United States Patent
Wang et al.

(10) Patent No.: US 10,815,308 B2
(45) Date of Patent: Oct. 27, 2020

(54) FIXAXFX BISPECIFIC ANTIBODY WITH COMMON LIGHT CHAIN

(71) Applicant: KYMAB LIMITED, Cambridge (GB)

(72) Inventors: Wei Wang, Cambridge (GB); E-Chiang Lee, Cambridge (GB); John Kenneth Blackwood, Cambridge (GB); Roberto Magliozzi, Cambridge (GB)

(73) Assignee: KYMAB LIMITED, Cambridge (GB)

( * ) Notice: Subject to any disclaimer, the term of this patent is extended or adjusted under 35 U.S.C. 154(b) by 0 days.

(21) Appl. No.: 16/722,452

(22) Filed: Dec. 20, 2019

(65) Prior Publication Data

US 2020/0199250 A1    Jun. 25, 2020

(30) Foreign Application Priority Data

| Dec. 21, 2018 | (GB) | .................................. | 1820977.5 |
| May 15, 2019 | (GB) | .................................. | 1906816.2 |
| Jun. 7, 2019 | (GB) | .................................. | 1908190.0 |

(51) Int. Cl.
   *C07K 16/36*   (2006.01)

(52) U.S. Cl.
   CPC .......... *C07K 16/36* (2013.01); *C07K 2317/31* (2013.01); *C07K 2317/522* (2013.01); *C07K 2317/565* (2013.01); *C07K 2317/92* (2013.01); *C07K 2317/94* (2013.01)

(58) Field of Classification Search
   None
   See application file for complete search history.

(56) References Cited

U.S. PATENT DOCUMENTS

| 8,062,635 | B2 * | 11/2011 | Hattori ................ | C07K 16/2866 424/136.1 |
| 9,334,331 | B2 * | 5/2016 | Igawa ..................... | C07K 16/40 |
| 2003/0219441 | A1 | 11/2003 | Thorpe | |
| 2005/0058640 | A1 | 3/2005 | Kerschbaumer | |
| 2016/0222129 | A1 | 8/2016 | Igawa | |

FOREIGN PATENT DOCUMENTS

| CA | 3027018 A1 | 2/2018 |
| WO | 0119992 | 3/2001 |
| WO | 2005025615 | 3/2005 |
| WO | 2005035753 | 4/2005 |
| WO | 2005035754 | 4/2005 |
| WO | 2005035756 | 4/2005 |
| WO | 2006109592 | 10/2006 |
| WO | 2012067176 | 5/2012 |
| WO | 2015194233 | 12/2015 |
| WO | 2016047656 | 3/2016 |
| WO | 2016166014 | 10/2016 |
| WO | 2016171202 | 10/2016 |
| WO | 2017110980 | 6/2017 |
| WO | 2017136820 | 8/2017 |
| WO | 2017200981 | 11/2017 |
| WO | 2018021450 | 2/2018 |
| WO | 2018047813 | 3/2018 |
| WO | 2018098363 | 5/2018 |
| WO | 2018141863 | 8/2018 |
| WO | 2018145125 | 8/2018 |
| WO | 2018234575 | 12/2018 |
| WO | 2019065795 | 4/2019 |
| WO | 2019096874 | 5/2019 |

OTHER PUBLICATIONS

Janeway et al., Immunobiology, 3rd edition, Garland Publishing Inc., 1997, pp. 3:1-3:21.*
Rudikoff et al., Proc Natl Acad Sci USA. Mar. 1982;79(6):1979-83.*
Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Kanyavuz et al., Nat Rev Immunol. Jun. 2019;19(6):355-368. doi: 10.1038/S41577-019-0126-7.*
Aleman, Maria M., et al. "Phospholipid-Independent Activity of Fviiia Mimetic Bispecific Antibodies in Plasma." Blood 132. Supplement 1 (2018): 2461-2461.
Brandstetter, Hans, et al. "X-ray structure of clotting factor IXa: active site and module structure related to Xase activity and hemophilia B." Proceedings of the National Academy of Sciences 92.21 (1995): 9796-9800.
Haemophilia (2014), 20(suppl. 3), 1-186.
Kitazawa, Takehisa, et al. "A bispecific antibody to factors IXa and X restores factor VIII hemostatic activity in a hemophilia A model." Nature medicine 18.10 (2012): 1570-1574.
Knappe, Sabrine et al. "Biospecific antibodies with light chain specificity for factor IXa and X improve thrombingeneration in hemophilia a plasma." 27th congress of the international society of thrombosis and homeostasis, Jul. 6-10, 2019, Melbourne, Australia, 1 pg.
Knobe, Karin, and Erik Berntorp. "New treatments in hemophilia: insights for the clinician." Therapeutic advances in hematology 3.3 (2012): 165-175.
Leksa, Nina C., et al. "Intrinsic differences between FVIII a mimetic bispecific antibodies and FVIII prevent assignment of FVIII☐equivalence." Journal of Thrombosis and Haemostasis 17.7 (2019): 1044-1052 Supplementary Material.
Leksa, Nina C., et al. "Intrinsic differences between FVIII a mimetic bispecific antibodies and FVIII prevent assignment of FVIII☐equivalence." Journal of Thrombosis and Haemostasis 17.7 (2019): 1044-1052.
Muto, Atsushi, et al. "Anti-factor IXa/X bispecific antibody ACE910 prevents joint bleeds in a longterm primate model of acquired hemophilia A." Blood, The Journal of the American Society of Hematology 124.20 (2014): 3165-3171.
Oldenburg J, Mahlangu JN, Kim B, et al. Emicizumab prophylaxis in hemophilia A with inhibitors. N Engl J Med. DOI: 10.1056/NEJMoa1703068, 29 pages.

(Continued)

*Primary Examiner* — Michael Szperka
(74) *Attorney, Agent, or Firm* — Riverside Law LLP

(57) ABSTRACT

Bispecific antigen binding molecules (e.g., antibodies) that bind blood clotting factors, factor IXa (FIXa) and factor X (FX), and enhance the FIXa-catalysed activation of FX to FXa. Use of the bispecific antigen binding molecules to control bleeding, by replacing natural cofactor FVIIIa which is deficient in patients with haemophilia A.

17 Claims, 54 Drawing Sheets

Specification includes a Sequence Listing.

(56) References Cited

OTHER PUBLICATIONS

Oldenburg, Johannes, et al. "Emicizumab prophylaxis in hemophilia A with inhibitors." New England Journal of Medicine 377.9 (2017): 809-818.

Sampei, Zenjiro, et al. "Identification and multidimensional optimization of an asymmetric bispecific IgG antibody mimicking the function of factor VIII cofactor activity." PloS one 8.2 (2013), 13 pages.

Shima, Midori, et al. "Factor VIII—mimetic function of humanized bispecific antibody in hemophilia A." New England Journal of Medicine 374.21 (2016): 2044-2053.

Smith, Eric J., et al. "A novel, native-format bispecific antibody triggering T-cell killing of B-cells is robustly active in mouse tumor models and cynomolgus monkeys." Scientific reports 5 (2015): 17943.

Tripodi, Armando. "Thrombin generation assay and its application in the clinical laboratory." Clinical chemistry 62.5 (2016): 699-707.

Uchida, Naoki, et al. "A first-in-human phase 1 study of ACE910, a novel factor VIII—mimetic bispecific antibody, in healthy subjects." Blood, The Journal of the American Society of Hematology 127.13 (2016): 1633-1641.

Young, Guy, et al. "Thrombin generation and whole blood viscoelastic assays in the management of hemophilia: current state of art and future perspectives." Blood, The Journal of the American Society of Hematology 121.11 (2013): 1944-1950.

International Search Report and Written Opinion for App No. PCT/EP2019/086808, dated Apr. 17, 2020, 20 pages.

Ido Paz-Priel et al.: "Immunogenicity of Emicizumab in People with Hemophilia A (PwHA): Results from the HAVEN 1-4 Studies", Blood, vol. 132, Nov. 29, 2018, p. 633, XP055683059.

Hoad R. B. et al.: "Characterisation of monoclonal antibodies to human factor X/Xa initial observations with a quantitative ELISA procedure", Journal of Immunological Methods, Elsevier Science Publishers B.V., Amsterdam, NL, vol. 136, No. 2, Feb. 15, 1991, pp. 269-278, XP023974087, ISSN: 0022-1759, DOI: 10.1016/0022-1759(91)90013-6 [retrieved on Feb. 15, 1991].

\* cited by examiner

A
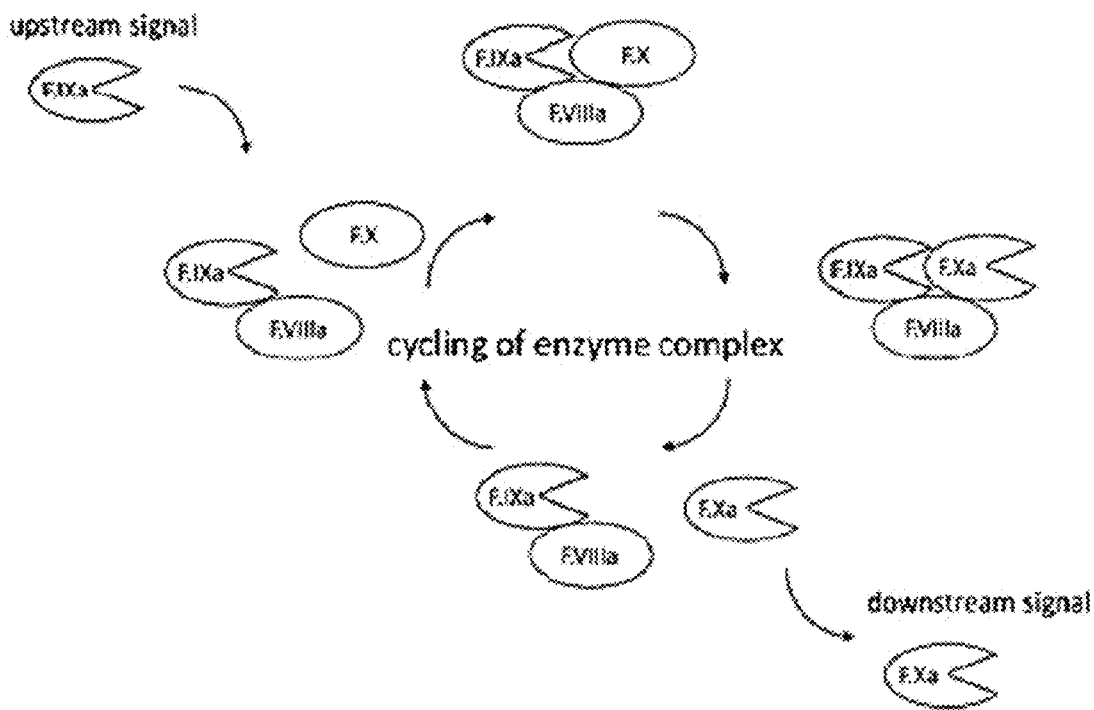
B
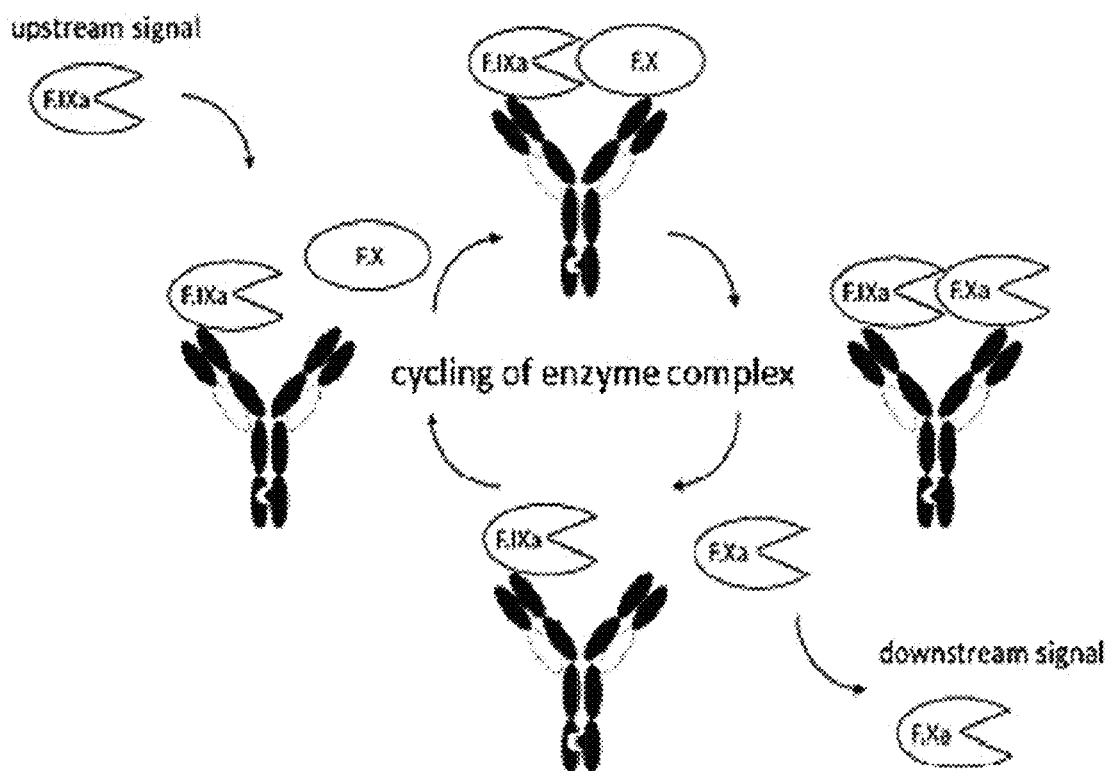
Figure 2

C

MQRVNMIMAESPGLITICLLGYLLSAECTVELDHENANKILNRPKR

| | | | | |
|---|---|---|---|---|
| YNSGKLEEFV | QGNLERECME | EKCSFEEARE | VFENTERTTE | 40 |
| FWKQYVDGDQ | CESNPCLNGG | SCKDDINSYE | CWCPFGFEGK | 80 |
| NCELDVTCNI | KNGRCEQFCK | NSADNKVVCS | CTEGYRLAEN | 120 |
| QKSCEPAVPF | PCGRVSVSQT | SKLTR AETVF | PDVDYVNSTE | 160 |
| AETILDNITQ | STQSFNDFTR | VVGGEDAKPG | QFPWQVVLNG | 200 |
| KVDAFCGGSI | VNEKWIVTAA | HCVETGVKIT | VVAGEHNIEE | 240 |
| TEHTEQKRNV | IRIIPHHNYN | AAINKYNHDI | ALLELDEPLV | 280 |
| LNSYVTPICI | ADKEYTNIFL | KFGSGYVSGW | GRVFHKGRSA | 320 |
| LVLQYLRVPL | VDRATCLRST | KFTIYNNMFC | AGFHEGGRDS | 360 |
| CQGDSGGPHV | TEVEGTSFLT | GIISWGEECA | MKGKYGIYTK | 400 |
| VSRYVNWIKE | KTKLT | | | 415 |

Figure 3

|   | 10 | 20 | 30 | 40 | 50 |
|---|---|---|---|---|---|
| | MGRPLHLVLL | SASLAGLLLL | GESLFIRREQ | ANNILARVTR | ANSFLEEMKK |
|   | 60 | 70 | 80 | 90 | 100 |
| | GHLERECMEE | TCSYEEAREV | FEDSDKTNEF | WNKYKDGDQC | ETSPCQNQGK |
|   | 110 | 120 | 130 | 140 | 150 |
| | CKDGLGEYTC | TCLEGFEGKN | CELFTRKLCS | LDNGDCDQFC | HEEQNSVVCS |
|   | 160 | 170 | 180 | 190 | 200 |
| | CARGYTLADN | GKACIPTGPY | PCGKQTLERR | KRSVAQATSS | SGEAPDSITW |
|   | 210 | 220 | 230 | 240 | 250 |
| | KPYDAADLDP | TENPFDLLDF | NQTQPERGDN | NLTRIVGGQE | CKDGECPWQA |
|   | 260 | 270 | 280 | 290 | 300 |
| | LLINEENEGF | CGGTILSEFY | ILTAAHCLYQ | AKRFKVRVGD | RNTEQEEGGE |
|   | 310 | 320 | 330 | 340 | 350 |
| | AVHEVEVVIK | HNRFTKETYD | FDIAVLRLKT | PITFRMNVAP | ACLPERDWAE |
|   | 360 | 370 | 380 | 390 | 400 |
| | STLMTQKTGI | VSGFGRTHEK | GRQSTRLKML | EVPYVDRNSC | KLSSSFIITQ |
|   | 410 | 420 | 430 | 440 | 450 |
| | NMFCAGYDTK | QEDACQGDSG | GPHVTRFKDT | YFVTGIVSWG | EGCARKGKYG |
|   | 460 | 470 | 480 |   |   |
| | IYTKVTAFLK | WIDRSMKTRG | LPKAKSHAPE | VITSSPLK |   |

(SEQ ID NO:468)

A

```
            <-----------FR1--------><-CDR1-><-----FR2--------><CDR2-->
(SEQ ID NO:470)  QVQLIQSGAEVKKPGASVKVSCKASRYSFTSYYMHWVRQAPGQGLEWMGIINPKSGST

<----------------FR3---------------><----CDR3----><---FR4--->
            SYAQKFQGRVTMTRDTSTSTVYMELSSLRSEDTAVYYCARDGYGSSSRCLQLWGQGTLVTVSS
```

B (SEQ ID NO:470)

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|
| Q | V | Q | L | I | Q | S | G | A | - | E | V | K | K | P | G | A | S | V | K |

| 21 | 22 | 23 | 24 | 25 | 26 | 27 | 28 | 29 | 30 | 31 | 32 | 33 | 34 | 35 | 36 | 37 | 38 | 39 | 40 |
|---|---|---|---|---|---|---|---|---|---|---|---|---|---|---|---|---|---|---|---|
| V | S | C | K | A | S | R | Y | S | F | - | - | - | T | S | Y | Y | M | H |

| 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|
| W | V | R | Q | A | P | G | Q | G | L | E | W | M | G | I | I | N | P | K | - |

| 61 | 62 | 63 | 64 | 65 | 66 | 67 | 68 | 69 | 70 | 71 | 72 | 73 | 74 | 75 | 76 | 77 | 78 | 79 | 80 |
|---|---|---|---|---|---|---|---|---|---|---|---|---|---|---|---|---|---|---|---|
| - | S | G | S | T | S | Y | A | Q | K | F | Q | - | G | R | V | T | M | T | R |

| 81 | 82 | 83 | 84 | 85 | 86 | 87 | 88 | 89 | 90 | 91 | 92 | 93 | 94 | 95 | 96 | 97 | 98 | 99 | 100 |
|---|---|---|---|---|---|---|---|---|---|---|---|---|---|---|---|---|---|---|---|
| D | T | S | T | S | T | V | Y | M | E | L | S | S | L | R | S | E | D | T | A |

| 101 | 102 | 103 | 104 | 105 | 106 | 107 | 108 | 109 | 110 | 111 | 111A | 112 | 113 | 114 |
|---|---|---|---|---|---|---|---|---|---|---|---|---|---|---|
| V | Y | Y | C | A | R | D | G | Y | G | S | S | S | R | C |

| 115 | 116 | 117 | 118 | 119 | 120 | 121 | 122 | 123 | 124 | 125 | 126 | 127 | 128 |
|---|---|---|---|---|---|---|---|---|---|---|---|---|---|
| L | Q | L | W | G | Q | G | T | L | V | T | V | S | S |

```
                    <----------FR1---------><--CDR1--><------FR2------><--CDR2-->
(SEQ ID NO:15)   812H(germline) EVQLVESGGGLVQPGGSLRLSCAASGFTFSNSYWMSWVRQAPGKGLEWVANIKQDGSEK
(SEQ ID NO:5)    812H           EVQLVESGGGFVQPGGSLRLSCAVSGFTFNSYWMSWVRQAPGKGLEWVANINQDGSEK
(SEQ ID NO:443)  812808         EVQLVESGGGFVQPGGSLRLSCAVSGFTFNSYWMSWVRQAPGKGLEWVANINQDGSEK
```

```
                    <-------------------FR3-------------------><----CDR3-----><---FR4--->
                 812H(germline) YYVDSVKGRFTISRDNAKNSLYLQMNSLRAEDTAVYYCARGTSYYYDYWGQGTTVTVSS
                 812H           FYVASVKGRFTMSRDNAKKSVYVQMNSLRAEDTAVYYCARGYSSSSYYGQWGQGTTVTVSS
                 812808         FYVASVKGRFTMSRDNAKKSVYVQMNSLRAEDTAVYYCARGYSSSSIKYYGQWGQGTTVTVSS
```

B

| 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|----|----|----|----|----|----|----|----|----|----|----|
| E | V | Q | L | V | E | S | G | G | -  | G  | F  | V  | Q  | P  | G  | G  | S  | L  | R  |

(SEQ ID NO:5)

| 21 | 22 | 23 | 24 | 25 | 26 | 27 | 28 | 29 | 30 | 31 | 32 | 33 | 34 | 35 | 36 | 37 | 38 | 39 | 40 |
|----|----|----|----|----|----|----|----|----|----|----|----|----|----|----|----|----|----|----|----|
| L  | S  | C  | A  | V  | S  | G  | F  | T  | F  | -  | -  | -  | -  | N  | S  | Y  | W  | M  | S  |

| 41 | 42 | 43 | 44 | 45 | 46 | 47 | 48 | 49 | 50 | 51 | 52 | 53 | 54 | 55 | 56 | 57 | 58 | 59 | 60 |
|----|----|----|----|----|----|----|----|----|----|----|----|----|----|----|----|----|----|----|----|
| W  | V  | R  | Q  | A  | P  | G  | K  | G  | L  | E  | W  | V  | A  | N  | I  | N  | Q  | D  | -  |

| 61 | 62 | 63 | 64 | 65 | 66 | 67 | 68 | 69 | 70 | 71 | 72 | 73 | 74 | 75 | 76 | 77 | 78 | 79 | 80 |
|----|----|----|----|----|----|----|----|----|----|----|----|----|----|----|----|----|----|----|----|
| -  | G  | S  | E  | K  | F  | Y  | V  | A  | S  | V  | K  | -  | G  | R  | F  | T  | M  | S  | R  |

| 81 | 82 | 83 | 84 | 85 | 86 | 87 | 88 | 89 | 90 | 91 | 92 | 93 | 94 | 95 | 96 | 97 | 98 | 99 | 100 |
|----|----|----|----|----|----|----|----|----|----|----|----|----|----|----|----|----|----|----|-----|
| D  | N  | A  | K  | K  | S  | V  | Y  | V  | Q  | M  | N  | S  | L  | R  | A  | E  | D  | T  | A   |

| 101 | 102 | 103 | 104 | 105 | 106 | 107 | 108 | 109 | 110 | 111 | 111A | 112A | 112 | 113 | 114 |
|-----|-----|-----|-----|-----|-----|-----|-----|-----|-----|-----|------|------|-----|-----|-----|
| V   | Y   | Y   | C   | A   | R   | E   | G   | Y   | S   | S   | S    | S    | Y   | Y   | G   |

| 115 | 116 | 117 | 118 | 119 | 120 | 121 | 122 | 123 | 124 | 125 | 126 | 127 | 128 |
|-----|-----|-----|-----|-----|-----|-----|-----|-----|-----|-----|-----|-----|-----|
| M   | D   | V   | W   | G   | Q   | G   | T   | T   | V   | T   | V   | S   | S   |

Figure 14

| Mutant ID | FR1 | CDR1 | FR2 | CDR2 |
|---|---|---|---|---|
| M0128H | EVQLVESGGGFVQPGGSLRLSCAVS (SEQ ID NO:132) | GFTFNSYW (SEQ ID NO:1) | MSWVRQAPGKGLEWVAN (SEQ ID NO:133) | INQDGSEK (SEQ ID NO:2) |
| N0436H | EVQLVESGGGFVQPGGSLRLSCAVS (SEQ ID NO:132) | GFTFNSYW (SEQ ID NO:1) | MSWVRQAPGKGLEWVAN (SEQ ID NO:133) | IKQDGSEK (SEQ ID NO:12) |
| N0511H | EVQLVESGGGFVQPGGSLRLSCAVS (SEQ ID NO:132) | GFTFNSYW (SEQ ID NO:1) | MSWVRQAPGKGLEWVAN (SEQ ID NO:133) | IKQDGSEK (SEQ ID NO:12) |
| N1091H | EVQLVESGGGFVQPGGSLRLSCAVS (SEQ ID NO:132) | GFTFNSYW (SEQ ID NO:1) | MSWVRQAPGKGLEWVAN (SEQ ID NO:133) | INQDGSRK (SEQ ID NO:436) |
| N1172H | EVQLVESGGGFVQPGGSLRLSCAVS (SEQ ID NO:132) | GFTFNSYW (SEQ ID NO:1) | MSWVRQAPGKGLEWVAN (SEQ ID NO:133) | INQDGSRK (SEQ ID NO:436) |
| N1280H | EVQLVESGGGFVQPGGSLRLSCAVS (SEQ ID NO:132) | GFRFNSYW (SEQ ID NO:441) | MSWVRQAPGKGLEWVAN (SEQ ID NO:133) | INQDGSRK (SEQ ID NO:436) |
| N1514H | EVQLVESGGGFVQPGGSLRLSCAVS (SEQ ID NO:132) | GFRFNSYW (SEQ ID NO:441) | MSWVRQAPGKGLEWVAN (SEQ ID NO:133) | INQMGSRK (SEQ ID NO:444) |
| N1527H | EVQLVESGGGFVQPGGSLRLSCAVS (SEQ ID NO:132) | GFRFNSYW (SEQ ID NO:441) | MSWVRQAPGKGLEWVAN (SEQ ID NO:133) | INQMGSRK (SEQ ID NO:447) |
| N1533H | EVQLVESGGGFVQPGGSLRLSCAVS (SEQ ID NO:132) | GFRFNSYW (SEQ ID NO:441) | MSWVRQAPGKGLEWVAN (SEQ ID NO:133) | INQDGFRK (SEQ ID NO:450) |

Figure 20

| Mutant ID | FR3 | CDR3 | FR4 |
|---|---|---|---|
| N0128H | FYVASVKGRFTMSRDNAKKSVYVQMNSLRAEDTAVYYC (SEQ ID NO: 134) | AREGYSSSSYYGMDV (SEQ ID NO: 3) | WGQGTTVTVSS (SEQ ID NO: 135) |
| N0436H | FYVASVKGRFTMSRDNAKKSVYVQMNSLRAEDTAVYYC (SEQ ID NO: 134) | AREGYSSISYYGMDV (SEQ ID NO: 171) | WGQGTTVTVSS (SEQ ID NO: 135) |
| N0511H | FYVASVKGRFTMSRDNAKKSVYVQMNSLRAEDTAVYYC (SEQ ID NO: 134) | AREGYSSIKYYGMDV (SEQ ID NO: 433) | WGQGTTVTVSS (SEQ ID NO: 135) |
| N1091H | FYVASVKGRFTMSRDNAKKSVYVQMNSLRAEDTAVYYC (SEQ ID NO: 134) | AREGYSSISYYGMDV (SEQ ID NO: 171) | WGQGTTVTVSS (SEQ ID NO: 135) |
| N1172H | FYVASVKGRFTMSRDNAKKSVYVQMNSLRAEDTAVYYC (SEQ ID NO: 134) | AREGYSSIKYYGMDV (SEQ ID NO: 433) | WGQGTTVTVSS (SEQ ID NO: 135) |
| N1480H | FYVASVKGRFTMSRDNAKKSVYVQMNSLRAEDTAVYYC (SEQ ID NO: 134) | AREGYSSIKYYGMDV (SEQ ID NO: 433) | WGQGTTVTVSS (SEQ ID NO: 135) |
| N1514H | FYVASVKGRFTMSRDNAKKSVYVQMNSLRAEDTAVYYC (SEQ ID NO: 134) | AREGYSSIKYYGMDV (SEQ ID NO: 433) | WGQGTTVTVSS (SEQ ID NO: 135) |
| N1927H | FYVASVKGRFTMSRDNAKKSVYVQMNSLRAEDTAVYYC (SEQ ID NO: 134) | AREGYSSIKYYGMDV (SEQ ID NO: 433) | WGQGTTVTVSS (SEQ ID NO: 135) |
| N1933H | FYVASVKGRFTMSRDNAKKSVYVQMNSLRAEDTAVYYC (SEQ ID NO: 134) | AREGYSSIKYYGMDV (SEQ ID NO: 433) | WGQGTTVTVSS (SEQ ID NO: 135) |

| T0201H | | | |
|---|---|---|---|
| ID | CDR1 | CDR2 | CDR3 |
| CL165509VH | RYSFTSYY (SEQ ID NO:462) | INPKSGST (SEQ ID NO:467) | ARDGYGSSSRCLQL (SEQ ID NO:468) |
| CDR3 single mutation | | | |
| T537H | RYSFTSYY (SEQ ID NO:462) | INPKSGST (SEQ ID NO:467) | ARDGYGSFSSRCLQL (SEQ ID NO:640) |
| T616H | RYSFTSYY (SEQ ID NO:462) | INPKSGST (SEQ ID NO:467) | ARDGYGSSSRCIQL (SEQ ID NO:641) |
| T638H | RYSFTSYY (SEQ ID NO:462) | INPKSGST (SEQ ID NO:467) | ARDGYGSSSRCLML (SEQ ID NO:642) |
| T596H | RYSFTSYY (SEQ ID NO:462) | INPKSGST (SEQ ID NO:467) | ARDGYGSSSRILQL (SEQ ID NO:643) |
| T598H | RYSFTSYY (SEQ ID NO:462) | INPKSGST (SEQ ID NO:467) | ARDGYGSSSRLLQL (SEQ ID NO:644) |
| T620H | RYSFTSYY (SEQ ID NO:462) | INPKSGST (SEQ ID NO:467) | ARDGYGSSSRQLQL (SEQ ID NO:645) |
| T606H | RYSFTSYY (SEQ ID NO:462) | INPKSGST (SEQ ID NO:467) | ARDGYGSSSRVLQL (SEQ ID NO:646) |
| CDR3 compound mutation | | | |
| T666H | RYSFTSYY (SEQ ID NO:462) | INPKSGST (SEQ ID NO:467) | ARDGYGSSSRIIQL (SEQ ID NO:520) |
| T667H | RYSFTSYY (SEQ ID NO:462) | INPKSGST (SEQ ID NO:467) | ARDGYGSSSRLIQL (SEQ ID NO:523) |
| T668H | RYSFTSYY (SEQ ID NO:462) | INPKSGST (SEQ ID NO:467) | ARDGYGSSSRQIQL (SEQ ID NO:526) |
| T669H | RYSFTSYY (SEQ ID NO:462) | INPKSGST (SEQ ID NO:467) | ARDGYGSSSRILML (SEQ ID NO:529) |
| T670H | RYSFTSYY (SEQ ID NO:462) | INPKSGST (SEQ ID NO:467) | ARDGYGSSSRLLML (SEQ ID NO:532) |
| T671H | RYSFTSYY (SEQ ID NO:462) | INPKSGST (SEQ ID NO:467) | ARDGYGSSSRQLML (SEQ ID NO:535) |
| T672H | RYSFTSYY (SEQ ID NO:462) | INPKSGST (SEQ ID NO:467) | ARDGYGSSSRIIML (SEQ ID NO:538) |
| T673H | RYSFTSYY (SEQ ID NO:462) | INPKSGST (SEQ ID NO:467) | ARDGYGSSSRLIML (SEQ ID NO:541) |
| T674H | RYSFTSYY (SEQ ID NO:462) | INPKSGST (SEQ ID NO:467) | ARDGYGSSSRQIML (SEQ ID NO:544) |
| T675H | RYSFTSYY (SEQ ID NO:462) | INPKSGST (SEQ ID NO:467) | ARDGYGSSSRVIQL (SEQ ID NO:547) |
| T676H | RYSFTSYY (SEQ ID NO:462) | INPKSGST (SEQ ID NO:467) | ARDGYGSSSRVLML (SEQ ID NO:550) |
| T677H | RYSFTSYY (SEQ ID NO:462) | INPKSGST (SEQ ID NO:467) | ARDGYGSSSRVIML (SEQ ID NO:553) |
| T678H | RYSFTSYY (SEQ ID NO:462) | INPKSGST (SEQ ID NO:467) | ARDGYGSFSSRIIQL (SEQ ID NO:556) |
| T679H | RYSFTSYY (SEQ ID NO:462) | INPKSGST (SEQ ID NO:467) | ARDGYGSFSSRILML (SEQ ID NO:559) |
| T680H | RYSFTSYY (SEQ ID NO:462) | INPKSGST (SEQ ID NO:467) | ARDGYGSFSSRIIML (SEQ ID NO:562) |
| T681H | RYSFTSYY (SEQ ID NO:462) | INPKSGST (SEQ ID NO:467) | ARDGYGSFSSRLIQL (SEQ ID NO:565) |
| T682H | RYSFTSYY (SEQ ID NO:462) | INPKSGST (SEQ ID NO:467) | ARDGYGSFSSRLLML (SEQ ID NO:568) |
| T683H | RYSFTSYY (SEQ ID NO:462) | INPKSGST (SEQ ID NO:467) | ARDGYGSFSSRLIML (SEQ ID NO:571) |
| T684H | RYSFTSYY (SEQ ID NO:462) | INPKSGST (SEQ ID NO:467) | ARDGYGSFSSRQIQL (SEQ ID NO:574) |
| T685H | RYSFTSYY (SEQ ID NO:462) | INPKSGST (SEQ ID NO:467) | ARDGYGSFSSRQLML (SEQ ID NO:577) |
| T686H | RYSFTSYY (SEQ ID NO:462) | INPKSGST (SEQ ID NO:467) | ARDGYGSFSSRQIML (SEQ ID NO:580) |
| T687H | RYSFTSYY (SEQ ID NO:462) | INPKSGST (SEQ ID NO:467) | ARDGYGSFSSRVIQL (SEQ ID NO:583) |
| T688H | RYSFTSYY (SEQ ID NO:462) | INPKSGST (SEQ ID NO:467) | ARDGYGSFSSRVLML (SEQ ID NO:586) |
| T689H | RYSFTSYY (SEQ ID NO:462) | INPKSGST (SEQ ID NO:467) | ARDGYGSFSSRVIML (SEQ ID NO:589) |

Figure 25

| CDR1 + CDR3 compound mutation | | | |
|---|---|---|---|
| T731H | RFSFTSYY (SEQ ID NO:592) | INPKSGST (SEQ ID NO:467) | ARDGYGSFSSRLIQL (SEQ ID NO:565) |
| T734H | RYHFTSYY (SEQ ID NO:595) | INPKSGST (SEQ ID NO:467) | ARDGYGSFSSRLIQL (SEQ ID NO:565) |
| T7376H | RYKFTSYY (SEQ ID NO:598) | INPKSGST (SEQ ID NO:467) | ARDGYGSFSSRLIQL (SEQ ID NO:565) |
| T742H | RYRFTSYY (SEQ ID NO:601) | INPKSGST (SEQ ID NO:467) | ARDGYGSFSSRLIQL (SEQ ID NO:565) |
| T774H | RYSFKSYY (SEQ ID NO:604) | INPKSGST (SEQ ID NO:467) | ARDGYGSFSSRLIQL (SEQ ID NO:565) |
| T285H | RYSFTAYY (SEQ ID NO:607) | INPKSGST (SEQ ID NO:467) | ARDGYGSFSSRLIQL (SEQ ID NO:565) |

| CDR2 + CDR3 compound mutation | | | |
|---|---|---|---|
| T850H | RYSFTSYY (SEQ ID NO:462) | LNPKSGST (SEQ ID NO:610) | ARDGYGSFSSRLIQL (SEQ ID NO:565) |
| T925H | RYSFTSYY (SEQ ID NO:462) | INPKIGST (SEQ ID NO:613) | ARDGYGSFSSRLIQL (SEQ ID NO:565) |
| T926H | RYSFTSYY (SEQ ID NO:462) | INPKKGST (SEQ ID NO:616) | ARDGYGSFSSRLIQL (SEQ ID NO:565) |
| T951H | RYSFTSYY (SEQ ID NO:462) | INPKSSST (SEQ ID NO:619) | ARDGYGSFSSRLIQL (SEQ ID NO:565) |
| T958H | RYSFTSYY (SEQ ID NO:462) | INPKSGDT (SEQ ID NO:622) | ARDGYGSFSSRLIQL (SEQ ID NO:565) |
| T989H | RYSFTSYY (SEQ ID NO:462) | INPKSGSR (SEQ ID NO:625) | ARDGYGSFSSRLIQL (SEQ ID NO:565) |
| T990H | RYSFTSYY (SEQ ID NO:462) | INPKSGSS (SEQ ID NO:628) | ARDGYGSFSSRLIQL (SEQ ID NO:565) |

Figure 25 (continued)

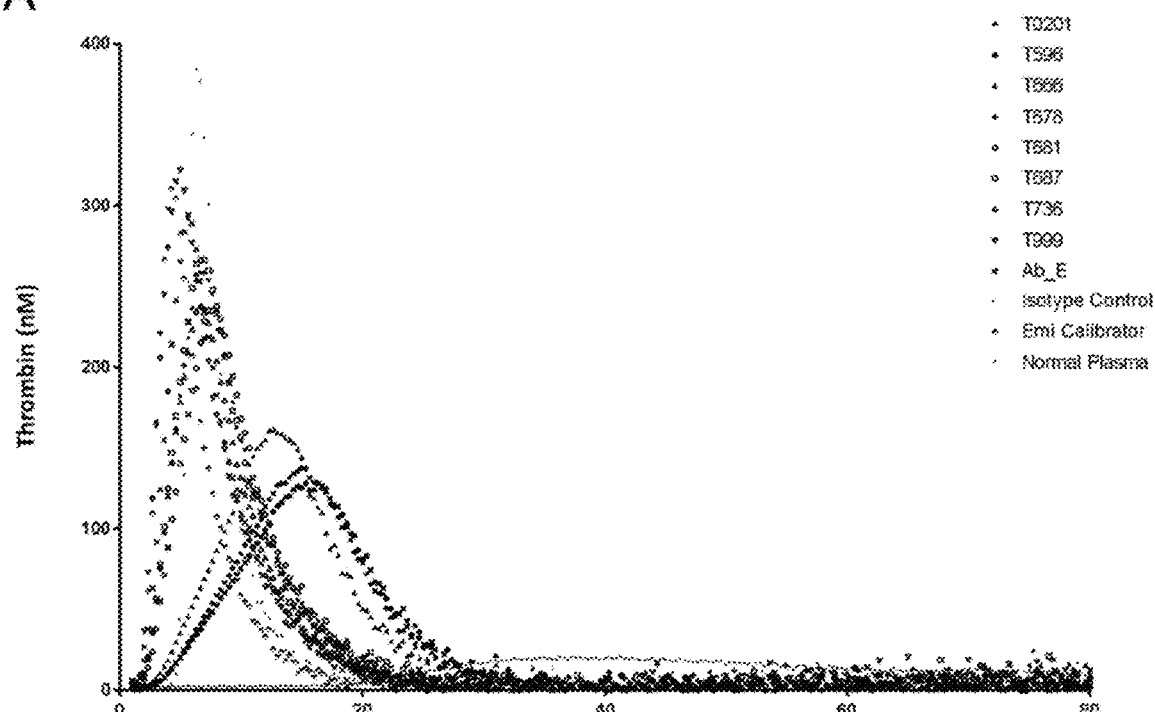
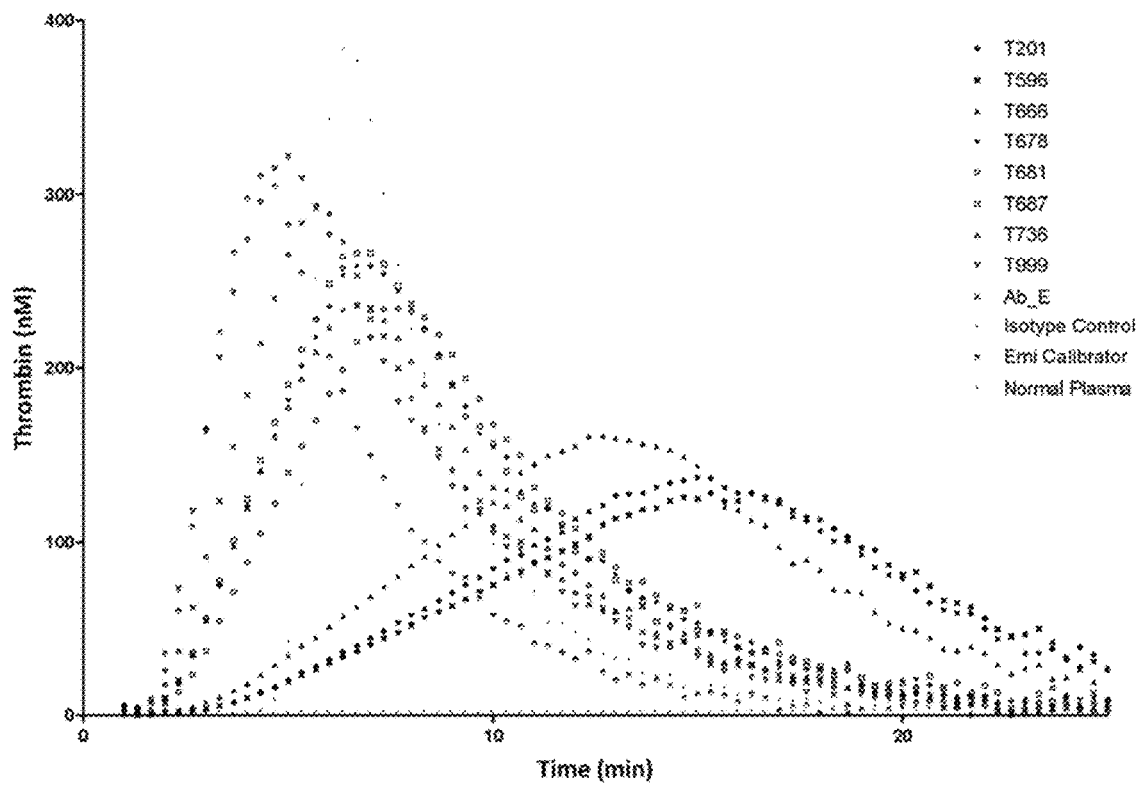
Figure 27

A
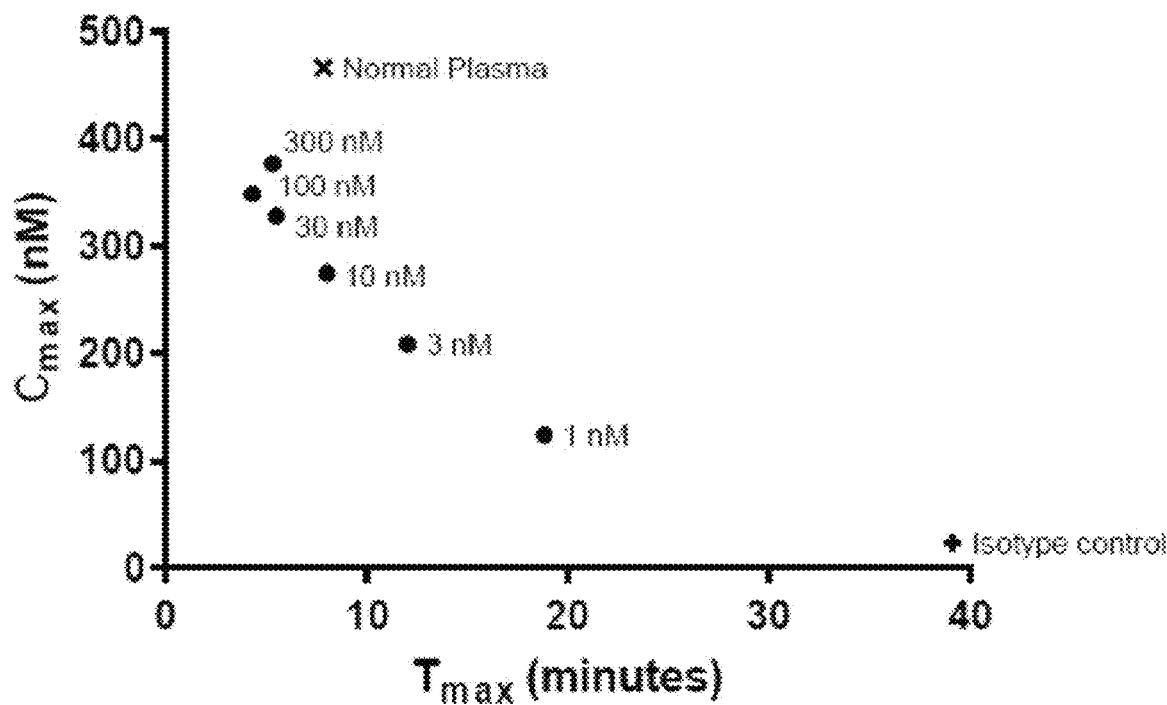
B
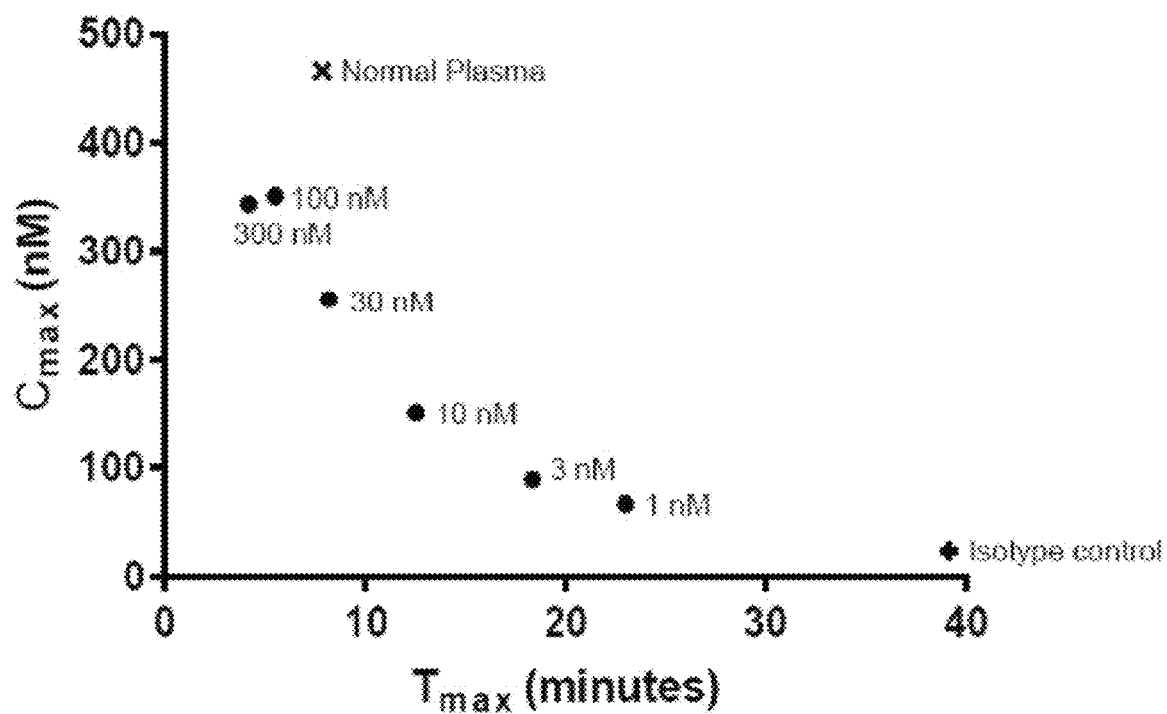
Figure 29

B

A

B
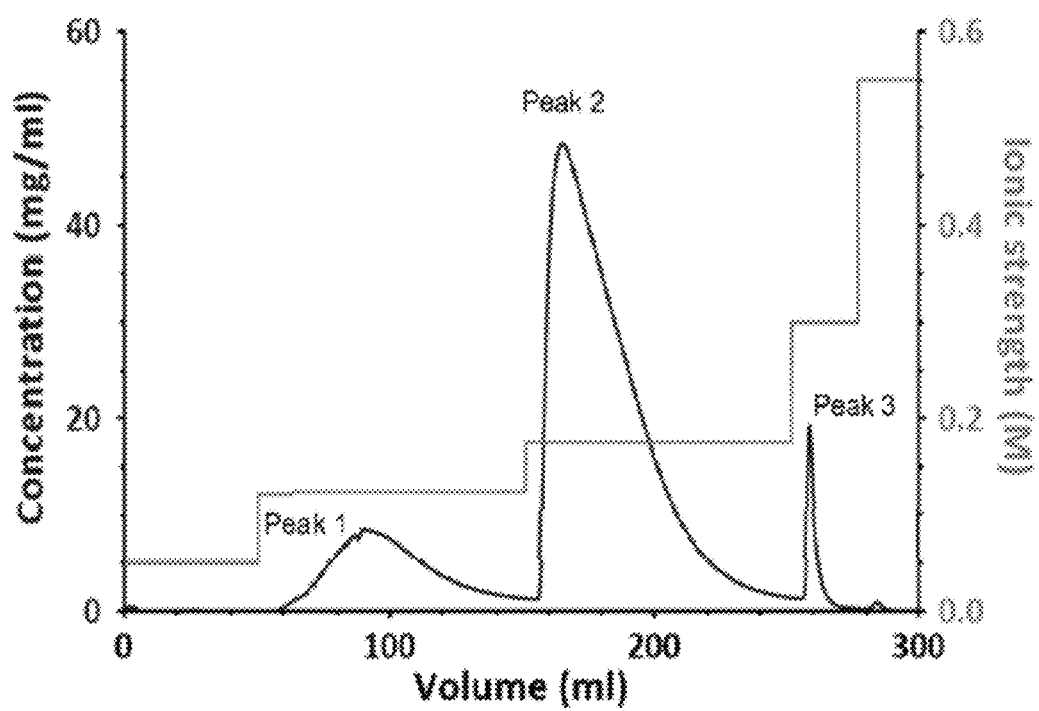
C
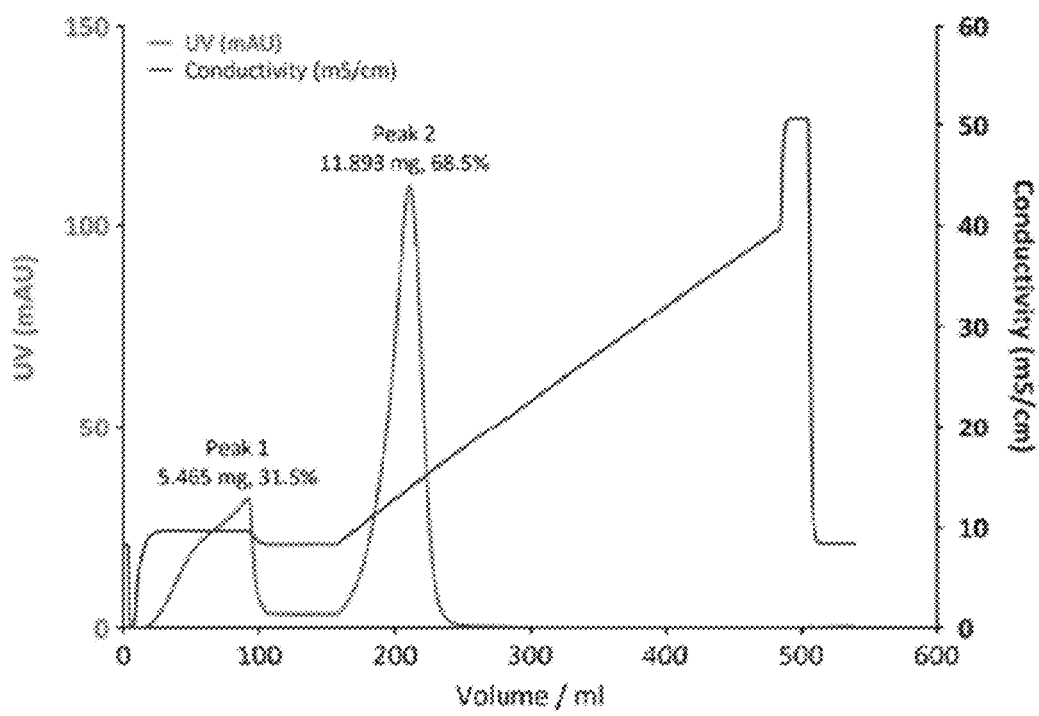
Figure 37 (continued)

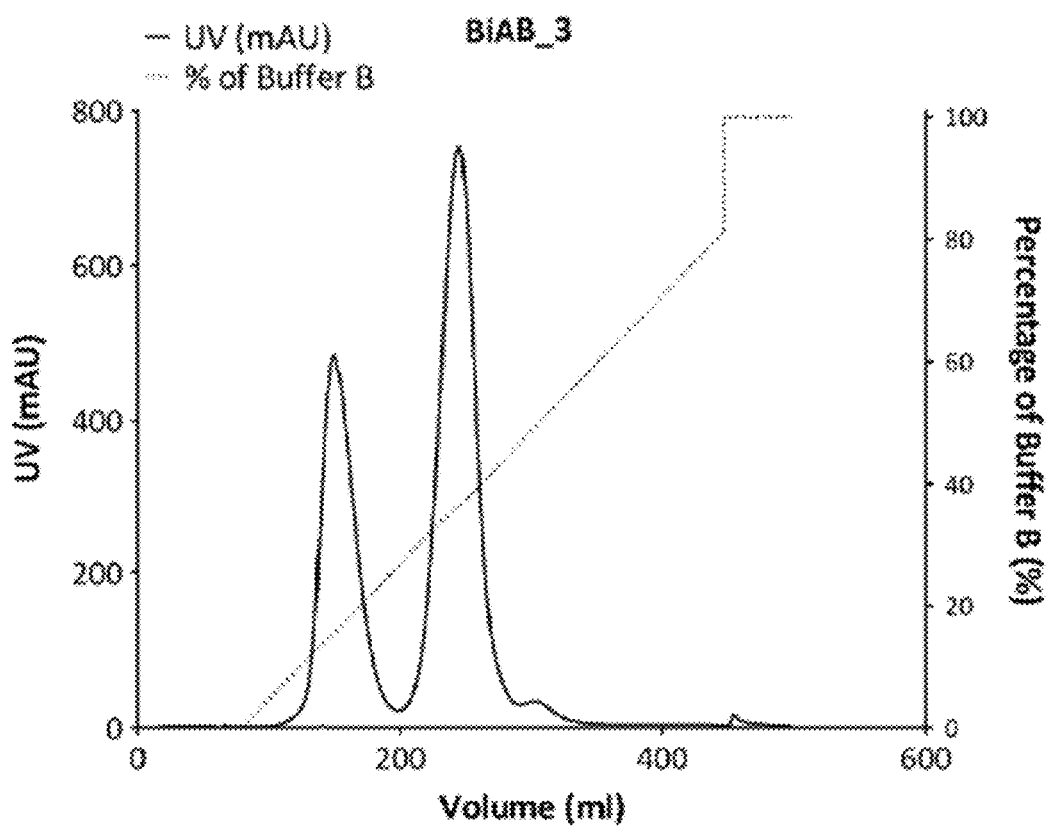
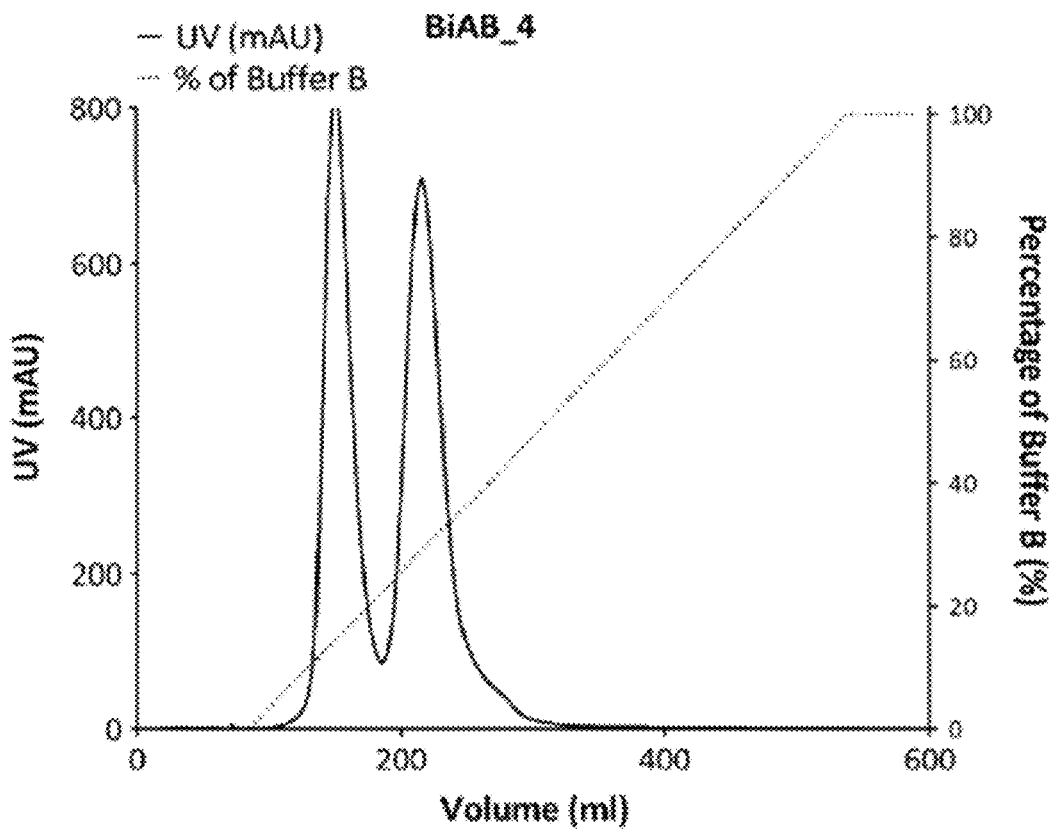
Figure 38 (continued)

SEQUENCE LISTING

<160> NUMBER OF SEQ ID NOS: 647

<210> SEQ ID NO 1
<211> LENGTH: 8
<212> TYPE: PRT
<213> ORGANISM: Homo sapiens

<400> SEQUENCE: 1

Gly Phe Thr Phe Asn Ser Tyr Trp
1               5

<210> SEQ ID NO 2
<211> LENGTH: 8
<212> TYPE: PRT
<213> ORGANISM: Homo sapiens

<400> SEQUENCE: 2

Ile Asn Gln Asp Gly Ser Glu Lys
1               5

<210> SEQ ID NO 3
<211> LENGTH: 15
<212> TYPE: PRT
<213> ORGANISM: Homo sapiens

<400> SEQUENCE: 3

Ala Arg Glu Gly Tyr Ser Ser Ser Tyr Tyr Gly Met Asp Val
1               5                   10                  15

<210> SEQ ID NO 4
<211> LENGTH: 367
<212> TYPE: DNA
<213> ORGANISM: Homo sapiens

<400> SEQUENCE: 4
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg gtggccaac ataaaccaag atggaagtga aaattctat      180 gtggcctctg tgaagggccg attcaccatg tccagagaca cgccaagaa atcagtgtat      240 gtacaaatga acagcctgag agccgaggac acggctgtgt attactgtgc gagagagggg    300
tatagtagtt cgtcctatta tggtatggac gtctgggggcc aagggaccac ggtcaccgtc    360
tcctcag                                                              367

<210> SEQ ID NO 5
<211> LENGTH: 122
<212> TYPE: PRT
<213> ORGANISM: Homo sapiens

<400> SEQUENCE: 5

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

```
Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 6
<211> LENGTH: 6
<212> TYPE: PRT
<213> ORGANISM: Homo sapiens

<400> SEQUENCE: 6

```
Asn Ile Gly Arg Lys Ser
1               5
```

<210> SEQ ID NO 7
<211> LENGTH: 3
<212> TYPE: PRT
<213> ORGANISM: Homo sapiens

<400> SEQUENCE: 7

```
Tyr Asp Ser
1
```

<210> SEQ ID NO 8
<211> LENGTH: 11
<212> TYPE: PRT
<213> ORGANISM: Homo sapiens

<400> SEQUENCE: 8

```
Gln Val Trp Asp Gly Ser Ser Asp His Trp Val
1               5                   10
```

<210> SEQ ID NO 9
<211> LENGTH: 325
<212> TYPE: DNA
<213> ORGANISM: Homo sapiens

<400> SEQUENCE: 9

```
tcctatgtgc tgactcagcc accctcagtg tcagtggccc caggagagac ggccaggatt     60
acctgtgggg gagacaacat tggaaggaaa agtgtgtact ggtaccagca gaagtcaggc    120
caggcccctg tgctggtcat ctattatgat agcgaccggc cctcagggat ccctgagcga    180
ttctctgggt ccaactctgg gaacacggcg accctgacca tcagcagggt cgaagccggg    240
gatgaggccg actattactg tcaggtgtgg gatggaagta gtgatcattg ggtgttcggc    300
ggagggacca agttgaccgt cctag                                          325
```

<210> SEQ ID NO 10
<211> LENGTH: 108
<212> TYPE: PRT
<213> ORGANISM: Homo sapiens

<400> SEQUENCE: 10

```
Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45
```

```
Tyr Asp Ser Asp Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Gly Ser Ser Asp His
                85                  90                  95

Trp Val Phe Gly Gly Gly Thr Lys Leu Thr Val Leu
            100                 105

<210> SEQ ID NO 11
<211> LENGTH: 8
<212> TYPE: PRT
<213> ORGANISM: Homo sapiens

<400> SEQUENCE: 11

Gly Phe Thr Phe Ser Ser Tyr Trp
 1               5

<210> SEQ ID NO 12
<211> LENGTH: 8
<212> TYPE: PRT
<213> ORGANISM: Homo sapiens

<400> SEQUENCE: 12

Ile Lys Gln Asp Gly Ser Glu Lys
 1               5

<210> SEQ ID NO 13
<211> LENGTH: 15
<212> TYPE: PRT
<213> ORGANISM: Homo sapiens

<400> SEQUENCE: 13

Ala Arg Glu Gly Tyr Ser Ser Tyr Tyr Tyr Gly Met Asp Val
 1               5                  10                  15

<210> SEQ ID NO 14
<211> LENGTH: 366
<212> TYPE: DNA
<213> ORGANISM: Homo sapiens

<400> SEQUENCE: 14
gaggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaagg ggctggagtg ggtggccaac ataaagcaag atggaagtga aaaatactat     180
gtggactctg tgaagggccg attcaccatc tccagagaca acgccaagaa ctcactgtat     240
ctgcaaatga acagcctgag agccgaggac acggctgtgt attactgtgc gagagagggg     300
tatagcagtt actactacta cggtatggac gtctggggcc aagggaccac ggtcaccgtc     360
tcctca                                                                366

<210> SEQ ID NO 15
<211> LENGTH: 122
<212> TYPE: PRT
<213> ORGANISM: Homo sapiens

<400> SEQUENCE: 15

Glu Val Gln Leu Val Glu Ser Gly Gly Gly Leu Val Gln Pro Gly Gly
 1               5                  10                  15
```

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Tyr Tyr Tyr Gly Met Asp Val Trp
            100                 105                 110

Gly Gln Gly Thr Thr Val Thr Val Ser Ser
            115                 120

<210> SEQ ID NO 16
<211> LENGTH: 366
<212> TYPE: DNA
<213> ORGANISM: Homo sapiens

<400> SEQUENCE: 16
gaggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaagg ggctggagtg ggtggccaac ataaaccaag atggaagtga aaaatactat     180
gtggactctg tgaagggccg attcaccatc tccagagaca acgccaagaa ctcactgtat     240
ctacaaatga acagcctgag agccgaggac acggctgtgt attactgtgc gagagagggg     300
tatagtagtt cgtcctatta tggtatggac gtctggggcc aagggaccac ggtcaccgtc     360
tcctca                                                                366

<210> SEQ ID NO 17
<211> LENGTH: 122
<212> TYPE: PRT
<213> ORGANISM: Homo sapiens

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Tyr Tyr Val Asp Ser Val
 50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

<210> SEQ ID NO 18
<211> LENGTH: 8
<212> TYPE: PRT

<210> SEQ ID NO 19
<211> LENGTH: 366
<212> TYPE: DNA
<213> ORGANISM: Homo sapiens

<400> SEQUENCE: 19

```
gaggtgcagc tggtggagtc tgggggaggc ttggtccagc ctgggggtc cctgagactc      60
tcctgtgtag cctctggatt catctttagt agctattgga tgagctgggt ccgccaggct    120
ccagggaagg gctggagtg gtggccaat ataaatcaag atggaagtga aaatactat       180
gtggactctg tgaagggccg attcaccatc tccagagaca cgccaagaa ctcactgtat     240
ctgcaaatga acagcctgag agccgaggac acggctgtgt attactgtgc gagagagggg   300
tatagcagtt cgtcctatta tggtatggac gtctggggcc aagggaccac ggtcaccgtc   360
tcctca                                                              366
```

<210> SEQ ID NO 20
<211> LENGTH: 122
<212> TYPE: PRT
<213> ORGANISM: Homo sapiens

<400> SEQUENCE: 20

Glu Val Gln Leu Val Glu Ser Gly Gly Gly Leu Val Gln Pro Gly Gly
1               5                   10                  15
Ser Leu Arg Leu Ser Cys Val Ala Ser Gly Phe Ile Phe Ser Ser Tyr
            20                  25                  30
Trp Met Ser Trp Val Arg Gln Ala Pro Gly Lys Gly Leu Glu Trp Val
        35                  40                  45
Ala Asn Ile Asn Gln Asp Gly Ser Glu Lys Tyr Tyr Val Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Glu Gly Tyr Ser Ser Ser Tyr Tyr Gly Met Asp Val Trp
            100                 105                 110
Gly Gln Gly Thr Thr Val Thr Val Ser Ser
        115                 120

<210> SEQ ID NO 21
<211> LENGTH: 366
<212> TYPE: DNA
<213> ORGANISM: Homo sapiens

<400> SEQUENCE: 21

```
gaggtgcagc tggtggagtc tgggggaggc ttggtccagc ctgggggtc cctgagactc      60
tcctgtgcag tctctggatt caccttaat agctattgga tgagctgggt ccgccaggct    120
ccagggaagg gctggagtg gtggccaac ataaaccaag atggaagtga aaattctat      180
gtggcctctg tgaagggccg attcaccatc tccagagaca cgccaagaa ctcagtgtat    240
ctacaaatga acagcctgag agccgaggac acggctgtgt attactgtgc gagagagggg   300
```

```
tatagtagtt cgtcctatta tggtatggac gtctggggcc aagggaccac ggtcaccgtc    360
tcctca                                                              366
```

<210> SEQ ID NO 22
<211> LENGTH: 122
<212> TYPE: PRT
<213> ORGANISM: Homo sapiens

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 23
<211> LENGTH: 8
<212> TYPE: PRT
<213> ORGANISM: Homo sapiens

<400> SEQUENCE: 23

```
Gly Phe Thr Phe Asn Asn Tyr Trp
1               5
```

<210> SEQ ID NO 24
<211> LENGTH: 15
<212> TYPE: PRT
<213> ORGANISM: Homo sapiens

<400> SEQUENCE: 24

```
Ala Arg Glu Gly Tyr Thr Asp Ser Ser Tyr Tyr Gly Met Asp Val
1               5                   10                  15
```

<210> SEQ ID NO 25
<211> LENGTH: 366
<212> TYPE: DNA
<213> ORGANISM: Homo sapiens

<400> SEQUENCE: 25

```
gaggtgcagc tggtggagtc tggggggaggc ctggtccagc ctggggggtc cctgagactc    60
tcctgtgcag tctctggatt cacctttaat aactattgga tgagctgggt ccgccaggct   120
ccagggaagg ggctggagtg gtggccaac ataaaccaag atggaagtga gaaattctat   180
gtggcctctg tgaagggccg attcatcatc tccagagaca cgccaaaaa ttcagtgtat   240 ctacaaatga acagcctgag agccgaggac acggctgtgt attactgtgc gagagagggg   300
tataccgatt cgtcctatta tggaatggac gtctggggcc aagggaccac ggtctccgtc   360
tcctca                                                              366
```

<210> SEQ ID NO 26
<211> LENGTH: 122
<212> TYPE: PRT
<213> ORGANISM: Homo sapiens

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Asn Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Ile Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Thr Asp Ser Ser Tyr Tyr Gly Met Asp Val Trp
            100                 105                 110

Gly Gln Gly Thr Thr Val Ser Val Ser Ser
        115                 120
```

<210> SEQ ID NO 27
<211> LENGTH: 366
<212> TYPE: DNA
<213> ORGANISM: Homo sapiens

<400> SEQUENCE: 27

```
gaggtgcagc tggtggagtc tgggggaggc ttggtccagc ctggggggtc cctgagactc      60
tcctgtgcag cctctggatt cacctttagt agctattgga tgagctgggt ccgccaggct     120
ccagggaagg ggctggagtg ggtggccaac ataaagcaag atggaagtga aaatactat      180
gtggactctg tgaagggccg attcaccatc tccagagaca acgccaagaa ctcactgtat     240
ctgcaaatga acagcctgag agccgaggac acggctgtgt attactgtgc gagagagggg    300
tatagcagtt cgtcctacta cggtatggac gtctggggcc aagggaccac ggtcaccgtc    360
tcctca                                                                366
```

<210> SEQ ID NO 28
<211> LENGTH: 122
<212> TYPE: PRT
<213> ORGANISM: Homo sapiens

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
```

```
                    85                  90                  95
Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

<210> SEQ ID NO 29
<211> LENGTH: 366
<212> TYPE: DNA
<213> ORGANISM: Homo sapiens

<400> SEQUENCE: 29
gaggtgcagc tggtggagtc tgggggaggc tttgtccagc ctgggggtc cctgagactc      60 tcctgtgcag tctctggatt cacctttaat agctattgga tgagctgggt ccgccaggct    120
ccagggaagg gctggagtg gtggccaac ataaaccaag atggaagtga gaaattctat      180
gtggcctctg tgaagggccg attcaccatc tccagagaca acgccaagaa ctcagtgtat    240
ctacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                               366

<210> SEQ ID NO 30
<211> LENGTH: 122
<212> TYPE: PRT
<213> ORGANISM: Homo sapiens

<400> SEQUENCE: 30

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

<210> SEQ ID NO 31
<211> LENGTH: 366
<212> TYPE: DNA
<213> ORGANISM: Homo sapiens

<400> SEQUENCE: 31
gaggtgcagc tggtggagtc tgggggaggc ttggtccagc ctgggggtc cctgagactc      60 tcctgtgcag tctctggatt cacctttaat agctattgga tgagctgggt ccgccaggct    120
ccagggaagg gctggagtg gtggccaac ataaaccaag atggaagtga gaaattctat      180
gtggcctctg tgaagggccg attcaccatg tccagagaca acgccaagaa ctcagtgtat    240
ctacaaatga acagcctgag agccgaggac acggctgtgt attactgtgc gagagagggg    300
```
tatagtagtt cgtcctatta tggtatggac gtctggggcc aagggaccac ggtcaccgtc    360
tcctca                                                              366

<210> SEQ ID NO 32
<211> LENGTH: 122
<212> TYPE: PRT
<213> ORGANISM: Homo sapiens

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Asn Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 33
<211> LENGTH: 366
<212> TYPE: DNA
<213> ORGANISM: Homo sapiens

<400> SEQUENCE: 33
gaggtgcagc tggtggagtc tgggggaggc ttggtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga aaattctat     180 gtggcctctg tgaagggccg attcaccatc tccagagaca acgccaagaa atcagtgtat    240
ctacaaatga acagcctgag agccgaggac acggctgtgt attactgtgc gagagaggg     300 tatagtagtt cgtcctatta tggtatggac gtctggggcc aagggaccac ggtcaccgtc    360
tcctca                                                              366

<210> SEQ ID NO 34
<211> LENGTH: 122
<212> TYPE: PRT
<213> ORGANISM: Homo sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

```
Lys Gly Arg Phe Thr Ile Ser Arg Asp Asn Ala Lys Lys Ser Val Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120
```

```
<210> SEQ ID NO 35
<211> LENGTH: 366
<212> TYPE: DNA
<213> ORGANISM: Homo sapiens

<400> SEQUENCE: 35
gaggtgcagc tggtggagtc tgggggaggc ttggtccagc ctggggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatc tccagagaca acgccaagaa ctcagtgtat    240
gtacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                                366
```

```
<210> SEQ ID NO 36
<211> LENGTH: 122
<212> TYPE: PRT
<213> ORGANISM: Homo sapiens

<400> SEQUENCE: 36

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Ile Ser Arg Asp Asn Ala Lys Asn Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120
```

```
<210> SEQ ID NO 37
<211> LENGTH: 366
<212> TYPE: DNA
<213> ORGANISM: Homo sapiens

<400> SEQUENCE: 37
gaggtgcagc tggtggagtc tgggggaggc tttgtccagc ctggggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
```

```
gtggcctctg tgaagggccg attcaccatc tccagagaca acgccaagaa atcagtgtat      240
gtacaaatga acagcctgag agccgaggac acggctgtgt attactgtgc gagagagggg      300
tatagtagtt cgtcctatta tggtatggac gtctggggcc aagggaccac ggtcaccgtc      360
tcctca                                                                  366
```

<210> SEQ ID NO 38
<211> LENGTH: 122
<212> TYPE: PRT
<213> ORGANISM: Homo sapiens

<400> SEQUENCE: 38

```
Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
                100                 105                 110

Gly Gln Gly Thr Thr Val Thr Val Ser Ser
            115                 120
```

<210> SEQ ID NO 39
<211> LENGTH: 366
<212> TYPE: DNA
<213> ORGANISM: Homo sapiens

<400> SEQUENCE: 39

```
gaggtgcagc tggtggagtc tgggggaggc tttgtccagc ctggggggtc cctgagactc       60
tcctgtgcag tctctggatt cacctttaat agctattgga tgagctgggt ccgccaggct      120
ccagggaagg ggctggagtg ggtggccaac ataaaccaag atggaagtga gaaattctat      180
gtggcctctg tgaagggccg attcaccatg tccagagaca acgccaagaa ctcagtgtat      240
gtacaaatga acagcctgag agccgaggac acggctgtgt attactgtgc gagagagggg      300
tatagtagtt cgtcctatta tggtatggac gtctggggcc aagggaccac ggtcaccgtc      360
tcctca                                                                  366
```

<210> SEQ ID NO 40
<211> LENGTH: 122
<212> TYPE: PRT
<213> ORGANISM: Homo sapiens

<400> SEQUENCE: 40

```
Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Asn Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
             100                 105                 110

Gly Gln Gly Thr Thr Val Thr Val Ser Ser
             115                 120

<210> SEQ ID NO 41
<211> LENGTH: 366
<212> TYPE: DNA
<213> ORGANISM: Homo sapiens

<400> SEQUENCE: 41

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
ctacaaatga acagcctgag agccgaggac acggctgtgt attactgtgc gagagagggg     300
tatagtagtt cgtcctatta tggtatggac gtctggggcc aagggaccac ggtcaccgtc     360
tcctca                                                                366
```

<210> SEQ ID NO 42
<211> LENGTH: 122
<212> TYPE: PRT
<213> ORGANISM: Homo sapiens

<400> SEQUENCE: 42

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
         35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
             100                 105                 110

Gly Gln Gly Thr Thr Val Thr Val Ser Ser
             115                 120

<210> SEQ ID NO 43
<211> LENGTH: 366
<212> TYPE: DNA
<213> ORGANISM: Homo sapiens

<400> SEQUENCE: 43

```
gaggtgcagc tggtggagtc tgggggaggc ttggtccagc ctggggggtc cctgagactc      60
```

```
tcctgtgcag tctctggatt cacctttaat agctattgga tgagctgggt ccgccaggct    120
ccagggaagg ggctggagtg ggtggccaac ataaaccaag atggaagtga aaattctat    180 gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                               366
```

<210> SEQ ID NO 44
<211> LENGTH: 122
<212> TYPE: PRT
<213> ORGANISM: Homo sapiens

<400> SEQUENCE: 44

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120
```

<210> SEQ ID NO 45
<211> LENGTH: 366
<212> TYPE: DNA
<213> ORGANISM: Homo sapiens

<400> SEQUENCE: 45

```
gaggtgcagc tggtggagtc tgggggaggc tttgtccagc ctggggggtc cctgagactc    60
tcctgtgcag tctctggatt cacctttaat agctattgga tgagctgggt ccgccaggct    120
ccagggaagg ggctggagtg ggtggccaac ataaaccaag atggaagtga aaattctat    180 gtggcctctg tgaagggccg attcaccatg tccagagaca acgccaagaa ctcagtgtat    240
ctacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                               366
```

<210> SEQ ID NO 46
<211> LENGTH: 122
<212> TYPE: PRT
<213> ORGANISM: Homo sapiens

<400> SEQUENCE: 46

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30
```

```
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Asn Ser Val Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
             100                 105                 110

Gly Gln Gly Thr Thr Val Thr Val Ser Ser
             115                 120

<210> SEQ ID NO 47
<211> LENGTH: 366
<212> TYPE: DNA
<213> ORGANISM: Homo sapiens

<400> SEQUENCE: 47
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg gtggccaac ataaaccaag atggaagtga aaattctat       180 gtggcctctg tgaagggccg attcaccatc tccagagaca cgccaagaa atcagtgtat     240 ctacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                               366

<210> SEQ ID NO 48
<211> LENGTH: 122
<212> TYPE: PRT
<213> ORGANISM: Homo sapiens

<400> SEQUENCE: 48

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Ile Ser Arg Asp Asn Ala Lys Lys Ser Val Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Ser Ser Tyr Tyr Gly Met Asp Val Trp
             100                 105                 110

Gly Gln Gly Thr Thr Val Thr Val Ser Ser
             115                 120

<210> SEQ ID NO 49
<211> LENGTH: 366
<212> TYPE: DNA
<213> ORGANISM: Homo sapiens
```

<400> SEQUENCE: 49

```
gaggtgcagc tggtggagtc tgggggaggc tttgtccagc ctggggggtc cctgagactc        60
tcctgtgcag tctctggatt cacctttaat agctattgga tgagctgggt ccgccaggct       120
ccagggaagg ggctggagtg ggtggccaac ataaaccaag atggaagtga aaattctat        180 gtggcctctg tgaagggccg attcaccatc tccagagaca acgccaagaa ctcagtgtat       240
gtacaaatga acagcctgag agccgaggac acggctgtgt attactgtgc gagagagggg       300
tatagtagtt cgtcctatta tggtatggac gtctggggcc aagggaccac ggtcaccgtc       360
tcctca                                                                  366
```

<210> SEQ ID NO 50
<211> LENGTH: 122
<212> TYPE: PRT
<213> ORGANISM: Homo sapiens

<400> SEQUENCE: 50

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Asn Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 51
<211> LENGTH: 366
<212> TYPE: DNA
<213> ORGANISM: Homo sapiens

<400> SEQUENCE: 51

```
gaggtgcagc tggtggagtc tgggggaggc ttggtccagc ctggggggtc cctgagactc        60
tcctgtgcag tctctggatt cacctttaat agctattgga tgagctgggt ccgccaggct       120
ccagggaagg ggctggagtg ggtggccaac ataaaccaag atggaagtga aaattctat        180 gtggcctctg tgaagggccg attcaccatg tccagagaca acgccaagaa atcagtgtat       240
ctacaaatga acagcctgag agccgaggac acggctgtgt attactgtgc gagagagggg       300
tatagtagtt cgtcctatta tggtatggac gtctggggcc aagggaccac ggtcaccgtc       360
tcctca                                                                  366
```

<210> SEQ ID NO 52
<211> LENGTH: 122
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Leu Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

<210> SEQ ID NO 53
<211> LENGTH: 366
<212> TYPE: DNA
<213> ORGANISM: Homo sapiens

<400> SEQUENCE: 53

```
gaggtgcagc tggtggagtc tgggggaggc ttggtccagc ctggggggtc cctgagactc      60
tcctgtgcag tctctggatt cacctttaat agctattgga tgagctgggt ccgccaggct     120
ccagggaagg ggctggagtg gtggccaac ataaaccaag atggaagtga gaaattctat     180
gtggcctctg tgaagggccg attcaccatg tccagagaca cgccaagaa ctcagtgtat     240
gtacaaatga acagcctgag agccgaggac acggctgtgt attactgtgc gagagagggg     300
tatagtagtt cgtcctatta tggtatggac gtctggggcc aagggaccac ggtcaccgtc     360
tcctca                                                                366
```

<210> SEQ ID NO 54
<211> LENGTH: 122
<212> TYPE: PRT
<213> ORGANISM: Homo sapiens

<400> SEQUENCE: 54

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Asn Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
            115                 120

-continued

<210> SEQ ID NO 55
<211> LENGTH: 366
<212> TYPE: DNA
<213> ORGANISM: Homo sapiens

<400> SEQUENCE: 55

```
gaggtgcagc tggtggagtc tgggggaggc ttggtccagc ctgggggtc cctgagactc      60 tcctgtgcag tctctggatt cacctttaat agctattgga tgagctgggt ccgccaggct    120
ccagggaagg ggctggagtg gtggccaac ataaaccaag atggaagtga gaaattctat    180
gtggcctctg tgaagggccg attcaccatc tccagagaca acgccaagaa atcagtgtat    240
gtacaaatga acagcctgag agccgaggac acggctgtgt attactgtgc gagagagggg    300
tatagtagtt cgtcctatta tggtatggac gtctggggcc aagggaccac ggtcaccgtc    360
tcctca                                                               366
```

<210> SEQ ID NO 56
<211> LENGTH: 122
<212> TYPE: PRT
<213> ORGANISM: Homo sapiens

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Ile Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120
```

<210> SEQ ID NO 57
<211> LENGTH: 8
<212> TYPE: PRT
<213> ORGANISM: Homo sapiens

<400> SEQUENCE: 57

```
Gly Tyr Thr Phe Thr Asn Tyr Ala
1               5
```

<210> SEQ ID NO 58
<211> LENGTH: 8
<212> TYPE: PRT
<213> ORGANISM: Homo sapiens

<400> SEQUENCE: 58

```
Ile Asn Ala Gly Asn Gly Phe Thr
1               5
```

<210> SEQ ID NO 59
<211> LENGTH: 15
<212> TYPE: PRT

<213> ORGANISM: Homo sapiens

<400> SEQUENCE: 59

Ala Arg Asp Trp Ala Ala Ala Ile Ser Tyr Tyr Gly Met Asp Val
1               5                   10                  15

<210> SEQ ID NO 60
<211> LENGTH: 367
<212> TYPE: DNA
<213> ORGANISM: Homo sapiens

<400> SEQUENCE: 60

```
caggtccagc ttgtgcagtc tggggctgag gtgaagaggc ctggggcctc agtgaaggtt     60
tcctgcaagg cttctggata caccttcact aactatgcta tacattgggt gcgccaggcc    120
cccggacaga ggcttgagtg gatgggatgg atcaacgctg gcaatggttt cacaaaatct    180
tcacagaagt tccggggcag agtcaccatt accagggaca catccgcgaa cacagcctac    240
atggaactga gcagcctcag atctgaagac acggctattt attactgtgc gagagattgg    300
gctgctgcta tctcttacta cggtatggac gtctggggcc aagggaccac ggtcaccgtc    360
tcctcag                                                              367
```

<210> SEQ ID NO 61
<211> LENGTH: 122
<212> TYPE: PRT
<213> ORGANISM: Homo sapiens

<400> SEQUENCE: 61

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Asn Tyr
                20                  25                  30

Ala Ile His Trp Val Arg Gln Ala Pro Gly Gln Arg Leu Glu Trp Met
            35                  40                  45

Gly Trp Ile Asn Ala Gly Asn Gly Phe Thr Lys Ser Ser Gln Lys Phe
    50                  55                  60

Arg Gly Arg Val Thr Ile Thr Arg Asp Thr Ser Ala Asn Thr Ala Tyr
65                  70                  75                  80

Met Glu Leu Ser Ser Leu Arg Ser Glu Asp Thr Ala Ile Tyr Tyr Cys
                85                  90                  95

Ala Arg Asp Trp Ala Ala Ala Ile Ser Tyr Tyr Gly Met Asp Val Trp
            100                 105                 110

Gly Gln Gly Thr Thr Val Thr Val Ser Ser
        115                 120

<210> SEQ ID NO 62
<211> LENGTH: 8
<212> TYPE: PRT
<213> ORGANISM: Homo sapiens

<400> SEQUENCE: 62

Ser Ser Asn Ile Gly Ser Asn Tyr
1               5

<210> SEQ ID NO 63
<211> LENGTH: 3
<212> TYPE: PRT
<213> ORGANISM: Homo sapiens

<400> SEQUENCE: 63

Arg Asn Thr
1

<210> SEQ ID NO 64
<211> LENGTH: 11
<212> TYPE: PRT
<213> ORGANISM: Homo sapiens

<400> SEQUENCE: 64

Ala Thr Trp Asp Asp Ser Leu Ser Ala Tyr Val
1               5                   10

<210> SEQ ID NO 65
<211> LENGTH: 331
<212> TYPE: DNA
<213> ORGANISM: Homo sapiens

<400> SEQUENCE: 65
cagtctgtcc tgactcagcc accctcagcg tctgggaccc ccgggcagag ggtcaccatc        60
tcttgttctg gaagcagctc caacatcgga agtaattatg tatactggta ccagcagctc       120
ccaggaacgg cccccaaact cctcatctat aggaatactc agcggccctc agaggtccct       180
gaccgattct ctggctccaa gtctggcgcc tcagcctccc tggccatcag tgggctccgg       240
tccgaggatg agactgatta ttactgtgca acatgggatg acagcctgag tgcttatgtc       300
ttcggaactg ggaccaaagt caccgtccta g                                       331

<210> SEQ ID NO 66
<211> LENGTH: 110
<212> TYPE: PRT
<213> ORGANISM: Homo sapiens

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
                20                  25                  30

Tyr Val Tyr Trp Tyr Gln Gln Leu Pro Gly Thr Ala Pro Lys Leu Leu
            35                  40                  45

Ile Tyr Arg Asn Thr Gln Arg Pro Ser Glu Val Pro Asp Arg Phe Ser
        50                  55                  60

Gly Ser Lys Ser Gly Ala Ser Ala Ser Leu Ala Ile Ser Gly Leu Arg
65                  70                  75                  80

Ser Glu Asp Glu Thr Asp Tyr Tyr Cys Ala Thr Trp Asp Asp Ser Leu
                85                  90                  95

Ser Ala Tyr Val Phe Gly Thr Gly Thr Lys Val Thr Val Leu
            100                 105                 110

<210> SEQ ID NO 67
<211> LENGTH: 8
<212> TYPE: PRT
<213> ORGANISM: Homo sapiens

<400> SEQUENCE: 67

Gly Phe Thr Phe Ser Ser Tyr Gly
1               5

<210> SEQ ID NO 68
<211> LENGTH: 8
<212> TYPE: PRT

<213> ORGANISM: Homo sapiens

<400> SEQUENCE: 68

Ile Trp Tyr Asp Gly Thr Asn Lys
1               5

<210> SEQ ID NO 69
<211> LENGTH: 15
<212> TYPE: PRT
<213> ORGANISM: Homo sapiens

<400> SEQUENCE: 69

Ala Arg Ser Gly Tyr Ser Ser Ser Trp Tyr Gly Ala Met Asp Val
1               5                   10                  15

<210> SEQ ID NO 70
<211> LENGTH: 367
<212> TYPE: DNA
<213> ORGANISM: Homo sapiens

<400> SEQUENCE: 70
caggtgcagc tggtggagtc tgggggaggc gtggtccagc ctggagggtc cctgagactc      60
tcctgtgcag cgtctggatt caccttcagt agctatggca tgcactgggt ccgccaggct     120
ccaggcgagg ggctggagtg ggtggcagtt atatggtatg atggaactaa taaatactat     180
gcagactcct tgaagggccg attcaccatc tccagagaca attccaagaa cacgctctat     240
ctgcaaatga acaggctgag agccgaggac acggctgtgt attactgtgc gaggtccggg     300
tatagcagca gctggtacgg cgctatggac gtctggggcc aagggaccac ggtcaccgtc     360
tcctcag                                                                367

<210> SEQ ID NO 71
<211> LENGTH: 122
<212> TYPE: PRT
<213> ORGANISM: Homo sapiens

<400> SEQUENCE: 71

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Glu Gly Leu Glu Trp Val
        35                  40                  45

Ala Val Ile Trp Tyr Asp Gly Thr Asn Lys Tyr Ala Asp Ser Leu
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Val Tyr Tyr Cys
                85                  90                  95

Ala Arg Ser Gly Tyr Ser Ser Ser Trp Tyr Gly Ala Met Asp Val Trp
            100                 105                 110

Gly Gln Gly Thr Thr Val Thr Val Ser Ser
        115                 120

<210> SEQ ID NO 72
<211> LENGTH: 9
<212> TYPE: PRT
<213> ORGANISM: Homo sapiens

<400> SEQUENCE: 72

```
Ser Ser Asp Val Gly Gly Tyr Tyr Tyr
1               5

<210> SEQ ID NO 73
<211> LENGTH: 3
<212> TYPE: PRT
<213> ORGANISM: Homo sapiens

<400> SEQUENCE: 73

Glu Val Asn
1

<210> SEQ ID NO 74
<211> LENGTH: 10
<212> TYPE: PRT
<213> ORGANISM: Homo sapiens

<400> SEQUENCE: 74

Ser Ser Tyr Ala Gly Ser Asn Thr Trp Val
1               5                   10

<210> SEQ ID NO 75
<211> LENGTH: 331
<212> TYPE: DNA
<213> ORGANISM: Homo sapiens
<400> SEQUENCE: 75
cagtctgccc tgactcagcc tccctccgcg tccgggtctc ctggacagtc agtcaccatc      60
tcctgcactg gaaccagcag tgacgttggt ggttattact atgtctcctg gtaccaacag     120
cacccaggca aagcccccaa actcatgatt tatgaggtca ataagcggcc ctcaggggtc     180
cctgatcgct tctctggctc caagtctggc atcacggcct ccctgaccgt ctctgggctc     240
cagtctgagg atgaggctga ttattactgc agctcatatg caggcagcaa cacttgggtg     300
ttcggcggag ggaccaagct gaccgtccta g                                    331

<210> SEQ ID NO 76
<211> LENGTH: 110
<212> TYPE: PRT
<213> ORGANISM: Homo sapiens

<400> SEQUENCE: 76

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Tyr Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Ile Thr Ala Ser Leu Thr Val Ser Gly Leu
65                  70                  75                  80

Gln Ser Glu Asp Glu Ala Asp Tyr Tyr Cys Ser Ser Tyr Ala Gly Ser
                85                  90                  95

Asn Thr Trp Val Phe Gly Gly Gly Thr Lys Leu Thr Val Leu
            100                 105                 110

<210> SEQ ID NO 77
<211> LENGTH: 8
<212> TYPE: PRT
```

```
<213> ORGANISM: Homo sapiens

<400> SEQUENCE: 77

Gly Tyr Thr Phe Thr Ser Tyr Ala
1               5

<210> SEQ ID NO 78
<211> LENGTH: 8
<212> TYPE: PRT
<213> ORGANISM: Homo sapiens

<400> SEQUENCE: 78

Ile Asn Ala Gly Asn Gly Ile Thr
1               5

<210> SEQ ID NO 79
<211> LENGTH: 15
<212> TYPE: PRT
<213> ORGANISM: Homo sapiens

<400> SEQUENCE: 79

Ala Arg Asp Trp Ala Ala Ala Ile Thr Tyr Tyr Gly Met Asp Val
1               5                   10                  15

<210> SEQ ID NO 80
<211> LENGTH: 367
<212> TYPE: DNA
<213> ORGANISM: Homo sapiens

<400> SEQUENCE: 80
caggtccagc ttgtgcagtc tggggctgag gtgaagaggc ctggggcctc agtgaaggtt    60
tcctgcaagg cttctggata caccttcaca agctacgcca tacattgggt gcgccaggcc   120
cccggacaga ggcttgagtg gatgggatgg atcaacgctg gcaatggtat cacaaaatct   180
tcacagaagt tccagggcag agtcaccatt accagggaca catccgcgaa cacagtttac   240
ctggaactga gcagcctcag atctgaagac acggctgttt attattgtgc gagagattgg   300
gctgctgcta tcacctacta cggtatggac gtctggggcc aagggaccac ggtcaccgtc   360
tcctcag                                                             367

<210> SEQ ID NO 81
<211> LENGTH: 122
<212> TYPE: PRT
<213> ORGANISM: Homo sapiens

<400> SEQUENCE: 81

Gln Val Gln Leu Val Gln Ser Gly Ala Glu Val Lys Arg Pro Gly Ala
1               5                   10                  15

Ser Val Lys Val Ser Cys Lys Ala Ser Gly Tyr Thr Phe Thr Ser Tyr
            20                  25                  30

Ala Ile His Trp Val Arg Gln Ala Pro Gly Gln Arg Leu Glu Trp Met
        35                  40                  45

Gly Trp Ile Asn Ala Gly Asn Gly Ile Thr Lys Ser Ser Gln Lys Phe
    50                  55                  60

Gln Gly Arg Val Thr Ile Thr Arg Asp Thr Ser Ala Asn Thr Val Tyr
65                  70                  75                  80

Leu Glu Leu Ser Ser Leu Arg Ser Glu Asp Thr Ala Val Tyr Tyr Cys
                85                  90                  95

Ala Arg Asp Trp Ala Ala Ala Ile Thr Tyr Tyr Gly Met Asp Val Trp
            100                 105                 110
```

Gly Gln Gly Thr Thr Val Thr Val Ser Ser
            115                 120

<210> SEQ ID NO 82
<211> LENGTH: 3
<212> TYPE: PRT
<213> ORGANISM: Homo sapiens

<400> SEQUENCE: 82

Arg Asn Asn
1

<210> SEQ ID NO 83
<211> LENGTH: 10
<212> TYPE: PRT
<213> ORGANISM: Homo sapiens

<400> SEQUENCE: 83

Phe Gly Ala Gly Thr Lys Val Thr Val Leu
1               5                   10

<210> SEQ ID NO 84
<211> LENGTH: 331
<212> TYPE: DNA
<213> ORGANISM: Homo sapiens

<400> SEQUENCE: 84
cagtctgtgc tgactcagcc accctcagtg tctgggaccc ccgggcagag ggtcaccatc        60
tcttgttctg gaagcagctc caacatcgga agtaattatg tatactggta ccagcagttc       120
ccaggaacgg cccccaaact cctcatctat aggaataatc agcggccctc agaggtccct       180
gaccgattct ctggctccaa gtctggcgcc tcagcctccc tggccatcag tgggctccgg       240
tccgaggatg agactgatta ttactgtgca acatgggatg acagcctgag tgcttatgtc       300
ttcggagctg ggaccaaagt caccgtccta g                                       331

<210> SEQ ID NO 85
<211> LENGTH: 110
<212> TYPE: PRT
<213> ORGANISM: Homo sapiens

<400> SEQUENCE: 85

Gln Ser Val Leu Thr Gln Pro Pro Ser Val Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Phe Pro Gly Thr Ala Pro Lys Leu Leu
        35                  40                  45

Ile Tyr Arg Asn Asn Gln Arg Pro Ser Glu Val Pro Asp Arg Phe Ser
    50                  55                  60

Gly Ser Lys Ser Gly Ala Ser Ala Ser Leu Ala Ile Ser Gly Leu Arg
65                  70                  75                  80

Ser Glu Asp Glu Thr Asp Tyr Tyr Cys Ala Thr Trp Asp Asp Ser Leu
                85                  90                  95

Ser Ala Tyr Val Phe Gly Ala Gly Thr Lys Val Thr Val Leu
            100                 105                 110

<210> SEQ ID NO 86
<211> LENGTH: 8
<212> TYPE: PRT

<213> ORGANISM: Homo sapiens

<400> SEQUENCE: 86

Glu Phe Thr Phe Ser Thr Ala Gly
1               5

<210> SEQ ID NO 87
<211> LENGTH: 8
<212> TYPE: PRT
<213> ORGANISM: Homo sapiens

<400> SEQUENCE: 87

Ile Ser Tyr Asp Gly Ser Asn Lys
1               5

<210> SEQ ID NO 88
<211> LENGTH: 15
<212> TYPE: PRT
<213> ORGANISM: Homo sapiens

<400> SEQUENCE: 88

Ala Lys Asp Phe Thr Met Val Arg Gly Val Ile Ile Met Asp Val
1               5                   10                  15

<210> SEQ ID NO 89
<211> LENGTH: 361
<212> TYPE: DNA
<213> ORGANISM: Homo sapiens

<400> SEQUENCE: 89

```
caggtgcagc tggtggagtc tgggggggc gtactccagc ctgggaagtc cctgagactc     60
tcctgtgcag cctctgaatt caccttcagt accgctggca tgcactgggt ccgccaggct   120
ccaggcaagg ggctggagtg ggtgactttt atatcatatg atggaagtaa taatactat   180
gcagactccg tgaagggccg attcaccatc tccagagaca attccaaggt gtatctgcaa   240
atgaacagcc tgagaactga ggacacggct gtgtattact gtgcgaaaga tttcactatg   300
gttcggggag ttattataat ggacgtctgg ggccaaggga ccacggtcac cgtctcctca   360
g                                                                   361
```

<210> SEQ ID NO 90
<211> LENGTH: 120
<212> TYPE: PRT
<213> ORGANISM: Homo sapiens

<400> SEQUENCE: 90

Gln Val Gln Leu Val Glu Ser Gly Gly Gly Val Leu Gln Pro Gly Lys
1               5                   10                  15

Ser Leu Arg Leu Ser Cys Ala Ala Ser Glu Phe Thr Phe Ser Thr Ala
            20                  25                  30

Gly Met His Trp Val Arg Gln Ala Pro Gly Lys Gly Leu Glu Trp Val
        35                  40                  45

Thr Phe Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Val Tyr Leu Gln
65                  70                  75                  80

Met Asn Ser Leu Arg Thr Glu Asp Thr Ala Val Tyr Tyr Cys Ala Lys
                85                  90                  95

Asp Phe Thr Met Val Arg Gly Val Ile Ile Met Asp Val Trp Gly Gln
            100                 105                 110

Gly Thr Thr Val Thr Val Ser Ser
        115                 120

<210> SEQ ID NO 91
<211> LENGTH: 6
<212> TYPE: PRT
<213> ORGANISM: Homo sapiens

<400> SEQUENCE: 91

Gln Asp Ile Ser Asn Tyr
1               5

<210> SEQ ID NO 92
<211> LENGTH: 3
<212> TYPE: PRT
<213> ORGANISM: Homo sapiens

<400> SEQUENCE: 92

Asp Ala Ser
1

<210> SEQ ID NO 93
<211> LENGTH: 9
<212> TYPE: PRT
<213> ORGANISM: Homo sapiens

<400> SEQUENCE: 93

Gln Gln Tyr Asp Asn Leu Pro Ile Thr
1               5

<210> SEQ ID NO 94
<211> LENGTH: 322
<212> TYPE: DNA
<213> ORGANISM: Homo sapiens

<400> SEQUENCE: 94

```
gacatccaga tgacccagtc tccatcctcc ctgtctgtat ctgtaggaga cagagtcacc      60
atcacttgcc aggcgagtca ggacattagc aactatttaa attggtatca gcagaaacca     120
gggaaagccc ctaagctcct gatctacgat gcatccaatt tggaaacagg ggtcccatca     180
aggttcagtg aagtggatc tgggacagat tttactttca tcatcagcag cctgcagcct     240
gaagatattg caacatatta ctgtcaacag tatgataatc tcccgatcac cttcggccaa     300
gggacacgac tggagatcaa ac                                              322
```

<210> SEQ ID NO 95
<211> LENGTH: 107
<212> TYPE: PRT
<213> ORGANISM: Homo sapiens

<400> SEQUENCE: 95

Asp Ile Gln Met Thr Gln Ser Pro Ser Ser Leu Ser Val Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Ile Ile Ser Ser Leu Gln Pro
65                  70                  75                  80

```
Glu Asp Ile Ala Thr Tyr Tyr Cys Gln Gln Tyr Asp Asn Leu Pro Ile
                85                  90                  95

Thr Phe Gly Gln Gly Thr Arg Leu Glu Ile Lys
            100                 105

<210> SEQ ID NO 96
<211> LENGTH: 8
<212> TYPE: PRT
<213> ORGANISM: Homo sapiens

<400> SEQUENCE: 96

Gly Gly Ser Ile Ser Ser Tyr Tyr
1               5

<210> SEQ ID NO 97
<211> LENGTH: 7
<212> TYPE: PRT
<213> ORGANISM: Homo sapiens

<400> SEQUENCE: 97

Ile Tyr Tyr Ser Gly Ser Thr
1               5

<210> SEQ ID NO 98
<211> LENGTH: 8
<212> TYPE: PRT
<213> ORGANISM: Homo sapiens

<400> SEQUENCE: 98

Ala Lys Gly Ala Ala Gly Asp Tyr
1               5

<210> SEQ ID NO 99
<211> LENGTH: 343
<212> TYPE: DNA
<213> ORGANISM: Homo sapiens

<400> SEQUENCE: 99
caggtgcagc tgcaggagtc gggcccagga ctggtgaagc cttcggagac cctgtccctc      60
acctgcactg tctctggtgg ctccatcagt agttattact ggagctggat ccggcagccc     120
ccagggaagg gactggagtg gattgggtat atctattaca gtgggagcac caactataac     180
ccctccctca agagtcgagt caacatatca gtagacacgt ccaagaacca gttctccctg     240
aggctgagtt ctgtgaccgc tgcggacacg gccgtgtatt attgtgcgaa agggcagct     300 ggggactact ggggccaggg aaccctggtc accgtctcct cag                       343

<210> SEQ ID NO 100
<211> LENGTH: 114
<212> TYPE: PRT
<213> ORGANISM: Homo sapiens

<400> SEQUENCE: 100

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
    50                  55                  60
```

Ser Arg Val Asn Ile Ser Val Asp Thr Ser Lys Asn Gln Phe Ser Leu
 65                  70                  75                  80

Arg Leu Ser Ser Val Thr Ala Ala Asp Thr Ala Val Tyr Tyr Cys Ala
                 85                  90                  95

Lys Gly Ala Ala Gly Asp Tyr Trp Gly Gln Gly Thr Leu Val Thr Val
            100                 105                 110

Ser Ser

<210> SEQ ID NO 101
<211> LENGTH: 6
<212> TYPE: PRT
<213> ORGANISM: Homo sapiens

<400> SEQUENCE: 101

Gln Ser Val Asn Ser Tyr
1               5

<210> SEQ ID NO 102
<211> LENGTH: 9
<212> TYPE: PRT
<213> ORGANISM: Homo sapiens

<400> SEQUENCE: 102

Gln Gln Arg Asn Asn Trp Pro Ile Thr
1               5

<210> SEQ ID NO 103
<211> LENGTH: 322
<212> TYPE: DNA
<213> ORGANISM: Homo sapiens

<400> SEQUENCE: 103
gaaattgtgt tggcacagtc tccagccacc ctgtctttgt ctccagggga aagagccacg    60
ttctcctgca gggccagtca gagtgttaac agctacttag cctggcacca acagaaacct   120
ggccaggctc ccaggctcct catctatgat gcatccaaca gggccactgg catcccagcc   180
aggttcagtg gcagtgggtc cgggacagac ttcactctca ccatcagcag cctagagcct   240
gaagattttg cagtttatta ctgtcagcag cgtaacaact ggcctatcac cttcggccaa   300
gggacacgac tggagatcaa ac                                            322

<210> SEQ ID NO 104
<211> LENGTH: 107
<212> TYPE: PRT
<213> ORGANISM: Homo sapiens

<400> SEQUENCE: 104

Glu Ile Val Leu Ala Gln Ser Pro Ala Thr Leu Ser Leu Ser Pro Gly
1               5                   10                  15

Glu Arg Ala Thr Phe Ser Cys Arg Ala Ser Gln Ser Val Asn Ser Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Asn Asn Trp Pro Ile
                85                  90                  95

Thr Phe Gly Gln Gly Thr Arg Leu Glu Ile Lys
            100                 105

<210> SEQ ID NO 105
<211> LENGTH: 8
<212> TYPE: PRT
<213> ORGANISM: Homo sapiens

<400> SEQUENCE: 105

Gly Gly Ser Ile Ser Lys Tyr Tyr
1               5

<210> SEQ ID NO 106
<211> LENGTH: 7
<212> TYPE: PRT
<213> ORGANISM: Homo sapiens

<400> SEQUENCE: 106

Ile Tyr Tyr Ser Gly Asn Thr
1               5

<210> SEQ ID NO 107
<211> LENGTH: 7
<212> TYPE: PRT
<213> ORGANISM: Homo sapiens

<400> SEQUENCE: 107

Ala Arg Gly Leu Gly Asp Tyr
1               5

<210> SEQ ID NO 108
<211> LENGTH: 340
<212> TYPE: DNA
<213> ORGANISM: Homo sapiens

<400> SEQUENCE: 108
caggtgcagc tgcaggagtc gggcccagga ctggtgaagc cttcggagac cctgtccctc      60
acctgcactg tctctggtgg ctccatcagt aaatactact ggagctggat ccggcagccc     120
ccagggaagg gactggagtg gattggatat atctattaca gtgggaacac ctaccagaat     180
ccctccctca agagtcgagt caccatatca atagacacgt ccaagaacca gatctccctg     240
aaggtgagct ctgtgaccgc tgcggacacg gccgtctatt actgtgcgag agggctgggg     300
gactactggg gccagggaac cctggtcacc gtctcctcag                           340

<210> SEQ ID NO 109
<211> LENGTH: 113
<212> TYPE: PRT
<213> ORGANISM: Homo sapiens

<400> SEQUENCE: 109

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Lys Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Asn Thr Tyr Gln Asn Pro Ser Leu Lys
    50                  55                  60

Ser Arg Val Thr Ile Ser Ile Asp Thr Ser Lys Asn Gln Ile Ser Leu
65                  70                  75                  80

Lys Val Ser Ser Val Thr Ala Ala Asp Thr Ala Val Tyr Tyr Cys Ala
                85                  90                  95

Arg Gly Leu Gly Asp Tyr Trp Gly Gln Gly Thr Leu Val Thr Val Ser
            100                 105                 110

Ser

<210> SEQ ID NO 110
<211> LENGTH: 6
<212> TYPE: PRT
<213> ORGANISM: Homo sapiens

<400> SEQUENCE: 110

Gln Ser Val Ser Ser Tyr
1               5

<210> SEQ ID NO 111
<211> LENGTH: 9
<212> TYPE: PRT
<213> ORGANISM: Homo sapiens

<400> SEQUENCE: 111

Gln Gln Arg Ser Asn Trp Pro Leu Thr
1               5

<210> SEQ ID NO 112
<211> LENGTH: 322
<212> TYPE: DNA
<213> ORGANISM: Homo sapiens

<400> SEQUENCE: 112
gaaattgtgt tgacacagtc tccagccacc ctgtctttgt ctccagggga aagagccacc     60
ctctcctgca gggccagtca gagtgttagc agctacttag cctggcacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcaa cgtagcaact ggcctctcac tttcggcgga   300
gggaccaagg tggagatcaa ac                                            322

<210> SEQ ID NO 113
<211> LENGTH: 107
<212> TYPE: PRT
<213> ORGANISM: Homo sapiens

<400> SEQUENCE: 113

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 114
<211> LENGTH: 8
<212> TYPE: PRT
<213> ORGANISM: Homo sapiens

<400> SEQUENCE: 114

Gly Gly Ser Ile Ser Arg Tyr Tyr
1               5

<210> SEQ ID NO 115
<211> LENGTH: 7
<212> TYPE: PRT
<213> ORGANISM: Homo sapiens

<400> SEQUENCE: 115

Ile Tyr Tyr Ser Gly Thr Thr
1               5

<210> SEQ ID NO 116
<211> LENGTH: 7
<212> TYPE: PRT
<213> ORGANISM: Homo sapiens

<400> SEQUENCE: 116

Ala Arg Gly Leu Gly Asp Phe
1               5

<210> SEQ ID NO 117
<211> LENGTH: 340
<212> TYPE: DNA
<213> ORGANISM: Homo sapiens

<400> SEQUENCE: 117
caggtgcagc tgcaggagtc gggcccagga ctggtgaagc cttcggagac cctgtccctc    60
acctgcagtg tctctggtgg ctccattagt agatattact ggagctggat ccggcagccc   120
ccagggaagg gactggagtg gattggatat atctattaca gtgggaccac ctactataac   180
ccctccctca gagtcgagt cacctttca gtagacacgt ccaagaccca gttctccctg   240
aaacttaact ctgtgaccgc tgcggacacg gccgtatatt actgtgcgag aggactgggg   300
gacttctggg gccggggaac cctggtcacc gtctcctcag                         340

<210> SEQ ID NO 118
<211> LENGTH: 113
<212> TYPE: PRT
<213> ORGANISM: Homo sapiens

<400> SEQUENCE: 118

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Ser Arg Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Thr Thr Tyr Tyr Asn Pro Ser Leu Lys
    50                  55                  60

Ser Arg Val Thr Phe Ser Val Asp Thr Ser Lys Thr Gln Phe Ser Leu
65                  70                  75                  80

Lys Leu Asn Ser Val Thr Ala Ala Asp Thr Ala Val Tyr Cys Ala
                85                  90                  95

Arg Gly Leu Gly Asp Phe Trp Gly Arg Gly Thr Leu Val Thr Val Ser
            100                 105                 110

Ser

<210> SEQ ID NO 119
<211> LENGTH: 6
<212> TYPE: PRT
<213> ORGANISM: Homo sapiens

<400> SEQUENCE: 119

Gln Ser Val Ser Gly Tyr
1               5

<210> SEQ ID NO 120
<211> LENGTH: 322
<212> TYPE: DNA
<213> ORGANISM: Homo sapiens

<400> SEQUENCE: 120
gaaattgtgt tgactcagtc tccagccacc ctgtcattgt ctccagggga aagggccacc      60
ctctcctgcc gggccagtca gagtgttagc ggctacttag cctggcacca acagaaacct     120
ggccaggctc ccaggctcct catctatgat gcatccaaca gggccactgg catcccagcc     180
agattcagtg gcagtgggtc tgggacagac ttcactctca ccatcagcag cctagagcct     240
gaagattttg cagtttatta ctgtcagcaa cgtagcaact ggcctctcac tttcggcgga     300
gggaccaagg tggagatcaa ac                                              322

<210> SEQ ID NO 121
<211> LENGTH: 107
<212> TYPE: PRT
<213> ORGANISM: Homo sapiens

<400> SEQUENCE: 121

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Gly Tyr
            20                  25                  30

Leu Ala Trp His Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 122
<211> LENGTH: 10
<212> TYPE: PRT
<213> ORGANISM: Homo sapiens

<400> SEQUENCE: 122

Gly Gly Ser Ile Ser Ser Gly Ile Tyr Tyr
1               5                   10

<210> SEQ ID NO 123

```
<211> LENGTH: 7
<212> TYPE: PRT
<213> ORGANISM: Homo sapiens

<400> SEQUENCE: 123

Ile Asn Asn Ser Gly Asn Thr
1               5

<210> SEQ ID NO 124
<211> LENGTH: 8
<212> TYPE: PRT
<213> ORGANISM: Homo sapiens

<400> SEQUENCE: 124

Ala Arg Gly Gly Ser Gly Asp Tyr
1               5

<210> SEQ ID NO 125
<211> LENGTH: 349
<212> TYPE: DNA
<213> ORGANISM: Homo sapiens

<400> SEQUENCE: 125
caggtgcagc tgcaggagtc gggcccagga ctggtgaagc cttcagagac cctgtccctc      60
acctgcactg tctctggtgg ctccatcagt agtggtatat actactggag ttggatccgc     120
cagcacccag ggaagggcct ggagtggatt ggatacatca ataacagtgg aacacctac      180 tacaacccgt ccctcaaggg tcgagttaac atatcagtag acacgtctaa gaaacagttc     240
tccctgaagc tgagctctgt gactgacgcg gacacggccg tctattactg tgcgaggggg     300
ggatcgggcg actactgggg ccagggaacc ctggtcaccg tctcctcag                 349

<210> SEQ ID NO 126
<211> LENGTH: 116
<212> TYPE: PRT
<213> ORGANISM: Homo sapiens

<400> SEQUENCE: 126

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Gly
                20                  25                  30

Ile Tyr Tyr Trp Ser Trp Ile Arg Gln His Pro Gly Lys Gly Leu Glu
            35                  40                  45

Trp Ile Gly Tyr Ile Asn Asn Ser Gly Asn Thr Tyr Tyr Asn Pro Ser
        50                  55                  60

Leu Lys Gly Arg Val Asn Ile Ser Val Asp Thr Ser Lys Lys Gln Phe
65                  70                  75                  80

Ser Leu Lys Leu Ser Ser Val Thr Asp Ala Asp Thr Ala Val Tyr Tyr
                85                  90                  95

Cys Ala Arg Gly Gly Ser Gly Asp Tyr Trp Gly Gln Gly Thr Leu Val
            100                 105                 110

Thr Val Ser Ser
        115

<210> SEQ ID NO 127
<211> LENGTH: 28
<212> TYPE: PRT
<213> ORGANISM: Homo sapiens

<400> SEQUENCE: 127
```

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys
            20                  25
```

<210> SEQ ID NO 128
<211> LENGTH: 6
<212> TYPE: PRT
<213> ORGANISM: Homo sapiens

<400> SEQUENCE: 128

```
Gln Ser Ile Asn Asn Tyr
1               5
```

<210> SEQ ID NO 129
<211> LENGTH: 9
<212> TYPE: PRT
<213> ORGANISM: Homo sapiens

<400> SEQUENCE: 129

```
Gln Gln Arg Asn Asn Trp Pro Pro Thr
1               5
```

<210> SEQ ID NO 130
<211> LENGTH: 322
<212> TYPE: DNA
<213> ORGANISM: Homo sapiens

<400> SEQUENCE: 130

| | |
|---|---|
| gaaattgtgt tgacacagtc tccagccacc ctgtctttgt ctccagggga aagagccacc | 60 |
| ctctcctgca ggaccagtca gagtattaac aactacttag cctggttcca acagaaacct | 120 |
| ggccaggctc ccaggctcct catctatgat gcatccaaca gggcccctgg catcccagcc | 180 |
| aggttcagtg gcagtgggtc tgggacagac ttcactctca ccatcagcag cctggagcct | 240 |
| gaagattttg tagtttattt ctgtcagcag cgtaacaact ggcctccgac attcggccaa | 300 |
| gggaccaagg tggaaatcaa ac | 322 |

<210> SEQ ID NO 131
<211> LENGTH: 107
<212> TYPE: PRT
<213> ORGANISM: Homo sapiens

<400> SEQUENCE: 131

```
Glu Ile Val Leu Thr Gln Ser Pro Ala Thr Leu Ser Leu Ser Pro Gly
1               5                   10                  15

Glu Arg Ala Thr Leu Ser Cys Arg Thr Ser Gln Ser Ile Asn Asn Tyr
            20                  25                  30

Leu Ala Trp Phe Gln Gln Lys Pro Gly Gln Ala Pro Arg Leu Leu Ile
        35                  40                  45

Tyr Asp Ala Ser Asn Arg Ala Pro Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Val Val Tyr Phe Cys Gln Gln Arg Asn Asn Trp Pro Pro
                85                  90                  95

Thr Phe Gly Gln Gly Thr Lys Val Glu Ile Lys
            100                 105
```

```
<210> SEQ ID NO 132
<211> LENGTH: 25
<212> TYPE: PRT
<213> ORGANISM: Homo sapiens

<400> SEQUENCE: 132

Glu Val Gln Leu Val Glu Ser Gly Gly Gly Phe Val Gln Pro Gly Gly
1               5                   10                  15

Ser Leu Arg Leu Ser Cys Ala Val Ser
            20                  25

<210> SEQ ID NO 133
<211> LENGTH: 17
<212> TYPE: PRT
<213> ORGANISM: Homo sapiens

<400> SEQUENCE: 133

Met Ser Trp Val Arg Gln Ala Pro Gly Lys Gly Leu Glu Trp Val Ala
1               5                   10                  15

Asn

<210> SEQ ID NO 134
<211> LENGTH: 38
<212> TYPE: PRT
<213> ORGANISM: Homo sapiens

<400> SEQUENCE: 134

Phe Tyr Val Ala Ser Val Lys Gly Arg Phe Thr Met Ser Arg Asp Asn
1               5                   10                  15

Ala Lys Lys Ser Val Tyr Val Gln Met Asn Ser Leu Arg Ala Glu Asp
            20                  25                  30

Thr Ala Val Tyr Tyr Cys
            35

<210> SEQ ID NO 135
<211> LENGTH: 11
<212> TYPE: PRT
<213> ORGANISM: Homo sapiens

<400> SEQUENCE: 135

Trp Gly Gln Gly Thr Thr Val Thr Val Ser Ser
1               5                   10

<210> SEQ ID NO 136
<211> LENGTH: 25
<212> TYPE: PRT
<213> ORGANISM: Homo sapiens

<400> SEQUENCE: 136

Ser Tyr Val Leu Thr Gln Pro Pro Ser Val Ser Val Ala Pro Gly Glu
1               5                   10                  15

Thr Ala Arg Ile Thr Cys Gly Gly Asp
            20                  25

<210> SEQ ID NO 137
<211> LENGTH: 17
<212> TYPE: PRT
<213> ORGANISM: Homo sapiens

<400> SEQUENCE: 137

Val Tyr Trp Tyr Gln Gln Lys Ser Gly Gln Ala Pro Val Leu Val Ile
1               5                   10                  15
```

Tyr

<210> SEQ ID NO 138
<211> LENGTH: 36
<212> TYPE: PRT
<213> ORGANISM: Homo sapiens

<400> SEQUENCE: 138

Asp Arg Pro Ser Gly Ile Pro Glu Arg Phe Ser Gly Ser Asn Ser Gly
1               5                   10                  15

Asn Thr Ala Thr Leu Thr Ile Ser Arg Val Glu Ala Gly Asp Glu Ala
            20                  25                  30

Asp Tyr Tyr Cys
        35

<210> SEQ ID NO 139
<211> LENGTH: 10
<212> TYPE: PRT
<213> ORGANISM: Homo sapiens

<400> SEQUENCE: 139

Phe Gly Gly Gly Thr Lys Leu Thr Val Leu
1               5                   10

<210> SEQ ID NO 140
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa = Thr or Ile
<220> FEATURE:
<221> NAME/KEY: MISC_FEATURE
<222> LOCATION: (5)..(5)
<223> OTHER INFORMATION: Xaa = Ser or Asn
<220> FEATURE:
<221> NAME/KEY: MISC_FEATURE
<222> LOCATION: (6)..(6)
<223> OTHER INFORMATION: Xaa = Ser or Asn

<400> SEQUENCE: 140

Gly Phe Xaa Phe Xaa Xaa Tyr Met
1               5

<210> SEQ ID NO 141
<211> LENGTH: 8
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = Asn or Lys

<400> SEQUENCE: 141

Ile Xaa Gln Asp Gly Ser Glu Lys
1               5

<210> SEQ ID NO 142
<211> LENGTH: 13
<212> TYPE: PRT
<213> ORGANISM: Homo sapiens
<220> FEATURE:
<221> NAME/KEY: MISC_FEATURE
<222> LOCATION: (6)..(6)
<223> OTHER INFORMATION: Xaa = Ser or Thr
<220> FEATURE:
<221> NAME/KEY: MISC_FEATURE

```
<222> LOCATION: (7)..(7)
<223> OTHER INFORMATION: Xaa = Ser or Asp
<220> FEATURE:
<221> NAME/KEY: MISC_FEATURE
<222> LOCATION: (8)..(8)
<223> OTHER INFORMATION: Xaa = Ser or Tyr
<220> FEATURE:
<221> NAME/KEY: MISC_FEATURE
<222> LOCATION: (9)..(9)
<223> OTHER INFORMATION: Xaa = Ser or Tyr

<400> SEQUENCE: 142

Ala Arg Glu Gly Tyr Xaa Xaa Xaa Xaa Gly Met Asp Val
1               5                   10

<210> SEQ ID NO 143
<211> LENGTH: 327
<212> TYPE: PRT
<213> ORGANISM: Homo sapiens

<400> SEQUENCE: 143

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
```

```
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 144
<211> LENGTH: 327
<212> TYPE: PRT
<213> ORGANISM: Artificial Sequence
<220> FEATURE:
<223> OTHER INFORMATION: IgG4ra

<400> SEQUENCE: 144

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
                100                 105                 110

Glu Phe Glu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
        210                 215                 220

Glu Pro Gln Val Cys Thr Leu Pro Pro Ser Gln Glu Glu Met Thr Lys
225                 230                 235                 240

Asn Gln Val Ser Leu Trp Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
```

<210> SEQ ID NO 145
<211> LENGTH: 327
<212> TYPE: PRT
<213> ORGANISM: Artificial Sequence
<220> FEATURE:
<223> OTHER INFORMATION: IgG4yb

<400> SEQUENCE: 145

```
Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Glu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
Trp Leu Asn Gly Lys Glu Tyr Lys Cys Lys Val Ser Asn Lys Gly Leu
        195                 200                 205
Pro Ser Ser Ile Glu Lys Thr Ile Ser Lys Ala Lys Gly Gln Pro Arg
    210                 215                 220
Glu Pro Gln Val Tyr Thr Leu Pro Pro Ser Gln Cys Glu Met Thr Lys
225                 230                 235                 240
Asn Gln Val Ser Leu Ser Cys Ala Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Val Ser
        275                 280                 285
Arg Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325
```

<210> SEQ ID NO 146
<211> LENGTH: 106
<212> TYPE: PRT

<213> ORGANISM: Homo sapiens

<400> SEQUENCE: 146

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 147
<211> LENGTH: 108
<212> TYPE: PRT
<213> ORGANISM: Homo sapiens

<400> SEQUENCE: 147

Lys Arg Thr Val Ala Ala Pro Ser Val Phe Ile Phe Pro Pro Ser Asp
1               5                   10                  15

Glu Gln Leu Lys Ser Gly Thr Ala Ser Val Val Cys Leu Leu Asn Asn
            20                  25                  30

Phe Tyr Pro Arg Glu Ala Lys Val Gln Trp Lys Val Asp Asn Ala Leu
        35                  40                  45

Gln Ser Gly Asn Ser Gln Glu Ser Val Thr Glu Gln Asp Ser Lys Asp
    50                  55                  60

Ser Thr Tyr Ser Leu Ser Ser Thr Leu Thr Leu Ser Lys Ala Asp Tyr
65                  70                  75                  80

Glu Lys His Lys Val Tyr Ala Cys Glu Val Thr His Gln Gly Leu Ser
                85                  90                  95

Ser Pro Val Thr Lys Ser Phe Asn Arg Gly Glu Cys
            100                 105

<210> SEQ ID NO 148
<211> LENGTH: 25
<212> TYPE: PRT
<213> ORGANISM: Homo sapiens

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 149
<211> LENGTH: 38
<212> TYPE: PRT
<213> ORGANISM: Homo sapiens

<400> SEQUENCE: 149

Tyr Tyr Val Asp Ser Val Lys Gly Arg Phe Thr Ile Ser Arg Asp Asn
1               5                   10                  15

-continued

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 150
<211> LENGTH: 25
<212> TYPE: PRT
<213> ORGANISM: Homo sapiens

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Val Ala Ser
            20                  25

<210> SEQ ID NO 151
<211> LENGTH: 25
<212> TYPE: PRT
<213> ORGANISM: Homo sapiens

<400> SEQUENCE: 151

Glu Val Gln Leu Val Glu Ser Gly Gly Gly Leu Val Gln Pro Gly Gly
1               5                   10                  15

Ser Leu Arg Leu Ser Cys Ala Val Ser
            20                  25

<210> SEQ ID NO 152
<211> LENGTH: 38
<212> TYPE: PRT
<213> ORGANISM: Homo sapiens

<400> SEQUENCE: 152

Phe Tyr Val Ala Ser Val Lys Gly Arg Phe Thr Ile Ser Arg Asp Asn
1               5                   10                  15

Ala Lys Asn Ser Val Tyr Leu Gln Met Asn Ser Leu Arg Ala Glu Asp
            20                  25                  30

Thr Ala Val Tyr Tyr Cys
        35

<210> SEQ ID NO 153
<211> LENGTH: 38
<212> TYPE: PRT
<213> ORGANISM: Homo sapiens

<400> SEQUENCE: 153

Phe Tyr Val Ala Ser Val Lys Gly Arg Phe Ile Ile Ser Arg Asp Asn
1               5                   10                  15

Ala Lys Asn Ser Val Tyr Leu Gln Met Asn Ser Leu Arg Ala Glu Asp
            20                  25                  30

Thr Ala Val Tyr Tyr Cys
        35

<210> SEQ ID NO 154
<211> LENGTH: 11
<212> TYPE: PRT
<213> ORGANISM: Homo sapiens

<400> SEQUENCE: 154

Trp Gly Gln Gly Thr Thr Val Ser Val Ser Ser
1               5                   10

<210> SEQ ID NO 155
<211> LENGTH: 38
<212> TYPE: PRT
<213> ORGANISM: Homo sapiens

<400> SEQUENCE: 155

Phe Tyr Val Ala Ser Val Lys Gly Arg Phe Thr Met Ser Arg Asp Asn
1               5                   10                  15

Ala Lys Asn Ser Val Tyr Leu Gln Met Asn Ser Leu Arg Ala Glu Asp
            20                  25                  30

Thr Ala Val Tyr Tyr Cys
        35

<210> SEQ ID NO 156
<211> LENGTH: 38
<212> TYPE: PRT
<213> ORGANISM: Homo sapiens

<400> SEQUENCE: 156

Phe Tyr Val Ala Ser Val Lys Gly Arg Phe Thr Ile Ser Arg Asp Asn
1               5                   10                  15

Ala Lys Lys Ser Val Tyr Leu Gln Met Asn Ser Leu Arg Ala Glu Asp
            20                  25                  30

Thr Ala Val Tyr Tyr Cys
        35

<210> SEQ ID NO 157
<211> LENGTH: 38
<212> TYPE: PRT
<213> ORGANISM: Homo sapiens

<400> SEQUENCE: 157

Phe Tyr Val Ala Ser Val Lys Gly Arg Phe Thr Ile Ser Arg Asp Asn
1               5                   10                  15

Ala Lys Asn Ser Val Tyr Val Gln Met Asn Ser Leu Arg Ala Glu Asp
            20                  25                  30

Thr Ala Val Tyr Tyr Cys
        35

<210> SEQ ID NO 158
<211> LENGTH: 38
<212> TYPE: PRT
<213> ORGANISM: Homo sapiens

<400> SEQUENCE: 158

Phe Tyr Val Ala Ser Val Lys Gly Arg Phe Thr Ile Ser Arg Asp Asn
1               5                   10                  15

Ala Lys Lys Ser Val Tyr Val Gln Met Asn Ser Leu Arg Ala Glu Asp
            20                  25                  30

Thr Ala Val Tyr Tyr Cys
        35

<210> SEQ ID NO 159
<211> LENGTH: 38
<212> TYPE: PRT
<213> ORGANISM: Homo sapiens

<400> SEQUENCE: 159

Phe Tyr Val Ala Ser Val Lys Gly Arg Phe Thr Met Ser Arg Asp Asn
1               5                   10                  15

Ala Lys Asn Ser Val Tyr Val Gln Met Asn Ser Leu Arg Ala Glu Asp
            20                  25                  30

Thr Ala Val Tyr Tyr Cys
         35

<210> SEQ ID NO 160
<211> LENGTH: 38
<212> TYPE: PRT
<213> ORGANISM: Homo sapiens

<400> SEQUENCE: 160

Phe Tyr Val Ala Ser Val Lys Gly Arg Phe Thr Met Ser Arg Asp Asn
1               5                   10                  15

Ala Lys Lys Ser Val Tyr Leu Gln Met Asn Ser Leu Arg Ala Glu Asp
            20                  25                  30

Thr Ala Val Tyr Tyr Cys
         35

<210> SEQ ID NO 161
<211> LENGTH: 15
<212> TYPE: PRT
<213> ORGANISM: Homo sapiens

<400> SEQUENCE: 161

Ala Arg Glu Gly Tyr Ala Ser Ser Ser Tyr Tyr Gly Met Asp Val
1               5                   10                  15

<210> SEQ ID NO 162
<211> LENGTH: 15
<212> TYPE: PRT
<213> ORGANISM: Homo sapiens

<400> SEQUENCE: 162

Ala Arg Glu Gly Tyr Ser Ala Ser Ser Tyr Tyr Gly Met Asp Val
1               5                   10                  15

<210> SEQ ID NO 163
<211> LENGTH: 15
<212> TYPE: PRT
<213> ORGANISM: Homo sapiens

<400> SEQUENCE: 163

Ala Arg Glu Gly Tyr Ser Ser Ala Ser Tyr Tyr Gly Met Asp Val
1               5                   10                  15

<210> SEQ ID NO 164
<211> LENGTH: 15
<212> TYPE: PRT
<213> ORGANISM: Homo sapiens

<400> SEQUENCE: 164

Ala Arg Glu Gly Tyr Ser Ser Ser Ala Tyr Tyr Gly Met Asp Val
1               5                   10                  15

<210> SEQ ID NO 165
<211> LENGTH: 15
<212> TYPE: PRT
<213> ORGANISM: Homo sapiens

<400> SEQUENCE: 165

Ala Arg Glu Gly Tyr Ser Ser Cys Ser Tyr Tyr Gly Met Asp Val
1               5                   10                  15

```
<210> SEQ ID NO 166
<211> LENGTH: 15
<212> TYPE: PRT
<213> ORGANISM: Homo sapiens

<400> SEQUENCE: 166

Ala Arg Glu Gly Tyr Ser Ser Asp Ser Tyr Tyr Gly Met Asp Val
1               5                   10                  15

<210> SEQ ID NO 167
<211> LENGTH: 15
<212> TYPE: PRT
<213> ORGANISM: Homo sapiens

<400> SEQUENCE: 167

Ala Arg Glu Gly Tyr Ser Ser Glu Ser Tyr Tyr Gly Met Asp Val
1               5                   10                  15

<210> SEQ ID NO 168
<211> LENGTH: 15
<212> TYPE: PRT
<213> ORGANISM: Homo sapiens

<400> SEQUENCE: 168

Ala Arg Glu Gly Tyr Ser Ser Phe Ser Tyr Tyr Gly Met Asp Val
1               5                   10                  15

<210> SEQ ID NO 169
<211> LENGTH: 15
<212> TYPE: PRT
<213> ORGANISM: Homo sapiens

<400> SEQUENCE: 169

Ala Arg Glu Gly Tyr Ser Ser Gly Ser Tyr Tyr Gly Met Asp Val
1               5                   10                  15

<210> SEQ ID NO 170
<211> LENGTH: 15
<212> TYPE: PRT
<213> ORGANISM: Homo sapiens

<400> SEQUENCE: 170

Ala Arg Glu Gly Tyr Ser Ser His Ser Tyr Tyr Gly Met Asp Val
1               5                   10                  15

<210> SEQ ID NO 171
<211> LENGTH: 15
<212> TYPE: PRT
<213> ORGANISM: Homo sapiens

<400> SEQUENCE: 171

Ala Arg Glu Gly Tyr Ser Ser Ile Ser Tyr Tyr Gly Met Asp Val
1               5                   10                  15

<210> SEQ ID NO 172
<211> LENGTH: 15
<212> TYPE: PRT
<213> ORGANISM: Homo sapiens

<400> SEQUENCE: 172

Ala Arg Glu Gly Tyr Ser Ser Lys Ser Tyr Tyr Gly Met Asp Val
1               5                   10                  15

<210> SEQ ID NO 173
<211> LENGTH: 15
```

```
<212> TYPE: PRT
<213> ORGANISM: Homo sapiens

<400> SEQUENCE: 173

Ala Arg Glu Gly Tyr Ser Ser Leu Ser Tyr Tyr Gly Met Asp Val
1               5                   10                  15

<210> SEQ ID NO 174
<211> LENGTH: 15
<212> TYPE: PRT
<213> ORGANISM: Homo sapiens

<400> SEQUENCE: 174

Ala Arg Glu Gly Tyr Ser Ser Met Ser Tyr Tyr Gly Met Asp Val
1               5                   10                  15

<210> SEQ ID NO 175
<211> LENGTH: 15
<212> TYPE: PRT
<213> ORGANISM: Homo sapiens

<400> SEQUENCE: 175

Ala Arg Glu Gly Tyr Ser Ser Asn Ser Tyr Tyr Gly Met Asp Val
1               5                   10                  15

<210> SEQ ID NO 176
<211> LENGTH: 15
<212> TYPE: PRT
<213> ORGANISM: Homo sapiens

<400> SEQUENCE: 176

Ala Arg Glu Gly Tyr Ser Ser Pro Ser Tyr Tyr Gly Met Asp Val
1               5                   10                  15

<210> SEQ ID NO 177
<211> LENGTH: 15
<212> TYPE: PRT
<213> ORGANISM: Homo sapiens

<400> SEQUENCE: 177

Ala Arg Glu Gly Tyr Ser Ser Gln Ser Tyr Tyr Gly Met Asp Val
1               5                   10                  15

<210> SEQ ID NO 178
<211> LENGTH: 15
<212> TYPE: PRT
<213> ORGANISM: Homo sapiens

<400> SEQUENCE: 178

Ala Arg Glu Gly Tyr Ser Ser Arg Ser Tyr Tyr Gly Met Asp Val
1               5                   10                  15

<210> SEQ ID NO 179
<211> LENGTH: 15
<212> TYPE: PRT
<213> ORGANISM: Homo sapiens

<400> SEQUENCE: 179

Ala Arg Glu Gly Tyr Ser Ser Thr Ser Tyr Tyr Gly Met Asp Val
1               5                   10                  15

<210> SEQ ID NO 180
<211> LENGTH: 15
<212> TYPE: PRT
<213> ORGANISM: Homo sapiens
```

<400> SEQUENCE: 180

Ala Arg Glu Gly Tyr Ser Ser Val Ser Tyr Tyr Gly Met Asp Val
1               5                   10                  15

<210> SEQ ID NO 181
<211> LENGTH: 15
<212> TYPE: PRT
<213> ORGANISM: Homo sapiens

<400> SEQUENCE: 181

Ala Arg Glu Gly Tyr Ser Ser Trp Ser Tyr Tyr Gly Met Asp Val
1               5                   10                  15

<210> SEQ ID NO 182
<211> LENGTH: 15
<212> TYPE: PRT
<213> ORGANISM: Homo sapiens

<400> SEQUENCE: 182

Ala Arg Glu Gly Tyr Ser Ser Tyr Ser Tyr Tyr Gly Met Asp Val
1               5                   10                  15

<210> SEQ ID NO 183
<211> LENGTH: 15
<212> TYPE: PRT
<213> ORGANISM: Homo sapiens

<400> SEQUENCE: 183

Ala Arg Glu Gly Tyr Ser Ser Ser Cys Tyr Tyr Gly Met Asp Val
1               5                   10                  15

<210> SEQ ID NO 184
<211> LENGTH: 15
<212> TYPE: PRT
<213> ORGANISM: Homo sapiens

<400> SEQUENCE: 184

Ala Arg Glu Gly Tyr Ser Ser Ser Asp Tyr Tyr Gly Met Asp Val
1               5                   10                  15

<210> SEQ ID NO 185
<211> LENGTH: 15
<212> TYPE: PRT
<213> ORGANISM: Homo sapiens

<400> SEQUENCE: 185

Ala Arg Glu Gly Tyr Ser Ser Ser Glu Tyr Tyr Gly Met Asp Val
1               5                   10                  15

<210> SEQ ID NO 186
<211> LENGTH: 15
<212> TYPE: PRT
<213> ORGANISM: Homo sapiens

<400> SEQUENCE: 186

Ala Arg Glu Gly Tyr Ser Ser Ser Phe Tyr Tyr Gly Met Asp Val
1               5                   10                  15

<210> SEQ ID NO 187
<211> LENGTH: 15
<212> TYPE: PRT
<213> ORGANISM: Homo sapiens

<400> SEQUENCE: 187

Ala Arg Glu Gly Tyr Ser Ser Ser Gly Tyr Tyr Gly Met Asp Val
1               5                   10                  15

<210> SEQ ID NO 188
<211> LENGTH: 15
<212> TYPE: PRT
<213> ORGANISM: Homo sapiens

<400> SEQUENCE: 188

Ala Arg Glu Gly Tyr Ser Ser Ser His Tyr Tyr Gly Met Asp Val
1               5                   10                  15

<210> SEQ ID NO 189
<211> LENGTH: 15
<212> TYPE: PRT
<213> ORGANISM: Homo sapiens

<400> SEQUENCE: 189

Ala Arg Glu Gly Tyr Ser Ser Ser Ile Tyr Tyr Gly Met Asp Val
1               5                   10                  15

<210> SEQ ID NO 190
<211> LENGTH: 15
<212> TYPE: PRT
<213> ORGANISM: Homo sapiens

<400> SEQUENCE: 190

Ala Arg Glu Gly Tyr Ser Ser Ser Lys Tyr Tyr Gly Met Asp Val
1               5                   10                  15

<210> SEQ ID NO 191
<211> LENGTH: 15
<212> TYPE: PRT
<213> ORGANISM: Homo sapiens

<400> SEQUENCE: 191

Ala Arg Glu Gly Tyr Ser Ser Ser Leu Tyr Tyr Gly Met Asp Val
1               5                   10                  15

<210> SEQ ID NO 192
<211> LENGTH: 15
<212> TYPE: PRT
<213> ORGANISM: Homo sapiens

<400> SEQUENCE: 192

Ala Arg Glu Gly Tyr Ser Ser Ser Met Tyr Tyr Gly Met Asp Val
1               5                   10                  15

<210> SEQ ID NO 193
<211> LENGTH: 15
<212> TYPE: PRT
<213> ORGANISM: Homo sapiens

<400> SEQUENCE: 193

Ala Arg Glu Gly Tyr Ser Ser Ser Asn Tyr Tyr Gly Met Asp Val
1               5                   10                  15

<210> SEQ ID NO 194
<211> LENGTH: 15
<212> TYPE: PRT
<213> ORGANISM: Homo sapiens

<400> SEQUENCE: 194

Ala Arg Glu Gly Tyr Ser Ser Ser Pro Tyr Tyr Gly Met Asp Val

```
<210> SEQ ID NO 195
<211> LENGTH: 15
<212> TYPE: PRT
<213> ORGANISM: Homo sapiens

<400> SEQUENCE: 195

Ala Arg Glu Gly Tyr Ser Ser Ser Gln Tyr Tyr Gly Met Asp Val
1               5                   10                  15

<210> SEQ ID NO 196
<211> LENGTH: 15
<212> TYPE: PRT
<213> ORGANISM: Homo sapiens

<400> SEQUENCE: 196

Ala Arg Glu Gly Tyr Ser Ser Ser Arg Tyr Tyr Gly Met Asp Val
1               5                   10                  15

<210> SEQ ID NO 197
<211> LENGTH: 15
<212> TYPE: PRT
<213> ORGANISM: Homo sapiens

<400> SEQUENCE: 197

Ala Arg Glu Gly Tyr Ser Ser Ser Thr Tyr Tyr Gly Met Asp Val
1               5                   10                  15

<210> SEQ ID NO 198
<211> LENGTH: 15
<212> TYPE: PRT
<213> ORGANISM: Homo sapiens

<400> SEQUENCE: 198

Ala Arg Glu Gly Tyr Ser Ser Ser Val Tyr Tyr Gly Met Asp Val
1               5                   10                  15

<210> SEQ ID NO 199
<211> LENGTH: 15
<212> TYPE: PRT
<213> ORGANISM: Homo sapiens

<400> SEQUENCE: 199

Ala Arg Glu Gly Tyr Ser Ser Ser Trp Tyr Tyr Gly Met Asp Val
1               5                   10                  15

<210> SEQ ID NO 200
<211> LENGTH: 15
<212> TYPE: PRT
<213> ORGANISM: Homo sapiens

<400> SEQUENCE: 200

Ala Arg Glu Gly Tyr Ser Ser Ser Tyr Tyr Tyr Gly Met Asp Val
1               5                   10                  15

<210> SEQ ID NO 201
<211> LENGTH: 15
<212> TYPE: PRT
<213> ORGANISM: Homo sapiens

<400> SEQUENCE: 201

Ala Arg Glu Gly Tyr Cys Ser Ser Tyr Tyr Gly Met Asp Val
1               5                   10                  15
```

<210> SEQ ID NO 202
<211> LENGTH: 15
<212> TYPE: PRT
<213> ORGANISM: Homo sapiens

<400> SEQUENCE: 202

Ala Arg Glu Gly Tyr Asp Ser Ser Ser Tyr Tyr Gly Met Asp Val
1               5                   10                  15

<210> SEQ ID NO 203
<211> LENGTH: 15
<212> TYPE: PRT
<213> ORGANISM: Homo sapiens

<400> SEQUENCE: 203

Ala Arg Glu Gly Tyr Glu Ser Ser Ser Tyr Tyr Gly Met Asp Val
1               5                   10                  15

<210> SEQ ID NO 204
<211> LENGTH: 15
<212> TYPE: PRT
<213> ORGANISM: Homo sapiens

<400> SEQUENCE: 204

Ala Arg Glu Gly Tyr Phe Ser Ser Ser Tyr Tyr Gly Met Asp Val
1               5                   10                  15

<210> SEQ ID NO 205
<211> LENGTH: 15
<212> TYPE: PRT
<213> ORGANISM: Homo sapiens

<400> SEQUENCE: 205

Ala Arg Glu Gly Tyr Gly Ser Ser Ser Tyr Tyr Gly Met Asp Val
1               5                   10                  15

<210> SEQ ID NO 206
<211> LENGTH: 15
<212> TYPE: PRT
<213> ORGANISM: Homo sapiens

<400> SEQUENCE: 206

Ala Arg Glu Gly Tyr His Ser Ser Ser Tyr Tyr Gly Met Asp Val
1               5                   10                  15

<210> SEQ ID NO 207
<211> LENGTH: 15
<212> TYPE: PRT
<213> ORGANISM: Homo sapiens

<400> SEQUENCE: 207

Ala Arg Glu Gly Tyr Ile Ser Ser Ser Tyr Tyr Gly Met Asp Val
1               5                   10                  15

<210> SEQ ID NO 208
<211> LENGTH: 15
<212> TYPE: PRT
<213> ORGANISM: Homo sapiens

<400> SEQUENCE: 208

Ala Arg Glu Gly Tyr Lys Ser Ser Ser Tyr Tyr Gly Met Asp Val
1               5                   10                  15

<210> SEQ ID NO 209

```
<211> LENGTH: 15
<212> TYPE: PRT
<213> ORGANISM: Homo sapiens

<400> SEQUENCE: 209

Ala Arg Glu Gly Tyr Leu Ser Ser Ser Tyr Tyr Gly Met Asp Val
1               5                   10                  15

<210> SEQ ID NO 210
<211> LENGTH: 15
<212> TYPE: PRT
<213> ORGANISM: Homo sapiens

<400> SEQUENCE: 210

Ala Arg Glu Gly Tyr Met Ser Ser Ser Tyr Tyr Gly Met Asp Val
1               5                   10                  15

<210> SEQ ID NO 211
<211> LENGTH: 15
<212> TYPE: PRT
<213> ORGANISM: Homo sapiens

<400> SEQUENCE: 211

Ala Arg Glu Gly Tyr Asn Ser Ser Ser Tyr Tyr Gly Met Asp Val
1               5                   10                  15

<210> SEQ ID NO 212
<211> LENGTH: 15
<212> TYPE: PRT
<213> ORGANISM: Homo sapiens

<400> SEQUENCE: 212

Ala Arg Glu Gly Tyr Pro Ser Ser Ser Tyr Tyr Gly Met Asp Val
1               5                   10                  15

<210> SEQ ID NO 213
<211> LENGTH: 15
<212> TYPE: PRT
<213> ORGANISM: Homo sapiens

<400> SEQUENCE: 213

Ala Arg Glu Gly Tyr Gln Ser Ser Ser Tyr Tyr Gly Met Asp Val
1               5                   10                  15

<210> SEQ ID NO 214
<211> LENGTH: 15
<212> TYPE: PRT
<213> ORGANISM: Homo sapiens

<400> SEQUENCE: 214

Ala Arg Glu Gly Tyr Arg Ser Ser Ser Tyr Tyr Gly Met Asp Val
1               5                   10                  15

<210> SEQ ID NO 215
<211> LENGTH: 15
<212> TYPE: PRT
<213> ORGANISM: Homo sapiens

<400> SEQUENCE: 215

Ala Arg Glu Gly Tyr Thr Ser Ser Ser Tyr Tyr Gly Met Asp Val
1               5                   10                  15

<210> SEQ ID NO 216
<211> LENGTH: 15
<212> TYPE: PRT
```

<213> ORGANISM: Homo sapiens

<400> SEQUENCE: 216

Ala Arg Glu Gly Tyr Val Ser Ser Tyr Tyr Gly Met Asp Val
1               5                   10                  15

<210> SEQ ID NO 217
<211> LENGTH: 15
<212> TYPE: PRT
<213> ORGANISM: Homo sapiens

<400> SEQUENCE: 217

Ala Arg Glu Gly Tyr Trp Ser Ser Tyr Tyr Gly Met Asp Val
1               5                   10                  15

<210> SEQ ID NO 218
<211> LENGTH: 15
<212> TYPE: PRT
<213> ORGANISM: Homo sapiens

<400> SEQUENCE: 218

Ala Arg Glu Gly Tyr Tyr Ser Ser Tyr Tyr Gly Met Asp Val
1               5                   10                  15

<210> SEQ ID NO 219
<211> LENGTH: 15
<212> TYPE: PRT
<213> ORGANISM: Homo sapiens

<400> SEQUENCE: 219

Ala Arg Glu Gly Tyr Ser Cys Ser Tyr Tyr Gly Met Asp Val
1               5                   10                  15

<210> SEQ ID NO 220
<211> LENGTH: 15
<212> TYPE: PRT
<213> ORGANISM: Homo sapiens

<400> SEQUENCE: 220

Ala Arg Glu Gly Tyr Ser Asp Ser Tyr Tyr Gly Met Asp Val
1               5                   10                  15

<210> SEQ ID NO 221
<211> LENGTH: 15
<212> TYPE: PRT
<213> ORGANISM: Homo sapiens

<400> SEQUENCE: 221

Ala Arg Glu Gly Tyr Ser Glu Ser Tyr Tyr Gly Met Asp Val
1               5                   10                  15

<210> SEQ ID NO 222
<211> LENGTH: 18
<212> TYPE: PRT
<213> ORGANISM: Homo sapiens

<400> SEQUENCE: 222

Thr Val Phe Leu Asp His Glu Asn Ala Asn Lys Ile Leu Asn Arg Pro
1               5                   10                  15

Lys Arg

<210> SEQ ID NO 223
<211> LENGTH: 15
<212> TYPE: PRT

-continued

<213> ORGANISM: Homo sapiens

<400> SEQUENCE: 223

Ala Arg Glu Gly Tyr Ser Phe Ser Ser Tyr Tyr Gly Met Asp Val
1               5                   10                  15

<210> SEQ ID NO 224
<211> LENGTH: 15
<212> TYPE: PRT
<213> ORGANISM: Homo sapiens

<400> SEQUENCE: 224

Ala Arg Glu Gly Tyr Ser Gly Ser Ser Tyr Tyr Gly Met Asp Val
1               5                   10                  15

<210> SEQ ID NO 225
<211> LENGTH: 15
<212> TYPE: PRT
<213> ORGANISM: Homo sapiens

<400> SEQUENCE: 225

Ala Arg Glu Gly Tyr Ser His Ser Ser Tyr Tyr Gly Met Asp Val
1               5                   10                  15

<210> SEQ ID NO 226
<211> LENGTH: 15
<212> TYPE: PRT
<213> ORGANISM: Homo sapiens

<400> SEQUENCE: 226

Ala Arg Glu Gly Tyr Ser Ile Ser Ser Tyr Tyr Gly Met Asp Val
1               5                   10                  15

<210> SEQ ID NO 227
<211> LENGTH: 15
<212> TYPE: PRT
<213> ORGANISM: Homo sapiens

<400> SEQUENCE: 227

Ala Arg Glu Gly Tyr Ser Lys Ser Ser Tyr Tyr Gly Met Asp Val
1               5                   10                  15

<210> SEQ ID NO 228
<211> LENGTH: 15
<212> TYPE: PRT
<213> ORGANISM: Homo sapiens

<400> SEQUENCE: 228

Ala Arg Glu Gly Tyr Ser Leu Ser Ser Tyr Tyr Gly Met Asp Val
1               5                   10                  15

<210> SEQ ID NO 229
<211> LENGTH: 15
<212> TYPE: PRT
<213> ORGANISM: Homo sapiens

<400> SEQUENCE: 229

Ala Arg Glu Gly Tyr Ser Met Ser Ser Tyr Tyr Gly Met Asp Val
1               5                   10                  15

<210> SEQ ID NO 230
<211> LENGTH: 15
<212> TYPE: PRT
<213> ORGANISM: Homo sapiens

```
<400> SEQUENCE: 230

Ala Arg Glu Gly Tyr Ser Asn Ser Ser Tyr Tyr Gly Met Asp Val
1               5                   10                  15

<210> SEQ ID NO 231
<211> LENGTH: 15
<212> TYPE: PRT
<213> ORGANISM: Homo sapiens

<400> SEQUENCE: 231

Ala Arg Glu Gly Tyr Ser Pro Ser Ser Tyr Tyr Gly Met Asp Val
1               5                   10                  15

<210> SEQ ID NO 232
<211> LENGTH: 15
<212> TYPE: PRT
<213> ORGANISM: Homo sapiens

<400> SEQUENCE: 232

Ala Arg Glu Gly Tyr Ser Gln Ser Ser Tyr Tyr Gly Met Asp Val
1               5                   10                  15

<210> SEQ ID NO 233
<211> LENGTH: 15
<212> TYPE: PRT
<213> ORGANISM: Homo sapiens

<400> SEQUENCE: 233

Ala Arg Glu Gly Tyr Ser Arg Ser Ser Tyr Tyr Gly Met Asp Val
1               5                   10                  15

<210> SEQ ID NO 234
<211> LENGTH: 15
<212> TYPE: PRT
<213> ORGANISM: Homo sapiens

<400> SEQUENCE: 234

Ala Arg Glu Gly Tyr Ser Thr Ser Ser Tyr Tyr Gly Met Asp Val
1               5                   10                  15

<210> SEQ ID NO 235
<211> LENGTH: 15
<212> TYPE: PRT
<213> ORGANISM: Homo sapiens

<400> SEQUENCE: 235

Ala Arg Glu Gly Tyr Ser Val Ser Ser Tyr Tyr Gly Met Asp Val
1               5                   10                  15

<210> SEQ ID NO 236
<211> LENGTH: 15
<212> TYPE: PRT
<213> ORGANISM: Homo sapiens

<400> SEQUENCE: 236

Ala Arg Glu Gly Tyr Ser Trp Ser Ser Tyr Tyr Gly Met Asp Val
1               5                   10                  15

<210> SEQ ID NO 237
<211> LENGTH: 15
<212> TYPE: PRT
<213> ORGANISM: Homo sapiens

<400> SEQUENCE: 237
```

Ala Arg Glu Gly Tyr Ser Tyr Ser Ser Tyr Tyr Gly Met Asp Val
1               5                   10                  15

<210> SEQ ID NO 238
<211> LENGTH: 367
<212> TYPE: DNA
<213> ORGANISM: Homo sapiens

<400> SEQUENCE: 238
gaggtgcagc tggtggagtc tggggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatgccagtt cgtcctatta tggtatggac gtctggggcc aagggaccac ggtcaccgtc   360
tcctcag                                                              367

<210> SEQ ID NO 239
<211> LENGTH: 367
<212> TYPE: DNA
<213> ORGANISM: Homo sapiens

<400> SEQUENCE: 239
gaggtgcagc tggtggagtc tggggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtgcct cgtcctatta tggtatggac gtctggggcc aagggaccac ggtcaccgtc   360
tcctcag                                                              367

<210> SEQ ID NO 240
<211> LENGTH: 367
<212> TYPE: DNA
<213> ORGANISM: Homo sapiens

<400> SEQUENCE: 240
gaggtgcagc tggtggagtc tggggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtg cctcctatta tggtatggac gtctggggcc aagggaccac ggtcaccgtc   360
tcctcag                                                              367

<210> SEQ ID NO 241
<211> LENGTH: 367
<212> TYPE: DNA
<213> ORGANISM: Homo sapiens

<400> SEQUENCE: 241
gaggtgcagc tggtggagtc tggggggaggc tttgtccagc ctggggggtc cctgagactc    60

```
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggcctatta tggtatggac gtctggggcc aagggaccac ggtcaccgtc    360
tcctcag                                                              367
```

<210> SEQ ID NO 242
<211> LENGTH: 367
<212> TYPE: DNA
<213> ORGANISM: Homo sapiens

<400> SEQUENCE: 242

```
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt gctcctatta tggtatggac gtctggggcc aagggaccac ggtcaccgtc    360
tcctcag                                                              367
```

<210> SEQ ID NO 243
<211> LENGTH: 367
<212> TYPE: DNA
<213> ORGANISM: Homo sapiens

<400> SEQUENCE: 243

```
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtg actcctatta tggtatggac gtctggggcc aagggaccac ggtcaccgtc    360
tcctcag                                                              367
```

<210> SEQ ID NO 244
<211> LENGTH: 367
<212> TYPE: DNA
<213> ORGANISM: Homo sapiens

<400> SEQUENCE: 244

```
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtg agtcctatta tggtatggac gtctggggcc aagggaccac ggtcaccgtc    360
tcctcag                                                              367
```

<210> SEQ ID NO 245
<211> LENGTH: 367
<212> TYPE: DNA
<213> ORGANISM: Homo sapiens

<400> SEQUENCE: 245

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg gtggccaac ataaaccaag atggaagtga gaaattctat     180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt ctcctatta tggtatggac gtctggggcc aagggaccac ggtcaccgtc    360
tcctcag                                                             367
```

<210> SEQ ID NO 246
<211> LENGTH: 367
<212> TYPE: DNA
<213> ORGANISM: Homo sapiens

<400> SEQUENCE: 246

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg gtggccaac ataaaccaag atggaagtga gaaattctat     180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtg ctcctatta tggtatggac gtctggggcc aagggaccac ggtcaccgtc    360
tcctcag                                                             367
```

<210> SEQ ID NO 247
<211> LENGTH: 367
<212> TYPE: DNA
<213> ORGANISM: Homo sapiens

<400> SEQUENCE: 247

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg gtggccaac ataaaccaag atggaagtga gaaattctat     180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtc actcctatta tggtatggac gtctggggcc aagggaccac ggtcaccgtc    360
tcctcag                                                             367
```

<210> SEQ ID NO 248
<211> LENGTH: 367
<212> TYPE: DNA
<213> ORGANISM: Homo sapiens

<400> SEQUENCE: 248

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg gtggccaac ataaaccaag atggaagtga gaaattctat     180
```

| | |
|---|---|
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagta tctcctatta tggtatggac gtctggggcc aagggaccac ggtcaccgtc | 360 |
| tcctcag | 367 |

<210> SEQ ID NO 249
<211> LENGTH: 367
<212> TYPE: DNA
<213> ORGANISM: Homo sapiens

<400> SEQUENCE: 249

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagta agtcctatta tggtatggac gtctggggcc aagggaccac ggtcaccgtc | 360 |
| tcctcag | 367 |

<210> SEQ ID NO 250
<211> LENGTH: 367
<212> TYPE: DNA
<213> ORGANISM: Homo sapiens

<400> SEQUENCE: 250

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtc tgtcctatta tggtatggac gtctggggcc aagggaccac ggtcaccgtc | 360 |
| tcctcag | 367 |

<210> SEQ ID NO 251
<211> LENGTH: 367
<212> TYPE: DNA
<213> ORGANISM: Homo sapiens

<400> SEQUENCE: 251

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagta tgtcctatta tggtatggac gtctggggcc aagggaccac ggtcaccgtc | 360 |
| tcctcag | 367 |

<210> SEQ ID NO 252
<211> LENGTH: 367
<212> TYPE: DNA
<213> ORGANISM: Homo sapiens

<400> SEQUENCE: 252

```
gaggtgcagc tggtggagtc tgggggaggc tttgtccagc ctgggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagta actcctatta tggtatggac gtctggggcc aagggaccac ggtcaccgtc   360
tcctcag                                                             367
```

<210> SEQ ID NO 253
<211> LENGTH: 367
<212> TYPE: DNA
<213> ORGANISM: Homo sapiens

<400> SEQUENCE: 253

```
gaggtgcagc tggtggagtc tgggggaggc tttgtccagc ctgggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtc cctcctatta tggtatggac gtctggggcc aagggaccac ggtcaccgtc   360
tcctcag                                                             367
```

<210> SEQ ID NO 254
<211> LENGTH: 367
<212> TYPE: DNA
<213> ORGANISM: Homo sapiens

<400> SEQUENCE: 254

```
gaggtgcagc tggtggagtc tgggggaggc tttgtccagc ctgggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtc agtcctatta tggtatggac gtctggggcc aagggaccac ggtcaccgtc   360
tcctcag                                                             367
```

<210> SEQ ID NO 255
<211> LENGTH: 367
<212> TYPE: DNA
<213> ORGANISM: Homo sapiens

<400> SEQUENCE: 255

```
gaggtgcagc tggtggagtc tgggggaggc tttgtccagc ctgggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
```

| | |
|---|---|
| tatagtagta gatcctatta tggtatggac gtctggggcc aagggaccac ggtcaccgtc | 360 |
| tcctcag | 367 |

<210> SEQ ID NO 256
<211> LENGTH: 367
<212> TYPE: DNA
<213> ORGANISM: Homo sapiens

<400> SEQUENCE: 256

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagta cctcctatta tggtatggac gtctggggcc aagggaccac ggtcaccgtc | 360 |
| tcctcag | 367 |

<210> SEQ ID NO 257
<211> LENGTH: 367
<212> TYPE: DNA
<213> ORGANISM: Homo sapiens

<400> SEQUENCE: 257

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtg tgtcctatta tggtatggac gtctggggcc aagggaccac ggtcaccgtc | 360 |
| tcctcag | 367 |

<210> SEQ ID NO 258
<211> LENGTH: 367
<212> TYPE: DNA
<213> ORGANISM: Homo sapiens

<400> SEQUENCE: 258

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtagtt ggtcctatta tggtatggac gtctggggcc aagggaccac ggtcaccgtc | 360 |
| tcctcag | 367 |

<210> SEQ ID NO 259
<211> LENGTH: 367
<212> TYPE: DNA
<213> ORGANISM: Homo sapiens

<400> SEQUENCE: 259

| | |
|---|---|
| gaggtgcagc tggtggagtc tgggggaggc tttgtccagc ctggggggtc cctgagactc | 60 |

```
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt actcctatta tggtatggac gtctggggcc aagggaccac ggtcaccgtc    360
tcctcag                                                              367
```

<210> SEQ ID NO 260
<211> LENGTH: 367
<212> TYPE: DNA
<213> ORGANISM: Homo sapiens

<400> SEQUENCE: 260

```
gaggtgcagc tggtggagtc tgggggaggc tttgtccagc ctgggggtc cctgagactc     60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgtgctatta tggtatggac gtctggggcc aagggaccac ggtcaccgtc    360
tcctcag                                                              367
```

<210> SEQ ID NO 261
<211> LENGTH: 367
<212> TYPE: DNA
<213> ORGANISM: Homo sapiens

<400> SEQUENCE: 261

```
gaggtgcagc tggtggagtc tgggggaggc tttgtccagc ctgggggtc cctgagactc     60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggactatta tggtatggac gtctggggcc aagggaccac ggtcaccgtc    360
tcctcag                                                              367
```

<210> SEQ ID NO 262
<211> LENGTH: 367
<212> TYPE: DNA
<213> ORGANISM: Homo sapiens

<400> SEQUENCE: 262

```
gaggtgcagc tggtggagtc tgggggaggc tttgtccagc ctgggggtc cctgagactc     60 tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cggagtatta tggtatggac gtctggggcc aagggaccac ggtcaccgtc    360
tcctcag                                                              367
```

<210> SEQ ID NO 263
<211> LENGTH: 367
<212> TYPE: DNA
<213> ORGANISM: Homo sapiens

<400> SEQUENCE: 263

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgttctatta tggtatggac gtctggggcc aagggaccac ggtcaccgtc    360
tcctcag                                                              367
```

<210> SEQ ID NO 264
<211> LENGTH: 367
<212> TYPE: DNA
<213> ORGANISM: Homo sapiens

<400> SEQUENCE: 264

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgggctatta tggtatggac gtctggggcc aagggaccac ggtcaccgtc    360
tcctcag                                                              367
```

<210> SEQ ID NO 265
<211> LENGTH: 367
<212> TYPE: DNA
<213> ORGANISM: Homo sapiens

<400> SEQUENCE: 265

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgcactatta tggtatggac gtctggggcc aagggaccac ggtcaccgtc    360
tcctcag                                                              367
```

<210> SEQ ID NO 266
<211> LENGTH: 367
<212> TYPE: DNA
<213> ORGANISM: Homo sapiens

<400> SEQUENCE: 266

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
```

```
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagtt cgatctatta tggtatggac gtctggggcc aagggaccac ggtcaccgtc    360
tcctcag                                                              367
```

<210> SEQ ID NO 267
<211> LENGTH: 367
<212> TYPE: DNA
<213> ORGANISM: Homo sapiens

<400> SEQUENCE: 267

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtt cgaagtatta tggtatggac gtctggggcc aagggaccac ggtcaccgtc   360
tcctcag                                                             367
```

<210> SEQ ID NO 268
<211> LENGTH: 367
<212> TYPE: DNA
<213> ORGANISM: Homo sapiens

<400> SEQUENCE: 268

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtt cgctgtatta tggtatggac gtctggggcc aagggaccac ggtcaccgtc   360
tcctcag                                                             367
```

<210> SEQ ID NO 269
<211> LENGTH: 367
<212> TYPE: DNA
<213> ORGANISM: Homo sapiens

<400> SEQUENCE: 269

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagtt cgatgtatta tggtatggac gtctggggcc aagggaccac ggtcaccgtc   360
tcctcag                                                             367
```

<210> SEQ ID NO 270
<211> LENGTH: 367
<212> TYPE: DNA

<213> ORGANISM: Homo sapiens

<400> SEQUENCE: 270

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca cgccaagaa atcagtgtat | 240 |
| gtacaaatga acagcctgag agccgaggac acggctgtgt attactgtgc gagagagggg | 300 |
| tatagtagtt cgaactatta tggtatggac gtctggggcc aagggaccac ggtcaccgtc | 360 |
| tcctcag | 367 |

<210> SEQ ID NO 271
<211> LENGTH: 367
<212> TYPE: DNA
<213> ORGANISM: Homo sapiens

<400> SEQUENCE: 271

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca cgccaagaa atcagtgtat | 240 |
| gtacaaatga acagcctgag agccgaggac acggctgtgt attactgtgc gagagagggg | 300 |
| tatagtagtt cgccctatta tggtatggac gtctggggcc aagggaccac ggtcaccgtc | 360 |
| tcctcag | 367 |

<210> SEQ ID NO 272
<211> LENGTH: 367
<212> TYPE: DNA
<213> ORGANISM: Homo sapiens

<400> SEQUENCE: 272

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca cgccaagaa atcagtgtat | 240 |
| gtacaaatga acagcctgag agccgaggac acggctgtgt attactgtgc gagagagggg | 300 |
| tatagtagtt cgcagtatta tggtatggac gtctggggcc aagggaccac ggtcaccgtc | 360 |
| tcctcag | 367 |

<210> SEQ ID NO 273
<211> LENGTH: 367
<212> TYPE: DNA
<213> ORGANISM: Homo sapiens

<400> SEQUENCE: 273

| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca cgccaagaa atcagtgtat | 240 |
| gtacaaatga acagcctgag agccgaggac acggctgtgt attactgtgc gagagagggg | 300 |

```
tatagtagtt cgagatatta tggtatggac gtctggggcc aagggaccac ggtcaccgtc    360
tcctcag                                                             367

<210> SEQ ID NO 274
<211> LENGTH: 367
<212> TYPE: DNA
<213> ORGANISM: Homo sapiens

<400> SEQUENCE: 274
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240 gtacaaatga acagcctgag agccgaggac acggctgtgt attactgtgc gagagagggg   300
tatagtagtt cgacctatta tggtatggac gtctggggcc aagggaccac ggtcaccgtc   360
tcctcag                                                             367

<210> SEQ ID NO 275
<211> LENGTH: 367
<212> TYPE: DNA
<213> ORGANISM: Homo sapiens

<400> SEQUENCE: 275
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240 gtacaaatga acagcctgag agccgaggac acggctgtgt attactgtgc gagagagggg   300
tatagtagtt cggtgtatta tggtatggac gtctggggcc aagggaccac ggtcaccgtc   360
tcctcag                                                             367

<210> SEQ ID NO 276
<211> LENGTH: 367
<212> TYPE: DNA
<213> ORGANISM: Homo sapiens

<400> SEQUENCE: 276
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240 gtacaaatga acagcctgag agccgaggac acggctgtgt attactgtgc gagagagggg   300
tatagtagtt cgtggtatta tggtatggac gtctggggcc aagggaccac ggtcaccgtc   360
tcctcag                                                             367

<210> SEQ ID NO 277
<211> LENGTH: 367
<212> TYPE: DNA
<213> ORGANISM: Homo sapiens

<400> SEQUENCE: 277
```

| | | |
|---|---|---|
| gaggtgcagc tggtggagtc tgggggaggc tttgtccagc ctggggggtc cctgagactc | 60 | |
| tcctgtgcag tctctggatt cacctttaat agctattgga tgagctgggt ccgccaggct | 120 | |
| ccagggaagg ggctggagtg ggtggccaac ataaaccaag atggaagtga gaaattctat | 180 | |
| gtggcctctg tgaagggccg attcaccatg tccagagaca cgccaagaa atcagtgtat | 240 | |
| gtacaaatga acagcctgag agccgaggac acggctgtgt attactgtgc gagagagggg | 300 | |
| tatagtagtt cgtactatta tggtatggac gtctggggcc aagggaccac ggtcaccgtc | 360 | |
| tcctcag | 367 | |

<210> SEQ ID NO 278
<211> LENGTH: 367
<212> TYPE: DNA
<213> ORGANISM: Homo sapiens

<400> SEQUENCE: 278

| | | |
|---|---|---|
| gaggtgcagc tggtggagtc tgggggaggc tttgtccagc ctggggggtc cctgagactc | 60 | |
| tcctgtgcag tctctggatt cacctttaat agctattgga tgagctgggt ccgccaggct | 120 | |
| ccagggaagg ggctggagtg ggtggccaac ataaaccaag atggaagtga gaaattctat | 180 | |
| gtggcctctg tgaagggccg attcaccatg tccagagaca cgccaagaa atcagtgtat | 240 | |
| gtacaaatga acagcctgag agccgaggac acggctgtgt attactgtgc gagagagggg | 300 | |
| tattgcagtt cgtcctatta tggtatggac gtctggggcc aagggaccac ggtcaccgtc | 360 | |
| tcctcag | 367 | |

<210> SEQ ID NO 279
<211> LENGTH: 367
<212> TYPE: DNA
<213> ORGANISM: Homo sapiens

<400> SEQUENCE: 279

| | | |
|---|---|---|
| gaggtgcagc tggtggagtc tgggggaggc tttgtccagc ctggggggtc cctgagactc | 60 | |
| tcctgtgcag tctctggatt cacctttaat agctattgga tgagctgggt ccgccaggct | 120 | |
| ccagggaagg ggctggagtg ggtggccaac ataaaccaag atggaagtga gaaattctat | 180 | |
| gtggcctctg tgaagggccg attcaccatg tccagagaca cgccaagaa atcagtgtat | 240 | |
| gtacaaatga acagcctgag agccgaggac acggctgtgt attactgtgc gagagagggg | 300 | |
| tatgacagtt cgtcctatta tggtatggac gtctggggcc aagggaccac ggtcaccgtc | 360 | |
| tcctcag | 367 | |

<210> SEQ ID NO 280
<211> LENGTH: 367
<212> TYPE: DNA
<213> ORGANISM: Homo sapiens

<400> SEQUENCE: 280

| | | |
|---|---|---|
| gaggtgcagc tggtggagtc tgggggaggc tttgtccagc ctggggggtc cctgagactc | 60 | |
| tcctgtgcag tctctggatt cacctttaat agctattgga tgagctgggt ccgccaggct | 120 | |
| ccagggaagg ggctggagtg ggtggccaac ataaaccaag atggaagtga gaaattctat | 180 | |
| gtggcctctg tgaagggccg attcaccatg tccagagaca cgccaagaa atcagtgtat | 240 | |
| gtacaaatga acagcctgag agccgaggac acggctgtgt attactgtgc gagagagggg | 300 | |
| tatgagagtt cgtcctatta tggtatggac gtctggggcc aagggaccac ggtcaccgtc | 360 | |
| tcctcag | 367 | |

<210> SEQ ID NO 281
<211> LENGTH: 367
<212> TYPE: DNA
<213> ORGANISM: Homo sapiens

<400> SEQUENCE: 281

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatttcagtt cgtcctatta tggtatggac gtctggggcc aagggaccac ggtcaccgtc     360
tcctcag                                                               367
```

<210> SEQ ID NO 282
<211> LENGTH: 367
<212> TYPE: DNA
<213> ORGANISM: Homo sapiens

<400> SEQUENCE: 282

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatggcagtt cgtcctatta tggtatggac gtctggggcc aagggaccac ggtcaccgtc     360
tcctcag                                                               367
```

<210> SEQ ID NO 283
<211> LENGTH: 367
<212> TYPE: DNA
<213> ORGANISM: Homo sapiens

<400> SEQUENCE: 283

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatcacagtt cgtcctatta tggtatggac gtctggggcc aagggaccac ggtcaccgtc     360
tcctcag                                                               367
```

<210> SEQ ID NO 284
<211> LENGTH: 367
<212> TYPE: DNA
<213> ORGANISM: Homo sapiens

<400> SEQUENCE: 284

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
```

```
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatatcagtt cgtcctatta tggtatggac gtctggggcc aagggaccac ggtcaccgtc    360
tcctcag                                                              367

<210> SEQ ID NO 285
<211> LENGTH: 367
<212> TYPE: DNA
<213> ORGANISM: Homo sapiens

<400> SEQUENCE: 285
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tataagagtt cgtcctatta tggtatggac gtctggggcc aagggaccac ggtcaccgtc    360
tcctcag                                                              367

<210> SEQ ID NO 286
<211> LENGTH: 367
<212> TYPE: DNA
<213> ORGANISM: Homo sapiens

<400> SEQUENCE: 286
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatctgagtt cgtcctatta tggtatggac gtctggggcc aagggaccac ggtcaccgtc    360
tcctcag                                                              367

<210> SEQ ID NO 287
<211> LENGTH: 367
<212> TYPE: DNA
<213> ORGANISM: Homo sapiens

<400> SEQUENCE: 287
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatatgagtt cgtcctatta tggtatggac gtctggggcc aagggaccac ggtcaccgtc    360
tcctcag                                                              367

<210> SEQ ID NO 288
<211> LENGTH: 367
```

<212> TYPE: DNA
<213> ORGANISM: Homo sapiens

<400> SEQUENCE: 288

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tataacagtt cgtcctatta tggtatggac gtctggggcc aagggaccac ggtcaccgtc    360
tcctcag                                                              367
```

<210> SEQ ID NO 289
<211> LENGTH: 367
<212> TYPE: DNA
<213> ORGANISM: Homo sapiens

<400> SEQUENCE: 289

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatcccagtt cgtcctatta tggtatggac gtctggggcc aagggaccac ggtcaccgtc    360
tcctcag                                                              367
```

<210> SEQ ID NO 290
<211> LENGTH: 367
<212> TYPE: DNA
<213> ORGANISM: Homo sapiens

<400> SEQUENCE: 290

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatcagagtt cgtcctatta tggtatggac gtctggggcc aagggaccac ggtcaccgtc    360
tcctcag                                                              367
```

<210> SEQ ID NO 291
<211> LENGTH: 367
<212> TYPE: DNA
<213> ORGANISM: Homo sapiens

<400> SEQUENCE: 291

```
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
```

```
gtacaaatga acagcctgag agccgaggac acggctgtgt attactgtgc gagagagggg      300
tatagaagtt cgtcctatta tggtatggac gtctggggcc aagggaccac ggtcaccgtc      360
tcctcag                                                                367
```

<210> SEQ ID NO 292
<211> LENGTH: 367
<212> TYPE: DNA
<213> ORGANISM: Homo sapiens

<400> SEQUENCE: 292

```
gaggtgcagc tggtggagtc tgggggaggc tttgtccagc ctgggggtc cctgagactc       60 tcctgtgcag tctctggatt caccttaat agctattgga tgagctgggt ccgccaggct       120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tataccagtt cgtcctatta tggtatggac gtctggggcc aagggaccac ggtcaccgtc    360
tcctcag                                                                367
```

<210> SEQ ID NO 293
<211> LENGTH: 367
<212> TYPE: DNA
<213> ORGANISM: Homo sapiens

<400> SEQUENCE: 293

```
gaggtgcagc tggtggagtc tgggggaggc tttgtccagc ctgggggtc cctgagactc       60 tcctgtgcag tctctggatt caccttaat agctattgga tgagctgggt ccgccaggct       120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tatgtgagtt cgtcctatta tggtatggac gtctggggcc aagggaccac ggtcaccgtc    360
tcctcag                                                                367
```

<210> SEQ ID NO 294
<211> LENGTH: 367
<212> TYPE: DNA
<213> ORGANISM: Homo sapiens

<400> SEQUENCE: 294

```
gaggtgcagc tggtggagtc tgggggaggc tttgtccagc ctgggggtc cctgagactc       60 tcctgtgcag tctctggatt caccttaat agctattgga tgagctgggt ccgccaggct       120
ccagggaagg ggctggagtg ggtggccaac ataaaccaag atggaagtga gaaattctat     180
gtggcctctg tgaagggccg attcaccatg tccagagaca acgccaagaa atcagtgtat     240
gtacaaatga acagcctgag agccgaggac acggctgtgt attactgtgc gagagagggg     300
tattggagtt cgtcctatta tggtatggac gtctggggcc aagggaccac ggtcaccgtc    360
tcctcag                                                                367
```

<210> SEQ ID NO 295
<211> LENGTH: 367
<212> TYPE: DNA
<213> ORGANISM: Homo sapiens

<400> SEQUENCE: 295

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tattacagtt cgtcctatta tggtatggac gtctggggcc aagggaccac ggtcaccgtc     360
tcctcag                                                              367
```

<210> SEQ ID NO 296
<211> LENGTH: 367
<212> TYPE: DNA
<213> ORGANISM: Homo sapiens

<400> SEQUENCE: 296

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagttgct cgtcctatta tggtatggac gtctggggcc aagggaccac ggtcaccgtc     360
tcctcag                                                              367
```

<210> SEQ ID NO 297
<211> LENGTH: 367
<212> TYPE: DNA
<213> ORGANISM: Homo sapiens

<400> SEQUENCE: 297

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtgact cgtcctatta tggtatggac gtctggggcc aagggaccac ggtcaccgtc     360
tcctcag                                                              367
```

<210> SEQ ID NO 298
<211> LENGTH: 367
<212> TYPE: DNA
<213> ORGANISM: Homo sapiens

<400> SEQUENCE: 298

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtgagt cgtcctatta tggtatggac gtctggggcc aagggaccac ggtcaccgtc     360
```

```
tcctcag                                                              367

<210> SEQ ID NO 299
<211> LENGTH: 367
<212> TYPE: DNA
<213> ORGANISM: Homo sapiens

<400> SEQUENCE: 299
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtttct cgtcctatta tggtatggac gtctggggcc aagggaccac ggtcaccgtc     360
tcctcag                                                              367

<210> SEQ ID NO 300
<211> LENGTH: 367
<212> TYPE: DNA
<213> ORGANISM: Homo sapiens

<400> SEQUENCE: 300
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtggct cgtcctatta tggtatggac gtctggggcc aagggaccac ggtcaccgtc     360
tcctcag                                                              367

<210> SEQ ID NO 301
<211> LENGTH: 367
<212> TYPE: DNA
<213> ORGANISM: Homo sapiens

<400> SEQUENCE: 301
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtcact cgtcctatta tggtatggac gtctggggcc aagggaccac ggtcaccgtc     360
tcctcag                                                              367

<210> SEQ ID NO 302
<211> LENGTH: 367
<212> TYPE: DNA
<213> ORGANISM: Homo sapiens

<400> SEQUENCE: 302
gaggtgcagc tggtggagtc tgggggaggc tttgtccagc ctggggggtc cctgagactc      60
tcctgtgcag tctctggatt cacctttaat agctattgga tgagctgggt ccgccaggct     120
```

```
ccagggaagg ggctggagtg ggtggccaac ataaaccaag atggaagtga gaaattctat      180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtatct cgtcctatta tggtatggac gtctggggcc aagggaccac ggtcaccgtc     360
tcctcag                                                                367
```

<210> SEQ ID NO 303
<211> LENGTH: 367
<212> TYPE: DNA
<213> ORGANISM: Homo sapiens

<400> SEQUENCE: 303

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtaagt cgtcctatta tggtatggac gtctggggcc aagggaccac ggtcaccgtc     360
tcctcag                                                                367
```

<210> SEQ ID NO 304
<211> LENGTH: 367
<212> TYPE: DNA
<213> ORGANISM: Homo sapiens

<400> SEQUENCE: 304

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtctgt cgtcctatta tggtatggac gtctggggcc aagggaccac ggtcaccgtc     360
tcctcag                                                                367
```

<210> SEQ ID NO 305
<211> LENGTH: 367
<212> TYPE: DNA
<213> ORGANISM: Homo sapiens

<400> SEQUENCE: 305

```
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg ggctggagtg ggtggccaac ataaaccaag atggaagtga gaaattctat     180
gtggcctctg tgaagggccg attcaccatg tccagagaca cgccaagaa atcagtgtat      240 gtacaaatga acagcctgag agccgaggac acggctgtgt attactgtgc gagagagggg     300
tatagtatgt cgtcctatta tggtatggac gtctggggcc aagggaccac ggtcaccgtc     360
tcctcag                                                                367
```

<210> SEQ ID NO 306

```
<211> LENGTH: 367
<212> TYPE: DNA
<213> ORGANISM: Homo sapiens

<400> SEQUENCE: 306
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtaact cgtcctatta tggtatggac gtctggggcc aagggaccac ggtcaccgtc    360
tcctcag                                                              367

<210> SEQ ID NO 307
<211> LENGTH: 367
<212> TYPE: DNA
<213> ORGANISM: Homo sapiens

<400> SEQUENCE: 307
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtccct cgtcctatta tggtatggac gtctggggcc aagggaccac ggtcaccgtc    360
tcctcag                                                              367

<210> SEQ ID NO 308
<211> LENGTH: 367
<212> TYPE: DNA
<213> ORGANISM: Homo sapiens

<400> SEQUENCE: 308
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtcagt cgtcctatta tggtatggac gtctggggcc aagggaccac ggtcaccgtc    360
tcctcag                                                              367

<210> SEQ ID NO 309
<211> LENGTH: 367
<212> TYPE: DNA
<213> ORGANISM: Homo sapiens

<400> SEQUENCE: 309
gaggtgcagc tggtggagtc tgggggaggc tttgtccagc ctgggggtc cctgagactc      60
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
```

| | |
|---|---|
| gtacaaatga acagcctgag agccgaggac acggctgtgt attactgtgc gagagagggg | 300 |
| tatagtagat cgtcctatta tggtatggac gtctggggcc aagggaccac ggtcaccgtc | 360 |
| tcctcag | 367 |

<210> SEQ ID NO 310
<211> LENGTH: 367
<212> TYPE: DNA
<213> ORGANISM: Homo sapiens

<400> SEQUENCE: 310

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtacct cgtcctatta tggtatggac gtctggggcc aagggaccac ggtcaccgtc | 360 |
| tcctcag | 367 |

<210> SEQ ID NO 311
<211> LENGTH: 367
<212> TYPE: DNA
<213> ORGANISM: Homo sapiens

<400> SEQUENCE: 311

| | |
|---|---|
| gaggtgcagc tggtggagtc tgggggaggc tttgtccagc ctggggggtc cctgagactc | 60 |
| tcctgtgcag tctctggatt cacctttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagtgtgt cgtcctatta tggtatggac gtctggggcc aagggaccac ggtcaccgtc | 360 |
| tcctcag | 367 |

<210> SEQ ID NO 312
<211> LENGTH: 367
<212> TYPE: DNA
<213> ORGANISM: Homo sapiens

<400> SEQUENCE: 312

| | |
|---|---|
| gaggtgcagc tggtggagtc tgggggaggc tttgtccagc ctggggggtc cctgagactc | 60 |
| tcctgtgcag tctctggatt caccttttaat agctattgga tgagctgggt ccgccaggct | 120 |
| ccagggaagg ggctggagtg ggtggccaac ataaaccaag atggaagtga gaaattctat | 180 |
| gtggcctctg tgaagggccg attcaccatg tccagagaca acgccaagaa atcagtgtat | 240 |
| gtacaaatga acagcctgag agccgaggac acggctgtgt attactgtgc gagagagggg | 300 |
| tatagttggt cgtcctatta tggtatggac gtctggggcc aagggaccac ggtcaccgtc | 360 |
| tcctcag | 367 |

<210> SEQ ID NO 313
<211> LENGTH: 367
<212> TYPE: DNA
<213> ORGANISM: Homo sapiens

<400> SEQUENCE: 313

```
gaggtgcagc tggtggagtc tgggggaggc tttgtccagc ctggggggtc cctgagactc    60
tcctgtgcag tctctggatt cacctttaat agctattgga tgagctgggt ccgccaggct   120
ccagggaagg ggctggagtg ggtggccaac ataaaccaag atggaagtga gaaattctat   180
gtggcctctg tgaagggccg attcaccatg tccagagaca cgccaagaa atcagtgtat    240
gtacaaatga acagcctgag agccgaggac acggctgtgt attactgtgc gagagagggg   300
tatagttact cgtcctatta tggtatggac gtctggggcc aagggaccac ggtcaccgtc   360
tcctcag                                                             367
```

<210> SEQ ID NO 314
<211> LENGTH: 122
<212> TYPE: PRT
<213> ORGANISM: Homo sapiens

<400> SEQUENCE: 314

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ala Ser Ser Tyr Tyr Gly Met Asp Val Trp
            100                 105                 110

Gly Gln Gly Thr Thr Val Thr Val Ser Ser
        115                 120
```

<210> SEQ ID NO 315
<211> LENGTH: 122
<212> TYPE: PRT
<213> ORGANISM: Homo sapiens

<400> SEQUENCE: 315

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ala Ser Ser Tyr Tyr Gly Met Asp Val Trp
            100                 105                 110

Gly Gln Gly Thr Thr Val Thr Val Ser Ser
        115                 120
```

<210> SEQ ID NO 316
<211> LENGTH: 122
<212> TYPE: PRT
<213> ORGANISM: Homo sapiens

<400> SEQUENCE: 316

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ala Ser Tyr Tyr Gly Met Asp Val Trp
            100                 105                 110

Gly Gln Gly Thr Thr Val Thr Val Ser Ser
        115                 120

<210> SEQ ID NO 317
<211> LENGTH: 122
<212> TYPE: PRT
<213> ORGANISM: Homo sapiens

<400> SEQUENCE: 317

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Ala Tyr Tyr Gly Met Asp Val Trp
            100                 105                 110

Gly Gln Gly Thr Thr Val Thr Val Ser Ser
        115                 120

<210> SEQ ID NO 318
<211> LENGTH: 122
<212> TYPE: PRT
<213> ORGANISM: Homo sapiens

<400> SEQUENCE: 318

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

```
Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Cys Ser Tyr Tyr Gly Met Asp Val Trp
                100                 105                 110

Gly Gln Gly Thr Thr Val Thr Val Ser Ser
            115                 120
```

<210> SEQ ID NO 319
<211> LENGTH: 122
<212> TYPE: PRT
<213> ORGANISM: Homo sapiens

<400> SEQUENCE: 319

```
Glu Val Gln Leu Val Glu Ser Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Asp Ser Tyr Tyr Gly Met Asp Val Trp
                100                 105                 110

Gly Gln Gly Thr Thr Val Thr Val Ser Ser
            115                 120
```

<210> SEQ ID NO 320
<211> LENGTH: 122
<212> TYPE: PRT
<213> ORGANISM: Homo sapiens

<400> SEQUENCE: 320

```
Glu Val Gln Leu Val Glu Ser Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Glu Ser Tyr Tyr Gly Met Asp Val Trp
                100                 105                 110
```

```
Gly Gln Gly Thr Thr Val Thr Val Ser Ser
        115                 120

<210> SEQ ID NO 321
<211> LENGTH: 122
<212> TYPE: PRT
<213> ORGANISM: Homo sapiens

<400> SEQUENCE: 321

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Phe Ser Tyr Tyr Gly Met Asp Val Trp
            100                 105                 110

Gly Gln Gly Thr Thr Val Thr Val Ser Ser
        115                 120

<210> SEQ ID NO 322
<211> LENGTH: 122
<212> TYPE: PRT
<213> ORGANISM: Homo sapiens

<400> SEQUENCE: 322

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Gly Ser Tyr Tyr Gly Met Asp Val Trp
            100                 105                 110

Gly Gln Gly Thr Thr Val Thr Val Ser Ser
        115                 120

<210> SEQ ID NO 323
<211> LENGTH: 122
<212> TYPE: PRT
<213> ORGANISM: Homo sapiens

<400> SEQUENCE: 323

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
```

```
            20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
             85                  90                  95

Ala Arg Glu Gly Tyr Ser Ser His Ser Tyr Tyr Gly Met Asp Val Trp
            100                 105                 110

Gly Gln Gly Thr Thr Val Thr Val Ser Ser
            115                 120

<210> SEQ ID NO 324
<211> LENGTH: 122
<212> TYPE: PRT
<213> ORGANISM: Homo sapiens

<400> SEQUENCE: 324

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
             85                  90                  95

Ala Arg Glu Gly Tyr Ser Ser Ile Ser Tyr Tyr Gly Met Asp Val Trp
            100                 105                 110

Gly Gln Gly Thr Thr Val Thr Val Ser Ser
            115                 120

<210> SEQ ID NO 325
<211> LENGTH: 122
<212> TYPE: PRT
<213> ORGANISM: Homo sapiens

<400> SEQUENCE: 325

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
             20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
             85                  90                  95

Ala Arg Glu Gly Tyr Ser Ser Lys Ser Tyr Tyr Gly Met Asp Val Trp
```

```
                    100                 105                 110

Gly Gln Gly Thr Thr Val Thr Val Ser Ser
            115                 120

<210> SEQ ID NO 326
<211> LENGTH: 122
<212> TYPE: PRT
<213> ORGANISM: Homo sapiens

<400> SEQUENCE: 326

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Leu Ser Tyr Tyr Gly Met Asp Val Trp
            100                 105                 110

Gly Gln Gly Thr Thr Val Thr Val Ser Ser
            115                 120

<210> SEQ ID NO 327
<211> LENGTH: 122
<212> TYPE: PRT
<213> ORGANISM: Homo sapiens

<400> SEQUENCE: 327

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Met Ser Tyr Tyr Gly Met Asp Val Trp
            100                 105                 110

Gly Gln Gly Thr Thr Val Thr Val Ser Ser
            115                 120

<210> SEQ ID NO 328
<211> LENGTH: 122
<212> TYPE: PRT
<213> ORGANISM: Homo sapiens

<400> SEQUENCE: 328

Glu Val Gln Leu Val Glu Ser Gly Gly Gly Phe Val Gln Pro Gly Gly
1               5                   10                  15
```

```
Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Asn Ser Tyr Tyr Gly Met Asp Val Trp
            100                 105                 110

Gly Gln Gly Thr Thr Val Thr Val Ser Ser
        115                 120

<210> SEQ ID NO 329
<211> LENGTH: 122
<212> TYPE: PRT
<213> ORGANISM: Homo sapiens

<400> SEQUENCE: 329

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Pro Ser Tyr Tyr Gly Met Asp Val Trp
            100                 105                 110

Gly Gln Gly Thr Thr Val Thr Val Ser Ser
        115                 120

<210> SEQ ID NO 330
<211> LENGTH: 145
<212> TYPE: PRT
<213> ORGANISM: Homo sapiens

<400> SEQUENCE: 330

Tyr Asn Ser Gly Lys Leu Glu Glu Phe Val Gln Gly Asn Leu Glu Arg
1               5                   10                  15

Glu Cys Met Glu Glu Lys Cys Ser Phe Glu Glu Ala Arg Glu Val Phe
            20                  25                  30

Glu Asn Thr Glu Arg Thr Thr Glu Phe Trp Lys Gln Tyr Val Asp Gly
        35                  40                  45

Asp Gln Cys Glu Ser Asn Pro Cys Leu Asn Gly Gly Ser Cys Lys Asp
    50                  55                  60

Asp Ile Asn Ser Tyr Glu Cys Trp Cys Pro Phe Gly Phe Glu Gly Lys
65                  70                  75                  80

Asn Cys Glu Leu Asp Val Thr Cys Asn Ile Lys Asn Gly Arg Cys Glu
                85                  90                  95
```

```
Gln Phe Cys Lys Asn Ser Ala Asp Asn Lys Val Val Cys Ser Cys Thr
                100                 105                 110

Glu Gly Tyr Arg Leu Ala Glu Asn Gln Lys Ser Cys Glu Pro Ala Val
            115                 120                 125

Pro Phe Pro Cys Gly Arg Val Ser Val Ser Gln Thr Ser Lys Leu Thr
130                 135                 140

Arg
145

<210> SEQ ID NO 331
<211> LENGTH: 270
<212> TYPE: PRT
<213> ORGANISM: Homo sapiens

<400> SEQUENCE: 331

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg Val Val Gly Gly Glu Asp Ala Lys Pro Gly Gln Phe Pro
        35                  40                  45

Trp Gln Val Val Leu Asn Gly Lys Val Asp Ala Phe Cys Gly Gly Ser
    50                  55                  60

Ile Val Asn Glu Lys Trp Ile Val Thr Ala Ala His Cys Val Glu Thr
65                  70                  75                  80

Gly Val Lys Ile Thr Val Val Ala Gly Glu His Asn Ile Glu Glu Thr
                85                  90                  95

Glu His Thr Glu Gln Lys Arg Asn Val Ile Arg Ile Ile Pro His His
            100                 105                 110

Asn Tyr Asn Ala Ala Ile Asn Lys Tyr Asn His Asp Ile Ala Leu Leu
        115                 120                 125

Glu Leu Asp Glu Pro Leu Val Leu Asn Ser Tyr Val Thr Pro Ile Cys
    130                 135                 140

Ile Ala Asp Lys Glu Tyr Thr Asn Ile Phe Leu Lys Phe Gly Ser Gly
145                 150                 155                 160

Tyr Val Ser Gly Trp Gly Arg Val Phe His Lys Gly Arg Ser Ala Leu
                165                 170                 175

Val Leu Gln Tyr Leu Arg Val Pro Leu Val Asp Arg Ala Thr Cys Leu
            180                 185                 190

Arg Ser Thr Lys Phe Thr Ile Tyr Asn Asn Met Phe Cys Ala Gly Phe
        195                 200                 205

His Glu Gly Gly Arg Asp Ser Cys Gln Gly Asp Ser Gly Gly Pro His
    210                 215                 220

Val Thr Glu Val Glu Gly Thr Ser Phe Leu Thr Gly Ile Ile Ser Trp
225                 230                 235                 240

Gly Glu Glu Cys Ala Met Lys Gly Lys Tyr Gly Ile Tyr Thr Lys Val
                245                 250                 255

Ser Arg Tyr Val Asn Trp Ile Lys Glu Lys Thr Lys Leu Thr
            260                 265                 270

<210> SEQ ID NO 332
<211> LENGTH: 235
<212> TYPE: PRT
<213> ORGANISM: Homo sapiens

<400> SEQUENCE: 332
```

```
Val Val Gly Gly Glu Asp Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Thr Gly Val Lys
                35                  40                  45

Ile Thr Val Val Ala Gly Glu His Asn Ile Glu Glu Thr Glu His Thr
    50                  55                  60

Glu Gln Lys Arg Asn Val Ile Arg Ile Ile Pro His His Asn Tyr Asn
65              70                  75                  80

Ala Ala Ile Asn Lys Tyr Asn His Asp Ile Ala Leu Leu Glu Leu Asp
                85                  90                  95

Glu Pro Leu Val Leu Asn Ser Tyr Val Thr Pro Ile Cys Ile Ala Asp
            100                 105                 110

Lys Glu Tyr Thr Asn Ile Phe Leu Lys Phe Gly Ser Gly Tyr Val Ser
                115                 120                 125

Gly Trp Gly Arg Val Phe His Lys Gly Arg Ser Ala Leu Val Leu Gln
130                 135                 140

Tyr Leu Arg Val Pro Leu Val Asp Arg Ala Thr Cys Leu Arg Ser Thr
145                 150                 155                 160

Lys Phe Thr Ile Tyr Asn Asn Met Phe Cys Ala Gly Phe His Glu Gly
                165                 170                 175

Gly Arg Asp Ser Cys Gln Gly Asp Ser Gly Gly Pro His Val Thr Glu
                180                 185                 190

Val Glu Gly Thr Ser Phe Leu Thr Gly Ile Ile Ser Trp Gly Glu Glu
                195                 200                 205

Cys Ala Met Lys Gly Lys Tyr Gly Ile Tyr Thr Lys Val Ser Arg Tyr
210                 215                 220

Val Asn Trp Ile Lys Glu Lys Thr Lys Leu Thr
225                 230                 235

<210> SEQ ID NO 333
<211> LENGTH: 35
<212> TYPE: PRT
<213> ORGANISM: Homo sapiens

<400> SEQUENCE: 333

Ala Glu Thr Val Phe Pro Asp Val Asp Tyr Val Asn Ser Thr Glu Ala
1               5                   10                  15

Glu Thr Ile Leu Asp Asn Ile Thr Gln Ser Thr Gln Ser Phe Asn Asp
            20                  25                  30

Phe Thr Arg
        35

<210> SEQ ID NO 334
<211> LENGTH: 461
<212> TYPE: PRT
<213> ORGANISM: Homo sapiens

<400> SEQUENCE: 334

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
                35                  40                  45
```

```
Ser Gly Lys Leu Glu Glu Phe Val Gln Gly Asn Leu Glu Arg Glu Cys
 50                  55                  60

Met Glu Glu Lys Cys Ser Phe Glu Glu Ala Arg Glu Val Phe Glu Asn
 65                  70                  75                  80

Thr Glu Arg Thr Thr Glu Phe Trp Lys Gln Tyr Val Asp Gly Asp Gln
                 85                  90                  95

Cys Glu Ser Asn Pro Cys Leu Asn Gly Gly Ser Cys Lys Asp Asp Ile
                100                 105                 110

Asn Ser Tyr Glu Cys Trp Cys Pro Phe Gly Phe Glu Gly Lys Asn Cys
            115                 120                 125

Glu Leu Asp Val Thr Cys Asn Ile Lys Asn Gly Arg Cys Glu Gln Phe
        130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
                180                 185                 190

Glu Thr Val Phe Pro Asp Val Asp Tyr Val Asn Ser Thr Glu Ala Glu
            195                 200                 205

Thr Ile Leu Asp Asn Ile Thr Gln Ser Thr Gln Ser Phe Asn Asp Phe
210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Ile Pro His His Asn
        290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
                340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
        435                 440                 445

Arg Tyr Val Asn Trp Ile Lys Glu Lys Thr Lys Leu Thr
450                 455                 460
```

<210> SEQ ID NO 335
<211> LENGTH: 488
<212> TYPE: PRT
<213> ORGANISM: Homo sapiens

<400> SEQUENCE: 335

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160

Gly Lys Ala Cys Ile Pro Thr Gly Pro Tyr Pro Cys Gly Lys Gln Thr
                165                 170                 175

Leu Glu Arg Arg Lys Arg Ser Val Ala Gln Ala Thr Ser Ser Ser Gly
            180                 185                 190

Glu Ala Pro Asp Ser Ile Thr Trp Lys Pro Tyr Asp Ala Ala Asp Leu
        195                 200                 205

Asp Pro Thr Glu Asn Pro Phe Asp Leu Leu Asp Phe Asn Gln Thr Gln
    210                 215                 220

Pro Glu Arg Gly Asp Asn Asn Leu Thr Arg Ile Val Gly Gly Gln Glu
225                 230                 235                 240

Cys Lys Asp Gly Glu Cys Pro Trp Gln Ala Leu Leu Ile Asn Glu Glu
                245                 250                 255

Asn Glu Gly Phe Cys Gly Gly Thr Ile Leu Ser Glu Phe Tyr Ile Leu
            260                 265                 270

Thr Ala Ala His Cys Leu Tyr Gln Ala Lys Arg Phe Lys Val Arg Val
        275                 280                 285

Gly Asp Arg Asn Thr Glu Gln Glu Glu Gly Gly Glu Ala Val His Glu
    290                 295                 300

Val Glu Val Val Ile Lys His Asn Arg Phe Thr Lys Glu Thr Tyr Asp
305                 310                 315                 320

Phe Asp Ile Ala Val Leu Arg Leu Lys Thr Pro Ile Thr Phe Arg Met
                325                 330                 335

Asn Val Ala Pro Ala Cys Leu Pro Glu Arg Asp Trp Ala Glu Ser Thr
            340                 345                 350

Leu Met Thr Gln Lys Thr Gly Ile Val Ser Gly Phe Gly Arg Thr His
        355                 360                 365

Glu Lys Gly Arg Gln Ser Thr Arg Leu Lys Met Leu Glu Val Pro Tyr
    370                 375                 380
```

-continued

```
Val Asp Arg Asn Ser Cys Lys Leu Ser Ser Phe Ile Ile Thr Gln
385                 390                 395                 400

Asn Met Phe Cys Ala Gly Tyr Asp Thr Lys Gln Glu Asp Ala Cys Gln
            405                 410                 415

Gly Asp Ser Gly Gly Pro His Val Thr Arg Phe Lys Asp Thr Tyr Phe
            420                 425                 430

Val Thr Gly Ile Val Ser Trp Gly Glu Gly Cys Ala Arg Lys Gly Lys
            435                 440                 445

Tyr Gly Ile Tyr Thr Lys Val Thr Ala Phe Leu Lys Trp Ile Asp Arg
            450                 455                 460

Ser Met Lys Thr Arg Gly Leu Pro Lys Ala Lys Ser His Ala Pro Glu
465                 470                 475                 480

Val Ile Thr Ser Ser Pro Leu Lys
                485

<210> SEQ ID NO 336
<211> LENGTH: 31
<212> TYPE: PRT
<213> ORGANISM: Homo sapiens

<400> SEQUENCE: 336

Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala
            20                  25                  30

<210> SEQ ID NO 337
<211> LENGTH: 9
<212> TYPE: PRT
<213> ORGANISM: Homo sapiens

<400> SEQUENCE: 337

Asn Asn Ile Leu Ala Arg Val Thr Arg
1               5

<210> SEQ ID NO 338
<211> LENGTH: 139
<212> TYPE: PRT
<213> ORGANISM: Homo sapiens

<400> SEQUENCE: 338

Ala Asn Ser Phe Leu Glu Glu Met Lys Lys Gly His Leu Glu Arg Glu
1               5                   10                  15

Cys Met Glu Glu Thr Cys Ser Tyr Glu Glu Ala Arg Glu Val Phe Glu
            20                  25                  30

Asp Ser Asp Lys Thr Asn Glu Phe Trp Asn Lys Tyr Lys Asp Gly Asp
            35                  40                  45

Gln Cys Glu Thr Ser Pro Cys Gln Asn Gln Gly Lys Cys Lys Asp Gly
        50                  55                  60

Leu Gly Glu Tyr Thr Cys Thr Cys Leu Glu Gly Phe Glu Gly Lys Asn
65                  70                  75                  80

Cys Glu Leu Phe Thr Arg Lys Leu Cys Ser Leu Asp Asn Gly Asp Cys
            85                  90                  95

Asp Gln Phe Cys His Glu Glu Gln Asn Ser Val Val Cys Ser Cys Ala
            100                 105                 110

Arg Gly Tyr Thr Leu Ala Asp Asn Gly Lys Ala Cys Ile Pro Thr Gly
            115                 120                 125
```

Pro Tyr Pro Cys Gly Lys Gln Thr Leu Glu Arg
    130                 135

<210> SEQ ID NO 339
<211> LENGTH: 254
<212> TYPE: PRT
<213> ORGANISM: Homo sapiens

<400> SEQUENCE: 339

Ile Val Gly Gly Gln Glu Cys Lys Asp Gly Glu Cys Pro Trp Gln Ala
1               5                   10                  15

Leu Leu Ile Asn Glu Glu Asn Glu Gly Phe Cys Gly Gly Thr Ile Leu
            20                  25                  30

Ser Glu Phe Tyr Ile Leu Thr Ala Ala His Cys Leu Tyr Gln Ala Lys
        35                  40                  45

Arg Phe Lys Val Arg Val Gly Asp Arg Asn Thr Glu Gln Glu Glu Gly
    50                  55                  60

Gly Glu Ala Val His Glu Val Glu Val Val Ile Lys His Asn Arg Phe
65                  70                  75                  80

Thr Lys Glu Thr Tyr Asp Phe Asp Ile Ala Val Leu Arg Leu Lys Thr
                85                  90                  95

Pro Ile Thr Phe Arg Met Asn Val Ala Pro Ala Cys Leu Pro Glu Arg
            100                 105                 110

Asp Trp Ala Glu Ser Thr Leu Met Thr Gln Lys Thr Gly Ile Val Ser
        115                 120                 125

Gly Phe Gly Arg Thr His Glu Lys Gly Arg Gln Ser Thr Arg Leu Lys
    130                 135                 140

Met Leu Glu Val Pro Tyr Val Asp Arg Asn Ser Cys Lys Leu Ser Ser
145                 150                 155                 160

Ser Phe Ile Ile Thr Gln Asn Met Phe Cys Ala Gly Tyr Asp Thr Lys
                165                 170                 175

Gln Glu Asp Ala Cys Gln Gly Asp Ser Gly Gly Pro His Val Thr Arg
            180                 185                 190

Phe Lys Asp Thr Tyr Phe Val Thr Gly Ile Val Ser Trp Gly Glu Gly
        195                 200                 205

Cys Ala Arg Lys Gly Lys Tyr Gly Ile Tyr Thr Lys Val Thr Ala Phe
    210                 215                 220

Leu Lys Trp Ile Asp Arg Ser Met Lys Thr Arg Gly Leu Pro Lys Ala
225                 230                 235                 240

Lys Ser His Ala Pro Glu Val Ile Thr Ser Ser Pro Leu Lys
                245                 250

<210> SEQ ID NO 340
<211> LENGTH: 122
<212> TYPE: PRT
<213> ORGANISM: Homo sapiens

<400> SEQUENCE: 340

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

```
Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Gln Ser Tyr Tyr Gly Met Asp Val Trp
            100                 105                 110

Gly Gln Gly Thr Thr Val Thr Val Ser Ser
            115                 120
```

<210> SEQ ID NO 341
<211> LENGTH: 122
<212> TYPE: PRT
<213> ORGANISM: Homo sapiens

<400> SEQUENCE: 341

```
Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Arg Ser Tyr Tyr Gly Met Asp Val Trp
            100                 105                 110

Gly Gln Gly Thr Thr Val Thr Val Ser Ser
            115                 120
```

<210> SEQ ID NO 342
<211> LENGTH: 122
<212> TYPE: PRT
<213> ORGANISM: Homo sapiens

<400> SEQUENCE: 342

```
Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Thr Ser Tyr Tyr Gly Met Asp Val Trp
            100                 105                 110

Gly Gln Gly Thr Thr Val Thr Val Ser Ser
            115                 120
```

<210> SEQ ID NO 343
<211> LENGTH: 122

```
<212> TYPE: PRT
<213> ORGANISM: Homo sapiens

<400> SEQUENCE: 343

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Val Ser Tyr Tyr Gly Met Asp Val Trp
            100                 105                 110

Gly Gln Gly Thr Thr Val Thr Val Ser Ser
        115                 120

<210> SEQ ID NO 344
<211> LENGTH: 122
<212> TYPE: PRT
<213> ORGANISM: Homo sapiens

<400> SEQUENCE: 344

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Trp Ser Tyr Tyr Gly Met Asp Val Trp
            100                 105                 110

Gly Gln Gly Thr Thr Val Thr Val Ser Ser
        115                 120

<210> SEQ ID NO 345
<211> LENGTH: 122
<212> TYPE: PRT
<213> ORGANISM: Homo sapiens

<400> SEQUENCE: 345

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
```

```
                    50                  55                  60
Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                     85                  90                  95

Ala Arg Glu Gly Tyr Ser Ser Tyr Ser Tyr Tyr Gly Met Asp Val Trp
                100                 105                 110

Gly Gln Gly Thr Thr Val Thr Val Ser Ser
            115                 120

<210> SEQ ID NO 346
<211> LENGTH: 122
<212> TYPE: PRT
<213> ORGANISM: Homo sapiens

<400> SEQUENCE: 346

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                     85                  90                  95

Ala Arg Glu Gly Tyr Ser Ser Ser Cys Tyr Tyr Gly Met Asp Val Trp
                100                 105                 110

Gly Gln Gly Thr Thr Val Thr Val Ser Ser
            115                 120

<210> SEQ ID NO 347
<211> LENGTH: 122
<212> TYPE: PRT
<213> ORGANISM: Homo sapiens

<400> SEQUENCE: 347

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                     85                  90                  95

Ala Arg Glu Gly Tyr Ser Ser Ser Asp Tyr Tyr Gly Met Asp Val Trp
                100                 105                 110

Gly Gln Gly Thr Thr Val Thr Val Ser Ser
            115                 120
```

```
<210> SEQ ID NO 348
<211> LENGTH: 122
<212> TYPE: PRT
<213> ORGANISM: Homo sapiens

<400> SEQUENCE: 348

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Tyr Tyr Gly Met Asp Val Trp
            100                 105                 110

Gly Gln Gly Thr Thr Val Thr Val Ser Ser
        115                 120

<210> SEQ ID NO 349
<211> LENGTH: 122
<212> TYPE: PRT
<213> ORGANISM: Homo sapiens

<400> SEQUENCE: 349

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Phe Tyr Tyr Gly Met Asp Val Trp
            100                 105                 110

Gly Gln Gly Thr Thr Val Thr Val Ser Ser
        115                 120

<210> SEQ ID NO 350
<211> LENGTH: 122
<212> TYPE: PRT
<213> ORGANISM: Homo sapiens

<400> SEQUENCE: 350

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

-continued

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Gly Tyr Tyr Gly Met Asp Val Trp
                100                 105                 110

Gly Gln Gly Thr Thr Val Thr Val Ser Ser
                115                 120

<210> SEQ ID NO 351
<211> LENGTH: 122
<212> TYPE: PRT
<213> ORGANISM: Homo sapiens

<400> SEQUENCE: 351

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser His Tyr Tyr Gly Met Asp Val Trp
                100                 105                 110

Gly Gln Gly Thr Thr Val Thr Val Ser Ser
                115                 120

<210> SEQ ID NO 352
<211> LENGTH: 122
<212> TYPE: PRT
<213> ORGANISM: Homo sapiens

<400> SEQUENCE: 352

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Ile Tyr Tyr Gly Met Asp Val Trp
                100                 105                 110

Gly Gln Gly Thr Thr Val Thr Val Ser Ser
                115                 120

<210> SEQ ID NO 353
<211> LENGTH: 122
<212> TYPE: PRT
<213> ORGANISM: Homo sapiens

<400> SEQUENCE: 353

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Lys Tyr Tyr Gly Met Asp Val Trp
            100                 105                 110

Gly Gln Gly Thr Thr Val Thr Val Ser Ser
        115                 120

<210> SEQ ID NO 354
<211> LENGTH: 122
<212> TYPE: PRT
<213> ORGANISM: Homo sapiens

<400> SEQUENCE: 354

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Leu Tyr Tyr Gly Met Asp Val Trp
            100                 105                 110

Gly Gln Gly Thr Thr Val Thr Val Ser Ser
        115                 120

<210> SEQ ID NO 355
<211> LENGTH: 122
<212> TYPE: PRT
<213> ORGANISM: Homo sapiens

<400> SEQUENCE: 355

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

```
Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Met Tyr Tyr Gly Met Asp Val Trp
                100                 105                 110

Gly Gln Gly Thr Thr Val Thr Val Ser Ser
            115                 120
```

<210> SEQ ID NO 356
<211> LENGTH: 122
<212> TYPE: PRT
<213> ORGANISM: Homo sapiens

<400> SEQUENCE: 356

```
Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Asn Tyr Tyr Gly Met Asp Val Trp
                100                 105                 110

Gly Gln Gly Thr Thr Val Thr Val Ser Ser
            115                 120
```

<210> SEQ ID NO 357
<211> LENGTH: 122
<212> TYPE: PRT
<213> ORGANISM: Homo sapiens

<400> SEQUENCE: 357

```
Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ser Pro Tyr Tyr Gly Met Asp Val Trp
                100                 105                 110
```

Gly Gln Gly Thr Thr Val Thr Val Ser Ser
            115                 120

<210> SEQ ID NO 358
<211> LENGTH: 122
<212> TYPE: PRT
<213> ORGANISM: Homo sapiens

<400> SEQUENCE: 358

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
            85                  90                  95

Ala Arg Glu Gly Tyr Ser Ser Gln Tyr Tyr Gly Met Asp Val Trp
            100                 105                 110

Gly Gln Gly Thr Thr Val Thr Val Ser Ser
            115                 120

<210> SEQ ID NO 359
<211> LENGTH: 122
<212> TYPE: PRT
<213> ORGANISM: Homo sapiens

<400> SEQUENCE: 359

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
            50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
            85                  90                  95

Ala Arg Glu Gly Tyr Ser Ser Ser Arg Tyr Tyr Gly Met Asp Val Trp
            100                 105                 110

Gly Gln Gly Thr Thr Val Thr Val Ser Ser
            115                 120

<210> SEQ ID NO 360
<211> LENGTH: 122
<212> TYPE: PRT
<213> ORGANISM: Homo sapiens

<400> SEQUENCE: 360

Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr

```
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Thr Tyr Tyr Gly Met Asp Val Trp
                100                 105                 110

Gly Gln Gly Thr Thr Val Thr Val Ser Ser
                115                 120

<210> SEQ ID NO 361
<211> LENGTH: 122
<212> TYPE: PRT
<213> ORGANISM: Homo sapiens

<400> SEQUENCE: 361

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Val Tyr Tyr Gly Met Asp Val Trp
                100                 105                 110

Gly Gln Gly Thr Thr Val Thr Val Ser Ser
                115                 120

<210> SEQ ID NO 362
<211> LENGTH: 122
<212> TYPE: PRT
<213> ORGANISM: Homo sapiens

<400> SEQUENCE: 362

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ser Trp Tyr Tyr Gly Met Asp Val Trp
```

100                 105                 110
Gly Gln Gly Thr Thr Val Thr Val Ser Ser
        115                 120

<210> SEQ ID NO 363
<211> LENGTH: 122
<212> TYPE: PRT
<213> ORGANISM: Homo sapiens

<400> SEQUENCE: 363

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Tyr Tyr Tyr Gly Met Asp Val Trp
            100                 105                 110

Gly Gln Gly Thr Thr Val Thr Val Ser Ser
        115                 120

<210> SEQ ID NO 364
<211> LENGTH: 122
<212> TYPE: PRT
<213> ORGANISM: Homo sapiens

<400> SEQUENCE: 364

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Cys Ser Ser Tyr Tyr Gly Met Asp Val Trp
            100                 105                 110

Gly Gln Gly Thr Thr Val Thr Val Ser Ser
        115                 120

<210> SEQ ID NO 365
<211> LENGTH: 122
<212> TYPE: PRT
<213> ORGANISM: Homo sapiens

<400> SEQUENCE: 365

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Asp Ser Ser Tyr Tyr Gly Met Asp Val Trp
            100                 105                 110

Gly Gln Gly Thr Thr Val Thr Val Ser Ser
            115                 120

<210> SEQ ID NO 366
<211> LENGTH: 122
<212> TYPE: PRT
<213> ORGANISM: Homo sapiens

<400> SEQUENCE: 366

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Glu Ser Ser Tyr Tyr Gly Met Asp Val Trp
            100                 105                 110

Gly Gln Gly Thr Thr Val Thr Val Ser Ser
            115                 120

<210> SEQ ID NO 367
<211> LENGTH: 122
<212> TYPE: PRT
<213> ORGANISM: Homo sapiens

<400> SEQUENCE: 367

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Phe Ser Ser Tyr Tyr Gly Met Asp Val Trp
            100                 105                 110

Gly Gln Gly Thr Thr Val Thr Val Ser Ser
            115                 120

<210> SEQ ID NO 368
<211> LENGTH: 122
<212> TYPE: PRT
<213> ORGANISM: Homo sapiens

<400> SEQUENCE: 368

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Gly Ser Ser Tyr Tyr Gly Met Asp Val Trp
            100                 105                 110

Gly Gln Gly Thr Thr Val Thr Val Ser Ser
            115                 120

<210> SEQ ID NO 369
<211> LENGTH: 122
<212> TYPE: PRT
<213> ORGANISM: Homo sapiens

<400> SEQUENCE: 369

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr His Ser Ser Tyr Tyr Gly Met Asp Val Trp
            100                 105                 110

Gly Gln Gly Thr Thr Val Thr Val Ser Ser
            115                 120

<210> SEQ ID NO 370
<211> LENGTH: 122
<212> TYPE: PRT
<213> ORGANISM: Homo sapiens

<400> SEQUENCE: 370

```
Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ile Ser Ser Tyr Tyr Gly Met Asp Val Trp
            100                 105                 110

Gly Gln Gly Thr Thr Val Thr Val Ser Ser
            115                 120
```

<210> SEQ ID NO 371
<211> LENGTH: 122
<212> TYPE: PRT
<213> ORGANISM: Homo sapiens

<400> SEQUENCE: 371

```
Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Lys Ser Ser Tyr Tyr Gly Met Asp Val Trp
            100                 105                 110

Gly Gln Gly Thr Thr Val Thr Val Ser Ser
            115                 120
```

<210> SEQ ID NO 372
<211> LENGTH: 122
<212> TYPE: PRT
<213> ORGANISM: Homo sapiens

<400> SEQUENCE: 372

```
Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80
```

```
Val Gln Met Asn Ser Leu Arg Ala Glu Asp Thr Ala Val Tyr Tyr Cys
                85                  90                  95

Ala Arg Glu Gly Tyr Leu Ser Ser Ser Tyr Tyr Gly Met Asp Val Trp
            100                 105                 110

Gly Gln Gly Thr Thr Val Thr Val Ser Ser
            115                 120
```

<210> SEQ ID NO 373
<211> LENGTH: 122
<212> TYPE: PRT
<213> ORGANISM: Homo sapiens

<400> SEQUENCE: 373

```
Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Met Ser Ser Ser Tyr Tyr Gly Met Asp Val Trp
            100                 105                 110

Gly Gln Gly Thr Thr Val Thr Val Ser Ser
            115                 120
```

<210> SEQ ID NO 374
<211> LENGTH: 122
<212> TYPE: PRT
<213> ORGANISM: Homo sapiens

<400> SEQUENCE: 374

```
Glu Val Gln Leu Val Glu Ser Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Asn Ser Ser Tyr Tyr Gly Met Asp Val Trp
            100                 105                 110

Gly Gln Gly Thr Thr Val Thr Val Ser Ser
            115                 120
```

<210> SEQ ID NO 375
<211> LENGTH: 122
<212> TYPE: PRT
<213> ORGANISM: Homo sapiens -continued

<400> SEQUENCE: 375

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Pro Ser Ser Tyr Tyr Gly Met Asp Val Trp
            100                 105                 110

Gly Gln Gly Thr Thr Val Thr Val Ser Ser
        115                 120

<210> SEQ ID NO 376
<211> LENGTH: 122
<212> TYPE: PRT
<213> ORGANISM: Homo sapiens

<400> SEQUENCE: 376

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Gln Ser Ser Tyr Tyr Gly Met Asp Val Trp
            100                 105                 110

Gly Gln Gly Thr Thr Val Thr Val Ser Ser
        115                 120

<210> SEQ ID NO 377
<211> LENGTH: 122
<212> TYPE: PRT
<213> ORGANISM: Homo sapiens

<400> SEQUENCE: 377

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr

```
                65                  70                  75                  80
Val Gln Met Asn Ser Leu Arg Ala Glu Asp Thr Ala Val Tyr Tyr Cys
                85                  90                  95

Ala Arg Glu Gly Tyr Arg Ser Ser Tyr Tyr Gly Met Asp Val Trp
            100                 105                 110

Gly Gln Gly Thr Thr Val Thr Val Ser Ser
            115                 120

<210> SEQ ID NO 378
<211> LENGTH: 122
<212> TYPE: PRT
<213> ORGANISM: Homo sapiens

<400> SEQUENCE: 378

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Thr Ser Ser Tyr Tyr Gly Met Asp Val Trp
            100                 105                 110

Gly Gln Gly Thr Thr Val Thr Val Ser Ser
            115                 120

<210> SEQ ID NO 379
<211> LENGTH: 122
<212> TYPE: PRT
<213> ORGANISM: Homo sapiens

<400> SEQUENCE: 379

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Val Ser Ser Tyr Tyr Gly Met Asp Val Trp
            100                 105                 110

Gly Gln Gly Thr Thr Val Thr Val Ser Ser
            115                 120

<210> SEQ ID NO 380
<211> LENGTH: 122
<212> TYPE: PRT
```

<213> ORGANISM: Homo sapiens

<400> SEQUENCE: 380

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Trp Ser Ser Tyr Tyr Gly Met Asp Val Trp
            100                 105                 110

Gly Gln Gly Thr Thr Val Thr Val Ser Ser
        115                 120

<210> SEQ ID NO 381
<211> LENGTH: 122
<212> TYPE: PRT
<213> ORGANISM: Homo sapiens

<400> SEQUENCE: 381

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Tyr Ser Ser Tyr Tyr Gly Met Asp Val Trp
            100                 105                 110

Gly Gln Gly Thr Thr Val Thr Val Ser Ser
        115                 120

<210> SEQ ID NO 382
<211> LENGTH: 122
<212> TYPE: PRT
<213> ORGANISM: Homo sapiens

<400> SEQUENCE: 382

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

```
Lys Gly Arg Phe Thr Met Ser Arg Asp Asn Ala Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Cys Ser Ser Tyr Tyr Gly Met Asp Val Trp
            100                 105                 110

Gly Gln Gly Thr Thr Val Thr Val Ser Ser
        115                 120
```

<210> SEQ ID NO 383
<211> LENGTH: 105
<212> TYPE: PRT
<213> ORGANISM: Homo sapiens

<400> SEQUENCE: 383

```
Glu Val Gln Leu Val Glu Ser Gly Gly Phe Val Gln Pro Gly Gly
 1               5                  10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Asp Ser Ser
            100                 105
```

<210> SEQ ID NO 384
<211> LENGTH: 122
<212> TYPE: PRT
<213> ORGANISM: Homo sapiens

<400> SEQUENCE: 384

```
Glu Val Gln Leu Val Glu Ser Gly Gly Phe Val Gln Pro Gly Gly
 1               5                  10                  15

Ser Leu Arg Leu Ser Cys Ala Val Ser Gly Phe Thr Phe Asn Ser Tyr
                20                  25                  30

Trp Met Ser Trp Val Arg Gln Ala Pro Gly Lys Gly Leu Glu Trp Val
            35                  40                  45

Ala Asn Ile Asn Gln Asp Gly Ser Glu Lys Phe Tyr Val Ala Ser Val
 50                  55                  60

Lys Gly Arg Phe Thr Met Ser Arg Asp Asn Ala Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Glu Ser Ser Tyr Tyr Gly Met Asp Val Trp
            100                 105                 110

Gly Gln Gly Thr Thr Val Thr Val Ser Ser
        115                 120
```

<210> SEQ ID NO 385
<211> LENGTH: 122
<212> TYPE: PRT
<213> ORGANISM: Homo sapiens -continued

```
<400> SEQUENCE: 385

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Phe Ser Tyr Tyr Gly Met Asp Val Trp
            100                 105                 110

Gly Gln Gly Thr Thr Val Thr Val Ser Ser
        115                 120

<210> SEQ ID NO 386
<211> LENGTH: 122
<212> TYPE: PRT
<213> ORGANISM: Homo sapiens

<400> SEQUENCE: 386

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Gly Ser Tyr Tyr Gly Met Asp Val Trp
            100                 105                 110

Gly Gln Gly Thr Thr Val Thr Val Ser Ser
        115                 120

<210> SEQ ID NO 387
<211> LENGTH: 122
<212> TYPE: PRT
<213> ORGANISM: Homo sapiens

<400> SEQUENCE: 387

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60
```

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser His Ser Ser Tyr Tyr Gly Met Asp Val Trp
            100                 105                 110

Gly Gln Gly Thr Thr Val Thr Val Ser Ser
            115                 120

<210> SEQ ID NO 388
<211> LENGTH: 122
<212> TYPE: PRT
<213> ORGANISM: Homo sapiens

<400> SEQUENCE: 388

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ile Ser Ser Tyr Tyr Gly Met Asp Val Trp
            100                 105                 110

Gly Gln Gly Thr Thr Val Thr Val Ser Ser
            115                 120

<210> SEQ ID NO 389
<211> LENGTH: 122
<212> TYPE: PRT
<213> ORGANISM: Homo sapiens

<400> SEQUENCE: 389

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Lys Ser Ser Tyr Tyr Gly Met Asp Val Trp
            100                 105                 110

Gly Gln Gly Thr Thr Val Thr Val Ser Ser
            115                 120

<210> SEQ ID NO 390
<211> LENGTH: 122

```
<212> TYPE: PRT
<213> ORGANISM: Homo sapiens

<400> SEQUENCE: 390

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Leu Ser Ser Tyr Tyr Gly Met Asp Val Trp
            100                 105                 110

Gly Gln Gly Thr Thr Val Thr Val Ser Ser
            115                 120

<210> SEQ ID NO 391
<211> LENGTH: 122
<212> TYPE: PRT
<213> ORGANISM: Homo sapiens

<400> SEQUENCE: 391

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Met Ser Ser Tyr Tyr Gly Met Asp Val Trp
            100                 105                 110

Gly Gln Gly Thr Thr Val Thr Val Ser Ser
            115                 120

<210> SEQ ID NO 392
<211> LENGTH: 122
<212> TYPE: PRT
<213> ORGANISM: Homo sapiens

<400> SEQUENCE: 392

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60
```

```
                    50                  55                  60
Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                     85                  90                  95

Ala Arg Glu Gly Tyr Ser Asn Ser Tyr Tyr Gly Met Asp Val Trp
                100                 105                 110

Gly Gln Gly Thr Thr Val Thr Val Ser Ser
            115                 120

<210> SEQ ID NO 393
<211> LENGTH: 122
<212> TYPE: PRT
<213> ORGANISM: Homo sapiens

<400> SEQUENCE: 393

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                     85                  90                  95

Ala Arg Glu Gly Tyr Ser Pro Ser Tyr Tyr Gly Met Asp Val Trp
                100                 105                 110

Gly Gln Gly Thr Thr Val Thr Val Ser Ser
            115                 120

<210> SEQ ID NO 394
<211> LENGTH: 122
<212> TYPE: PRT
<213> ORGANISM: Homo sapiens

<400> SEQUENCE: 394

Glu Val Gln Leu Val Glu Ser Gly Gly Gly Phe Val Gln Pro Gly Gly
  1               5                  10                  15

Ser Leu Arg Leu Ser Cys Ala Val Ser Gly Phe Thr Phe Asn Ser Tyr
                 20                  25                  30

Trp Met Ser Trp Val Arg Gln Ala Pro Gly Lys Gly Leu Glu Trp Val
             35                  40                  45

Ala Asn Ile Asn Gln Asp Gly Ser Glu Lys Phe Tyr Val Ala Ser Val
         50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                     85                  90                  95

Ala Arg Glu Gly Tyr Ser Gln Ser Tyr Tyr Gly Met Asp Val Trp
                100                 105                 110

Gly Gln Gly Thr Thr Val Thr Val Ser Ser
            115                 120
```

```
<210> SEQ ID NO 395
<211> LENGTH: 122
<212> TYPE: PRT
<213> ORGANISM: Homo sapiens

<400> SEQUENCE: 395

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Arg Ser Tyr Tyr Gly Met Asp Val Trp
            100                 105                 110

Gly Gln Gly Thr Thr Val Thr Val Ser Ser
        115                 120

<210> SEQ ID NO 396
<211> LENGTH: 122
<212> TYPE: PRT
<213> ORGANISM: Homo sapiens

<400> SEQUENCE: 396

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Thr Ser Tyr Tyr Gly Met Asp Val Trp
            100                 105                 110

Gly Gln Gly Thr Thr Val Thr Val Ser Ser
        115                 120

<210> SEQ ID NO 397
<211> LENGTH: 122
<212> TYPE: PRT
<213> ORGANISM: Homo sapiens

<400> SEQUENCE: 397

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45
```

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Val Ser Ser Tyr Tyr Gly Met Asp Val Trp
            100                 105                 110

Gly Gln Gly Thr Thr Val Thr Val Ser Ser
            115                 120

<210> SEQ ID NO 398
<211> LENGTH: 122
<212> TYPE: PRT
<213> ORGANISM: Homo sapiens

<400> SEQUENCE: 398

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Trp Ser Ser Tyr Tyr Gly Met Asp Val Trp
            100                 105                 110

Gly Gln Gly Thr Thr Val Thr Val Ser Ser
            115                 120

<210> SEQ ID NO 399
<211> LENGTH: 122
<212> TYPE: PRT
<213> ORGANISM: Homo sapiens

<400> SEQUENCE: 399

Glu Val Gln Leu Val Glu Ser Gly Gly Gly Phe Val Gln Pro Gly Gly
 1               5                  10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Glu Lys Phe Tyr Val Ala Ser Val
        50                  55                  60

Lys Gly Arg Phe Thr Met Ser Arg Asp Asn Ala Lys Lys Ser Val Tyr
 65                  70                  75                  80

Val Gln Met Asn Ser Leu Arg Ala Glu Asp Thr Ala Val Tyr Tyr Cys
                85                  90                  95

Ala Arg Glu Gly Tyr Ser Tyr Ser Ser Tyr Tyr Gly Met Asp Val Trp
            100                 105                 110

Gly Gln Gly Thr Thr Val Thr Val Ser Ser
            115                 120

```
<210> SEQ ID NO 400
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu, Val, Arg, Trp, Gln, Lys, His,
      Glu, Asn, Met or Ser

<400> SEQUENCE: 400

Ala Arg Glu Gly Tyr Ser Ser Xaa Ser Tyr Tyr Gly Met Asp Val
1               5                   10                  15

<210> SEQ ID NO 401
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu, Val, Arg, Trp, Gln, Lys, His,
      Glu, Asn or Met

<400> SEQUENCE: 401

Ala Arg Glu Gly Tyr Ser Ser Xaa Ser Tyr Tyr Gly Met Asp Val
1               5                   10                  15

<210> SEQ ID NO 402
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu, Val, Arg, Trp, Gln or Lys

<400> SEQUENCE: 402

Ala Arg Glu Gly Tyr Ser Ser Xaa Ser Tyr Tyr Gly Met Asp Val
1               5                   10                  15

<210> SEQ ID NO 403
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ile, Leu or Val

<400> SEQUENCE: 403

Ala Arg Glu Gly Tyr Ser Ser Xaa Ser Tyr Tyr Gly Met Asp Val
1               5                   10                  15

<210> SEQ ID NO 404
<211> LENGTH: 642
<212> TYPE: DNA
<213> ORGANISM: Homo sapiens

<400> SEQUENCE: 404
tcctatgtgc tgactcagcc accctcagtg tcagtggccc caggagagac ggccaggatt      60
acctgtgggg gagacaacat tggaaggaaa agtgtgtact ggtaccagca gaagtcaggc     120
caggcccctg tgctggtcat ctattatgat agcgaccggc cctcagggat ccctgagcga     180
ttctctgggt ccaactctgg gaacacggcg accctgacca tcagcagggt cgaagccggg     240
```

```
gatgaggccg actattactg tcaggtgtgg gatggaagta gtgatcattg ggtgttcggc    300
ggagggacca agttgaccgt cctaggtcag cccaaggctg cccctcggt cactctgttc     360 ccaccctcct ctgaggagct tcaagccaac aaggccacac tggtgtgtct cataagtgac    420
ttctacccgg gagccgtgac agtggcctgg aaggcagata gcagcccgt caaggcggga    480 gtggagacca ccacccctc caaacaaagc aacaacaagt acgcggccag cagctacctg     540
agcctgacgc ctgagcagtg gaagtcccac aaaagctaca gctgccaggt cacgcatgaa    600
gggagcaccg tggagaagac agtggcccct acagaatgtt ca                       642
```

<210> SEQ ID NO 405
<211> LENGTH: 214
<212> TYPE: PRT
<213> ORGANISM: Homo sapiens

<400> SEQUENCE: 405

```
Ser Tyr Val Leu Thr Gln Pro Pro Ser Val Ser Val Ala Pro Gly Glu
1               5                   10                  15

Thr Ala Arg Ile Thr Cys Gly Gly Asp Asn Ile Gly Arg Lys Ser Val
            20                  25                  30

Tyr Trp Tyr Gln Gln Lys Ser Gly Gln Ala Pro Val Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Gly Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

<210> SEQ ID NO 406
<211> LENGTH: 8
<212> TYPE: PRT
<213> ORGANISM: Homo sapiens
<220> FEATURE:
<221> NAME/KEY: MISC_FEATURE
<222> LOCATION: (3)..(3)
<223> OTHER INFORMATION: Xaa is Arg or Thr

<400> SEQUENCE: 406

```
Gly Phe Xaa Phe Asn Ser Tyr Trp
1               5
```

```
<210> SEQ ID NO 407
<211> LENGTH: 8
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: Xaa is Asp, Gly or Trp
<220> FEATURE:
<221> NAME/KEY: MISC_FEATURE
<222> LOCATION: (6)..(6)
<223> OTHER INFORMATION: Xaa is Ser or Phe
<220> FEATURE:
<221> NAME/KEY: MISC_FEATURE
<222> LOCATION: (7)..(7)
<223> OTHER INFORMATION: Xaa is Glu or Arg

<400> SEQUENCE: 407

Ile Asn Gln Xaa Gly Xaa Xaa Lys
1               5

<210> SEQ ID NO 408
<211> LENGTH: 15
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is Ser or Ile
<220> FEATURE:
<221> NAME/KEY: MISC_FEATURE
<222> LOCATION: (9)..(9)
<223> OTHER INFORMATION: Xaa is Ser or Lys

<400> SEQUENCE: 408

Ala Arg Glu Gly Tyr Ser Ser Xaa Xaa Tyr Tyr Gly Met Asp Val
1               5                   10                  15

<210> SEQ ID NO 409
<211> LENGTH: 325
<212> TYPE: PRT
<213> ORGANISM: Artificial Sequence
<220> FEATURE:
<223> OTHER INFORMATION: IgG4 human heavy chain constant region with P
      (hinge) mutation and K439E

<400> SEQUENCE: 409

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140
```

```
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
290                 295                 300

Cys Ser Val Met His Glu Ala Leu His Asn His Tyr Thr Gln Glu Ser
305                 310                 315                 320

Leu Ser Leu Ser Pro
                325

<210> SEQ ID NO 410
<211> LENGTH: 325
<212> TYPE: PRT
<213> ORGANISM: Artificial Sequence
<220> FEATURE:
<223> OTHER INFORMATION: IgG4 human heavy chain constant region with P
      (hinge) mutation and E356K

<400> SEQUENCE: 410

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Tyr
```

|  | 165 | | | 170 | | | 175 | | |
|---|---|---|---|---|---|---|---|---|---|

Asn Ser Thr Tyr Arg Val Val Ser Val Leu Thr Val Leu His Gln Asp
        180                         185                     190

Trp Leu Asn Gly Lys Glu Tyr Lys Cys Lys Val Ser Asn Lys Gly Leu
    195                         200                     205

Pro Ser Ser Ile Glu Lys Thr Ile Ser Lys Ala Lys Gly Gln Pro Arg
210                       215                     220

Glu Pro Gln Val Tyr Thr Leu Pro Pro Ser Gln Lys Glu Met Thr Lys
225                     230                  235               240

Asn Gln Val Ser Leu Thr Cys Leu Val Lys Gly Phe Tyr Pro Ser Asp
        245                   250                  255

Ile Ala Val Glu Trp Glu Ser Asn Gly Gln Pro Glu Asn Asn Tyr Lys
         260                  265                270

Thr Thr Pro Pro Val Leu Asp Ser Asp Gly Ser Phe Phe Leu Tyr Ser
     275                   280                  285

Lys Leu Thr Val Asp Lys Ser Arg Trp Gln Glu Gly Asn Val Phe Ser
    290                    295                300

Cys Ser Val Met His Glu Ala Leu His Asn His Tyr Thr Gln Lys Ser
305              310                 315              320

Leu Ser Leu Ser Pro
        325

<210> SEQ ID NO 411
<211> LENGTH: 975
<212> TYPE: DNA
<213> ORGANISM: Artificial Sequence
<220> FEATURE:
<223> OTHER INFORMATION: IgG4-P E356K encoding nucleic acid

<400> SEQUENCE: 411

```
gcttccacca agggacccag cgttttccct ctggctcctt gctccagatc cacctccgag    60
tctacagctg ctctgggctg cctggtcaag gactactttc ctgagcctgt gaccgtgtcc   120
tggaactctg gcgctctgac atctggcgtg cacacctttc cagctgtgct gcagtcctcc   180
ggcctgtact ctctgtcctc tgtcgtgacc gtgccttcca gctctctggg aacccagacc   240
tacacctgta atgtggacca caagccttcc aacaccaagg tggacaagcg cgtggaatct   300
aagtacggcc ctccttgtcc tccatgtcct gctccagagt ttctcggcgg acccccgtg   360
tttctgttcc ctccaaagcc taaggacacc ctgatgatct ctcggacccc tgaagtgacc   420
tgcgtggtgg tggatgtgtc caagaggat cccgaggtgc agttcaattg gtacgtggac   480
ggcgtggaag tgcacaatgc caagaccaag cctagagagg aacagtacaa ctccacctac   540
agagtggtgt ccgtgctgac cgtgctgcac caggattggc tgaacggcaa agagtacaag   600
tgcaaggtgt ccaacaaggg cctgcctagc tccatcgaaa agaccatctc caaggccaag   660
ggccagcctc gagaacccca ggtttacacc ctgcctccaa gccaaggga atgaccaag   720
aaccaggtgt ccctgacctg tctcgtgaag ggcttctacc cctccgatat cgccgtggaa   780
tgggagtcta atggccagcc agagaacaac tacaagacca cctccagt gctggactcc   840
gacggctcat tctttctgta ctccaagctg acagtggaca gtcccggtg gcaagagggc   900
aacgtgttct cctgctctgt gatgcacgag gccctgcaca accactacac ccaagagtcc   960
ctgtctctgt cccct                                                   975
```

<210> SEQ ID NO 412
<211> LENGTH: 975

<212> TYPE: DNA
<213> ORGANISM: Homo sapiens

<400> SEQUENCE: 412

```
gcttccacca agggacccag cgtgttccct ctggctcctt gctccagatc cacctccgag      60
tctacagctg ctctgggctg cctggtcaag gactactttc ctgagcctgt gaccgtgtct     120
tggaactctg gcgctctgac atctggcgtg cacacctttc cagctgtgct gcagtcctcc     180
ggcctgtact ctctgtcctc tgtcgtgacc gtgccttcca gctctctggg aacccagacc     240
tacacctgta atgtggacca caagccttcc aacaccaagg tggacaagcg cgtggaatct     300
aagtacggcc ctccttgtcc tccatgtcct gctccagagt ttctcggcgg acctccgtg     360
tttctgttcc ctccaaagcc taaggacacc ctgatgatct ctcggacccc tgaagtgacc     420
tgcgtggtgg tggatgtgtc caagaggat cccgaggtgc agttcaattg gtacgtggac     480
ggcgtggaag tgcacaacgc caagaccaag cctagagagg aacagtacaa ctccacctac     540
agagtggtgt ccgtgctgac cgtgctgcac caggattggc tgaacggcaa agagtacaag     600
tgcaaggtgt ccaacaaggg cctgcctagc tccatcgaaa agaccatctc caaggccaag     660
ggccagcctc gagaacccca ggtttacacc ctgcctccaa gccagaaaga gatgaccaag     720
aaccaggtgt ccctgacctg cctcgtgaag ggcttctacc cttccgatat cgccgtggaa     780
tgggagagca atggccagcc agagaacaac tacaagacca cacctcctgt gctggactcc     840
gatggctcat tctttctgta ctccaagctg acagtggaca agtcccggtg gcaagagggc     900
aacgtgttct cctgctctgt gatgcacgag gccctgcaca accactacac ccagaagtcc     960
ctgtctctgt ccccct                                                      975
```

<210> SEQ ID NO 413
<211> LENGTH: 639
<212> TYPE: DNA
<213> ORGANISM: Homo sapiens

<400> SEQUENCE: 413

```
tacgtgctga cccagcctcc ttccgtgtct gttgctcctg gcgagacagc cagaatcacc      60
tgtggcggcg ataacatcgg ccggaagtcc gtgtactggt atcagcagaa gtccggccag     120
gctcctgtgc tggtcatcta ctacgactcc gaccggcctt ctggcatccc tgagagattc     180
tccggctcca actccggcaa taccgccaca ctgaccatct ccagagtgga agctggcgac     240
gaggccgact actactgcca agtgtgggac ggctcctctg accactgggt tttcggcgga     300
ggcaccaagc tgacagtgct gggacaacct aaggccgctc cttctgtgac cctgtttcct     360
ccatcctccg aggaactgca ggccaacaag gctaccctcg tgtgcctgat ctccgacttt     420
taccctggcg ctgtgaccgt ggcctggaag gctgatagtt ctcctgtgaa ggccggcgtg     480
gaaaccacca ccttccaa gcagtccaac aacaaatacg ccgcctcctc ctacctgtct     540
ctgacccctg aacagtggaa gtcccacaag tcctactctt gccaagtgac ccacgagggc     600
tccaccgtgg aaaagacagt ggctcctacc gagtgctcc                            639
```

<210> SEQ ID NO 414
<211> LENGTH: 213
<212> TYPE: PRT
<213> ORGANISM: Homo sapiens

<400> SEQUENCE: 414

```
Tyr Val Leu Thr Gln Pro Pro Ser Val Ser Val Ala Pro Gly Glu Thr
1               5                   10                  15
```

```
Ala Arg Ile Thr Cys Gly Gly Asp Asn Ile Gly Arg Lys Ser Val Tyr
             20                  25                  30

Trp Tyr Gln Gln Lys Ser Gly Gln Ala Pro Val Leu Val Ile Tyr Tyr
         35                  40                  45

Asp Ser Asp Arg Pro Ser Gly Ile Pro Glu Arg Phe Ser Gly Ser Asn
     50                  55                  60

Ser Gly Asn Thr Ala Thr Leu Thr Ile Ser Arg Val Glu Ala Gly Asp
 65                  70                  75                  80

Glu Ala Asp Tyr Tyr Cys Gln Val Trp Asp Gly Ser Ser Asp His Trp
                 85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Lys Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 415
<211> LENGTH: 321
<212> TYPE: DNA
<213> ORGANISM: Homo sapiens

<400> SEQUENCE: 415
tacgtgctga cccagcctcc ttccgtgtct gttgctcctg gcgagacagc cagaatcacc      60
tgtggcggcg ataacatcgg ccggaagtcc gtgtactggt atcagcagaa gtccggccag     120
gctcctgtgc tggtcatcta ctacgactcc gaccggcctt ctggcatccc tgagagattc     180
tccggctcca actccggcaa taccgccaca ctgaccatct ccagagtgga agctggcgac     240
gaggccgact actactgcca agtgtgggac ggctcctctg accactgggt tttcggcgga     300
ggcaccaagc tgacagtgct g                                                321

<210> SEQ ID NO 416
<211> LENGTH: 107
<212> TYPE: PRT
<213> ORGANISM: Homo sapiens

<400> SEQUENCE: 416

Tyr Val Leu Thr Gln Pro Pro Ser Val Ser Val Ala Pro Gly Glu Thr
 1               5                  10                  15

Ala Arg Ile Thr Cys Gly Gly Asp Asn Ile Gly Arg Lys Ser Val Tyr
             20                  25                  30

Trp Tyr Gln Gln Lys Ser Gly Gln Ala Pro Val Leu Val Ile Tyr Tyr
         35                  40                  45

Asp Ser Asp Arg Pro Ser Gly Ile Pro Glu Arg Phe Ser Gly Ser Asn
     50                  55                  60
```

Ser Gly Asn Thr Ala Thr Leu Thr Ile Ser Arg Val Glu Ala Gly Asp
65                  70                  75                  80

Glu Ala Asp Tyr Tyr Cys Gln Val Trp Asp Gly Ser Ser Asp His Trp
                85                  90                  95

Val Phe Gly Gly Gly Thr Lys Leu Thr Val Leu
            100                 105

<210> SEQ ID NO 417
<211> LENGTH: 24
<212> TYPE: PRT
<213> ORGANISM: Homo sapiens

<400> SEQUENCE: 417

Tyr Val Leu Thr Gln Pro Pro Ser Val Ser Val Ala Pro Gly Glu Thr
1               5                   10                  15

Ala Arg Ile Thr Cys Gly Gly Asp
            20

<210> SEQ ID NO 418
<211> LENGTH: 1341
<212> TYPE: DNA
<213> ORGANISM: Artificial Sequence
<220> FEATURE:
<223> OTHER INFORMATION: Nucleic acid encoding N1280H-IgG4-P K439E

<400> SEQUENCE: 418
gaagtgcagc tggttgaatc tggcggcgga tttgttcagc ctggcggctc tctgagactg      60
tcctgtgctg tgtccggctt ccggttcaac tcctactgga tgtcctgggt ccgacaggct     120
cctggcaaag gactggaatg ggtcgccaac atcaaccagg acggctcccg gaagttctac     180
gtggcctctg tgaagggcag attcaccatg tctcgggaca cgccaagaa atccgtgtac     240
gtgcagatga actccctgag agccgaggac accgccgtgt actactgtgc tagagagggc     300
tactcctcca tcaagtacta cggcatggac gtgtggggcc agggcacaac cgtgacagtc     360
tcttccgctt ccaccaaggg acccagcgtt ttccctctgg ctccttgctc cagatccacc     420
tccgagtcta cagctgctct gggctgcctg gtcaaggact actttcctga gcctgtgacc     480
gtgtcctgga actctggcgc tctgacatct ggcgtgcaca ccttccagc tgtgctgcag     540
tcctccggcc tgtactctct gtcctctgtc gtgaccgtgc cttccagctc tctgggaacc     600
cagacctaca cctgtaatgt ggaccacaag ccttccaaca ccaaggtgga caagcgcgtg     660
gaatctaagt acggccctcc ttgtcctcca tgtcctgctc agagtttct cggcggaccc     720
tccgtgtttc tgttccctcc aaagcctaag acaccctga tgatctctcg acccctgaa     780
gtgacctgcg tggtggtgga tgtgtcccaa gaggatcccg aggtgcagtt caattggtac     840
gtggacggcg tggaagtgca caatgccaag accaagccta gaggaacagta caactcc     900
acctacagag tggtgtccgt gctgaccgtg ctgcaccagg attggctgaa cggcaaagag     960
tacaagtgca aggtgtccaa caagggcctg cctagctcca tcgaaaagac catctccaag    1020
gccaagggcc agcctcgaga acccaggtt acaccctgc tccaagcca gaggaaatg     1080
accaagaacc aggtgtccct gacctgtctc gtgaagggct ctacccctc cgatatcgcc    1140
gtggaatggg agtctaatgg ccagccagag acaactaca gaccacacc tccagtgctg    1200
gactccgacg gctcattctt tctgtactcc aagctgacag tggacaagtc ccggtggcaa    1260
gagggcaacg tgttctcctg ctctgtgatg cacgaggccc tgcacaacca ctacacccaa    1320
gagtccctgt ctctgtcccc t                                               1341

<210> SEQ ID NO 419
<211> LENGTH: 447
<212> TYPE: PRT
<213> ORGANISM: Artificial Sequence
<220> FEATURE:
<223> OTHER INFORMATION: N1280H-IgG4-P K439E amino acid sequence

<400> SEQUENCE: 419

Glu Val Gln Leu Val Glu Ser Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Glu Ser Leu Ser Leu Ser Pro
            435                 440                 445

<210> SEQ ID NO 420
<211> LENGTH: 1338
<212> TYPE: DNA
<213> ORGANISM: Artificial Sequence
<220> FEATURE:
<223> OTHER INFORMATION: Nucleic acid encoding T0999H-IgG4-P E356K

<400> SEQUENCE: 420

```
caggttcagc tgattcagtc cggcgccaaa gtgaagaaac ctggcgcctc tgtgaaggtg      60
tcctgcaagg cctctcggta caagttcacc tcctactaca tgcactgggt ccgacaggcc     120
cctggacaag gattggagtg gatgggcatc atcaaccca  agtccggctc cacctcttac     180
gcccagaaat ccagggcag  agtgaccatg accagagaca cctctacctc caccgtgtac     240
atggaactgt ccagcctgag atccgaggac accgccgtgt actactgtgc cagagatggc     300
tacggcagct ctccagact  gatccagttg tggggcagg  gcacactggt cacagtgtcc     360
tctgcttcca ccaagggacc cagcgtgttc cctctggctc cttgctccag atccacctcc     420
gagtctacac tgctctgggg ctgcctggtc aaggactact tcctgagcc  tgtgaccgtg     480
tcttggaact ctggcgctct gacatctggc gtgcacacct tccagctgt  gctgcagtcc     540
tccggcctgt actctctgtc ctctgtcgtg accgtgcctt ccagctctct gggaacccag     600
acctacacct gtaatgtgga ccacaagcct tccaacacca aggtggacaa gcgcgtggaa     660
tctaagtacg ccctcccttg tcctccatgt cctgctccag agtttctcgg cggaccctcc     720
gtgtttctgt tccctccaaa gcctaaggac accctgatga tctctcggac ccctgaagtg     780
acctgcgtgg tggtggatgt gtcccaagag gatcccgagg tgcagttcaa ttggtacgtg     840
gacggcgtgg aagtgcacaa cgccaagacc aagcctagag aggaacagta caactccacc     900
tacagagtgg tgtccgtgct gaccgtgctg caccaggatt ggctgaacgg caaagagtac     960
aagtgcaagg tgtccaacaa gggcctgcct agctccatcg aaaagaccat ctccaaggcc    1020
aagggccagc ctcgagaacc ccaggtttac accctgcctc caagccagaa agagatgacc    1080
aagaaccagg tgtccctgac ctgcctcgtg aagggcttct accttccga  tatcgccgtg    1140
gaatgggaga gcaatggcca gccagagaac aactacaaga ccacacctcc tgtgctggac    1200
tccgatggct cattctttct gtactccaag ctgacagtgg acaagtcccg gtggcaagag    1260
ggcaacgtgt tctcctgctc tgtgatgcac gaggccctgc acaaccacta cacccagaag    1320
tccctgtctc tgtcccct                                                  1338
```

<210> SEQ ID NO 421
<211> LENGTH: 446
<212> TYPE: PRT
<213> ORGANISM: Artificial Sequence
<220> FEATURE:
<223> OTHER INFORMATION: T0999H-IgG4-P E356K amino acid sequence

<400> SEQUENCE: 421

```
Gln Val Gln Leu Ile Gln Ser Gly Ala Lys Val Lys Lys Pro Gly Ala
1               5                   10                  15

Ser Val Lys Val Ser Cys Lys Ala Ser Arg Tyr Lys Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
```

```
              405                 410                 415
Arg Trp Gln Glu Gly Asn Val Phe Ser Cys Ser Val Met His Glu Ala
        420                 425                 430

Leu His Asn His Tyr Thr Gln Lys Ser Leu Ser Leu Ser Pro
        435                 440                 445

<210> SEQ ID NO 422
<211> LENGTH: 8
<212> TYPE: PRT
<213> ORGANISM: Homo sapiens

<400> SEQUENCE: 422

Gly Phe Thr Phe Asn Ser Tyr Trp
1               5

<210> SEQ ID NO 423
<211> LENGTH: 1341
<212> TYPE: DNA
<213> ORGANISM: Artificial Sequence
<220> FEATURE:
<223> OTHER INFORMATION: Nucleic acid encoding N1454H-IgG4-P K439E

<400> SEQUENCE: 423
gaagtgcagc tggttgaatc tggcggcgga tttgttcagc ctggcggctc tctgagactg     60
tcctgtgctg tgtccggctt ccggttcaac tcctactgga tgtcctgggt ccgacaggct    120
cctggcaaag gactggaatg ggtcgccaac atcaaccagg acggctcccg aagttctac    180
gtggcctctg tgaagggcag attcaccatg tctcgggaca cgccaagaa agaggtgtac    240
gtgcagatga actccctgag agccgaggac accgccgtgt actactgtgc tagagagggc    300
tactcctcca tcaagtacta cggcatggac gtgtggggcc agggcacaac cgtgacagtc    360
tcttccgctt ccaccaaggg acccagcgtt ttccctctgg ctccttgctc cagatccacc    420
tccgagtcta cagctgctct gggctgcctg gtcaaggact actttcctga gcctgtgacc    480
gtgtcctgga actctggcgc tctgacatct ggcgtgcaca cctttccagc tgtgctgcag    540
tcctccggcc tgtactctct gtcctctgtc gtgaccgtgc cttccagctc tctgggaacc    600
cagacctaca cctgtaatgt ggaccacaag ccttccaaca ccaaggtgga caagcgcgtg    660
gaatctaagt acggcccctc cttgtcctcca tgtcctgctc cagagtttct cggcggaccc    720
tccgtgtttc tgttccctcc aaagcctaag gacaccctga tgatctctcg gacccctgaa    780
gtgacctgcg tggtggtgga tgtgtcccaa gaggatcccg aggtgcagtt caattggtac    840
gtggacggcg tggaagtgca caatgccaag accaagccta gaggaacga gtacaactcc    900
acctacagag tggtgtccgt gctgaccgtg ctgcaccagg attggctgaa cggcaaagag    960
tacaagtgca aggtgtccaa caagggcctg cctagctcca tcgaaaagac catctccaag   1020
gccaagggcc agcctcgaga accccaggtt tacaccctgc ctccaagcca agaggaaatg   1080
accaagaacc aggtgtccct gacctgtctc gtgaagggct ctaccccctc cgatatcgcc   1140
gtggaatggg agtctaatgg ccagccagag aacaactaca gaccacacc tccagtgctg   1200
gactccgacg gctcattctt tctgtactcc aagctgacag tggacaagtc ccggtggcaa   1260
gagggcaacg tgttctcctg ctctgtgatg cacgaggccc tgcacaacca ctacacccaa   1320
gagtccctgt ctctgtcccc t                                              1341

<210> SEQ ID NO 424
<211> LENGTH: 447
<212> TYPE: PRT
```

<210> ORGANISM: Artificial Sequence
<220> FEATURE:
<223> OTHER INFORMATION: N1454H-IgG4-P K439E amino acid sequence

<400> SEQUENCE: 424

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
50                  55                  60

Lys Gly Arg Phe Thr Met Ser Arg Asp Asn Ala Lys Lys Glu Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
```

```
                385             390             395             400
Asp Ser Asp Gly Ser Phe Phe Leu Tyr Ser Lys Leu Thr Val Asp Lys
                    405                 410                 415

Ser Arg Trp Gln Glu Gly Asn Val Phe Ser Cys Ser Val Met His Glu
                420                 425                 430

Ala Leu His Asn His Tyr Thr Gln Glu Ser Leu Ser Leu Ser Pro
            435                 440                 445
```

<210> SEQ ID NO 425
<211> LENGTH: 1341
<212> TYPE: DNA
<213> ORGANISM: Artificial Sequence
<220> FEATURE:
<223> OTHER INFORMATION: Nucleic acid encoding N1441H-IgG4-P K439E

<400> SEQUENCE: 425

```
gaagtgcagc tggttgaatc tggcggcgga tttgttcagc ctggcggctc tctgagactg      60
tcctgtgctg tgtccggctt ccggttcaac tcctactgga gtgtccgggt ccgacaggct     120
cctggcaaag gactggaatg ggtcgccaac atcaaccagg acggctcccg gaagttctac     180
gtggcctctg tgaagggcag attcaccatg tctcgggaca cgccgacaa gtccgtgtac      240
gtgcagatga actccctgag agccgaggac accgccgtgt actactgtgc tagagagggc     300
tactcctcca tcaagtacta cggcatggac gtgtggggcc agggcacaac cgtgacagtc     360
tcttccgctt ccaccaaggg acccagcgtt ttccctctgg ctccttgctc cagatccacc     420
tccgagtcta cagctgctct gggctgcctg gtcaaggact actttcctga gcctgtgacc     480
gtgtcctgga actctggcgc tctgacatct ggcgtgcaca cctttccagc tgtgctgcag     540
tcctccggcc tgtactctct gtcctctgtc gtgaccgtgc cttccagctc tctgggaacc     600
cagacctaca cctgtaatgt ggaccacaag ccttccaaca ccaaggtgga caagcgcgtg     660
gaatctaagt acggcccctc cttgtcctcca tgtcctgctc cagagtttct cggcggaccc    720
tccgtgtttc tgttccctcc aaagcctaag gacaccctga tgatctctcg gacccctgaa     780
gtgacctgcg tggtggtgga tgtgtcccaa gaggatcccg aggtgcagtt caattggtac     840
gtggacggcg tggaagtgca caacgccaag accaagccta gaggaacag tacaactcc       900
acctacagag tggtgtccgt gctgaccgtg ctgcaccagg attggctgaa cggcaaagag     960
tacaagtgca aggtgtccaa caagggcctg cctagctcca tcgaaaagac catctccaag    1020
gccaagggcc agcctcgaga acccaggtt tacaccctgc ctccaagcca agaggaaatg     1080
accaagaacc aggtgtccct gacctgtctc gtgaagggct ctaccccctc cgatatcgcc    1140
gtggaatggg agtctaatgg ccagccagag aacaactaca agaccacacc tccagtgctg    1200
gactccgacg gctcattctt tctgtactcc aagctgacag tggacaagtc ccggtggcaa    1260
gagggcaacg tgttctcctg ctctgtgatg cacgaggccc tgcacaacca ctacacccaa    1320
gagtccctgt ctctgtcccc t                                              1341
```

<210> SEQ ID NO 426
<211> LENGTH: 447
<212> TYPE: PRT
<213> ORGANISM: Artificial Sequence
<220> FEATURE:
<223> OTHER INFORMATION: N1441H-IgG4-P K439E amino acid sequence

<400> SEQUENCE: 426

```
Glu Val Gln Leu Val Glu Ser Gly Gly Gly Phe Val Gln Pro Gly Gly
1               5                   10                  15
```

```
Ser Leu Arg Leu Ser Cys Ala Val Ser Gly Phe Arg Phe Asn Ser Tyr
         20                  25                  30
Trp Met Ser Trp Val Arg Gln Ala Pro Gly Lys Gly Leu Glu Trp Val
         35                  40                  45
Ala Asn Ile Asn Gln Asp Gly Ser Arg Lys Phe Tyr Val Ala Ser Val
 50                  55                  60
Lys Gly Arg Phe Thr Met Ser Arg Asp Asn Ala Asp Lys Ser Val Tyr
 65                  70                  75                  80
Val Gln Met Asn Ser Leu Arg Ala Glu Asp Thr Ala Val Tyr Tyr Cys
             85                  90                  95
Ala Arg Glu Gly Tyr Ser Ser Ile Lys Tyr Tyr Gly Met Asp Val Trp
                100                 105                 110
Gly Gln Gly Thr Thr Val Thr Val Ser Ser Ala Ser Thr Lys Gly Pro
            115                 120                 125
Ser Val Phe Pro Leu Ala Pro Cys Ser Arg Ser Thr Ser Glu Ser Thr
130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
            180                 185                 190
Val Pro Ser Ser Ser Leu Gly Thr Gln Thr Tyr Thr Cys Asn Val Asp
        195                 200                 205
His Lys Pro Ser Asn Thr Lys Val Asp Lys Arg Val Glu Ser Lys Tyr
    210                 215                 220
Gly Pro Pro Cys Pro Pro Cys Pro Ala Pro Glu Phe Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser Gln Glu Asp
            260                 265                 270
Pro Glu Val Gln Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Gly Leu Pro Ser Ser Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Gln Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Glu Gly Asn Val Phe Ser Cys Ser Val Met His Glu
            420                 425                 430
```

Ala Leu His Asn His Tyr Thr Gln Glu Ser Leu Ser Leu Ser Pro
            435                 440                 445

<210> SEQ ID NO 427
<211> LENGTH: 1341
<212> TYPE: DNA
<213> ORGANISM: Artificial Sequence
<220> FEATURE:
<223> OTHER INFORMATION: Nucleic acid encoding N1442H-IgG4-P K439E

<400> SEQUENCE: 427

```
gaagtgcagc tggttgaatc tggcggcgga tttgttcagc ctggcggctc tctgagactg      60
tcctgtgctg tgtccggctt ccggttcaac tcctactgga gtgtcctggt ccgacaggct     120
cctggcaaag gactggaatg ggtcgccaac atcaaccagg acggctcccg aagttctac      180
gtggcctctg tgaagggcag attcaccatg tctcgggaca cgccgagaa gtccgtgtac      240
gtgcagatga actccctgag agccgaggac accgccgtgt actactgtgc tagagagggc     300
tactcctcca tcaagtacta cggcatggac gtgtggggcc agggcacaac cgtgacagtc     360
tcttccgctt ccaccaaggg acccagcgtt ttccctctgg ctccttgctc cagatccacc     420
tccgagtcta cagctgctct gggctgcctg gtcaaggact actttcctga gcctgtgacc     480
gtgtcctgga actctggcgc tctgacatct ggcgtgcaca cctttccagc tgtgctgcag     540
tcctccggcc tgtactctct gtcctctgtc gtgaccgtgc cttccagctc tctgggaacc     600
cagacctaca cctgtaatgt ggaccacaag ccttccaaca ccaaggtgga caagcgcgtg     660
gaatctaagt acggccctcc ttgtcctcca tgtcctgctc cagagtttct cggcggaccc     720
tccgtgtttc tgttccctcc aaagcctaag gacaccctga tgatctctcg gacccctgaa     780
gtgacctgcg tggtggtgga tgtgtcccaa gaggatcccg aggtgcagtt caattggtac     840
gtggacggcg tggaagtgca caacgccaag accaagccta gagaggaaca gtacaactcc     900
acctacagag tggtgtccgt gctgaccgtg ctgcaccagg attggctgaa cggcaaagag     960
tacaagtgca aggtgtccaa caagggcctg cctagctcca tcgaaaagac catctccaag    1020
gccaagggcc agcctcgaga acccccaggtt tacaccctgc ctccaagcca gaggaaatg    1080
accaagaacc aggtgtccct gacctgtctc gtgaagggct ctaccccctc cgatatcgcc    1140
gtggaatggg agtctaatgg ccagccagag aacaactaca agaccacacc tccagtgctg    1200
gactccgacg gctcattctt tctgtactcc aagctgacag tggacaagtc ccggtggcaa    1260
gagggcaacg tgttctcctg ctctgtgatg cacgaggccc tgcacaacca ctacacccaa    1320
gagtccctgt ctctgtcccc t                                             1341
```

<210> SEQ ID NO 428
<211> LENGTH: 447
<212> TYPE: PRT
<213> ORGANISM: Artificial Sequence
<220> FEATURE:
<223> OTHER INFORMATION: N1442H-IgG4-P K439E amino acid sequence

<400> SEQUENCE: 428

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val

```
            50                  55                  60
Lys Gly Arg Phe Thr Met Ser Arg Asp Asn Ala Glu Lys Ser Val Tyr
 65                  70                  75                  80

Val Gln Met Asn Ser Leu Arg Ala Glu Asp Thr Ala Val Tyr Tyr Cys
                 85                  90                  95

Ala Arg Glu Gly Tyr Ser Ser Ile Lys Tyr Tyr Gly Met Asp Val Trp
                100                 105                 110

Gly Gln Gly Thr Thr Val Thr Val Ser Ser Ala Ser Thr Lys Gly Pro
                115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Thr Cys Asn Val Asp
                195                 200                 205

His Lys Pro Ser Asn Thr Lys Val Asp Lys Arg Val Glu Ser Lys Tyr
210                 215                 220

Gly Pro Pro Cys Pro Pro Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
                420                 425                 430

Ala Leu His Asn His Tyr Thr Gln Glu Ser Leu Ser Leu Ser Pro
                435                 440                 445

<210> SEQ ID NO 429
<211> LENGTH: 1338
<212> TYPE: DNA
<213> ORGANISM: Artificial Sequence
```

<220> FEATURE:
<223> OTHER INFORMATION: Nucleic acid encoding T0736H-IgG4-P E356K

<400> SEQUENCE: 429

```
caggttcagc tgattcagtc tggcgccgaa gtgaagaaac ctggcgcctc tgtgaaggtg      60
tcctgcaagg cctctcggta caagttcacc tcctactaca tgcactgggt ccgacaggcc     120
cctggacaag gattggagtg gatgggcatc atcaacccca gtccggctca cctcttac      180
gcccagaaat ccagggcag agtgaccatg accagagaca cctctacctc caccgtgtac     240
atggaactgt ccagcctgag atccgaggac accgccgtgt actactgtgc cagagatggc     300
tacggcagct ctccaggct gatccagttg tggggacagg gcacactggt caccgtgtcc     360
tctgcttcta ccaagggacc cagcgtgttc cctctggctc cttgctccag atccacctcc     420
gagtctacag ctgctctggg ctgcctggtc aaggactact tcctgagcc tgtgaccgtg     480
tcttggaact ctggcgctct gacatctggc gtgcacacct ttccagctgt gctgcagtcc     540
tccggcctgt actctctgtc ctctgtcgtg accgtgcctt ccagctctct gggaacccag     600
acctacacct gtaatgtgga ccacaagcct tccaacacca aggtggacaa gcgcgtggaa     660
tctaagtacg gccctccttg tcctccatgt cctgctccag agtttctcgg cggaccctcc     720
gtgtttctgt tccctccaaa gcctaaggac accctgatga tctctcggac ccctgaagtg     780
acctgcgtgg tggtggatgt gtcccaagag atcccgagg tgcagttcaa ttggtacgtg     840
gacggcgtgg aagtgcacaa cgccaagacc aagcctagag aggaacagta caactccacc     900
tacagagtgg tgtccgtgct gaccgtgctg caccaggatt ggctgaacgg caaagagtac     960
aagtgcaagg tgtccaacaa gggcctgcct agctccatcg aaaagaccat ctccaaggcc    1020
aagggccagc ctcgagaacc ccaggtttac accctgcctc caagccagaa agagatgacc    1080
aagaaccagg tgtccctgac ctgcctcgtg aagggcttct acccttccga tatcgccgtg    1140
gaatgggaga gcaatggcca gccagagaac aactacaaga ccacacctcc tgtgctggac    1200
tccgatggct cattctttct gtactccaag ctgacagtgg acaagtcccg gtggcaagag    1260
ggcaacgtgt tctcctgctc tgtgatgcac gaggccctgc acaaccacta cacccagaag    1320
tccctgtctc tgtcccct                                                   1338
```

<210> SEQ ID NO 430
<211> LENGTH: 446
<212> TYPE: PRT
<213> ORGANISM: Artificial Sequence
<220> FEATURE:
<223> OTHER INFORMATION: T0736H-IgG4-P E356K amino acid sequence

<400> SEQUENCE: 430

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Lys Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Asp Gly Tyr Gly Ser Phe Ser Arg Leu Ile Gln Leu Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Cys Ser Arg Ser Thr Ser Glu Ser Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Thr Cys Asn Val Asp His
        195                 200                 205

Lys Pro Ser Asn Thr Lys Val Asp Lys Arg Val Glu Ser Lys Tyr Gly
        210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Lys Glu Met Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro
        435                 440                 445

<210> SEQ ID NO 431
<211> LENGTH: 1338
<212> TYPE: DNA
<213> ORGANISM: Artificial Sequence
<220> FEATURE:
<223> OTHER INFORMATION: Nucleic acid encoding T0687H-IgG4-P E356K

<400> SEQUENCE: 431
caggttcagc tgattcagtc tggcgccgaa gtgaagaaac tggcgcctc tgtgaaggtg    60 tcctgcaagg cctccagata ctccttcacc tcctactaca tgcactgggt ccgacaggcc   120

```
cctggacaag gattggagtg gatgggcatc atcaacccca agtccggctc cacctcttac    180
gcccagaaat tccagggcag agtgaccatg accagagaca cctctacctc caccgtgtac    240
atggaactgt ccagcctgag atccgaggac accgccgtgt actactgtgc cagagatggc    300
tacggctcct tcagcagagt gatccagttg tggggccagg gcacactggt cacagtgtcc    360
tctgcttcca ccaagggacc cagcgtgttc cctctggctc cttgctccag atccacctcc    420
gagtctacag ctgctctggg ctgcctggtc aaggactact tcctgagcc tgtgaccgtg     480 tcttggaact ctggcgctct gacatctggc gtgcacacct tccagctgt gctgcagtcc     540 tccggcctgt actctctgtc ctctgtcgtg accgtgcctt ccagctctct gggaacccag    600
acctacacct gtaatgtgga ccacaagcct tccaacacca aggtggacaa gcgcgtggaa    660
tctaagtacg gcctccttg tcctccatgt cctgctccag agtttctcgg cggacccctcc   720 gtgtttctgt tcctccaaa gcctaaggac accctgatga tctctcggac ccctgaagtg    780
acctgcgtgg tggtggatgt gtcccaagag gatcccgagg tgcagttcaa ttggtacgtg    840
gacggcgtgg aagtgcacaa cgccaagacc aagcctagag aggaacagta caactccacc    900
tacagagtgg tgtccgtgct gaccgtgctg caccaggatt ggctgaacgg caaagagtac    960
aagtgcaagg tgtccaacaa gggcctgcct agctccatcg aaaagaccat ctccaaggcc   1020
aagggccagc ctcgagaacc ccaggtttac accctgcctc caagccagaa agagatgacc   1080
aagaaccagg tgtccctgac ctgcctcgtg aagggcttct acccttccga tatcgccgtg   1140
gaatgggaga gcaatggcca gccagagaac aactacaaga ccacacctcc tgtgctggac   1200
tccgatggct cattctttct gtactccaag ctgacagtgg acaagtcccg gtggcaagag   1260
ggcaacgtgt tctcctgctc tgtgatgcac gaggccctgc acaaccacta cacccagaag   1320
tccctgtctc tgtccccct                                                1338
```

<210> SEQ ID NO 432
<211> LENGTH: 446
<212> TYPE: PRT
<213> ORGANISM: Artificial Sequence
<220> FEATURE:
<223> OTHER INFORMATION: T0687H-IgG4-P E356K amino acid sequence

<400> SEQUENCE: 432

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Val Ile Gln Leu Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
            180                 185                 190

Pro Ser Ser Ser Leu Gly Thr Gln Thr Tyr Thr Cys Asn Val Asp His
                195                 200                 205

Lys Pro Ser Asn Thr Lys Val Asp Lys Arg Val Glu Ser Lys Tyr Gly
            210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Lys Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Pro
            435                 440                 445

<210> SEQ ID NO 433
<211> LENGTH: 15
<212> TYPE: PRT
<213> ORGANISM: Homo sapiens

<400> SEQUENCE: 433

Ala Arg Glu Gly Tyr Ser Ser Ile Lys Tyr Tyr Gly Met Asp Val
1               5                   10                  15

<210> SEQ ID NO 434
<211> LENGTH: 366
<212> TYPE: DNA
<213> ORGANISM: Homo sapiens

<400> SEQUENCE: 434
gaggtgcagc tggtggagtc tgggggaggc tttgtccagc ctggggggtc cctgagactc      60
```

```
tcctgtgcag tctctggatt cacctttaat agctattgga tgagctgggt ccgccaggct    120
ccagggaagg ggctggagtg ggtggccaac ataaaccaag atggaagtga gaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagta tcaagtatta tggtatggac gtctggggcc aagggaccac ggtcaccgtc    360
tcctca                                                                366
```

<210> SEQ ID NO 435
<211> LENGTH: 122
<212> TYPE: PRT
<213> ORGANISM: Homo sapiens

<400> SEQUENCE: 435

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Thr Phe Asn Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
        115                 120
```

<210> SEQ ID NO 436
<211> LENGTH: 8
<212> TYPE: PRT
<213> ORGANISM: Homo sapiens

<400> SEQUENCE: 436

```
Ile Asn Gln Asp Gly Ser Arg Lys
1               5
```

<210> SEQ ID NO 437
<211> LENGTH: 366
<212> TYPE: DNA
<213> ORGANISM: Homo sapiens

<400> SEQUENCE: 437

```
gaggtgcagc tggtggagtc tgggggaggc tttgtccagc ctggggggtc cctgagactc     60
tcctgtgcag tctctggatt cacctttaat agctattgga tgagctgggt ccgccaggct    120
ccagggaagg ggctggagtg ggtggccaac ataaaccaag atggaagtag aaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagta tctcctatta tggtatggac gtctggggcc aagggaccac ggtcaccgtc    360
tcctca                                                                366
```

<210> SEQ ID NO 438

```
<211> LENGTH: 122
<212> TYPE: PRT
<213> ORGANISM: Homo sapiens

<400> SEQUENCE: 438
```

| Glu | Val | Gln | Leu | Val | Glu | Ser | Gly | Gly | Gly | Phe | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Val | Ser | Gly | Phe | Thr | Phe | Asn | Ser | Tyr |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Asn | Ile | Asn | Gln | Asp | Gly | Ser | Arg | Lys | Phe | Tyr | Val | Ala | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Met | Ser | Arg | Asp | Asn | Ala | Lys | Lys | Ser | Val | Tyr |
|---|---|---|---|---|---|---|---|---|---|---|---|---|---|---|---|
| 65 | | | | | 70 | | | | | 75 | | | | | 80 |

| Val | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Gly | Tyr | Ser | Ile | Ser | Tyr | Tyr | Gly | Met | Asp | Val | Trp |
|---|---|---|---|---|---|---|---|---|---|---|---|---|---|---|
| | | | 100 | | | | | 105 | | | | | 110 | |

| Gly | Gln | Gly | Thr | Thr | Val | Thr | Val | Ser | Ser |
|---|---|---|---|---|---|---|---|---|---|
| | | | 115 | | | | | 120 | |

```
<210> SEQ ID NO 439
<211> LENGTH: 366
<212> TYPE: DNA
<213> ORGANISM: Homo sapiens
<400> SEQUENCE: 439
gaggtgcagc tggtggagtc tgggggaggc tttgtccagc ctggggggtc cctgagactc      60
tcctgtgcag tctctggatt cacctttaat agctattgga tgagctgggt ccgccaggct     120
ccagggaagg gctggagtg gtggccaac ataaaccaag atggaagtag aaaattctat       180
gtggcctctg tgaagggccg attcaccatg tccagagaca cgccaagaa tcagtgtat       240
gtacaaatga acagcctgag agccgaggac acggctgtgt attactgtgc gagagagggg    300
tatagtagta tcaagtatta tggtatggac gtctggggcc aagggaccac ggtcaccgtc    360
tcctca                                                                366

<210> SEQ ID NO 440
<211> LENGTH: 122
<212> TYPE: PRT
<213> ORGANISM: Homo sapiens

<400> SEQUENCE: 440
```

| Glu | Val | Gln | Leu | Val | Glu | Ser | Gly | Gly | Gly | Phe | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Val | Ser | Gly | Phe | Thr | Phe | Asn | Ser | Tyr |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Val |
|---|---|---|---|---|---|---|---|---|---|---|---|---|---|---|---|
| | | 35 | | | | | 40 | | | | | 45 | | | |

| Ala | Asn | Ile | Asn | Gln | Asp | Gly | Ser | Arg | Lys | Phe | Tyr | Val | Ala | Ser | Val |
|---|---|---|---|---|---|---|---|---|---|---|---|---|---|---|---|
| | 50 | | | | | 55 | | | | | 60 | | | | |

| Lys | Gly | Arg | Phe | Thr | Met | Ser | Arg | Asp | Asn | Ala | Lys | Lys | Ser | Val | Tyr |
|---|---|---|---|---|---|---|---|---|---|---|---|---|---|---|---|
| 65 | | | | | 70 | | | | | 75 | | | | | 80 |

| Val | Gln | Met | Asn | Ser | Leu | Arg | Ala | Glu | Asp | Thr | Ala | Val | Tyr | Tyr | Cys |
|---|---|---|---|---|---|---|---|---|---|---|---|---|---|---|---|
| | | | | 85 | | | | | 90 | | | | | 95 | |

| Ala | Arg | Glu | Gly | Tyr | Ser | Ser | Ile | Lys | Tyr | Tyr | Gly | Met | Asp | Val | Trp |
|---|---|---|---|---|---|---|---|---|---|---|---|---|---|---|---|

```
                    100                 105                 110
Gly Gln Gly Thr Thr Val Thr Val Ser Ser
            115                 120

<210> SEQ ID NO 441
<211> LENGTH: 8
<212> TYPE: PRT
<213> ORGANISM: Homo sapiens

<400> SEQUENCE: 441

Gly Phe Arg Phe Asn Ser Tyr Trp
1               5

<210> SEQ ID NO 442
<211> LENGTH: 366
<212> TYPE: DNA
<213> ORGANISM: Homo sapiens

<400> SEQUENCE: 442
gaggtgcagc tggtggagtc tgggggaggc tttgtccagc ctggggggtc cctgagactc      60
tcctgtgcag tctctggatt cagatttaat agctattgga tgagctgggt ccgccaggct    120
ccagggaagg ggctggagtg ggtggccaac ataaaccaag atggaagtag aaaattctat    180
gtggcctctg tgaagggccg attcaccatg tccagagaca acgccaagaa atcagtgtat    240
gtacaaatga acagcctgag agccgaggac acggctgtgt attactgtgc gagagagggg    300
tatagtagta tcaagtatta tggtatggac gtctggggcc aagggaccac ggtcaccgtc    360
tcctca                                                              366

<210> SEQ ID NO 443
<211> LENGTH: 122
<212> TYPE: PRT
<213> ORGANISM: Homo sapiens

<400> SEQUENCE: 443

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
            115                 120

<210> SEQ ID NO 444
<211> LENGTH: 8
<212> TYPE: PRT
<213> ORGANISM: Homo sapiens

<400> SEQUENCE: 444

Ile Asn Gln Gly Gly Ser Arg Lys
1               5
```

<210> SEQ ID NO 445
<211> LENGTH: 366
<212> TYPE: DNA
<213> ORGANISM: Homo sapiens

<400> SEQUENCE: 445

```
gaggtgcagc tggtggagtc tgggggaggc tttgtccagc ctggggggtc cctgagactc    60
tcctgtgcag tctctggatt cagatttaat agctattgga tgagctgggt ccgccaggct   120
ccagggaagg ggctggagtg ggtggccaac ataaaccaag gcggaagtag aaaattctat   180
gtggcctctg tgaagggccg attcaccatg tccagagaca acgccaagaa atcagtgtat   240
gtacaaatga acagcctgag agccgaggac acggctgtgt attactgtgc gagagagggg   300
tatagtagta tcaagtatta tggtatggac gtctggggcc aagggaccac ggtcaccgtc   360
tcctca                                                              366
```

<210> SEQ ID NO 446
<211> LENGTH: 122
<212> TYPE: PRT
<213> ORGANISM: Homo sapiens

<400> SEQUENCE: 446

Glu Val Gln Leu Val Glu Ser Gly Gly Gly Phe Val Gln Pro Gly Gly
1               5                   10                  15
Ser Leu Arg Leu Ser Cys Ala Val Ser Gly Phe Arg Phe Asn Ser Tyr
            20                  25                  30
Trp Met Ser Trp Val Arg Gln Ala Pro Gly Lys Gly Leu Glu Trp Val
        35                  40                  45
Ala Asn Ile Asn Gln Gly Gly Ser Arg Lys Phe Tyr Val Ala Ser Val
    50                  55                  60
Lys Gly Arg Phe Thr Met Ser Arg Asp Asn Ala Lys Lys Ser Val Tyr
65                  70                  75                  80
Val Gln Met Asn Ser Leu Arg Ala Glu Asp Thr Ala Val Tyr Tyr Cys
                85                  90                  95
Ala Arg Glu Gly Tyr Ser Ser Ile Lys Tyr Tyr Gly Met Asp Val Trp
            100                 105                 110
Gly Gln Gly Thr Thr Val Thr Val Ser Ser
        115                 120

<210> SEQ ID NO 447
<211> LENGTH: 8
<212> TYPE: PRT
<213> ORGANISM: Homo sapiens

<400> SEQUENCE: 447

Ile Asn Gln Trp Gly Ser Arg Lys
1               5

<210> SEQ ID NO 448
<211> LENGTH: 366
<212> TYPE: DNA
<213> ORGANISM: Homo sapiens

<400> SEQUENCE: 448

```
gaggtgcagc tggtggagtc tgggggaggc tttgtccagc ctggggggtc cctgagactc    60
tcctgtgcag tctctggatt cagatttaat agctattgga tgagctgggt ccgccaggct   120
```

```
ccagggaagg ggctggagtg ggtggccaac ataaaccaat ggggaagtag aaaattctat      180
gtggcctctg tgaagggccg attcaccatg tccagagaca acgccaagaa atcagtgtat      240
gtacaaatga acagcctgag agccgaggac acggctgtgt attactgtgc gagagagggg      300
tatagtagta tcaagtatta tggtatggac gtctggggcc aagggaccac ggtcaccgtc      360
tcctca                                                                 366
```

<210> SEQ ID NO 449
<211> LENGTH: 122
<212> TYPE: PRT
<213> ORGANISM: Homo sapiens

<400> SEQUENCE: 449

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Trp Gly Ser Arg Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
        115                 120

<210> SEQ ID NO 450
<211> LENGTH: 8
<212> TYPE: PRT
<213> ORGANISM: Homo sapiens

<400> SEQUENCE: 450

Ile Asn Gln Asp Gly Phe Arg Lys
1               5

<210> SEQ ID NO 451
<211> LENGTH: 366
<212> TYPE: DNA
<213> ORGANISM: Homo sapiens

<400> SEQUENCE: 451

```
gaggtgcagc tggtggagtc tgggggaggc tttgtccagc ctggggggtc cctgagactc      60
tcctgtgcag tctctggatt cagatttaat agctattgga tgagctgggt ccgccaggct      120
ccagggaagg ggctggagtg gtggccaac ataaaccaag atggattcag aaaattctat       180
gtggcctctg tgaagggccg attcaccatg tccagagaca acgccaagaa atcagtgtat      240
gtacaaatga acagcctgag agccgaggac acggctgtgt attactgtgc gagagagggg      300
tatagtagta tcaagtatta tggtatggac gtctggggcc aagggaccac ggtcaccgtc      360
tcctca                                                                 366
```

<210> SEQ ID NO 452
<211> LENGTH: 122
<212> TYPE: PRT

<213> ORGANISM: Homo sapiens

<400> SEQUENCE: 452

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Phe Arg Lys Phe Tyr Val Ala Ser Val
    50                  55                  60

Lys Gly Arg Phe Thr Met Ser Arg Asp Asn Ala Lys Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
        115                 120

<210> SEQ ID NO 453
<211> LENGTH: 366
<212> TYPE: DNA
<213> ORGANISM: Homo sapiens

<400> SEQUENCE: 453
gaggtgcagc tggttgaatc tggcggcgga tttgttcagc ctggcggctc tctgagactg     60
agctgtgccg tgtccggctt ccggttcaac agctactgga tgtcctgggt ccgacaggcc    120
cctggcaaag gacttgagtg gtcgccaac atcaaccagg acggcagccg gaagttttac     180
gtggcctctg tgaagggcag attcaccatg agccgggaca cgccaagaa agaggtgtac     240
gtgcagatga acagcctgag agccgaggac accgccgtgt actattgtgc cagagagggc    300
tacagcagca tcaagtacta cggcatggac gtgtggggcc agggcacaac agtgacagtc    360
tcttct                                                                366

<210> SEQ ID NO 454
<211> LENGTH: 122
<212> TYPE: PRT
<213> ORGANISM: Homo sapiens

<400> SEQUENCE: 454

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Lys Lys Glu Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

```
Gly Gln Gly Thr Thr Val Thr Val Ser Ser
        115                 120
```

<210> SEQ ID NO 455
<211> LENGTH: 366
<212> TYPE: DNA
<213> ORGANISM: Homo sapiens

<400> SEQUENCE: 455

```
gaggtgcagc tggttgaatc tggcggcgga tttgttcagc ctggcggctc tctgagactg      60
agctgtgccg tgtccggctt ccggttcaac agctactgga tgtcctgggt ccgacaggcc     120
cctggcaaag gacttgagtg gtcgccaac atcaaccagg acggcagccg gaagttttac      180
gtggcctctg tgaagggcag attcaccatg agccgggaca cgccgacaa aagcgtgtac      240
gtgcagatga acagcctgag agccgaggac accgccgtgt actattgtgc cagagagggc     300
tacagcagca tcaagtacta cggcatggac gtgtggggcc agggcacaac agtgacagtc     360
tcttct                                                                366
```

<210> SEQ ID NO 456
<211> LENGTH: 122
<212> TYPE: PRT
<213> ORGANISM: Homo sapiens

<400> SEQUENCE: 456

```
Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Asp Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
        115                 120
```

<210> SEQ ID NO 457
<211> LENGTH: 366
<212> TYPE: DNA
<213> ORGANISM: Homo sapiens

<400> SEQUENCE: 457

```
gaggtgcagc tggttgaatc tggcggcgga tttgttcagc ctggcggctc tctgagactg      60
agctgtgccg tgtccggctt ccggttcaac agctactgga tgtcctgggt ccgacaggcc     120
cctggcaaag gacttgagtg gtcgccaac atcaaccagg acggcagccg gaagttttac      180
gtggcctctg tgaagggcag attcaccatg agccgggaca cgccgagaa aagcgtgtac      240
gtgcagatga acagcctgag agccgaggac accgccgtgt actattgtgc cagagagggc     300
tacagcagca tcaagtacta cggcatggac gtgtggggcc agggcacaac agtgacagtc     360
tcttct                                                                366
```

<210> SEQ ID NO 458
<211> LENGTH: 122
<212> TYPE: PRT
<213> ORGANISM: Homo sapiens

<400> SEQUENCE: 458

Glu Val Gln Leu Val Glu Ser Gly Gly Gly Phe Val Gln Pro Gly Gly
1               5                   10                  15

Ser Leu Arg Leu Ser Cys Ala Val Ser Gly Phe Arg Phe Asn Ser Tyr
            20                  25                  30

Trp Met Ser Trp Val Arg Gln Ala Pro Gly Lys Gly Leu Glu Trp Val
        35                  40                  45

Ala Asn Ile Asn Gln Asp Gly Ser Arg Lys Phe Tyr Val Ala Ser Val
    50                  55                  60

Lys Gly Arg Phe Thr Met Ser Arg Asp Asn Ala Glu Lys Ser Val Tyr
65                  70                  75                  80

Val Gln Met Asn Ser Leu Arg Ala Glu Asp Thr Ala Val Tyr Tyr Cys
                85                  90                  95

Ala Arg Glu Gly Tyr Ser Ser Ile Lys Tyr Tyr Gly Met Asp Val Trp
            100                 105                 110

Gly Gln Gly Thr Thr Val Thr Val Ser Ser
        115                 120

<210> SEQ ID NO 459
<211> LENGTH: 38
<212> TYPE: PRT
<213> ORGANISM: Homo sapiens

<400> SEQUENCE: 459

Phe Tyr Val Ala Ser Val Lys Gly Arg Phe Thr Met Ser Arg Asp Asn
1               5                   10                  15

Ala Asp Lys Ser Val Tyr Val Gln Met Asn Ser Leu Arg Ala Glu Asp
            20                  25                  30

Thr Ala Val Tyr Tyr Cys
        35

<210> SEQ ID NO 460
<211> LENGTH: 38
<212> TYPE: PRT
<213> ORGANISM: Homo sapiens

<400> SEQUENCE: 460

Phe Tyr Val Ala Ser Val Lys Gly Arg Phe Thr Met Ser Arg Asp Asn
1               5                   10                  15

Ala Glu Lys Ser Val Tyr Val Gln Met Asn Ser Leu Arg Ala Glu Asp
            20                  25                  30

Thr Ala Val Tyr Tyr Cys
        35

<210> SEQ ID NO 461
<211> LENGTH: 38
<212> TYPE: PRT
<213> ORGANISM: Homo sapiens

<400> SEQUENCE: 461

Phe Tyr Val Ala Ser Val Lys Gly Arg Phe Thr Met Ser Arg Asp Asn
1               5                   10                  15

Ala Lys Lys Glu Val Tyr Val Gln Met Asn Ser Leu Arg Ala Glu Asp
            20                  25                  30

```
<210> SEQ ID NO 462
<211> LENGTH: 8
<212> TYPE: PRT
<213> ORGANISM: Homo sapiens

<400> SEQUENCE: 462

Arg Tyr Ser Phe Thr Ser Tyr Tyr
1               5

<210> SEQ ID NO 463
<211> LENGTH: 8
<212> TYPE: PRT
<213> ORGANISM: Homo sapiens

<400> SEQUENCE: 463

Ile Asn Pro Lys Thr Gly Asp Thr
1               5

<210> SEQ ID NO 464
<211> LENGTH: 14
<212> TYPE: PRT
<213> ORGANISM: Homo sapiens

<400> SEQUENCE: 464

Ala Arg Asp Gly Tyr Gly Ser Ser Ala Arg Cys Leu Gln Leu
1               5                   10

<210> SEQ ID NO 465
<211> LENGTH: 363
<212> TYPE: DNA
<213> ORGANISM: Homo sapiens

<400> SEQUENCE: 465
caggtgcagc tggtgcagtc tggggctgag gtgaaaaagc ctggggcctc agtgaaggtt      60
tcctgcaagg catctagata cagcttcacc agctactatc tgcattgggt gcgacaggcc     120
cctggacaag gcttgagtg gatgggaata atcaacccta aaactggtga cacaagctac     180
gcacagaagt tccagggcag agtcaccatg accagggaca cgtccacgac cacagtctac     240
atggagctga gcagcctgag atctgaggac acggccgtgt attactgtgc gagagatggg     300
tatggcagct cggcccggtg cctccagctc tggggccagg gcaccctggt caccgtctcc     360
tca                                                                  363

<210> SEQ ID NO 466
<211> LENGTH: 121
<212> TYPE: PRT
<213> ORGANISM: Homo sapiens

<400> SEQUENCE: 466

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Leu His Trp Val Arg Gln Ala Pro Gly Gln Gly Leu Glu Trp Met
        35                  40                  45

Gly Ile Ile Asn Pro Lys Thr Gly Asp Thr Ser Tyr Ala Gln Lys Phe
    50                  55                  60
```

(preceding continuation)

Thr Ala Val Tyr Tyr Cys
        35

```
Gln Gly Arg Val Thr Met Thr Arg Asp Thr Ser Thr Thr Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Ser Ser Ala Arg Cys Leu Gln Leu Trp Gly
            100                 105                 110

Gln Gly Thr Leu Val Thr Val Ser Ser
        115                 120
```

<210> SEQ ID NO 467
<211> LENGTH: 8
<212> TYPE: PRT
<213> ORGANISM: Homo sapiens

<400> SEQUENCE: 467

```
Ile Asn Pro Lys Ser Gly Ser Thr
 1               5
```

<210> SEQ ID NO 468
<211> LENGTH: 14
<212> TYPE: PRT
<213> ORGANISM: Homo sapiens

<400> SEQUENCE: 468

```
Ala Arg Asp Gly Tyr Gly Ser Ser Ser Arg Cys Leu Gln Leu
 1               5                   10
```

<210> SEQ ID NO 469
<211> LENGTH: 363
<212> TYPE: DNA
<213> ORGANISM: Homo sapiens

<400> SEQUENCE: 469

```
caggtgcagt tgatacagtc tggggctgag gtgaagaagc ctggggcctc agtgaaggtt     60
tcctgcaagg catctagata cagcttcacc agctactata tgcactgggt gcgacaggcc    120
cctggacaag ggcttgagtg gatgggaata atcaaccctaaa aagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct cgtcccggtg cctccagctc tggggccagg gcaccctggt caccgtctcc    360
tca                                                                  363
```

<210> SEQ ID NO 470
<211> LENGTH: 121
<212> TYPE: PRT
<213> ORGANISM: Homo sapiens

<400> SEQUENCE: 470

```
Gln Val Gln Leu Ile Gln Ser Gly Ala Glu Val Lys Lys Pro Gly Ala
 1               5                  10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Tyr Ala Gln Lys Phe
        50                  55                  60

Gln Gly Arg Val Thr Met Thr Arg Asp Thr Ser Thr Thr Thr Val Tyr
 65                  70                  75                  80
```

```
Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120
```

<210> SEQ ID NO 471
<211> LENGTH: 363
<212> TYPE: DNA
<213> ORGANISM: Homo sapiens

<400> SEQUENCE: 471

```
caggtgcagc tgatacagtc tggggctgag gtgcagaagc ctggggcctc agtgaaggtt      60
tcctgcaagg catctagata cagcttcacc agctactata tgcactgggt gcgacaggcc     120
cctggacaag ggcttgagtg gatgggaata atcaaccctc aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccggtg cctccagctc tggggccagg gcaccctggt caccgtctcc     360
tca                                                                   363
```

<210> SEQ ID NO 472
<211> LENGTH: 121
<212> TYPE: PRT
<213> ORGANISM: Homo sapiens

<400> SEQUENCE: 472

```
Gln Val Gln Leu Ile Gln Ser Gly Ala Glu Val Gln Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120
```

<210> SEQ ID NO 473
<211> LENGTH: 363
<212> TYPE: DNA
<213> ORGANISM: Homo sapiens

<400> SEQUENCE: 473

```
caggtgcagc tggtgcagtc tggggctgag gtgaagaagc ctggggcctc agtgaaggtt      60
tcctgcaagg catctagata cagcttcacc agctactata tgcactgggt gcgacaggcc     120
cctggacaag ggcttgagtg gatgggaata atcaaccctc aaagtggtag tacaagttac     180
gcacagaagt tccagggcag agtcaccatg accagggaca cgtccacgag cacagtctac     240
```

```
atggagctga tcagcctgag atctgaggac acggccgtgt attactgtgc gagagatggg    300
tatggcagct cgtccggtg cctccagctc tggggccagg gcaccctggt caccgtctcc    360
tca                                                                  363
```

<210> SEQ ID NO 474
<211> LENGTH: 121
<212> TYPE: PRT
<213> ORGANISM: Homo sapiens

<400> SEQUENCE: 474

```
Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ile Ser Leu Arg Ser Glu Asp Thr Ala Val Tyr Tyr Cys
                85                  90                  95

Ala Arg Asp Gly Tyr Gly Ser Ser Ser Arg Cys Leu Gln Leu Trp Gly
            100                 105                 110

Gln Gly Thr Leu Val Thr Val Ser Ser
        115                 120
```

<210> SEQ ID NO 475
<211> LENGTH: 363
<212> TYPE: DNA
<213> ORGANISM: Homo sapiens

<400> SEQUENCE: 475

```
caggtgcagc tggtgcagtc tggggctgag gtgcagaaga ctggggcctc agtgaaggtt    60
tcctgcaagg catctagata cagcttcacc agctactata tgcactgggt gcgacaggcc   120
cctggacaag ggcttgagtg gatgggaata atcaacccta aaagtggtag tacaagttac   180
gcacagaagt tccagggcag agtcaccatg accaggaca cgtccacgag cacagtctac   240
atggagctga gcagcctgag atctgaggac acggccgtgt attactgtgc gagagatggg   300
tatggcagct cgtccggtg cctccagctc tggggccagg gcaccctggt caccgtctcc   360
tca                                                                  363
```

<210> SEQ ID NO 476
<211> LENGTH: 121
<212> TYPE: PRT
<213> ORGANISM: Homo sapiens

<400> SEQUENCE: 476

```
Gln Val Gln Leu Val Gln Ser Gly Ala Glu Val Gln Lys Thr Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60
```

Gln Gly Arg Val Thr Met Thr Arg Asp Thr Ser Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120

<210> SEQ ID NO 477
<211> LENGTH: 8
<212> TYPE: PRT
<213> ORGANISM: Homo sapiens

<400> SEQUENCE: 477

Ile Asn Pro Lys Ser Gly Asp Thr
1               5

<210> SEQ ID NO 478
<211> LENGTH: 363
<212> TYPE: DNA
<213> ORGANISM: Homo sapiens

<400> SEQUENCE: 478
caggtgcagc tggtgcagtc tggggctgag gtgaagaagc ctggggcctc agtgaaggtt      60
tcctgcaagg catctagata cagcttcacc agctactata tgcactgggt gcgacaggcc    120
cctggacaag gcttgagtg gatgggaata atcaacccta aaagtggtga cacaagctac     180
gcacagaagt tccagggcag agtcaccatg accagggaca cgtccacgag cacagtctac    240
atggagctga acagcctgag atctgaggac acggccgtgt attactgtgc gagagatggg    300
tatggcagct cggcccggtg cctccagctc tggggccagg gcgccctggt caccgtctcc    360
tca                                                                  363

<210> SEQ ID NO 479
<211> LENGTH: 121
<212> TYPE: PRT
<213> ORGANISM: Homo sapiens

<400> SEQUENCE: 479

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Asp Thr Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Asn Ser Leu Arg Ser Glu Asp Thr Ala Val Tyr Tyr Cys
                85                  90                  95

Ala Arg Asp Gly Tyr Gly Ser Ser Ala Arg Cys Leu Gln Leu Trp Gly
            100                 105                 110

Gln Gly Thr Leu Val Thr Val Ser Ser
        115                 120

<210> SEQ ID NO 480
<211> LENGTH: 363
<212> TYPE: DNA
<213> ORGANISM: Homo sapiens

<400> SEQUENCE: 480
caggtgcagc tggtgcagtc tggggctgag gtgaagaagc ctggggcctc agtgaaggtt    60
tcctgcaagg catctagata cagcttcacc agctactata tgcactgggt gcgacaggcc   120
cctggacaag gcttgagtg gatgggaata atcaaccctaaaagtggtga cacaagctac    180 gcacagaagt tccagggcag agtcaccatg accagggaca cgtccacgag cacagtctac   240
atggacctga gcagcctgag atctgaggac acggccgtgt attactgtgc gagagatggg   300
tatggcagct cggcccggtg cctccagctc tggggccagg gcaccctggt caccgtctcc   360
tca                                                                 363

<210> SEQ ID NO 481
<211> LENGTH: 121
<212> TYPE: PRT
<213> ORGANISM: Homo sapiens

<400> SEQUENCE: 481

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Asp Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Asp Gly Tyr Gly Ser Ser Ala Arg Cys Leu Gln Leu Trp Gly
            100                 105                 110

Gln Gly Thr Leu Val Thr Val Ser Ser
        115                 120

<210> SEQ ID NO 482
<211> LENGTH: 363
<212> TYPE: DNA
<213> ORGANISM: Homo sapiens

<400> SEQUENCE: 482
caggtgcagc tggtgcagtc tggggctgag gtgaagaaga ctggggcctc agtgaaggtt    60
tcctgcaagg catctagata cagcttcacc agctactata tgcactgggt gcgacaggcc   120
cctggacaag gcttgagtg gatgggaata atcaaccctaaaagtggtag tacaagttac    180 gcacagaagt tccagggcag agtcaccatg accagggaca cgtccacgag cacagtctac   240
atggagctga gcagcctgag atctgaggac acggccgtgt attactgtgc gagagatggg   300
tatggcagct cgtcccggtg cctccagctc tggggccagg gcaccctggt caccgtctcc   360
tca                                                                 363

<210> SEQ ID NO 483
<211> LENGTH: 121
<212> TYPE: PRT

<213> ORGANISM: Homo sapiens

<400> SEQUENCE: 483

Gln Val Gln Leu Val Gln Ser Gly Ala Glu Val Lys Lys Thr Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
            115                 120

<210> SEQ ID NO 484
<211> LENGTH: 363
<212> TYPE: DNA
<213> ORGANISM: Homo sapiens

<400> SEQUENCE: 484
caggtgcagc tggtgcagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaacccta aaagtggtag tacaagttac     180
gaacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccggtg cctccagctc tggggccagg gcaccctggt caccgtctcc     360
tca                                                                  363

<210> SEQ ID NO 485
<211> LENGTH: 121
<212> TYPE: PRT
<213> ORGANISM: Homo sapiens

<400> SEQUENCE: 485

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Glu Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120

<210> SEQ ID NO 486
<211> LENGTH: 363
<212> TYPE: DNA
<213> ORGANISM: Homo sapiens

<400> SEQUENCE: 486
caggtgcagc tggtgcagtc tggggctgag gtgcaaaagc ctggggcctc agtgaaggtt    60
tcctgcaagg catctagata cagcttcacc agctactatc tgcattgggt gcgacaggcc   120
cctggacaag gcttgagtg gatgggaata atcaaccctaa aaactggtga cacaagctac   180
gcacagaagt tccagggcag agtcaccatg accagggaca cgtccacgac cacagtctac   240
atggagctga gcagcctgag atctgaggac acggccgtgt attactgtgc gagagatggg   300
tatggcagct cggcccggtg cctccagctc tggggccagg gcaccctggt caccgtctcc   360
tca                                                                  363

<210> SEQ ID NO 487
<211> LENGTH: 121
<212> TYPE: PRT
<213> ORGANISM: Homo sapiens

<400> SEQUENCE: 487

Gln Val Gln Leu Val Gln Ser Gly Ala Glu Val Gln Lys Pro Gly Ala
1               5                   10                  15

Ser Val Lys Val Ser Cys Lys Ala Ser Arg Tyr Ser Phe Thr Ser Tyr
            20                  25                  30

Tyr Leu His Trp Val Arg Gln Ala Pro Gly Gln Gly Leu Glu Trp Met
        35                  40                  45

Gly Ile Ile Asn Pro Lys Thr Gly Asp Thr Ser Tyr Ala Gln Lys Phe
    50                  55                  60

Gln Gly Arg Val Thr Met Thr Arg Asp Thr Ser Thr Thr Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ala Arg Cys Leu Gln Leu Trp Gly
            100                 105                 110

Gln Gly Thr Leu Val Thr Val Ser Ser
        115                 120

<210> SEQ ID NO 488
<211> LENGTH: 363
<212> TYPE: DNA
<213> ORGANISM: Homo Sapiens

<400> SEQUENCE: 488
caggtgcagc tggtgcagtc tggggctgag gtgaagaagc ctggggcctc agtgaaggtt    60
tcctgcaagg catctagata cagcttcacc agctactata tgcactgggt gcgacaggcc   120
cctggacaag gcttgagtg gatgggaata atcaaccctaa aaagtggtag tacaagttac   180
gcacagaagt tccagggcag agtcaccatg accagggaca cgtccacgag cacagtctac   240
atggagctga acagcctgag atctgaggac acggccgtgt attactgtgc gagagatggg   300
tatggcagct cgtccggtg cctccagctc tggggccagg gcaccctggt caccgtctcc   360
tca                                                                  363

<210> SEQ ID NO 489
<211> LENGTH: 8
<212> TYPE: PRT
<213> ORGANISM: Homo Sapiens

<400> SEQUENCE: 489

Gly Phe Thr Phe Asn Ser Tyr Trp
1               5

<210> SEQ ID NO 490
<211> LENGTH: 8
<212> TYPE: PRT
<213> ORGANISM: Homo Sapiens

<400> SEQUENCE: 490

Gly Phe Thr Phe Asn Ser Tyr Trp
1               5

<210> SEQ ID NO 491
<211> LENGTH: 8
<212> TYPE: PRT
<213> ORGANISM: Homo Sapiens

<400> SEQUENCE: 491

Gly Phe Thr Phe Asn Ser Tyr Trp
1               5

<210> SEQ ID NO 492
<211> LENGTH: 8
<212> TYPE: PRT
<213> ORGANISM: Homo Sapiens

<400> SEQUENCE: 492

Gly Phe Thr Phe Asn Ser Tyr Trp
1               5

<210> SEQ ID NO 493
<211> LENGTH: 8
<212> TYPE: PRT
<213> ORGANISM: Homo Sapiens

<400> SEQUENCE: 493

Gly Phe Thr Phe Asn Ser Tyr Trp
1               5

<210> SEQ ID NO 494
<211> LENGTH: 8
<212> TYPE: PRT
<213> ORGANISM: Homo Sapiens

<400> SEQUENCE: 494

Gly Phe Thr Phe Asn Ser Tyr Trp
1               5

<210> SEQ ID NO 495
<211> LENGTH: 8
<212> TYPE: PRT
<213> ORGANISM: Homo Sapiens

<400> SEQUENCE: 495

Gly Phe Thr Phe Asn Ser Tyr Trp
1               5

<210> SEQ ID NO 496

```
<211> LENGTH: 8
<212> TYPE: PRT
<213> ORGANISM: Homo Sapiens

<400> SEQUENCE: 496

Gly Phe Thr Phe Asn Ser Tyr Trp
1               5

<210> SEQ ID NO 497
<211> LENGTH: 8
<212> TYPE: PRT
<213> ORGANISM: Homo Sapiens

<400> SEQUENCE: 497

Gly Phe Thr Phe Asn Ser Tyr Trp
1               5

<210> SEQ ID NO 498
<211> LENGTH: 8
<212> TYPE: PRT
<213> ORGANISM: Homo Sapiens

<400> SEQUENCE: 498

Gly Phe Thr Phe Asn Ser Tyr Trp
1               5

<210> SEQ ID NO 499
<211> LENGTH: 121
<212> TYPE: PRT
<213> ORGANISM: Homo Sapiens

<400> SEQUENCE: 499

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Asn Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120

<210> SEQ ID NO 500
<211> LENGTH: 363
<212> TYPE: DNA
<213> ORGANISM: Homo Sapiens

<400> SEQUENCE: 500
caggtgcagc tggtgcagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaaccta aaagtggtag tacaagttac      180
gcacagaagt tccagggcag agtcaccatg accagggaca cgtccacgag cacagtctac     240
```

```
atggacctga gcagcctgag atctgaggac acggccgtgt attactgtgc gagagatggg    300
tatggcagct cgtcccggtg cctccagctc tggggccagg gcaccctggt caccgtctcc    360
tca                                                                  363
```

<210> SEQ ID NO 501
<211> LENGTH: 121
<212> TYPE: PRT
<213> ORGANISM: Homo Sapiens

<400> SEQUENCE: 501

```
Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Asp Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120
```

<210> SEQ ID NO 502
<211> LENGTH: 8
<212> TYPE: PRT
<213> ORGANISM: Homo Sapiens

<400> SEQUENCE: 502

```
Gly Phe Ser Phe Thr Ser Tyr Tyr
1               5
```

<210> SEQ ID NO 503
<211> LENGTH: 8
<212> TYPE: PRT
<213> ORGANISM: Homo Sapiens

<400> SEQUENCE: 503

```
Ile Asn Pro Arg Ser Gly Ser Thr
1               5
```

<210> SEQ ID NO 504
<211> LENGTH: 14
<212> TYPE: PRT
<213> ORGANISM: Homo Sapiens

<400> SEQUENCE: 504

```
Ala Arg Asp Gly Tyr Gly Ser Ser Ser Arg Cys Phe Gln Tyr
1               5                   10
```

<210> SEQ ID NO 505
<211> LENGTH: 363
<212> TYPE: DNA
<213> ORGANISM: Homo Sapiens

<400> SEQUENCE: 505

```
caggtgcagc tggtgcagtc tggggctgag gtgaagaagc tggggcctc agtgaaggtt        60 tcctgcaagg catctggatt ctccttcacc agctactata tacactgggt gcgccaggcc      120
cctggacaag gacttgagtg gatgggaata atcaaccta gaagtggtag cacaagctac       180
gctcagaagt tccagggcag agtcaccatg accagggaca cgtccacgaa acagtctac       240 atggacctga gcagcctgag atctgaggac acggccgtat attactgtgc gagagatggg      300
tatggcagct cgtcccgatg cttccagtac tggggccagg gcaccctggt caccgtctcc      360
tca                                                                    363
```

<210> SEQ ID NO 506
<211> LENGTH: 121
<212> TYPE: PRT
<213> ORGANISM: Homo Sapiens

<400> SEQUENCE: 506

Gln Val Gln Leu Val Gln Ser Gly Ala Glu Val Lys Lys Pro Gly Ala
1               5                   10                  15

Ser Val Lys Val Ser Cys Lys Ala Ser Gly Phe Ser Phe Thr Ser Tyr
            20                  25                  30

Tyr Ile His Trp Val Arg Gln Ala Pro Gly Gln Gly Leu Glu Trp Met
        35                  40                  45

Gly Ile Ile Asn Pro Arg Ser Gly Ser Thr Ser Tyr Ala Gln Lys Phe
    50                  55                  60

Gln Gly Arg Val Thr Met Thr Arg Asp Thr Ser Thr Asn Thr Val Tyr
65                  70                  75                  80

Met Asp Leu Ser Ser Leu Arg Ser Glu Asp Thr Ala Val Tyr Tyr Cys
                85                  90                  95

Ala Arg Asp Gly Tyr Gly Ser Ser Arg Cys Phe Gln Tyr Trp Gly
            100                 105                 110

Gln Gly Thr Leu Val Thr Val Ser Ser
        115                 120

<210> SEQ ID NO 507
<211> LENGTH: 8
<212> TYPE: PRT
<213> ORGANISM: Homo Sapiens

<400> SEQUENCE: 507

Ile Asn Pro Lys Ser Gly Thr Thr
1               5

<210> SEQ ID NO 508
<211> LENGTH: 363
<212> TYPE: DNA
<213> ORGANISM: Homo Sapiens

<400> SEQUENCE: 508

```
caggtgcagc tggtgcagtc tggggctgag gtgaagaaga ctggggcctc agtgaaggtt       60
tcctgcaagg catctagata cagcttcacc agctactata tgcactgggt gcgacaggcc      120
cctggacaag ggcttgagtg gatgggaata atcaacccta aaagtggtac tacaagttac      180
gcacagaagt tccagggcag agtcaccatg accagggaca cgtccacgag cacagtctac      240
atggaactga gcagcctgag atctgaggac acggccgtgt attactgtgc gagagatggg      300
tatggcagct cgtcccggtg cctccagctc tggggccagg gcaccctggt caccgtctcc      360
tca                                                                    363
```

<210> SEQ ID NO 509
<211> LENGTH: 121
<212> TYPE: PRT
<213> ORGANISM: Homo Sapiens

<400> SEQUENCE: 509

Gln Val Gln Leu Val Gln Ser Gly Ala Glu Val Lys Lys Thr Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Thr Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120

<210> SEQ ID NO 510
<211> LENGTH: 363
<212> TYPE: DNA
<213> ORGANISM: Homo Sapiens

<400> SEQUENCE: 510
caggtgcagc tggtgcagtc tggggctgag gtgaagaaga ctggggcctc agtgaaggtt     60
tcctgccagg catctagata cagcttcacc agctactata tgcactgggt gcgacaggcc    120
cctggacaag gcttgagtg gatgggaata atcaaccctaa aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct cgtcccggtg cctccagctc tggggccagg gcaccctggt caccgtctcc    360
tca                                                                  363

<210> SEQ ID NO 511
<211> LENGTH: 121
<212> TYPE: PRT
<213> ORGANISM: Homo Sapiens

<400> SEQUENCE: 511

Gln Val Gln Leu Val Gln Ser Gly Ala Glu Val Lys Lys Thr Gly Ala
1               5                   10                  15

Ser Val Lys Val Ser Cys Gln Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120

<210> SEQ ID NO 512
<211> LENGTH: 363
<212> TYPE: DNA
<213> ORGANISM: Homo Sapiens

<400> SEQUENCE: 512
caggtgcagc tggtgcagtc tggggctgag gtgaagaagc ctggggcctc agtgaaggtt      60
tcctgcaagg catctagata cagcttcacc agctactata tgcactgggt gcgacaggcc     120
ccgggacaag gcttgagtg gatgggaata atcaaccctc aaagtggtag tacaagttac      180
gcacagaagt tccagggcag agtcaccatg accagggaca cgtccacgag cacagtctac     240
atggagctga gcagcctgag atctgaggac acggccgtgt attactgtgc gagagatggg    300
tatggcagct cgtcccggtg cctccagctc tggggccagg gcaccctggt caccgtctcc    360
tca                                                                  363

<210> SEQ ID NO 513
<211> LENGTH: 121
<212> TYPE: PRT
<213> ORGANISM: Homo Sapiens

<400> SEQUENCE: 513

Gln Val Gln Leu Val Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Cys Leu Gln Leu Trp Gly
            100                 105                 110

Gln Gly Thr Leu Val Thr Val Ser Ser
        115                 120

<210> SEQ ID NO 514
<211> LENGTH: 363
<212> TYPE: DNA
<213> ORGANISM: Homo Sapiens

<400> SEQUENCE: 514
caggtgcagc tggtgcagtc tggggctgag gtgaagaagc ctggggcctc agtgaaggtt      60
tcctgcaagg catctagata cagcttcacc agctactatt tgcactgggt gcgacaggcc    120
cctggacaag gcttgagtg gatgggaata atcaaccctc aaagtggtag tacaagttac     180
gcacagaagt tccagggcag agtcaccatg accagggaca cgtccacgag cacagtctac    240
atggagctga gcagcctgag atctgaggac acggccgtgt attactgtgc gagagatggg   300

```
tatggcagct cgtcccggtg cctccagctc tggggccagg gcaccctggt caccgtctcc    360
tca                                                                  363
```

<210> SEQ ID NO 515
<211> LENGTH: 121
<212> TYPE: PRT
<213> ORGANISM: Homo Sapiens

<400> SEQUENCE: 515

Gln Val Gln Leu Val Gln Ser Gly Ala Glu Val Lys Lys Thr Gly Ala
1               5                   10                  15

Ser Val Lys Val Ser Cys Gln Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Cys Leu Gln Leu Trp Gly
            100                 105                 110

Gln Gly Thr Leu Val Thr Val Ser Ser
        115                 120

<210> SEQ ID NO 516
<211> LENGTH: 363
<212> TYPE: DNA
<213> ORGANISM: Homo Sapiens

<400> SEQUENCE: 516

```
caggtgcagc tggtgcagtc tggggctgag gtgacgaagc tggggcctc agtgaaggtt    60 tcctgcaagg catctagata cagcttcacc agctactata tgcactgggt gcgacaggcc   120
cctggacaag gcttgagtg gatgggaata atcaaccccta aaagtggtag tacaagttac   180
gcacagaagt tccagggcag agtcaccatg accagggaca cgtccacgag cacagtctac   240
atggagctga gcagcctgag atctgaggac acggccgtgt attactgtgc gagagatggg   300
tatggcagct cgtcccggtg cctccagctc tggggccagg gcaccctggt caccgtctcc   360
tca                                                                  363
```

<210> SEQ ID NO 517
<211> LENGTH: 121
<212> TYPE: PRT
<213> ORGANISM: Homo Sapiens

<400> SEQUENCE: 517

Gln Val Gln Leu Val Gln Ser Gly Ala Glu Val Thr Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr

```
                65                  70                  75                  80
Met Glu Leu Ser Ser Leu Arg Ser Glu Asp Thr Ala Val Tyr Tyr Cys
                        85                  90                  95

Ala Arg Asp Gly Tyr Gly Ser Ser Arg Cys Leu Gln Leu Trp Gly
                100                 105                 110

Gln Gly Thr Leu Val Thr Val Ser Ser
        115                 120
```

<210> SEQ ID NO 518
<211> LENGTH: 120
<212> TYPE: PRT
<213> ORGANISM: Homo Sapiens

<400> SEQUENCE: 518

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Tyr Ser Ser Gly Ala Glu Tyr Phe Gln His Trp Gly Gln
                100                 105                 110

Gly Thr Leu Val Thr Val Ser Ser
        115                 120
```

<210> SEQ ID NO 519
<211> LENGTH: 19
<212> TYPE: PRT
<213> ORGANISM: Homo Sapiens

<400> SEQUENCE: 519

```
Met Ala Trp Thr Ala Leu Leu Leu Gly Leu Leu Ser His Cys Thr Gly
1               5                   10                  15

Ser Val Thr
```

<210> SEQ ID NO 520
<211> LENGTH: 14
<212> TYPE: PRT
<213> ORGANISM: Homo Sapiens

<400> SEQUENCE: 520

```
Ala Arg Asp Gly Tyr Gly Ser Ser Ser Arg Ile Ile Gln Leu
1               5                   10
```

<210> SEQ ID NO 521
<211> LENGTH: 363
<212> TYPE: DNA
<213> ORGANISM: Homo Sapiens

<400> SEQUENCE: 521

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
```

```
cctggacaag ggcttgagtg gatgggaata atcaacccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct cgtcccggat catccagctc tggggccagg gcaccctggt caccgtctcc    360
tca                                                                  363
```

<210> SEQ ID NO 522
<211> LENGTH: 121
<212> TYPE: PRT
<213> ORGANISM: Homo Sapiens

<400> SEQUENCE: 522

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Ile Ile Gln Leu Trp Gly
            100                 105                 110

Gln Gly Thr Leu Val Thr Val Ser Ser
        115                 120
```

<210> SEQ ID NO 523
<211> LENGTH: 14
<212> TYPE: PRT
<213> ORGANISM: Homo Sapiens

<400> SEQUENCE: 523

```
Ala Arg Asp Gly Tyr Gly Ser Ser Ser Arg Leu Ile Gln Leu
1               5                   10
```

<210> SEQ ID NO 524
<211> LENGTH: 363
<212> TYPE: DNA
<213> ORGANISM: Homo Sapiens

<400> SEQUENCE: 524

```
caggtgcagt tgatacagtc tggggctgag gtgaagaagc tggggcctc agtgaaggtt    60 tcctgcaagg catctagata cagcttcacc agctactata tgcactgggt gcgacaggcc    120
cctggacaag ggcttgagtg gatgggaata atcaaccccta aaagtggtag tacaagttac   180
gcacagaagt tccagggcag agtcaccatg accagggaca cgtccacgag cacagtctac    240
atggagctga gcagcctgag atctgaggac acggccgtgt attactgtgc gagagatggg    300
tatggcagct cgtcccggct gatccagctc tggggccagg gcaccctggt caccgtctcc    360
tca                                                                  363
```

<210> SEQ ID NO 525
<211> LENGTH: 121
<212> TYPE: PRT

<213> ORGANISM: Homo Sapiens

<400> SEQUENCE: 525

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Leu Ile Gln Leu Trp Gly
            100                 105                 110

Gln Gly Thr Leu Val Thr Val Ser Ser
        115                 120

<210> SEQ ID NO 526
<211> LENGTH: 14
<212> TYPE: PRT
<213> ORGANISM: Homo Sapiens

<400> SEQUENCE: 526

Ala Arg Asp Gly Tyr Gly Ser Ser Arg Gln Ile Gln Leu
1               5                   10

<210> SEQ ID NO 527
<211> LENGTH: 363
<212> TYPE: DNA
<213> ORGANISM: Homo Sapiens

<400> SEQUENCE: 527
caggtgcagt tgatacagtc tggggctgag gtgaagaagc ctggggcctc agtgaaggtt       60
tcctgcaagg catctagata cagcttcacc agctactata tgcactgggt gcgacaggcc      120
cctggacaag gcttgagtg gatgggaata atcaacccta aaagtggtag tacaagttac      180
gcacagaagt tccagggcag agtcaccatg accaggaca cgtccacgag cacagtctac      240
atggagctga gcagcctgag atctgaggac acggccgtgt attactgtgc gagagatggg      300
tatggcagct cgtcccggca gatccagctc tggggccagg gcaccctggt caccgtctcc      360
tca                                                                   363

<210> SEQ ID NO 528
<211> LENGTH: 121
<212> TYPE: PRT
<213> ORGANISM: Homo Sapiens

<400> SEQUENCE: 528

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe

```
            50                  55                  60
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                     85                  90                  95

Ala Arg Asp Gly Tyr Gly Ser Ser Arg Gln Ile Gln Leu Trp Gly
                100                 105                 110

Gln Gly Thr Leu Val Thr Val Ser Ser
            115                 120

<210> SEQ ID NO 529
<211> LENGTH: 14
<212> TYPE: PRT
<213> ORGANISM: Homo Sapiens

<400> SEQUENCE: 529

Ala Arg Asp Gly Tyr Gly Ser Ser Arg Ile Leu Met Leu
 1               5                  10

<210> SEQ ID NO 530
<211> LENGTH: 363
<212> TYPE: DNA
<213> ORGANISM: Homo Sapiens

<400> SEQUENCE: 530
caggtgcagt tgatacagtc tgggcctgag gtgaagaagc ctggggcctc agtgaaggtt    60
tcctgcaagg catctagata cagcttcacc agctactata tgcactgggt gcgacaggcc   120
cctggacaag gcttgagtg gatgggaata atcaaccctaa aaagtggtag tacaagttac   180
gcacagaagt tccagggcag agtcaccatg accaggaca cgtccacgag cacagtctac   240
atggagctga gcagcctgag atctgaggac acggccgtgt attactgtgc gagagatggg   300
tatggcagct cgtcccggat cctcatgctc tggggccagg gcaccctggt caccgtctcc   360
tca                                                                 363

<210> SEQ ID NO 531
<211> LENGTH: 121
<212> TYPE: PRT
<213> ORGANISM: Homo Sapiens

<400> SEQUENCE: 531

Gln Val Gln Leu Ile Gln Ser Gly Ala Glu Val Lys Lys Pro Gly Ala
 1               5                  10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
     50                  55                  60

Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Ser Ser Arg Ile Leu Met Leu Trp Gly
                100                 105                 110

Gln Gly Thr Leu Val Thr Val Ser Ser
            115                 120
```

<210> SEQ ID NO 532
<211> LENGTH: 14
<212> TYPE: PRT
<213> ORGANISM: Homo Sapiens

<400> SEQUENCE: 532

Ala Arg Asp Gly Tyr Gly Ser Ser Ser Arg Leu Leu Met Leu
1               5                   10

<210> SEQ ID NO 533
<211> LENGTH: 363
<212> TYPE: DNA
<213> ORGANISM: Homo Sapiens

<400> SEQUENCE: 533
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaaccctd aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccggct gctcatgctc tggggccagg gcaccctggt caccgtctcc     360
tca                                                                    363

<210> SEQ ID NO 534
<211> LENGTH: 121
<212> TYPE: PRT
<213> ORGANISM: Homo Sapiens

<400> SEQUENCE: 534

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Leu Leu Met Leu Trp Gly
            100                 105                 110

Gln Gly Thr Leu Val Thr Val Ser Ser
        115                 120

<210> SEQ ID NO 535
<211> LENGTH: 14
<212> TYPE: PRT
<213> ORGANISM: Homo Sapiens

<400> SEQUENCE: 535

Ala Arg Asp Gly Tyr Gly Ser Ser Ser Arg Gln Leu Met Leu
1               5                   10

<210> SEQ ID NO 536
<211> LENGTH: 363

```
<212> TYPE: DNA
<213> ORGANISM: Homo Sapiens

<400> SEQUENCE: 536
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag ggcttgagtg gatgggaata atcaacccta aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccggca gctcatgctc tggggccagg gcaccctggt caccgtctcc     360
tca                                                                   363

<210> SEQ ID NO 537
<211> LENGTH: 121
<212> TYPE: PRT
<213> ORGANISM: Homo Sapiens

<400> SEQUENCE: 537

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Gln Leu Met Leu Trp Gly
            100                 105                 110

Gln Gly Thr Leu Val Thr Val Ser Ser
        115                 120

<210> SEQ ID NO 538
<211> LENGTH: 14
<212> TYPE: PRT
<213> ORGANISM: Homo Sapiens

<400> SEQUENCE: 538

Ala Arg Asp Gly Tyr Gly Ser Ser Ser Arg Ile Ile Met Leu
1               5                   10

<210> SEQ ID NO 539
<211> LENGTH: 363
<212> TYPE: DNA
<213> ORGANISM: Homo Sapiens

<400> SEQUENCE: 539
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag ggcttgagtg gatgggaata atcaacccta aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
```

```
tatggcagct cgtcccggat catcatgctc tggggccagg gcaccctggt caccgtctcc      360
tca                                                                    363
```

<210> SEQ ID NO 540
<211> LENGTH: 121
<212> TYPE: PRT
<213> ORGANISM: Homo Sapiens

<400> SEQUENCE: 540

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Ile Ile Met Leu Trp Gly
            100                 105                 110

Gln Gly Thr Leu Val Thr Val Ser Ser
        115                 120
```

<210> SEQ ID NO 541
<211> LENGTH: 14
<212> TYPE: PRT
<213> ORGANISM: Homo Sapiens

<400> SEQUENCE: 541

```
Ala Arg Asp Gly Tyr Gly Ser Ser Ser Arg Leu Ile Met Leu
1               5                   10
```

<210> SEQ ID NO 542
<211> LENGTH: 363
<212> TYPE: DNA
<213> ORGANISM: Homo Sapiens

<400> SEQUENCE: 542

```
caggtgcagt tgatacagtc tggggctgag gtgaagaagc ctggggcctc agtgaaggtt       60
tcctgcaagg catctagata cagcttcacc agctactata tgcactgggt gcgacaggcc     120
cctggacaag gcttgagtg gatgggaata atcaacccta aaagtggtag tacaagttac      180
gcacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccggct gatcatgctc tggggccagg gcaccctggt caccgtctcc     360
tca                                                                    363
```

<210> SEQ ID NO 543
<211> LENGTH: 121
<212> TYPE: PRT
<213> ORGANISM: Homo Sapiens

<400> SEQUENCE: 543

```
Gln Val Gln Leu Ile Gln Ser Gly Ala Glu Val Lys Lys Pro Gly Ala
```

```
              1               5                  10                 15
            Ser Val Lys Val Ser Cys Lys Ala Ser Arg Tyr Ser Phe Thr Ser Tyr
                         20                  25                 30

Tyr Met His Trp Val Arg Gln Ala Pro Gly Gln Gly Leu Glu Trp Met
                     35                  40                 45

Gly Ile Ile Asn Pro Lys Ser Gly Ser Thr Ser Tyr Ala Gln Lys Phe
                 50                  55                 60

Gln Gly Arg Val Thr Met Thr Arg Asp Thr Ser Thr Ser Thr Val Tyr
            65                  70                  75                 80

Met Glu Leu Ser Ser Leu Arg Ser Glu Asp Thr Ala Val Tyr Tyr Cys
                             85                  90                 95

Ala Arg Asp Gly Tyr Gly Ser Ser Ser Arg Leu Ile Met Leu Trp Gly
                        100                 105                110

Gln Gly Thr Leu Val Thr Val Ser Ser
                        115                 120
```

```
<210> SEQ ID NO 544
<211> LENGTH: 14
<212> TYPE: PRT
<213> ORGANISM: Homo Sapiens

<400> SEQUENCE: 544

Ala Arg Asp Gly Tyr Gly Ser Ser Ser Arg Gln Ile Met Leu
1               5                  10
```

```
<210> SEQ ID NO 545
<211> LENGTH: 363
<212> TYPE: DNA
<213> ORGANISM: Homo Sapiens

<400> SEQUENCE: 545
caggtgcagt tgatacagtc tggggctgag gtgaagaagc ctggggcctc agtgaaggtt     60
tcctgcaagg catctagata cagcttcacc agctactata tgcactgggt gcgacaggcc    120
cctggacaag ggcttgagtg gatgggaata atcaacccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct cgtcccggca gatcatgctc tggggccagg gcaccctggt caccgtctcc    360
tca                                                                  363
```

```
<210> SEQ ID NO 546
<211> LENGTH: 121
<212> TYPE: PRT
<213> ORGANISM: Homo Sapiens

<400> SEQUENCE: 546

Gln Val Gln Leu Ile Gln Ser Gly Ala Glu Val Lys Lys Pro Gly Ala
1               5                  10                 15

Ser Val Lys Val Ser Cys Lys Ala Ser Arg Tyr Ser Phe Thr Ser Tyr
                20                  25                 30

Tyr Met His Trp Val Arg Gln Ala Pro Gly Gln Gly Leu Glu Trp Met
            35                  40                 45

Gly Ile Ile Asn Pro Lys Ser Gly Ser Thr Ser Tyr Ala Gln Lys Phe
        50                  55                 60

Gln Gly Arg Val Thr Met Thr Arg Asp Thr Ser Thr Ser Thr Val Tyr
65                  70                  75                 80
```

-continued

```
Met Glu Leu Ser Ser Leu Arg Ser Glu Asp Thr Ala Val Tyr Tyr Cys
            85                  90                  95

Ala Arg Asp Gly Tyr Gly Ser Ser Arg Gln Ile Met Leu Trp Gly
        100                 105                 110

Gln Gly Thr Leu Val Thr Val Ser Ser
        115                 120

<210> SEQ ID NO 547
<211> LENGTH: 14
<212> TYPE: PRT
<213> ORGANISM: Homo Sapiens

<400> SEQUENCE: 547

Ala Arg Asp Gly Tyr Gly Ser Ser Arg Val Ile Gln Leu
1               5                   10

<210> SEQ ID NO 548
<211> LENGTH: 363
<212> TYPE: DNA
<213> ORGANISM: Homo Sapiens

<400> SEQUENCE: 548
caggtgcagt tgatacagtc tgggctgag gtgaagaagc ctggggcctc agtgaaggtt      60
tcctgcaagg catctagata cagcttcacc agctactata tgcactgggt gcgacaggcc    120
cctggacaag gcttgagtg gatgggaata atcaaccctaa aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct cgtcccgggt gatccagctc tggggccagg gcaccctggt caccgtctcc    360
tca                                                                  363

<210> SEQ ID NO 549
<211> LENGTH: 121
<212> TYPE: PRT
<213> ORGANISM: Homo Sapiens

<400> SEQUENCE: 549

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Val Ile Gln Leu Trp Gly
        100                 105                 110

Gln Gly Thr Leu Val Thr Val Ser Ser
        115                 120

<210> SEQ ID NO 550
<211> LENGTH: 14
<212> TYPE: PRT
<213> ORGANISM: Homo Sapiens
```

<400> SEQUENCE: 550

Ala Arg Asp Gly Tyr Gly Ser Ser Ser Arg Val Leu Met Leu
1               5                   10

<210> SEQ ID NO 551
<211> LENGTH: 363
<212> TYPE: DNA
<213> ORGANISM: Homo Sapiens

<400> SEQUENCE: 551
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag ggcttgagtg gatgggaata atcaacccta aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccgggt gctcatgctc tggggccagg gcaccctggt caccgtctcc     360
tca                                                                   363

<210> SEQ ID NO 552
<211> LENGTH: 121
<212> TYPE: PRT
<213> ORGANISM: Homo Sapiens

<400> SEQUENCE: 552

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Ser Arg Val Leu Met Leu Trp Gly
            100                 105                 110

Gln Gly Thr Leu Val Thr Val Ser Ser
        115                 120

<210> SEQ ID NO 553
<211> LENGTH: 14
<212> TYPE: PRT
<213> ORGANISM: Homo Sapiens

<400> SEQUENCE: 553

Ala Arg Asp Gly Tyr Gly Ser Ser Ser Arg Val Ile Met Leu
1               5                   10

<210> SEQ ID NO 554
<211> LENGTH: 363
<212> TYPE: DNA
<213> ORGANISM: Homo Sapiens

<400> SEQUENCE: 554

```
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag ggcttgagtg gatgggaata atcaacccta aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct cgtcccgggt gatcatgctc tggggccagg gcaccctggt caccgtctcc     360
tca                                                                  363
```

<210> SEQ ID NO 555
<211> LENGTH: 121
<212> TYPE: PRT
<213> ORGANISM: Homo Sapiens

<400> SEQUENCE: 555

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Arg Val Ile Met Leu Trp Gly
            100                 105                 110

Gln Gly Thr Leu Val Thr Val Ser Ser
        115                 120
```

<210> SEQ ID NO 556
<211> LENGTH: 14
<212> TYPE: PRT
<213> ORGANISM: Homo Sapiens

<400> SEQUENCE: 556

```
Ala Arg Asp Gly Tyr Gly Ser Phe Ser Arg Ile Ile Gln Leu
1               5                   10
```

<210> SEQ ID NO 557
<211> LENGTH: 363
<212> TYPE: DNA
<213> ORGANISM: Homo Sapiens

<400> SEQUENCE: 557

```
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag ggcttgagtg gatgggaata atcaacccta aaagtggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct ctcccggat catccagctc tggggccagg gcaccctggt caccgtctcc     360
tca                                                                  363
```

<210> SEQ ID NO 558
<211> LENGTH: 121
<212> TYPE: PRT
<213> ORGANISM: Homo Sapiens

<400> SEQUENCE: 558

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Ile Ile Gln Leu Trp Gly
            100                 105                 110

Gln Gly Thr Leu Val Thr Val Ser Ser
        115                 120

<210> SEQ ID NO 559
<211> LENGTH: 14
<212> TYPE: PRT
<213> ORGANISM: Homo Sapiens

<400> SEQUENCE: 559

Ala Arg Asp Gly Tyr Gly Ser Phe Ser Arg Ile Leu Met Leu
1               5                   10

<210> SEQ ID NO 560
<211> LENGTH: 363
<212> TYPE: DNA
<213> ORGANISM: Homo Sapiens

<400> SEQUENCE: 560
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag gcttgagtg gatgggaata atcaacccta aaagtggtag tacaagttac   180
gcacagaagt tccagggcag agtcaccatg accaggaca cgtccacgag cacagtctac   240
atggagctga gcagcctgag atctgaggac acggccgtgt attactgtgc gagagatggg   300
tatggcagct ctcccggat cctcatgctc tggggccagg gcaccctggt caccgtctcc   360
tca   363

<210> SEQ ID NO 561
<211> LENGTH: 121
<212> TYPE: PRT
<213> ORGANISM: Homo Sapiens

<400> SEQUENCE: 561

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
         35                  40                  45

Gly Ile Ile Asn Pro Lys Ser Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Ser Phe Ser Arg Ile Leu Met Leu Trp Gly
            100                 105                 110

Gln Gly Thr Leu Val Thr Val Ser Ser
        115                 120

<210> SEQ ID NO 562
<211> LENGTH: 14
<212> TYPE: PRT
<213> ORGANISM: Homo Sapiens

<400> SEQUENCE: 562

Ala Arg Asp Gly Tyr Gly Ser Phe Ser Arg Ile Ile Met Leu
1               5                   10

<210> SEQ ID NO 563
<211> LENGTH: 363
<212> TYPE: DNA
<213> ORGANISM: Homo Sapiens

<400> SEQUENCE: 563
caggtgcagt tgatacagtc tggggctgag gtgaagaagc ctggggcctc agtgaaggtt      60
tcctgcaagg catctagata cagcttcacc agctactata tgcactgggt gcgacaggcc    120
cctggacaag ggcttgagtg gatgggaata atcaacccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggat catcatgctc tggggccagg gcaccctggt caccgtctcc    360
tca                                                                  363

<210> SEQ ID NO 564
<211> LENGTH: 121
<212> TYPE: PRT
<213> ORGANISM: Homo Sapiens

<400> SEQUENCE: 564

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
             20                  25                  30

Tyr Met His Trp Val Arg Gln Ala Pro Gly Gln Gly Leu Glu Trp Met
         35                  40                  45

Gly Ile Ile Asn Pro Lys Ser Gly Ser Thr Ser Tyr Ala Gln Lys Phe
 50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                 85                  90                  95

Ala Arg Asp Gly Tyr Gly Ser Phe Ser Arg Ile Ile Met Leu Trp Gly
            100                 105                 110

Gln Gly Thr Leu Val Thr Val Ser Ser
        115                 120

<210> SEQ ID NO 565
<211> LENGTH: 14
<212> TYPE: PRT
<213> ORGANISM: Homo Sapiens

<400> SEQUENCE: 565

Ala Arg Asp Gly Tyr Gly Ser Phe Ser Arg Leu Ile Gln Leu
1               5                   10

<210> SEQ ID NO 566
<211> LENGTH: 363
<212> TYPE: DNA
<213> ORGANISM: Homo Sapiens

<400> SEQUENCE: 566
caggtgcagt tgatacagtc tggggctgag gtgaagaagc ctggggcctc agtgaaggtt      60
tcctgcaagg catctagata cagcttcacc agctactata tgcactgggt gcgacaggcc    120
cctggacaag gcttgagtg gatgggaata atcaaccta aaagtggtag tacaagttac     180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggct gatccagctc tggggccagg gcaccctggt caccgtctcc    360
tca                                                                  363

<210> SEQ ID NO 567
<211> LENGTH: 121
<212> TYPE: PRT
<213> ORGANISM: Homo Sapiens

<400> SEQUENCE: 567

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 568
<211> LENGTH: 14
<212> TYPE: PRT
<213> ORGANISM: Homo Sapiens

<400> SEQUENCE: 568

Ala Arg Asp Gly Tyr Gly Ser Phe Ser Arg Leu Leu Met Leu
1               5                   10

<210> SEQ ID NO 569
<211> LENGTH: 363
<212> TYPE: DNA
<213> ORGANISM: Homo Sapiens

<400> SEQUENCE: 569

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaaccta aaagtggtag tacaagttac   180
gcacagaagt tccagggcag agtcaccatg accaggaca cgtccacgag cacagtctac   240
atggagctga gcagcctgag atctgaggac acggccgtgt attactgtgc gagagatggg   300
tatggcagct ctcccggct gctcatgctc tggggccagg gcaccctggt caccgtctcc   360
tca                                                                  363
```

<210> SEQ ID NO 570
<211> LENGTH: 121
<212> TYPE: PRT
<213> ORGANISM: Homo Sapiens

<400> SEQUENCE: 570

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Leu Met Leu Trp Gly
            100                 105                 110

Gln Gly Thr Leu Val Thr Val Ser Ser
        115                 120
```

<210> SEQ ID NO 571
<211> LENGTH: 14
<212> TYPE: PRT
<213> ORGANISM: Homo Sapiens

<400> SEQUENCE: 571

```
Ala Arg Asp Gly Tyr Gly Ser Phe Ser Arg Leu Ile Met Leu
1               5                   10
```

<210> SEQ ID NO 572
<211> LENGTH: 363
<212> TYPE: DNA
<213> ORGANISM: Homo Sapiens

<400> SEQUENCE: 572

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaaccta aaagtggtag tacaagttac   180
```

-continued

```
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggct gatcatgctc tggggccagg gcaccctggt caccgtctcc     360
tca                                                                  363
```

<210> SEQ ID NO 573
<211> LENGTH: 121
<212> TYPE: PRT
<213> ORGANISM: Homo Sapiens

<400> SEQUENCE: 573

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Met Leu Trp Gly
            100                 105                 110

Gln Gly Thr Leu Val Thr Val Ser Ser
        115                 120
```

<210> SEQ ID NO 574
<211> LENGTH: 14
<212> TYPE: PRT
<213> ORGANISM: Homo Sapiens

<400> SEQUENCE: 574

```
Ala Arg Asp Gly Tyr Gly Ser Phe Ser Arg Gln Ile Gln Leu
1               5                   10
```

<210> SEQ ID NO 575
<211> LENGTH: 363
<212> TYPE: DNA
<213> ORGANISM: Homo Sapiens

<400> SEQUENCE: 575

```
caggtgcagt tgatacagtc tggggctgag gtgaagaagc ctggggcctc agtgaaggtt    60
tcctgcaagg catctagata cagcttcacc agctactata tgcactgggt gcgacaggcc    120
cctggacaag gcttgagtg gatgggaata atcaacccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggca gatccagctc tggggccagg gcaccctggt caccgtctcc     360
tca                                                                  363
```

<210> SEQ ID NO 576
<211> LENGTH: 121
<212> TYPE: PRT
<213> ORGANISM: Homo Sapiens

<400> SEQUENCE: 576

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Gln Ile Gln Leu Trp Gly
            100                 105                 110

Gln Gly Thr Leu Val Thr Val Ser Ser
        115                 120

<210> SEQ ID NO 577
<211> LENGTH: 14
<212> TYPE: PRT
<213> ORGANISM: Homo Sapiens

<400> SEQUENCE: 577

Ala Arg Asp Gly Tyr Gly Ser Phe Ser Arg Gln Leu Met Leu
1               5                   10

<210> SEQ ID NO 578
<211> LENGTH: 363
<212> TYPE: DNA
<213> ORGANISM: Homo Sapiens

<400> SEQUENCE: 578
caggtgcagt tgatacagtc tgggctgag gtgaagaagc ctggggcctc agtgaaggtt      60
tcctgcaagg catctagata cagcttcacc agctactata tgcactgggt gcgacaggcc    120
cctggacaag ggcttgagtg gatgggaata atcaaccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggca gctcatgctc tggggccagg gcaccctggt caccgtctcc    360
tca                                                                  363

<210> SEQ ID NO 579
<211> LENGTH: 121
<212> TYPE: PRT
<213> ORGANISM: Homo Sapiens

<400> SEQUENCE: 579

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

```
Gln Gly Arg Val Thr Met Thr Arg Asp Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Gln Leu Met Leu Trp Gly
            100                 105                 110

Gln Gly Thr Leu Val Thr Val Ser Ser
        115                 120
```

<210> SEQ ID NO 580
<211> LENGTH: 14
<212> TYPE: PRT
<213> ORGANISM: Homo Sapiens

<400> SEQUENCE: 580

```
Ala Arg Asp Gly Tyr Gly Ser Phe Ser Arg Gln Ile Met Leu
1               5                   10
```

<210> SEQ ID NO 581
<211> LENGTH: 363
<212> TYPE: DNA
<213> ORGANISM: Homo Sapiens

<400> SEQUENCE: 581

```
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaaccta aaagtggtag tacaagttac       180
gcacagaagt tccagggcag agtcaccatg accagggaca cgtccacgag cacagtctac     240
atggagctga gcagcctgag atctgaggac acggccgtgt attactgtgc gagagatggg     300
tatggcagct ctcccggca gatcatgctc tggggccagg gcaccctggt caccgtctcc     360
tca                                                                   363
```

<210> SEQ ID NO 582
<211> LENGTH: 121
<212> TYPE: PRT
<213> ORGANISM: Homo Sapiens

<400> SEQUENCE: 582

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Gln Ile Met Leu Trp Gly
            100                 105                 110

Gln Gly Thr Leu Val Thr Val Ser Ser
        115                 120
```

```
<210> SEQ ID NO 583
<211> LENGTH: 14
<212> TYPE: PRT
<213> ORGANISM: Homo Sapiens

<400> SEQUENCE: 583

Ala Arg Asp Gly Tyr Gly Ser Phe Ser Arg Val Ile Gln Leu
1               5                   10

<210> SEQ ID NO 584
<211> LENGTH: 363
<212> TYPE: DNA
<213> ORGANISM: Homo Sapiens

<400> SEQUENCE: 584
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaaccta aaagtggtag tacaagttac      180
gcacagaagt tccagggcag agtcaccatg accaggaca cgtccacgag cacagtctac      240
atggagctga gcagcctgag atctgaggac acggccgtgt attactgtgc gagagatggg     300
tatggcagct ctcccgggt gatccagctc tggggccagg gcaccctggt caccgtctcc     360
tca                                                                   363

<210> SEQ ID NO 585
<211> LENGTH: 121
<212> TYPE: PRT
<213> ORGANISM: Homo Sapiens

<400> SEQUENCE: 585

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Val Ile Gln Leu Trp Gly
            100                 105                 110

Gln Gly Thr Leu Val Thr Val Ser Ser
        115                 120

<210> SEQ ID NO 586
<211> LENGTH: 14
<212> TYPE: PRT
<213> ORGANISM: Homo Sapiens

<400> SEQUENCE: 586

Ala Arg Asp Gly Tyr Gly Ser Phe Ser Arg Val Leu Met Leu
1               5                   10

<210> SEQ ID NO 587
<211> LENGTH: 363
<212> TYPE: DNA
```

<213> ORGANISM: Homo Sapiens

<400> SEQUENCE: 587

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaaccctaa aaagtggtag tacaagttac   180
gcacagaagt tccagggcag agtcaccatg accagggaca cgtccacgag cacagtctac   240
atggagctga gcagcctgag atctgaggac acggccgtgt attactgtgc gagagatggg   300
tatggcagct ctcccgggt gctcatgctc tggggccagg gcaccctggt caccgtctcc   360
tca                                                                 363
```

<210> SEQ ID NO 588
<211> LENGTH: 121
<212> TYPE: PRT
<213> ORGANISM: Homo Sapiens

<400> SEQUENCE: 588

Gln Val Gln Leu Ile Gln Ser Gly Ala Glu Val Lys Lys Pro Gly Ala
1               5                   10                  15
Ser Val Lys Val Ser Cys Lys Ala Ser Arg Tyr Ser Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Lys Ser Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Asp Gly Tyr Gly Ser Phe Ser Arg Val Leu Met Leu Trp Gly
            100                 105                 110
Gln Gly Thr Leu Val Thr Val Ser Ser
        115                 120

<210> SEQ ID NO 589
<211> LENGTH: 14
<212> TYPE: PRT
<213> ORGANISM: Homo Sapiens

<400> SEQUENCE: 589

Ala Arg Asp Gly Tyr Gly Ser Phe Ser Arg Val Ile Met Leu
1               5                   10

<210> SEQ ID NO 590
<211> LENGTH: 363
<212> TYPE: DNA
<213> ORGANISM: Homo Sapiens

<400> SEQUENCE: 590

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaaccctaa aaagtggtag tacaagttac   180
gcacagaagt tccagggcag agtcaccatg accagggaca cgtccacgag cacagtctac   240
atggagctga gcagcctgag atctgaggac acggccgtgt attactgtgc gagagatggg   300
```

```
tatggcagct tctcccgggt gatcatgctc tggggccagg gcaccctggt caccgtctcc    360
tca                                                                 363
```

<210> SEQ ID NO 591
<211> LENGTH: 121
<212> TYPE: PRT
<213> ORGANISM: Homo Sapiens

<400> SEQUENCE: 591

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Val Ile Met Leu Trp Gly
            100                 105                 110

Gln Gly Thr Leu Val Thr Val Ser Ser
        115                 120

<210> SEQ ID NO 592
<211> LENGTH: 8
<212> TYPE: PRT
<213> ORGANISM: Homo Sapiens

<400> SEQUENCE: 592

Arg Phe Ser Phe Thr Ser Tyr Tyr
1               5

<210> SEQ ID NO 593
<211> LENGTH: 363
<212> TYPE: DNA
<213> ORGANISM: Homo Sapiens

<400> SEQUENCE: 593

```
caggtgcagt tgatacagtc tggggctgag gtgaagaagc ctggggcctc agtgaaggtt    60
tcctgcaagg catctagatt cagcttcacc agctactata tgcactgggt gcgacaggcc   120
cctggacaag ggcttgagtg gatgggaata atcaaccctaaaagtggtag tacaagttac   180 gcacagaagt tccagggcag agtcaccatg accagggaca cgtccacgag cacagtctac   240
atggagctga gcagcctgag atctgaggac acggccgtgt attactgtgc gagagatggg   300
tatggcagct tctcccggct gatccagctc tggggccagg gcaccctggt caccgtctcc   360
tca                                                                  363
```

<210> SEQ ID NO 594
<211> LENGTH: 121
<212> TYPE: PRT
<213> ORGANISM: Homo Sapiens

<400> SEQUENCE: 594

Gln Val Gln Leu Ile Gln Ser Gly Ala Glu Val Lys Lys Pro Gly Ala
1               5                   10                  15

Ser Val Lys Val Ser Cys Lys Ala Ser Arg Phe Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 595
<211> LENGTH: 8
<212> TYPE: PRT
<213> ORGANISM: Homo Sapiens

<400> SEQUENCE: 595

Arg Tyr His Phe Thr Ser Tyr Tyr
1               5

<210> SEQ ID NO 596
<211> LENGTH: 363
<212> TYPE: DNA
<213> ORGANISM: Homo Sapiens

<400> SEQUENCE: 596
caggtgcagt tgatacagtc tgggctgag gtgaagaagc ctggggcctc agtgaaggtt     60
tcctgcaagg catctagata ccacttcacc agctactata tgcactgggt gcgacaggcc    120
cctggacaag ggcttgagtg gatgggaata atcaaccccta aaagtggtag tacaagttac   180
gcacagaagt tccagggcag agtcaccatg accaggaca cgtccacgag cacagtctac    240
atggagctga gcagcctgag atctgaggac acggccgtgt attactgtgc gagagatggg   300
tatggcagct ctcccggct gatccagctc tggggccagg gcaccctggt caccgtctcc    360
tca                                                                 363

<210> SEQ ID NO 597
<211> LENGTH: 121
<212> TYPE: PRT
<213> ORGANISM: Homo Sapiens

<400> SEQUENCE: 597

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr His Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                    85                  90                  95
Ala Arg Asp Gly Tyr Gly Ser Phe Ser Arg Leu Ile Gln Leu Trp Gly
                100                 105                 110

Gln Gly Thr Leu Val Thr Val Ser Ser
        115                 120

<210> SEQ ID NO 598
<211> LENGTH: 8
<212> TYPE: PRT
<213> ORGANISM: Homo Sapiens

<400> SEQUENCE: 598

Arg Tyr Lys Phe Thr Ser Tyr Tyr
1               5

<210> SEQ ID NO 599
<211> LENGTH: 363
<212> TYPE: DNA
<213> ORGANISM: Homo Sapiens

<400> SEQUENCE: 599
caggtgcagt tgatacagtc tggggctgag gtgaagaagc ctggggcctc agtgaaggtt      60
tcctgcaagg catctagata caagttcacc agctactata tgcactgggt gcgacaggcc    120
cctggacaag gcttgagtg gatgggaata atcaacccta aaagtggtag tacaagttac     180
gcacagaagt tccagggcag agtcaccatg accagggaca cgtccacgag cacagtctac    240
atggagctga gcagcctgag atctgaggac acggccgtgt attactgtgc gagagatggg    300
tatggcagct tctcccggct gatccagctc tggggccagg gcaccctggt caccgtctcc    360
tca                                                                  363

<210> SEQ ID NO 600
<211> LENGTH: 121
<212> TYPE: PRT
<213> ORGANISM: Homo Sapiens

<400> SEQUENCE: 600

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Lys Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
                100                 105                 110

Gln Gly Thr Leu Val Thr Val Ser Ser
        115                 120

<210> SEQ ID NO 601
<211> LENGTH: 8
<212> TYPE: PRT
<213> ORGANISM: Homo Sapiens
```

<400> SEQUENCE: 601

Arg Tyr Arg Phe Thr Ser Tyr Tyr
1               5

<210> SEQ ID NO 602
<211> LENGTH: 363
<212> TYPE: DNA
<213> ORGANISM: Homo Sapiens

<400> SEQUENCE: 602
caggtgcagt tgatacagtc tggggctgag gtgaagaagc ctggggcctc agtgaaggtt      60
tcctgcaagg catctagata cagattcacc agctactata tgcactgggt gcgacaggcc     120
cctggacaag ggcttgagtg gatgggaata atcaaccctc aaagtggtag tacaagttac     180
gcacagaagt tccagggcag agtcaccatg accaggggaca cgtccacgag cacagtctac     240
atggagctga gcagcctgag atctgaggac acggccgtgt attactgtgc gagagatggg     300
tatggcagct ctcccggct gatccagctc tggggccagg gcaccctggt caccgtctcc     360
tca                                                                  363

<210> SEQ ID NO 603
<211> LENGTH: 121
<212> TYPE: PRT
<213> ORGANISM: Homo Sapiens

<400> SEQUENCE: 603

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Arg Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Ser Phe Ser Arg Leu Ile Gln Leu Trp Gly
            100                 105                 110

Gln Gly Thr Leu Val Thr Val Ser Ser
        115                 120

<210> SEQ ID NO 604
<211> LENGTH: 8
<212> TYPE: PRT
<213> ORGANISM: Homo Sapiens

<400> SEQUENCE: 604

Arg Tyr Ser Phe Lys Ser Tyr Tyr
1               5

<210> SEQ ID NO 605
<211> LENGTH: 363
<212> TYPE: DNA
<213> ORGANISM: Homo Sapiens

<400> SEQUENCE: 605
caggtgcagt tgatacagtc tggggctgag gtgaagaagc ctggggcctc agtgaaggtt      60

-continued

```
tcctgcaagg catctagata cagcttcaag agctactata tgcactgggt gcgacaggcc    120
cctggacaag ggcttgagtg gatgggaata atcaacccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggct gatccagctc tggggccagg gcaccctggt caccgtctcc    360
tca                                                                 363
```

<210> SEQ ID NO 606
<211> LENGTH: 121
<212> TYPE: PRT
<213> ORGANISM: Homo Sapiens

<400> SEQUENCE: 606

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Lys Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 607
<211> LENGTH: 8
<212> TYPE: PRT
<213> ORGANISM: Homo Sapiens

<400> SEQUENCE: 607

Arg Tyr Ser Phe Thr Ala Tyr Tyr
1               5

<210> SEQ ID NO 608
<211> LENGTH: 363
<212> TYPE: DNA
<213> ORGANISM: Homo Sapiens

<400> SEQUENCE: 608

```
caggtgcagt tgatacagtc tggggctgag gtgaagaagc ctggggcctc agtgaaggtt    60
tcctgcaagg catctagata cagcttcacc gcctactata tgcactgggt gcgacaggcc    120
cctggacaag ggcttgagtg gatgggaata atcaacccta aaagtggtag tacaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggct gatccagctc tggggccagg gcaccctggt caccgtctcc    360
tca                                                                 363
```

-continued

```
<210> SEQ ID NO 609
<211> LENGTH: 121
<212> TYPE: PRT
<213> ORGANISM: Homo Sapiens

<400> SEQUENCE: 609

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ala Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 610
<211> LENGTH: 8
<212> TYPE: PRT
<213> ORGANISM: Homo Sapiens

<400> SEQUENCE: 610

Leu Asn Pro Lys Ser Gly Ser Thr
1               5

<210> SEQ ID NO 611
<211> LENGTH: 363
<212> TYPE: DNA
<213> ORGANISM: Homo Sapiens

<400> SEQUENCE: 611
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata ctgaacccta aaagtggtag tacaagttac   180
gcacagaagt tccagggcag agtcaccatg accagggaca cgtccacgag cacagtctac   240
atggagctga gcagcctgag atctgaggac acggccgtgt attactgtgc gagagatggg   300
tatggcagct ctcccggct gatccagctc tggggccagg gcaccctggt caccgtctcc   360
tca                                                                 363

<210> SEQ ID NO 612
<211> LENGTH: 121
<212> TYPE: PRT
<213> ORGANISM: Homo Sapiens

<400> SEQUENCE: 612

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
```

```
                35                  40                  45
Gly Ile Leu Asn Pro Lys Ser Gly Ser Thr Ser Tyr Ala Gln Lys Phe
        50                  55                  60
Gln Gly Arg Val Thr Met Thr Arg Asp Thr Ser Thr Ser Thr Val Tyr
 65                 70                  75                  80
Met Glu Leu Ser Ser Leu Arg Ser Glu Asp Thr Ala Val Tyr Tyr Cys
                85                  90                  95
Ala Arg Asp Gly Tyr Gly Ser Phe Ser Arg Leu Ile Gln Leu Trp Gly
            100                 105                 110
Gln Gly Thr Leu Val Thr Val Ser Ser
            115                 120
```

<210> SEQ ID NO 613
<211> LENGTH: 8
<212> TYPE: PRT
<213> ORGANISM: Homo Sapiens

<400> SEQUENCE: 613

```
Ile Asn Pro Lys Ile Gly Ser Thr
 1               5
```

<210> SEQ ID NO 614
<211> LENGTH: 363
<212> TYPE: DNA
<213> ORGANISM: Homo Sapiens

<400> SEQUENCE: 614

```
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaaccct aaatcggtag tacaagttac     180
gcacagaagt tccagggcag agtcaccatg accagggaca cgtccacgag cacagtctac     240
atggagctga gcagcctgag atctgaggac acggccgtgt attactgtgc gagagatggg     300
tatggcagct ctcccggct gatccagctc tggggccagg gcaccctggt caccgtctcc     360
tca                                                                   363
```

<210> SEQ ID NO 615
<211> LENGTH: 121
<212> TYPE: PRT
<213> ORGANISM: Homo Sapiens

<400> SEQUENCE: 615

```
Gln Val Gln Leu Ile Gln Ser Gly Ala Glu Val Lys Lys Pro Gly Ala
 1               5                  10                  15
Ser Val Lys Val Ser Cys Lys Ala Ser Arg Tyr Ser Phe Thr Ser Tyr
                20                  25                  30
Tyr Met His Trp Val Arg Gln Ala Pro Gly Gln Gly Leu Glu Trp Met
            35                  40                  45
Gly Ile Ile Asn Pro Lys Ile Gly Ser Thr Ser Tyr Ala Gln Lys Phe
        50                  55                  60
Gln Gly Arg Val Thr Met Thr Arg Asp Thr Ser Thr Ser Thr Val Tyr
 65                 70                  75                  80
Met Glu Leu Ser Ser Leu Arg Ser Glu Asp Thr Ala Val Tyr Tyr Cys
                85                  90                  95
Ala Arg Asp Gly Tyr Gly Ser Phe Ser Arg Leu Ile Gln Leu Trp Gly
            100                 105                 110
```

```
Gln Gly Thr Leu Val Thr Val Ser Ser
        115                 120
```

<210> SEQ ID NO 616
<211> LENGTH: 8
<212> TYPE: PRT
<213> ORGANISM: Homo Sapiens

<400> SEQUENCE: 616

```
Ile Asn Pro Lys Lys Gly Ser Thr
1               5
```

<210> SEQ ID NO 617
<211> LENGTH: 363
<212> TYPE: DNA
<213> ORGANISM: Homo Sapiens

<400> SEQUENCE: 617

```
caggtgcagt tgatacagtc tggggctgag gtgaagaagc ctggggcctc agtgaaggtt     60
tcctgcaagg catctagata cagcttcacc agctactata tgcactgggt gcgacaggcc    120
cctggacaag ggcttgagtg gatgggaata atcaacccta aaaagggtag tacaagttac    180
gcacagaagt tccagggcag agtcaccatg accaggaca cgtccacgag cacagtctac     240
atggagctga gcagcctgag atctgaggac acggccgtgt attactgtgc gagagatggg    300
tatggcagct ctcccggct gatccagctc tggggccagg gcaccctggt caccgtctcc    360
tca                                                                 363
```

<210> SEQ ID NO 618
<211> LENGTH: 121
<212> TYPE: PRT
<213> ORGANISM: Homo Sapiens

<400> SEQUENCE: 618

```
Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Lys Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120
```

<210> SEQ ID NO 619
<211> LENGTH: 8
<212> TYPE: PRT
<213> ORGANISM: Homo Sapiens

<400> SEQUENCE: 619

```
Ile Asn Pro Lys Ser Ser Ser Thr
1               5
```

<210> SEQ ID NO 620
<211> LENGTH: 363
<212> TYPE: DNA
<213> ORGANISM: Homo Sapiens

<400> SEQUENCE: 620

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaaccca aaagtagcag tacaagttac    180
gcacagaagt tccagggcag agtcaccatg accaggaca cgtccacgag cacagtctac    240
atggagctga gcagcctgag atctgaggac acggccgtgt attactgtgc gagagatggg   300
tatggcagct ctcccggct gatccagctc tggggccagg gcaccctggt caccgtctcc    360
tca                                                                 363
```

<210> SEQ ID NO 621
<211> LENGTH: 121
<212> TYPE: PRT
<213> ORGANISM: Homo Sapiens

<400> SEQUENCE: 621

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Ser Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 622
<211> LENGTH: 8
<212> TYPE: PRT
<213> ORGANISM: Homo Sapiens

<400> SEQUENCE: 622

Ile Asn Pro Lys Ser Gly Asp Thr
1               5

<210> SEQ ID NO 623
<211> LENGTH: 363
<212> TYPE: DNA
<213> ORGANISM: Homo Sapiens

<400> SEQUENCE: 623

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaaccta aaagtggtga cacaagttac    180
```

```
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggct gatccagctc tggggccagg gcaccctggt caccgtctcc     360
tca                                                                  363
```

<210> SEQ ID NO 624
<211> LENGTH: 121
<212> TYPE: PRT
<213> ORGANISM: Homo Sapiens

<400> SEQUENCE: 624

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Asp Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 625
<211> LENGTH: 8
<212> TYPE: PRT
<213> ORGANISM: Homo Sapiens

<400> SEQUENCE: 625

Ile Asn Pro Lys Ser Gly Ser Arg
1               5

<210> SEQ ID NO 626
<211> LENGTH: 363
<212> TYPE: DNA
<213> ORGANISM: Homo Sapiens

<400> SEQUENCE: 626

```
caggtgcagt tgatacagtc tggggctgag gtgaagaagc ctggggcctc agtgaaggtt    60
tcctgcaagg catctagata cagcttcacc agctactata tgcactgggt gcgacaggcc   120
cctggacaag ggcttgagtg gatgggaata atcaacccta aaagtggtag tagaagttac    180
gcacagaagt tccagggcag agtcaccatg accagggaca cgtccacgag cacagtctac    240
atggagctga gcagcctgag atctgaggac acggccgtgt attactgtgc gagagatggg    300
tatggcagct ctcccggct gatccagctc tggggccagg gcaccctggt caccgtctcc     360
tca                                                                  363
```

<210> SEQ ID NO 627
<211> LENGTH: 121
<212> TYPE: PRT
<213> ORGANISM: Homo Sapiens -continued

<400> SEQUENCE: 627

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Arg Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
            100                 105                 110

Gln Gly Thr Leu Val Thr Val Ser Ser
        115                 120

<210> SEQ ID NO 628
<211> LENGTH: 8
<212> TYPE: PRT
<213> ORGANISM: Homo Sapiens

<400> SEQUENCE: 628

Ile Asn Pro Lys Ser Gly Ser Ser
1               5

<210> SEQ ID NO 629
<211> LENGTH: 363
<212> TYPE: DNA
<213> ORGANISM: Homo Sapiens

<400> SEQUENCE: 629
caggtgcagt tgatacagtc tggggctgag gtgaagaagc ctggggcctc agtgaaggtt      60
tcctgcaagg catctagata cagcttcacc agctactata tgcactgggt gcgacaggcc     120
cctggacaag gcttgagtg gatgggaata atcaaccta aaagtggtag tagcagttac       180
gcacagaagt tccagggcag agtcaccatg accaggaca cgtccacgag cacagtctac      240
atggagctga gcagcctgag atctgaggac acggccgtgt attactgtgc gagagatggg     300
tatggcagct ctcccggct gatccagctc tggggccagg gcaccctggt caccgtctcc      360
tca                                                                  363

<210> SEQ ID NO 630
<211> LENGTH: 121
<212> TYPE: PRT
<213> ORGANISM: Homo Sapiens

<400> SEQUENCE: 630

Gln Val Gln Leu Ile Gln Ser Gly Ala Glu Val Lys Lys Pro Gly Ala
1               5                   10                  15

Ser Val Lys Val Ser Cys Lys Ala Ser Arg Tyr Ser Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Lys Ser Gly Ser Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
                100                 105                 110

Gln Gly Thr Leu Val Thr Val Ser Ser
            115                 120

<210> SEQ ID NO 631
<211> LENGTH: 363
<212> TYPE: DNA
<213> ORGANISM: Homo Sapiens

<400> SEQUENCE: 631
caggttcagc tgattcagtc cggcgccaaa gtgaagaaac ctggcgcctc tgtgaaggtg      60
tcctgcaagg cctctcggta caagttcacc tcctactaca tgcactgggt ccgacaggcc    120
cctggacaag gattggagtg gatgggcatc atcaacccca gtccggctc acctcttac      180 gcccagaaat tccagggcag agtgaccatg accagagaca cctctacctc caccgtgtac    240
atggaactgt ccagcctgag atccgaggac accgccgtgt actactgtgc cagagatggc    300
tacggcagct ctccagact gatccagttg tggggccagg gcacactggt cacagtgtcc      360
tct                                                                   363

<210> SEQ ID NO 632
<211> LENGTH: 121
<212> TYPE: PRT
<213> ORGANISM: Homo Sapiens

<400> SEQUENCE: 632

Gln Val Gln Leu Ile Gln Ser Gly Ala Lys Val Lys Lys Pro Gly Ala
1               5                   10                  15

Ser Val Lys Val Ser Cys Lys Ala Ser Arg Tyr Lys Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Lys Ser Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Tyr Gly Ser Phe Ser Arg Leu Ile Gln Leu Trp Gly
                100                 105                 110

Gln Gly Thr Leu Val Thr Val Ser Ser
            115                 120

<210> SEQ ID NO 633
<211> LENGTH: 318
<212> TYPE: DNA
<213> ORGANISM: Homo Sapiens

<400> SEQUENCE: 633
ggacaaccta aggccgctcc ttctgtgacc ctgtttcctc catcctccga ggaactgcag    60
gccaacaagg ctaccctcgt gtgcctgatc tccgactttt accctggcgc tgtgaccgtg    120
gcctggaagg ctgatagttc tcctgtgaag gccggcgtgg aaaccaccac accttccaag    180

```
cagtccaaca acaaatacgc cgcctcctcc tacctgtctc tgacccctga acagtggaag    240
tcccacaagt cctactcttg ccaagtgacc cacgagggct ccaccgtgga aaagacagtg    300
gctcctaccg agtgctcc                                                  318
```

<210> SEQ ID NO 634
<211> LENGTH: 8
<212> TYPE: PRT
<213> ORGANISM: Homo Sapiens
<220> FEATURE:
<221> NAME/KEY: MISC_FEATURE
<222> LOCATION: (7)..(7)
<223> OTHER INFORMATION: Xaa is Arg or Glu

<400> SEQUENCE: 634

Ile Asn Gln Asp Gly Ser Xaa Lys
1               5

<210> SEQ ID NO 635
<211> LENGTH: 15
<212> TYPE: PRT
<213> ORGANISM: Homo Sapiens
<220> FEATURE:
<221> NAME/KEY: MISC_FEATURE
<222> LOCATION: (9)..(9)
<223> OTHER INFORMATION: Xaa is Lys or Ser

<400> SEQUENCE: 635

Ala Arg Glu Gly Tyr Ser Ser Ile Xaa Tyr Tyr Gly Met Asp Val
1               5                   10                  15

<210> SEQ ID NO 636
<211> LENGTH: 8
<212> TYPE: PRT
<213> ORGANISM: Homo Sapiens
<220> FEATURE:
<221> NAME/KEY: MISC_FEATURE
<222> LOCATION: (3)..(3)
<223> OTHER INFORMATION: Xaa is Lys or Ser

<400> SEQUENCE: 636

Arg Tyr Xaa Phe Thr Ser Tyr Tyr
1               5

<210> SEQ ID NO 637
<211> LENGTH: 14
<212> TYPE: PRT
<213> ORGANISM: Homo Sapiens
<220> FEATURE:
<221> NAME/KEY: MISC_FEATURE
<222> LOCATION: (8)..(8)
<223> OTHER INFORMATION: Xaa is Phe or Ser
<220> FEATURE:
<221> NAME/KEY: MISC_FEATURE
<222> LOCATION: (11)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is Ile or Leu

<400> SEQUENCE: 637

Ala Arg Asp Gly Tyr Gly Ser Xaa Ser Arg Xaa Xaa Gln Leu
1               5                   10

<210> SEQ ID NO 638
<211> LENGTH: 14
<212> TYPE: PRT

```
<213> ORGANISM: Homo Sapiens
<220> FEATURE:
<221> NAME/KEY: MISC_FEATURE
<222> LOCATION: (8)..(8)
<223> OTHER INFORMATION: Xaa is Phe or Ser
<220> FEATURE:
<221> NAME/KEY: MISC_FEATURE
<222> LOCATION: (11)..(11)
<223> OTHER INFORMATION: Xaa is Leu or Val
<220> FEATURE:
<221> NAME/KEY: MISC_FEATURE
<222> LOCATION: (12)..(12)
<223> OTHER INFORMATION: Xaa is Ile or Leu

<400> SEQUENCE: 638

Ala Arg Asp Gly Tyr Gly Ser Xaa Ser Arg Xaa Xaa Gln Leu
1               5                   10

<210> SEQ ID NO 639
<211> LENGTH: 14
<212> TYPE: PRT
<213> ORGANISM: Homo Sapiens
<220> FEATURE:
<221> NAME/KEY: MISC_FEATURE
<222> LOCATION: (11)..(11)
<223> OTHER INFORMATION: Xaa is Leu or Val

<400> SEQUENCE: 639

Ala Arg Asp Gly Tyr Gly Ser Phe Ser Arg Xaa Ile Gln Leu
1               5                   10

<210> SEQ ID NO 640
<211> LENGTH: 15
<212> TYPE: PRT
<213> ORGANISM: Homo sapiens

<400> SEQUENCE: 640

Ala Arg Asp Gly Tyr Gly Ser Phe Ser Ser Arg Cys Leu Gln Leu
1               5                   10                  15

<210> SEQ ID NO 641
<211> LENGTH: 14
<212> TYPE: PRT
<213> ORGANISM: Homo sapiens

<400> SEQUENCE: 641

Ala Arg Asp Gly Tyr Gly Ser Ser Ser Arg Cys Ile Gln Leu
1               5                   10

<210> SEQ ID NO 642
<211> LENGTH: 14
<212> TYPE: PRT
<213> ORGANISM: Homo sapiens

<400> SEQUENCE: 642

Ala Arg Asp Gly Tyr Gly Ser Ser Ser Arg Cys Leu Met Leu
1               5                   10

<210> SEQ ID NO 643
<211> LENGTH: 14
<212> TYPE: PRT
<213> ORGANISM: Homo sapiens

<400> SEQUENCE: 643

Ala Arg Asp Gly Tyr Gly Ser Ser Ser Arg Ile Leu Gln Leu
1               5                   10
```

```
<210> SEQ ID NO 644
<211> LENGTH: 14
<212> TYPE: PRT
<213> ORGANISM: Homo sapiens

<400> SEQUENCE: 644

Ala Arg Asp Gly Tyr Gly Ser Ser Ser Arg Leu Leu Gln Leu
1               5                   10

<210> SEQ ID NO 645
<211> LENGTH: 14
<212> TYPE: PRT
<213> ORGANISM: Homo sapiens

<400> SEQUENCE: 645

Ala Arg Asp Gly Tyr Gly Ser Ser Ser Arg Gln Leu Gln Leu
1               5                   10

<210> SEQ ID NO 646
<211> LENGTH: 14
<212> TYPE: PRT
<213> ORGANISM: Homo sapiens

<400> SEQUENCE: 646

Ala Arg Asp Gly Tyr Gly Ser Ser Ser Arg Val Leu Gln Leu
1               5                   10

<210> SEQ ID NO 647
<211> LENGTH: 8
<212> TYPE: PRT
<213> ORGANISM: Homo sapiens

<400> SEQUENCE: 647

Gly Phe Lys Phe Asn Ser Tyr Trp
1               5
```

FIXAXFX BISPECIFIC ANTIBODY WITH COMMON LIGHT CHAIN

FIELD OF THE INVENTION

This invention relates to bispecific antigen-binding molecules (e.g., antibodies) that bind factor IXa and factor X clotting factors in the blood coagulation cascade. Such bispecifics functionally substitute for factor VIII by activating factor X, restoring blood clotting ability to patients who are deficient in FVIII, i.e., patients who have type A haemophilia.

BACKGROUND

Haemophilia is an inherited condition in which the blood has a reduced ability to clot, owing to loss of function (partial or total) of one of the many clotting factors. Haemophilia A is a deficiency in blood clotting factor VIII (FVIII). The disease has mild, moderate and severe forms, depending on the degree to which the patient retains any residual FVIII function and on the balance of other components in the blood coagulation cascade. If untreated, haemophilia A leads to uncontrolled bleeding, which can result in severe disability, especially through damage to joints from haemarthrosis events. The disease is often life-limiting and can be life-threatening. The global incidence of haemophilia A is believed to be around 1:10,000. Haemophilia B (deficiency of a different blood clotting factor, factor IX) is less common, with an incidence of around 1:50,000. Both diseases are X-linked so are usually found in males, the incidence of haemophilia A in male births thus being around 1 in 5,000.

Preventing bleeding episodes is essential to improving patients' quality of life and reducing the risk of fatal blood loss. For haemophilia A, the missing co-factor can be replaced by administration of FVIII. FVIII for administration to a patient may be recombinantly expressed or it may be purified from blood plasma. Typically, patients on this treatment self-inject with FVIII every 48 hours or 3× per week.

Treatment with FVIII is not a perfect solution. A serious drawback is that it can trigger production of allo-antibodies in the body. This renders treatment with FVIII ineffective, as the allo-antibodies bind the FVIII and prevent its activity, putting the patient in a dangerous situation if a bleed occurs. Such inhibitory antibodies develop in about 30% of patients treated with FVIII for severe haemophilia.

Treatment with plasma-derived FVIII, rather than the recombinant form, has been reported to have a lower risk of triggering inhibitory antibodies in patients. This may be due to the plasma-derived form retaining Von Willebrand factor (VWF), which is found naturally in association with FVIII and may mask immunogenic epitopes. However, no form of FVIII has yet been produced that completely avoids the risk of inhibitory antibodies.

Despite being possibly more immunogenic, recombinant FVIII offers some advantages over the plasma-derived form, since being more stable it is easier and cheaper to store and transport. The risk of transmitting infections via products from donated blood plasma is now much reduced compared with the 1980s when viruses such as hepatitis C and HIV were inadvertently spread to recipients of infected blood products, but of course the need for strict safety controls remains.

New recombinant forms of FVIII have been developed, such as the B-domain truncated polypeptide turoctocog alfa (NovoEight®). However, such products are ineffective for patients that develop neutralising antibodies against FVIII. Some patients successfully undergo immune tolerance induction to prevent anti-FVIII antibodies from developing. However, there remains a substantial demand for alternatives to FVIII for use in patients who have, or are at risk of developing, inhibitory antibodies.

One such alternative is recombinant factor VIIa, known as activated eptacog alfa (NovoSeven®). However, it has a short half-life and must be injected every few hours. Its use is largely restricted to rescue therapy or providing haemostatic cover during surgery in haemophiliacs who have inhibitory antibodies, rather than being a viable option for long term protective treatment.

Another available product is FEIBA (Factor Eight Inhibitor Bypassing Activity), an activated prothrombin complex concentrate (aPCC), which similarly can be used to control bleeding episodes and to prevent bleeding during surgical interventions in haemophiliac patients who have inhibitors to factor VIII.

A variety of other alternative therapies are currently being pursued, such as gene therapy, suppression of anti-thrombin using siRNA, and an antibody to TFPI (Tissue factor Pathway Inhibitor), concizumab.

One approach is a humanised bispecific IgG antibody targeting both factor IXa (FIXa) and factor X (FX). The bispecific antibody binds FIXa with one arm and FX with the other arm, bringing these two co-factors together and thereby promoting FIXa-catalysed activation of FX in the same way that FVIII does. Thus, the antibody functionally replaces FVIII in the blood coagulation cascade (FIG. 1). As its structure is completely different from FVIII, the antibody cannot be neutralised by anti-FVIII antibodies and so is suitable for patients who have developed, or are at risk of developing, allo-antibodies to administered FVIII.

In 2012, Kitazawa et al reported isolation of a FIXa/X bispecific antibody which was able to activate FX, from a screen of approximately 40,000 anti-FIXa/X bispecific antibodies that had been produced by immunising 92 laboratory animals with human FIXa or FX and co-transfecting the anti-FIXa and anti-FX antibody genes into host cells for expression [1]. The selected antibody was refined to generate a humanised antibody designated hBS23, which showed coagulation activity in FVIII-deficient plasma and in vivo haemostatic activity in primates [1]. A more potent version of this antibody, designated hBS910 [2], entered clinical trials under the investigational drug name ACE910, INN emicizumab [3]. The development of ACE910 took place in one of the leading antibody groups globally. Nevertheless, it took more than 7 years to engineer a molecule with the appropriate in vivo efficacy and with biochemical and biophysical properties suitable for clinical scale manufacturing.

In a phase I study of 48 healthy male subjects receiving ACE910 subcutaneously at doses up to 1 mg/kg, 2 subjects tested positive for anti-ACE910 antibodies [4]. The antibody was reported to have a linear pharmacokinetic profile and a half-life of about 4-5 weeks [4]. Emicizumab was subsequently administered to 18 Japanese patients with severe haemophilia A, at weekly subcutaneous doses of up to 3 mg/kg, and was reported to reduce the episodic use of clotting factors to control bleeding in these patients [5]. In December 2016, emicizumab was reported to have met its primary endpoint in a phase III clinical trial for reducing bleeding in patients with haemophilia A (the "HAVEN 1" study). A statistically significant reduction in the number of bleeds was reported for patients treated with emicizumab prophylaxis compared with those receiving no prophylactic treatment. The study was also reported to have met all secondary endpoints, including a statistically significant reduction in the number of bleeds over time with emicizumab prophylaxis treatment in an intra-patient comparison in people who had received prior bypassing agent prophylaxis treatment. The efficacy data on emicizumab are therefore encouraging, although safety concerns were heightened by the death of a patient on the HAVEN 1 study. The approved drug carries a boxed warning regarding the risk of thrombotic microangiopathy and thromboembolism in patients receiving aPCC in combination with emicizumab. As noted above, aPCC is used to control bleeding in patients who have inhibitory antibodies to FVIII, a key patient group for treatment with the bispecific antibody.

It is important to note that management of haemophilia requires continuous treatment for a patient's lifetime, beginning at the point of diagnosis—which is usually in infancy—and calls for a therapy that will be tolerated without adverse effects and that will remain effective over several decades or even a century. Long term safety, including low immunogenicity, is therefore of greater significance for an anti-haemophilia antibody compared with antibodies that are intended to be administered over a shorter duration such as a period of weeks, months or even a few years.

WO2018/098363 described bispecific antibodies binding to FIX and FX, isolated from a human antibody yeast library (Adimab). WO2018/098363 disclosed that increasing the affinity of the anti-FIXa arm of a bispecific antibody results in an increase in FVIIIa activity (represented by decreased blood clotting time in an assay). A bispecific antibody "BS-027125" was generated by affinity maturation of an initially selected "parent" antibody, which increased the affinity of its FIXa-binding arm. BS-027125 was reported to achieve approximately 90% FVIIIa-like activity in a one-stage clotting assay. When compared with emicizumab, BS-027125 was reported to exhibit much higher affinity binding to factor FIX zymogen, FIXa and FX zymogen, and much lower binding (no detected binding) to FXa. The FIX-binding arm, "BIIB-9-1336" reportedly showed selective binding for FIXa (activated FIX) in preference to FIX zymogen (mature FIX prior to proteolytic activation), and was found to bind an epitope overlapping with the FIXa epitope bound by FVIIIa. The FX-binding arm, "BIIB-12-917", reportedly showed selective binding to FX zymogen, lacked detectable binding to (activated) FXa, and bound an epitope of FX that lies within the activation peptide (which is present in FX zymogen but not FXa). Further mutations were then introduced into selected FIX-binding antibodies, including BIIB-9-1336, to generate libraries from which to select for antibodies with even further increased specificity and/or affinity for FIXa.

WO2018/141863 and WO2018/145125 also described anti-FIXaxFX bispecific antibodies and their use as procoagulants for treating or reducing bleeding.

SUMMARY OF THE INVENTION

The present invention relates to improved bispecific antigen-binding molecules that bind blood clotting factors FIXa and FX. The bispecific antigen-binding molecules of the present invention enhance the FIXa-catalysed activation of FX to FXa, and can effectively replace the natural cofactor FVIIIa which is missing in patients with haemophilia A, to restore the ability of the patients' blood to clot. See FIG. 2.

As reported here, the inventors succeeded in generating a number of bispecific antigen-binding molecules having suitable qualities for development as therapeutic products, including very high potency in enhancing FX activation. Described are bispecific antigen-binding molecules having novel binding sites for anti-FIXa and anti-FX, which can be used to effectively substitute for FVIIIa in the blood clotting cascade. In particular, an anti-FIXa binding site is described which is highly active in combination with an array of different anti-FX binding sites and can thus be incorporated into a variety of different FIXa-FX bispecifics, providing flexibility for selection of bispecific antibodies with further desired characteristics such as ease of manufacture.

The inventors have designed bispecific antibodies which combine a potent FVIII mimetic activity (as indicated by high performance in in vitro assays) with robust biochemical and biophysical properties suitable for clinical scale manufacturing (including expression, bispecific molecular assembly, purification and formulation), and which are of fully human origin, thereby minimising the risk of immunogenicity in human in vivo therapy.

Aspects of the invention are set out in the appended claims, and further embodiments and preferred features of the invention are described below.

In a first aspect, the present invention relates to bispecific antigen-binding molecules comprising (i) a FIXa binding polypeptide arm comprising a FIXa binding site, and (ii) a FX binding polypeptide arm comprising a FX binding site. The FIXa and/or the FX binding polypeptide arm may comprise an antibody Fv region comprising the FIXa or FX binding site respectively. An antibody Fv region is an antibody VH-VL domain pair. The VH domain comprises HCDR1, HCDR2 and HCDR3 in a VH domain framework, and the VL domain comprises LCDR1, LCDR2 and LCDR3 in a VL domain framework. The polypeptide arm may comprise an antibody heavy chain (optionally one comprising an IgG constant region) and/or an antibody light chain.

Antigen-binding molecules of the present invention may thus comprise
 first and second antibody Fv regions, the first and second antibody Fv regions comprising binding sites for FIXa and for FX respectively, and
 a half-life extending region for prolonging the half-life of the molecule in vivo.

The half-life extending region may be a heterodimerisation region, comprising a first polypeptide covalently linked (e.g., as a fusion protein) to the first antibody Fv region and a second polypeptide covalently linked (e.g., as a fusion protein) to the second antibody Fv region, wherein the two polypeptides pair covalently and/or non-covalently with one another. The first and second polypeptides of the heterodimerisation region may have identical or different amino acid sequences. The heterodimerisation region may comprise one or more antibody constant domains, e.g., it may be an antibody Fc region.

Bispecific antigen-binding molecules of the present invention are able to bind FIXa through the FIXa binding site of the FIXa binding polypeptide arm and to bind FX through the FX binding site of the FX binding polypeptide arm, and thereby enhance the FIXa-catalysed activation of FX to FXa. This may be determined in an in vitro FX activation assay as described herein.

The FIXa binding site may be provided by a set of complementarity determining regions (CDRs) in the FIXa binding polypeptide arm, the set of CDRs comprising HCDR1, HCDR2, HCDR3 and LCDR1, LCDR2 and LCDR3. Optionally, HCDR1 is SEQ ID NO: 406, HCDR2 is SEQ ID NO: 407 and HCDR3 is SEQ ID NO: 408. Optionally, LCDR1 is SEQ ID NO: 6, LCDR2 is SEQ ID NO: 7 and LCDR3 is SEQ ID NO: 8.

The set of HCDRs in the FIXa binding polypeptide arm may be the set of HCDRs of any anti-FIX VH domain shown herein, such as any shown in Table S-9A, any identified in Table N, or any of the VH domains N0128H, N0436H, N0511H, N1091H, N1172H, N1280H, N1314H, N1327H or N1333H shown in FIG. 20. HCDR1 may be SEQ ID NO: 441. HCDR2 may be SEQ ID NO: 634 or SEQ ID NO: 436. HCDR3 may be SEQ ID NO: 635 or SEQ ID NO: 433. The CDRs may be the N1280 CDRs, wherein HCDR1 is SEQ ID NO: 441, HCDR2 is SEQ ID NO: 436 and HCDR3 is SEQ ID NO: 533. Alternatively the CDRs may be the N1333H CDRs.

The set of LCDRs in the FIXa binding polypeptide arm may be the set of LCDRs of any anti-FIX VL domain shown herein. The LCDRs may be the LCDRs of 0128L as shown in Table S-50. LCDR1 may be SEQ ID NO: 6, LCDR2 may be SEQ ID NO: 7 and/or LCDR3 may be SEQ ID NO: 8.

Optionally, one or more amino acids in the set of CDRs may be mutated to differ from these sequences. For example, the set of CDRs may comprise 1, 2, 3, 4 or 5 amino acid alterations, the altered residue or residues being in any one or more of the heavy or light chain CDRs. For example the set of CDRs may comprise one or two conservative substitutions. The choice of mutations, e.g., substitutions, can be informed by the information and analysis provided in the Examples herein.

The FIXa binding polypeptide arm may comprise an antibody VH domain comprising a set of HCDRs HCDR1, HCDR2 and HCDR3. The sequence of HCDR1 may be SEQ ID NO: 406, optionally with one or two amino acid alterations (e.g., substitutions). The sequence of HCDR2 may be SEQ ID NO: 407, optionally with one or two amino acid alterations (e.g., substitutions). The sequence of HCDR3 may be SEQ ID NO: 408, optionally with one or two amino acid alterations (e.g., substitutions).

The FIXa binding polypeptide arm may comprise an antibody VL domain comprising a set of LCDRs LCDR1, LCDR2 and LCDR3. The sequence of LCDR1 may be SEQ ID NO: 6, optionally with one or two amino acid alterations (e.g., substitutions). The sequence of LCDR2 may be SEQ ID NO: 7, optionally with one or two amino acid alterations (e.g., substitutions). The sequence of LCDR3 may be SEQ ID NO: 8, optionally with one or two amino acid alterations (e.g., substitutions).

The antibody Fv region of the FIXa binding polypeptide arm may comprise a VH domain generated through recombination of immunoglobulin heavy chain v, d and j gene segments, wherein the v gene segment is VH3-7 (e.g., VH3-7*01), wherein the j gene segment is JH6 (e.g. JH6*02), and optionally wherein the d gene segment is DH1-26 (e.g., DH1-26*01), and/or it may comprise a VL domain generated through recombination of immunoglobulin light chain v and j gene segments, wherein the v gene segment is VL3-21 (e.g., VL3-21*d01) and the j gene segment is JL2 (e.g., JL2*01). In another embodiment, a VL domain may be one that is generated through recombination of immunoglobulin light chain v and j gene segments, wherein the v gene segment is VL3-21 (e.g., VL3-21*d01) and the j gene segment is JL3 (e.g., JL3*02).

The amino acid sequence of the VH domain of a FIXa polypeptide binding arm may share at least 90% sequence identity with a VH domain shown in FIG. 20, e.g., the N1280H VH domain. Sequence identity may be at least 95%, at least 97%, at least 98% or at least 99%. Optionally the VH domain is one of the anti-FIX VH domains shown herein, such as any shown in Table S-9A, any identified in Table N, or any of the VH domains N0128H, N0436H, N0511H, N1091H, N1172H, N1280H, N1314H, N1327H or N1333H shown in FIG. 20. Optionally the VH domain is N1280H, N1333H, N1441, N1442 or N1454. Optionally the anti-FIXa VH domain comprises the amino acid sequence of any of said VH domains (e.g., N1280H) with up to 5 amino acid substitutions, i.e., 1, 2, 3, 4 or 5 substitutions. Substitutions may optionally be in one or more framework regions, e.g., there may be 1 or 2 substitutions in FR3, optionally at IMGT position 84 and/or IMGT position 86.

The amino acid sequence of the VL domain may share at least 90% sequence identity with SEQ ID NO: 10 (0128L). Sequence identity may be at least 95%, at least 96%, at least 97%, at least 98% or at least 99%. Optionally the VL domain amino acid sequence is SEQ ID NO: 10. The VL domain amino acid sequence may alternatively be SEQ ID NO: 416.

The FX binding site may be provided by a set of CDRs in the FX binding polypeptide arm. The FX binding polypeptide arm may comprise an antibody VH-VL domain pair (i.e., an antibody Fv region), the VH domain comprising HCDR1, HCDR2 and HCDR3 in a framework, and the VL domain comprising LCDR1, LCDR2 and LCDR3 in a framework.

The FX binding site may be provided by the HCDRs of any anti-FX VH domain identified herein (e.g., any set of HCDR1, HCDR2 and HCDR3 of a VH domain shown in Table S10-C and/or in FIG. 11) and the 0128L LCDRs.

The FX binding polypeptide arm may comprise a VH domain having at least 90% amino acid sequence identity with a VH domain disclosed herein, including any in Table S-10C and/or in FIG. 11—for example the T0687H, T0736H or T0999H VH domain. Sequence identity may be at least 95%, at least 96%, at least 97%, at least 98% or at least 99%. Optionally the VH domain comprises the amino acid sequence of said VH domain with up to 5 amino acid substitutions, i.e., 1, 2, 3, 4 or 5 substitutions. Substitutions may optionally be in one or more framework regions.

The FX binding polypeptide arm may comprise a VH domain having at least 90% amino acid sequence identity with the T0201 VH domain (shown in FIG. 11). Sequence identity may be at least 95%, at least 96%, at least 97%, at least 98% or at least 99%. Optionally the VH domain comprises the amino acid sequence of said VH domain with up to 5 amino acid substitutions, i.e., 1, 2, 3, 4 or 5 substitutions. Substitutions may optionally be in one or more framework regions.

The FX binding polypeptide arm may comprise any VH domain amino acid sequence identified herein, such as any shown in Table S-10C, any identified in Table T or any from FIG. 11. Optionally the VH domain is T0201 H, T0687H, T0736H or T0999H.

The FX binding polypeptide arm may comprise a VL domain having at least 90% amino acid sequence identity with the 0128L VL domain SEQ ID NO: 10. Sequence identity may be at least 95%, at least 96%, at least 97%, at least 98% or at least 99%. Optionally the VL domain comprises the amino acid sequence of the 0128L VL domain with up to 5 amino acid substitutions, i.e., 1, 2, 3, 4 or 5 substitutions. Optionally the VL domain amino acid sequence is SEQ ID NO: 10. Alternatively the VL domain sequence is SEQ ID NO: 416.

The FX binding polypeptide arm may comprise an antibody Fv region comprising
  a VH domain generated through recombination of immunoglobulin heavy chain v, d and j gene segments, wherein the v and j gene segments are IGHV1-46 (e.g., VH1-46*03) and IGHJ1 (e.g., JH1*01), and optionally wherein the d gene segment is IGHD6-6 (e.g., DH6-6*01), and a VL domain generated through recombination of immunoglobulin light chain v and j gene segments, wherein the v and j gene segments are IGLV3-21 (e.g., VL3-21*d01) and IGLJ2 (e.g., JL2*01) or IGLJ3 (e.g., JL3*02).

Accordingly, one aspect of the present invention is a bispecific antibody that binds FIXa and FX and catalyses FIXa-mediated activation of FX, wherein the antibody comprises two immunoglobulin heavy-light chain pairs, wherein a first heavy-light chain pair comprises a FIXa binding Fv region comprising a first VH domain paired with a first VL domain, and a second heavy-light chain pair comprises a FX binding Fv region comprising a second VH domain paired with a second VL domain, wherein the first VH domain comprises a set of HCDRs comprising HCDR1, HCDR2 and HCDR3 with amino acid sequences defined wherein HCDR1 is SEQ ID NO: 406, HCDR2 is SEQ ID NO: 407 and HCDR3 is SEQ ID NO: 408, and/or wherein the first VH domain is at least 95 identical to the N1280H VH domain at the amino acid sequence level;

the second VH domain is at least 95% identical to the T0201H VH domain at the amino acid sequence level, and the first VL domain and the second VL domain each comprise a set of LCDRs comprising LCDR1, LCDR2 and LCDR3 with amino acid sequences defined wherein LCDR1 is SEQ ID NO: 6, LCDR2 is SEQ ID NO: 7 and LCDR3 is SEQ ID NO: 8, and/or wherein the first VL domain and the second VL domain are at least 95% identical to the 0128L VL domain SEQ ID NO: 10 at the amino acid sequence level.

Another aspect of the present invention is a bispecific antibody that binds FIXa and FX and catalyses FIXa-mediated activation of FX, wherein the antibody comprises two immunoglobulin heavy-light chain pairs, wherein a first heavy-light chain pair comprises a FIXa binding Fv region comprising a first VH domain paired with a first VL domain, and a second heavy-light chain pair comprises a FX binding Fv region comprising a second VH domain paired with a second VL domain, wherein the first VH domain is a product of recombination of human immunoglobulin heavy chain v, d and j gene segments, wherein the v gene segment is IGHV3-7 (e.g., VH3-7*01) and the j gene segment is IGHJ6 (e.g., JH6*02), the second VH domain is a product of recombination of human immunoglobulin heavy chain v, d and j gene segments, wherein the v gene segment is IGHV1-46 (e.g., VH1-46*03) and the j gene segment is IGHJ1 (e.g., JH1*01), and optionally wherein the d gene segment is IGHD6-6 (e.g., DH6-6*01), and the first VL domain and the second VL domain are both products of recombination of human immunoglobulin light chain v and j gene segments, wherein the v gene segment is IGLV3-21 (e.g., VL3-21*d01) and the j gene segment is IGLJ2 (e.g., JL2*01) or IGLJ3 (e.g., JL3*02).

Another aspect of the present invention is a bispecific antibody that binds FIXa and FX and catalyses FIXa-mediated activation of FX, wherein the antibody comprises two immunoglobulin heavy-light chain pairs, wherein a first heavy-light chain pair comprises a FIXa binding Fv region comprising a first VH domain paired with a first VL domain, and a second heavy-light chain pair comprises a FX binding Fv region comprising a second VH domain paired with a second VL domain, wherein the first VH domain has at least 95% amino acid sequence identity with the N1280H VH domain, the second VH domain has at least 95% amino acid sequence identity with the T0201H VH domain, and the first VL domain and the second VL domain each have at least 95% amino acid sequence identity with the 0128L VL domain.

The first VH domain may comprise a set of HCDRs comprising HCDR1, HCDR2 and HCDR3 with amino acid sequences defined wherein HCDR1 is SEQ ID NO: 406, HCDR2 is SEQ ID NO: 407 and HCDR3 is SEQ ID NO: 408.

The first VH domain may have at least 96%, at least 97%, at least 98% or at least 99% amino acid sequence identity to N1280H. The first VH domain may comprise a set of N1280H HCDRs comprising N1280H HCDR1, N1280H HCDR2 and N1280H HCDR3. For example, it may be the N1280H VH domain. Alternatively, the VH domain may be the N1441H, N1442H or N1454H VH domain.

Amino acid sequences of example VH domains and sets of VH CDRs are shown in FIG. 20 and/or in Table S-9A. The first VH domain of the bispecific antibody may be, or may have at least 95%, at least 96%, at least 97%, at least 98% or at least 99% amino acid sequence identity to, any of these VH domains. Optionally it may comprise a VH domain amino acid sequence having up to 5 amino acid substitutions, i.e., 1, 2, 3, 4 or 5 substitutions compared with said VH domain. Substitutions are optionally in framework regions.

Examples of residues and substitutions that may be retained or introduced in the first VH domain include the following (defined with reference to N1280H, with IMGT numbering as shown in FIG. 14):

Substitution of another residue (e.g., Asp, Glu, His, Asn, Gln, Met, Thr, Gly, Ser, Ala, Ile, Leu, Val or Tyr) at Lys84 in FR3, e.g., Lys84Asp or Lys84Glu; and Substitution of another residue at Ser86 in FR3, e.g., a negatively charged residue such as Glu (Ser86Glu).

Further examples include:

Substitution of a negatively charged residue (e.g., Asp or Glu) or His at one or more of Gln3, Val5, Gly9, Gly11, Gly16, Gly17 and Leu21 FR1, such as any of Gln3Asp, Gln3Glu, Gln3His, Val5Glu, Gly9Glu, Gly11Asp, Gly11Glu, Gly11His, Gly16Glu, Gly17Asp, Gly17Glu or Leu21Asp;

Substitution of a negatively charged residue at Val68 and/or Val71 in FR3, e.g., Val68Asp, Val68Glu or Val71Glu;

Substitution of His, Gln or Leu at Arg75 in FR3;

Substitution of Ser, Thr, Gly, Leu or Lys at Arg80 in FR3; and

Substitution of Asp or His at Asn82 in FR3.

Any one or more of the above-listed sequence features may be included.

The second VH domain may be, or may have at least 95%, at least 96%, at least 97%, at least 98% or at least 99% amino acid sequence identity to T0201H or any other VH domain shown in FIG. 11 and/or in Table S-10C. Optionally it may comprise a VH domain amino acid sequence having up to 5 amino acid substitutions, i.e., 1, 2, 3, 4 or 5 substitutions compared with said VH domain. Substitutions are optionally in framework regions. The second VH domain may comprise an HCDR1 which is the T0201H HCDR1, an HCDR2 which is the T0201H HCDR1, and/or an HCDR3 which is the T0201H HCDR3. Amino acid sequences of these CDRs are shown in FIGS. 11 and 12 and in Table S-10C. Further example CDRs are indicated in FIG. 12 and in Table T. For example, the second VH domain may comprise:
an HCDR1 which is the T0201 HCDR1 or the T0736 HCDR1,
an HCDR2 which is the T0201 HCDR2, and/or
an HCDR3 which is the T0201 HCDR3, the T0687 HCDR3 or the T0736 HCDR3.

Optionally, HCDR1 is SEQ ID NO: 636 or SEQ ID NO: 598. Optionally, HCDR2 is SEQ ID NO: 467. Optionally, HCDR3 is SEQ ID NO: 637, SEQ ID NO: 638, SEQ ID NO: 639 or SEQ ID NO: 565.

Examples of residues and substitutions that may be retained or introduced in the second VH domain include the following (defined with reference to T0201H, with IMGT numbering as shown in FIG. 13):
Substitution of another amino acid residue at Cys114, e.g., wherein the substituted residue is Ile, Gln, Arg, Val or Trp, (preferably Ile, Val or Leu);
Substitution of another positively charged residue for Gln3 in FR1, e.g., Gln3Arg or Gln3Lys;
Germlining of residues in framework regions, e.g., Ile5Val (substitution of valine for isoleucine at residue 5 in FR1), or replacement of a non-germline residue in a framework region by a different non-germline residue, e.g., Ile5Arg (substitution of arginine for isoleucine at residue 5 in FR1);
Substitution of another amino acid residue (e.g., Lys, Ala or Gly) at Glu11 in FR1, e.g., Glu11Lys;
Substitution of a positively charged amino acid residue for Gly16 in FR1, e.g., Gly16Arg;
Presence of Met at position 39 in FR2, or alternatively Leu at this position;
Presence of Ser at position 62 and/or position 64 in CDR2;
Substitution of Tyr at Phe71 in FR3;
Substitution of a positively charged residue at Thr82 in FR3, e.g., Thr82Arg or Thr82Lys; Presence of Ser at position 85 in FR3, or alternatively Thr at this position;
Substitution of a positively charged residue at Thr86 in FR3, e.g., Thr86Arg or Thr86Lys.

Any one or more of the above-listed sequence features may be included.

The FIXa binding polypeptide arm and the FX binding polypeptide arm may each comprise an antibody Fv, wherein the VL domain of each Fv has an identical amino acid sequence, i.e. the bispecific antigen-binding molecule has a common VL domain. The molecule may have a common light chain comprising a variable region and a constant region, optionally a human lambda constant region.

The bispecific antigen-binding molecule may be a tetrameric immunoglobulin comprising
a first pair of antibody heavy and light chains (heavy-light chain pair) comprising a FIXa binding Fv region,
a second heavy-light chain pair comprising a FX binding Fv region,
wherein each heavy chain comprises a VH domain and a constant region, and each light chain comprises a VL domain and a constant region, and wherein the first and second heavy-light chain pairs associate through heterodimerisation of their heavy chain constant regions to form the immunoglobulin tetramer.

As noted, the light chain may be a common light chain, i.e., the light chain of the first and second heavy-light chain pairs has an identical amino acid sequence. Each heavy-light chain pair may comprise the 0128L CL constant domain paired with a CH1 domain. The sequence of the light chain may be SEQ ID NO: 405. Alternatively the sequence of the light chain may be SEQ ID NO: 414. Exemplary immunoglobulin isotypes include human IgG, e.g., IgG4, optionally with engineered constant domains such as IgG4 PE.

The Fc domain of a bispecific antibody may be engineered to promote heterodimerisation over homodimerisation. For example, the heavy chain constant region of the first heavy-light chain pair may comprise a different amino acid sequence from the heavy chain constant region of the second heavy-light chain pair, wherein the different amino acid sequences are engineered to promote heterodimerisation of the heavy chain constant regions. Examples include knobs-into-holes mutations or charge pair mutations. Alternatively, the heavy chain constant region of the first heavy-light chain pair may be identical to the heavy chain constant region of the second heavy-light chain pair, in which case it is expected that both homodimers and heterodimers will assemble, and these will be subsequently separated using one or more purification steps in the antibody manufacturing process to isolate the desired heterodimer comprising one anti-FIXa arm and one anti-FX arm.

An advantageous feature of bispecific antibodies exemplified here is that they have been generated from human immunoglobulin gene segments, using the Kymouse platform. Unlike antibodies generated from immunisation of normal laboratory animals, which may require "humanisation" steps such as grafting of mouse CDRs into human antibody variable domains and iterative refinement of the engineered variable domains to mitigate a loss of function resulting from these changes, the antibodies of the present invention were generated and selected from the outset with fully human antibody variable domains. The use of a fully human antibody is of special relevance in the context of haemophilia treatment, where low immunogenicity is paramount, as noted above. The low immunogenicity of the bispecific antibodies of the present invention renders them suitable for treatment of haemophilia A patients, including those with or without inhibitory antibodies to other treatments such as FVIII. Patients receiving antigen-binding molecules of the present invention should be at minimal risk of developing an immunogenic response to the therapy.

The mode of action of the bispecific molecules is also associated with a good safety profile, with low risk of complications such as deep vein thrombosis and pulmonary embolism. Activity of the bispecific molecules is comparable with that of natural FVIII and a mechanism of action that is integrated within the existing blood coagulation pathway, being activated only in the context of upstream triggering of the natural clotting cascade.

Bispecific antibodies according to the present invention have shown strong activity in a number of functionally relevant assays for FVIII mimetic activity, including factor Xase assay, activated partial thromboplastin time (aPTT) assay and thrombin generation assay (TGA), as exemplified herein.

Other desirable features include long-half life (reducing the required frequency of administration) and amenability of the molecules to formulation at high concentration (facilitating subcutaneous injection in the home setting).

Patient compliance is recognised to be a significant issue for long term self-administered therapy, especially among teenage and young adult patients. For a treatment to succeed in the field, its administration schedule should be simple for the patient to understand and follow with minimum inconvenience. Long intervals between administered doses are desirable, but reducing dose frequency without sacrificing therapeutic activity requires a product with both a long in vivo half life and a sufficient efficacy at "trough" concentrations towards the end of a dosing period. Antigen-binding molecules according to the present invention desirably have a long in vivo half life. This can be facilitated by inclusion of an Fc region which undergoes recycling in vivo via FcRn. Antigen-binding molecules according to the present invention also preferably maintain high functional activity at low concentration. We found that bispecific antibodies according to the present invention have a thrombogenic activity similar to that of emicizumab but with an increase in thrombogenic activity that is most pronounced at lower concentrations. Data disclosed herein indicate that bispecific antibodies according to the present invention possess a thrombogenic activity that is the same as or surpasses that of emicizumab at concentrations in at least the range of 1 to 300 nM, for example when the antibody and emicizumab are tested at the following concentrations:

1-30 nM, e.g., at 1 nM, at 3 nM, at 10 nM and/or at 30 nM; 100-300 nM, e.g., at 100 nM and/or at 300 nM.

Activity can be measured in the thrombin generation assay described herein. Effective activity at low concentrations may help to ensure that protection against bleeds is maintained towards the end of a dosing period—the in vivo concentration of the antibody being lowest in the final days before the next dose is due. It may also assist in protecting areas of the body which are relatively poorly perfused by the circulation—including the joints, which are a common site of problematic bleeding in haemophiliac patients.

Further aspects of the invention relate to pharmaceutical compositions comprising the bispecific antigen-binding molecules and their use in medicine including for the treatment of haemophilia A, as set out in the appended claims and described in the present disclosure.

Monospecific antibodies are also provided as aspects of the present invention. Thus, an anti-FIXa antibody may comprise two copies of a first heavy-light chain pair as defined herein. An anti-FX antibody may comprise two copies of a second heavy-light chain pair as defined herein.

Further aspects include nucleic acid molecules encoding sequences of the antibodies described herein, host cells containing such nucleic acids, and methods of producing the antibodies by culturing the host cells and expressing and optionally isolating or purifying the antibodies. The expressed antibody is thereby obtained. VH and VL domains of antibodies described herein may similarly be produced and are aspects of the present invention. Suitable production methods of antibodies include large-scale expression from host cells (e.g, mammalian cells) in a bioreactor by continuous or batch culture (e.g., fed batch culture).

BRIEF DESCRIPTION OF THE DRAWINGS

Aspects and embodiments of the invention will now be described in more detail, with reference to the drawings, in which:

FIG. 3 shows the amino acid sequence (SEQ ID NO: 334) of factor IX, with residue numbering for the mature protein. The signal peptide (straight underlined) is cleaved after secretion. The propeptide (wave underlined) is cleaved on maturation. Mature factor IX contains a light chain (residues 1-145) and a heavy chain (residues 146-415). The activation peptide (boxed) is cleaved on activation, generating activated factor IXa which contains a light chain (residues 1-145) and a heavy chain (residues 181-415, bold) joined by a disulphide bridge between Cys132 and Cys289.

FIG. 4 shows the amino acid sequence (SEQ ID NO: 335) of factor X, with residue numbering. Residues 1-31 are a signal peptide (straight underlined). Residues 32-40 are a propeptide (wave underlined). The FX light chain is residues 41-179. The FX heavy chain is residues 183-488. The FXa heavy chain is residues 235-488 (bold).

FIG. 11 is an amino acid sequence alignment of a selection of anti-FX VH domains from the T0200H B cell cluster. Germline sequence (SEQ ID NO: 518) is shown for comparison. CDRs are boxed.

FIG. 12 identifies mutants of the T0201H VH domain in which the terminal four residues of CDR3 were individually mutated to other amino acids. For example the T0590H VH domain is a Cys114Ala mutant of the T0201H VH domain, i.e., in which the cysteine at IMGT position 114 is replaced by alanine.

FIG. 13 shows the amino acid sequence of VH domain T0201H, annotated in (A) to show FR1, CDR1, FR2, CDR2, FR3, CDR3 and FR4, and in (B) to show IMGT numbering.

FIG. 14 shows the amino acid sequence of VH domain N0128H, aligned against N192H and N1280H and annotated in (A) to show FR1, CDR1, FR2, CDR2, FR3, CDR3 and FR4, and in (B) to show IMGT numbering.

FIG. 20 shows VH domain amino acid sequences of N0128H, N0436H, N0511H, N1091H, N1172H, N1280H, N1314H, N1327H and N1333H, annotated to identify their framework regions and CDRs.

FIG. 25 identifies CDRs of VH domains which were progressively improved for FVIII mimetic activity during the mutagenesis process. Black shading ident

DETAILED DESCRIPTION

Blood Coagulation

Figure 1:
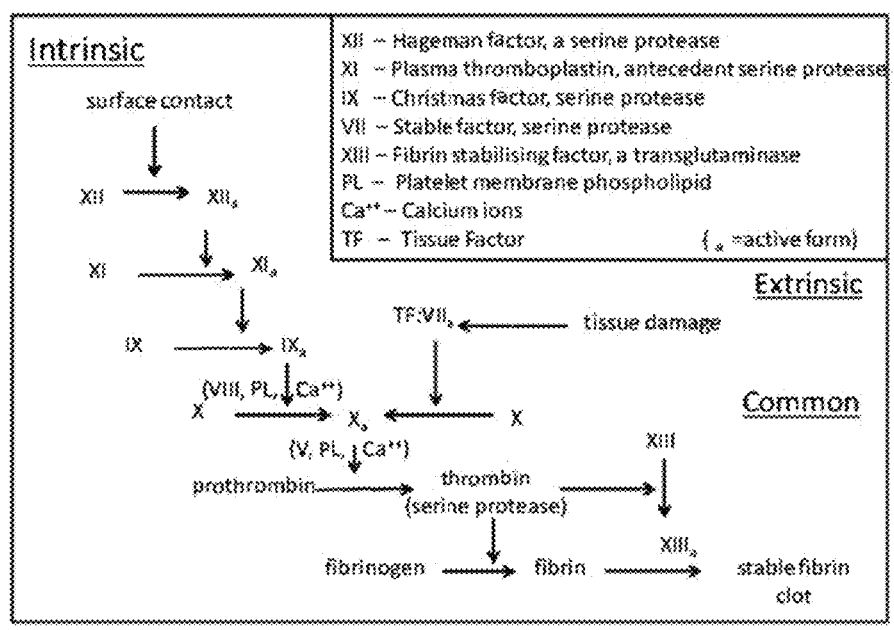
FIG. 1 illustrates the blood coagulation cascade [6].

The blood coagulation cascade is diagrammed in FIG. 1. Coagulation or clotting is one of the most important biological processes which stops blood loss from a damaged vessel to allow the vessel to be repaired. The mechanism of coagulation involves activation, adhesion, and aggregation of platelets along with deposition and maturation of fibrin. Misregulation of coagulation can result in excessive bleeding (haemophilia) or obstructive clotting (thrombosis). Coagulation is highly conserved in all mammals. It is controlled by a complex network of coagulation factors. Coagulation is initiated when the endothelium lining the blood vessel is damaged. The exposure of subendothelial tissue factor (TF) to plasma factor VII (FVII) leads to primary haemostasis (extrinsic pathway): a loose plug is formed at the site of injury. Activation of additional coagulation factors, especially factor IX (FIX) and factor VIII (FVIII), leads to secondary haemostasis (intrinsic pathway): fibrin strands are formed to strengthen the plug. Extrinsic and intrinsic pathways ultimately converge to a common point: the formation of the factor Xa/Va complex which together with calcium and bound on a phospholipid surface generate thrombin (factor IIa) from prothrombin (factor II).

Figure 2:
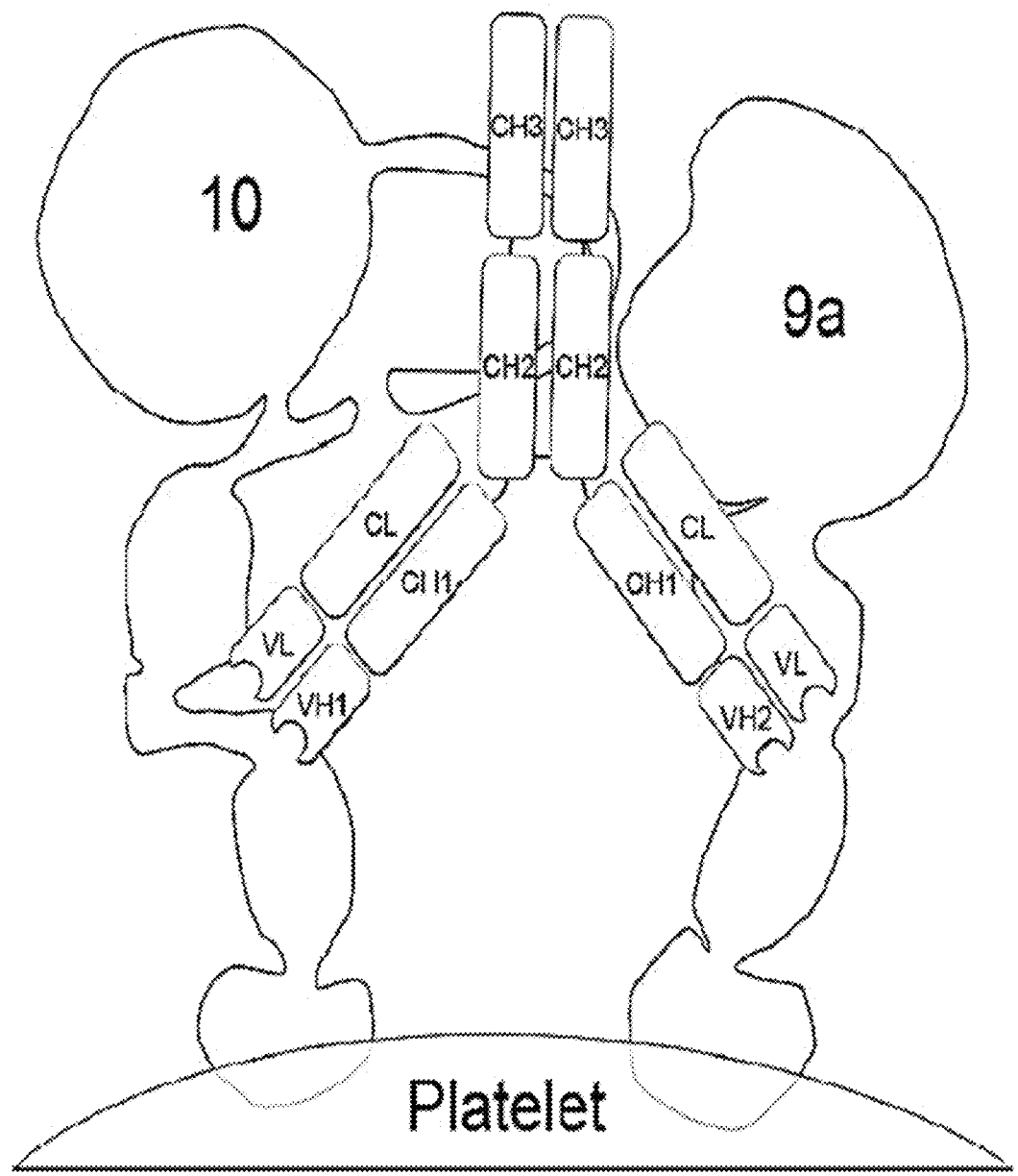
FIG. 2 shows (A) co-factor action of FVIIIa interacting with FIXa and FX; (B) co-factor action of bispecific antibody interacting with FIXa and FX; and (C) bispecific antibody interacting with FIXa (9a) and FX (10) on the surface of a platelet. Bispecific antibody in this embodiment is a four chain molecule having two disulphide-linked heavy chains each comprising (N to C) domains VH1-CH1-CH2-CH3 and two identical light chains (common light chain) comprising (N to C) domains VL-CL. In this illustration, binding site comprising VH1-VL binds to FX and binding site comprising VH2-VL binds to FXa.

FVIII is cleaved by thrombin or factor Xa (FXa), and the resultant factor VIIIa (FVIIIa) presents a heterotrimeric structure consisting of the A1 subunit, the A2 subunit, and the light chain. Upon activation and in the presence of calcium ions and a phospholipid surface (on platelets), FVIIIa binds via its light chain and A2 subunit to FIXa and simultaneously binds via its A1 subunit to FX, forming an active intrinsic "tenase" or "Xase" complex in which the FVIIIa cofactor brings FIXa and FX into proximity and also allosterically enhances the catalytic rate constant of FIXa. See FIG. 2a. Factor X is activated by the serine protease activity of FIXa, and the clotting cascade continues, culminating in the deposition of fibrin, the structural polymer of the blood clot.

Haemophilia arise through a deficiency in the Xase complex, due either to a lack of FVIII cofactor activity (haemophilia A) or a lack of FIX enzyme activity (haemophilia B).

Factor IX (FIX)

Factor IX is a serine protease which requires factor VIII as a cofactor. It circulates in blood as an inactive precursor, which is activated through intrinsic or extrinsic pathway at the time of haemostatic challenge, as discussed above.

Unless the context requires otherwise, factor IX referred to herein is human factor IX, and factor IXa is human factor IXa.

The amino acid sequence of human factor IX is shown in FIG. 3. The factor IX gene is approximately 34 kb in length and contains 8 exons. The transcript comprises a short 5' untranslated region, an open reading frame plus stop codon and a 3' untranslated region. The ORF encodes a 461 amino acid pre-pro-protein in which the pre-sequence (signal peptide) directs factor IX for secretion, the propeptide sequence provides a binding domain for a vitamin K dependent carboxylase, which carboxylates certain glutamic acid residues in the adjacent GLA domain, and the remainder represents the factor IX zymogen, which enters into circulation after removal of the pre- and pro-sequences. The mature 415 residue FIX protein contains, from N to C terminus: a GLA domain in which 12 glutamic acid residues are post-translationally γ-carboxylated, two epidermal growth factor (EGF)-like domains, an activation peptide sequence and a catalytic serine protease domain. FIX is activated by either activated factor XI generated through the intrinsic pathway, or by the TF/FVIIa complex of the extrinsic pathway. Either way, activation involves cleavage of the peptide bond following R145 (α-cleavage) and of the peptide bond following R180 (β-cleavage), releasing an activation peptide corresponding to the intervening sequence, and thereby generating the activated FIXa molecule, which has an N terminal light chain (GLA-EGF-EGF) and a C terminal heavy chain (catalytic domain) joined by a disulphide bridge between C132 of the light chain and C289 of the heavy chain. Residue numbering refers to amino acids in the mature FIX polypeptide sequence. On the phospholipid surface where the Xase complex forms, it is the GLA domain of FIXa which associates with the phospholipid, while the catalytic domain stands high (>70 Å) above the phospholipid surface and is modulated by the A2 domain of FVIIIa [7, 8].

The molecular basis of haemophilia B—deficiency in FIXa activity—is diverse, including a variety of point mutations, nonsense mutations, mRNA splice site mutations, deletions, insertions, or mis-sense mutations at activation cleavage sites [9].

The catalytic (protease) domain of activated FIX (FIXa) is involved in binding to FVIIIa. Residue E245 in this domain binds calcium ions, and mutations at this position may reduce binding to FVIII and lead to haemophilia B, for example the substitution E245V. Mutations within the FIX helix formed by residues 330-338 are also linked with reduced binding to FVIII and consequently to haemophilia B.

Non-pathogenic mutations in factor IX have also been reported, including single nucleotide polymorphisms (SNPs) and length polymorphisms—reviewed in [9]. These include the MnII SNP in exon 6, resulting in T/A substitution at residue 148 (Malmo polymorphism), which is relatively common among white and black American populations [9].

Factor X (FX)

Unless the context requires otherwise, factor X referred to herein is human factor X, and factor Xa is human factor Xa. The amino acid sequence of human FX is shown in FIG. 4.

FX is also known as Stuart-Prower factor. It is a serine endopeptidase. FX can be activated, by hydrolysis, into factor Xa by either factor IX (together with its cofactor, factor FVIII, as described above) or factor VII (with its cofactor, tissue factor). FX acts by cleaving prothrombin in two places—at an Arg-Thr bond and then at an Arg-Ile bond, to yield the active thrombin.

Antigen-Binding

A desirable feature of the bispecific antigen-binding molecule is that it binds FIXa and FX in a manner that allows the bound FIXa to activate the bound FX.

To bring FIXa and FX together and thereby promote the activation of FX by FIXa, the bispecific antigen-binding molecule may bind these two cofactors simultaneously. Binding may occur sequentially, e.g., an initial binary complex may form between a first binding arm and its cognate antigen, followed by binding of the second binding arm to its cognate antigen. In principle these two binding events may occur in either sequence, i.e., FIXa followed by FX, or FX followed by FIXa. The molecular choreography is influenced by the relative affinities of the two binding sites for their respective antigens. In a population of bispecific antigen-binding molecules, FIXa and FX, a number of different complexes are expected to exist in parallel. Thus the pool will comprise free antigen-binding molecule, free FIXa, free FX, FIXa complexed with antigen-binding molecule, FX complexed with antigen-binding molecule, and a tertiary complex of FIX, FX and antigen-binding molecule, with each of these species being present in different proportions according to the relative on-rates and off-rates of the individual interactions.

It may be preferable for a bispecific antigen-binding molecule to have a higher affinity for FIXa than for FX. Such a bispecific molecule would be envisaged to form an initial complex with FIXa, which in turn would bind and activate FX. The relatively low affinity for FX reduces the proportion of FX that is bound in incomplete antibody-antigen complexes (i.e., without FIXa). A potential advantage of this is that it allows a greater proportion of FX to remain free to engage with any FVIII that may be present in a patient's blood. Haemophilia A encompasses a range of deficiencies in FVIII, ranging from mild deficiency to total absence of functional FVIII. For those patients who retain some functional FVIII, it may be desirable to retain this natural activity as far as possible. Thus, it may be desirable to provide a bispecific antigen-binding molecule in which the FX binding arm does not compete with FVIII for binding to FX.

Preferably the FX binding arm has a higher affinity for FX than for FXa. A low affinity for FXa promotes release of the activated product, completing the role of the FVIII-mimetic molecule in the coagulation cascade and freeing the FX binding site for re-use. In various embodiments, a bispecific described herein (e.g., antibody IXAX-1280.0999.0325 or antibody IXAX-1441.0999.0325), the FX binding arm of such a bispecific (e.g., binding arm comprising T0999H VH domain), or an anti-FX monospecific antibody comprising a homodimer of two such arms, has at least 2-fold higher, at least 3-fold higher, at least 4-fold higher, at least 5-fold higher, at least 10-fold higher, at least 100-fold higher affinity for FX than for FXa, e.g., at least 1000-fold higher affinity for FX than for FXa, and optionally does not show significant binding to FXa, e.g., as measured by ELISA. For example, in various embodiments the bispecific, FX binding arm or anti-FX monospecific antibody (e.g., TINA-0999.0325) does not bind human FXa as determined by ELISA and with reference to a negative control IgG. As an alternative to ELISA, affinity may be measured by SPR and the affinity for FX compared with affinity for FXa.

FIXa Binding

The FIXa binding arm of a bispecific antigen-binding molecule may bind the light chain and/or the heavy chain of FIXa. Initial studies indicated that FIXa binding arms of the N128 lineage described in the Examples do not bind the FIXa light chain in isolation (in the absence of the heavy chain).

A bispecific antigen-binding molecule of the present invention (or FIXa binding polypeptide arm thereof) may thus be one which binds a FIXa molecule comprising a heavy chain and a light chain, and which does not bind the FIX light chain in the absence of the heavy chain. Optionally, the FIXa binding arm recognises an epitope formed by, or stabilised by, the combination of the FIXa heavy and light chains. It may for example make contact only with the light chain in the FIXa molecule, binding an epitope that is exposed or stabilised only when the light chain is present in combination with the heavy chain in the FIXa molecule. Alternatively, it may contact an epitope comprising one or more residues from both the light chain and the heavy chain, or comprising residues of the heavy chain alone.

An antigen-binding molecule according to the present invention, or a FIXa-binding polypeptide arm thereof, may bind the EC domain of human FIXa with an affinity (measured as $K_D$) of 10 mM or less, preferably 5 mM or less, more preferably 1 mM or less. For example, $K_D$ may be between 1 nM and 3 µM.

The $K_D$ for binding human FIXa may be between 0.1 µM and 1 µM, e.g., between 0.15 and 0.3 µM. The $K_D$ may be 0.6 µM or less, 0.5 µM or less, 0.4 µM or less, 0.3 µM or less, 0.25 µM or less, or 2 µM or less. The $K_D$ may be at least 0.1 µM, for example at least 0.2 µM. It may be 0.1 µM-0.5 µM.

The $K_D$ may be between 10 and 100 nM, e.g., between 25 and 75 nM.

The $K_D$ may be 50 nM or less, 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less. The $K_D$ may be at least 0.001 nM, for example at least 0.01 nM or at least 0.1 nM. The $K_D$ may be between 0.1-10 nM.

An antigen-binding molecule according to the present invention, or a FIXa-binding polypeptide arm thereof, may bind human FIX with an affinity (measured as $K_D$) between 0.1 µM and 1 µM, e.g., between 0.15 and 0.3 µM. The $K_D$ may be 0.6 µM or less, 0.5 µM or less, 0.4 µM or less, 0.3 µM or less, 0.25 µM or less, or 2 µM or less. The $K_D$ may be at least 0.1 µM, for example at least 0.2 µM.

The $K_D$ of interaction with FIX may be comparable to the $K_D$ of interaction with FIXa, e.g., there may be difference of less than 25%, optionally less than 10%, in the FIXa-binding arm's affinity for FIX compared with the affinity for FIXa. There may be no statistically significant difference in $K_D$ of interaction with FIX compared with FIXa.

As described elsewhere herein, affinity may be determined using surface plasmon resonance (SPR), e.g., with the binding arm coupled to a solid surface, optionally as a dimer (e.g., as monospecific IgG), with the antigen in solution as analyte, at 25° C.

FX Binding

An antigen-binding molecule according to the present invention, or a FX-binding polypeptide arm thereof, may bind the EC domain of human FX with a $K_D$ of 10 mM or less, preferably 5 mM or less, more preferably 1 mM or less. For example, $K_D$ may be between 5 µM and 1 nM, e.g., between 5 µM and 10 nM.

The $K_D$ may be between 0.1 µM and 2 µM, e.g., between 0.1 µM and 1 µM, e.g., between 0.15 and 0.3 µM. The $K_D$ may be 0.6 µM or less, 0.5 µM or less, 0.4 µM or less, 0.3 µM or less, or 0.25 µM or less. The $K_D$ may be at least 0.1 µM.

The $K_D$ may be 50 nM or less, 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less. The $K_D$ may be at least 0.001 nM, for example at least 0.01 nM or at least 0.1 nM. For example, the $K_D$ may be between 1-100 nM. $K_D$ may be between 1-10 nM.

As described elsewhere herein, affinity may be determined using surface plasmon resonance (SPR), e.g., with the binding arm coupled to a solid surface, optionally as a dimer (e.g., as monospecific IgG), with the antigen in solution as analyte, at 25° C.

Measurement of Antigen-Binding Affinity

The affinity of an antigen-binding molecule for binding FIX, FIXa, FX and FXa may be quantified in terms of the equilibrium dissociation constant $K_D$, the ratio Ka/Kd of the association or on-rate (Ka) and the dissociation or off-rate (kd) of the binding interaction. $K_D$, Ka and Kd for antigen binding can be measured using surface plasmon resonance (SPR). Example SPR procedure and conditions are set out in Example 10.

Quantification of affinity may be performed using SPR with the antigen-binding polypeptide arm in monovalent form, e.g., antibody Fab or Fv comprising the antigen binding site, or heterodimeric immunoglobulin (e.g., IgG) having a single antigen-binding arm for the antigen in question. Alternatively, it may be convenient to determine affinity for the antigen-binding polypeptide arm in bivalent form, for example IgG comprising homodimeric antigen-binding arms. SPR may comprise coating dimers of the antigen-binding polypeptide arm on to a biosensor chip (directly or indirectly), exposing the antigen-binding polypeptide arms to antigen in buffered solution at a range of concentrations, detecting binding, and calculating the equilibrium dissociation constant $K_D$ for the binding interaction. SPR may be performed at 25° C. A suitable buffered solution is 150 mM NaCl, 0.05% detergent (e.g., P20) and 3 mM EDTA, pH 7.6. HBS-P 1× (10 mM HEPES pH 7.4, 150 mM NaCl, 3 mM EDTA, 0.05% polysorbate 20 pH 7.6) with 2.5 mM $CaCl_2$. is an example buffer. The binding data can be fitted to a 1:1 model using standard algorithms, which may be inherent to the instrument used. A variety of SPR instruments are known, such as Biacore™, ProteOn XPR36™ (Bio-Rad®), and KinExA® (Sapidyne Instruments, Inc).

Cross-Reactivity

Regulatory bodies may require candidate therapeutic molecules to have demonstrated therapeutic efficacy in laboratory animals before they advance to human clinical trials. An example of an acquired haemophilia A animal model is a cynomolgus monkey that is rendered deficient in blood clotting through administration of a FVIII-neutralising antibody or a small molecule inhibitor against FVIII, thereby replicating the phenotype of a human haemophilia A patient. To enable testing of bispecific antigen-binding molecules in animal models, it is desirable for the binding site of each arm to be cross-reactive with the corresponding antigen from one or more non-human mammals. Thus, the FIXa binding site of the antigen-binding molecule may bind murine (e.g., mouse or rat), rabbit or non-human primate (e.g., cynomolgus monkey) FIXa as well as human FIXa, and the FX binding site may bind murine (e.g., mouse or rat), rabbit or non-human primate (e.g., cynomolgus monkey) FXa as well as human FXa.

One way to quantify the extent of species cross-reactivity of an antigen-binding molecule (or, more precisely, of its antigen binding site) is as the fold-difference in its affinity for antigen or one species compared with antigen of another species, e.g., fold difference in affinity for human antigen vs cynomolgus antigen. Affinity may be quantified as $K_D$, referring to the equilibrium dissociation constant of the binding of the antigen to the antigen-binding molecule. $K_D$ may be determined by SPR as described elsewhere herein.

A species cross-reactive binding molecule may have a fold-difference in affinity for binding human and non-human antigen that is 30-fold or less, 25-fold or less, 20-fold or less, 15-fold or less, 10-fold or less or 5-fold or less. To put it another way, the $K_D$ of binding the extracellular domain of the human antigen may be within 30-fold, 25-fold, 20-fold, 15-fold, 10-fold or 5-fold of the $K_D$ of binding the extracellular domain of the non-human antigen.

Preferably, the binding affinities of human and non-human antigen are within a range of 10-fold or less, more preferably within 5-fold or within 2-fold. $K_D$ for binding non-human FIXa, e.g., as determined by surface plasmon resonance, may be up to 10-fold (preferably up to 5-fold or up to 2-fold) greater or up to 10-fold lower (preferably up to 5-fold or up to 2-fold lower) than the Kd for binding human FIXa. Similarly, $K_D$ for binding non-human FX, e.g., as determined by SPR, may be up to 10-fold (preferably up to 5-fold or up to 2-fold) greater or up to 10-fold (preferably up to 5-fold or up to 2-fold) lower than the Kd for binding human FX. Methods of determining affinity are described elsewhere herein.

Binding molecules can also be considered species cross-reactive if the $K_D$ for binding antigen of both species meets a threshold value, e.g., if the $K_D$ of binding human antigen and the $K_D$ of binding non-human antigen are both 10 mM or less, preferably 5 mM or less, more preferably 1 mM or less. The $K_D$ may be 10 nM or less, 5 nM or less, 2 nM or less, or 1 nM or less. The $K_D$ may be 0.9 nM or less, 0.8 nM or less, 0.7 nM or less, 0.6 nM or less, 0.5 nM or less, 0.4 nM or less, 0.3 nM or less, 0.2 nM or less, or 0.1 nM or less.

While species cross-reactivity for binding antigen of different species may be advantageous, selectivity of the FIXa binding arm and the FX binding arm for their respective antigens is nevertheless desirable to avoid unwanted side effects. Thus, within the body, FIX/FIXa and FX/FXa are preferably the only antigens bound by the antigen-binding molecule.

Enhancement of FIXa-Mediated Activation of FX

The ability of a bispecific antigen-binding molecule to enhance the FIXa-mediated activation of FX to FXa may be determined in assays in vitro or in vivo.

Figure 7:
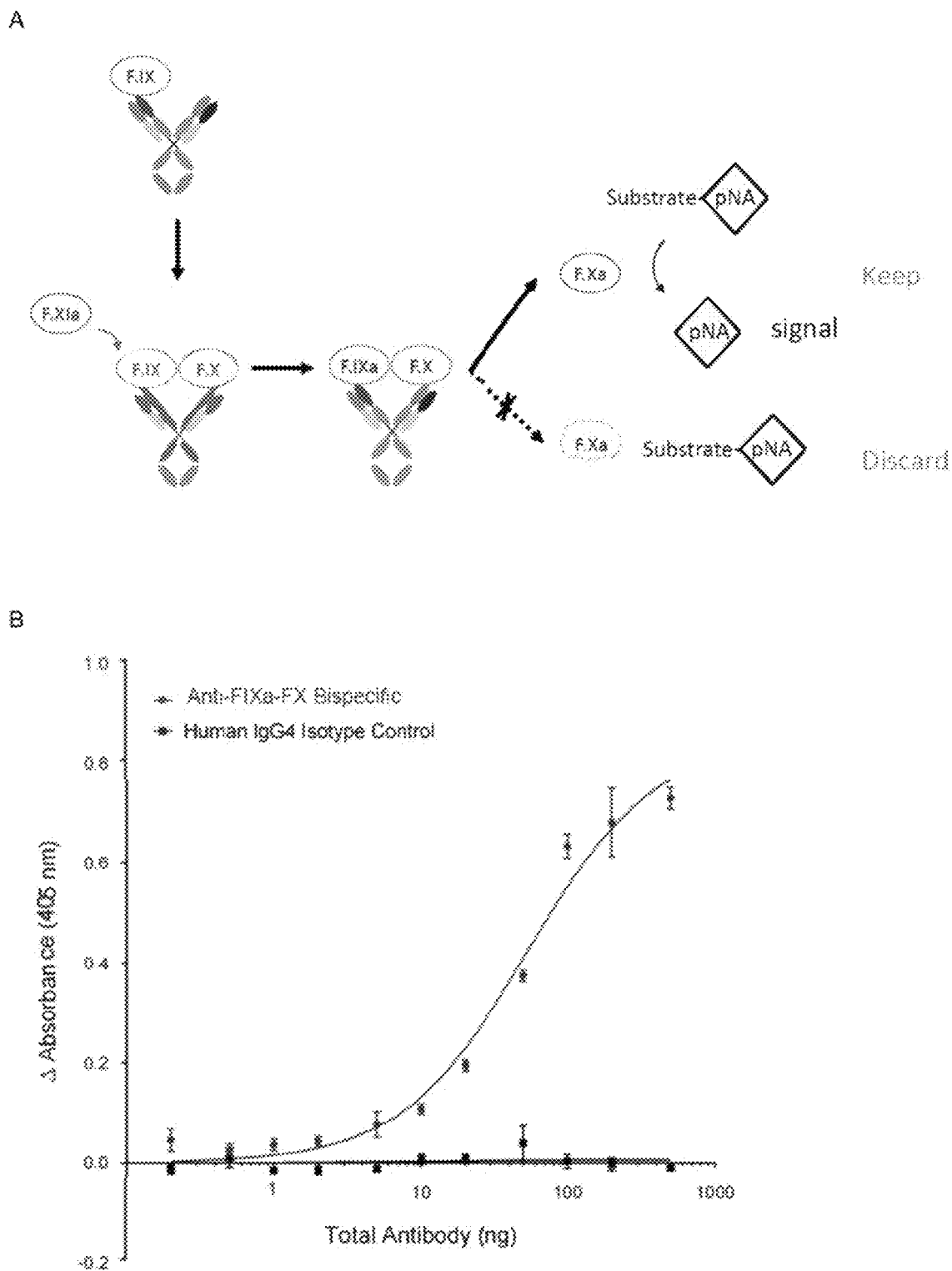
FIG. 7 illustrates (A) principles of in vitro assay for FVIII mimetic activity of a bispecific molecule (FXase or tenase assay); and (B) example data from the assay showing positive result for FIXa-FX bispecific molecule compared with negative control.

A suitable in vitro assay is the FX activation assay exemplified in Example 3 and Example 7 and illustrated in FIG. 7. The assay comprises
(i) contacting the bispecific antigen-binding molecule with FIXa and FX under conditions suitable for formation of FXa (e.g., in the presence of phospholipid, in buffered solution at 37° C.)
(ii) adding substrate that is cleavable by FXa to generate a detectable product, and
(iii) detecting, and optionally quantifying, the presence of the detectable product.

A detailed protocol is set out in Example 7.

The level of product may be compared with a control assay in which FIXa-FX bispecific antigen-binding molecule is absent from the reaction mixture. Significant difference in product level in the assay with the bispecific compared with control indicates that the bispecific is able to enhance FIXa-mediated activation of FX. FVIII may be included as a positive control.

The level of product may be compared with an assay in which the FIXa-FX bispecific antigen-binding molecule is emicizumab. A bispecific according to the present invention may enhance the FIXa-mediated activation of FX to FXa to the same or similar extent (e.g., within 10% difference or within 5% difference) as emicizumab, or to a greater extent (e.g., more than 10% more activation of FX to FXa than is achieved with emicizumab as measured by the level of detectable product). Preferably the bispecific antibody enhances the FIXa-mediated activation of FX to FXa to at least the same extent as emicizumab. The assay is typically performed at physiological temperature of 37 degrees C. Suitable concentrations of bispecific for use in the assay are indicated in the Examples herein, e.g., 12.5 µg/ml (10.4 nM) or 125 nM.

Another suitable assay is to measure the activated partial thromboplastin time (aPTT) in FVIII-deficient plasma, which may be performed in the presence or the absence of inhibitors and can be used to compare the activity of bispecific molecules with recombinant human FVIII. This assay is exemplified in Example 8. aPTT is an end point assay which provides a global overview of blood clot formation and provides coagulation time as the assay readout. FVIII-deficient plasma would typically have a coagulation time of around 80-90 seconds in the aPTT assay. Bispecific antigen binding molecules of the present invention are effective to reduce the coagulation time in an aPTT assay (compared with a negative control). The coagulation time of human FVIII-deficient in an aPTT assay with a bispecific antigen binding molecule according to the present invention may for example be the same as or less than that of the coagulation time with recombinant human FVIIIa. Physiological clotting time for normal (FVIII+) human plasma is typically <40 seconds, e.g., in the range of 37-34 s. Similar values are achievable with FVIII-deficient plasma upon provision of activated FVIIIa, which provides a convenient way of standardising the assay through calibration of the apparatus/measurement against reference values. Alternatively, coagulation time of normal (FVIII+) human plasma may be used for reference, the aPTT assay being begun by induction of coagulation through the addition of calcium. The assay is typically performed at physiological temperature of 37 degrees C. Suitable concentrations of bispecific for use in the assay are indicated in the Examples herein, and include 0.1 mg/ml (44 nM), 0.3 mg/ml (133 nM) and 0.5 mg/ml (222 nM).

A bispecific antigen-binding molecule of the present invention may give a coagulation time in the aPTT assay of within 10 seconds of that of FVIIIa (i.e., up to 10 seconds more than or up to 10 seconds less than the coagulation time of the aPTT assay with FVIIIa). Preferably, the coagulation time in the aPTT assay with a bispecific antigen binding molecule of the invention is less than that with FVIIIa. The bispecific antigen-binding molecule may reduce the coagulation time to less than 40 seconds, less than 35 seconds, or less than 30 seconds. The coagulation time may be between 20 and 40 seconds, e.g., between 20 and 30 seconds. Preferably the coagulation time is 22-28 seconds, e.g., 24-26 seconds.

Another measure of function is the rate at which thrombin is generated in FVIII-deficient blood plasma in the presence of the bispecific antigen-binding molecule. Activity of a bispecific antibody may be measured in a thrombin generation assay (TGA) [10]. A number of thrombin generation assays have been described, as recently reviewed [11]. Essentially, a TGA comprises measuring the conversion (activation) of prothrombin to thrombin over time following addition of a test molecule (here, the candidate bispecific antibody), where thrombin is detected via its cleavage of a substrate to form a detectable product.

With reference to FIG. 1, it will be remembered that the extrinsic tissue factor (TF) pathway exists to initiate the coagulation cascade. Cells expressing TF normally reside outside of the vasculature, and upon tissue damage such TF-bearing cells come into contact with circulating platelets. TF acts as a co-factor to facilitate the activation of small amounts of factors IX and X by factor VIIa. Activated factor Xa and factor V form a prothrombinase complex on TF-bearing cells, generating a limited amount of thrombin. The newly generated thrombin activates platelets which have accumulated at the site of injury and factor XI which is present on the platelets. Platelet bound FXIa is required to ensure further activation of FIXa. Given the TGA is an ex vivo assay, TF-bearing cells are absent and a coagulation trigger must be supplied to initiate the cascade. Commercial assays typically use a recombinant TF/phospholipid mixture to initiate coagulation [11]. The TGA method exemplified herein (see Example 13) uses a factor IXa/phospholipid mixture as the trigger, although other upstream activators such as FXIa could be used.

To perform the TGA, FVIII-deficient plasma is contacted with (i) the trigger reagent, (ii) a substrate convertable by thrombin to a detectable product, e.g., a fluorogenic or chromogenic substrate which produces a visually detectable product on cleavage by thrombin, and (iii) the test molecule (e.g., bispecific antibody), to create conditions under which the presence of FVIII-mimetic activity would result in thrombin generation and hence a signal from the detectable product. Typically, the plasma will lack free metal ions such as calcium, which are required in the blood clotting cascade (FIG. 1). $Ca^{2+}$ ions may be supplied (e.g., as $CaCl_2$ in solution) to initiate the assay, e.g., it may be contained within the substrate solution. Following initiation, generation of the detectable product (representing generation of thrombin) is monitored (preferably continuously, or at frequent intervals, e.g., about every 20 seconds) over time, e.g., by detecting fluorescence or colour. A plate reader may be used, e.g., to monitor conversion of a fluorogenic substrate into a fluorophore. TGA is performed at physiological temperature of 37 degrees C.

Figure 26:
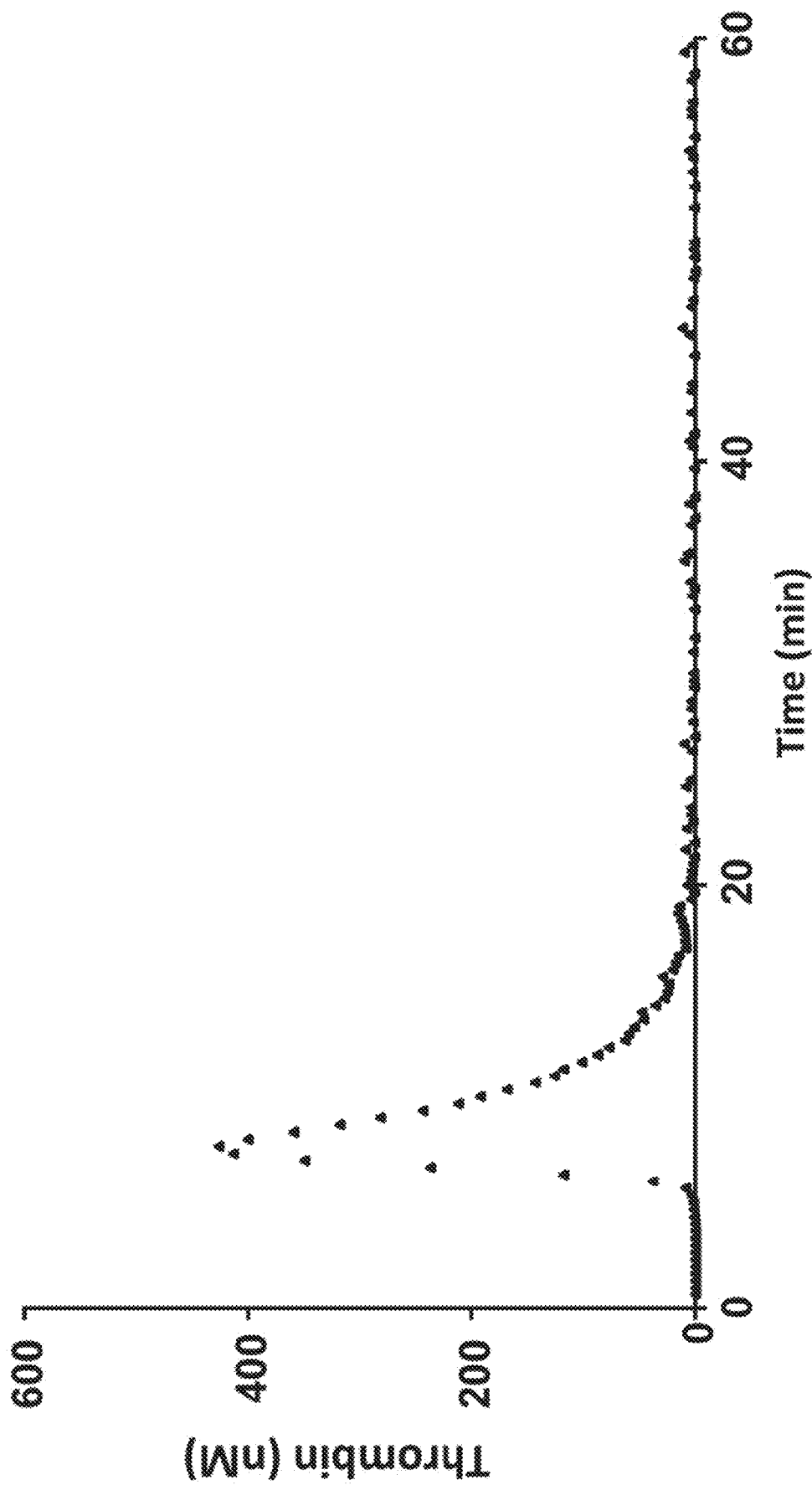

Fluorescence may be converted to thrombin concentration by calibrating against known concentrations of thrombin added to control plasma. A thrombogram may then be generated (FIG. 26, FIG. 27).

Preferably, bispecific antibodies (or other test molecules) are suitably purified for use in the TGA (e.g., by protein A chromatography and ion exchange chromatography or hydrophobic interaction chromatography), e.g., to provide the bispecific in a composition of at least 95 bispecific heterodimer (i.e., no more than 5% homodimeric or other antibody contaminants should be present). Preferably the test molecule is provided as close to 100% purity as possible. It may be about 98, 99% or 100% pure bispecific.

Approximate reference ranges for plasma from healthy individuals in a fluorogenic TGA are Cmax 200 to 450 nM and Tmax 5 to 8 minutes [11]. Activity in a TGA can also be compared against published representative thrombin generation curves for plasma from healthy individuals, patients with severe FVIII deficiency and patients with severe FVIII deficiency after FVIII infusion [12]. For standardisation, performance in the TGA may also be compared against a calibrator which represents a positive control molecule at known concentration. A dilution series of the test bispecific may be compared against the calibrator at a series of known fixed concentrations. A suitable calibrator is an emicizumab calibrator. Emicizumab calibrator is available commercially, prepared from FVIII immunodepleted citrated human plasma spiked with 100 μg/mL emicizumab (Hemlibra®) and further comprising buffer and stabilisers. It is supplied in lyophilised form and is reconstituted in water before use in the TGA. The exact concentration of emicizumab in the calibrator phial is known, so the activity of a test bispecific molecule in the assay can be compared against the activity of the calibrator after normalising for concentration. As an alternative control for comparison of a bispecific antibody against emicizumab, performance of the test bispecific antibody in the TGA may be compared against performance of a control bispecific antibody having the amino acid sequence of emicizumab, wherein the test bispecific antibody and the bispecific antibody having the amino acid sequence of emicizumab are tested under identical conditions in the TGA.

The TGA may be used to characterise six aspects of thrombin generation: lag time (lag), time to peak (Tmax), maximal peak height (Cmax), endogenous thrombin potential (ETP), velocity index (VI) and the "tail start" or return to baseline. The lag time represents the initiation phase before the thrombin peak begins to be generated, where addition of a trigger results in the activation of the coagulation cascade. Once initiated, large amounts of thrombin are quickly generated during the propagation phase. The time to peak represents the time taken (Tmax) to reach maximal thrombin peak height (Cmax), the ETP represents the total amount of thrombin generated and the velocity index characterises the slope between the lag time and the time to peak. The return to baseline (tail start) reflects the inhibition (by activated protein C) of thrombin formation and the inactivation (by antithrombin) of thrombin already formed. The Cmax and/or Tmax is typically the key measure used to represent activity in the TGA. References values in the TGA (e.g., Cmax, Tmax, lagtime etc.) may be determined for the bispecific at a fixed concentration, e.g., 1 nM, 3 nM, 10 nM, 30 nM, 100 nM or 300 nM. Parameters may be measured a series of concentrations, e.g., at 1 nM, 3 nM, 10 nM, 30 nM, 100 nM and 300 nM and/or other concentrations to obtain a complete dose response curve, allowing EC50 values to then be determined. The dose response curve can be fitted using a non-linear log(antibody) vs response variable slope model (e.g., variable slope 4 parameter logistic regression model, which may be performed using GraphPad Prism v8.0.0). EC50 is the concentration of test molecule (e.g., antibody) at which half-maximal effect is reached (half way between baseline and maximal value of the measured parameter). EC50 can be determined from the dose response curve. Worked examples with EC50 data are presented in Example 14 herein.

In one embodiment, the TGA comprises:
(a) contacting FVIII-deficient plasma lacking free calcium ions with
  (i) a trigger reagent comprising a factor IXa/phospholipid mixture,
  (ii) a solution comprising a fluorogenic substrate (e.g., 2 nM ZGGR-AMC fluorogenic substrate) which produces a visually detectable fluorophore on cleavage by thrombin, and calcium ions (e.g., 100 mM CaCl2)), (for example, the FluCa reagent from Stago), and
  (iii) the bispecific antibody (e.g., at a purity of 95%-100%, e.g., 99%-100%),
(b) incubating the plasma at 37 degrees C. under conditions in which the presence of FVIII-mimetic activity would result in thrombin generation and hence a signal from the fluorophore,
(c) detecting fluorescence over time to monitor conversion of the fluorogenic substrate to fluorophore,
(d) calibrating detected fluorescence against fluorescence from solutions of thrombin at predetermined concentrations, and
(e) determining one or more parameters of a thrombogram, wherein said parameters are:
  maximal thrombin peak height (Cmax) that is reached,
  time taken (Tmax) to reach maximal thrombin peak height, and/or
  length of the initiation phase before the thrombin peak begins to be generated (lag time).

Said one or more parameters are determined at a series of concentrations of the bispecific antibody to obtain a complete dose response curve including baseline and top plateau (maximal value) of response. A dose response curves may be fitted to the data points using a non-linear log [antibody] vs response parameter variable slope model (4 parameter logistic regression model). EC50 is determined from said dose response curve. Said one or more parameters, or EC50 for said one or more parameters, may be compared between the test bispecific antibody and emicizumab (e.g., emicizumab calibrator, as available from Enzyme Research Laboratories).

A bispecific antibody according to the present invention preferably exhibits a potency that is similar to or greater than that of emicizumab in a fluorimetric TGA. Higher potency may be represented by lower EC50 for one or more parameters in said assay, e.g., Cmax, Tmax or lagtime. As demonstrated in the Examples herein, embodiments of the present invention consistently demonstrated greater potency than emicizumab at lower concentrations. See, for example, the results presented in FIG. 29, FIG. 30, FIG. 31, FIG. 33 and FIG. 34.

The maximal response (e.g., highest Cmax, lowest Tmax, shortest lagtime, etc) in the fluorimetric TGA is also noteworthy. Maximal response is the level at which the measured parameter (e.g., Cmax) plateaus with increasing antibody concentration, and represents the maximum achievable level (e.g., the maximal Cmax). An excessive maximal response may be associated with increased risks of overdosing the bispecific molecule, including risk of consumption coagulopathy or disseminated intravascular coagulation (DIC) which is characterised by abnormally increased activation of procoagulant pathways. Hypercoagulability may compromise patient safety through coagulopathy events such as arterial/venous thrombosis, embolism and thrombotic microangiopathy, and would thus narrow the therapeutic window, i.e., the range of dose or plasma concentration at which a beneficial effect is achieved without unacceptable side effects or risk of adverse events.

Since emicizumab has received regulatory approval based on a safety profile deemed acceptable in human clinical trials, the maximal response of emicizumab in the TGA represent established safe limits. Optionally, bispecifics of the present invention have a maximal Cmax and/or maximal Tmax response in the TGA which is not more than 20% (e.g., not more than 15 or not more than 10%) different from that of emicizumab. These reference values may be determined using an emicizumab calibrator or a sequence identical analogue of emicizumab.

Bispecifics of the present invention may demonstrate maximal responses in the TGA as follows:
Cmax in the TGA not exceeding 500 nM. Optionally the maximal response for Cmax does not exceed 450 nM, e.g., does not exceed 400 nM. Maximal response for Cmax may be between 200 and 450 nM, e.g., between 250 and 350 nM; and/or
Tmax in the TGA not lower than a maximal response of 1 minute. Optionally the maximal response for Tmax is not less than 5 minutes, not less than 4 minutes, not less than 3 minutes or not less than 2 minutes. Maximal response for Tmax may be between 2 and 10 minutes, e.g., between 2 and 8 minutes or between 5 and 8 minutes.

A bispecific antigen-binding molecule according to the present invention may have a Cmax in the range of 100 to 450 nM (e.g., 200 to 450 nM) as determined by fluorimetric TGA, e.g., wherein the bispecific antibody is at a concentration of 100 nM or 300 nM in said assay. The Cmax is preferably at least 200 nM, more preferably at least 250 nM or at least 300 nM. The Cmax of the bispecific may be the same or similar to (e.g., within 10% difference from) the Cmax of emicizumab, or it may be greater than that of emicizumab. The bispecific may have a Cmax EC50 in said assay that is within 10% of the Cmax EC50 of emicizumab, or that is lower. Where the EC50 is lower than that of emicizumab, there may be at least a 2-fold, at least a 3-fold, at least a 4-fold or at least a 5-fold difference in Cmax EC50 in the TGA between the bispecific of the present invention and emicizumab. Optionally the Cmax EC50 in the TGA may be up to 10-fold, up to 15-fold or up to 20-fold different. EC50 of the Cmax for the bispecific antigen-binding molecule in the fluorimetric TGA may be less than 50 nM, e.g., between 1 nM and 50 nM, between 5 nM and 20 nM, or between 5 nM and 10 nM.

A bispecific antigen-binding molecule according to the present invention may have a Tmax of 8 minutes or under, e.g., in the range of 4 to 8 minutes, as determined by fluorimetric TGA, e.g., wherein the bispecific antibody is at a concentration of 100 nM or 300 nM in said assay. The Tmax of the bispecific may be the same or similar to (e.g., within 10% difference from) the Tmax of emicizumab, or it may be less than that of emicizumab. The bispecific may have a Tmax EC50 in said assay that is within 10% of the Tmax EC50 of emicizumab, or that is lower.

EC50 of the Tmax for the bispecific antigen-binding molecule in the fluorimetric TGA may be less than 5 nM, e.g., less than 3 nM or less than 2 nM. It may be between 1 nM and 5 nM, e.g., between 1 nM and 2 nM.

A bispecific antigen-binding molecule according to the present invention may have a lag time of 2-6 minutes as determined by fluorometric TGA, e.g., wherein the bispecific antibody is at a concentration of 100 nM or 300 nM in said assay. The lagtime of the bispecific may be the same or similar to (e.g., within 10% difference from) the lagtime of emicizumab, or it may be lower than that of emicizumab. The bispecific may have a lagtime EC50 in said assay that is within 10% of the lagtime EC50 of emicizumab, or that is lower.

Bispecific Antigen-Binding Molecules

The bispecific antigen-binding molecule comprises a FIXa binding polypeptide arm and a FX binding polypeptide arm. It may be a multi-chain or single-chain polypeptide molecule. While the FIXa binding polypeptide arm and the FX binding polypeptide arm represent different moieties of the bispecific molecule, one polypeptide can optionally form all or part of both the FIXa binding arm and the FX binding arm.

A polypeptide binding arm is the region of the bispecific molecule that comprises the binding site for one of the antigens (FIXa or FX). One or both antigen-binding sites of a bispecific molecule can be provided by a set of complementarity determining regions (or peptide loops) in a polypeptide arm, wherein the polypeptide arm is any suitable scaffold polypeptide whether that of an antibody (e.g., an antibody Fv region) or a non-antibody molecule. A binding arm may comprise one or more than one (e.g., two) polypeptides or parts (e.g., domains) thereof.

The invention is described in detail herein with reference to bispecific antibodies, wherein at least one of the antigen binding polypeptide arms is provided by a set of CDRs in an antibody VH and/or VL domain, optionally an Fv region.

Antibodies are immunoglobulins or molecules comprising immunoglobulin domains. Antibodies may be IgG, IgM, IgA, IgD or IgE molecules or molecules including antigen-specific antibody fragments thereof. The term "antibody" covers any polypeptide or protein comprising an antibody antigen-binding site. An antibody antigen-binding site (paratope) is the part of an antibody that binds to and is complementary to the epitope of its target antigen. The term "epitope" refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulphonyl groups, and, in certain embodiments, may have specific three-dimensional structural characteristics, and/or specific charge characteristics.

An antibody antigen-binding site is provided by a set of complementarity determining regions (CDRs) in an antibody VH and/or VL domain, and is capable of binding the antigen. In an example, the antibody binding site is provided by a single variable domain, e.g., a heavy chain variable domain (VH domain) or a light chain variable domain (VL domain). In another example, the binding site is provided by a VH/VL pair (an Fv) or two or more such pairs.

The antibody variable domains are the portions of the light and heavy chains of antibodies that include amino acid sequences of complementarity determining regions (CDRs; ie., CDR1, CDR2, and CDR3), and framework regions (FRs). Thus, within each of the VH and VL domains are CDRs and FRs. A VH domain comprises a set of HCDRs, and a VL domain comprises a set of LCDRs. VH refers to the variable domain of the heavy chain. VL refers to the variable domain of the light chain. Each VH and VL is typically composed of three CDRs and four FRs, arranged from amino-terminus to carboxy-terminus in the following order: FR1, CDR1, FR2, CDR2, FR3, CDR3, FR4. Amino acid positions assigned to CDRs and FRs may be defined according to IMGT nomenclature. An antibody may comprise an antibody VH domain comprising a VH CDR1, CDR2 and CDR3 and a framework. It may alternatively or also comprise an antibody VL domain comprising a VL CDR1, CDR2 and CDR3 and a framework. Example sequences of antibody VH and VL domains and CDRs form part of the present disclosure. The CDRs are defined according to the IMGT system [13]. All VH and VL sequences, CDR sequences, sets of CDRs and sets of HCDRs and sets of LCDRs disclosed herein represent aspects and embodiments of the invention. As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

An antibody may comprise one or more CDRs, e.g. a set of CDRs, within an antibody framework. The framework regions may be of human germline gene segment sequences. Thus, the antibody may be a human antibody having a VH domain comprising a set of HCDRs in a human germline framework. Normally the antibody also has a VL domain comprising a set of LCDRs, e.g. in a human germline framework. An antibody "gene segment", e.g., a VH gene segment, D gene segment, or JH gene segment refers to oligonucleotide having a nucleic acid sequence from which that portion of an antibody is derived, e.g., a VH gene segment is an oligonucleotide comprising a nucleic acid sequence that corresponds to a polypeptide VH domain from FR1 to part of CDR3. Human v, d and j gene segments recombine to generate the VH domain, and human v and j segments recombine to generate the VL domain. The D domain or region refers to the diversity domain or region of an antibody chain. J domain or region refers to the joining domain or region of an antibody chain. Somatic hypermutation may result in an antibody VH or VL domain having framework regions that do not exactly match or align with the corresponding gene segments, but sequence alignment can be used to identify the closest gene segments and thus identify from which particular combination of gene segments a particular VH or VL domain is derived. When aligning antibody sequences with gene segments, the antibody amino acid sequence may be aligned with the amino acid sequence encoded by the gene segment, or the antibody nucleotide sequence may be aligned directly with the nucleotide sequence of the gene segment. Germline gene segments corresponding to framework regions of example antibodies described herein are indicated in Table S-12.

An antibody may be a whole immunoglobulin, including constant regions, or may be an antibody fragment. An antibody fragment is a portion of an intact antibody, for example comprising the antigen binding and/or variable region of the intact antibody. The antibody fragment may include one or more constant region domains.

An antibody of the invention may be a human antibody or a chimaeric antibody comprising human variable regions and non-human (e.g., mouse) constant regions. The antibody of the invention for example has human variable regions, and optionally also has human constant regions.

Thus, antibodies optionally include constant regions or parts thereof, e.g., human antibody constant regions or parts thereof, such as a human IgG4 constant region. For example, a VL domain may be attached at its C-terminal end to antibody light chain kappa or lambda constant domains. Similarly, an antibody VH domain may be attached at its C-terminal end to all or part (e.g. a CH1 domain or Fc region) of an immunoglobulin heavy chain constant region derived from any antibody isotype, e.g. IgG, IgA, IgE and IgM and any of the isotype sub-classes, such as IgG1 or IgG4.

Digestion of whole (bivalent) immunoglobulins with the enzyme papain results in two identical (monovalent) antigen-binding fragments known as "Fab" fragments, and an "Fc" fragment. The Fc has no antigen-binding activity but has the ability to crystallize. "Fab" when used herein refers to a fragment of an antibody that includes one constant and one variable domain of each of the heavy and light chains. The term "Fc region" herein is used to define a C-terminal region of an immunoglobulin heavy chain, including native-sequence Fc regions and variant Fc regions. The "Fc fragment" refers to the carboxy-terminal portions of both H chains held together by disulphides.

Digestion of antibodies with the enzyme pepsin results in a bivalent F(ab')2 fragment in which the two arms of the antibody molecule remain linked. The F(ab')2 fragment is a bivalent fragment including two Fab fragments linked by a disulphide bridge at the hinge region. Single-chain antibodies (e.g., scFv) are another fragment. Two different monovalent monospecific antibody fragments such as scFv may be linked together to form a bivalent bispecific antibody.

"Fv" when used herein refers to the minimum fragment of an antibody that retains both antigen-recognition and antigen-binding sites. This region consists of a dimer of one heavy and one light chain variable domain in tight, non-covalent or covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognise and bind antigen, although usually at a lower affinity than the entire binding site.

Preferably, the bispecific antibody is a dual binding antibody, i.e., a bispecific antibody in which both antigen binding domains are formed by a VH/VL pair. Dual binding antibodies include FIT-Ig (see WO2015/103072, incorporated herein by reference), mAb-dAb, dock and lock, Fab-arm exchange, SEEDbody, Triomab, LUZ-Y, Fcab, Kλ-body, orthogonal Fab, scDiabody-Fc, diabody-Fc, tandem scFv-Fc, Fab-scFv-Fc, Fab-scFv, intrabody, BITE, diabody, DART, TandAb, scDiabody, scDiabody-CH3, Diabody-CH3, Triple body, Miniantibody, minibody, scFv-CH3 KIH, scFv-CH-CL-scFv, F(ab')2-scFv, scFv-KIH, Fab-scFv-Fc, tetravalent HCab, ImmTAC, knobs-in-holes, knobs-in-holes with common light chain, knobs-in-holes with common light chain and charge pairs, charge pairs, charge pairs with common light chain, DT-IgG, DutaMab, IgG(H)-scFv, scFv-(H)IgG, IgG(L)-scFv, scFv-(L)IgG, IgG (L,H)-Fv, IgG(H)-V, V(H)-IgG, IgG(L)-V, V(L)-IgG, KIH IgG-scFab, 2scFv-IgG, IgG-2scFv and scFv4-Ig.

In one embodiment, the bispecific antibody is a bispecific IgG comprising a FIXa-binding polypeptide arm and a FX-binding polypeptide arm, each polypeptide arm comprising a heavy chain and a light chain. The IgG is a tetrameric immunoglobulin comprising a first pair of antibody heavy and light chains (heavy-light chain pair) comprising a FIXa binding Fv region, a second heavy-light chain pair comprising a FX binding Fv region, wherein each heavy chain comprises a VH domain and a constant region, and each light chain comprises a VL domain and a constant region, and wherein the first and second heavy-light chain pairs associate through heterodimerisation of their heavy chain constant regions to form the immunoglobulin tetramer.

Figure 5:
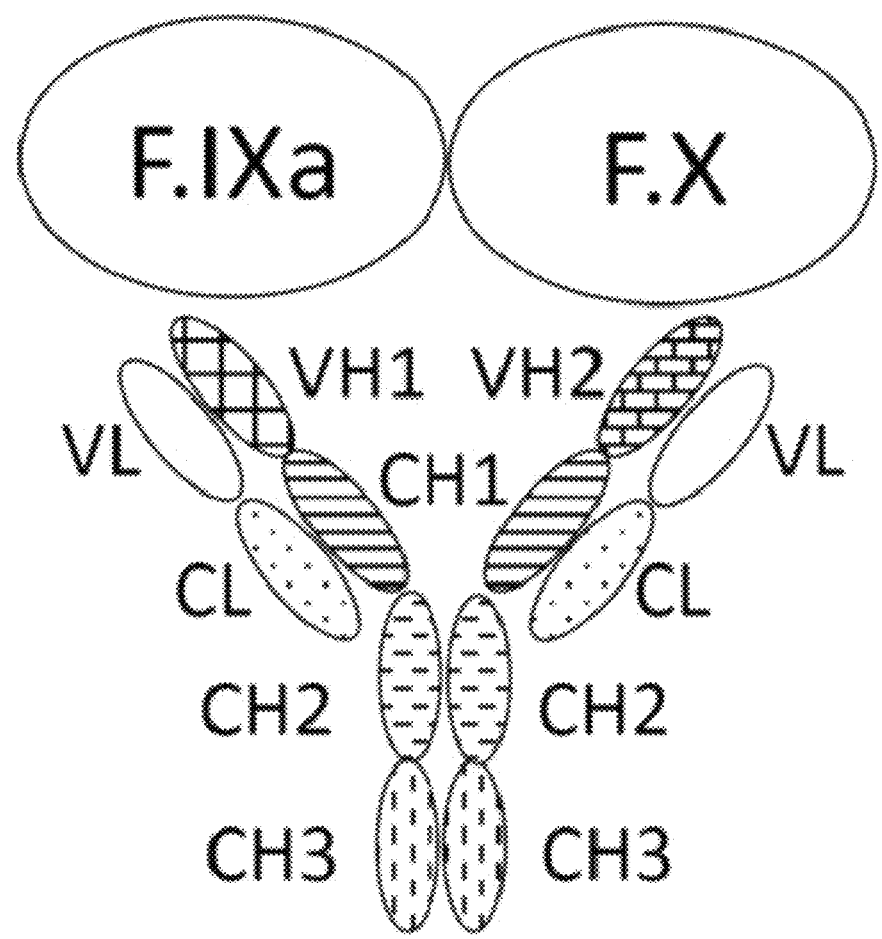
FIG. 5 shows an embodiment of the invention: bispecific IgG with common light chain.

Optionally, the two polypeptide arms comprise a common light chain, so the light chain of the first and second heavy-light chain pairs has an identical amino acid sequence (FIG. 5). Alternatively the two polypeptide arms may comprise different light chains.

Bispecific antibody may be monovalent for binding FIXa and for binding FX.

Antibody Constant Regions

As discussed above, antibodies can be provided in various isotypes and with different constant regions. The Fc region of antibodies is recognised by Fc receptors and determines the ability of the antibody to mediate cellular effector functions, including antibody-dependent cell-mediated cytotoxicity (ADCC) activity, complement dependent cytotoxicity (CDC) activity and antibody-dependent cell phagocytosis (ADCP) activity. These cellular effector functions involve recruitment of cells bearing Fc receptors to the site of the target cells, resulting in killing of the antibody-bound cell.

In the context of the present invention it is desirable to avoid cellular effector functions such as ADCC, ADCP and/or CDC. Therefore, bispecific antigen-binding molecules according to the present invention may lack Fc effector function, for example they may contain Fc regions that do not mediate ADCC, ADCP and/or CDC, or they may lack Fc regions or lack antibody constant regions entirely. An antibody may have a constant region which is effector null.

An antibody may have a heavy chain constant region that binds one or more types of Fc receptor but does not induce cellular effector functions, i.e., does not mediate ADCC, CDC or ADCP activity. Such a constant region may be unable to bind the particular Fc receptor(s) responsible for triggering ADCC, CDC or ADCP activity.

An antibody may have a heavy chain constant region that does not bind Fcγ receptors, for example the constant region may comprise a Leu235Glu mutation (i.e., where the wild type leucine residue is mutated to a glutamic acid residue), which may be referred to as an "E" mutation, e.g., IgG4-E. Another optional mutation for a heavy chain constant region is Ser228Pro ("P" mutation), which increases stability by reducing Fab arm exchange. A heavy chain constant region may be an IgG4 comprising both the Leu235Glu mutation and the Ser228Pro mutation (EU numbering). This "IgG4-PE" heavy chain constant region is effector null. An alternative effector null human constant region is a disabled IgG1.

Antibody constant regions may be engineered to have an extended half life in vivo. Examples include "YTE" mutations and other half-life extending mutations (Dall'Acqua, Kiener & Wu, JBC 281(33):23514-23524 2006 and WO02/060919, incorporated by reference herein). The triple mutation YTE is a substitution of 3 amino acids in the IgG CH2 domain, these mutations providing tyrosine at residue 252, threonine at residue 254 and glutamic acid at residue 256, numbered according to the EU index of Kabat. As described in the referenced publications, the YTE modification increases the half-life of the antibody compared with the half-life of a corresponding antibody having a human CH2 wild type domain. To provide an increased duration of efficacy in vivo, antibodies of the present invention may include antibody constant regions (e.g., IgG constant regions, e.g., IgG CH2 domains) that have one or more mutations that increase the half life of the antibody compared with the corresponding wild type human constant region (e.g., IgG, e.g., IgG CH2 domain). Half-life may be determined by standard methods, such as are described in WO02/060919.

In some embodiments, a gamma-carboxyglutamic acid-rich (Gla) domain or other membrane-binding domain is included in the bispecific antibody (e.g., at the C terminus of the Fc), to promote localisation of the antibody to the phospholipid membrane at the platelet surface (via interaction between the Gla domain and the membrane), thereby increasing the local concentration of bispecific antibody where FIX and FX are naturally present in vivo. WO2018/145125 described a FVIII mimetic protein comprising a FIX/FX bispecific antibody and a membrane binding domain, e.g., a platelet binding domain such as a C1, C2 domain, a PH domain, a GLA domain or a membrane binding domain of a platelet membrane glycoprotein. As described therein, the membrane-binding domain may be linked to the C terminal of one or both of the heavy chain constant domains of the bispecific antibody. Bispecific antigen binding molecules of the present invention may optionally include the features and molecular formats described in WO2018/145125.

As discussed below, in bispecific IgG formats or other antibody formats where the different antigen binding arms are heterodimerised via constant regions, the constant regions may be engineered to promote heterodimer formation over homodimer formation and/or to facilitate purification of heterodimers from a mixture of different species.

The anti-FIXaxFX bispecific antibody emicizumab contains a heavy chain constant region which includes features designed to promote its assembly, purification and/or therapeutic performance. A bispecific antibody according to the present invention may comprise any one or more of these features. Thus it may comprise a human IgG4 (e.g., IgHG4*03) heavy chain constant region amino acid sequence comprising one or more of the following changes (EU numbering):

Lys196Gln in CH1;
Ser228Pro in the hinge region (P mutation);
Phe296Tyr in the DE turn of CH2;
Glu356Lys in CH3;
Lys439Glu in CH3;
Leu445Pro in CH3;
Deletion of Gly446;
Deletion of Lys447.

One each of the mutations Glu356Lys and Lys439Glu are included in the two oppositely paired heavy chain constant regions within the Fc of the heterodimeric bispecific, i.e., one heavy chain constant region comprises Glu356 and Lys439Glu and the other heavy chain constant region comprises Glu356Lys and Lys439 (see the discussion on charge pairing below).

A bispecific antibody according to the present invention may comprise an Fc region that has any one or more of the features that are present in the Fc region of emicizumab. It may comprise the Fc region of emicizumab. In one embodiment, the amino acid sequences of the heavy chain constant regions are the amino acid sequences of the emicizumab heavy chain constant regions.

Example amino acid sequences for heavy chain constant regions are shown in Table S-100.

Engineering of Bispecific Antibodies to Facilitate Heterodimer Formation and/or Purification One of the difficulties with using bispecific antibodies in the clinic has historically been the difficulty of producing them in large quantities and at pharmaceutical grade purity. The "traditional" bispecific IgG format comprises two different pairs of heavy and light chains, thus 4 different polypeptide chains, which if expressed together could assemble into 10 different potential antibody molecules. The mixture of species will include homodimers (homodimeric anti-FIXa binding arms and homodimeric anti-FX binding arms), molecules in which one or both light chains are swapped between the H-L pairs, as well as the "correct" bispecific heterodimeric structure.

Alternative molecular formats have been developed which avoid this potential mis-pairing, and several examples are provided herein. These include F(ab')2, e.g., prepared by chemical coupling or leucine zipper (fos:jun) assembly, diabodies, and scFv heterodimers. Nevertheless, it remains desirable to be able to use bispecific IgG, to reflect the native structure of antibodies in the bloodstream and to minimise immunogenicity of the administered therapeutic molecule. Additionally, a full length bispecific antibody may have a longer serum half-life.

"Knobs into holes" technology for making bispecific antibodies was described in [14] and in U.S. Pat. No. 5,731,168, both incorporated herein by reference. The principle is to engineer paired CH3 domains of heterodimeric heavy chains so that one CH3 domain contains a "knob" and the other CH3 domains contains a "hole" at a sterically opposite position. Knobs are created by replacing small amino acid side chain at the interface between the CH3 domains, while holes are created by replacing large side chains with smaller ones. The knob is designed to insert into the hole, to favour heterodimerisation of the different CH3 domains while destabilising homodimer formation. In in a mixture of antibody heavy and light chains that assemble to form a bispecific antibody, the proportion of IgG molecules having paired heterodimeric heavy chains is thus increased, raising yield and recovery of the active molecule Mutations Y349C and/or T366W may be included to form "knobs" in an IgG CH3 domain. Mutations E356C, T366S, L368A and/or Y407V may be included to form "holes" in an IgG CH3 domain. Knobs and holes may be introduced into any human IgG CH3 domain, e.g., an IgG1, IgG2, IgG3 or IgG4 CH3 domain. A preferred example is IgG4. As noted, the IgG4 may include further modifications such as the "P" and/or "E" mutations. An example IgG4-PE sequence and other example constant regions including knobs-into-holes mutations are shown in Table S-100. The IgG4 type a ("ra") sequence contains substitutions Y349C and T366W ("knobs"), and the IgG4 type b ("yb") sequence contains substitutions E356C, T366S, L368A, and Y407V ("holes"). Both ra and yb also contain the "P" substitution at position 228 in the hinge (S228P), to stabilise the hinge region of the heavy chain. Both ra and yb also contain the "E" substitution in the CH2 region at position 235 (L235S), to abolish binding to FcγR. Thus the relevant sequence of the IgG4-PE heavy chain is ppcpPcpapefEggps (SEQ ID NO: 401). A bispecific antigen binding molecule of the present invention may contain an IgG4 PE human heavy chain constant region (e.g., SEQ ID NO: 143), optionally two such paired constant regions, optionally wherein one has "knobs" mutations and one has "holes" mutations, e.g., wherein one heavy chain constant region has a sequence SEQ ID NO: 144 (knobs) and one heavy chain constant region has a sequence SEQ ID NO: 145 (holes).

A further advance in bispecific IgG engineering was the idea of using a common light chain, as described in WO98/50431. Bispecific antibodies comprising two heavy-light chain pairs were described, in which the variable light chains of both heavy-light chain pairs had a common sequence. WO98/50431 described combining the common light chain approach with specific complementary interactions in the heavy chain heterodimerisation interface (such as knobs-into-holes) to promote heterodimer formation and hinder homodimer formation. In combination, these approaches enhance formation of the desired heterodimer relative to undesired heterodimers and homodimers.

While knobs-into-holes technology involves engineering amino acid side chains to create complementary molecular shapes at the interface of the paired CH3 domains in the bispecific heterodimer, another way to promote heterodimer formation and hinder homodimer formation is to engineer the amino acid side chains to have opposite charges. Association of CH3 domains in the heavy chain heterodimers is favoured by the pairing of oppositely charged residues, while paired positive charges or paired negative charges would make homodimer formation less energetically favourable. WO2006/106905 described a method for producing a heteromultimer composed of more than one type of polypeptide (such as a heterodimer of two different antibody heavy chains) comprising a substitution in an amino acid residue forming an interface between said polypeptides such that heteromultimer association will be regulated, the method comprising:

(a) modifying a nucleic acid encoding an amino acid residue forming the interface between polypeptides from the original nucleic acid, such that the association between polypeptides forming one or more multimers will be inhibited in a heteromultimer that may form two or more types of multimers;

(b) culturing host cells such that a nucleic acid sequence modified by step (a) is expressed; and (c) recovering said heteromultimer from the host cell culture, wherein the modification of step (a) is modifying the original nucleic acid so that one or more amino acid residues are substituted at the interface such that two or more amino acid residues, including the mutated residue(s), forming the interface will carry the same type of positive or negative charge.

An example of this is to suppress association between heavy chains by introducing electrostatic repulsion at the interface of the heavy chain homodimers, for example by modifying amino acid residues that contact each other at the interface of the CH3 domains, including:

positions 356 and 439
positions 357 and 370
positions 399 and 409,
the residue numbering being according to the EU numbering system.

By modifying one or more of these pairs of residues to have like charges (both positive or both negative) in the CH3 domain of a first heavy chain, the pairing of heavy chain homodimers is inhibited by electrostatic repulsion. By engineering the same pairs or pairs of residues in the CH3 domain of a second (different) heavy chain to have an opposite charge compared with the corresponding residues in the first heavy chain, the heterodimeric pairing of the first and second heavy chains is promoted by electrostatic attraction.

Amino acids at the heavy chain constant region CH3 interface were modified to introduce charge pairs, the mutations being listed in Table 1 of WO2006/106905. It was reported that modifying the amino acids at heavy chain positions 356, 357, 370, 399, 409 and 439 to introduce charge-induced molecular repulsion at the CH3 interface had the effect of increasing efficiency of formation of the intended bispecific antibody. For example, one heavy chain constant region may be an IgG4 constant region containing mutation K439E (positively charged Lys replaced by negatively charged Glu) and the other heavy chain constant region may be an IgG4 constant region containing mutation E356K (negatively charged Glu replaced by positively charged Lys), using EU numbering. "Charge pairing" results from spatial proximity of residues 439 and 356 in an Fc region assembled from heterodimerisation of these two constant regions.

Where two different heavy chain constant regions are used, these may be connected to the two different VH domains of the antibody in either orientation. For example, a first heavy chain may comprise an anti-FIX VH domain and a constant region comprising K439E, and a second heavy chain may comprise an anti-FX VH domain and a constant region comprising E356K, or a first heavy chain may comprise an anti-FIX VH domain and a constant region comprising E356K, and a second heavy chain may comprise an anti-FX VH domain and a constant region comprising K439E.

WO2006/106905 also exemplified bispecific IgG antibodies binding FX and FIXa in which the CH3 domains of IgG4 were engineered with knobs-into-holes mutations. Type a Type a (IgG4γa) was an IgG4 substituted at Y349C and T366W, and type b (IgG4γb) was an IgG4 substituted at E356C, T366S, L368A, and Y407V.

In another example, introduction of charge pairs in the antibody VH and VL domains was used to inhibit the formation of "incorrect" VH-VL pairs (pairing of VH from one antibody with VL of the other antibody). In one example, Q residues in the VH and VL were changed to K or R (positive), or to E or D (negative), to inhibit hydrogen bonding between the Q side chains and to introduce electrostatic repulsion.

Further examples of charge pairs were disclosed in WO2013/157954, which described a method for producing a heterodimeric CH3 domain-comprising molecule from a single cell, the molecule comprising two CH3 domains capable of forming an interface. The method comprised providing in the cell (a) a first nucleic acid molecule encoding a first CH3 domain-comprising polypeptide chain, this chain comprising a K residue at position 366 according to the EU numbering system and (b) a second nucleic acid molecule encoding a second CH3 domain-comprising polypeptide chain, this chain comprising a D residue at position 351 according to the EU numbering system, the method further comprising the step of culturing the host cell, allowing expression of the two nucleic acid molecules and harvesting the heterodimeric CH3 domain-comprising molecule from the culture.

Further methods of engineering electrostatic interactions in polypeptide chains to promote heterodimer formation over homodimer formation were described in WO2011/143545.

Another example of engineering at the CH3-CH3 interface is strand-exchange engineered domain (SEED) CH3 heterodimers. The CH3 domains are composed of alternating segments of human IgA and IgG CH3 sequences, which form pairs of complementary SEED heterodimers referred to as "SEED-bodies" [15; WO2007/110205].

Bispecifics have also been produced with heterodimerised heavy chains that are differentially modified in the CH3 domain to alter their affinity for binding to a purification reagent such as Protein A. WO2010/151792 described a heterodimeric bispecific antigen-binding protein comprising a first polypeptide comprising, from N-terminal to C-terminal, a first epitope-binding region that selectively binds a first epitope, an immunoglobulin constant region that comprises a first CH3 region of a human IgG selected from IgG1, IgG2, and IgG4; and a second polypeptide comprising, from N-terminal to C-terminal, a second epitope-binding region that selectively binds a second epitope, an immunoglobulin constant region that comprises a second CH3 region of a human IgG selected from IgG1, IgG2, and IgG4, wherein the second CH3 region comprises a modification that reduces or eliminates binding of the second CH3 domain to Protein A.

The Fc region may thus comprise one or more mutations to promote differential purification of the active heterodimer from homodimer species. The CH3 of one heavy chain constant region may comprise the mutation His435Arg and/or Tyr436Phe (EU numbering) [16] while the CH3 of the other heavy chain constant region lacks said mutations. Emicizumab, for example, comprises an Fc region in which one CH3 comprises His435 and the other CH3 comprises His435Arg.

The bispecifics of the present invention may employ any of these techniques and molecular formats as desired.

Generating and Modifying Antibodies

Methods for identifying and preparing antibodies are well known. Isolated (optionally mutated) nucleic acid encoding antibodies (or heavy-light chain pairs or polypeptide binding arms thereof) described herein may be introduced into host cells, e.g., CHO cells as discussed. Host cells are then cultured under conditions for expression of the antibody (or of the antibody heavy and/or light chain variable domain, heavy-light chain pair, or polypeptide binding arm) to produce the desired antibody format. Some possible antibody formats are described herein, e.g., whole immunoglobulins, antigen-binding fragments, and other designs.

Variable domain amino acid sequence variants of any of the VH and VL domains or CDRs whose sequences are specifically disclosed herein and may be employed in accordance with the present invention, as discussed.

Alterations to nucleic acid encoding the antibody heavy and/or light chain variable domain may be performed, such as mutation of residues and generation of variants, as described herein. There are many reasons why it may be desirable to create variants, which include optimising the antibody sequence for large-scale manufacturing, facilitating purification, enhancing stability or improving suitability for inclusion in a desired pharmaceutical formulation. Protein engineering work can be performed at one or more target residues in the antibody sequence, e.g., to substituting one amino acid with an alternative amino acid (optionally, generating variants containing all naturally occurring amino acids at this position, with the possible exception of Cys and Met), and monitoring the impact on function and expression to determine the best substitution. It is in some instances undesirable to substitute a residue with Cys or Met, or to introduce these residues into a sequence, as to do so may generate difficulties in manufacturing—for instance through the formation of new intramolecular or intermolecular cysteine-cysteine bonds. Where a lead candidate has been selected and is being optimised for manufacturing and clinical development, it will generally be desirable to change its antigen-binding properties as little as possible, or at least to retain the affinity and potency of the parent molecule. However, variants may also be generated in order to modulate key antibody characteristics such as affinity, cross-reactivity or neutralising potency.

One or more amino acid mutations may optionally be made in framework regions of an antibody VH or VL domain disclosed herein. For example, one or more residues that differ from the corresponding human germline segment sequence may be reverted to germline. Human germline gene segment sequences corresponding to VH and VL domains of example antibodies herein are indicated in Table S-12.

In a bispecific antigen binding molecule, an antigen-binding site may comprise a set of H and/or L CDRs of any of the disclosed anti-FIX or anti-FX antibodies with one or more amino acid mutations within the disclosed set of H and/or L CDRs. The mutation may be an amino acid substitution, deletion or insertion. Thus for example there may be one or more amino acid substitutions within the disclosed set of H and/or L CDRs. For example, there may be up to 12, 11, 10, 9, 8, 7, 6, 5, 4, 3 or 2 mutations e.g. substitutions, within the set of H and/or L CDRs. For example, there may be up to 6, 5, 4, 3 or 2 mutations, e.g. substitutions, in HCDR3 and/or there may be up to 6, 5, 4, 3, or 2 mutations, e.g. substitutions, in LCDR3.

An antibody may comprise a VH domain that has at least 60, 70, 80, 85, 90, 95, 98 or 99 amino acid sequence identity with a VH domain as shown in the Tables, and/or comprising a VL domain that has at least 60, 70, 80, 85, 90, 95, 98 or 99% amino acid sequence identity with a VL domain of any of those antibodies. Algorithms that can be used to calculate % identity of two amino acid sequences include e.g. BLAST, FASTA, or the Smith-Waterman algorithm, e.g. employing default parameters. Particular variants may include one or more amino acid sequence alterations (addition, deletion, substitution and/or insertion of an amino acid residue).

Alterations may be made in one or more framework regions and/or one or more CDRs. Variants are optionally provided by CDR mutagenesis. The alterations normally do not result in loss of function, so an antibody comprising a thus-altered amino acid sequence may retain an ability to bind its antigen. It may retain the same quantitative binding ability as an antibody in which the alteration is not made, e.g. as measured in an assay described herein. The antibody comprising a thus-altered amino acid sequence may have an improved ability to bind its antigen.

Alteration may comprise replacing one or more amino acid residue with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring.

The term "variant" as used herein refers to a peptide or nucleic acid that differs from a parent polypeptide or nucleic acid by one or more amino acid or nucleic acid deletions, substitutions or additions, yet retains one or more specific functions or biological activities of the parent molecule. Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

In some aspects, one can use "synthetic variants", "recombinant variants", or "chemically modified" polynucleotide variants or polypeptide variants isolated or generated using methods well known in the art. "Modified variants" can include conservative or non-conservative amino acid changes, as described below. Polynucleotide changes can result in amino acid substitutions, additions, deletions, fusions and truncations in the polypeptide encoded by the reference sequence. Some aspects include insertion variants, deletion variants or substituted variants with substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties (e.g., acidic, basic, positively or negatively charged, polar or nonpolar, etc.). Conservative amino acid substitutions include replacement of a leucine with an isoleucine or valine, an aspartate with a glutamate, or a threonine with a serine. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

One can select the amino acid that will substitute an existing amino acid based on the location of the existing amino acid, including its exposure to solvents (i.e., if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119(1986); 205-218 and S. French and B. Robson, J. Mol. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

The invention includes methods of producing polypeptide binding arms containing VH and/or VL domain variants of the antibody VH and/or VL domains shown in the Tables herein. FIXa binding polypeptide arms comprising variant VH domains may be produced by a method comprising (i) providing, by way of addition, deletion, substitution or insertion of one or more amino acids in the amino acid sequence of a parent antibody VH domain, an antibody VH domain that is an amino acid sequence variant of the parent antibody VH domain, wherein the parent antibody VH domain is a VH domain shown in FIG. 20, e.g., N1280H, or is a VH domain comprising the heavy chain complementarity determining regions of any of those VH domains, (ii) optionally combining the VH domain thus provided with a VL domain, to provide a VH/VL combination, and (iii) testing the VH domain or VH/VL domain combination thus provided to identify an antibody with one or more desired characteristics.

The VH domain may be any VH domain whose sequence is shown in Table S-9A or FIG. 20, or any VH domain comprising a set of HCDRs (HCDR1, HCDR2 and HCDR3) of a VH domain shown in Table S-9A or FIG. 20.

Desired characteristics of FIXa-binding polypeptide arms, and of bispecific anti-FIXa/FX binding molecules comprising them, are detailed elsewhere herein. For example, the method may comprise confirming that the VH domain or VH/VL domain combination binds FIXa as described herein.

When VL domains are included in the method, the VL domain may be the N0128L VL domain or may be a variant provided by way of addition, deletion, substitution or insertion of one or more amino acids in the amino acid sequence of the N0128L VL domain, or may be a VL domain comprising the light chain complementarity determining regions of the N0128L VL domain. The VL domain may be the 0325L VL domain.

Methods of generating variant antibodies may optionally comprise producing copies of the antibody or VH/VL domain combination. Methods may further comprise producing a bispecific antibody comprising the FIXa binding polypeptide arm, for example by expression of encoding nucleic acid. Suitable methods of expression, including recombinant expression in host cells, are set out in detail herein.

Encoding Nucleic Acids and Methods of Expression

Isolated nucleic acid may be provided, encoding bispecific antigen binding molecules, e.g., bispecific antibodies, according to the present invention. Nucleic acid may be DNA and/or RNA. Genomic DNA, cDNA, mRNA or other RNA, of synthetic origin, or any combination thereof can encode an antibody.

The present invention provides constructs in the form of plasmids, vectors, transcription or expression cassettes which comprise at least one polynucleotide as above. Exemplary nucleotide sequences are included in the Tables. Reference to a nucleotide sequence as set out herein encompasses a DNA molecule with the specified sequence, and encompasses a RNA molecule with the specified sequence in which U is substituted for T, unless context requires otherwise.

The present invention also provides a recombinant host cell that comprises one or more nucleic acids encoding the antigen binding molecule. Methods of producing the encoded molecule may comprise expression from the nucleic acid, e.g., by culturing recombinant host cells containing the nucleic acid. The bispecific molecule may thus be obtained, and may be isolated and/or purified using any suitable technique, then used as appropriate. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals.

The expression of antibodies and antibody fragments in prokaryotic cells is well established in the art. A common bacterial host is *E. coli*. Expression in eukaryotic cells in culture is also available to those skilled in the art as an option for production. Mammalian cell lines available in the art for expression of a heterologous polypeptide include Chinese hamster ovary (CHO) cells, HeLa cells, baby hamster kidney cells, NSO mouse melanoma cells, YB2/0 rat myeloma cells, human embryonic kidney cells, human embryonic retina cells and many others.

Vectors may contain appropriate regulatory sequences, including promoter sequences, terminator sequences, polyadenylation sequences, enhancer sequences, marker genes and other sequences as appropriate. Nucleic acid encoding an antibody can be introduced into a host cell. Nucleic acid can be introduced to eukaryotic cells by various methods, including calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques include calcium chloride transformation, electroporation and transfection using bacteriophage. The introduction may be followed by expressing the nucleic acid, e.g., by culturing host cells under conditions for expression of the gene, then optionally isolating or purifying the antibody.

Nucleic acid of the invention may be integrated into the genome (e.g. chromosome) of the host cell. Integration may be promoted by inclusion of sequences that promote recombination with the genome, in accordance with standard techniques. Nucleic acid encoding a bispecific may be integrated into genomic DNA of a host (e.g., CHO) cell, e.g., into chromosomal DNA, and the resulting recombinant cell may be cultured to express the bispecific. A cell line development process may comprise introducing nucleic acid encoding the bispecific into multiple host cells, and selecting a cell line which expresses a desired level of bispecific antibody (e.g., at least 95% heterodimer, with no more than 5% homodimeric contaminants) at the desired yield (e.g., at least 0.5 g/L or at least 1 g/L). Preferably the cell line will retain stable expression over a number of generations in cell culture, and thus it may maintain these levels of production over a at least 60 generations for example.

The present invention also provides a method that comprises using nucleic acid described herein in an expression system in order to express the bispecific antigen binding molecule. Desirably, the antigen-binding molecules are expressed at a yield of at least 0.5 g/L in the cell supernatant after initial fermentation, preferably at a yield of >2 g/L. Solubility should be >10 mg/ml, preferably >50 mg/ml, without significant aggregation or degradation of the molecules.

To provide medicines suitable for global treatment, antibodies can be produced on a large scale, for instance in cell culture volumes of at least 100 litres or at least 200 litres, e.g., between 100-250 litres. Batch culture, particularly fed-batch culture, is now commonly used for production of biotherapeutics for clinical and commercial use, and such methods may suitably be used in the present invention to generate the antibodies, followed by purification and formulation steps as noted herein. Bioreactors may be metal (e.g., stainless steel) vessels or may be single-use bioreactors.

Formulation and Administration

The bispecific antigen-binding molecules ("bispecifics") according to the present invention, and their encoding nucleic acid molecules, will usually be provided in isolated form. The bispecifics VH and/or VL domains, and nucleic acids may be provided purified from their natural environment or their production environment. Isolated antigen-binding molecules and isolated nucleic acid will be free or substantially free of material with which they are naturally associated, such as other polypeptides or nucleic acids with which they are found in vivo, or the environment in which they are prepared (e.g., cell culture) when such preparation is by recombinant DNA technology in vitro. Optionally an isolated antigen-binding molecule or nucleic acid (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature.

Bispecific antibody may be purified (e.g., from cell culture supernatant) by protein A chromatography and/or ion exchange chromatography. The bispecific antibody may be produced by a method comprising expressing two antibody heavy chains and common light chain from cultured host cells comprising encoding nucleic acids, obtaining cell culture comprising the bispecific antibody and monospecific antibodies assembled from the antibody heavy chains and common light chain, isolating the bispecific antibody and monospecific antibodies from the cell culture (e.g., using protein A chromatography), and purifying the bispecific antibody from the monospecific antibodies (e.g., using cation exchange chromatography).

Bispecifics or their encoding nucleic acids may be formulated with diluents or adjuvants and still for practical purposes be isolated—for example they may be mixed with carriers if used to coat microtitre plates for use in immunoassays, and may be mixed with pharmaceutically acceptable carriers or diluents when used in therapy. As described elsewhere herein, other active ingredients may also be included in therapeutic preparations. The antigen binding molecules may be glycosylated, either naturally in vivo or by systems of heterologous eukaryotic cells such as CHO cells, or they may be (for example if produced by expression in a prokaryotic cell) unglycosylated. The invention encompasses antibodies having a modified glycosylation pattern.

Typically, an isolated product constitutes at least about 5%, at least about 10%, at least about 25%, or at least about 50% of a given sample. A bispecific may be substantially free from proteins or polypeptides or other contaminants that are found in its natural or production environment that would interfere with its therapeutic, diagnostic, prophylactic, research or other use.

As discussed elsewhere herein, expression of antibody heavy and light chains for a bispecific antibody may generate unwanted homodimeric species (anti-FIX and anti-FX antibodies) in addition to the active heterodimeric bispecific antibody. Preferably a bispecific is provided in a composition in which the heterodimeric bispecific antibody is represents at least 95% of the total antibody, with homodimeric antibody contaminants being present at 5% or less. The composition may comprise at least 98% or at least 99% heterodimeric bispecific, with homodimeric contaminants representing 0-2% or 0-1% respectively.

The invention provides therapeutic compositions comprising the bispecifics described herein. Therapeutic compositions comprising nucleic acid encoding such bispecifics are also provided. Encoding nucleic acids are described in more detail elsewhere herein and include DNA and RNA, e.g., mRNA. In therapeutic methods described herein, use of nucleic acid encoding the bispecific, and/or of cells containing such nucleic acid, may be used as alternatives (or in addition) to compositions comprising the bispecific molecule itself. Cells containing nucleic acid encoding the bispecific, optionally wherein the nucleic acid is stably integrated into the genome, thus represent medicaments for therapeutic use in a patient. Nucleic acid encoding the bispecific may be introduced into human cells derived from the intended patient and modified ex vivo. Administration of cells containing the encoding nucleic acid to the patient provides a reservoir of cells capable of expressing the bispecific, which may provide therapeutic benefit over a longer term compared with administration of isolated nucleic acid or the isolated bispecific molecule. Nucleic acid encoding the bispecific may be provided for use in gene therapy, comprising introducing the encoding nucleic acid into cells of the patient in vivo, so that the nucleic acid is expressed in the patient's cells and provides a therapeutic effect such as compensating for hereditary factor VIII deficiency.

Compositions may contain suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311. Compositions may comprise the antibody or nucleic acid in combination with medical injection buffer.

Bispecifics, or their encoding nucleic acids, may be formulated for the desired route of administration to a patient, e.g., in liquid (optionally aqueous solution) for injection. An example buffer in which to formulate the bispecific for injection is an aqueous solution of 20 mM sodium acetate, 150 mM arginine hydrochloride, 0.05% w/v polysorbate 80 pH 5.2.

Various delivery systems are known and can be used to administer the pharmaceutical composition of the invention. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. The antigen-binding molecules are preferably administered by subcutaneous injection.

The pharmaceutical composition can be also delivered in a vesicle, in particular a liposome (see Langer (1990) Science 249:1527-1533; Treat et al. (1989) in Liposomes in the Therapy of Infectious Disease and Cancer, Lopez Berestein and Fidler (eds.), Liss, New York, pp. 353-365; Lopez-Berestein, ibid., pp. 317-327; see generally ibid.).

In certain situations, the pharmaceutical composition can be delivered in a controlled release system. In one embodiment, a pump may be used (see Langer, supra; Sefton (1987) CRC Crit. Ref. Biomed. Eng. 14:201). In another embodiment, polymeric materials can be used; see, Medical Applications of Controlled Release, Langer and Wise (eds.), CRC Pres., Boca Raton, Fla. (1974). In yet another embodiment, a controlled release system can be placed in proximity of the composition's target, thus requiring only a fraction of the systemic dose (see, e.g., Goodson, in Medical Applications of Controlled Release, supra, vol. 2, pp. 115-138, 1984).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared can be filled in an appropriate ampoule. A pharmaceutical composition of the present invention can be delivered subcutaneously or intravenously with a standard needle and syringe. It is envisaged that treatment will not be restricted to use in the clinic. Therefore, subcutaneous injection using a needle-free device is also advantageous. With respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded. Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPENTMI, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPENT™, OPTIPEN PRO™, OPTIPEN STARLET™, and OPTICLIKT™ (Sanofi-Aventis, Frankfurt, Germany), to name only a few. Examples of disposable pen delivery devices having applications in subcutaneous delivery of a pharmaceutical composition of the present invention include, but certainly are not limited to the SOLOSTAR™ pen (Sanofi-Aventis), the FLEXPEN™ (Novo Nordisk), and the KWIKPEN™ (Eli Lilly).

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, the aforesaid antibody may be contained in about 5 to about 100 mg and in about 10 to about 250 mg for the other dosage forms.

The bispecific, nucleic acid, or composition comprising it, may be contained in a medical container such as a phial, syringe, IV container or an injection device. In an example, the bispecific, nucleic acid or composition is in vitro, and may be in a sterile container. In an example, a kit is provided comprising the bispecific, packaging and instructions for use in a therapeutic method as described herein.

One aspect of the invention is a composition comprising a bispecific or nucleic acid of the invention and one or more pharmaceutically acceptable excipients, examples of which are listed above. "Pharmaceutically acceptable" refers to approved or approvable by a regulatory agency of the USA Federal or a state government or listed in the U.S. Pharmacopeia or other generally recognized pharmacopeia for use in animals, including humans. A pharmaceutically acceptable carrier, excipient, or adjuvant can be administered to a patient, together with a bispecific agent, e.g., any antibody or polypeptide molecule described herein, and does not destroy the pharmacological activity thereof and is nontoxic when administered in doses sufficient to deliver a therapeutic amount of the agent.

In some embodiments, the bispecific will be the sole active ingredient in a composition according to the present invention. Thus, a composition may consist of the antibody or it may consist of the bispecific with one or more pharmaceutically acceptable excipients. However, compositions according to the present invention optionally include one or more additional active ingredients.

Where required (for example, for management of acute bleeds), the bispecific may be combined with one or more other treatments for haemophilia, including recombinant factor VIII (e.g., turoctocog alfa) or recombinant factor VIIa (e.g., eptacog alfa). The functional properties and safety profile of bispecifics described herein are believed to be suitable for their safe combination with such further therapeutic agents. The bispecific may be combined with recombinant factor Va (FVa), for example an activated variant FVa as described in U.S. Ser. No. 10/407,488.

Other therapeutic agents that it may be desirable to administer with bispecific or nucleic acids according to the present invention include analgaesic agents. Any such agent or combination of agents may be administered in combination with, or provided in compositions with antibodies or nucleic acids according to the present invention, whether as a combined or separate preparation. The bispecific or nucleic acid according to the present invention may be administered separately and sequentially, or concurrently and optionally as a combined preparation, with another therapeutic agent or agents such as those mentioned.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

Bispecifics, and their encoding nucleic acids, can be used as therapeutic agents. Patients herein are generally mammals, typically humans. A bispecific or nucleic acid may be administered to a mammal, e.g., by any route of administration mentioned herein.

Administration is normally in a "therapeutically effective amount", this being an amount that produces the desired effect for which it is administered, sufficient to show benefit to a patient. The exact amount will depend on the purpose of the treatment, and will be ascertainable by one skilled in the art using known techniques (see, for example, Lloyd (1999) The Art, Science and Technology of Pharmaceutical Compounding). Prescription of treatment, e.g. decisions on dosage etc, is within the responsibility of general practitioners and other medical doctors and may depend on the severity of the symptoms and/or progression of a disease being treated. A therapeutically effective amount or suitable dose of bispecific or nucleic acid can be determined by comparing its in vitro activity and in vivo activity in an animal model. Methods for extrapolation of effective dosages in mice and other test animals to humans are known.

Bispecifics may be administered in an amount in one of the following ranges per dose:
  about 10 µg/kg body weight to about 100 mg/kg body weight,
  about 50 µg/kg body weight to about 5 mg/kg body weight,
  about 100 µg/kg body weight to about 10 mg/kg body weight,
  about 100 µg/kg body weight to about 20 mg/kg body weight,
  about 0.5 mg/kg body weight to about 20 mg/kg body weight, or
  about 5 mg/kg body weight or lower, for example less than 4, less than 3, less than 2, or less than 1 mg/kg of the antibody.

The dose of antigen-binding molecule administered may be up to 1 mg/kg. It may be formulated at lower strength for paediatric populations, for example 30-150 mg/mL. The bispecific molecule may be packaged in smaller quantities for a paediatric population, e.g., it may be provided in phials of 25-75 mg, e.g., 30 or 60 mg.

In methods of treatment described herein, one or more doses may be administered. In some cases, a single dose may be effective to achieve a long-term benefit. Thus, the method may comprise administering a single dose of the bispecific, its encoding nucleic acid, or the composition. Alternatively, multiple doses may be administered, usually sequentially and separated by a period of days, weeks or months. Optionally, the bispecific may be administered to a patient once a month, or less frequently, e.g., every two months or every three months.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilised (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well. In the context of the invention, treatment may be preventative treatment.

Long half-life is a desirable feature in the bispecifics of the present invention. Extended half-life translates to less frequent administration, with fewer injections being required to maintain a therapeutically effective concentration of the molecule in the bloodstream. The in vivo half life of antigen-binding molecules of the present invention in humans may be 7, 8, 9, 10, 11, 12, 13, 14, 15, 16, 17, 18, 19, 20 or 21 days, or longer. The in vivo half life of antigen-binding molecules in non-human primates such as cynomolgus monkeys may be 7, 8, 9, 10, 11, 12, 13, 14, 15, 16, 17, 18, 19, 20 or 21 days, or longer.

Maintenance of 1% of normal FVIII activity is considered to be a minimum for prophylactic use in haemophilia [1]. In a paper reporting a human clinical trial with ACE910 (emicizumab), in silico population pharmacokinetic modelling and simulations suggested that a weekly dose of 1 mg/kg resulted in a plasma concentration of at least about 300 nM (45 µg/ml), producing a continuous haemostatic effect of at least 10% of normal FVIII activity [4]. This dose was also reported to be well tolerated in patients.

Based on that data, a plasma concentration range of approximately 30 nM (~4.5 µg/ml) to 300 nM (~45 µg/ml) would correspond to effective FVIII activity of 1-10%, assuming a linear relationship between antibody concentration and FVIII activity and comparable antibody activity.

Bispecifics according to the present invention exhibit exceptionally high activity at concentrations in the range of 30 nM (~4.5 µg/ml) to 300 nM (~45 µg/ml), maintaining strong thrombin generation activity even at relatively low doses. As evidenced by its high potency (see, e.g., Example 14), a bispecific antibody according to the present invention may exhibit therapeutic efficacy at a lower plasma concentration than emicizumab. Therefore it may provide greater therapeutic benefit at an equivalent dose, and it may provide equivalent therapeutic benefit at a lower dose, compared with emicizumab. Patients can thus benefit from smaller and/or less frequent injections, and healthcare providers can benefit from lower associated costs.

The US FDA currently (in guidance issued October 2018) recommends that emicizumab be administered at a loading dose of 3 mg/kg by subcutaneous injection once weekly for the first 4 weeks, followed by a maintenance dose of:
  1.5 mg/kg once every week, or
  3 mg/kg once every 2 weeks, or
  6 mg/kg once every 4 weeks.

Antigen-binding molecules according to the present invention may be provided for administration at regular intervals of one week, two weeks, three weeks, four weeks, or one month.

In a preferred embodiment, the bispecific is administered by subcutaneous injection.

Therapeutic Use

The bispecific antigen-binding molecules of the present invention may be used in a method of treatment of the human or animal body by therapy. Therapeutic indications for the molecules include:
  use to treat haemophilia A,
  use to treat hereditary factor VIII deficiency,
  use to significantly decrease the number of bleeding incidents in haemophilia A patients,
  use to substitute for factor VIII function,
  and/or
  use to promote blood coagulation.

Patients are typically human patients. The patient may be a human diagnosed with haemophilia A or hereditary factor VIII deficiency, or a human who has lower (or absent) factor VIII expression or activity compared with wild type. The patient may be a paediatric patient (e.g., from 2 to less than 18 years of age) or may be an adult. The patient may be a human male. The patient may or may not have inhibitors to factor VIII.

A bispecific molecule of the present invention, or a composition comprising such a bispecific molecule or its encoding nucleic acid, may be used or provided for use in any such method. Use of the bispecific molecule, or of a composition comprising it or its encoding nucleic acid, for the manufacture of a medicament for use in any such method is also envisaged. The method typically comprises administering the antibody or composition to a mammal, e.g., a human patient. Suitable formulations and methods of administration are described elsewhere herein.

There is a presently unmet need for treatment of haemophilia A patients who develop inhibitory allo-antibodies to FVIII. Antigen-binding molecules of the present invention are suitable for use in such patients. Accordingly, in some aspects, a patient treated with a bispecific antigen binding molecule according to the present invention may be resistant to treatment with FVIII owing to the presence of inhibitory antibodies in the bloodstream. Resistance to treatment can be manifested in a reduction of efficacy of the therapy. Such resistance may be detected in in vitro assays (e.g. aPTT assay) with a blood plasma sample from the patient, wherein the therapeutic molecule does not reduce coagulation time to the same level as in an assay with control FVIII-deficient plasma (the latter lacking inhibitory antibodies to the therapeutic molecule).

Patients receiving other treatments for haemophilia, such as bispecific antibodies to FIXa and FX, may also develop inhibitory antibodies to those therapeutic antibodies. As noted, use of human antibodies such as those of the present invention should minimise the risk of this, but inhibitory antibodies may nevertheless be generated in some patients who receive antigen binding molecules of the present invention or other bispecific antigen binding molecules to FIXa and FX. A patient treated with a bispecific antigen binding molecule according to the present invention may be resistant to treatment to a different bispecific antigen binding molecule for FIXa and FX owing to the presence of inhibitory antibodies in the bloodstream. The patient may be resistant to treatment with emicizumab.

Since inhibitory antibodies may be generated through long term therapeutic administration of a drug product, it may be beneficial for patients to alternate or cycle between multiple different treatments, to reduce the risk of their developing inhibitory antibodies. Thus, a bispecific antigen binding molecule of the present invention may be administered to a patient who has previously received treatment with a different FVIIIa-activity replacing polypeptide drug, e.g., a bispecific antigen binding molecule for FIXa and FX, optionally emicizumab, even where the patient has not (yet) developed inhibitory antibodies. Similarly, emicizumab or other bispecific antigen binding molecules for FIXa and FX, and other FVIIIa-activity replacing polypeptide drugs generally, may be administered to patients who were previously treated with a bispecific antigen binding molecule of the present invention. Regiments of treatment may comprise administration of a first FVIII-activity replacing polypeptide drug for a first period (e.g., between one and six months, or between six months and one year), followed by switching to a different FVIII-activity replacing polypeptide drug for a second period (e.g. between one and six months, or between six months and one year), followed by switching back to the first drug or switching to yet another FVIII-activity replacing polypeptide drug. The different amino acid sequences of the different drug treatments should ensure that a patient at risk of developing inhibitory antibodies to one drug is no longer at risk of developing inhibitory antibodies to the first drug (e.g., emicizumab) following switching to a different drug (e.g., a molecule of the present invention). The cycling period may be varied or shortened, according to convenience and the preferences of the patient and doctor.

It will be recognised that administration of the encoding nucleic acid represents an alternative therapy, and may be performed in place of administering the polypeptide drug directly.

As noted, the bispecific antigen-binding molecules of the present invention are believed to have a strong safety profile, associated with no (or minimal) incidents of hypersensitivity reactions, development of allo-antibodies, organ toxicity or other adverse events leading to discontinuation of the therapy.

Clauses

The following numbered clauses represent embodiments of the invention and are part of the description.

1. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, and
a second heavy-light chain pair comprises a FX binding Fv region comprising a second VH domain paired with a second VL domain, wherein
the first VH domain comprises a set of HCDRs comprising HCDR1, HCDR2 and HCDR3 with amino acid sequences defined wherein HCDR1 is SEQ ID NO: 406, HCDR2 is SEQ ID NO: 407 and HCDR3 is SEQ ID NO: 408, and/or wherein the first VH domain is at least 95 identical to the N1280H VH domain at the amino acid sequence level;
the second VH domain is at least 95% identical to the T0201H VH domain SEQ ID NO: 470 at the amino acid sequence level, and
the first VL domain and the second VL domain each comprise a set of LCDRs comprising LCDR1, LCDR2 and LCDR3 with amino acid sequences defined wherein LCDR1 is SEQ ID NO: 6, LCDR2 is SEQ ID NO: 7 and LCDR3 is SEQ ID NO: 8, and/or wherein the first VL domain and the second VL domain are at least 95% identical to the 0128L VL domain SEQ ID NO: 10 at the amino acid sequence level.

2. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, and
a second heavy-light chain pair comprises a FX binding Fv region comprising a second VH domain paired with a second VL domain, wherein
the first VH domain is a product of recombination of human immunoglobulin heavy chain v, d and j gene segments, wherein the v gene segment is IGHV3-7 (e.g., VH3-7*01) and the j gene segment is IGHJ6 (e.g., JH6*02),
the second VH domain is a product of recombination of human immunoglobulin heavy chain v, d and j gene segments, wherein the v gene segment is IGHV1-46 (e.g., VH1-46*03) and the j gene segment is IGHJ1 (e.g., JH1*01), and optionally wherein the d gene segment is IGHD6-6 (e.g., DH6-6*01), and
the first VL domain and the second VL domain are both products of recombination of human immunoglobulin light chain v and j gene segments, wherein the v gene segment is IGLV3-21 (e.g., VL3-21*d01) and the j gene segment is IGLJ2 (e.g., JL2*01) or IGLJ3 (e.g., JL3*02).

3. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, and
a second heavy-light chain pair comprises a FX binding Fv region comprising a second VH domain paired with a second VL domain, wherein
the first VH domain has at least 95% amino acid sequence identity with the N1280H VH domain SEQ ID NO: 443,
the second VH domain has at least 95% amino acid sequence identity with the T0201H VH domain SEQ ID NO: 470, and the first VL domain and the second VL domain each have at least 95% amino acid sequence identity with the 0128L VL domain SEQ ID NO: 10.

4. Bispecific antibody according to any preceding clause, wherein the first VH domain comprises a set of HCDRs comprising HCDR1, HCDR2 and HCDR3 with amino acid sequences defined wherein HCDR1 is SEQ ID NO: 406, HCDR2 is SEQ ID NO: 407 and HCDR3 is SEQ ID NO: 408.

5. Bispecific antibody according to clause 4, wherein the first VH domain comprises HCDR1 SEQ ID NO: 441.

6. Bispecific antibody according to clause 4 or clause 5, wherein the first VH domain comprises HCDR2 SEQ ID NO: 634.

7. Bispecific antibody according to any of clauses 4 to 6, wherein the first VH domain comprises HCDR2 SEQ ID NO: 436.

8. Bispecific antibody according to any of clauses 4 to 7, wherein the first VH domain comprises HCDR3 SEQ ID NO: 635.

9. Bispecific antibody according to any of clauses 4 to 8, wherein the first VH domain comprises HCDR3 SEQ ID NO: 433.

10. Bispecific antibody according to any preceding clause, wherein the first VH domain has at least 96%, at least 97%, at least 98% or at least 99% amino acid sequence identity to N1280H.

11. Bispecific antibody according to any preceding clause, wherein the the first VH domain comprises a set of N1280H HCDRs comprising N1280H HCDR1 SEQ ID NO: 441, N1280H HCDR2 SEQ ID NO: 436 and N1280H HCDR3 SEQ ID NO: 433.

12. Bispecific antibody according to clause 10 or clause 11, wherein the first VH domain is the N1280H VH domain SEQ ID NO: 443.

13. Bispecific antibody according to any of clauses 1 to 11, wherein the first VH domain is the N1454H VH domain SEQ ID NO: 454.

14. Bispecific antibody according to any of clauses 1 to 11, wherein the first VH domain is the N1441H VH domain SEQ ID NO: 456.

15. Bispecific antibody according to any of clauses 1 to 11, wherein the first VH domain is the N1442H VH domain SEQ ID NO: 458.

16. Bispecific antibody according to any of clauses 1 to 3, wherein the first VH domain has at least 96%, at least 97%, at least 98% or at least 99% amino acid sequence identity to N1333H.

17. Bispecific antibody according to clause 16, wherein the first VH domain comprises a set of N1333H CDRs comprising N1333H CDR1, N1333H CDR2 and N1333H CDR3.

18. Bispecific antibody according to clause 16 or clause 17, wherein the first VH domain is the N1333H VH domain.

19. Bispecific antibody according to any of clauses 1 to 3, wherein the first VH domain has at least 96%, at least 97%, at least 98% or at least 99% amino acid sequence identity to N1327H.

20. Bispecific antibody according to clause 19, wherein the the first VH domain comprises a set of N1327H HCDRs comprising N1327H HCDR1, N1327H HCDR2 and N1327H HCDR3.

21. Bispecific antibody according to clause 19 or clause 20, wherein the first VH domain is the N1327H VH domain.

22. Bispecific antibody according to any of clauses 1 to 3, wherein the first VH domain has at least 96%, at least 97%, at least 98% or at least 99% amino acid sequence identity to N1314H.

23. Bispecific antibody according to clause 22, wherein the the first VH domain comprises a set of N1314H HCDRs comprising N1314H HCDR1, N1314H HCDR2 and N1314H HCDR3.

24. Bispecific antibody according to clause 22 or clause 23, wherein the first VH domain is the N1314H VH domain.

25. Bispecific antibody according to any of clauses 1 to 3, wherein the first VH domain has at least 96%, at least 97%, at least 98% or at least 99% amino acid sequence identity to N1172H.

26. Bispecific antibody according to clause 25, wherein the the first VH domain comprises a set of N1172H HCDRs comprising N1172H HCDR1, N1172H HCDR2 and N1172H HCDR3.

27. Bispecific antibody according to clause 25 or clause 26, wherein the first VH domain is the N1172H VH domain.

28. Bispecific antibody according to any of clauses 1 to 3, wherein the first VH domain has at least 96%, at least 97%, at least 98% or at least 99% amino acid sequence identity to N1091H.

29. Bispecific antibody according to clause 28, wherein the the first VH domain comprises a set of N1091H HCDRs comprising N1091H HCDR1, N1091H HCDR2 and N1091H HCDR3.

30. Bispecific antibody according to clause 28 or clause 29, wherein the first VH domain is the N1091H VH domain.

31. Bispecific antibody according to any of clauses 1 to 3, wherein the first VH domain has at least 96%, at least 97%, at least 98% or at least 99% amino acid sequence identity to N0511H.

32. Bispecific antibody according to clause 31, wherein the the first VH domain comprises a set of N0511H HCDRs comprising N0511H HCDR1, N0511H HCDR2 and N0511H HCDR3.

33. Bispecific antibody according to clause 31 or clause 32, wherein the first VH domain is the N0511H VH domain.

34. Bispecific antibody according to any of clauses 1 to 3, wherein the first VH domain has at least 96%, at least 97%, at least 98% or at least 99% amino acid sequence identity to N0436H.

35. Bispecific antibody according to clause 34, wherein the the first VH domain comprises a set of N0436H HCDRs comprising N0436H HCDR1, N0436H HCDR2 and N0436H HCDR3.

36. Bispecific antibody according to clause 34 or clause 35, wherein the first VH domain is the N0436H VH domain.

37. Bispecific antibody according to any preceding clause, wherein the second VH domain has at least 95%, at least 96%, at least 97%, at least 98% or at least 99% amino acid sequence identity to T0201H VH domain SEQ ID NO: 470.

38. Bispecific antibody according to clause 37, wherein the second VH domain comprises an HCDR1 which is the T0201H HCDR1 SEQ ID NO: 462, an HCDR2 which is the T0201H HCDR2 SEQ ID NO: 467, and/or an HCDR3 which is the T0201H HCDR3 SEQ ID NO: 468.

39. Bispecific antibody according to any preceding clause wherein the second VH domain comprises HCDR1 SEQ ID NO: 636.

40. Bispecific antibody according to clause 39, wherein the second VH domain comprises HCDR1 SEQ ID NO: 598.

41. Bispecific antibody according to any preceding clause, wherein the second VH domain comprises HCDR2 SEQ ID NO: 467.

42. Bispecific antibody according to any preceding clause, wherein the second VH domain comprises HCDR3 SEQ ID NO: 637.
43. Bispecific antibody according to clause 42, wherein the second VH domain comprises HCDR3 SEQ ID NO: 638.
44. Bispecific antibody according to clause 43, wherein the second VH domain comprises HCDR3 SEQ ID NO: 639.
45. Bispecific antibody according to clause 44, wherein the second VH domain comprises HCDR3 SEQ ID NO: 565.
46. Bispecific antibody according to clause 44, wherein the second VH domain comprises HCDR3 SEQ ID NO: 583.
47. Bispecific antibody according to any of clauses 37 to 45, wherein the second VH domain comprises SEQ ID NO: 632.
48. Bispecific antibody according to any of clauses 37 to 45, wherein the second VH domain comprises SEQ ID NO: 600.
49. Bispecific antibody according to any of clauses 37 to 46, wherein the second VH domain comprises SEQ ID NO: 585.
50. Bispecific antibody according to clause 38, wherein the the second VH domain comprises a set of T0201H HCDRs comprising T0201H HCDR1, T0201H HCDR2 and T0201H HCDR3.
51. Bispecific antibody according to clause 37, clause 38 or clause 50, wherein the second VH domain is the T0201H VH domain, optionally with a substitution at Cys114.
52. Bispecific antibody according to clause 51, wherein the substitution at Cys114 is Ile, Gln, Arg, Val or Trp.
53. Bispecific antibody according to any of clauses 1 to 38, wherein the second VH domain comprises a set of T0638H HCDRs comprising T0638H HCDR1, T0638H HCDR2 and T0638H HCDR3.
54. Bispecific antibody according to clause 53, wherein the second VH domain is the T0638 VH domain, optionally with a substitution at Cys114.
55. Bispecific antibody according to clause 54, wherein the substitution at Cys114 is Ile, Gln,
  Arg, Val or Trp.
56. Bispecific antibody according to any preceding clause, wherein the first VL domain and the second VL domain each have at least 96%, at least 97%, at least 98% or at least 99 amino acid sequence identity with 0128L SEQ ID NO: 10.
57. Bispecific antibody according to any preceding clause, wherein the first VL domain and the second VL domain each comprise a set of 0128L CDRs comprising 0128L LCDR1 SEQ ID NO: 6, 0128L LCDR2 SEQ ID NO: 7 and 0128L LCDR3 SEQ ID NO: 8.
58. Bispecific antibody according to any preceding clause, wherein the first VL domain and the second VL domain are identical in amino acid sequence.
59. Bispecific antibody according to clause 58, wherein the first VL domain and the second VL domain comprise the 0325L amino acid sequence SEQ ID NO: 416.
60. Bispecific antibody according to clause 58 or clause 59, wherein the first VL domain and the second VL domain comprise the 0128L amino acid sequence SEQ ID NO: 10.
61. Bispecific antibody according to any preceding clause, wherein each heavy-light chain pair further comprises a CL constant domain paired with a CH1 domain.
62. Bispecific antibody according to any preceding clause, wherein the heavy-light chain pairs comprise a common light chain.
63. Bispecific antibody according to clause 62, wherein the common light chain comprises the CL amino acid sequence SEQ ID NO: 146 of the 0128L light chain.
64. Bispecific antibody according to clause 63, wherein the common light chain is the 0325L light chain SEQ ID NO: 414.
65. Bispecific antibody according to clause 63, wherein the common light chain is the 0128L light chain SEQ ID NO: 405.
66. Bispecific antibody according to any preceding clause, wherein the heavy chain of each heavy-light chain comprises a heavy chain constant region and wherein the first and second heavy-light chain pairs associate to form tetrameric immunoglobulin through dimerisation of the heavy chain constant regions.
67. Bispecific antibody according to clause 66, wherein the heavy chain constant region of the first heavy-light chain pair comprises a different amino acid sequence from the heavy chain constant region of the second heavy-light chain pair, wherein the different amino acid sequences are engineered to promote heterodimerisation of the heavy chain constant regions.
68. Bispecific antibody according to clause 67, wherein the heavy chain constant regions comprise knobs-into-holes mutations or charge pair mutations.
69. Bispecific antibody according to clause 67, wherein the heavy chain constant region of one (e.g., the first) heavy-light chain pair is a human IgG4 constant region comprising substitution K439E and wherein the heavy chain constant region of the other (e.g., the second) heavy-light chain pair is an IgG4 region comprising substitution E356K, wherein constant region numbering is according to the EU numbering system.
70. Bispecific antibody according to any of clauses 66 to 69, wherein the heavy chain constant region of one or both heavy-light chain pairs is a human IgG4 constant region comprising substitution S228P, wherein constant region numbering is according to the EU numbering system.
71. Bispecific antibody according to any of clauses 66 to 70, wherein the heavy chain constant region of one (e.g., the first) heavy-light chain pair comprises SEQ ID NO: 409 and the heavy chain constant region of the other (e.g., the second) heavy-light chain pair comprises SEQ ID NO: 410.
72. Bispecific antibody according to any of clauses 66 to 71, comprising
  a first heavy chain comprising a first VH domain amino acid sequence SEQ ID NO: 443 or SEQ ID NO: 456,
  a second heavy chain comprising a second VH domain amino acid sequence SEQ ID NO: 632, and
  a common light chain comprising a VL domain amino acid sequence SEQ ID NO: 416.
73. Bispecific antibody according to any of clauses 66 to 72, comprising
  a first heavy chain comprising amino acid sequence SEQ ID NO: 419,
  a second heavy chain comprising amino acid sequence SEQ ID NO: 421, and
  a common light chain comprising amino acid sequence SEQ ID NO: 414.
74. Bispecific antibody according to any of clauses 66 to 71, comprising
  a first heavy chain comprising amino acid sequence SEQ ID NO: 424
  a second heavy chain comprising amino acid sequence SEQ ID NO: 421, and
  a common light chain comprising amino acid sequence SEQ ID NO: 414.
75. Bispecific antibody according to any of clauses 66 to 72, comprising
  a first heavy chain comprising amino acid sequence SEQ ID NO: 426
  a second heavy chain comprising amino acid sequence SEQ ID NO: 421, and a common light chain comprising amino acid sequence SEQ ID NO: 414.

76. Bispecific antibody according to any of clauses 66 to 71, comprising
a first heavy chain comprising amino acid sequence SEQ ID NO: 428
a second heavy chain comprising amino acid sequence SEQ ID NO: 430, and
a common light chain comprising amino acid sequence SEQ ID NO: 414.

77. Bispecific antibody according to any of clauses 66 to 71, comprising
a first heavy chain comprising amino acid sequence SEQ ID NO: 428
a second heavy chain comprising amino acid sequence SEQ ID NO: 432, and
a common light chain comprising amino acid sequence SEQ ID NO: 414.

78. Bispecific antibody according to clause 66, wherein the heavy chain constant region of the first heavy-light chain pair is identical to the heavy chain constant region of the second heavy-light chain pair.

79. Bispecific antibody according to any of clauses 1 to 68, wherein the antibody is human IgG.

80. Bispecific antibody according to clause 79, wherein the antibody is human IgG4.

81. Bispecific antibody according to clause 79 or clause 80, wherein the IgG comprises the IgG4-PE heavy chain constant region SEQ ID NO: 143, optionally engineered with one or more amino acid substitutions to promote heterodimerisation.

82. Bispecific antibody according to clause 79 or clause 80, wherein the antibody comprises the Fc region of emicizumab.

83. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, wherein the first VH domain is at least 98% identical in amino acid sequence to the N1280H VH domain SEQ ID NO: 443, and
a second heavy-light chain pair comprises a FX binding Fv region comprising a second VH domain paired with a second VL domain, wherein the second VH domain is at least 98 identical in amino acid sequence to the T0999H VH domain SEQ ID NO: 632, and wherein
the first and second heavy-light chain pairs each comprise a common light chain comprising the 0325L light chain amino acid sequence SEQ ID NO: 414.

84. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, wherein the first VH domain is at least 98% identical in amino acid sequence to the N1454H VH domain SEQ ID NO: 454, and
a second heavy-light chain pair comprises a FX binding Fv region comprising a second VH domain paired with a second VL domain, wherein the second VH domain is at least 98 identical in amino acid sequence to the T0999H VH domain SEQ ID NO: 632, and wherein
the first and second heavy-light chain pairs each comprise a common light chain comprising the 0325L light chain amino acid sequence SEQ ID NO: 414.

85. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, wherein the first VH domain is at least 98% identical in amino acid sequence to the N1441H VH domain SEQ ID NO: 456, and
a second heavy-light chain pair comprises a FX binding Fv region comprising a second VH domain paired with a second VL domain, wherein the second VH domain is at least 98 identical in amino acid sequence to the T0999H VH domain SEQ ID NO: 632, and wherein
the first and second heavy-light chain pairs each comprise a common light chain comprising the 0325L light chain amino acid sequence SEQ ID NO: 414.

86. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, wherein the first VH domain is at least 98% identical in amino acid sequence to the N1442H VH domain SEQ ID NO: 458, and
a second heavy-light chain pair comprises a FX binding Fv region comprising a second VH domain paired with a second VL domain, wherein the second VH domain is at least 98 identical in amino acid sequence to the T0736H VH domain SEQ ID NO: 600, and wherein
the first and second heavy-light chain pairs each comprise a common light chain comprising the 0325L light chain amino acid sequence SEQ ID NO: 414.

87. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, wherein the first VH domain is at least 98% identical in amino acid sequence to the N1442H VH domain SEQ ID NO: 458, and
a second heavy-light chain pair comprises a FX binding Fv region comprising a second VH domain paired with a second VL domain, wherein the second VH domain is at least 98 identical in amino acid sequence to the T0687H VH domain SEQ ID NO: 585, and wherein
the first and second heavy-light chain pairs each comprise a common light chain comprising the 0325L light chain amino acid sequence SEQ ID NO: 414.

88. Bispecific antibody that binds FIXa and FX and catalyses FIXa-mediated activation of FX, wherein the antibody comprises two immunoglobulin heavy-light chain pairs, wherein
a first heavy-light chain pair comprises a FIXa binding Fv region comprising a first VH domain paired with a first VL domain, wherein the first VH domain is at least 98% identical in amino acid sequence to the N1333H VH domain, and
a second heavy-light chain pair comprises a FX binding Fv region comprising a second VH domain paired with a second VL domain, wherein the second VH domain is at least 98 identical in amino acid sequence to the T0638H VH domain, and wherein the first and second heavy-light chain pairs each comprise a common light chain comprising the 0128L light chain amino acid sequence SEQ ID NO: 405.

89. Bispecific antibody according to any preceding clause, which reduces the coagulation time of FVIII-deficient human blood plasma to less than 40 seconds in an aPTT assay.

90. Bispecific antibody according to clause 89, which reduces the coagulation time of FVIII-deficient human blood plasma to less than 30 seconds in an aPTT assay.

91. Bispecific antibody according to clause 90, which reduces the coagulation time of FVIII-deficient human blood plasma to 22-28 seconds in an aPTT assay.

92. Bispecific antibody according to clause 91, which reduces the coagulation time of FVIII-deficient human blood plasma to 24-26 seconds in an aPTT assay.

93. Bispecific antibody according to any preceding clause, which enhances the FIXa-mediated activation of FX to FXa to the same or similar extent as emicizumab in a FXase assay.

94. Bispecific antibody according to any preceding clause, which enhances the FIXa-mediated activation of FX to FXa to at least the same extent as emicizumab.

95. Bispecific antibody according to any of clauses 89 to 94, wherein said coagulation time or FIXa-mediated activation is as determined at an antibody concentration of 0.1 mg/ml, 0.3 mg/ml or 0.5 mg/ml at 37 degrees C.

96. Bispecific antibody according to any preceding clause, wherein the antibody has an EC50 for Cmax in a fluorometric thrombin generation assay (TGA) that is within 10% of or is lower than the Cmax EC50 of emicizumab in said assay, and/or wherein the antibody generates a maximal response of Cmax between 200 and 450 nM thrombin in a fluorometric TGA.

98. Bispecific antibody according to clause 96, wherein the antibody has an EC50 of less than 50 nM for Cmax in a fluorometric TGA.

99. Bispecific antibody according to clause 98, which has an EC50 of less than 10 nM for Cmax in a fluorometric TGA.

100. Bispecific antibody according to any preceding clause, wherein the maximal response of Cmax is between 250 nM and 400 nM.

101. Bispecific antibody according to any preceding clause, wherein the antibody has an EC50 for Tmax in a fluorometric TGA that is within 10% of, or is lower than, the Tmax EC50 of emicizumab in said assay, and/or wherein the antibody generates a maximal response of Tmax between 1 and 10 minutes.

102. Bispecific antibody according to any preceding clause, wherein the antibody has an EC50 of less than 5 nM for Tmax in a fluorometric TGA.

103. Bispecific antibody according to clause 102, wherein the EC50 for Tmax is less than 2 nM.

104. Bispecific antibody according to any preceding clause, wherein the antibody generates a maximal response of Tmax between 2 and 8 minutes in a fluorometric TGA.

105. Anti-FIXa antibody comprising two copies of the first heavy-light chain pair as defined in any preceding clause.

106. Anti-FX antibody comprising two copies of the second heavy-light chain pair as defined in any of clauses 1 to 104.

107. Isolated nucleic acid encoding an antibody according to any preceding clause.

108. A host cell in vitro comprising recombinant DNA encoding an antibody heavy chain comprising a first VH domain as defined in any of clauses 1 to 104, an antibody heavy chain comprising a second VH domain as defined in any of clauses 1 to 104, and/or an antibody light chain comprising a first or second VL domain as defined in any of clauses 1 to 104.

109. A host cell according to clause 108 comprising recombinant DNA encoding a first heavy chain comprising amino acid sequence SEQ ID NO: 419 or SEQ ID NO: 426, a second heavy chain comprising amino acid sequence SEQ ID NO: 421, and a common light chain comprising amino acid sequence SEQ ID NO: 414.

110. A population of host cells in vitro, wherein each host cell comprises recombinant DNA encoding a bispecific antibody according to any of clauses 1 to 104.

111. A kit for production of a bispecific antibody according to any of clauses 1 to 104, comprising an antibody heavy chain comprising a first VH domain as defined in any of clauses 1 to 104, or nucleic acid encoding said heavy chain, an antibody heavy chain comprising a second VH domain as defined in any of clauses 1 to 104, or nucleic acid encoding said heavy chain, an antibody light chain comprising a first VL domain as defined in any of clauses 1 to 104, or nucleic acid encoding said light chain, and an antibody light chain comprising a second VL domain as defined in any of clauses 1 to 104, or nucleic acid encoding said light chain.

112. A kit according to clause 111, comprising a first heavy chain comprising amino acid sequence SEQ ID NO: 419 or SEQ ID NO: 426, or nucleic acid encoding said first heavy chain, a second heavy chain comprising amino acid sequence SEQ ID NO: 421, or nucleic acid encoding said second heavy chain, and a common light chain comprising amino acid sequence SEQ ID NO: 414, or nucleic acid encoding said common light chain.

113. A kit according to clause 111 or clause 112, wherein said amino acid sequences or said nucleic acids are provided in cells.

114. A kit according to clause 111 or clause 112, wherein said amino acid sequences or said nucleic acids are provided in cell-free buffered aqueous media.

115. A kit according to any of clauses 111 to 114, wherein each of said amino acid sequences or each of said nucleic acids is provided in a separate phial.

116. A method of producing a bispecific antibody according to any of clauses 1 to 104, comprising culturing host cells according to clause 108 or clause 109 under conditions for expression of the bispecific antibody, and recovering the bispecific antibody from the host cell culture.

117. A method according to clause 116, comprising culturing the host cells in a vessel comprising a volume of at least 100 litres.

118. A method according to clause 117, wherein the vessel is of stainless steel or is a single-use bioreactor.

119. A composition comprising a bispecific antibody according to any of clauses 1 to 104, or isolated nucleic acid according to clause 107, in solution with a pharmaceutically acceptable excipient.

120. A composition according to clause 119, wherein the bispecific antibody or nucleic acid is in sterile aqueous solution.

121. A composition according to clause 119 or clause 120, comprising a bispecific antibody according to any of clauses 1 to 104 wherein the bispecific antibody is at least 95% pure such that the composition comprises no more than 5% homodimeric antibody contaminants.

122. A composition according to clause 121, wherein the bispecific antibody is at least 99 pure such that the composition comprises no more than 1% homodimeric antibody contaminants.

123. A method of controlling bleeding in a patient, comprising administering a composition according to any of clauses 119 to 122 to the patient.

124. A composition according to any of clauses 119 to 122 for use in a method of treatment of the human body by therapy.

125. A composition according to any of clauses 119 to 122 for use in a method of controlling bleeding in a patient.

125. Use of a bispecific antibody according to any of clauses 1 to 104 for the manufacture of a medicament for controlling bleeding in a haemophilia A patient.

126. A method according to clause 123, or a composition for use or use according to clause 125, wherein the patient is a haemophilia A patient.

127. A method or a composition for use according to clause 126, wherein the patient is resistant to treatment with FVIII owing to the presence of inhibitory antibodies in the bloodstream.

128. A method or a composition for use according to clause 126 or clause 127, wherein the patient is resistant to treatment with another bispecific antibody to FIXa and FX owing to the presence of inhibitory antibodies in the bloodstream.

129. A method or a composition for use according to clause 128, wherein the patient is resistant to treatment with emicizumab.

130. A method of reducing development of inhibitory anti-drug antibodies in a haemophilia A patient undergoing treatment with a polypeptide that replaces FVIIIa activity, comprising administering a first FVIIIa-activity replacing polypeptide drug to the patient for a period of 1-12 months, switching the patient to a second, different FVIIIa-activity replacing polypeptide drug for a period of 1-12 months, and switching the patient to either the first antigen-binding molecule or to a third, different FVIIIa-activity replacing polypeptide drug for a period of 1-12 months, wherein the first, second or third FVIIIa-activity replacing polypeptide drug is a bispecific antibody according to any of clauses 1 to 104, and wherein in each case the FVIIIa-activity replacing polypeptide drug or its encoding nucleic acid is administered in a therapeutically effective amount to functionally replace FVIIIa in the patient, and wherein the risk of the patient developing inhibitory anti-drug antibodies to any of the FVIIIa-activity replacing polypeptide drug is reduced compared with a patient continuing to receive treatment with that FVIIIa-activity replacing polypeptide drug.

131. A composition comprising a FVIIIa-activity replacing polypeptide drug or its encoding nucleic acid, for use in a method of treating a haemophilia A patient while reducing development of inhibitory anti-drug antibodies, or use of a FVIIIa-activity replacing polypeptide drug or its encoding nucleic acid for the manufacture of a medicament for use in a method of treating a haemophilia A patient while reducing development of inhibitory anti-drug antibodies, the method comprising administering a first FVIIIa-activity replacing polypeptide drug to the patient for a period of 1-12 months, switching the patient to a second, different FVIIIa-activity replacing polypeptide drug for a period of 1-12 months, and switching the patient to either the first antigen-binding molecule or to a third, different FVIIIa-activity replacing polypeptide drug for a period of 1-12 months, wherein the first, second or third FVIIIa-activity replacing polypeptide drug is a bispecific antibody according to any of clauses 1 to 104, and wherein in each case the FVIIIa-activity replacing polypeptide drug or its encoding nucleic acid is administered in a therapeutically effective amount to functionally replace FVIIIa in the patient, and wherein the risk of the patient developing inhibitory anti-drug antibodies to any of the FVIIIa-activity replacing polypeptide drug is reduced compared with a patient continuing to receive treatment with that FVIIIa-activity replacing polypeptide drug.

132. A method according to clause 130, or a composition for use or use according to clause 131, wherein the first, second and third FVIIIa-activity replacing polypeptide drugs are recombinant or plasma-derived FVIII, emicizumab, and a bispecific antibody according to any of clauses 1 to 104, in any order.

133. A method, composition for use or use according to any of clauses 123 to 132 wherein the treatment comprises subcutaneous administration of the composition to the patient.

Equivalents: Those skilled in the art will recognise, or be able to ascertain using no more than routine experimentation, many equivalents to the specific embodiments of the invention described herein. Such equivalents are intended to be within the scope of protection of the appended claims.

EXAMPLES

Bispecific IgG antibodies comprising Fv binding sites for human FIXa and human FX were generated as described in PCT/EP2018/066836 filed on 22 Jun. 2018 entitled "Bispecific antibodies for factor IX and factor X" (WO2018/234575). As described therein, an extensive campaign of immunisation and screening led to the identification of an anti-FIXa antibody NINA-0128 which, when paired in IgG format with any of a selection of different anti-FX binding Fvs, showed outstanding activity in functional screens including a tenase assay and aPTT assay. NINA-0128 comprises VH domain N0128H and VL domain 0128L. A number of variants of the N0128H VH domain were generated and tested, resulting in further improvements in function in a bispecific format, including for example the N0436H VH domain.

Building on that work, bispecific IgG were designed with the VL domain of NINA-0128 as a common light chain. A panel of anti-FX antibodies were generated in vivo in a transgenic mouse comprising human immunoglobulin genes. These were co-expressed with NINA-0128 as the anti-FIX binding arm, using the 0128L VL domain in a common light chain including a human constant region. One VH domain, T0200, showed outstanding activity in the bispecific format and was selected for further development. Structurally related antibodies obtained from the same immunised animal as the T0200H clone, included further anti-FX VH domains that performed even better than the T0200H VH domain in bispecific IgG4 with an anti-FIX VH domain and the 0128L common light chain.

Meanwhile, further anti-FIXa antibody variants were generated, introducing mutations in the VH domain while retaining the common 0128L VL domain. The anti-FIXa N0436H VH domain sequence was optimised by substituting all possible amino acids at each position in CDR1, CDR2 and CDR3, expressing the resulting VH domain variants in the context of bispecific antibodies comprising the common light chain, evaluating the variant bispecific antibodies in a range of functional assays, identifying mutations associated with increased functional activity, and generating further variants including combinations of mutations associated with increased functional activity.

Improved T0200H VH domain variants were combined with improved N0436H VH domain variants, each paired with the N0128L common light chain, and repeated rounds of optimisation, screening and selection were conducted.

Figure 6:
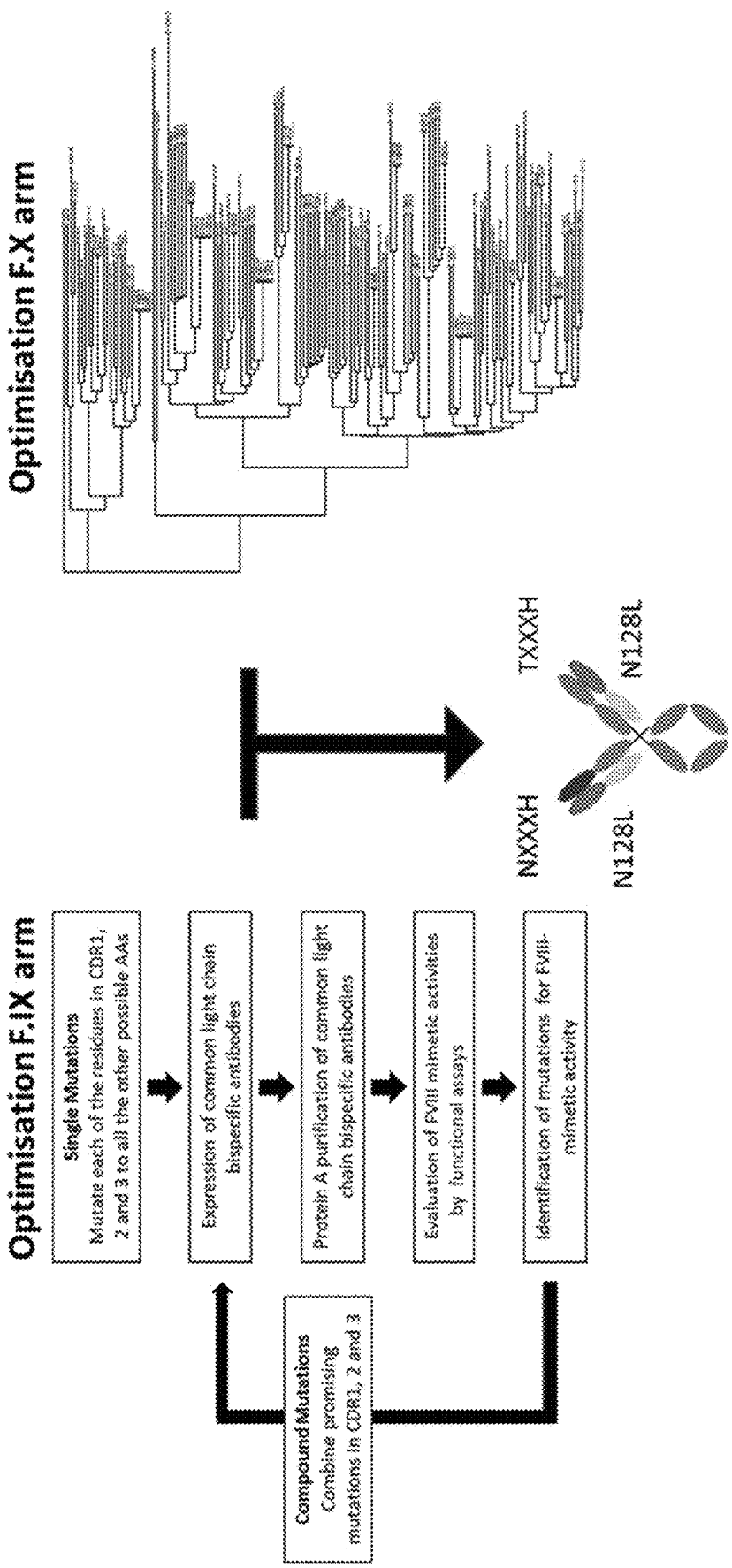
FIG. 6 summarises the process of optimising the anti-FIXa VH domain sequence N0436H and the anti-FX VH domain sequence T0200 for functional combination with each other and for pairing with the N0128L common VL domain.

FIG. 6 shows a simplified overview of the screening program.

Very strong FVIII mimetic activity was achieved with common light chain bispecific antibodies including the optimised sequences. The following bispecific antibodies are examples of strong performers, as indicated by functional characterisation in a range of disease-relevant assays. Nomenclature of the bispecific antibodies which have a common light chain is IXAX-nnnn.tttt.llll, wherein nnnn is a 4 digit numerical identifier of the anti-FIX VH domain, tttt is a 4 digit identifier of the anti-FX VH domain, and llll is a 4 digit numerical identifier of the common VL domain:

IXAX-0128.0201.0128 (anti-FIXa VH domain N0128H; anti-FX VH domain T0201H; 0128L common light chain)
IXAX-0436.0201.0128
IXAX-0511.0201.0128
IXAX-1091.0201.0128
IXAX-1172.0201.0128
IXAX-1280.0201.0128
IXAX-1341.0201.0128
IXAX-1327.0201.0128
IXAX-1333.0201.0128

Figure 11:
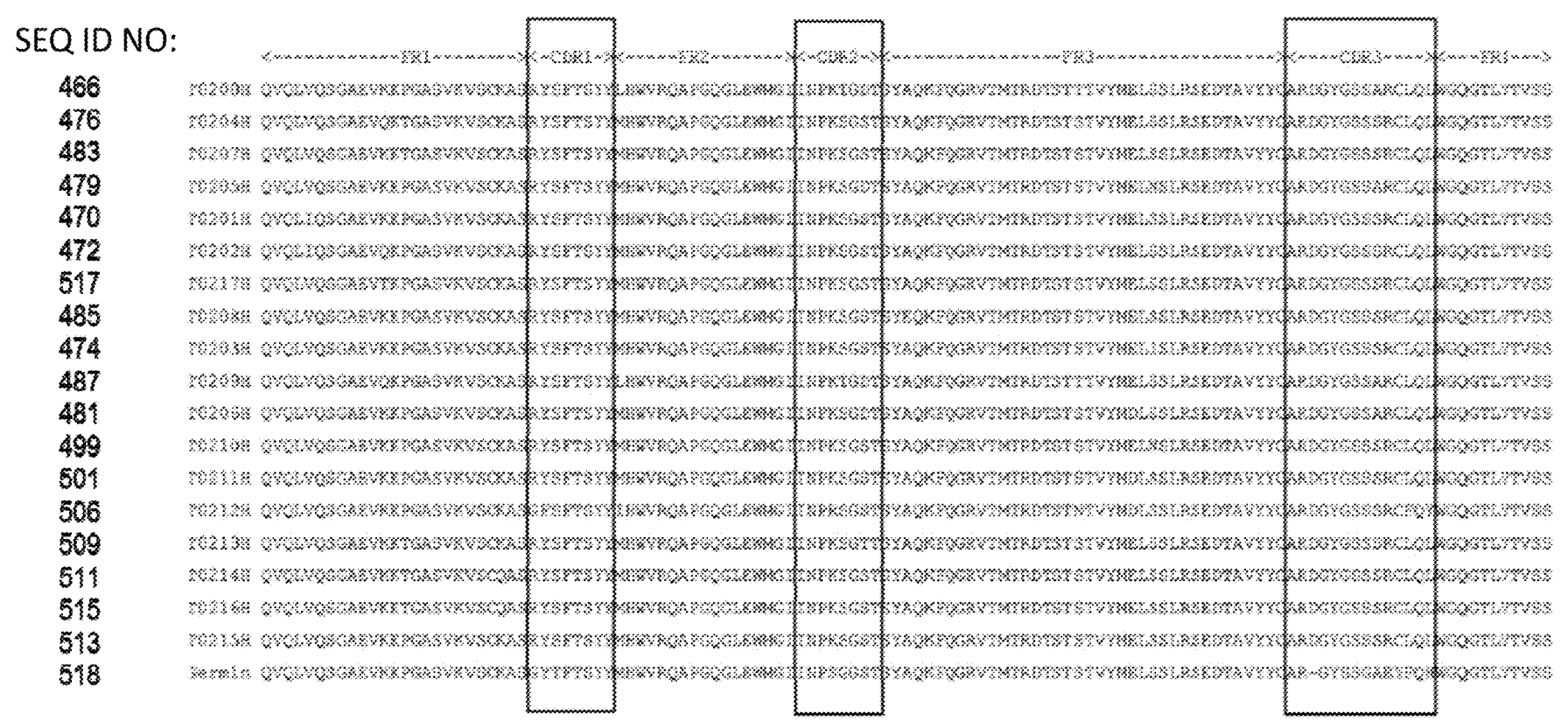

Other high performing anti-FX VH domains which combine well with the above and other anti-FIX VH domains in bispecific antibodies were those of the T0201H lineage and variants thereof such as those listed in FIG. 11 and other related sequences. Particularly good results were obtained with bispecific antibodies including an anti-FIX VH domain, an anti-FX VH domain and a common light chain selected from the following:

| anti-FIX VH domain: | anti-FX VH domain: | common VL domain: |
|---|---|---|
| N0436H | T0201H | 0128L |
| N0511H | T0596H | 0325L |
| N1091H | T0616H | |
| N1172H | T0638H | |
| N1280H | T0666H | |
| N1327H | T0678H | |
| N1333H | T0681H | |
| N1341H | T0687H | |
| N1441H | T0736H | |
| N1442H | T0999H | |
| N1454H | | |

For example,
IXAX-1280.0999.0325
IXAX-1454.0999.0325
IXAX-1441.0999.0325
IXAX-1441.0736.0325
IXAX-1442.0687.0325

The bispecific antibodies described here represent candidate pharmaceutical drug molecules for therapeutic use as described herein. They may offer a vital healthcare option for patients by providing an alternative to existing treatments such as emicizumab, especially in patients for whom such existing treatments are no longer effective due to the presence of anti-drug antibodies.

In these Examples, the reference antibody AbE or Antibody E is a bispecific antibody having the heavy and light chain amino acid sequences of emicizumab [3].

Example 1. Creation of Anti-FX Antibody Panel with Common Light Chain

Transgenic mice expressing a common light chain comprising the 0128L VL domain of were immunised with human factor X. Antigen specific B cells were single cell sorted by flow cytometry and the VH and VL sequences were retrieved by next generation sequencing (NGS). 200 anti-FX heavy chains were identified by NGS analysis of the single cell sorted lymphocytes. Further bulk NGS analysis was performed on bone marrow and lymph node tissues harvested from the same transgenic animals.

Example 2. Creation of Anti-FIXaxFIX Bispecific Antibodies with Common Light Chain Each anti-FX heavy chain was expressed in HEK293 cells as bispecific antibody comprising the anti-FIX N0128H heavy chain and the 0128L common light chain. The bispecific antibodies were purified by Protein A substantially as described in PCT/EP2018/066836 filed on 22 Jun. 2018 entitled "Bispecific antibodies for factor IX and factor X", which is incorporated by reference herein.

Example 3. Initial Screening of Anti-FX Arms Using Activation Coagulation Factor VIII (FVIIIa)-Like Activity Assay (FXase or Tenase Assay)

200 bispecific antibodies comprising a range of different anti-FX heavy chains, each in combination with the N0128H anti-FIX heavy chain and 0128L common VL domain, were screened using a factor Xa generation assay. This functional screening detects FVIIIa-mimetic activity, i.e., ability to enhance (catalyse) the FIXa-mediated activation of FX to FXa, in vitro by enzymatic "FXase" assay. In this assay, the test bispecific molecule is contacted with FIXa and FX in the presence of phospholipid, under conditions suitable for formation of FXa. A substrate for FXa is added which, when cleaved by FXa, generates a detectable product. Detection of this product in the presence of test bispecific antibody is compared with a negative control in which no test antibody is present (a control antibody may be included). The detected signal is quantified by recording absorbance of the reaction solution at 405 nm. Absorbance is measured across a range of antibody concentrations in the assay and an EC50 value is calculated as a measure of the bispecific antibody potency in this assay. Significant difference of EC50 between test antibody and control indicates that the test antibody is able to enhance FIXa-mediated activation of FX. FIG. 7.

Results

Figure 8:
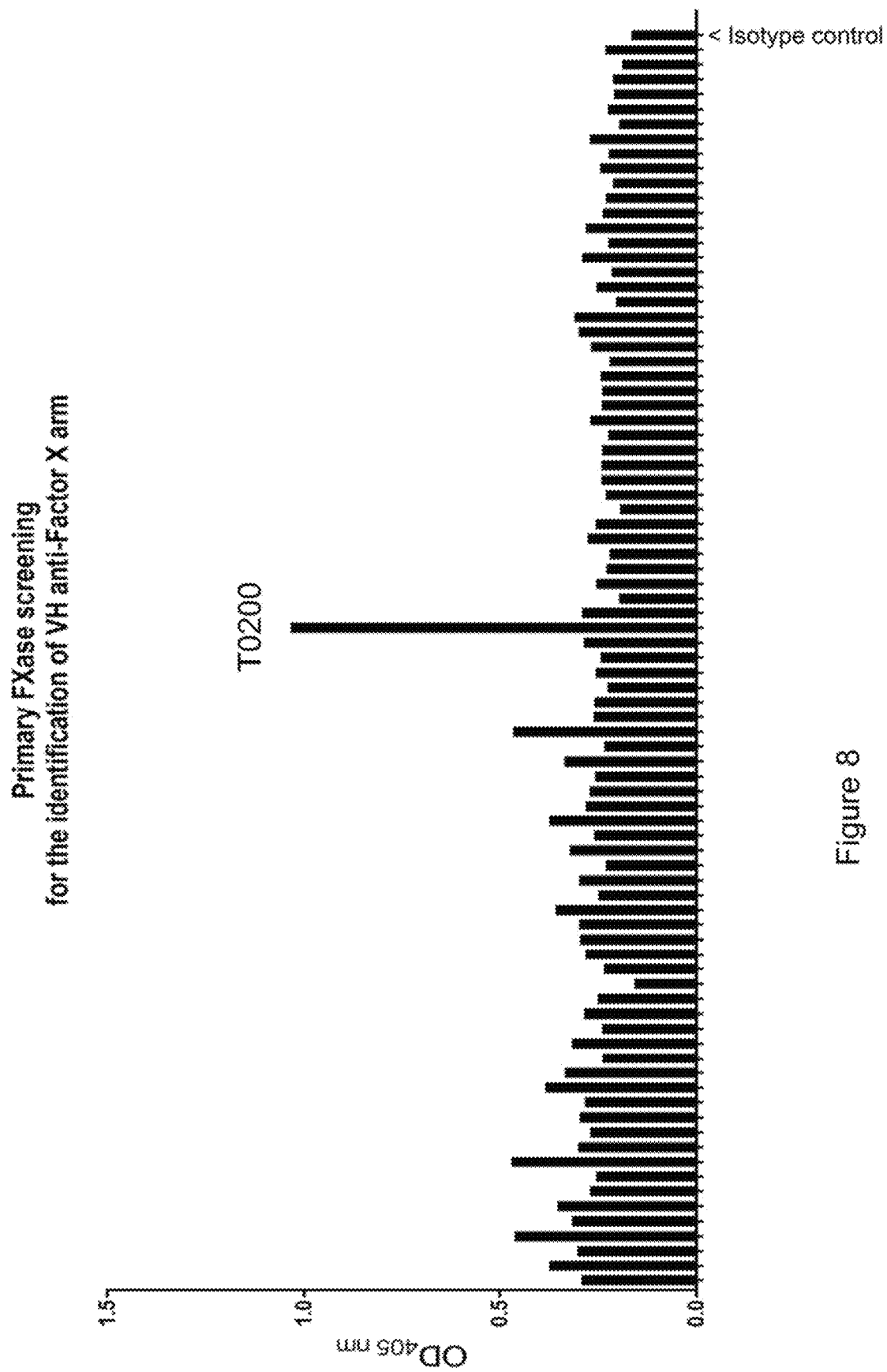
FIG. 8 shows the results of screening bispecific antibodies having various anti-FX arms in the FXase assay (standard reaction conditions). The bispecific antibody panel comprises a range of anti-FX VH test domains, each in combination with the N0128H anti-FIX VH domain and 0128L common VL domain.

Among all the bispecific antibodies assayed, a single one showed outstanding FXase activity: the N0128H anti-FIX heavy chain and T0200H anti-FX heavy chain, paired with 0128L common VL domain, had markedly higher FXase activity than all others in the panel. FIG. 8.

Materials & Methods—Standard FXase Reaction Conditions 7.5 µL FIX (3.75 µg/mL) and 5 µL supernatant from the Expi293 cells producing the recombinant antibodies (Example 8) were added to each well of an assay plate and incubated at room temperature for 1 hour. A mixture of 2.5 µL FXIa (10 ng/mL), 5 µL FX (50 ng/mL), 0.05 µL phospholipid (10 mg/mL) and 5 µL TBSB-S buffer was added to each well to initiate enzymatic reaction (FIXa cleavage of FX to generate FXa), and incubated at 37° C. for 1 hour. After 60 minutes, the reaction was terminated by adding 5 µL of 0.5 M EDTA. After adding 10 µL S2765 substrate solution to each well, absorbance at 405 nm (reference wavelength 655 nm) was measured for 30 minutes (one reading per 10 minutes). All reactions were performed at 37° C. unless otherwise stated.

TBSB:
Tris buffered saline containing 0.1% bovine serum albumin
To make 7.5 mL TBSB:
0.1 mL 7.5% BSA solution (Sigma)
7.4 mL 1×TBS solution (diluted from 20×TBS solution ThermoFisher)
TBSB-S:
TBSB containing 5 mM CaCl2 and 1 mM MgCl2
To make 100 mL TBSB-S:
99.4 mL TBSB
0.5 mL 1M CaCl2) (Sigma)
0.1 mL 1M MgCl2 (Sigma)
FXIa Stock Solution (10 µg/mL):
Add 10 mL TBSB-S to 0.1 mg FXIa (Enzyme Research Laboratories) to make 10 µg/mL stock solution.
Dilute to 10 ng/mL (1:1,000) working solution before use.
F.IXa Stock Solution (5 µg/mL)
Add 100 mL TBSB-S to 0.5 mg FIXa (HFIXa 1080) (Enzyme Research Laboratories) to make 5 µg/mL stock solution.
Dilute to 1.0 µg/mL (1:5) working solution before use.
FIX Stock Solution (37.5 µg/mL):
Add 13.3 mL TBSB-S to 0.5 mg FIX (Enzyme Research Laboratories) to make 37.5 µg/mL stock solution.
Dilute to 3.75 µg/mL (1:10) working solution before use.
FX Working Solution (50 µg/mL):
Add 16 mL TBSB-S to 0.8 mg FX (Enzyme Research Laboratories) to make 50 µg/mL working solution.
No further dilution is needed before use.
S2765 Stock Solution:
25 mg S2765 (Chromogenix) chromogenic substrate (0.035 mmol)
To make 2 mM stock solution:
Add 17.493 mL water to the vial and dissolve with shaking.
Polybrene Solution:
To make 0.6 g/L hexadimethrine bromide stock solution:
Add 0.15 g hexadimethrine bromide (Sigma) to 250 mL water.
Dilute to 0.6 mg/L (1:1,000) working solution before use.
S2765 Substrate Working Solution
A 1:1 mixture of 2 mM S-2765 stock solution and 0.6 mg/L polybrene solution.

Example 4. Identification of Anti-FX T0200H VH Domain

The bispecific antibody designated IXAX.0128.0200.0128, comprising N0128H anti-FIX VH domain, T0200H anti-FX VH domain and 0128L common light chain, demonstrated high FXase activity compared with the other bispecific antibodies. The T0200H VH domain was chosen for further development to attempt production of yet further improved bispecific antibodies.

Example 5. Optimisation of Anti-FX T0200H VH Domain

Phylogenetic Analysis

Figure 9:
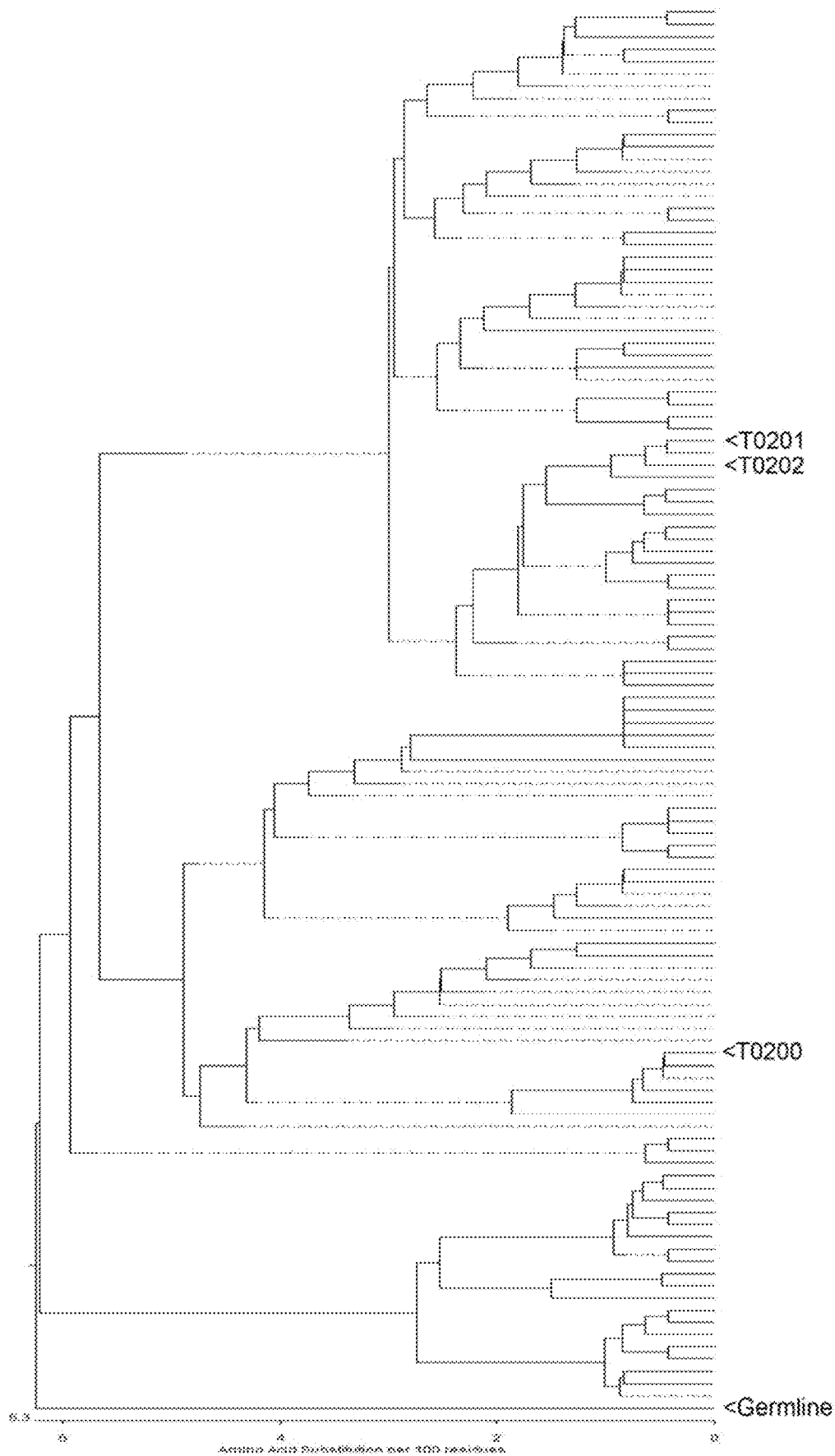
FIG. 9 illustrates the B cell cluster identified for the lineage of the anti-FX T0200H domain.

From the bulk NGS (Example 1) and phylogenetic analysis, 113 anti-FX heavy chains were identified as belonging to the same lymphocyte cluster as the anti-FX heavy chain T0200H. The cluster represents B cells that appear to share a common evolutionary lineage. The anti-FX heavy chains within the cluster shared approximately 95% sequence identity with T0200H at the amino acid level. FIG. 9.

The 113 anti-FX heavy chains were expressed in bispecific antibodies with a panel of different anti-FIX heavy chains and the 0128L common light chain, and screened by FXase assay.

Figure 10:
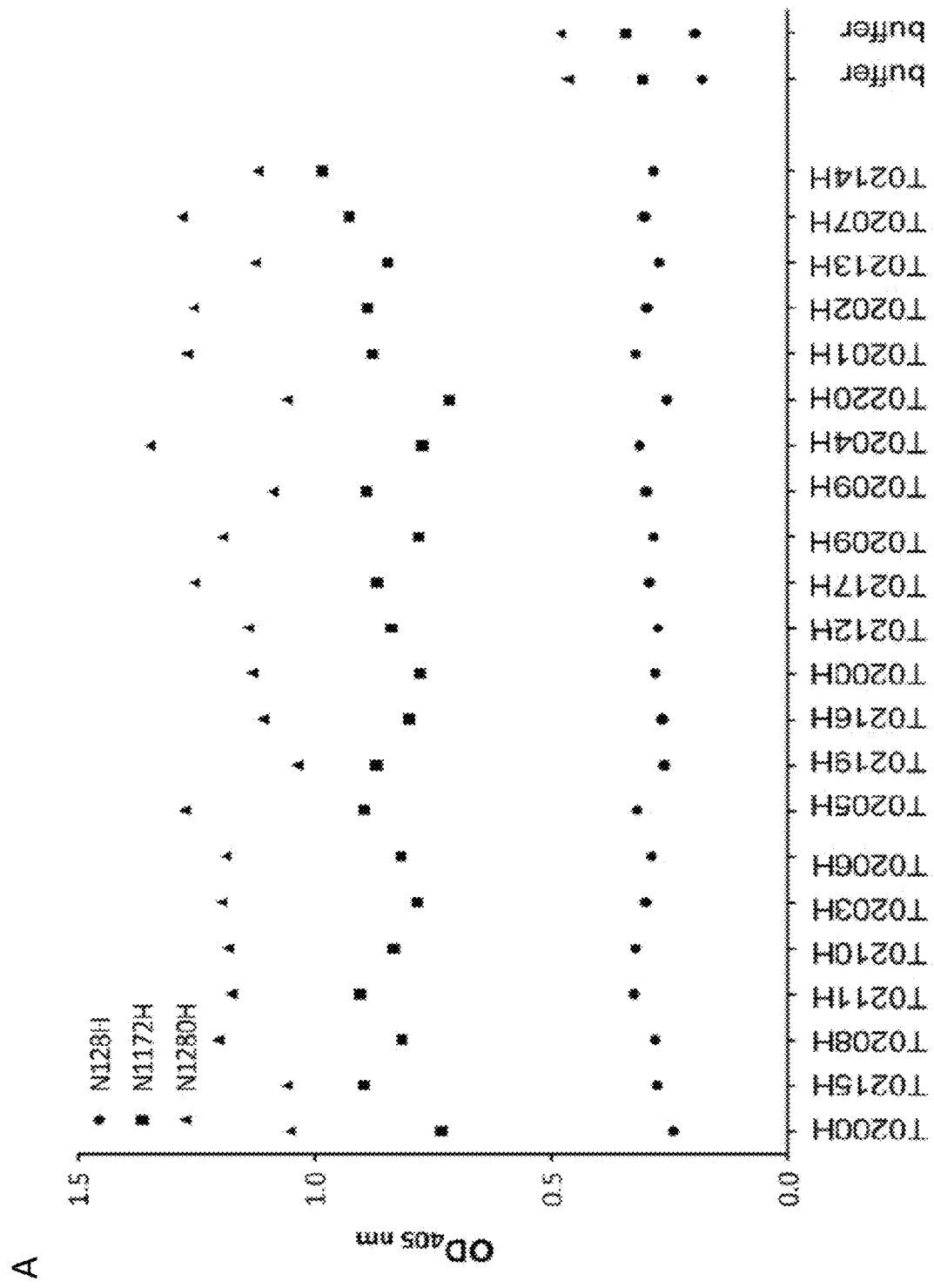
FIG. 10 shows the results of screening optimised bispecific antibodies in the FXase assay. (A) FXase activity for IgG4 bispecific antibodies comprising named anti-FX VH domain combined with the N0128H, N1172H or N1280H anti-FIX VH domain and 0128L common light chain. OD at 405 nm at 10 minutes (600s). (B) FXase activity for IgG4 bispecific antibodies comprising named anti-FX VH domain combined with the N1280H anti-FIX VH domain and N0128L common light chain.
Figure 10:
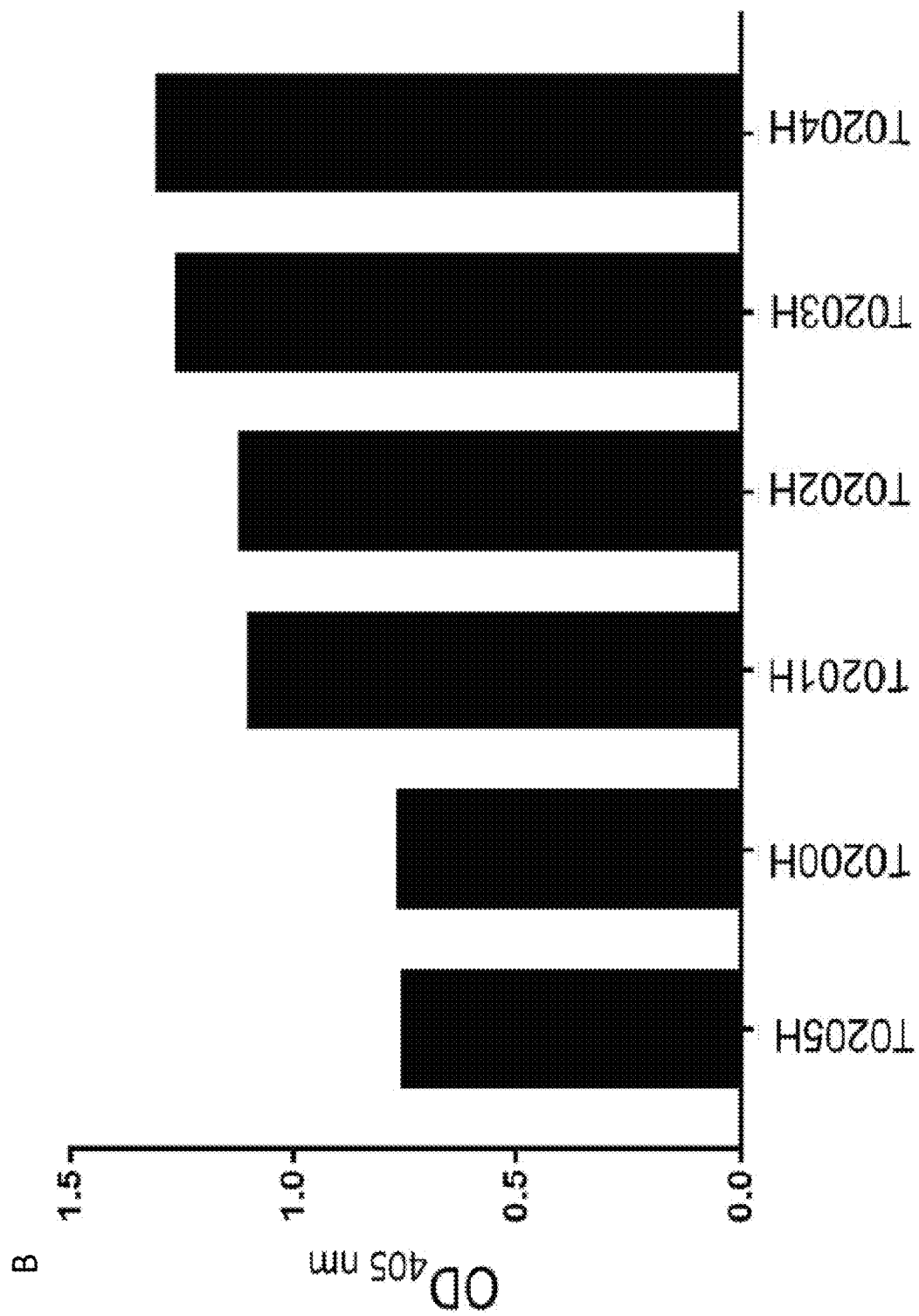
Figure 15:
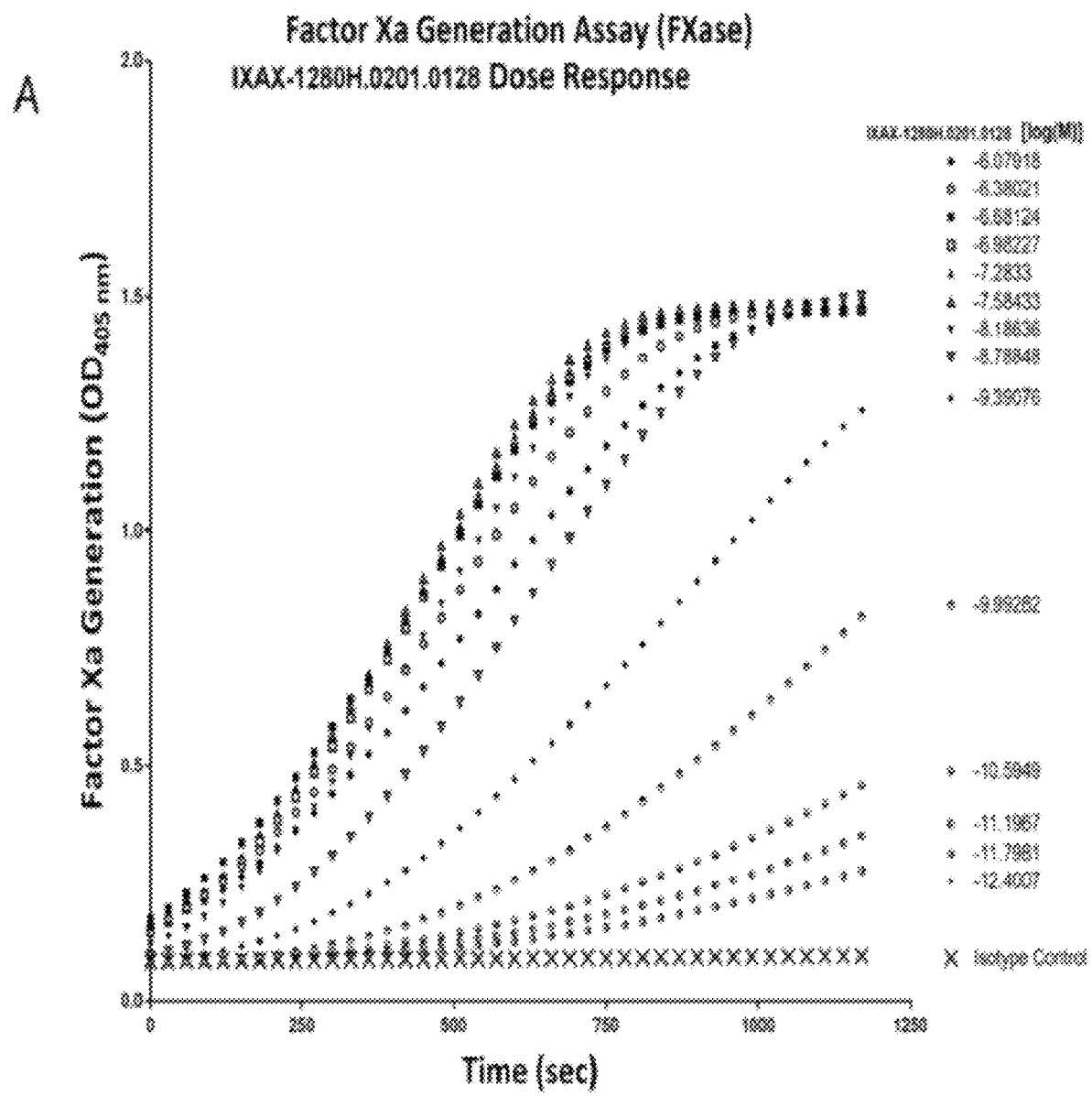
FIG. 15 shows the kinetics of activity of (A) IXAX-1280.0201.0128 and of (B) the comparator antibody AbE in the FXase assay. Antibody was purified by Protein A and is composed of a homodimer/heterodimer mixture.
Figure 15:
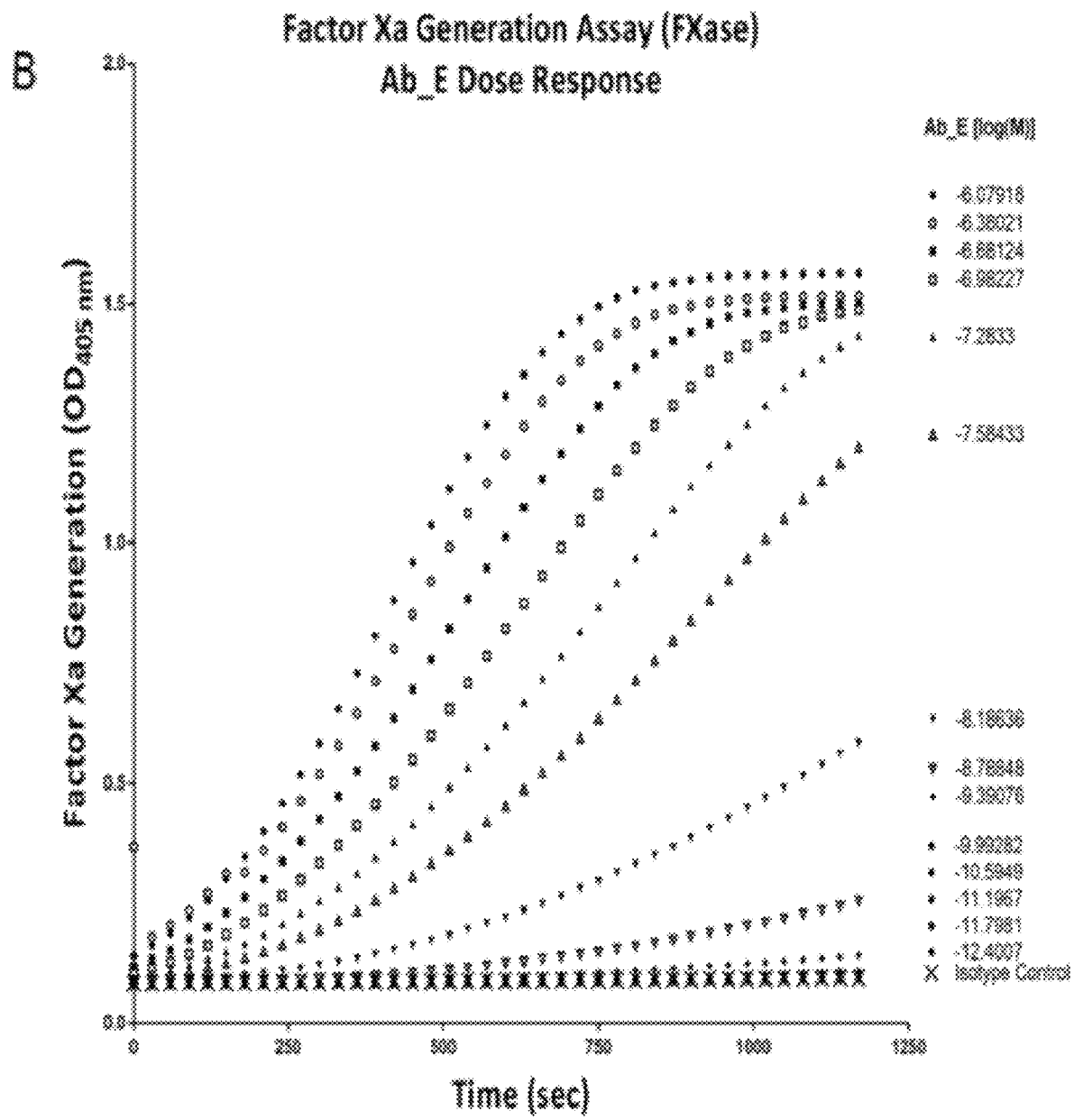
Figure 16:
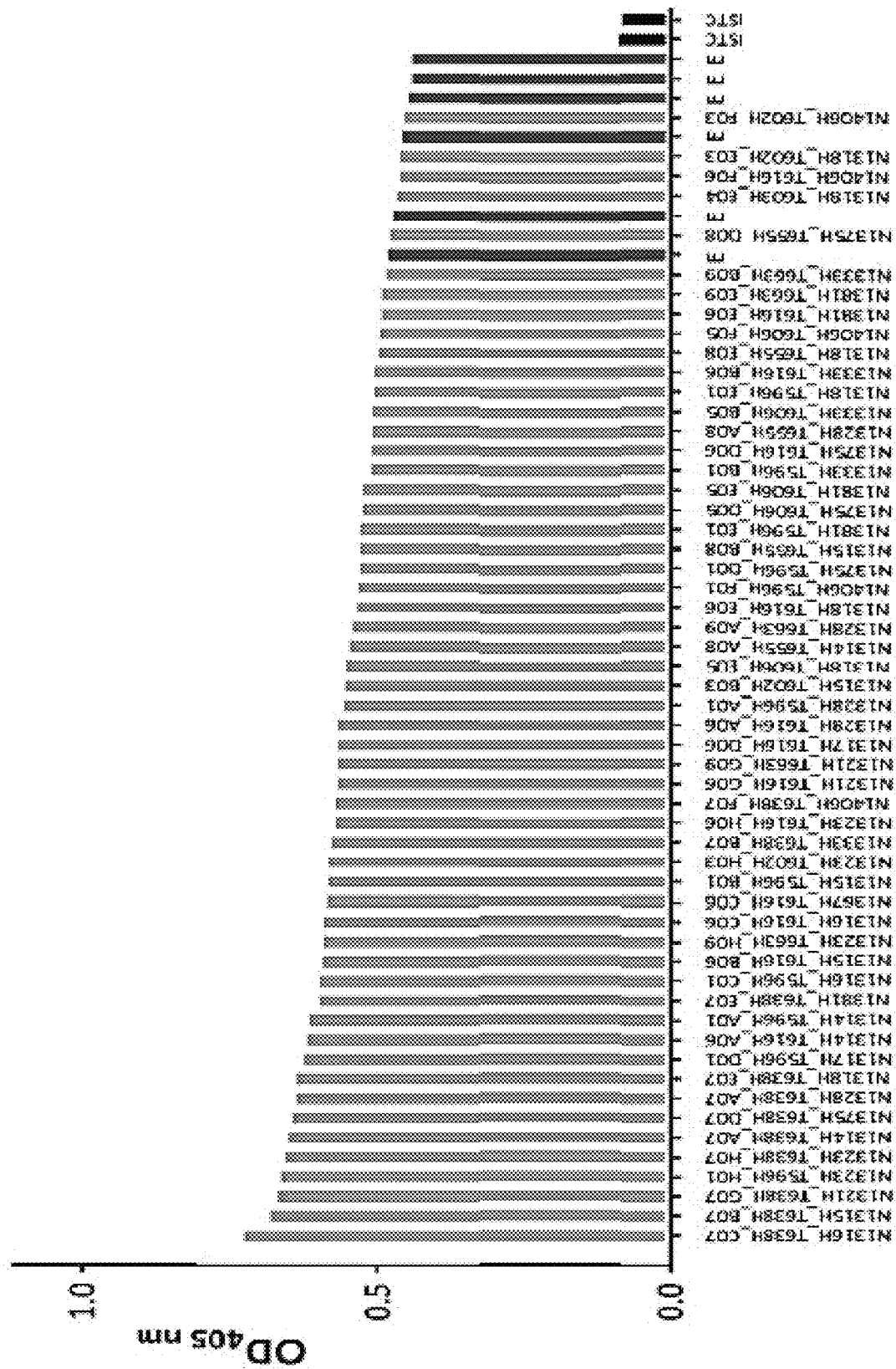
FIG. 16 shows results of bispecific antibodies in Xase assay. "E" is Antibody E positive control. FXase activities are plotted as OD405 nm at 10 minutes for samples normalised to 12.5 µg/mL (10.4 nM) final concentration. Bispecific antibodies are ranked in order of activity.
Figure 17:
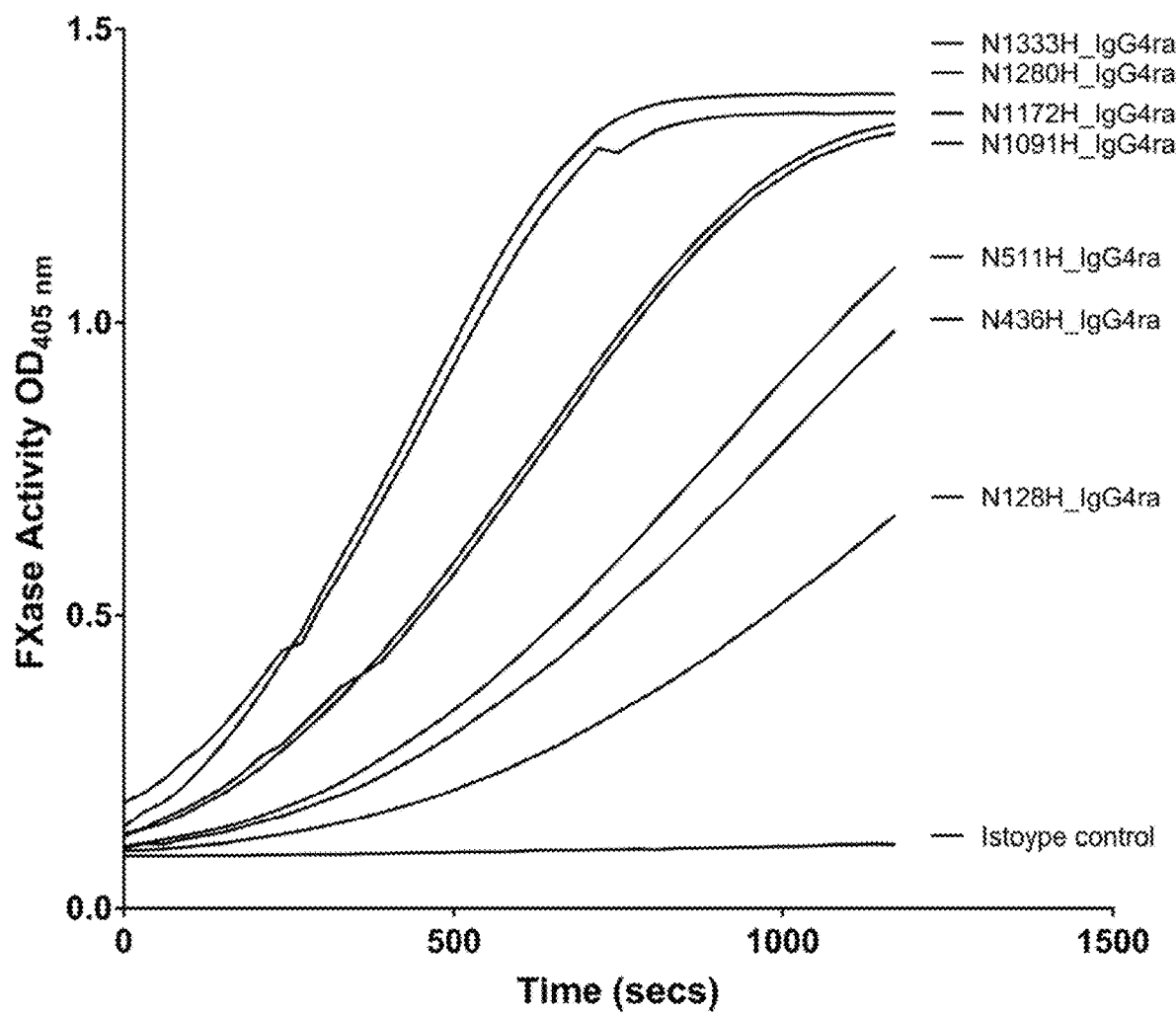
FIG. 17 shows the effect of bispecific antibody optimisation on FVIII mimetic activity (FXase). Results are shown for of bispecific antibodies, each having the named VH domain in the anti-FIXa arm and T0638H VH domain in the anti-FX arm, both paired with the 0128L common light chain VL domain. FVIII mimetic activity (FXase) was measured using an in vitro chromogenic Factor X activation assay at 405 nm (Y-axis) as a function of time in seconds (X-axis). Optimised bispecific antibodies are individually labelled. A human IgG4 isotype control demonstrates no FVIII mimetic activity. The key shows the name of the VH domain in the antibody to the right of its corresponding graph in order of maximal FXase activity, i.e., N1333H>N1280H>N1172H>N1091H>N0511H>N0436H>N0128H> control.

We identified several anti-FX-heavy chains that showed increased FXase activity compared with the T0200H VH domain when assayed as bispecific antibodies. FIG. 10 shows example data from the Xase assay.

A selection of the most active FX arm sequences is shown in FIG. 11. These VH domains were designated T0201H to T0217H respectively. Those with the strongest activity in bispecific format were T0204, T0207, T0205 and T0201 (FIG. 10*b*).

Using amino acid sequence comparisons, and supported by the functional data, we identified several amino acid residues in frameworks and CDR regions of the anti-FX heavy chains that differ in the most active VH domains and may contribute to the enhanced biological activity compared with T0200H. For example, one or more of the following amino acid features of the VH domain may increase the FVIII-mimetic activity of bispecific antibodies containing the VH domain (IMGT residue numbering):

Replacement of valine (V) by isoleucine (I) at position 5 in FR1;
Replacement of lysine (K) by glutamine (Q) at position 13 in FR1;
Replacement of leucine (L) by methionine (M) at position 39 in FR2;
Replacement of threonine (T) by serine (S) at position 62 in CDR2;
Replacement of aspartate (D) by serine (S) at position 64 in CDR2;
Replacement of threonine (T) by serine (S) at position 85 in FR3;
Replacement of alanine (A) by serine (S) at position 112 in the CDR3.

Nevertheless it is clear that activity is high even without these amino acid substitutions, since T0200H itself shows strong activity in a bispecific antibody, and none of these substitutions was consistently present in all of the top VH domains (FIG. 11).

Targeted Mutagenesis for Functional Optimisation

Figure 12:
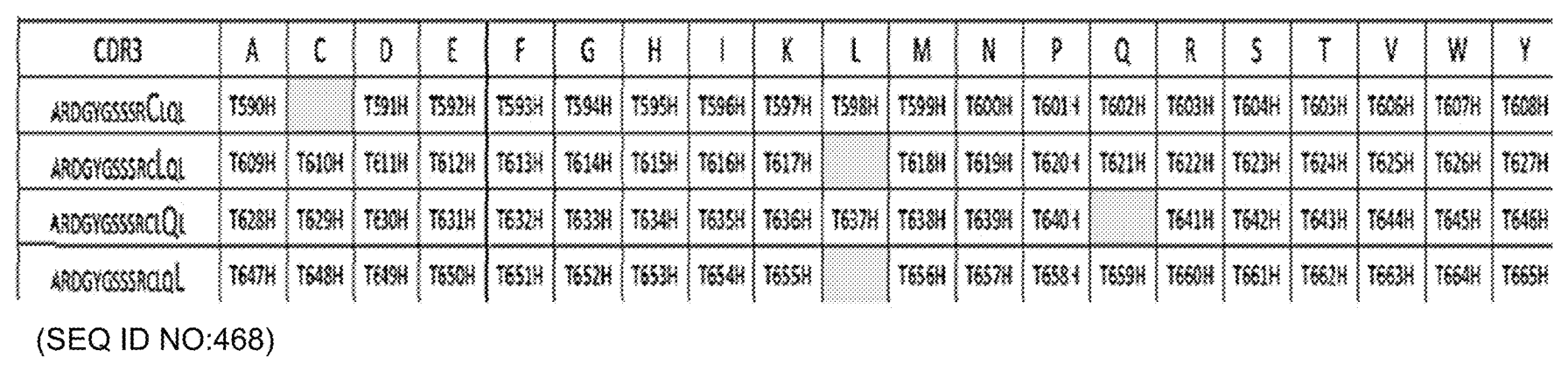

The CDR3 of VH domain T0201H was systematically mutated to provide a library of VH domains in which the residue at each position was individually replaced by another amino acid. The resulting VH domains were named T0XXXH, where XXX numbers are shown in FIG. 12 for the mutants of IMGT positions 114 (Cys), 115 (Leu), 116 (Gln) and 117 (Leu). Refer to FIG. 13 for IMGT numbering.

Removal of Potential Developmental Liability

An unpaired cysteine (C) residue present in CDR3 was identified as a high-risk sequence motif. This unpaired cysteine, present at position 114 in the CDR3 of T0200H and all 113 further anti-FX VH domains identified from the bulk NGS analysis, represents a liability for the development of the bispecific antibody. We screened VH domains containing substitutions of all other amino acids for the cysteine at this position in T0201H. These new variants were expressed with N1280H (see Example 6) and 0128L common light chain as IgG4 bispecific antibodies, purified by Protein A and screened for FVIII mimetic activity by FXase assay. Replacement of cysteine at position 114 with isoleucine (I), glutamine (Q), arginine (R), valine (V) or tryptophan (W) resulted in bispecifics antibodies with FVIII mimetic activity similar to bispecific antibodies having the T0201H or T0202H VH domains. We conclude C114 can be replaced with a variety of other amino acids and still maintain FVIII mimetic activity.

Example 6. Systematic Sequence Optimisation of Anti-FIX VH

Each amino acid residue in CDR1, CDR2 and CDR3 was individually mutated to generate single position mutants of the anti-FIX N0128H heavy chain. The anti-FIX heavy chain variants thus generated were expressed in bispecific format, paired with anti-FX heavy chain T0201H and N0128L common VL domain in HEK293.

Protein A purified bispecific antibodies were assayed for biological activity by FXase (Example 7) and aPTT to look for amino acid changes that improved the FVIII-mimetic activity of the bispecific antibody. Improved variants were then combined to generate double or triple mutants in the CDR1, CDR2 and CDR3 regions.

Table N identifies mutants of the N0128H VH domain in which one or more residues of the CDRs are mutated to other amino acids. For example the N0436H VH domain is a Ser→Ile mutant of the N0128H VH domain, i.e., in which the serine at IMGT position 111A in CDR3 is replaced by isoleucine. Further residue mutations were introduced on top of initial single mutations. For example the N0511H VH domain is a Ser112ALys mutant of the N0436H VH domain, i.e., in which the serine at IMGT position 112A in CDR3 is replaced by lysine. N1172H is a Glu64Arg mutant of the N0511H VH domain, i.e., in which the glutamate at IMGT position 64 in CDR2 is replaced by arginine. N1280H is a Thr29Arg mutant of the N1172H VH domain, i.e., in which the Thr at IMGT position 29 in CDR1 is replaced by arginine. The other named VH domains can be identified from Table N in the same manner.

Refer to FIG. 14 for IMGT numbering.

Example 7. Screening of Improved Bispecific Antibodies in FXase Assay

Anti-FX arms comprising the VH domain variants generated as described in Example 5 were combined with anti-FIX arms comprising the VH domain variants generated as described in Example 6, each paired with the 0128L common VL domain, to generate FIXAxFX bispecific antibodies, and screened for functional activity in the tenase assay.

Results

Example data are shown:

FIG. 10.

FIG. 15.

FIG. 16.

Highly active bispecific antibodies were identified for several combinations of anti-FIX VH and anti-FX VH domains, each paired with the 0128L common VL domain. Examples of anti-FIX VH and anti-FX VH domain combinations are shown in FIG. 16.

The identity of the anti-FX VH domain appeared to have a stronger influence than the identity of the anti-FIX VH domain for these bispecific arm combinations, with T0638H, T0616H, T0596H and T0663H being among the highest-performing anti-FX VH domains. These anti-FX domains performed well in combination with a variety of anti-FIX arms, including variants of N1280H such as those indicated in FIG. 16. Anti-FIX VH domain sequences are identified by reference to appended Table N. Anti-FX VH domain sequences are identified by reference to FIG. 12.

FVIII-mimetic activity of N128 bispecific antibody was sequentially optimised by modifying amino acid residues in any of the three CDRs. Several amino acid residues were identified to increase FVIII mimetic activity across the CDRs and these mutations were combined to maximise activity. The FVIII mimetic activity of antibodies with the N0128H VH domain was progressively improved with further VH domains in the following order: N0128H→N0436H→N0511H→N1091H→N01172H→N1280H→N1333H. FIG. 17.

Materials & Methods—Modified FXase Reaction Conditions.

Initial screening for bispecific antibody FVIII mimetic activity was assessed using the Standard FXase Reaction Conditions set out above in Example 3. As the FVIII mimetic activity of the bispecific antibody increased, the Standard FXase reaction conditions were no longer sufficient to detect improvements in FXase activity. Therefore, more sensitive Modified FXase Reaction Conditions were established.

This modified assay differs from the Standard FXase Reaction Conditions in the following ways: FXIa is not used, the activated form of Factor IX (FIXa) is used and there is no incubation step. All FXase reagents are mixed with a bispecific antibody and the generation of FXa is detected by recording the absorbance of the reaction solution 40 to 50 times every 30 seconds at 405 nm using an Envision plate reader set to 37° C.

18.45 µl TBSB-S buffer was mixed with 0.05 µl phospholipid (10 mg/ml) and mixed vigorously by pipetting to disperse the phospholipid. To this mixture 1.5 µl FIXa (1 µg/ml) and 5 µl of FX (50 µg/ml), was combined with 5 µl of polybrene (0.6 mg/L) and 5 µl S2765 (4 mM), all pre-warmed to 37° C. Finally, 5 ul of bispecific antibody being investigated for FXase activity was added. Absorbance at 405 nm (reference wavelength 655 nm) was recorded 40 to 50 times every 30 seconds.

Example 8. Screening of Improved Bispecific Antibodies in Plasma Coagulation Assay Anti-FX arms comprising the VH domain variants generated as described in Example 5 were combined with anti-FIX arms comprising the VH domain variants generated as described in Example 6, each paired with the 0128L common VL domain, to generate FIXaxFX bispecific antibodies. To determine the ability of the bispecific antibodies of the present invention to correct the coagulation ability of the blood of haemophilia A patients, the effect of these antibodies on the activated partial thromboplastin time (aPTT) using FVIII deficient plasma was examined.

A mixture of 5 µL of bispecific antibody solution having a variety of concentrations, 20 µL of FVIII deficient plasma (Helena Biosciences), and 25 µL of aPTT reagent (APTT Si L Minus, Helena Biosciences) was warmed at 37° C. for 3 minutes. The coagulation reaction was initiated by adding 25 µL of 25 mM $CaCl_2$ (Helena Biosciences) to the mixture. The time period until coagulation was measured. Apparatus used for this was C-4 4 channel coagulation analyser (Helena Biosciences).

Figure 18:
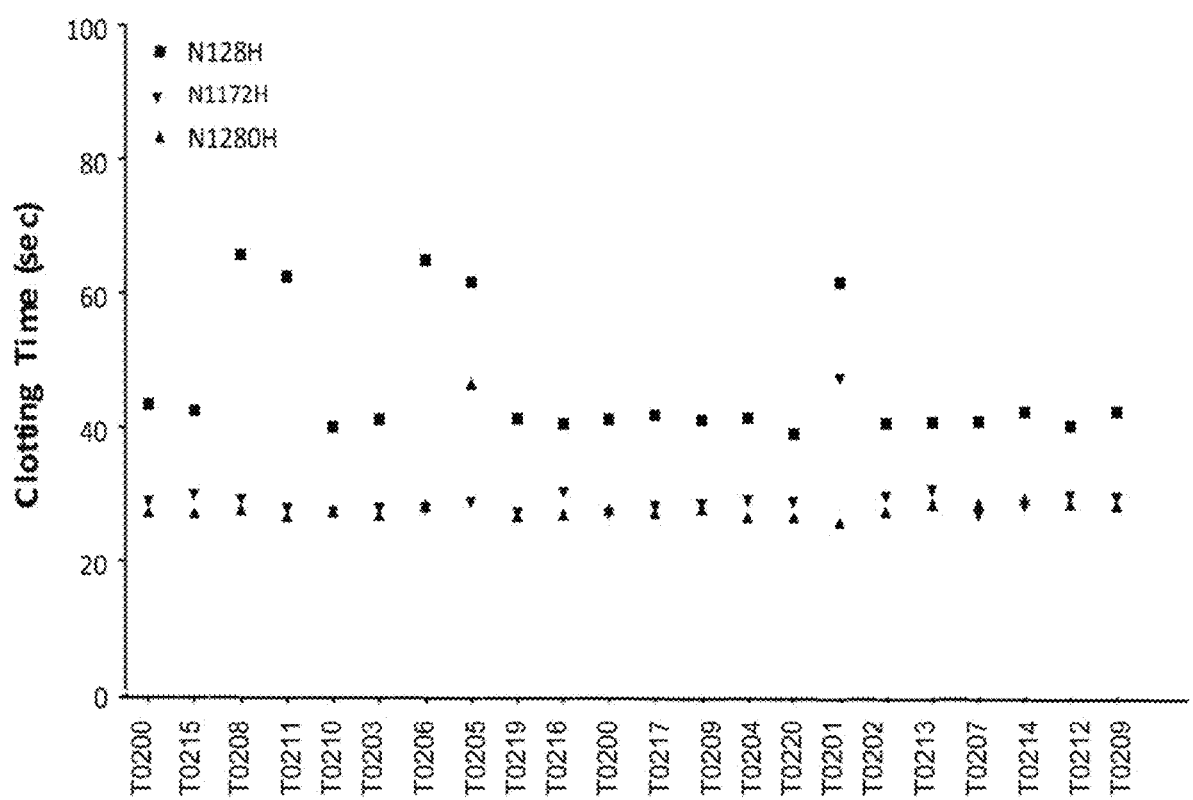
FIG. 18 shows aPTT assay results for IgG4 bispecific antibodies comprising named anti-FX VH domain combined with the N0128H, N1172H or N1280H anti-FIX VH domain and 0128L common light chain.

A sample of results is shown in FIG. 18.

Concentration dependency was subsequently determined for bispecific antibodies that exhibited the highest coagulation time-reducing effect.

Figure 19:
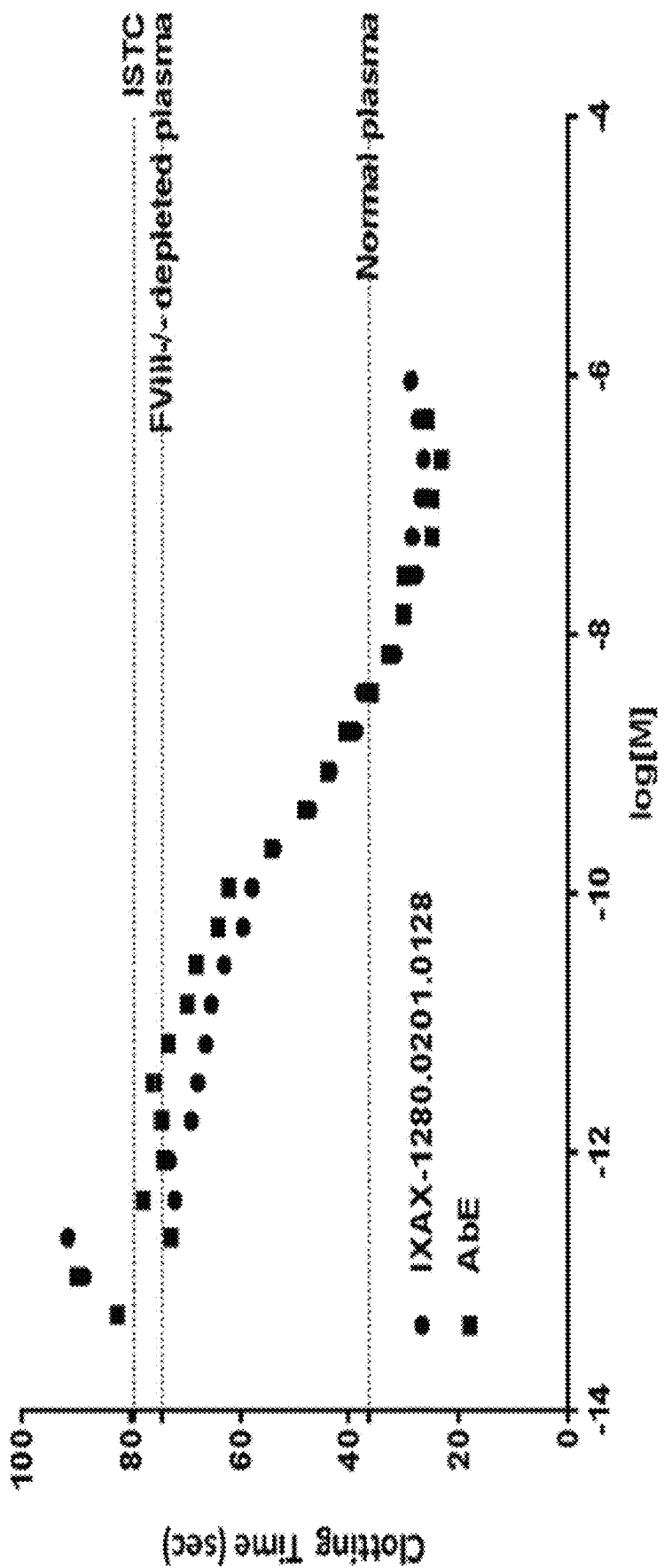
FIG. 19 shows a dose response for IXAX-1280.0201.0128 bispecific antibody (purified on Protein A) in a one-stage activated aPTT clotting assay using FVIII-depleted human plasma.

For example, IXAX-1280.0201.0128 IgG4 antibody demonstrated a dose dependent decrease in aPTT, comparable to the reference antibody AbE (positive control). FIG. 19. No reduction in aPTT was observed for an isotype control antibody. Note that the antibody preparation used for this assay was the result of a one-step purification on Protein A and as such contained residual anti-FIX monospecific antibodies and residual anti-FX monospecific antibodies in addition to the desired bispecific fraction.

Example 9. Analysis of Anti-FIX VH Domains in Bispecific Antibodies

Considering data from a variety of functional assays including those described in Example 7 and Example 8, it was noted that the anti-FX VH domain T0201 and its sequence variants performed well in combination with a variety of anti-FIX VH domains in bispecific antibodies with the common light chain. For example, anti-FIX VH domains N0128H, N0436H, N0511H, N1091H, N1172H, N1280H, N1314H, N1327H and N1333H all gave good functional activity in the bispecific antibodies. These anti-FIX VH domains share a close structural relationship. FIG. 20. Their performance could be further enhanced by fine tuning of residues through substitution (Table N) and combining substitutions associated with improved activity.

Example 10. Affinity for Antigen-Binding

Binding affinity and the kinetics of antibody-antigen interaction were determined using SPR. Affinity and kinetics of purified test antibodies (all IgG4PE) were compared to comparator anti-FIX antibody AbN or comparator anti-FX antibody AbT as positive control and to an isotype control (ISTC) as negative control.

Binding Affinity for FIX

The anti-FIX antibodies analysed showed binding to FIX in the affinity range of approximately 0.18 µM to 0.3 µM and fast association ($k_{on}$) and dissociation ($k_{off}$) rates for FIX. The anti-FIX antibodies analysed showed slightly higher binding affinity to FIX and higher association rate compared to the comparator antibody AbN. No binding to FIX was observed with ISTC. Table E-10-1.

TABLE E-10-1

Binding affinity and kinetic constants on-rate (kon) and off-rate (koff) of anti-FIX antibodies. Anti-FIXa monospecific antibody nomenclature: NINA-hhhh.llll, wherein hhhh is the numeric identifier of the VH domain (e.g., N0436H) and llll is the numeric identifier of the VL domain (e.g., 0128L).

| Captured anti-FIX antibody | $k_{on}$ (1/Ms) | $k_{off}$ (1/s) | $K_D$ (M) |
|---|---|---|---|
| NINA-0128 (n = 2 average) | $2.92 \times 10^5$ | $5.76 \times 10^{-2}$ | $1.98 \times 10^{-7}$ |
| NINA-0436.0128 | $2.46 \times 10^5$ | $4.53 \times 10^{-2}$ | $1.84 \times 10^{-7}$ |
| NINA-0438.0128 | $2.30 \times 10^5$ | $6.73 \times 10^{-2}$ | $2.93 \times 10^{-7}$ |
| NINA-0440.0128 | $1.85 \times 10^5$ | $5.35 \times 10^{-2}$ | $2.89 \times 10^{-7}$ |
| NINA-0442.0128 | $1.94 \times 10^5$ | $4.71 \times 10^{-2}$ | $2.42 \times 10^{-7}$ |
| NINA-0444.0128 | $2.16 \times 10^5$ | $4.45 \times 10^{-2}$ | $2.06 \times 10^{-7}$ |
| NINA-0445.0128 | $2.04 \times 10^5$ | $5.44 \times 10^{-2}$ | $2.67 \times 10^{-7}$ |
| NINA-0456.0128 | $1.51 \times 10^5$ | $3.96 \times 10^{-2}$ | $2.63 \times 10^{-7}$ |
| NINA-0460.0128 | $1.75 \times 10^5$ | $3.18 \times 10^{-2}$ | $1.81 \times 10^{-7}$ |
| AbN | $3.06 \times 10^4$ | $4.26 \times 10^{-2}$ | $1.39 \times 10^{-6}$ |
| ISTC | No binding | No binding | No binding |

Binding Affinity for FX

The anti-FX antibodies analysed showed binding to FX in the affinity range of approximately 0.1 µM to 1.4 µM and fast association ($k_{on}$) and dissociation ($k_{off}$) rate for FX. No binding to FX was observed with ISTC.

The anti-FX antibodies analysed similar binding affinity to FX compared to the benchmark antibody AbT.

TABLE E-10-2

Binding affinity and kinetic constants on-rate (kon) and off-rate (koff) of anti-FX antibodies. Anti-FX monospecific antibody nomenclature: TINA-hhhh.llll, wherein hhhh is the numeric identifier of the VH domain (e.g., N0201H) and llll is the numeric identifier of the VL domain (e.g., 0128L).

| Captured anti-FX antibody (IgG4PE) | $k_{on}$ (1/Ms) | $k_{off}$ (1/s) | $K_D$ (M) |
|---|---|---|---|
| TINA-0200.0128 (n = 2 average) | $1.03 \times 10^5$ | $1.15 \times 10^{-1}$ | $1.13 \times 10^{-6}$ |
| TINA-0215.0128 | $6.84 \times 10^4$ | $7.87 \times 10^{-2}$ | $1.15 \times 10^{-6}$ |
| TINA-0211.0128 | $6.57 \times 10^4$ | $4.47 \times 10^{-2}$ | $6.80 \times 10^{-7}$ |
| TINA-0210.0128 | $7.64 \times 10^4$ | $7.44 \times 10^{-2}$ | $9.74 \times 10^{-7}$ |
| TINA-0203.0128 | $6.80 \times 10^4$ | $5.98 \times 10^{-2}$ | $8.80 \times 10^{-7}$ |
| TINA-0206.0128 | $6.72 \times 10^4$ | $6.67 \times 10^{-2}$ | $9.92 \times 10^{-7}$ |
| TINA-0205.0128 | $6.26 \times 10^4$ | $8.53 \times 10^{-2}$ | $1.36 \times 10^{-6}$ |
| TINA-0219.0128 | $1.01 \times 10^5$ | $9.11 \times 10^{-2}$ | $9.05 \times 10^{-7}$ |
| TINA-0217.0128 | $1.02 \times 10^5$ | $5.74 \times 10^{-2}$ | $5.64 \times 10^{-7}$ |
| TINA-0209.0128 | $5.90 \times 10^4$ | $6.79 \times 10^{-2}$ | $1.15 \times 10^{-6}$ |
| TINA-0204.0128 | $1.09 \times 10^5$ | $7.85 \times 10^{-2}$ | $7.18 \times 10^{-7}$ |
| TINA-0220.0128 | $5.38 \times 10^4$ | $5.60 \times 10^{-2}$ | $1.04 \times 10^{-6}$ |
| TINA-0201.0128 | $8.67 \times 10^4$ | $5.02 \times 10^{-2}$ | $5.79 \times 10^{-7}$ |
| TINA-0202.0128 | $8.87 \times 10^4$ | $7.20 \times 10^{-2}$ | $8.12 \times 10^{-7}$ |
| TINA-0213.0128 | $9.69 \times 10^4$ | $1.33 \times 10^{-1}$ | $1.37 \times 10^{-6}$ |
| TINA-0207.0128 | $1.66 \times 10^5$ | $1.41 \times 10^{-1}$ | $8.47 \times 10^{-7}$ |
| TINA-0214.0128 | $1.20 \times 10^5$ | $5.58 \times 10^{-2}$ | $4.66 \times 10^{-7}$ |
| AbN | No binding | No binding | No binding |
| AbT | $4.13 \times 10^4$ | $2.72 \times 10^{-2}$ | $6.60 \times 10^{-7}$ |
| hIgG4PE ISTC | No binding | No binding | No binding |

Materials & Methods

SPR was used to determine the binding affinity ($K_D$) to FIX or FX respectively, the kinetic constants on-rate ($k_{on}$) and off-rate ($k_{off}$). Analyses was performed using a Biacore 8K (GE Healthcare) system.

Anti-human IgG Fc antibody was immobilised on CM4 chip (GE Healthcare) according to the manufacturer's instructions. The chip surface was activated by amine coupling and subsequently blocked with 1M ethanolamine. The immobilisation run was performed at 25° C. using HBS-EP as immobilisation running buffer.

Monospecific antibodies (referred as ligand) which had been purified on Protein A were captured onto the anti-human IgG Fc CM4 surface at approximately 2 µg/ml. The ligands were injected for 60 seconds at 10 µl/min in all the active channels of all 8 flow channels. The run was performed at 25° C. using neutral pH HBS-P 1×+CaCl$_2$ 2.5 mM as running buffer.

Human FIX (MW ~55 KDa) or human FX (MW ~58 KDa) was reconstituted at 1 mg/ml in the running buffer and used as analyte. The analyte was injected in multiple cycle kinetics (MCK) mode at 3 concentrations (1.5 μM, 500 nM and 166.7 nM) with 120 seconds association phase and 200 seconds (for FIX) or 300 seconds (for FX) dissociation phase, at flow rate 30 μl/sec in both active and reference channels. Three injections of 10 mM Glycine pH 1.5 for 60 sec. at 10 μl/min were used for the regeneration phase.

For the anti-FIX analysis, ISTC antibody hIgG4PE was captured at 1 μg/ml for 60 seconds at 10 μl/min in the reference channel. hIgG4PE ISTC and hIgG1 ISTC were also captured in the active channel as a negative control. The monospecific antibody AbN was used as positive control.

For the anti-FX analysis, the hIgG4PE ISTC was also captured in the active channel as a negative control. The monospecific antibody AbT was used as positive control.

The values for association rate constant (kon), dissociation rate constant (koff) and dissociation constant (KD) were calculated from the binding data by BIAevaluation software. Data were reference and buffer subtracted and fitted into one step biomolecular reaction (Langmuir 1:1) model. The first 30 seconds of dissociation were evaluated in the model.

Example 11. Simultaneous Binding of Bispecific Antibody to FX and FIX

Figure 21:
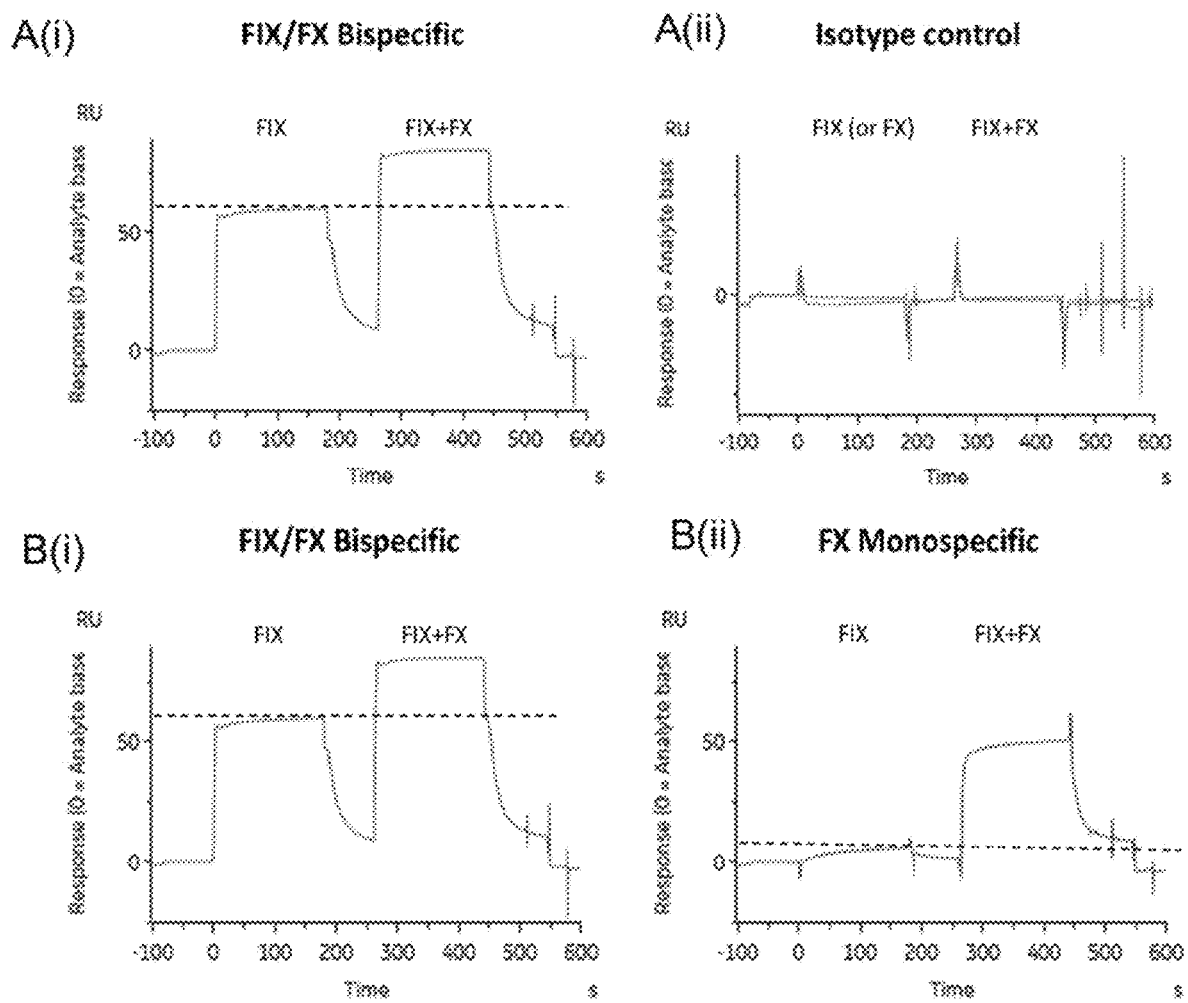
FIG. 21 is an SPR sensorgram of bispecific antibody binding to antigen, where simultaneous binding to FIX and FX is demonstrated, compared with sensorgram of (A) isotype control antibody or (B) monospecific antibody.

The ability of FIX×FX bispecific antibody IXAX-0436.0202.0128 to bind simultaneously to FIX and FX was demonstrated using SPR. The binding kinetics of the purified bispecific antibody was compared to an isotype control (ISTC). Sensorgrams of the binding indicated that the bispecific antibody bound simultaneously to FIX and FX while no binding to FIX and FX was observed with ISTC. FIG. 21A.

FIX was flown over the surface captured with the bispecific antibody to allow the binding with the first analyte. The interaction between the bispecific antibody generated a baseline response as indicated in the sensogram FIG. 21. The following injection of the second analyte, FX, generated a further increase in signal indicating that FX binds the bispecific antibody already in complex with FIX.

Contrarily no binding to FIX or FX was observed when FIX and FX were flown over the surface where an isotype control was captured, demonstrating the specificity of interaction between FI and FX to the bispecific antibody. FIG. 21A.

Sensorgram for the bispecific antibody can also be compared with sensorgram for monospecific antibody. When the antibody captured is an anti-FX monospecific the same series of injection does not give any significant response when FIX is flown over instead when the second injection is performed (1:1 mixture) approximately 50 response units (RU) are observed while with the bispecific the response is 25 RU higher. FIG. 21B.

A key feature of the FVII-mimetic bispecific antibody is the ability to bind simultaneously FIX and FX, to promote the conversion of FX into FXa by FIXa. The binding observed represents a biophysical confirmation that the bispecific antibodies described herein can interact simultaneously with Factor IX and Factor IX, which is in agreement with the functional data described in the accompanying Examples.

Materials & Methods

SPR analysis was performed using a Biacore 8K (GE Healthcare) system.

An anti-human IgG Fc antibody was immobilised on CM4 chip (GE Healthcare) according to the manufacturer's instructions. The chip surface was activated by amine coupling and subsequently blocked with 1M ethanolamine. The immobilisation run was performed at 25° C. using HBS-EP as immobilisation running buffer.

Bispecific antibody (ligand), which had been purified by Protein A capture followed by ion exchange chromatography, was captured on to the anti-human IgG Fc CM4 surface at approximately 2 μg/ml. The ligand was injected at 10 μg/ml for 60 seconds at 10 μl/min in one active channel. The run was performed at 25° C. using neutral pH HBS-P 1×+CaCl$_2$ 2.5 mM as running buffer.

Human FIX and human FX (analytes) were reconstituted at 1.15 mg/ml in the running buffer and used as analytes. Analytes were injected at 10 μM alone or mixed 1:1 (10 μM 10 μM) at 10 μl/min for 180 seconds.

An isotype control hIgG4PE antibody was captured at 10 μg/ml for 60 seconds at 10 μl/min in the reference channel as negative control. A blank injection of buffer was performed for all the samples to be used in the double referencing process. Three injections of 10 mM glycine pH 1.5 for 30 seconds at 30 μl/min were used for the regeneration phase. The data were referenced and buffer subtracted and fitted into Langmuir 1:1 model.

Example 12. Further Optimisation of Anti-FX VH

The anti-FIX binding arm of the bispecific antibody was "fixed" as a VH domain comprising the CDRs of N1280H and a VL domain comprising the CDRs of 0128L, while further refinements were made to the anti-FX VH domain to improve performance. 0128L was used as a common light chain.

Table T identifies mutants of the T0201H VH domain in which one or more residues of the CDRs are mutated to other amino acids. The table shows the name given to each variant VH domain having the identified mutation. In each case, residues other than those indicated are left unchanged. For example, the T0616H VH domain is a Leu115Ile mutant of the T0201H VH domain, i.e., in which the leucine (L) at IMGT position 115 in CDR3 is replaced by isoleucine (I). Further residue changes were introduced to the variants containing the single mutations in the T0201H VH domain, resulting in further variants representing combinations of different mutations in the T0201H VH domain. For example, the T0687H VH domain is a Ser111APhe, Cys114Val, Leu115Ile mutant of the T0201H VH domain, i.e., in which the serine at IMGT position 111A in CDR3 is replaced by phenylalanine (T0537H mutation), the cysteine at IMGT position 114 in CDR3 is replaced by valine (T0606H mutation), and the leucine at IMGT position 115 is replaced by isoleucine (T0616H mutation). Sequences of other named anti-FX VH domains can be identified from Table T in the same manner. Refer to FIG. 13 for IMGT numbering.

Bispecific antibodies, purified by Protein A chromatography, were tested for functional activity to look for improvement over the parent bispecific comprising T0201H VH domain.

Improved antibodies were identified in the FXase assay (using Modified FXase Reaction Conditions as detailed in Example 7) and aPTT assay (method as detailed in Example 8).

Mutagenesis of HCDR3 produced improvements in FVIII mimetic activity. HCDRs of VH domains demonstrating improved activity are indicated in FIG. 25. For example, each of the following substitutions and combinations of substitutions in the T0201H VH domain CDR3 was found to improve FVIII mimetic activity (name of resulting VH domain indicated in brackets) (non-exhaustive list):
  Gln116Met in CDR3 (T0638H VH);
  Leu115Ile in CDR3 (T0616H VH);
  Ser111APhe in CDR3 (T0537H VH);
  Cys114Ile Leu115Ile (T0666H VH);
  Ser111APhe Cys114Ile Leu115Ile (T0678H VH);
  Ser111APhe Cys114Leu Leu115Ile (T0681H VH);
  Ser111APhe Cys114Val Leu115Ile (T0687H).

Concluding the HCDR3 mutagenesis of T0201H, the VH domains T0687H, T0678H and T0681H demonstrated the strongest activity in the bispecific antibodies.

Functional activity of the bispecific antibodies was still further improved through mutagenesis of HCDR1 and HCDR2 in the anti-FX arm. Starting with T0681H, each amino acid residue of CDR1 and CDR2 was systematically replaced by all other possible amino acids, generating the VH domains numbered T0690H to T0993H identified in Table T.

aPTT and TGA analyses were also conducted to support functional assessment of HCDR1 variants. The VH domains T0736 (S29K mutation), T0713, T0734, T0742, T0774 and T0785 showed improved activity compared with T0681H. Based on the functional analyses of HCDR1 variants of T0681H, VH domain T0736H was selected as the top performer. As compared with T0201H, T0736H combines a Ser29Lys substitution in CDR1 with the Ser111APhe Cys114Val and Leu115Ile substitutions in CDR3.

FXase, aPTT and TGA analyses were also conducted to support functional assessment of HCDR2 variants. Based on the functional analyses of HCDR2 variants of T0681H, the following VH domains were identified to have improved activity compared with T0681H: T0926H (S62K), T850H (I56L), T0925H (S62L), T0951H (G63S), T0958H (S64D), T0989 (T65R) and T0990H (T65S).

Selected CDR1 and CDR2 variants were then combined with selected CDR3, generating further VH domain variants to investigate possible further improvements in activity.

Figure 22:
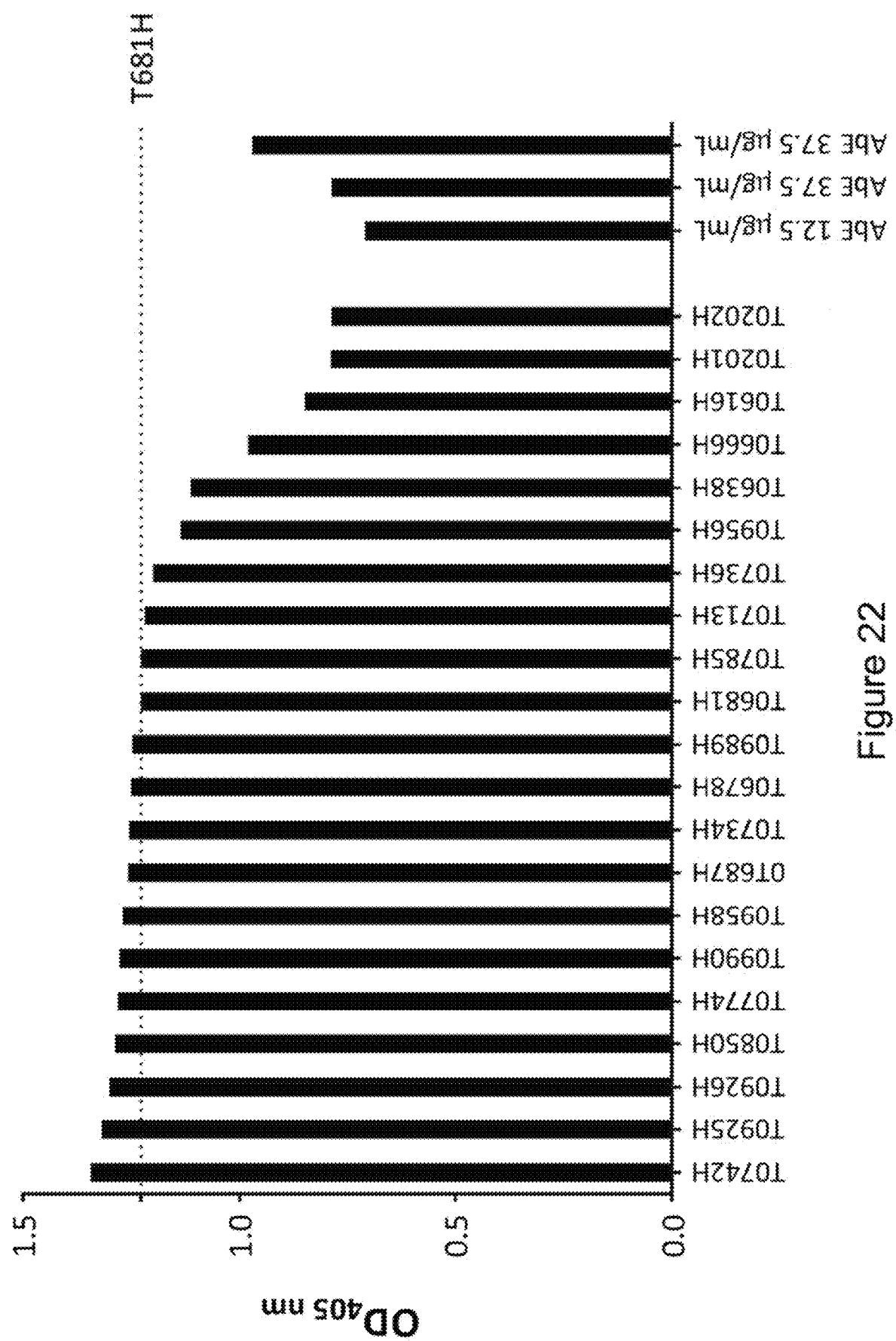
FIG. 22 presents summary results of FXase assays for selected CDR1 and CDR2 sequence variants of T0681H. Except where indicated for AbE controls, samples were purified by Protein A chromatography and their final concentrations normalised to 12.5 µg/mL (10.4 nM). 3 samples of AbE positive control antibody are included: (i) protein A purified; 12.5 µg/mL; (ii) protein A purified; 37.5 µg/mL; (iii) protein A purified followed by further purification by ion exchange chromatography; 37.5 µg/mL. All data shown were sampled at the 10 minute time-point.
Figure 23:
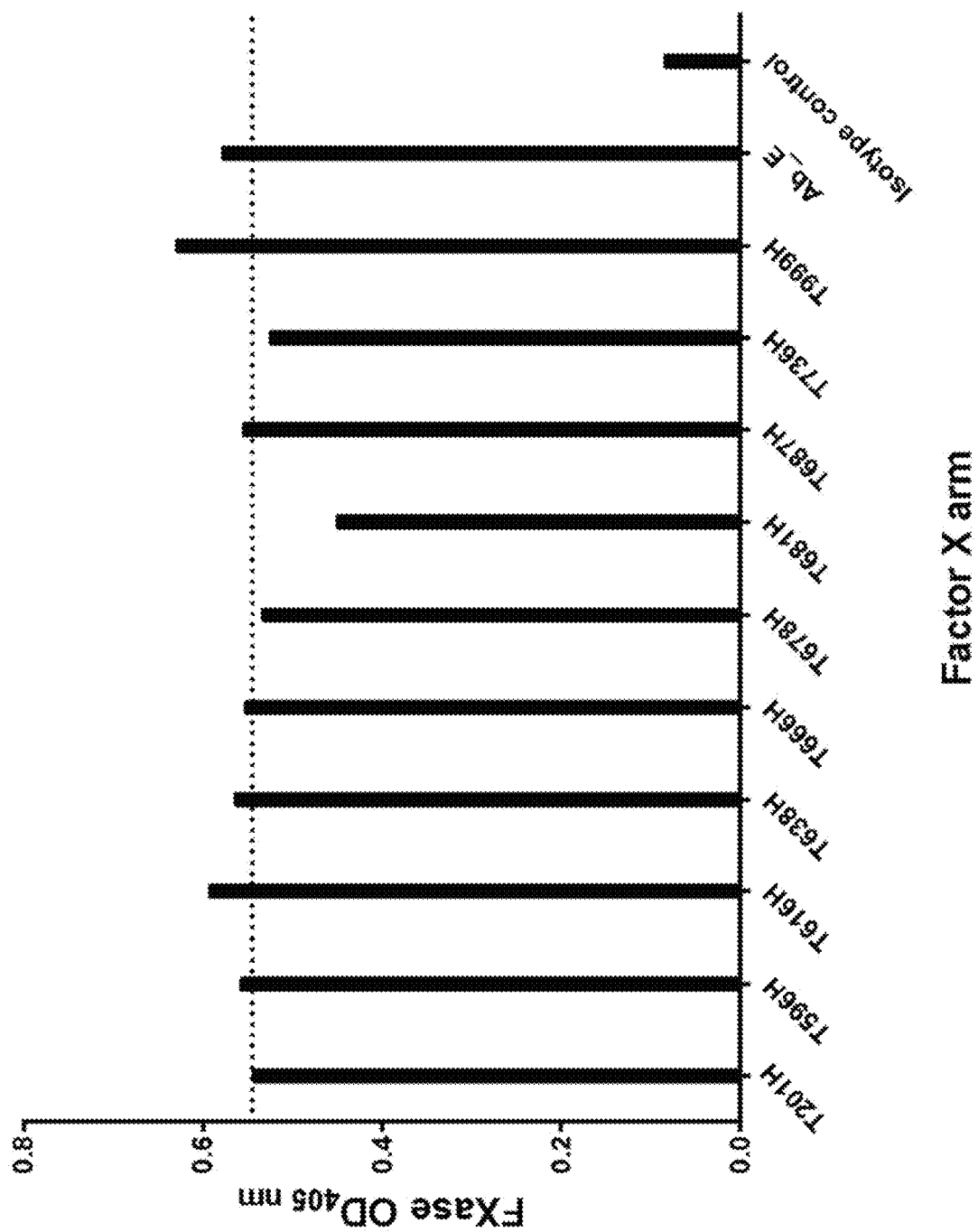
FIG. 23 summarises the effect of T0201H CDR1, CDR2 and CDR3 mutagenesis on bispecific antibody FXase activity in vitro. Bispecific antibody anti-FX T0201H variant VH domains were expressed with anti-FIX N01280H arm and N128_IgL common light chain in HEK cells, purified by Protein A chromatography and normalised by concentration to 0.15 mg/ml (125 nM final concentration). In vitro FXase assay was performed using 5 µl of purified material. Data shown are at 10 minute time point. Dotted line represents FXase activity of T0201H.
Figure 24:
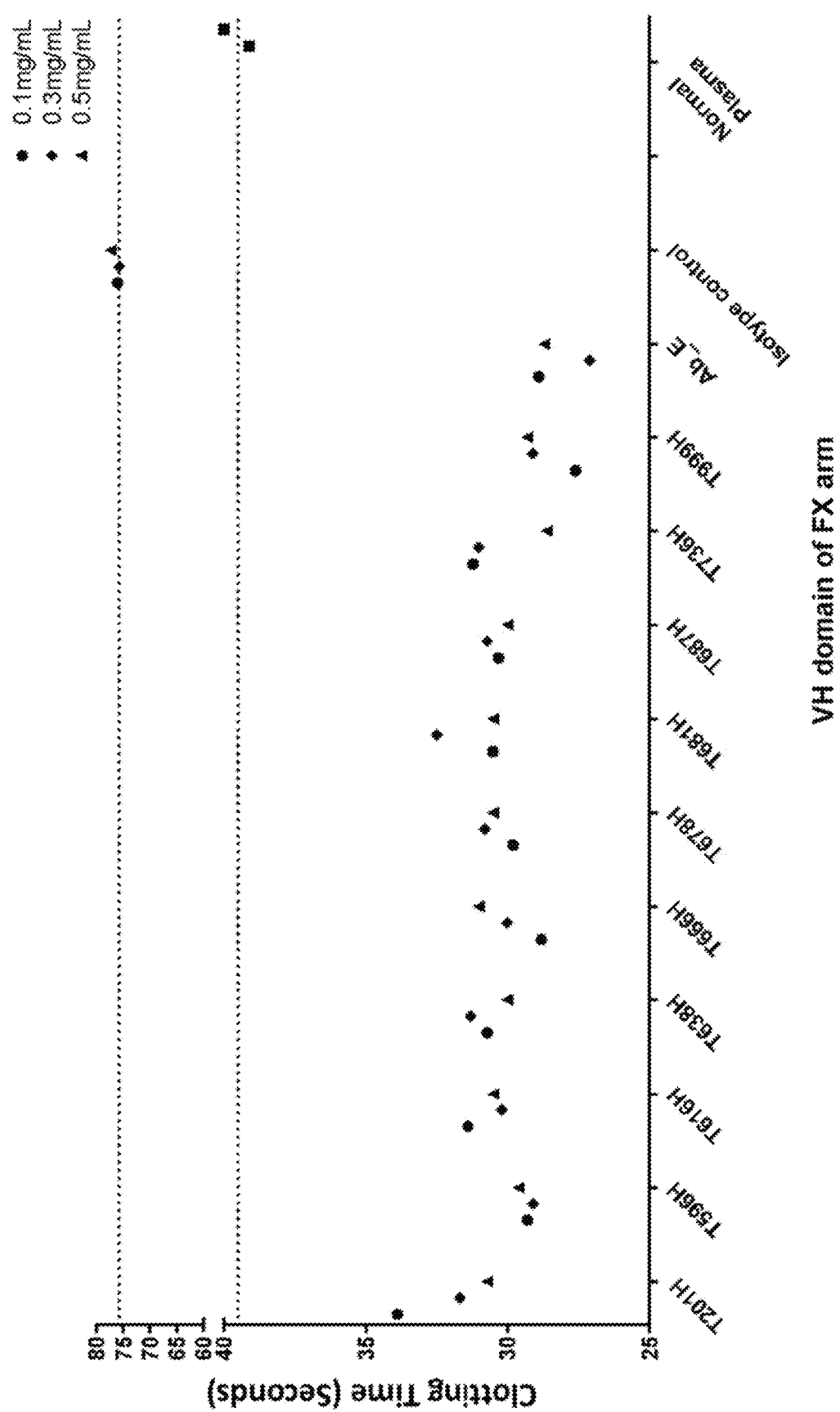
FIG. 24 presents summary results of aPTT clotting assays investigating the effect of sequence variation in the anti-FX T0201H VH domain on bispecific antibody activity. Clotting time (seconds) was recorded after spiking FVIII deficient plasma with bispecific antibodies comprising the named anti-FX VH arm, anti-FIX N01280H arm and N128_IgL common light chain. Bispecific antibodies were expressed in HEK cells, purified by Protein A chromatography and analysed at three different concentrations 0.1 mg/ml, 0.3 mg/ml and 0.5 mg/ml. Dotted lines indicate the clotting times of FVIII deficient plasma spiked with a human IgG4 isotype control or normal pooled human plasma spiked with PBS.

FXase assay data for high-performing antibodies are summarised in FIG. 22 and FIG. 23. The aPTT assay data are summarised in FIG. 24.

Bispecific antibodies comprising the VH domains shown in FIGS. 22 and 23 demonstrated improved or similar clotting times compared with bispecific antibodies comprising T0201H, with T0999H demonstrating the shortest clotting time in aPTT assay.

FXase activity and clotting times were comparable with the comparator bispecific antibody AbE.

FIG. 25 identifies CDRs of VH domains which were progressively improved for FVIII mimetic activity during the mutagenesis process.

Example 13. Strong Activity of Bispecific Antibodies in a Thrombin Generation Assay The thrombin generation assay (TGA) detects the activation of prothrombin to thrombin in blood plasma. As thrombin is generated it converts a fluorogenic substrate into a fluorophore, which is continuously monitored by a plate reader. The TGA provides a robust measure of the ability of bispecific antibodies to substitute for FVIII in the coagulation cascade in FVIII-deficient plasma, and kinetics of thrombin generation in the TGA are believed to be highly reliable as an indicator of in vivo therapeutic performance of FVIII-mimetic drugs.

Results

To establish a suitable concentration for factor IXa as a TGA trigger, we initially performed TGAs with a fixed concentration of bispecific antibody whilst varying the concentration of FIXa present in the trigger reagent. We determined that a stock solution of 1 ml MP reagent containing 222 nM FIXa is sufficient to trigger thrombin generation for normal pooled human plasma (final concentration, 0.33 nM FIXa) with a Cmax of 418.11 nM thrombin, a Tmax of 7.67 minutes and a lagtime of 5.83 minutes. FIG. 26. These values are comparable with the reference range in healthy adults (see, e.g., Table 3 of ref [11]) and validate the use of FIXa as a TGA trigger.

Figure 28:
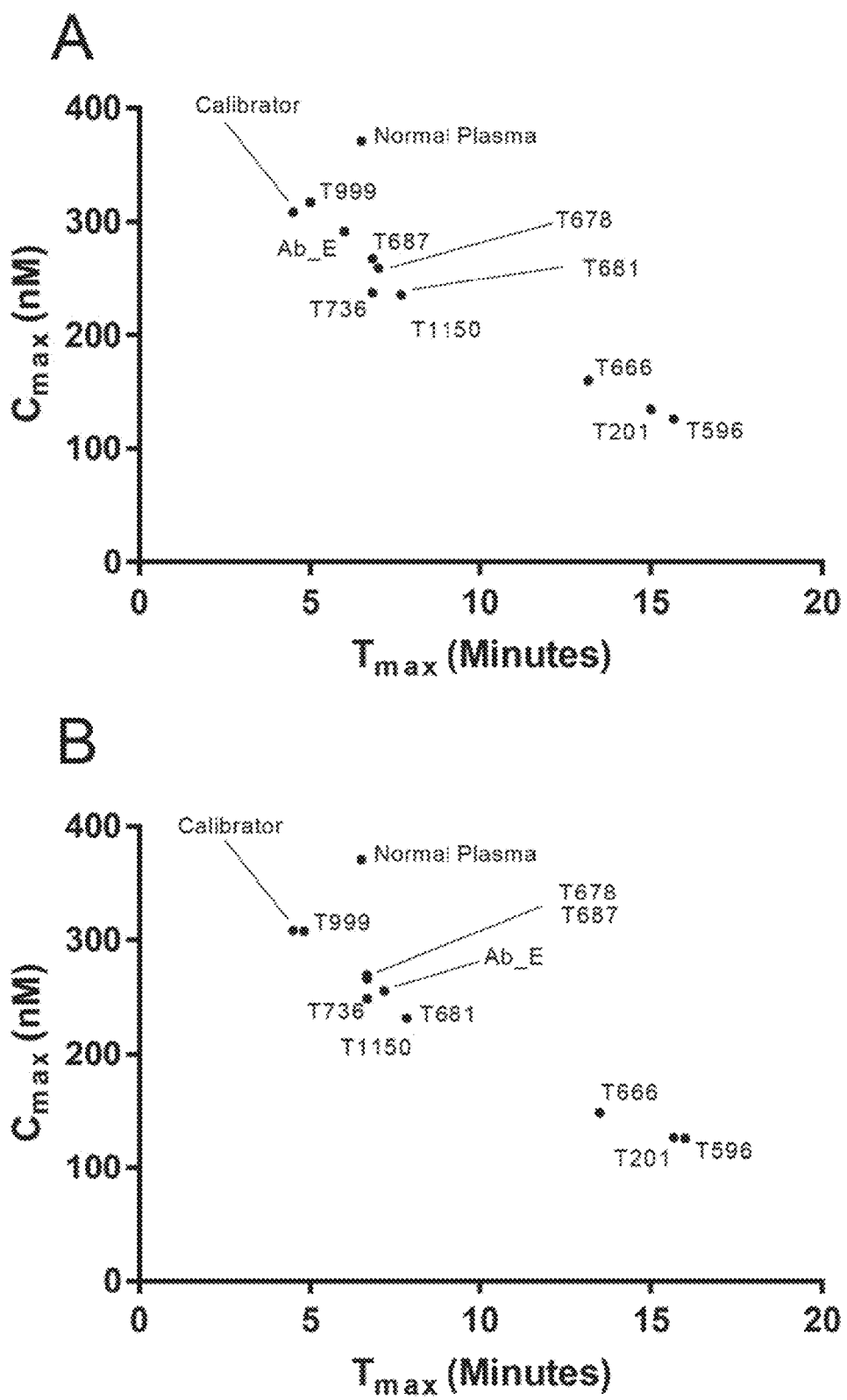

Bispecific antibody VH domain T0201H and CDR1, CDR2 and CDR3 combinatorial variants of T0201H were expressed with FIX N1280H arm and N0128 common light chain in HEK cells, purified by protein A chromatography and analysed at a final concentration of 133 nM and 80 nM. The VH domain variants exhibited shortening lagtime, increasing Cmax and shorter time to peak compared with T0201H, with T0999 demonstrating the largest thrombin peak height and shortest time to peak at both concentrations analysed. Performance of at least IXAX-1280.0999.0128 was comparable with that of AbE and of the emicizumab calibrator. AbE demonstrated a lagtime, peak height and time to peak of 2.5 mins, 291.8 nM and 6.0 minutes respectively, and IXAX-1280.0999.0128 demonstrated a lagtime, peak height and time to peak of 2.0 mins, 317.2 nM and 5 minutes. FIG. 27. FIG. 28. As illustrated in FIG. 27 and in order of increasing Tmax, we observed a Tmax of 5, 6.83, 6.83, 7, 7.67, 13.17, 15 and 15.67 minutes for bispecific antibodies comprising T0999, T0687, T0736, T0678, T0681, T0666, T0201 and T0596 respectively.

TABLE E13-1

Recorded parameters from TGA carried out on FVIII deficient plasma spiked with CDR1, CDR2 and CDR3 single and combinatorial mutants of T0201H in bispecific antibody IXAX-1280.0201.0128 at final concentration of 133 nM. ETP = endogenous thrombin potential.

| VH | T0201 | T0596 | T0666 | T0678 | T0681 | T0687 | T0736 | T0999 | AbE | Isotype Control |
|---|---|---|---|---|---|---|---|---|---|---|
| Lagtime (min) | 5.0 | 5.2 | 4.5 | 2.7 | 3.0 | 2.7 | 2.7 | 2.0 | 2.5 | 18.0 |
| ETP (nmol/L thrombin × min) | 1774.4 | 1724.2 | 1883.6 | 2053.5 | 1932.4 | 2077.5 | 1805.4 | 2099.8 | 1951.9 | −1.0 |
| Maximal Peak Height (nM) | 134.9 | 126.4 | 160.4 | 259.6 | 235.6 | 267.8 | 237.5 | 317.2 | 291.8 | 19.9 |
| Time to peak (min) | 15.0 | 15.7 | 13.2 | 7.0 | 7.7 | 6.8 | 6.8 | 5.0 | 6.0 | 38.3 |

TABLE E13-1-continued

Recorded parameters from TGA carried out on FVIII deficient plasma spiked with CDR1, CDR2 and CDR3 single and combinatorial mutants of T0201H in bispecific antibody IXAX-1280.0201.0128 at final concentration of 133 nM. ETP = endogenous thrombin potential.

| VH | T0201 | T0596 | T0666 | T0678 | T0681 | T0687 | T0736 | T0999 | AbE | Isotype Control |
|---|---|---|---|---|---|---|---|---|---|---|
| Velocity Index (nM/min) | 13.5 | 12.0 | 18.5 | 59.9 | 50.5 | 64.4 | 57.1 | 105.7 | 83.6 | 1.0 |
| Tail Start (min) | 39.0 | 39.8 | 37.0 | 29.8 | 30.2 | 29.5 | 28.2 | 26.7 | 27.3 | −1.0 |

TABLE E13-2

Recorded parameters from TGA carried out on FVIII deficient plasma spiked with CDR1, CDR2 and CDR3 single and combinatorial mutants of T0201H in bispecific antibody IXAX-1280.0201.0128 at final concentration of 80 nM. ETP = endogenous thrombin potential. Refer to FIG. 27.

| VH | T0201 | T0596 | T0666 | T0678 | T0681 | T0687 | T0736 | T0999 | AbE | Isotype Control |
|---|---|---|---|---|---|---|---|---|---|---|
| Lagtime (min) | 5.0 | 5.3 | 4.7 | 2.7 | 3.0 | 2.7 | 2.7 | 2.0 | 3.0 | 19.0 |
| ETP (nmol/L thrombin × min) | 1766.2 | 1793.8 | 1757.9 | 1975.4 | 1891.7 | 1927.1 | 1933.3 | 1986.1 | 1878.6 | −1.0 |
| Maximal Peak Height (nM) | 126.6 | 125.9 | 148.2 | 269.7 | 231.4 | 266.2 | 248.9 | 308.0 | 255.8 | 19.7 |
| Time to peak (min) | 15.7 | 16.0 | 13.5 | 6.7 | 7.8 | 6.7 | 6.7 | 4.8 | 7.2 | 39.0 |
| Velocity Index (nM/min) | 11.9 | 11.8 | 16.8 | 67.4 | 47.9 | 66.5 | 62.2 | 109.2 | 61.6 | 1.0 |
| Tail Start (min) | 41.0 | 41.5 | 37.0 | 28.7 | 29.8 | 29.5 | 30.0 | 26.8 | 29.8 | −1.0 |

TABLE E13-2

Recorded parameters from TGA carried out with (i) emicizumab calibrator and (ii) normal pooled plasma spiked with PBS. The emicizumab calibrator is originally 100 ug/ml = 0.1 mg/ml = 666.666 nM. Dilution 125/80 = 1.5625 (80 plasma, 20 Calibrator/MP, 20 FluCa, 5 PBS spike) provides final emicizumab concentration of 426.6 nM for the calibrator. Refer to FIG. 27.

| | Calibrator | Normal Plasma |
|---|---|---|
| Lagtime (min) | 2.0 | 4.8 |
| Endogenous Thrombin Potential (ETP) (nmol/L thrombin × min) | 1538.0 | 1425.7 |
| Maximal Peak Height (nM) | 308.6 | 371.2 |
| Time to peak (min) | 4.5 | 6.5 |
| Velocity Index (nM/min) | 124.1 | 222.7 |
| Tail Start (min) | 23.7 | 22.7 |

For a dose response TGA, bispecific antibody IXAX-1280.0999.0128 was expressed in HEK cells, purified by Protein A chromatography and bispecific heterodimer purified by ion exchange chromatography. Using 0.3 nM FIXa trigger, dose response of Cmax (nM) and Tmax (min) in the TGA was carried out on FVIII deficient plasma spiked with bispecific antibody IXAX-1280.0999.0128 and compared against emicizumab calibrator. Both bispecific antibodies demonstrated a linear decrease in Cmax with increasing antibody concentration. IXAX-1280.0999.0128 achieved a greater Cmax than the calibrator antibody, this increase being more pronounced at lower bispecific antibody concentrations. See FIG. 29.

TABLE E13-3

Recorded parameters from TGA carried out on FVIII deficient plasma spiked with CDR1, CDR2 and CDR3 single and combinatorial mutants of T0201H in bispecific antibody IXAX-1280.0201.0128. Refer to FIG. 29.

| | IXAX-1280.0999.0128 Dose Response FIxa Trigger (0.3 nM) | | | | | | Normal Plasma | Isotype Control |
|---|---|---|---|---|---|---|---|---|
| | 300 nM | 100 nM | 30 nM | 10 nM | 3 nM | 1 nM | | |
| Lagtime (min) | 2 | 1.83 | 2.17 | 3.33 | 4.5 | 5.83 | 6.17 | 18 |
| Endogenous Thrombin Potential (ETP) (nmol/L thrombin × min) | 2703 | 2170 | 2266 | 2311 | 2208 | 2088 | 1629 | −1 |
| Maximal Peak Height (nM) | 377.14 | 348.38 | 327.7 | 274.76 | 208.45 | 124.11 | 466.31 | 23.47 |
| Time to peak (min) | 5.33 | 4.33 | 5.5 | 8 | 12 | 18.83 | 7.83 | 39.17 |

TABLE E13-3-continued

Recorded parameters from TGA carried out on FVIII deficient plasma spiked
with CDR1, CDR2 and CDR3 single and combinatorial mutants of T0201H
in bispecific antibody IXAX-1280.0201.0128. Refer to FIG. 29.

| | IXAX-1280.0999.0128 Dose Response FIxa Trigger (0.3 nM) | | | | | | | |
|---|---|---|---|---|---|---|---|---|
| | 300 nM | 100 nM | 30 nM | 10 nM | 3 nM | 1 nM | Normal Plasma | Isotype Control |
| Velocity Index (nM/min) | 113.14 | 140.01 | 98.31 | 58.88 | 27.82 | 9.62 | 279.78 | 1.11 |
| Tail Start (min) | 28.67 | 26.83 | 28.67 | 31.5 | 35.33 | 44.5 | 23.33 | −1 |

TABLE E13-4

Recorded parameters from TGA carried out with
emicizumab calibrator. Refer to FIG. 29

| | Emicizumab Calibrator Dose Response FIxa Trigger (0.3 nM) | | | | | | | |
|---|---|---|---|---|---|---|---|---|
| | 300 nM | 100 nM | 30 nM | 10 nM | 3 nM | 1 nM | Normal Plasma | Isotype Control |
| Lagtime (min) | 2 | 2.33 | 3 | 4.33 | 5.5 | 6.67 | 6.17 | 18 |
| Endogenous Thrombin Potential (ETP) (nmol/L thrombin × min) | 1884 | 2363 | 2075 | 1733 | 1524 | 1634 | 1629 | −1 |
| Maximal Peak Height (nM) | 343.94 | 351.58 | 255.87 | 152.08 | 89.33 | 67.38 | 466.31 | 23.47 |
| Time to peak (min) | 4.17 | 5.5 | 8.17 | 12.5 | 18.33 | 23 | 7.83 | 39.17 |
| Velocity Index (nM/min) | 160.26 | 111.69 | 50.03 | 18.67 | 6.96 | 4.13 | 279.78 | 1.11 |
| Tail Start (min) | 25 | 27.67 | 29.33 | 35.33 | 43.33 | 58.17 | 23.33 | −1 |

Materials & Methods

For the initial experimental work to establish a suitable concentration of factor IXa as a TGA trigger, 80 µl normal pooled plasma, taken from healthy individuals (Helena Biosciences), was mixed with 20 µl of trigger reagent (Microparticle (MP) reagent which is composed of phospholipids only containing varying amounts of FIXa) in Immulon 2HB transparent U-bottom 96 well plates (ThermoFisher #3665). All reagents were used according to manufacturers instructions, pre-warmed to 37° C. in a water bath.

Once a final concentration of 0.33 nM FIXa was determined to be sufficient to trigger thrombin generation for normal plasma, the same assay conditions including 0.3 nM FIXa were applied with FVIII-depleted plasma in calibrated automated thrombogram assays.

FVIII immunodepleted plasma (Helena Biosciences) was mixed with 20 µl of trigger reagent (Microparticle (MP) reagent which is composed of phospholipids only containing 222 nM FIXa, final concentration 0.33 nM) in Immulon 2HB transparent U-bottom 96 well plates. All reagents were used according to manufacturers instructions, pre-warmed to 37° C. in a water bath. A TGA dose response was carried out starting at 300 nM of test bispecific antibody or of emicizumab calibrator ((emicizumab spiked into FVIII deficient plasma (Enzyme Research Laboratories)) with a 1 in 3 dilution series over five points. A human IgG4 isotype control antibody was used as negative control, and normal (FVIII+ve) pooled plasma spiked with PBS was used as positive control.

Samples were measured in duplicate, accompanied by duplicate calibrator wells containing a thrombin calibrator (containing a pre-determined quantity of thrombin) in the same plasma. The 96 well plate was warmed to 37° C. in a Fluoroskan Ascent plate reader (Thermo) for 10 minutes. Thrombin generation commenced upon addition of 20 µl FluCa reagent (fluorogenic substrate, ZGGR-AMC (2.5 mM), in buffer containing 100 mM $CaCl_2$). TGA reagents were obtained from Stago. Increase in fluorescence over time was monitored by the plate reader.

A thrombin calibrator curve was run alongside each sample being investigated. Using a calibrator, with a known concentration of thrombin, the amount of thrombin generated in a sample under investigation can be calculated from the fluorescent signal obtained using software ThrombinoscopeBV. Fluorescence from test wells was calibrated against fluorescence from the thrombin calibrator wells, to determine the equivalent thrombin generated in the test wells.

Run data were analysed using Stago analysis software. The amount of thrombin generated was determined using the thrombin calibrator curve with known activity. The following aspects of the thrombogram were determined: lag time (minutes), endogenous thrombin potential (ETP; area under the thrombogram, nM thrombin/minute), peak height (Cmax; nM thrombin), time to peak (Tmax/minutes), velocity index (VI; nM/minute, slope between lag time and time to peak) and tail start (minutes; time at which the thrombin generation has come to an end).

Example 14. Dose Response and Potency in Thrombin Generation Assay

To evaluate the maximal thrombin peak height (Cmax, nM Thrombin) and time to peak (Tmax, minutes) of bispecific antibody IXAX-1280.0999.0325 we performed thrombin generation assays (TGA) in human FVIII-depleted plasma using a full antibody concentration dose response according to the method set out in Example 13. Data generated from dose response curves was fitted using a non-linear log [antibody] vs response parameter variable slope model (4 parameter logistic regression model). AbE was included for comparison. IXAX-1280.0999.0325 and AbE used in this assay were determined by mass spectrometry to be close to 100% heterodimer, with no homodimeric contaminants detected.

Figure 30:
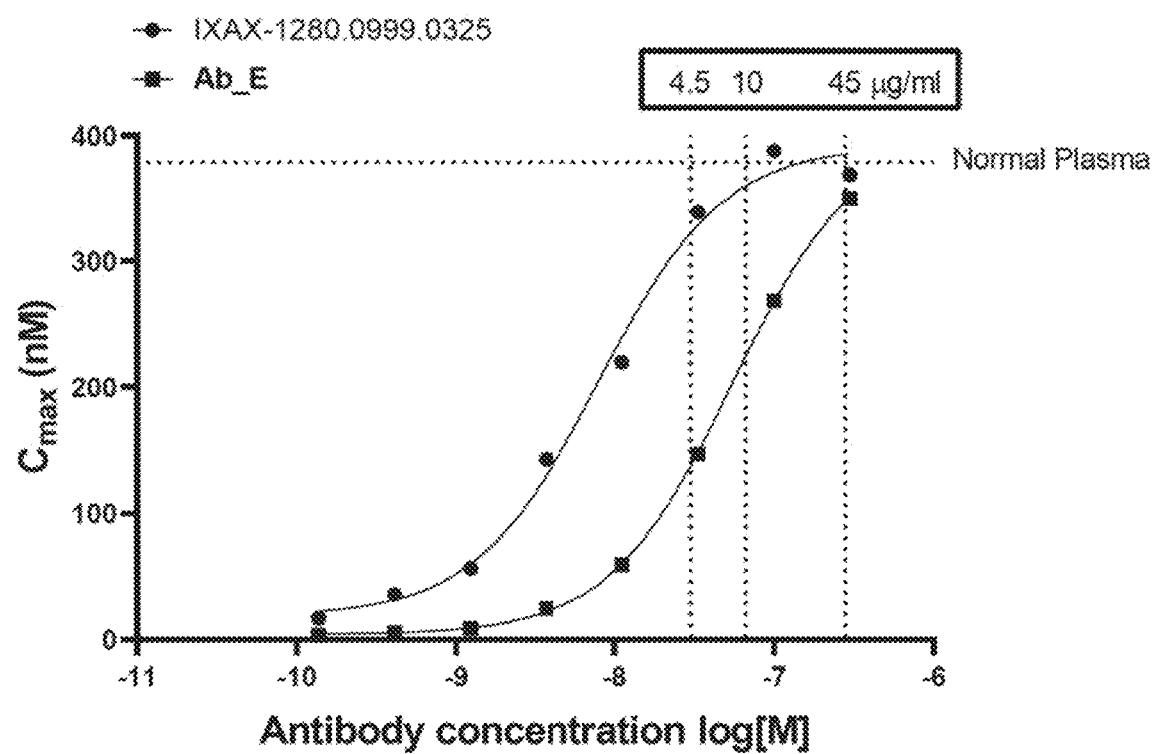
Figure 31:
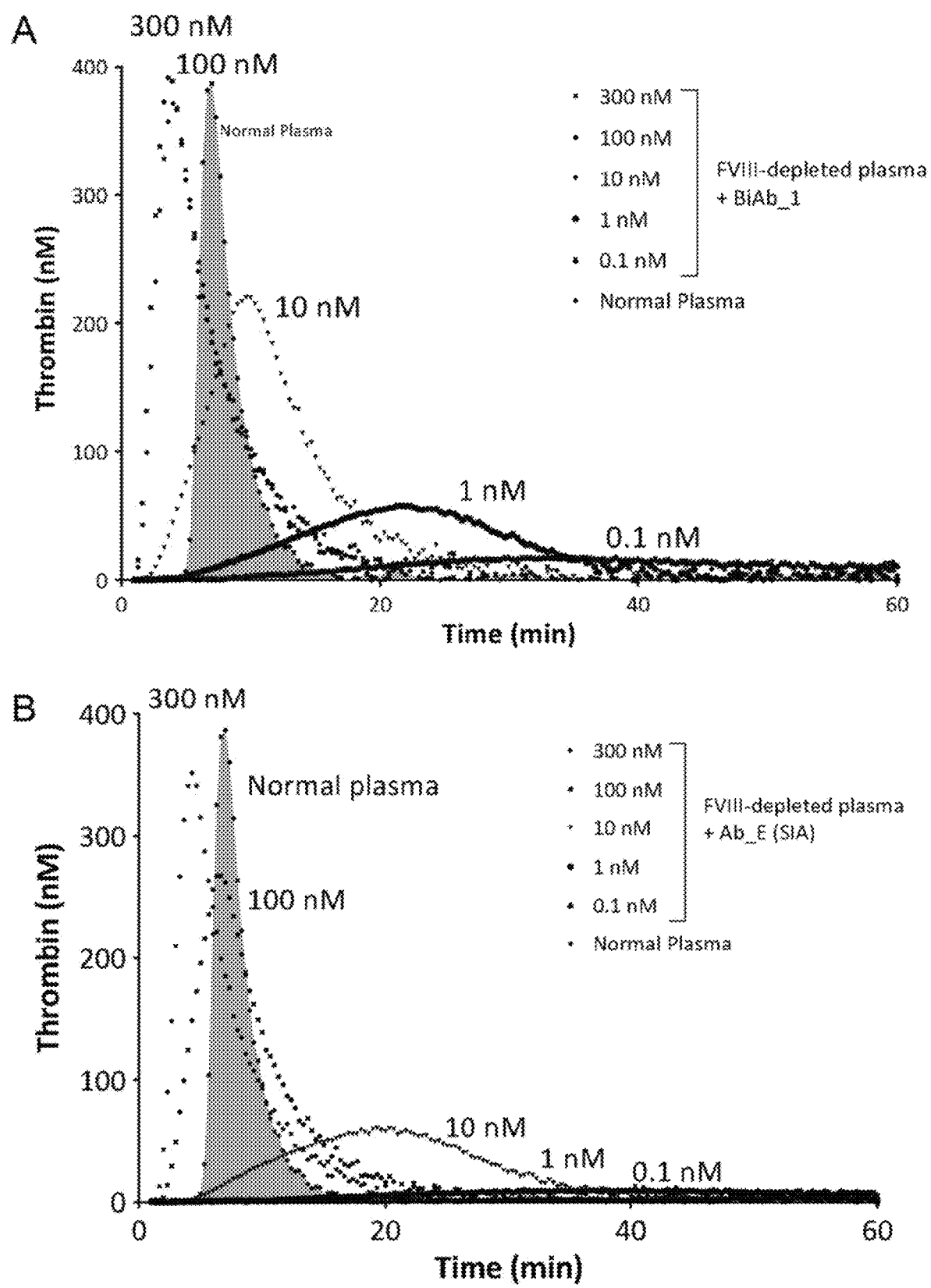

Over a prospective therapeutic window spanning 300 to 30 nM, equivalent to 45 to 4.5 µg/ml, we observed equivalent (within 10%) or greater Cmax (nM Thrombin) values for IXAX-1280.0999.0325 compared to AbE at all concentrations analysed (FIG. 30). Cmax of IXAX-1280.0999.0325 was close to that of a normal plasma control when the concentrations of the bispecific antibody were between 100 and 300 nM (FIG. 30 and FIG. 31). In contrast, Cmax of AbE only reached the normal level when IgG concentration is 300 nM. In this study, the EC50 of IXAX-1280.0999.0325 (8.0 nM) was approximately 15% of the EC50 of AbE (54.4 nM).

Using the Cmax curve, it can be predicted that IXAX-1280.0999.0325 can achieve the same activity as 45 µg/mL of emicizumab when its concentration is equal to or greater than 8 µg/mL, which suggests a potential efficacy advantage with IXAX-1280.0999.0325 compared with emicizumab.

Figure 32:
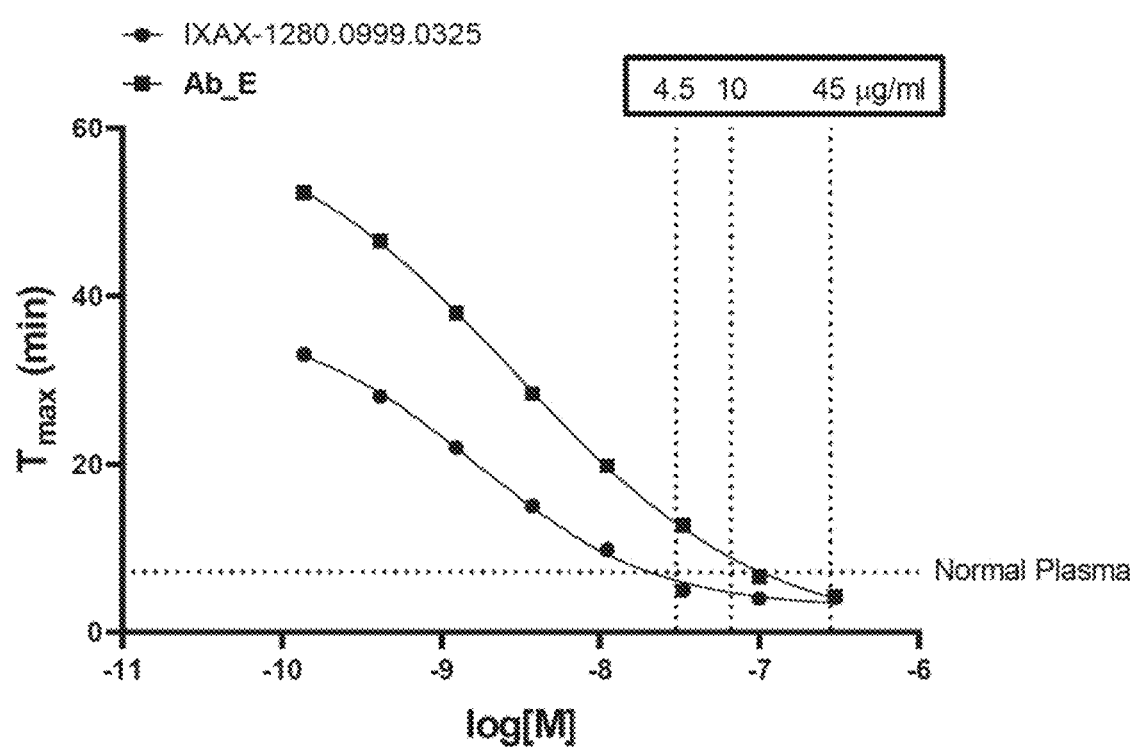

Analysis of the same dose response but with respect to Tmax, we observed equivalent (within 10%) or less than (or reduced) Tmax values for IXAX-1280.0999.0325 compared to AbE at all concentrations analysed (FIG. 32). Calculated EC50 values based on Tmax values obtained are 1.65 nM for IXAX-1280.0999.0325 (circle) compared to 2.8 nM for AbE (square).

In respect to the therapeutic ranges indicated in FIGS. 30 and 32, we observe with IXAX-1280.0999.0325 Cmax and Tmax dose response curves which are greater and lower compared to AbE, respectively.

TABLE E14-1

Non-linear fit of Cmax. Best fit values for log of antibody concentration vs Cmax. Variable slope (4 parameters).

|  | IXAX-1280.0999.0325 | Ab_E |
| --- | --- | --- |
| Bottom | 18.20 | 4.053 |
| Top | 392.0 | 399.9 |
| LogEC50 | −8.098 | −7.264 |
| HillSlope | 1.111 | 1.135 |
| EC50 | 7.984e−009 | 5.440e−008 |
| Span | 373.8 | 395.8 |

TABLE E14-2

Non-linear fit of Tmax. Best fit values for log of antibody concentration vs Cmax. Variable slope (4 parameters).

|  | IXAX-1280.0999.0325 | Ab_E |
| --- | --- | --- |
| Bottom | 2.888 | −0.2454 |
| Top | 37.14 | 62.16 |

TABLE E14-2-continued

Non-linear fit of Tmax. Best fit values for log of antibody concentration vs Cmax. Variable slope (4 parameters).

|  | IXAX-1280.0999.0325 | Ab_E |
| --- | --- | --- |
| LogEC50 | −8.781 | −8.548 |
| HillSlope | −0.7713 | −0.5577 |
| EC50 | 1.654e−009 | 2.829e−009 |
| Span | 34.25 | 62.41 |

The activities of three further bispecific antibodies (BiAb 2, 3 and 4) were also assessed in the TGA and compared against the performance of IXAX-1280.0999.0325 (BiAb 1) and commercially available emicizumab calibrator (Enzyme Research Laboratories) in commercially available human FVIII-depleted plasma (Helena Biosciences). BiAbs were as follows, each including heavy chain constant regions SEQ ID NO: 409 and SEQ ID NO: 410 respectively in the two heavy chains, and lambda light chain constant region SEQ ID NO: 146 in the common light chain:

1. IXAX-1280.0999.0325. Anti-FIX heavy chain SEQ ID NO: 419, anti-FX heavy chain SEQ ID NO: 421, common light chain SEQ ID NO: 414.
2. IXAX-1454.0999.0325. Anti-FIX heavy chain SEQ ID NO: 424, anti-FX heavy chain SEQ ID NO: 421, common light chain SEQ ID NO: 414.
3. IXAX-1441.0999.0325. Anti-FIX heavy chain SEQ ID NO: 426, anti-FX heavy chain SEQ ID NO: 421, common light chain SEQ ID NO: 414.
4. IXAX-1442.0736.0325. Anti-FIX heavy chain SEQ ID NO: 428, anti-FX heavy chain SEQ ID NO: 430, common light chain SEQ ID NO: 414.

Figure 33:
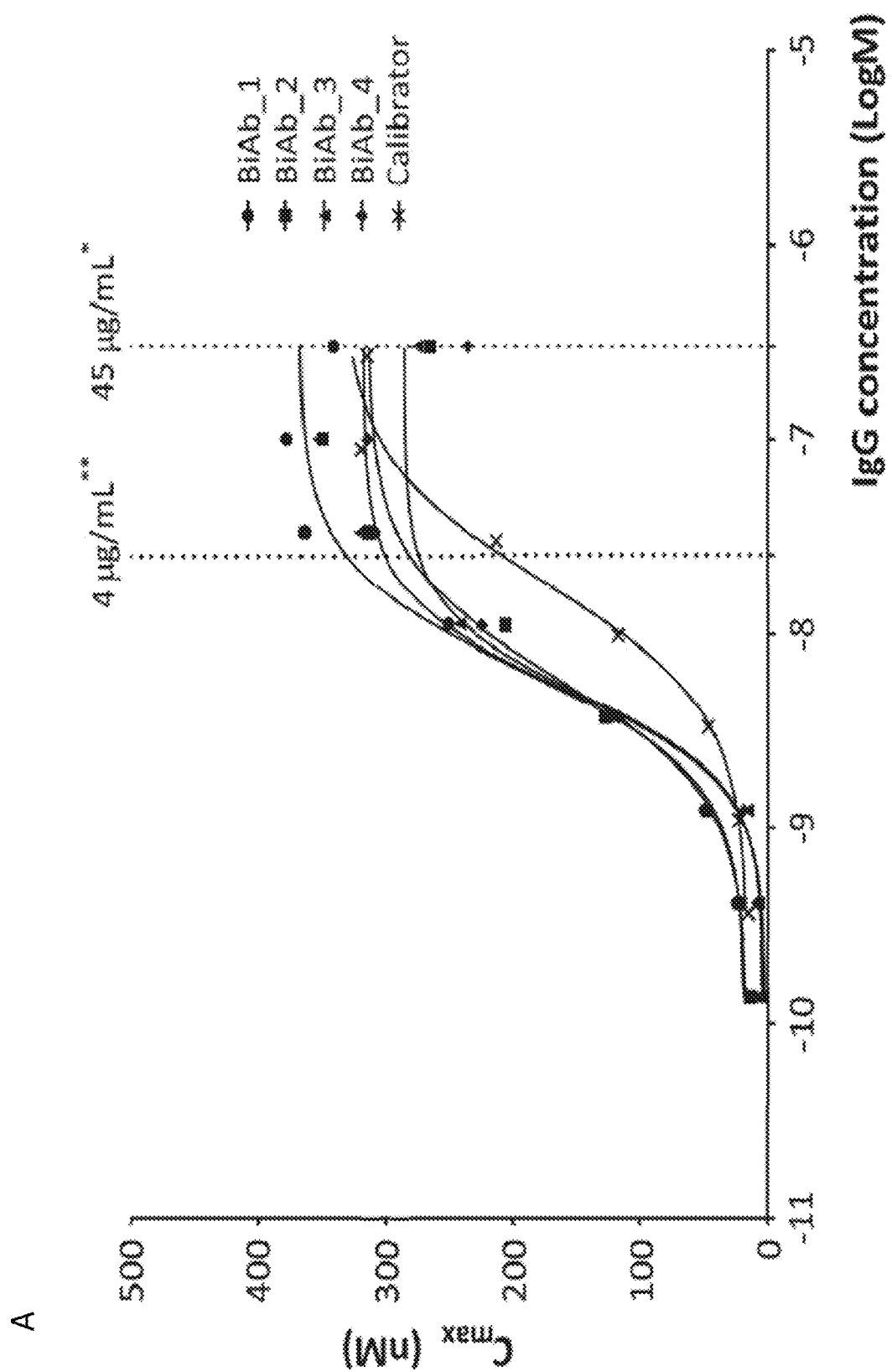
Figure 33:
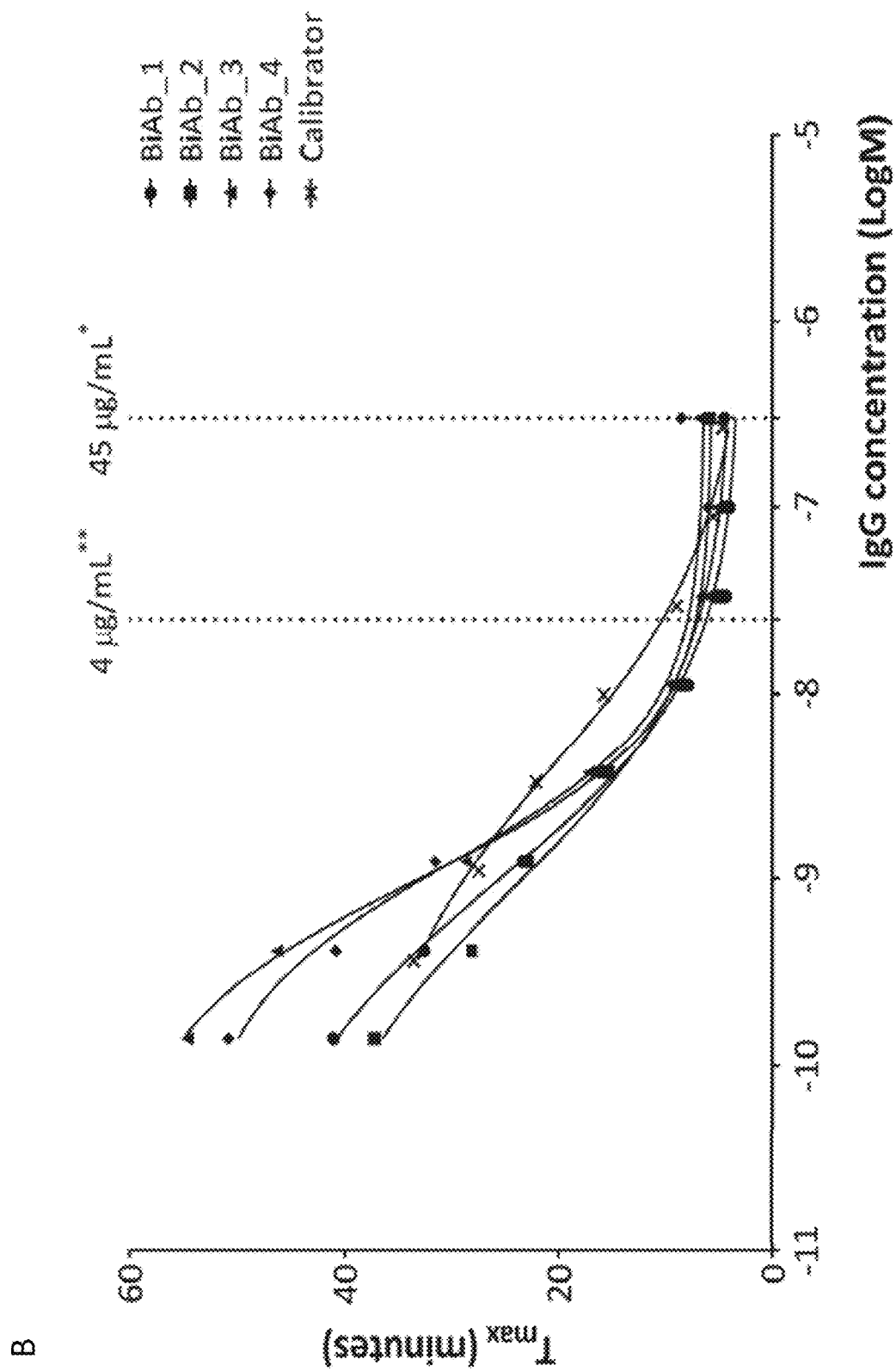

BiAb_1, 2, 3 and 4 dose-dependently increased thrombin peak height (Cmax), and dose-dependently decreased time to peak (Tmax) in the same manner as emicizumab. The top of Cmax curve of BiAb_1 was measured at about 368 nM, higher than that of emicizumab (334.8 nM). EC50 (Cmax) of BiAb_1, 2, 3, and 4 were similar to each other and had calculated EC50s of 6.45 nM, 5.87 nM, 5.2 nM and 4.81 nM respectively, representing EC50s between 26% and 35% of the EC50 of emicizumab (18.33 nM). FIG. 33 A. Calculated EC50 (Tmax) values for BiAb_1 to BiAb_4 were 0.56 nM, 0.65 nM, 1.08 nM and 0.93 nM respectively, compared with 2.53 nM for emicizumab. FIG. 33 B.

Figure 34:
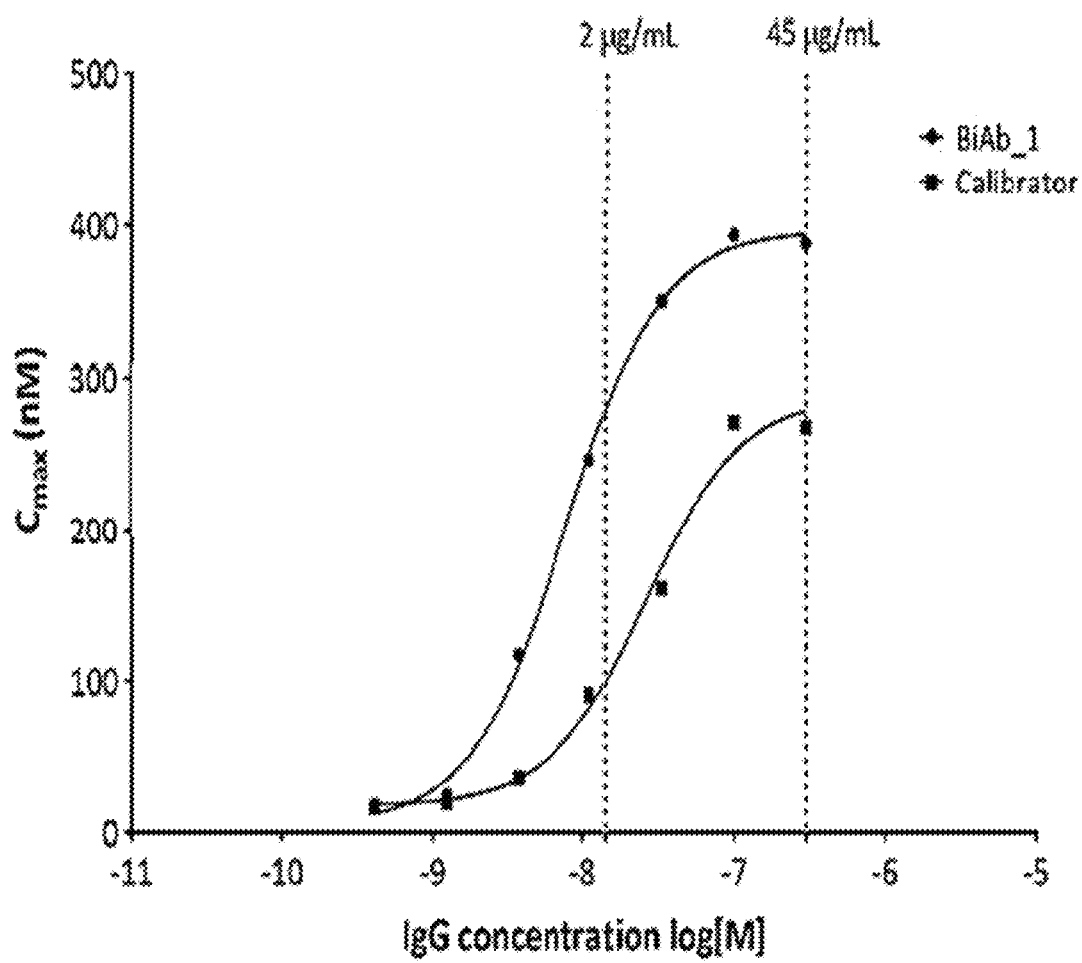
Figure 34:
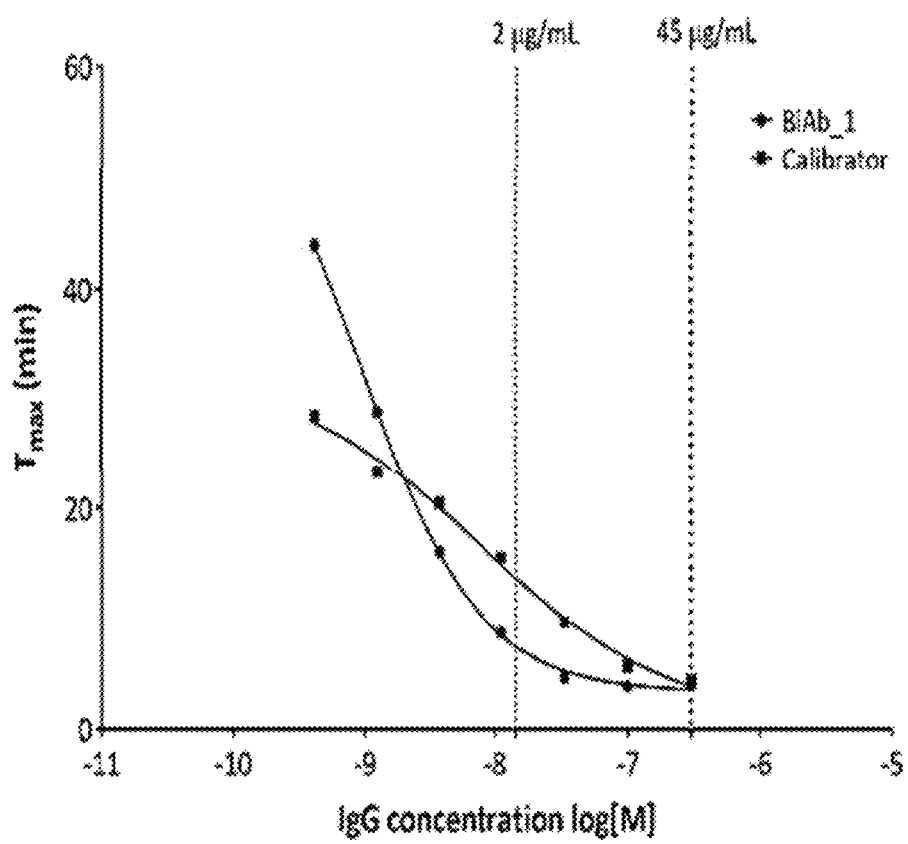

In a third study, BiAb_1 (IXAX-1280.0999.0325) was again compared with commercially available emicizumab calibrator by using TGA assay in human FVIII-depleted plasma. BiAb_1 dose-dependently increased thrombin peak height (Cmax), and dose-dependently decreased time to peak (Tmax). FIG. 34. The top of Cmax curve for BiAb_1 was about 396.5 nM, higher than that of emicizumab (286.3 nM). EC50 of BiAb_1 was 7.7 nM, approximately 30% of the EC50 of emicizumab (25.9 nM).

Assay to assay variation is observed between the TGA as shown in FIG. 34, FIG. 33 and FIG. 30, in which BiAb_1 exhibited Cmax of approximately 400 nM, 375 nM and 375 nM respectively and in which emicizumab exhibited Cmax of 275 nM, 300 nM and 350 nM. Despite variation in the absolute readings, the trends observed were the same in each instance of the TGA.

In summary, TGA data with either the commercially available emicizumab calibrator or the generated reference antibody AbE consistently indicated an efficacy advantage for BiAb_1 (IXAX-1280.0999.0325) compared with emicizumab. An advantage was also observed with the other antibodies tested (BiAb_2, BiAb_3 and BiAb_4).

According to an FDA multi-disciplinary review of emicizumab, a median annualized bleeding rate (ABR) of 0 would be achieved at emicizumab steady state trough plasma concentration ≥45 µg/mL[17]. Using the Cmax curves from the TGA described above, it is predicted that BiAb_1 can achieve the same activity as 45 µg/mL of emicizumab when its concentration is equal to or greater than about 2-4 µg/mL. This observation suggests a potential efficacy and/or dosing advantage with respect to emicizumab. The differences in activity potentially mean that the bispecific antibody can achieve the same therapeutic effect when administered at lower dose and/or less frequently than emicizumab, representing a clinical advantage. Although the higher Cmax indicates the potential for a more powerful procoagulant capability, the magnitude of this increase is unlikely to be associated with safety concerns.

Example 15. Affinities of Optimised Antibody Arms

Affinity and kinetics of purified anti-FIX and anti-FX antibodies for binding to their respective antigens was determined by SPR as described in Example 10 above.

The anti-FIX antibodies showed binding to FIX with an affinity range of approximately 0.05 µM-0.3 µM (50-300 nM), with a general trend of increasing affinity (lower $K_D$) and faster off-rate correlating with greater activity in the bispecific antibody. Table E15-1.

TABLE E15-1

| Captured anti-FIX IgG | $k_{on}$ (1/MS) | $k_{off}$ (1/s) | $K_D$ (M) |
|---|---|---|---|
| Isotype control antibody | No binding | No binding | No binding |
| AbN | $3.64 \times 10^4$ | $6.48 \times 10^{-2}$ | $1.78 \times 10^{-6}$ |
| NINA-0128 | $1.37 \times 10^5$ | $4.92 \times 10^{-2}$ | $3.59 \times 10^{-7}$ |
| NINA-0436.0128 | $1.46 \times 10^5$ | $5.23 \times 10^{-2}$ | $3.59 \times 10^{-7}$ |
| NINA-0511.0128 | $1.34 \times 10^5$ | $1.75 \times 10^{-2}$ | $1.31 \times 10^{-7}$ |
| NINA-1091.0128 | $1.61 \times 10^5$ | $3.52 \times 10^{-2}$ | $2.18 \times 10^{-7}$ |
| NINA-1172.0128 | $2.25 \times 10^5$ | $1.71 \times 10^{-2}$ | $7.64 \times 10^{-8}$ |
| NINA-1280.0128 | $1.92 \times 10^5$ | $1.00 \times 10^{-2}$ | $5.23 \times 10^{-8}$ |

The anti-FX antibodies showed binding to FX with an affinity range of approximately 0.3-3 µM. Table E15-2. Anti-FX antibody MONA was included as a control low affinity antibody with VH and VL domains from an IgM clone obtained from the single cell sorting (Example 1).

TABLE E15-2

| Captured anti-FX IgG | $k_{on}$ (1/MS) | $k_{off}$ (1/s) | $K_D$ (M) |
|---|---|---|---|
| Isotype control antibody | No binding | No binding | No binding |
| AbT | $2.50 \times 10^4$ | $3.85 \times 10^{-2}$ | $1.54 \times 10^{-6}$ |
| TINA-0200.0128 | $4.43 \times 10^4$ | $1.12 \times 10^{-1}$ | $2.52 \times 10^{-6}$ |
| TINA-0201.0128 | $5.90 \times 10^4$ | $4.82 \times 10^{-2}$ | $8.16 \times 10^{-7}$ |
| TINA-0202.0128 | $5.13 \times 10^4$ | $7.09 \times 10^{-2}$ | $1.38 \times 10^{-6}$ |
| TINA-0616.0128 | $4.19 \times 10^4$ | $2.22 \times 10^{-2}$ | $5.30 \times 10^{-7}$ |
| TINA-0638.0128 | $6.99 \times 10^4$ | $2.32 \times 10^{-2}$ | $3.33 \times 10^{-7}$ |
| TINA-0666.0128 | $4.49 \times 10^4$ | $4.17 \times 10^{-2}$ | $9.27 \times 10^{-7}$ |
| MONA_IgG4PE | $5.36 \times 10^4$ | $5.24 \times 10^{-2}$ | $9.78 \times 10^{-7}$ |

Example 16. Initial Biophysical Assessment

To evaluate expression of the bispecific antibodies, IXAX-1172.0201.0128 was chosen as a representative antibody for minipool analysis. Minipool analysis allows screening of CHO stably transfected cells expressing large amounts (at least 1 g/l) of heterodimeric bispecific antibody and represents a means of evaluating stable bispecific antibody expression.

Using standard Lonza fed-batch overgrowth protocols for stably transfected CHO-K1 cells, bispecific antibodies were expressed. After transfection, 5000 viable cells were aliquoted per well to generate multiple minipools. 8 were taken forward based on antibody titres as measured by Octet.

Cells were harvested, filtered and purified by Protein A chromatography to isolate the antibodies from the supernatant. Antibody concentration (mg) was quantified by OD280, total amount of antibody (mg) was calculated accordingly based on volume of sample and a purification yield (mg/L) assigned according to cell culture volume. The relative percentages of heterodimer and homodimers in each of the 8 minipool samples was determined using imaged capillary isoelectric focusing (icIEF) (Protein Simple, Maurice). Homodimer and heterodimer peaks were assigned using transiently expressed reference homodimer arms for FIX and FX.

Figure 35:
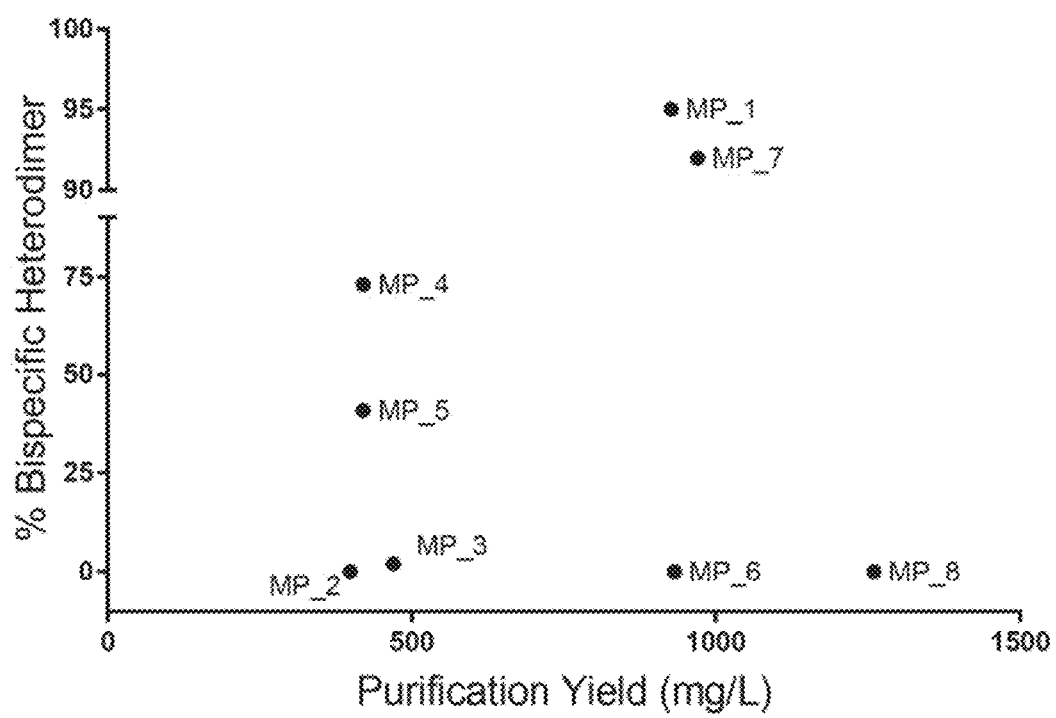
FIG. 35 shows purification yield and % heterodimer for bispecific antibody IXAX-1172.0201.0128 expressed from 8 independent minipools of stably transfected CHO cells.

We were able to isolate stably transfected cells expressing approximately 1 g/L bispecific antibody with up to approximately 95% heterodimer (e.g., as shown for MP_1 and MP_7, FIG. 35).

Figure 36:
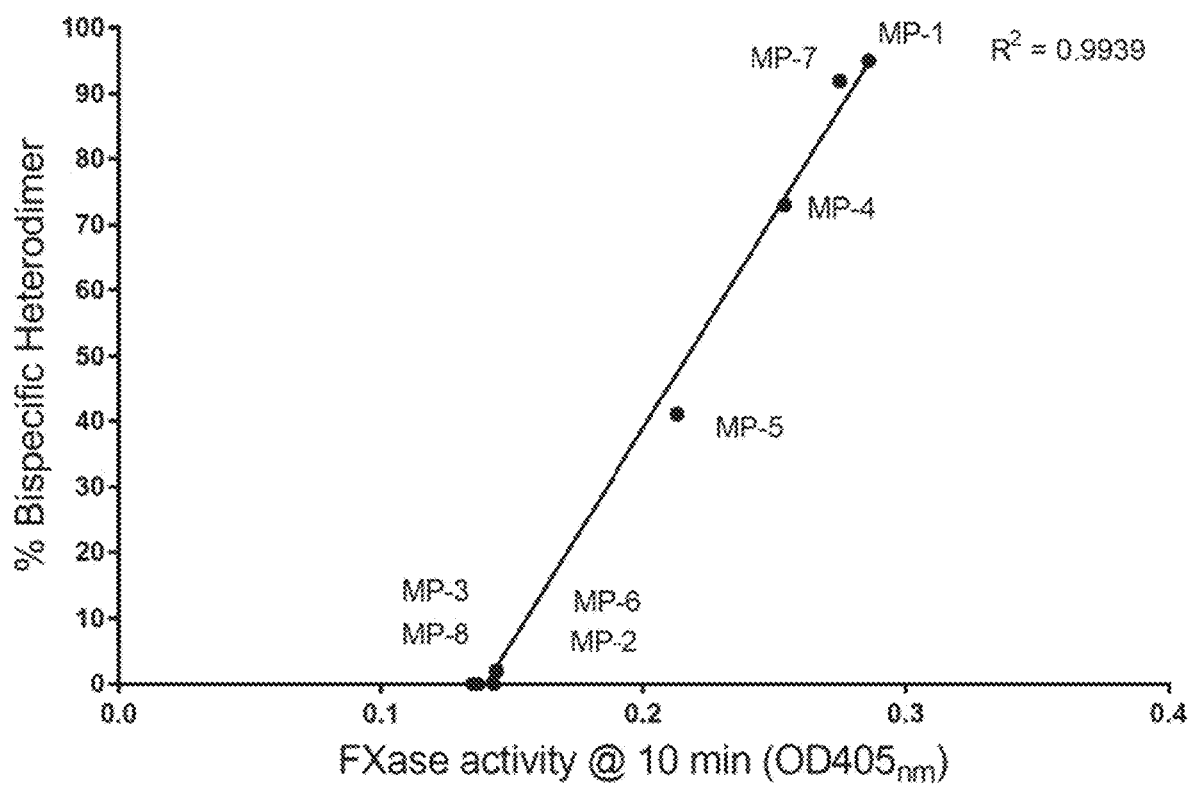
FIG. 36 plots the correlation between bispecific antibody activity by FXase assay (activity at 10 min) and % heterodimer for bispecific antibody IXAX-1172.0201.0128 normalised to 0.3 mg/ml expressed from 8 independent minipools. Pearson's correlation coefficient was calculated as 0.9939.

Bispecific antibody activity in FXase assay correlated with % heterodimer with a Pearson's correlation coefficient of 0.99 (FIG. 36).

Example 17. Purification of Bispecific Antibody

Co-expression of the two heavy chains and one common light chain of a bispecific antibody generates a composition comprising the bispecific antibody plus monospecific antibody byproducts. These may be separated by ion exchange chromatography, exploiting differences in the isoelectric point of the bispecific heterodimer compared with the monospecific homodimers.

Bispecific antibody IXAX-1280.0999.0128 comprises anti-FIX heavy chain SEQ ID NO: 419, anti-FX heavy chain SEQ ID NO: 421 and common light chain SEQ ID NO: 405. The bispecific antibody was purified following co-expression of these polypeptides in HEK cells, using protein A chromatography to isolate the antibodies from cell supernatant, followed by ion exchange chromatography to isolate the heterodimer.

Bispecific antibody IXAX-0436.0201.0128 comprises anti-FIX heavy chain comprising VH domain SEQ ID NO: 324 and an IgG4 human heavy chain constant region with P (hinge) mutation and K439E, anti-FX heavy chain comprising VH domain SEQ ID NO: 470 and IgG4 human heavy chain constant region with P (hinge) mutation and E356K, and common light chain SEQ ID NO: 405.

Bispecific antibody IXAX-0436.0202.0128 comprises anti-FIX heavy chain comprising VH domain SEQ ID NO: 324 and an IgG4 human heavy chain constant region with P (hinge) mutation and K439E, anti-FX heavy chain comprising VH domain SEQ ID NO: 472 and IgG4 human heavy chain constant region with P (hinge) mutation and E356K, and common light chain SEQ ID NO: 405.

Bispecific antibody IXAX-1172.0201.0128 comprises anti-FIX heavy chain comprising VH domain SEQ ID NO: 440 and an IgG4 human heavy chain constant region with P (hinge) mutation and K439E, anti-FX heavy chain comprising VH domain SEQ ID NO: 470 and an IgG4 human heavy chain constant region with P (hinge) mutation and E356K, and common light chain SEQ ID NO: 405.

Ion exchange chromatography cleanly separated each antibody composition into its component parts. Baseline separation was observed. Anti-FIXxFX heterodimeric bispecific antibody is separated from homodimeric contaminant anti-FIX and/or anti-FX monospecific antibodies.

Figure 37:
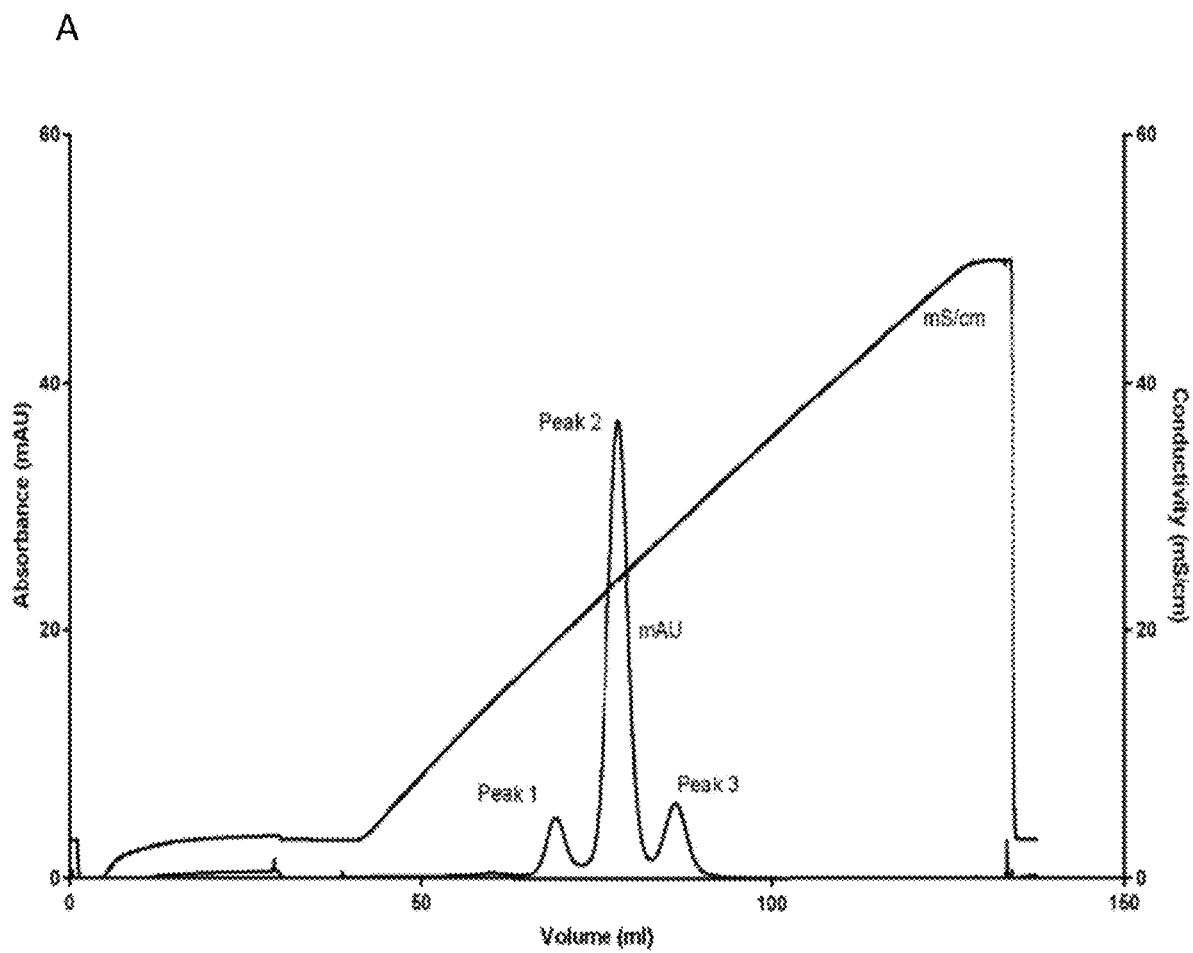
FIG. 37 (A) shows separation of IXAX-1280.0999.0128 by ion exchange chromatography on a 1 ml CaptoSP ImpRes column and a linear NaCl gradient up to 500 nM in 20 nM sodium phosphate, pH 6.0. Absorbance, mAU (milli absorbance unit); conductivity, mS/cm (milli Siemens per centimetre). Peak 1 is NINA-1280.0128 monospecific anti-FIX antibody. Peak 2 is IXAX-1280.0999.0128 bispecific antibody. Peak 3 is TINA-0999.0128 monospecific anti-FX antibody. (B) shows separation of IXAX-0436.0202.0128 by ion exchange chromatography with stepwise elution. Peak 1 is NINA-0436.0128 monospecific anti-FIX antibody. Peak 2 is IXAX-0436.0202.0128 bispecific antibody. Peak 3 is TINA-0202.0128 moospecific anti-FX antibody. (C) shows separation of IXAX-1172.0201.0128 by ion exchange chromatography. Peak 1 is NINA-1172.0128 anti-FIX monospecific antibody. Peak 2 is IXAX-1172.0201.0128 bispecific antibody.

FIG. 37a shows successful purification of IXAX-1280.0999.0128 from a composition comprising the bispecific antibody mixed with anti-FIX homodimer NINA-1280.0128 and anti-FX homodimer TINA-0999.0128.

FIG. 37b shows successful purification of IXAX-0436.0202.0128 from a composition comprising the bispecific antibody mixed with anti-FIX homodimer NINA-0436.0128 and anti-FX homodimer TINA-0202.0128. The chromatogram represents cation ion exchange purification of N436 bispecific antibody from homodimer contaminants using a series of stepwise elutions using increasing concentrations of NaCl up to 500 nM in Sodium acetate pH 5. Peak 1 represents anti-FIX homodimer antibody; peak 2, anti-FIX/FX bispecific antibody and peak 3 represents anti-FX homodimer antibody. Peak 1, 2 and 3 make up 18%, 79% and 3% total peak area respectively.

FIG. 37c shows successful purification of IXAX-1172.0201.0128 from a composition comprising the bispecific antibody and anti-FIX homodimer NINA-1172.0128. The column purification here yielded 31.5% anti-FIX homodimer and 68.5% bispecific heterodimer. The chromatogram represents cation ion exchange purification of N1172 bispecific antibody from anti-FIX homodimer contaminants using an initial stepwise elution to remove weakly bound Peak 1 (anti-FIX homodimer) followed by a gradient elution using increasing concentrations of NaCl to elute the anti-FIX/FX bispecific. The presence of anti-FX homodimer was not detected.

Materials & Methods

For IXAX-1280.0999.0128 purification, bispecific antibody was transiently expressed in Expi293F HEK cells. Cell culture supernatant was harvested, filtered and loaded on to a 5 ml HiTrap MabSelect Sure (MSS) column (GE Healthcare) equilibrated with 1× phosphate buffered saline (PBS). The column was washed with 5 column volumes of PBS and bound antibody was eluted using IgG elute (ThermoFisher). Eluted bispecific antibody was dialysed into 1×PBS overnight at 4° C. and concentrated using a centrifugal filter unit with a 10 kDa molecular weight cut off.

Chromatography was performed at room temperature. A 1 ml HiTrap Capto SP column (GE Healthcare) was equilibrated with 20 mM sodium phosphate, pH 6.0 and 0.5 mg of Protein A purified material, diluted 1:20 in equilibration buffer (20 mM sodium phosphate, pH 6.0), was loaded on to the column. The column was subsequently washed with 10 column volumes of equilibration buffer followed by a linear gradient (100% B over 90 column volumes to 500 mM NaCl) to elute the bispecific antibody and monospecific contaminants. In this process, buffer is progressively changed from A (20 mM sodium phosphate, pH 6.0, no salt) to B (buffer A with the addition of 500 mM NaCl) over 90 cv at a flow rate of 1 ml/min for the 1 ml column.

For IXAX-0436.0202.0128 purification, a stepwise gradient including washes at three different ionic strengths was applied using varied proportions of Buffer A (50 mM sodium acetate, pH 5) and Buffer B (50 nM sodium acetate and 500 mM sodium chloride).

For IXAX-1172.0201.0128 purification. an initial stepwise elution was used to remove weakly bound Peak 1 (anti-FIX homodimer) followed by a gradient elution using increasing concentrations of NaCl to elute the anti-FIX/FX bispecific.

Subsequently, the following bispecific antibodies were expressed in CHO cells:

5. IXAX-1280.0999.0325. Anti-FIX heavy chain SEQ ID NO: 419, anti-FX heavy chain SEQ ID NO: 421, common light chain SEQ ID NO: 414.
6. IXAX-1454.0999.0325. Anti-FIX heavy chain SEQ ID NO: 424, anti-FX heavy chain SEQ ID NO: 421, common light chain SEQ ID NO: 414.
7. IXAX-1441.0999.0325. Anti-FIX heavy chain SEQ ID NO: 426, anti-FX heavy chain SEQ ID NO: 421, common light chain SEQ ID NO: 414.
8. IXAX-1442.0736.0325. Anti-FIX heavy chain SEQ ID NO: 428, anti-FX heavy chain SEQ ID NO: 430, common light chain SEQ ID NO: 414.
9. IXAX-1442.0687.0325. Anti-FIX heavy chain SEQ ID NO: 428, anti-FX heavy chain SEQ ID NO: 421, common light chain SEQ ID NO: 414.

Each of these bispecific antibodies includes heavy chain constant regions SEQ ID NO:
409 and SEQ ID NO: 410 respectively for the two heavy chains, and lambda light chain constant region SEQ ID NO: 146 in the common light chain.

The titres observed from transient expression of each of antibodies 1 to 5 above in CHO cells were comparable to titres for a monospecific isotype control antibody. Stable pools and mini-pools (up to 4,000 cells seeded after transfection) were also generated. Although the stable pools produced low percentages (11-19%) of heterodimeric antibody, mini-pools with titres up to 4.9 g/l and percentages of heterodimers up to 82% were established from a limited number of screened mini-pools.

After protein A purification, cation exchange chromatography was used to remove homodimeric by-products to generate high-purity materials suitable for use in functional assays and for developability screening.

Figure 38:
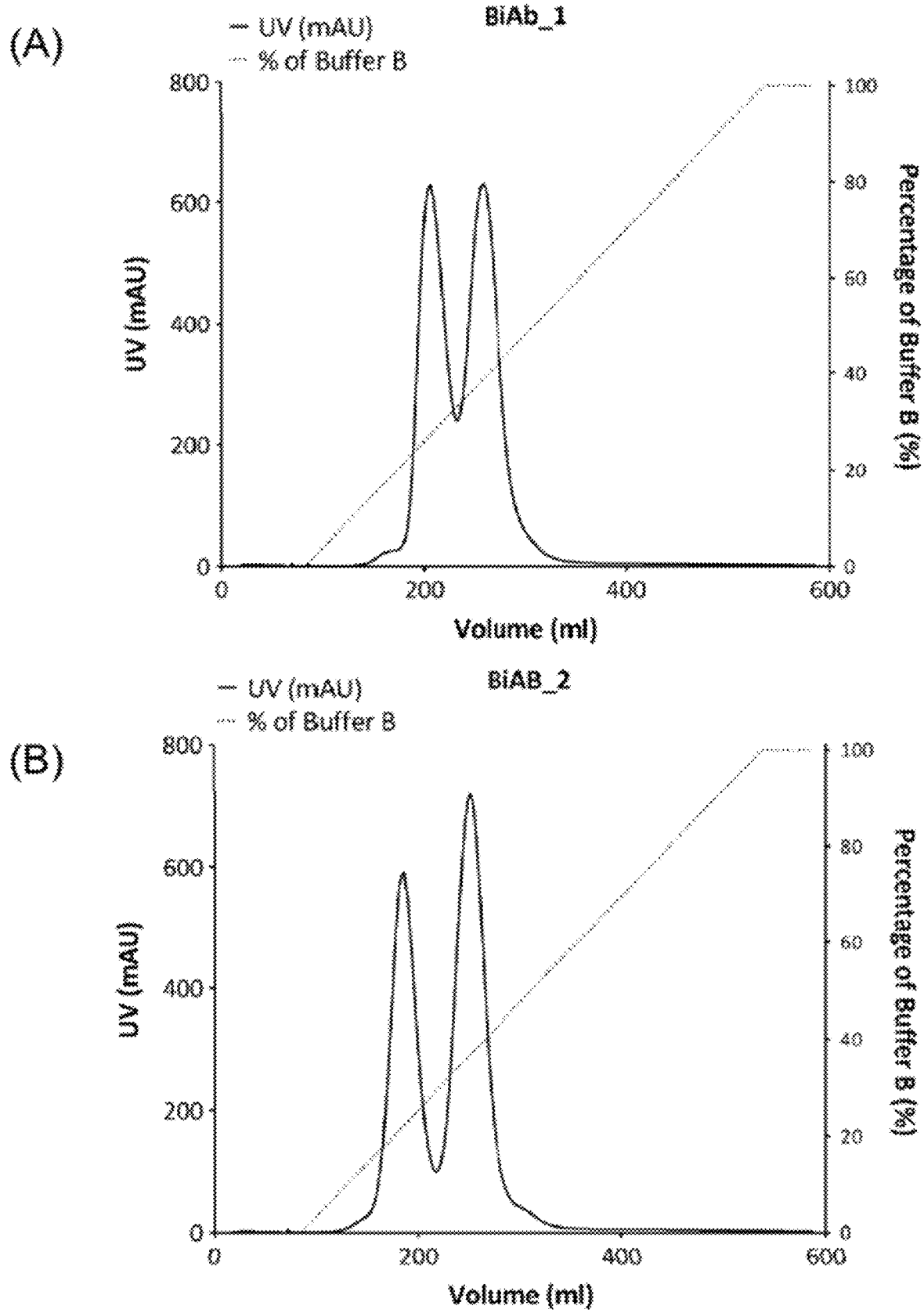
FIG. 38 shows cation exchange purification of purified FIX/FX heterodimers for each of bispecific antibodies (A) IXAX-1280.0999.0325 (B) IXAX-1454.0999.0325 (C) IXAX-1441.0999.0325 and (D) IXAX-1442.0736.0325.

Using a gradient cation exchange method, antibodies 1 to 4 were separated from the homodimeric by-products, providing 91-96% heterodimer in the eluted material. Thus, even with this preliminary purification method we were able to obtain 91-96% pure heterodimer. FIG. 38. No comparable homodimer/heterodimer separation was observed for antibody 5 using this technique.

Example 18. Quality Assessment by Mass Spectrometry

The structural integrity of therapeutic monoclonal antibodies can be compromised by multiple types of post-translational modifications which result in product heterogeneity. Mass spectrometry (MS) was used to characterize and evaluate the quality of the bispecific antibodies after cation exchange purification.

After cation exchange separation as described in Example 17, the three different species (anti-FIX/anti-FX heterodimer, anti-FIX homodimer and anti-FX homodimer respectively) in the eluted composition of BiAb_1 IXAX-1280.0999.0325 were analysed by MS. Molecular weights (MW) of the three molecules determined by MS matched the theoretical MW predicted by amino acid sequences of BiAb_1. MS results thus confirmed the identity and the purity of FIX/FX heterodimer after cation exchange purification.

Example 19. Stability Assessment

After purification as described in Example 17, BiAb_1, 2, 3 and 4 respectively were buffer exchanged to either buffer 1 (sodium acetate, pH 5.5) or buffer 2 (citrate/phosphate, pH 6.0), stored for 2 weeks at 4° C., for 4 weeks at 25° C., or underwent 1× freeze/thaw cycle. The concentration of IgG was measured before and after treatment to calculate the loss of antibodies due to the treatment. SEC-HPLC was also performed before and after treatment to monitor for bispecific antibody degradation and aggregation. No obvious loss or degradation of BiAb_1, 2, 3 or 4 was observed. These four bispecific antibodies were thus all stable in both buffer 1 and buffer 2.

Example 20. Dose Response and Potency in FXase Assay

Figure 39:
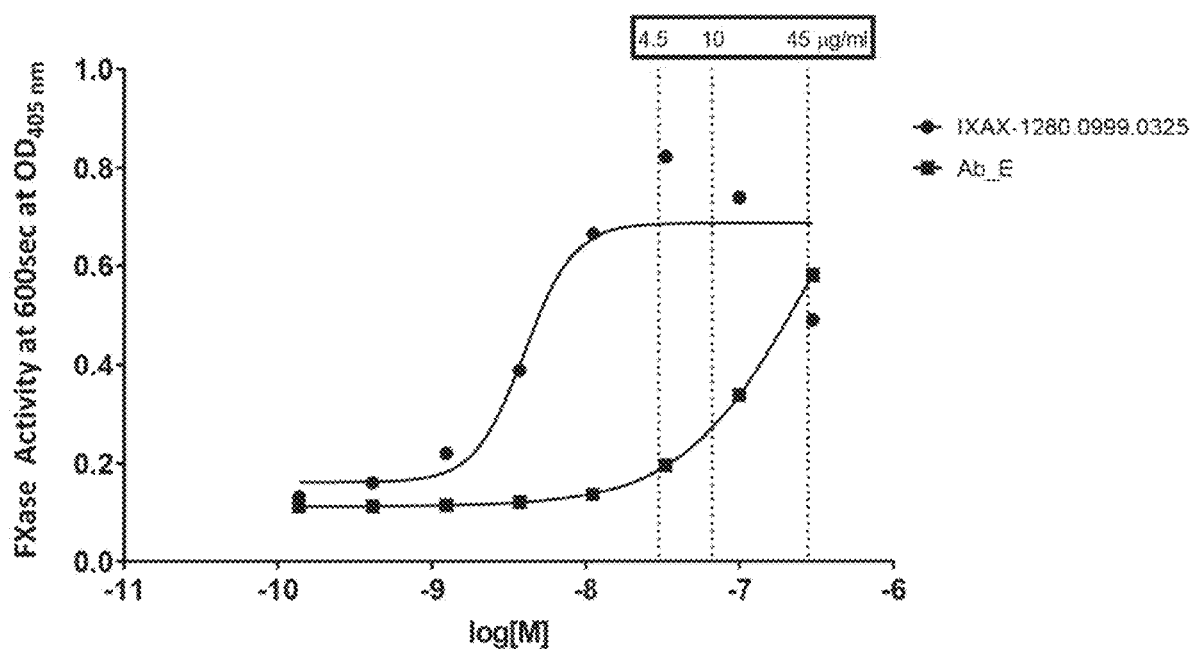
FIG. 39 shows dose response in the FXase assay with IXAX-1280.0999.0325 and AbE. Dotted lines indicate antibody concentration corresponding to 4.5 µg/ml, 10 µg/ml and 45 µg/ml.

A FXase kinetic assay was conducted to measure the factor VIII mimetic activity of IXAX-1280.0999.0325 and AbE in a dose response to determine their EC50 values as per Example 7. Data generated from dose response curves was fitted using a non-linear log[antibody] vs response parameter variable slope model (4 parameter logistic regression model). FIG. 39. The y-axis are plotted OD405 nm values at a 600 second assay timepoint. The EC50 values for both IXAX-1280.0999.0325 and AbE were calculated from a non-linear regression curve of the data, giving an EC50 of 3.99 nM for IXAX-1280.0999.0325 and EC50 of 261.2 nM for AbE. These are approximations since the dose response curve was incomplete. Despite this it is evident that IXAX-1280.0999.0325 has a significantly lower EC50 than AbE. The activity of IXAX-1280.0999.0325 and AbE is dose dependent. IXAX-1280.0999.0325 demonstrated higher FVIII mimetic activity, in particular at lower concentrations, compared with AbE.

TABLE E20-1

Kinetic FXase best fit values for log of antibody concentration vs response. Variable slope (4 parameters).

|  | IXAX-1280.0999.0325 | Ab_E |
|---|---|---|
| Bottom | 0.1620 | 0.1103 |
| Top | 0.6872 | 0.9858 |
| LogEC50 | −8.399 | −6.583 |
| HillSlope | 2.707 | 1.087 |
| EC50 | 3.993e−009 | 2.612e−007 |
| Span | 0.5252 | 0.8756 |

Example 21. Hyphen Assay Dose Response

A chromogenic assay (HYPHEN BioMed), which analyses factor Xa production in human plasma, was used to measure the factor VIII mimetic activity of IXAX-1280.0999.0325 and AbE. In this assay, FXa generation is proportional to the OD405 measured after chromogenic substrate addition. Antibody concentration dose response curves were generated and fitted using a non-linear log [antibody] vs response parameter variable slope model (4 parameter logistic regression model). EC50 values based on the dose responses were calculated. An EC50 value of 5.92 nM was calculated for IXAX-1280.0999.0325 compared with 15.43 nM for AbE.

Figure 40:
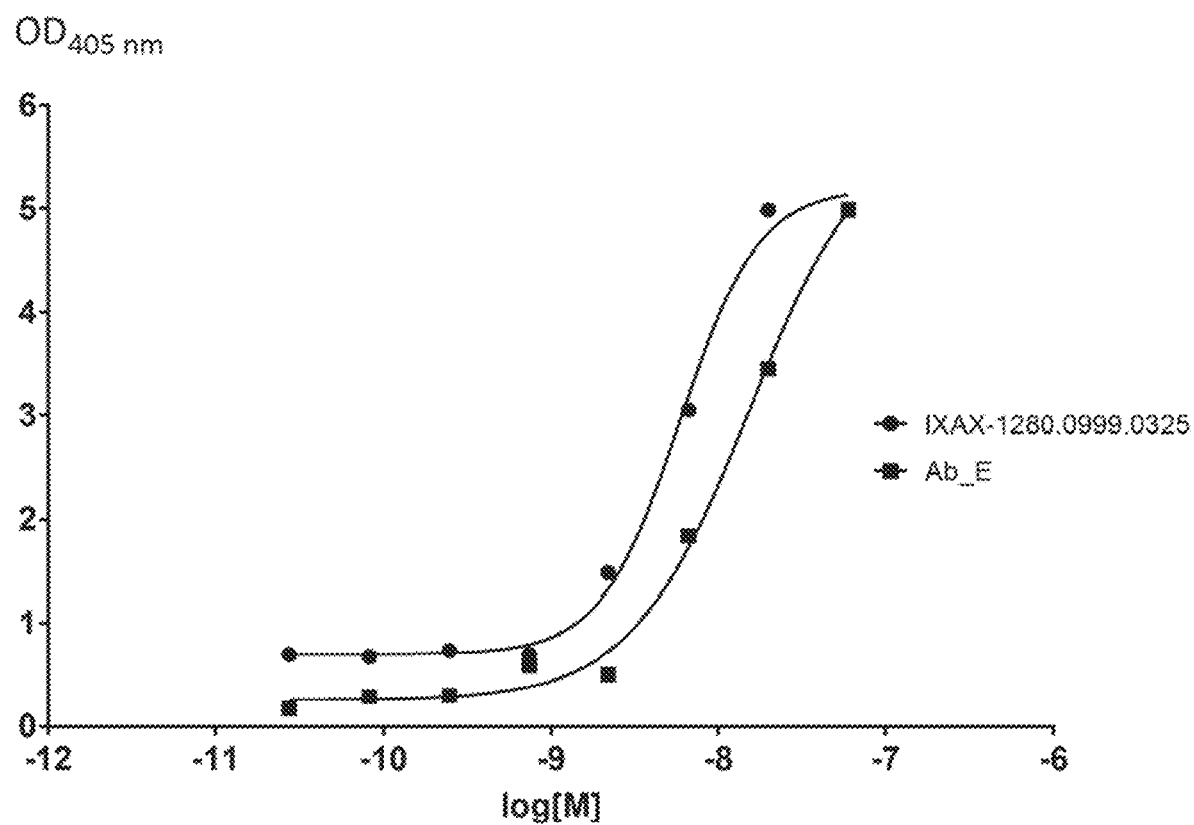
FIG. 40 shows dose response in a chromogenic FVIII mimetic activity Hyphen assay with IXAX-1280.0999.0325 and AbE.

IXAX-1280.0999.0325 consistently achieved greater FVIII mimetic ability than AbE over almost all concentrations. At 60 nM the A405 nm had saturated at 4.988 for both molecules. IXAX-1280.0999.0325 retained this saturation at 20 nM while AbE presented with a decreased A405 nm of 3.457. At the lowest concentration of 0.028 nM, IXAX-1280.0999.0325 displayed over 4-fold greater absorbance than AbE. The calculated EC50 values confirm that IXAX-1280.0999.0325 shows a superior potency when comparing to AbE across a dose response assay. FIG. 40.

TABLE E21-1

Hyphen FXase EC50. Best fit values for log of antibody concentration vs response. Variable slope (4 parameters).

|  | IXAX-1280.0999.0325 | Ab_E |
|---|---|---|
| Bottom | 0.7007 | 0.2581 |
| Top | 5.195 | 5.861 |
| LogEC50 | −8.227 | −7.812 |
| HillSlope | 1.848 | 1.231 |
| EC50 | 5.924e−009 | 1.543e−008 |
| Span | 4.495 | 5.603 |

Materials & Methods

The BIOPHEN FVIII:C (Ref. 221402) kit was used following manufacture's assay protocol. Briefly, FVIII deficient plasma (Helena Biosciences Europe) was diluted 1:40 using Tris-BSA buffer (R4) and 45 µl was added to a clear bottom 96-well plate. 5 µl of bispecific antibody was added to the diluted plasma. 50 µl each of reagent R1 (FX) and R2 (FIXa), pre-incubated to 37° C., was added to each well and incubated at 37° C. for five minutes. Subsequently, 50 µl of reagent R3 (SXa-11, chromogenic reagent) was added, mixed and incubated for an additional five minutes, exactly. Addition of 50 µl 20% acetic acid terminated the reaction. Generation of Factor Xa was monitored through the ability of factor Xa to cleave a specific factor Xa substrate (SXa-11). Cleavage of this substrate releases the coloured product, pNA, which can be monitored using a spectrophotometer at 405 nM and compared to a blank sample.

IXAX-1280.0999.0325 and AbE used in this assay were determined by mass spectrometry to be close to 100% heterodimer, with no (or low levels of) homodimeric contaminants detected.

IXAX-1280.0999.0325 and AbE samples were diluted using a 1:3 dilution series with PBS as diluent. 5 µL volume was added to 45 µL factor VIII deficient plasma. The final concentrations (nM) of each sample in the dilution series (when assayed) were: 60.0, 20.0, 6.67, 2.22, 0.741, 0.247, 0.082, and 0.028. Concentrations were converted to log(M) and plotted. A non-linear regression was plotted on the graph to enable EC50 calculation.

Example 22. Dose Response and Potency in Plasma Coagulation Assay

We evaluated the activated partial thromboplastin time (aPTT) of bispecific antibody AbE against IXAX-1280.0999.0325 using a full antibody concentration dose response (method according to Example 8). Data generated from dose response curves were fitted using a non-linear log[antibody] vs response parameter variable slope model (4 parameter logistic regression model).

Figure 41:
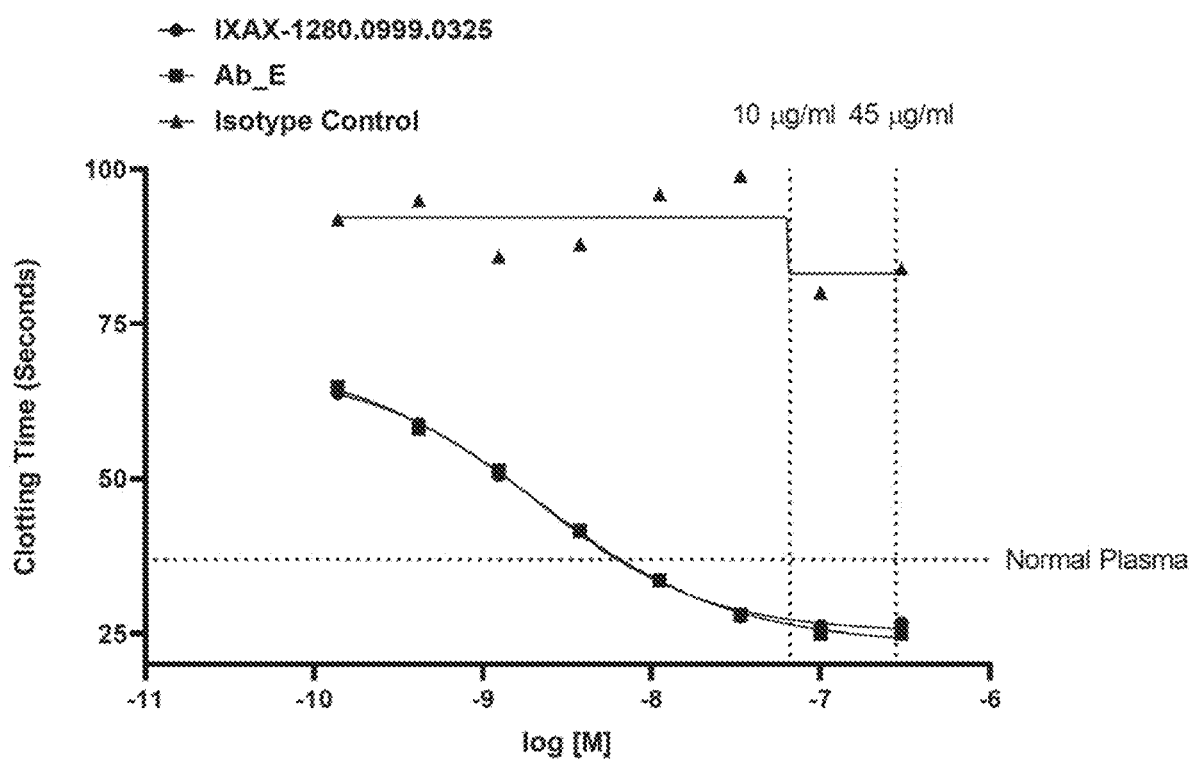
FIG. 41 shows dose response in the aPTT assay with IXAX-1280.0999.0325 and AbE. Vertical dotted lines represent 66.6 nM (10 µg/ml) and 300 nM (45 µg/ml) final antibody concentration; horizontal lines represent aPTT value of normal pooled plasma collected from healthy volunteers.

Over the concentration values analysed we observed equivalent aPTT values (within 10%) for IXAX-1280.0999.0325 compared to AbE at all concentrations analysed (FIG. 41). Dose response curves were compared to a human IgG4 monoclonal antibody isotype control, which demonstrated no haemostatic efficacy. Calculated EC50 values based on aPTT values obtained were 2.1 nM for IXAX-1280.0999.0325 (circle) compared with 2.0 nM for AbE (square).

With respect to a prospective therapeutic range of 30-300 nM, we observe with IXAX-1280.0999.0325 an aPTT dose response curve equivalent to that of AbE.

IXAX-1280.0999.0325 and AbE used in this assay were determined by mass spectrometry to be 100% heterodimer, with no homodimeric contaminants detected.

Example 23. Activity in the Presence of Anti-FVIII Inhibitory Antibodies

Factor VIII replacement therapy can become ineffective for treating patients with haemophilia A if the patient develops alloantibodies against the exogenously administered FVIII. Inhibitory anti-FVIII alloantibodies may block the binding of FIX, phospholipid and von Willebrand factor to FVIII, rendering it inactive.

Advantageously, therapeutic bispecific antibodies are insensitive to the presence of FVIII alloantibodies in a patient's blood, as the alloantibodies have specificity to FVIII. This is confirmed by the ability of a bispecific antibody to functionally restore haemostasis in plasma taken from an inhibitor patient. In this Example, we demonstrate this using two haemostatic assays: activated partial thromboplastin time (aPTT) and Thrombin Generation Assay (TGA) using plasma from a patient with haemophilia A having inhibitory alloantibodies (referred to as "inhibitor plasma"). A restoration of clotting time indicated that the bispecific antibodies analysed are functional in the presence of a FVIII inhibitory alloantibody. Thus, the data presented here indicate that IXAX-1280.0999.0325 and IXAX-1441.0999.0325 will be able to functionally rescue clotting time in patients who have inhibitory alloantibodies against FVIII.

The Bethesda assay or the Nijmegen-Modified Bethesda assay is used measure the titre of alloantibodies against FVIII. In these assays, different dilutions of patient's plasma are mixed with an equal volume of 'normal' plasma and left to incubate for a period of time and the level of FVIII is measured. Presence of an inhibitor is indicated when a decrease in residual FVIII is observed. The unit of measurement in these assays are known as Bethesda Units (BU)—a higher BU indicating greater inhibition and lower residual FVIII activity. The experiments described here used patient plasma having a specific inhibitor level of 70 BU.

aPTT

Figure 42:
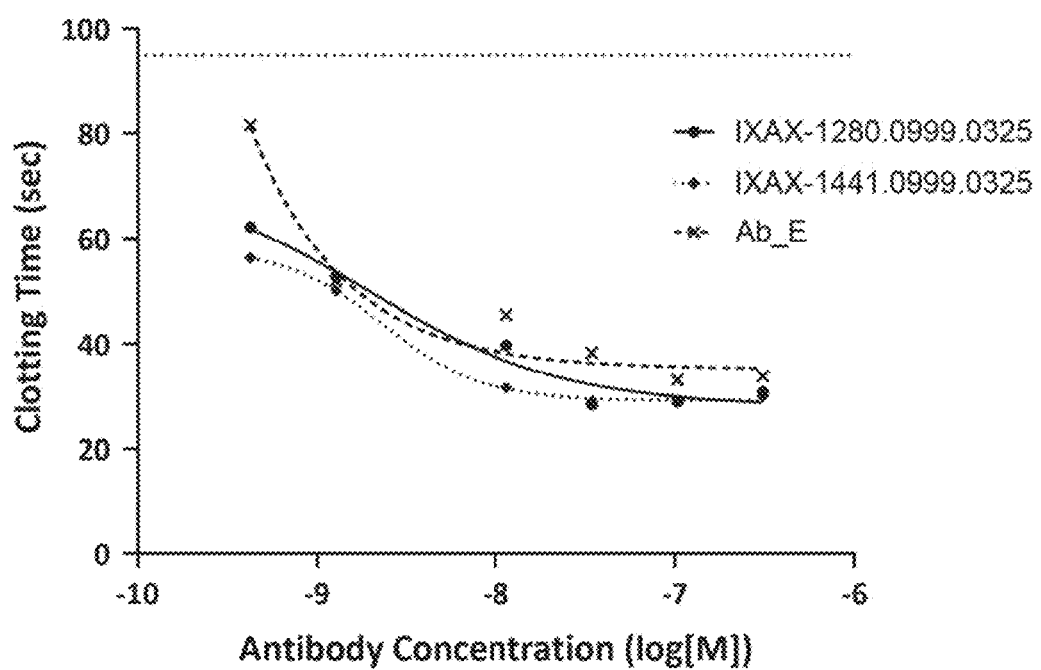
FIG. 42 presents results of aPTT clotting time assays investigating the effect of bispecific antibodies IXAX-1280.0999.0325 (circle), IXAX-1441.0999.0325 (diamond) and AbE (cross) in inhibitor plasma. Dose responses are shown for these antibodies in a one-stage aPTT clotting assay using plasma obtained from a patient with haemophilia A demonstrating a specific inhibitor level of 70 BU to FVIII. Dotted horizontal line indicates the clotting time of the inhibitor plasma spiked with a human IgG4 isotype control.

IgG4 bispecific antibodies IXAX-1280.0999.0325, IXAX-1441.0999.0325 and AbE were expressed in CHO cells then purified by Protein A chromatography followed by cation exchange chromatography to separate active heterodimer from contaminating homodimers and analysed at six different concentrations 300, 100, 33.3, 11.1, 3.7 and 1.23 nM by aPTT. aPTT was carried out as per Example 8. Data generated from dose response curves were fitted using a non-linear log[antibody] vs response parameter variable slope model (4 parameter logistic regression model). Both IXAX-1280.0999.0325 and IXAX-1441.0999.0325 IgG4 antibodies were able to rescue the clotting defect in the inhibitor patient sample in a similar manner to AbE. FIG. 42.

Thrombin Generation Assay

Thrombin generation in inhibitor plasma (70 BU) was determined using for IXAX-1280.0999.0325, IXAX-1441.0999.0325 and AbE IgG4 bispecific antibodies following purification on Protein A followed by cation exchange chromatography. A thrombin generation assay was used as per Example 13. A thrombin peak was observed for all bispecific antibodies, indicating that both IXAX-1280.0999.0325 and IXAX-1441.0999.0325 can functionally restore haemostasis in plasma containing inhibitory alloantibodies to FVIII, in a similar way to AbE.

Figure 43:
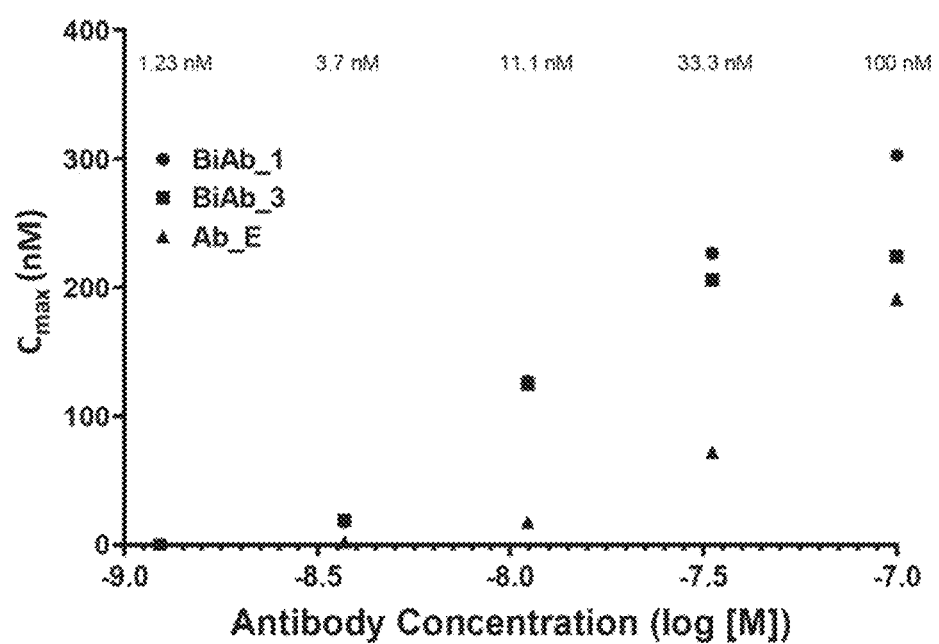
FIG. 43 shows a thrombin peak height (Cmax) dose response for IgG4 bispecific antibodies IXAX-1280.0999.0325, IXAX-1441.0999.0325 and AbE (all purified on Protein A, followed by cation exchange chromatography) in a thrombin generation assay with plasma obtained from a patient with haemophilia A demonstrating a specific inhibitor level of 70 BU to FVIII. Bispecific antibody concentrations in nM are indicated for each dilution.
Figure 44:
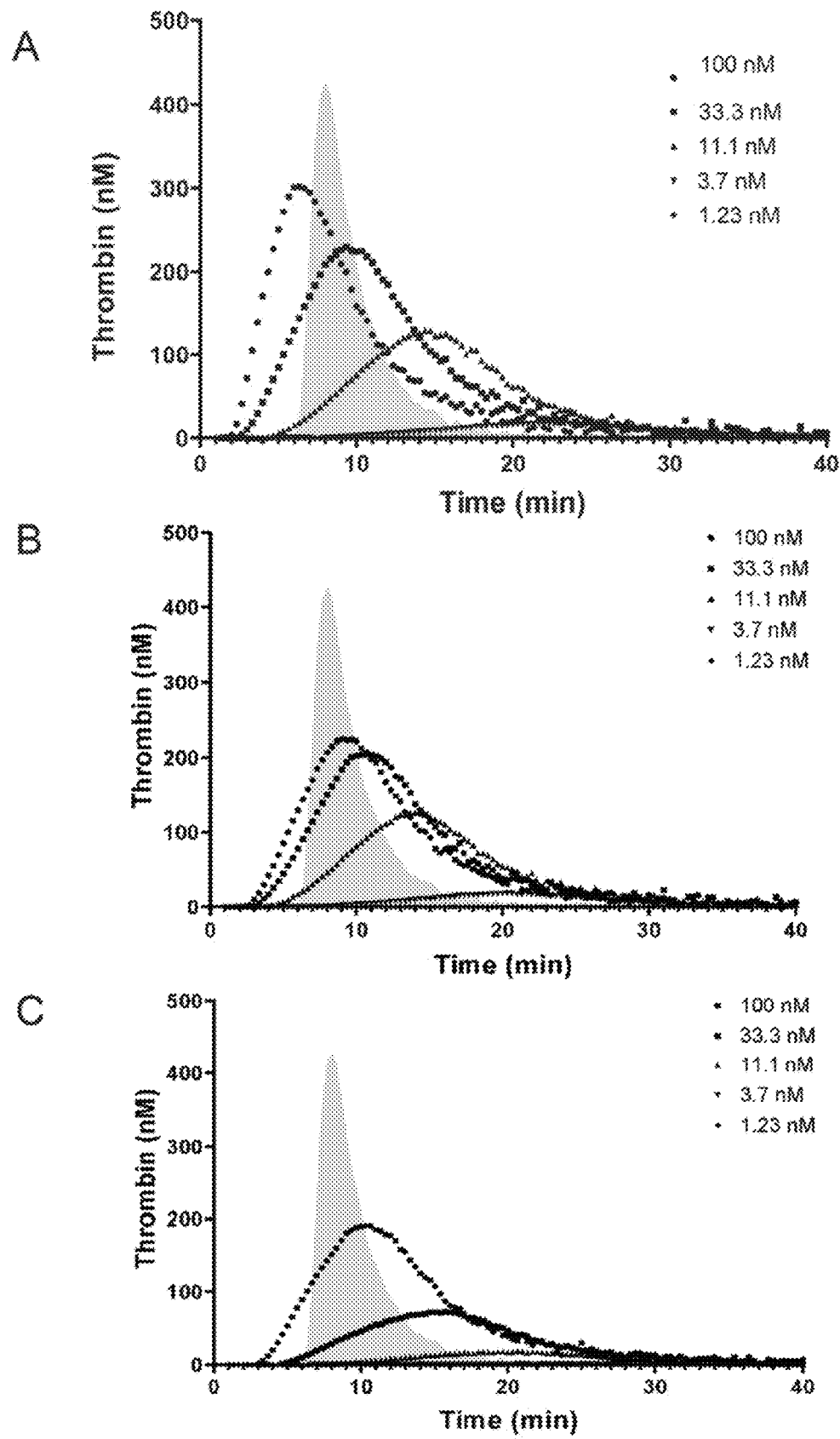
FIG. 44 shows a dose response for IgG4 bispecific antibodies (A) IXAX-1280.0999.0325, (B) IXAX-1441.0999.0325 and (C) AbE (all purified on Protein A, followed by cation exchange chromatography) in a thrombin generation assay with plasma obtained from a patient with haemophilia A demonstrating a specific inhibitor level of 70 BU to FVIII. Bispecific antibody concentrations analysed are 100, 33.3, 11.1, 3.7 and 1.23 nM. Grey shaded area indicates thrombin generation of normal pooled plasma. TGA trigger is FIXa.

A dose response for each bispecific antibody was carried out and the peak thrombin height (Cmax) was determined. FIG. 43. In the concentration range analysed, the Cmax dose responses for IXAX-1280.0999.0325 and IXAX-1441.0999.0325 were greater than the Cmax of AbE, indicating greater thrombin burst, and the Tmax dose responses for IXAX-1280.0999.0325 and IXAX-1441.0999.0325 were lower than the Tmax of AbE, indicating faster thrombin burst. FIG. 44.

REFERENCES

1 Kitazawa et al., A bispecific antibody to factors IXa and X restores factor VIII hemostatic activity in hemophilia A model, Nat. Med. 18(10):1570-1574 2012

2 Sampei et al., Identification and Multidimensional Optimization of an Asymmetric Bispecific IgG Antibody Mimicking the Function of Factor VIII Cofactor Activity, PLOS ONE 8(2) 2013

3 WHO Drug Information, Recommended INN List 75, Vol 30 No 1 2016

4 Uchida et al., A first-in-human phase 1 study of ACE910, a novel factor VIII-mimetic bispecific antibody, in healthy subjects, Blood 127(13):1633-1641 2015

5 Shima et al., Factor VIII-Mimetic Function of Humanized Bispecific Antibody in Hemophilia A, N Engl J Med 374:2044-2053 2016

6 Diagram by Dr Graham Beards, based on information in Pallister CJ and Watson MS (2010) Haematology, UK: Scion Publishing, pp. 336-347 ISBN: 1-904842-39-9

7 Fay, Activation of factor VIII and mechanisms of cofactor action, Blood Reviews, 18:1-15 2004

8 Brandstetter et al., X-ray structure of clotting factor IXa: Active site and module structure related to Xase activity and hemophilia B, PNAS 92:9796-9800 1995

9 Bowen, Haemophilia A and haemophilia B: molecular insights, Mol. Pathol. 55:1-18 2002

10 Tripodi, A. Thrombin Generation Assay and Its Application in the Clinical Laboratory, Clinical Chemistry 62(5):699-707 2016

11 Kintigh, Monagle & Ignjatovic, A review of commercially available thrombin generation assays, Res Pract Thromb Haemost 2:42-48 2018.

12 Young, et al., Thrombin generation and whole blood viscoelastic assays in the management of hemophilia: current state of art and future perspectives, Blood 121 (11):1944-1950 2013

13 Lefranc MP, IMGT unique numbering for immunoglobulin and T cell receptor variable domains and Ig superfamily V-like domains, Dev Comp Immunol. 27(1):55-77 2003

14 Ridgway et al., Protein Eng. 9:617-621 1996

15 Davis J H et al., PEDS 23:195-202

16 Smith, et al., A novel, native-format bispecific antibody triggering T-cell killing of B-cells is robustly active in mouse tumor models and cynomolgus monkeys, Scientific Reports 5:17943 2015

17 FDA multidisciplinary review of emicizumab, Center for Drug Evaluation and Research, application number 761083Orig1s000 (BLA 761083, Hemlibra®, emicizumab-kxwh), currently available at accessdata.fda.gov/drugsatfda_docs/nda/2017/761083Orig1s000MultidisciplineR.pdf FIXa Binding Arm VH Domain Polypeptide Sequences

TABLE S-9A

Anti-FIXa VH domain sequences and CRDs

| Ab VH | HCDR1 | HCDR2 | HCDR3 | VH nucleotide sequence | VH amino acid sequence |
|---|---|---|---|---|---|
| N0192H | SEQ ID NO: 11 GFTFSSYW | SEQ ID NO: 12 IKQDGSEK | SEQ ID NO: 13 AREGYSSSSYYGMDV | SEQ ID NO: 14<br>GAGGTGCAGCTGGTGGAGTCTGGGGGAGGCTTGGTCCAGCCTGGGGGGTCCCT<br>GAGACTCTCCTGTGCAGCCTCTGGATTCACCTTTAGTAGCTATTGGATGAGCT<br>GGGTCCGCCAGGCTCCAGGGAAGGGGCTGGAGTGGGTGGCCAACATAAAGCAA<br>GATGGAAGTGAGAAATACTATGTGGACTCTGTGAAGGGCCGATTCACCATCTC<br>CAGAGACAACGCCAAGAACTCACTGTATCTGCAAATGAACAGCCTGAGAGCCG<br>AGGACACGGCTGTGTATTACTGTGCGAGAGAGGGGTATAGCAGTTACTACTAC<br>TACGGTATGGACGTCTGGGGCCAAGGGACCACGGTCACCGTCTCCTCA | SEQ ID NO: 15<br>EVQLVESGGGLVQPGGSL<br>RLSCAASGFTFSSYWMSW<br>VRQAPGKGLEWVANIKQD<br>GSEKYYVDSVKGRFTISR<br>DNAKNSLYLQMNSLRAED<br>TAVYYCAREGYSSYYYYG<br>MDVWGQGTTVTVSS |
| N0212H | SEQ ID NO: 11 GFTFSSYW | SEQ ID NO: 2 INQDGSEK | SEQ ID NO: 3 AREGYSSSSYYGMDV | SEQ ID NO: 16<br>GAGGTGCAGCTGGTGGAGTCTGGGGGAGGCTTGGTCCAGCCTGGGGGGTCCCT<br>GAGACTCTCCTGTGCAGCCTCTGGATTCACCTTTAGTAGCTATTGGATGAGCT<br>GGGTCCGCCAGGCTCCAGGGAAGGGGCTGGAGTGGGTGGCCAACATAAACCAA<br>GATGGAAGTGAGAAATACTATGTGGACTCTGTGAAGGGCCGATTCACCATCTC<br>CAGAGACAACGCCAAGAACTCACTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 17<br>EVQLVESGGGLVQPGGSL<br>RLSCAASGFTFSSYWMSW<br>VRQAPGKGLEWVANINQD<br>GSEKYYVDSVKGRFTISR<br>DNAKNSLYLQMNSLRAED<br>TAVYYCAREGYSSSSYYG<br>MDVWGQGTTVTVSS |
| N0205H | SEQ ID NO: 18 GFIFSSYW | SEQ ID NO: 2 INQDGSEK | SEQ ID NO: 3 AREGYSSSSYYGMDV | SEQ ID NO: 19<br>GAGGTGCAGCTGGTGGAGTCTGGGGGAGGCTTGGTCCAGCCTGGGGGGTCCCT<br>GAGACTCTCCTGTGTGGCATCTGGATTCATCTTTAGTAGCTATTGGATGAGCT<br>GGGTCCGCCAGGCTCCAGGGAAGGGGCTGGAGTGGGTGGCCAATATAAATCAA<br>GATGGAAGTGAGAAATACTATGTGGACTCTGTGAAGGGCCGATTCACCATCTC<br>CAGAGACAACGCCAAGAACTCACTGTATCTGCAAATGAACAGCCTGAGAGCCG<br>AGGACACGGCTGTGTATTACTGTGCGAGAGAGGGGTATAGCAGTTCGTCCTAT<br>TATGGTATGGACGTCTGGGGCCAAGGGACCACGGTCACCGTCTCCTCA | SEQ ID NO: 20<br>EVQLVESGGGLVQPGGSL<br>RLSCVASGFIFSSYWMSW<br>VRQAPGKGLEWVANINQD<br>GSEKYYVDSVKGRFTISR<br>DNAKNSLYLQMNSLRAED<br>TAVYYCAREGYSSSSYYG<br>MDVWGQGTTVTVSS |
| N0211H | SEQ ID NO: 1 GFTFNSYW | SEQ ID NO: 2 INQDGSEK | SEQ ID NO: 3 AREGYSSSSYYGMDV | SEQ ID NO: 21<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAACTCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 22<br>EVQLVESGGGLVQPGGSL<br>RLSCAVSGFTFNSYWMSW<br>VRQAPGKGLEWVANINQD<br>GSEKFYVASVKGRFTISR<br>DNAKNSVYLQMNSLRAED<br>TAVYYCAREGYSSSSYYG<br>MDVWGQGTTVTVSS |
| N0203H | SEQ ID NO: 23 GFTFNNYW | SEQ ID NO: 2 INQDGSEK | SEQ ID NO: 24 AREGYTDSSYYGMDV | SEQ ID NO: 25<br>GAGGTGCAGCTGGTGGAGTCTGGGGGAGGCCTGGTCCAGCCTGGGGGGTCCCT<br>GAGACTCTCCTGTGCAGTCTCTGGATTCACCTTTAATAACTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCATCATCTC<br>CAGAGACAACGCCAAAAATTCAGTGTATCTACAAATGAACAGCCTGAGAGCCG<br>AGGACACGGCTGTGTATTACTGTGCGAGAGAGGGGTATACCGATTCGTCCTAT<br>TATGGAATGGACGTCTGGGGCCAAGGGACCACGGTCTCCGTCTCCTCA | SEQ ID NO: 26<br>EVQLVESGGGLVQPGGSL<br>RLSCAVSGFTFNNYWMSW<br>VRQAPGKGLEWVANINQD<br>GSEKFYVASVKGRFIISR<br>DNAKNSVYLQMNSLRAED<br>TAVYYCAREGYTDSSYYG<br>MDVWGQGTTVSVSS |
| N0128H | SEQ ID NO: 1 GFTFNSYW | SEQ ID NO: 2 INQDGSEK | SEQ ID NO: 3 AREGYSSSSYYGMDV | SEQ ID NO: 4<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCAG | SEQ ID NO: 5<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSSYYG<br>MDVWGQGTTVTVSS |
| N0215H | SEQ ID NO: 11 GFTFSSYW | SEQ ID NO: 12 IKQDGSEK | SEQ ID NO: 3 AREGYSSSSYYGMDV | SEQ ID NO: 27<br>GAGGTGCAGCTGGTGGAGTCTGGGGGAGGCTTGGTCCAGCCTGGGGGGTCCCT<br>GAGACTCTCCTGTGCAGCCTCTGGATTCACCTTTAGTAGCTATTGGATGAGCT<br>GGGTCCGCCAGGCTCCAGGGAAGGGGCTGGAGTGGGTGGCCAACATAAAGCAA<br>GATGGAAGTGAGAAATACTATGTGGACTCTGTGAAGGGCCGATTCACCATCTC<br>CAGAGACAACGCCAAGAACTCACTGTATCTGCAAATGAACAGCCTGAGAGCCG<br>AGGACACGGCTGTGTATTACTGTGCGAGAGAGGGGTATAGCAGTTCGTCCTAC<br>TACGGTATGGACGTCTGGGGCCAAGGGACCACGGTCACCGTCTCCTCA | SEQ ID NO: 28<br>EVQLVESGGGLVQPGGSL<br>RLSCAASGFTFSSYWMSW<br>VRQAPGKGLEWVANIKQD<br>GSEKYYVDSVKGRFTISR<br>DNAKNSLYLQMNSLRAED<br>TAVYYCAREGYSSSSYYG<br>MDVWGQGTTVTVSS |
| N0216H | SEQ ID NO: 1 GFTFNSYW | SEQ ID NO: 2 INQDGSEK | SEQ ID NO: 3 AREGYSSSSYYGMDV | SEQ ID NO: 29<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAACTCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO:<br>EVQLVESGGGFVQPGGSL<br>RLSCAVSGFTFNSYWMSW<br>VRQAPGKGLEWVANINQD<br>GSEKFYVASVKGRFTISR<br>DNAKNSVYLQMNSLRAED<br>TAVYYCAREGYSSSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0217H | SEQ ID NO: 1 GFTFNSYW | SEQ ID NO: 2 INQDGSEK | SEQ ID NO: 3 AREGYSSSSYYGMDV | SEQ ID NO: 31<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAACTCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 32<br>EVQLVESGGGLVQPGGSL<br>RLSCAVSGFTFNSYWMSW<br>VRQAPGKGLEWVANINQD<br>GSEKFYVASVKGRFTMSR<br>DNAKNSVYLQMNSLRAED<br>TAVYYCAREGYSSSSYYG<br>MDVWGQGTTVTVSS |
| N0218H | SEQ ID NO: 1 GFTFNSYW | SEQ ID NO: 2 INQDGSEK | SEQ ID NO: 3 AREGYSSSSYYGMDV | SEQ ID NO: 33<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAAATCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 34<br>EVQLVESGGGLVQPGGSL<br>RLSCAVSGFTFNSYWMSW<br>VRQAPGKGLEWVANINQD<br>GSEKFYVASVKGRFTISR<br>DNAKNSVYLQMNSLRAED<br>TAVYYCAREGYSSSSYYG<br>MDVWGQGTTVTVSS |
| N0219H | SEQ ID NO: 1 GFTFNSYW | SEQ ID NO: 2 INQDGSEK | SEQ ID NO: 3 AREGYSSSSYYGMDV | SEQ ID NO: 35<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAACTCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 36<br>EVQLVESGGGLVQPGGSL<br>RLSCAVSGFTFNSYWMSW<br>VRQAPGKGLEWVANINQD<br>GSEKFYVASVKGRFTISR<br>DNAKNSVYVQMNSLRAED<br>TAVYYCAREGYSSSSYYG<br>MDVWGQGTTVTVSS |
| N0220H | SEQ ID NO: 1 GFTFNSYW | SEQ ID NO: 2 INQDGSEK | SEQ ID NO: 3 AREGYSSSSYYGMDV | SEQ ID NO: 37<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 38<br>EVQLVESGGGFVQPGGSL<br>RLSCAVSGFTFNSYWMSW<br>VRQAPGKGLEWVANINQD<br>GSEKFYVASVKGRFTISR<br>DNAKKSVYVQMNSLRAED<br>TAVYYCAREGYSSSSYYG<br>MDVWGQGTTVTVSS |
| N0221H | SEQ ID NO: 1 GFTFNSYW | SEQ ID NO: 2 INQDGSEK | SEQ ID NO: 3 AREGYSSSSYYGMDV | SEQ ID NO: 39<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAACTCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 40<br>EVQLVESGGGFVQPGGSL<br>RLSCAVSGFTFNSYWMSW<br>VRQAPGKGLEWVANINQD<br>GSEKFYVASVKGRFTMSR<br>DNAKNSVYVQMNSLRAED<br>TAVYYCAREGYSSSSYYG<br>MDVWGQGTTVTVSS |
| N0222H | SEQ ID NO: 1 GFTFNSYW | SEQ ID NO: 2 INQDGSEK | SEQ ID NO: 3 AREGYSSSSYYGMDV | SEQ ID NO: 41<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 42<br>EVQLVESGGGFVQPGGSL<br>RLSCAVSGFTFNSYWMSW<br>VRQAPGKGLEWVANINQD<br>GSEKFYVASVKGRFTMSR<br>DNAKNSVYLQMNSLRAED<br>TAVYYCAREGYSSSSYYG<br>MDVWGQGTTVTVSS |
| N0223H | SEQ ID NO: 1 GFTFNSYW | SEQ ID NO: 2 INQDGSEK | SEQ ID NO: 3 AREGYSSSSYYGMDV | SEQ ID NO: 43<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAACTCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 44<br>EVQLVESGGGLVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSSYYG<br>MDVWGQGTTVTVSS |
| N0224H | SEQ ID NO: 1 GFTFNSYW | SEQ ID NO: 2 INQDGSEK | SEQ ID NO: 3 AREGYSSSSYYGMDV | SEQ ID NO: 45<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAACTCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 46<br>EVQLVESGGGFVQPGGSL<br>RLSCAVSGFTFNSYWMSW<br>VRQAPGKGLEWVANINQD<br>GSEKFYVASVKGRFTMSR<br>DNAKNSVYLQMNSLRAED<br>TAVYYCAREGYSSSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0225H | SEQ ID NO: 1 GFTFNSYW | SEQ ID NO: 2 INQDGSEK | SEQ ID NO: 3 AREGYSSSSYYGMDV | SEQ ID NO: 47<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAAATCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 48<br>EVQLVESGGGFVQPGGSL<br>RLSCAVSGFTFNSYWMSW<br>VRQAPGKGLEWVANINQD<br>GSEKFYVASVKGRFTISR<br>DNAKKSVYLQMNSLRAED<br>TAVYYCAREGYSSSSYYG<br>MDVWGQGTTVTVSS |
| N0226H | SEQ ID NO: 1 GFTFNSYW | SEQ ID NO: 2 INQDGSEK | SEQ ID NO: 3 AREGYSSSSYYGMDV | SEQ ID NO: 49<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAACTCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 50<br>EVQLVESGGGFVQPGGSL<br>RLSCAVSGFTFNSYWMSW<br>VRQAPGKGLEWVANINQD<br>GSEKFYVASVKGRFTISR<br>DNAKNSVYVQMNSLRAED<br>TAVYYCAREGYSSSSYYG<br>MDVWGQGTTVTVSS |
| N0227H | SEQ ID NO: 1 GFTFNSYW | SEQ ID NO: 2 INQDGSEK | SEQ ID NO: 3 AREGYSSSSYYGMDV | SEQ ID NO: 51<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATCTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 52<br>EVQLVESGGGLVQPGGSL<br>RLSCAVSGFTFNSYWMSW<br>VRQAPGKGLEWVANINQD<br>GSEKFYVASVKGRFTMSR<br>DNAKKSVYLQMNSLRAED<br>TAVYYCAREGYSSSSYYG<br>MDVWGQGTTVTVSS |
| N0228H | SEQ ID NO: 1 GFTFNSYW | SEQ ID NO: 2 INQDGSEK | SEQ ID NO: 3 AREGYSSSSYYGMDV | SEQ ID NO: 53<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAACTCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 54<br>EVQLVESGGGLVQPGGSL<br>RLSCAVSGFTFNSYWMSW<br>VRQAPGKGLEWVANINQD<br>GSEKFYVASVKGRFTMSR<br>DNAKNSVYVQMNSLRAED<br>TAVYYCAREGYSSSSYYG<br>MDVWGQGTTVTVSS |
| N0229H | SEQ ID NO: 1 GFTFNSYW | SEQ ID NO: 2 INQDGSEK | SEQ ID NO: 3 AREGYSSSSYYGMDV | SEQ ID NO: 55<br>GAGGTGCAGCTGGTGGAGTCTGGGGGAGGCTTGGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATCTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTCCTAT<br>TATGGTATGGACGTCTGGGGCCAAGGGACCACGGTCACCGTCTCCTCA | SEQ ID NO: 56<br>EVQLVESGGGLVQPGGSL<br>RLSCAVSGFTFNSYWMSW<br>VRQAPGKGLEWVANINQD<br>GSEKFYVASVKGRFTISR<br>DNAKKSVYVQMNSLRAED<br>TAVYYCAREGYSSSSYYG<br>MDVWGQGTTVTVSS |
| | SEQ ID NO: 140 HCDR1 consensus GFTFSSYWI GF(T/I)F(S/N)(S/N)YW | SEQ ID NO: 141 HCDR2 consensus INQDGSEK I(N/K)QDGSEK | SEQ ID NO: 142 HCDR3 consensus AREGYSSSSYYGMDV TDYY AREGY(S/T)(S/D)(S/Y)YYGMDV | | |
| N0420H | SEQ ID NO: 1 | SEQ ID NO: 2 | SEQ ID NO: 161 AREGYASSSYYGMDV | SEQ ID NO: 238<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATGCCAGTTCGTCCTAT<br>TATGGTATGGACGTCTGGGGCCAAGGGACCACGGTCACCGTCTCCTCAG | SEQ ID NO: 314<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYASSSYYG<br>MDVWGQGTTVTVSS |
| N0421H | SEQ ID NO: 1 | SEQ ID NO: 2 | SEQ ID NO: 162 AREGYSASSSYYGMDV | SEQ ID NO: 239<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTGCCTCGTCCTAT<br>TATGGTATGGACGTCTGGGGCCAAGGGACCACGGTCACCGTCTCCTCAG | SEQ ID NO: 315<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSASSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0422H | SEQ ID NO: 1 | SEQ ID NO: 2 | SEQ ID NO: 240 AREGYSS ASYYGMD V | SEQ ID NO: 163 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTGCCTCCTAT TATGGTATGGACGTCTGGGGCCAAGGGACCACGGTCACCGTCTCCTCAG | SEQ ID NO: 316 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSASYYG MDVWGQGTTVTVSS |
| N0423H | SEQ ID NO: 1 | SEQ ID NO: 2 | SEQ ID NO: 241 AREGYSS SAYYGMD V | SEQ ID NO: 164 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGGCCTAT TATGGTATGGACGTCTGGGGCCAAGGGACCACGGTCACCGTCTCCTCAG | SEQ ID NO: 317 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSAYYG MDVWGQGTTVTVSS |
| N0430H | SEQ ID NO: 1 | SEQ ID NO: 2 | SEQ ID NO: 242 AREGYSS CSYYGMD V | SEQ ID NO: 165 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTGCTCCTAT TATGGTATGGACGTCTGGGGCCAAGGGACCACGGTCACCGTCTCCTCAG | SEQ ID NO: 318 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSCSYYG MDVWGQGTTVTVSS |
| N0431H | SEQ ID NO: 1 | SEQ ID NO: 2 | SEQ ID NO: 243 AREGYSS DSYYGMD V | SEQ ID NO: 166 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTGACTCCTAT TATGGTATGGACGTCTGGGGCCAAGGGACCACGGTCACCGTCTCCTCAG | SEQ ID NO: 319 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSDSYYG MDVWGQGTTVTVSS |
| N0432H | SEQ ID NO: 1 | SEQ ID NO: 2 | SEQ ID NO: 244 AREGYSS ESYYGMD V | SEQ ID NO: 167 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTGAGTCCTAT TATGGTATGGACGTCTGGGGCCAAGGGACCACGGTCACCGTCTCCTCAG | SEQ ID NO: 320 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSESYYG MDVWGQGTTVTVSS |
| N0433H | SEQ ID NO: 1 | SEQ ID NO: 2 | SEQ ID NO: 245 AREGYSS FSYYGMD V | SEQ ID NO: 168 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTTCTCCTAT TATGGTATGGACGTCTGGGGCCAAGGGACCACGGTCACCGTCTCCTCAG | SEQ ID NO: 321 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSFSYYG MDVWGQGTTVTVSS |
| N0434H | SEQ ID NO: 1 | SEQ ID NO: 2 | SEQ ID NO: 246 AREGYSS GSYYGMD V | SEQ ID NO: 169 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTGGCTCCTAT TATGGTATGGACGTCTGGGGCCAAGGGACCACGGTCACCGTCTCCTCAG | SEQ ID NO: 322 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSGSYYG MDVWGQGTTVTVSS |
| N0435H | SEQ ID NO: 1 | SEQ ID NO: 2 | SEQ ID NO: 247 AREGYSS HSYYGMD V | SEQ ID NO: 170 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTCACTCCTAT TATGGTATGGACGTCTGGGGCCAAGGGACCACGGTCACCGTCTCCTCAG | SEQ ID NO: 323 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSHSYYG MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0436H | SEQ ID NO: 1 | SEQ ID NO: 2 | SEQ ID NO: 171 AREGYSS ISYYGMD V | SEQ ID NO: 248<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCTCCTAT<br>TATGGTATGGACGTCTGGGGCCAAGGGACCACGGTCACCGTCTCCTCAG | SEQ ID NO: 324<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSISYYG<br>MDVWGQGTTVTVSS |
| N0437H | SEQ ID NO: 1 | SEQ ID NO: 2 | SEQ ID NO: 172 AREGYSS KSYYGMD V | SEQ ID NO: 249<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTAAGTCCTAT<br>TATGGTATGGACGTCTGGGGCCAAGGGACCACGGTCACCGTCTCCTCAG | SEQ ID NO: 325<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSKSYYG<br>MDVWGQGTTVTVSS |
| N0438H | SEQ ID NO: 1 | SEQ ID NO: 2 | SEQ ID NO: 173 AREGYSS LSYYGMD V | SEQ ID NO: 250<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTCTGTCCTAT<br>TATGGTATGGACGTCTGGGGCCAAGGGACCACGGTCACCGTCTCCTCAG | SEQ ID NO: 326<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSLSYYG<br>MDVWGQGTTVTVSS |
| N0439H | SEQ ID NO: 1 | SEQ ID NO: 2 | SEQ ID NO: 174 AREGYSS MSYYGMD V | SEQ ID NO: 251<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATGTCCTAT<br>TATGGTATGGACGTCTGGGGCCAAGGGACCACGGTCACCGTCTCCTCAG | SEQ ID NO: 327<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSMSYYG<br>MDVWGQGTTVTVSS |
| N0440H | SEQ ID NO: 1 | SEQ ID NO: 2 | SEQ ID NO: 175 AREGYSS NSYYGMD V | SEQ ID NO: 252<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTAACTCCTAT<br>TATGGTATGGACGTCTGGGGCCAAGGGACCACGGTCACCGTCTCCTCAG | SEQ ID NO: 328<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSNSYYG<br>MDVWGQGTTVTVSS |
| N0441H | SEQ ID NO: 1 | SEQ ID NO: 2 | SEQ ID NO: 176 AREGYSS PSYYGMD V | SEQ ID NO: 253<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTCCCTCCTAT<br>TATGGTATGGACGTCTGGGGCCAAGGGACCACGGTCACCGTCTCCTCAG | SEQ ID NO: 329<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSPSYYG<br>MDVWGQGTTVTVSS |
| N0442H | SEQ ID NO: 1 | SEQ ID NO: 2 | SEQ ID NO: 177 AREGYSS QSYYGMD V | SEQ ID NO: 254<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTCAGTCCTAT<br>TATGGTATGGACGTCTGGGGCCAAGGGACCACGGTCACCGTCTCCTCAG | SEQ ID NO: 340<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSQSYYG<br>MDVWGQGTTVTVSS |
| N0443H | SEQ ID NO: 1 | SEQ ID NO: 2 | SEQ ID NO: 178 AREGYSS RSYYGMD V | SEQ ID NO: 255<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTAGATCCTAT<br>TATGGTATGGACGTCTGGGGCCAAGGGACCACGGTCACCGTCTCCTCAG | SEQ ID NO: 341<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSRSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0444H | SEQ ID NO: 1 | SEQ ID NO: 2 | SEQ ID NO: 179 AREGYSS TSYYGMD V | SEQ ID NO: 256<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTACCTCCTAT<br>TATGGTATGGACGTCTGGGGCCAAGGGACCACGGTCACCGTCTCCTCAG | SEQ ID NO: 342<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSTSYYG<br>MDVWGQGTTVTSS |
| N0445H | SEQ ID NO: 1 | SEQ ID NO: 2 | SEQ ID NO: 180 AREGYSS VSYYGMD V | SEQ ID NO: 257<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTGTGTCCTAT<br>TATGGTATGGACGTCTGGGGCCAAGGGACCACGGTCACCGTCTCCTCAG | SEQ ID NO: 343<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSVSYYG<br>MDVWGQGTTVTSS |
| N0446H | SEQ ID NO: 1 | SEQ ID NO: 2 | SEQ ID NO: 181 AREGYSS WSYYGMD V | SEQ ID NO: 258<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTGGTCCTAT<br>TATGGTATGGACGTCTGGGGCCAAGGGACCACGGTCACCGTCTCCTCAG | SEQ ID NO: 344<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSWSYYG<br>MDVWGQGTTVTSS |
| N0447H | SEQ ID NO: 1 | SEQ ID NO: 2 | SEQ ID NO: 182 AREGYSS YSYYGMD V | SEQ ID NO: 259<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTACTCCTAT<br>TATGGTATGGACGTCTGGGGCCAAGGGACCACGGTCACCGTCTCCTCAG | SEQ ID NO: 345<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSYSYYG<br>MDVWGQGTTVTSS |
| N0448H | SEQ ID NO: 1 | SEQ ID NO: 2 | SEQ ID NO: 183 AREGYSS SCYYGMD V | SEQ ID NO: 260<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTGCTAT<br>TATGGTATGGACGTCTGGGGCCAAGGGACCACGGTCACCGTCTCCTCAG | SEQ ID NO: 346<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSCYYG<br>MDVWGQGTTVTSS |
| N0449H | SEQ ID NO: 1 | SEQ ID NO: 2 | SEQ ID NO: 184 AREGYSS SDYYGMD V | SEQ ID NO: 261<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGGACTAT<br>TATGGTATGGACGTCTGGGGCCAAGGGACCACGGTCACCGTCTCCTCAG | SEQ ID NO: 347<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSDYYG<br>MDVWGQGTTVTSS |
| N0450H | SEQ ID NO: 1 | SEQ ID NO: 2 | SEQ ID NO: 185 AREGYSS SEYYGMD V | SEQ ID NO: 262<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGGAGTAT<br>TATGGTATGGACGTCTGGGGCCAAGGGACCACGGTCACCGTCTCCTCAG | SEQ ID NO: 348<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSEYYG<br>MDVWGQGTTVTSS |
| N0451H | SEQ ID NO: 1 | SEQ ID NO: 2 | SEQ ID NO: 186 AREGYSS SFYYGMD V | SEQ ID NO: 263<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTTCTAT<br>TATGGTATGGACGTCTGGGGCCAAGGGACCACGGTCACCGTCTCCTCAG | SEQ ID NO: 349<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSFYYG<br>MDVWGQGTTVTSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0452H | SEQ ID NO: 1 | SEQ ID NO: 2 | SEQ ID NO: 187 AREGYSS SGYYGMD V | SEQ ID NO: 264 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGGGGTAT TATGGTATGGACGTCTGGGGCCAAGGGACCACGGTCACCGTCTCCTCAG | SEQ ID NO: 350 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSGYYG MDVWGQGTTVTVSS |
| N0453H | SEQ ID NO: 1 | SEQ ID NO: 2 | SEQ ID NO: 188 AREGYSS SHYYGMD V | SEQ ID NO: 265 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGCACTAT TATGGTATGGACGTCTGGGGCCAAGGGACCACGGTCACCGTCTCCTCAG | SEQ ID NO: 351 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSHYYG MDVWGQGTTVTVSS |
| N0454H | SEQ ID NO: 1 | SEQ ID NO: 2 | SEQ ID NO: 189 AREGYSS SIYYGMD V | SEQ ID NO: 266 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGATCTAT TATGGTATGGACGTCTGGGGCCAAGGGACCACGGTCACCGTCTCCTCAG | SEQ ID NO: 352 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSIYYG MDVWGQGTTVTVSS |
| N0455H | SEQ ID NO: 1 | SEQ ID NO: 2 | SEQ ID NO: 190 AREGYSS SKYYGMD V | SEQ ID NO: 267 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGAAGTAT TATGGTATGGACGTCTGGGGCCAAGGGACCACGGTCACCGTCTCCTCAG | SEQ ID NO: 353 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSKYYG MDVWGQGTTVTVSS |
| N0456H | SEQ ID NO: 1 | SEQ ID NO: 2 | SEQ ID NO: 191 AREGYSS SLYYGMD V | SEQ ID NO: 268 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGCTGTAT TATGGTATGGACGTCTGGGGCCAAGGGACCACGGTCACCGTCTCCTCAG | SEQ ID NO: 354 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSLYYG MDVWGQGTTVTVSS |
| N0457H | SEQ ID NO: 1 | SEQ ID NO: 2 | SEQ ID NO: 192 AREGYSS SMYYGMD V | SEQ ID NO: 269 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGATGTAT TATGGTATGGACGTCTGGGGCCAAGGGACCACGGTCACCGTCTCCTCAG | SEQ ID NO: 355 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSMYYG MDVWGQGTTVTVSS |
| N0458H | SEQ ID NO: 1 | SEQ ID NO: 2 | SEQ ID NO: 193 AREGYSS SNYYGMD V | SEQ ID NO: 270 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGAACTAT TATGGTATGGACGTCTGGGGCCAAGGGACCACGGTCACCGTCTCCTCAG | SEQ ID NO: 356 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSNYYG MDVWGQGTTVTVSS |
| N0459H | SEQ ID NO: 1 | SEQ ID NO: 2 | SEQ ID NO: 194 AREGYSS SPYYGMD V | SEQ ID NO: 271 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTAGTTCGCCCTAT TATGGTATGGACGTCTGGGGCCAAGGGACCACGGTCACCGTCTCCTCAG | SEQ ID NO: 357 EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYSSSPYYG MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0460H | SEQ ID NO: 1 | SEQ ID NO: 2 | SEQ ID NO: 195 AREGYSS SQYYGMD V | SEQ ID NO: 272<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGAGTAT<br>TATGGTATGGACGTCTGGGGCCAAGGGACCACGGTCACCGTCTCCTCAG | SEQ ID NO: 358<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSQYYG<br>MDVWGQGTTVTVSS |
| N0461H | SEQ ID NO: 1 | SEQ ID NO: 2 | SEQ ID NO: 196 AREGYSS SRYYGMD V | SEQ ID NO: 273<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGAGATAT<br>TATGGTATGGACGTCTGGGGCCAAGGGACCACGGTCACCGTCTCCTCAG | SEQ ID NO: 359<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSRYYG<br>MDVWGQGTTVTVSS |
| N0462H | SEQ ID NO: 1 | SEQ ID NO: 2 | SEQ ID NO: 197 AREGYSS STYYGMD V | SEQ ID NO: 274<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGACCTAT<br>TATGGTATGGACGTCTGGGGCCAAGGGACCACGGTCACCGTCTCCTCAG | SEQ ID NO: 360<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSTYYG<br>MDVWGQGTTVTVSS |
| N0463H | SEQ ID NO: 1 | SEQ ID NO: 2 | SEQ ID NO: 198 AREGYSS SVYYGMD V | SEQ ID NO: 275<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGGTTAT<br>TATGGTATGGACGTCTGGGGCCAAGGGACCACGGTCACCGTCTCCTCAG | SEQ ID NO: 361<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSVYYG<br>MDVWGQGTTVTVSS |
| N0464H | SEQ ID NO: 1 | SEQ ID NO: 2 | SEQ ID NO: 199 AREGYSS SWYYGMD V | SEQ ID NO: 276<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTGGTAT<br>TATGGTATGGACGTCTGGGGCCAAGGGACCACGGTCACCGTCTCCTCAG | SEQ ID NO: 362<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSWYYG<br>MDVWGQGTTVTVSS |
| N0465H | SEQ ID NO: 1 | SEQ ID NO: 2 | SEQ ID NO: 200 AREGYSS SYYYGMD V | SEQ ID NO: 277<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTTCGTACTAT<br>TATGGTATGGACGTCTGGGGCCAAGGGACCACGGTCACCGTCTCCTCAG | SEQ ID NO: 363<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSSSYYYG<br>MDVWGQGTTVTVSS |
| N0467H | SEQ ID NO: 1 | SEQ ID NO: 2 | SEQ ID NO: 201 AREGYCS SSYYGMD V | SEQ ID NO: 278<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGTATTGCAGTTCGTCCTAT<br>TATGGTATGGACGTCTGGGGCCAAGGGACCACGGTCACCGTCTCCTCAG | SEQ ID NO: 364<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYCSSSYYG<br>MDVWGQGTTVTVSS |
| N0468H | SEQ ID NO: 1 | SEQ ID NO: 2 | SEQ ID NO: 202 AREGYDS SSYYGMD V | SEQ ID NO: 279<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATGACAGTTCGTCCTAT<br>TATGGTATGGACGTCTGGGGCCAAGGGACCACGGTCACCGTCTCCTCAG | SEQ ID NO: 365<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYDSSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0469H | SEQ ID NO: 1 | SEQ ID NO: 2 | SEQ ID NO: 203 AREGYES SSYYGMD V | SEQ ID NO: 280<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATGAGAGTTCGTCCTAT TATGGTATGGACGTCTGGGGCCAAGGGACCACGGTCACCGTCTCCTCAG | SEQ ID NO: 366<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYESSSYYG MDVWGQGTTVTVSS |
| N0470H | SEQ ID NO: 1 | SEQ ID NO: 2 | SEQ ID NO: 204 AREGYFS SSYYGMD V | SEQ ID NO: 281<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATTTCAGTTCGTCCTAT TATGGTATGGACGTCTGGGGCCAAGGGACCACGGTCACCGTCTCCTCAG | SEQ ID NO: 367<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYFSSSYYG MDVWGQGTTVTVSS |
| N0471H | SEQ ID NO: 1 | SEQ ID NO: 2 | SEQ ID NO: 205 AREGYGS SSYYGMD V | SEQ ID NO: 282<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATGGCAGTTCGTCCTAT TATGGTATGGACGTCTGGGGCCAAGGGACCACGGTCACCGTCTCCTCAG | SEQ ID NO: 368<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYGSSSYYG MDVWGQGTTVTVSS |
| N0472H | SEQ ID NO: 1 | SEQ ID NO: 2 | SEQ ID NO: 206 AREGYHS SSYYGMD V | SEQ ID NO: 283<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATCACAGTTCGTCCTAT TATGGTATGGACGTCTGGGGCCAAGGGACCACGGTCACCGTCTCCTCAG | SEQ ID NO: 369<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYHSSSYYG MDVWGQGTTVTVSS |
| N0473H | SEQ ID NO: 1 | SEQ ID NO: 2 | SEQ ID NO: 207 AREGYIS SSYYGMD V | SEQ ID NO: 284<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATATCAGTTCGTCCTAT TATGGTATGGACGTCTGGGGCCAAGGGACCACGGTCACCGTCTCCTCAG | SEQ ID NO: 370<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYISSSYYG MDVWGQGTTVTVSS |
| N0474H | SEQ ID NO: 1 | SEQ ID NO: 2 | SEQ ID NO: 208 AREGYKS SSYYGMD V | SEQ ID NO: 285<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAAGAGTTCGTCCTAT TATGGTATGGACGTCTGGGGCCAAGGGACCACGGTCACCGTCTCCTCAG | SEQ ID NO: 371<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYKSSSYYG MDVWGQGTTVTVSS |
| N0465H | SEQ ID NO: 1 | SEQ ID NO: 2 | SEQ ID NO: 209 AREGYLS SSYYGMD V | SEQ ID NO: 286<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATCTGAGTTCGTCCTAT TATGGTATGGACGTCTGGGGCCAAGGGACCACGGTCACCGTCTCCTCAG | SEQ ID NO: 372<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYLSSSYYG MDVWGQGTTVTVSS |
| N0476H | SEQ ID NO: 1 | SEQ ID NO: 2 | SEQ ID NO: 210 AREGYMS SSYYGMD V | SEQ ID NO: 287<br>GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATATGAGTTCGTCCTAT TATGGTATGGACGTCTGGGGCCAAGGGACCACGGTCACCGTCTCCTCAG | SEQ ID NO: 373<br>EVQLVESGGGFVQPGGSL RLSCAVSGFTFNSYWMSW VRQAPGKGLEWVANINQD GSEKFYVASVKGRFTMSR DNAKKSVYVQMNSLRAED TAVYYCAREGYMSSSYYG MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0477H | SEQ ID NO: 1 | SEQ ID NO: 2 | SEQ ID NO: 211 AREGYNSSSYYGMDV | SEQ ID NO: 288<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAACAGTTCGTCCTAT<br>TATGGTATGGACGTCTGGGGCCAAGGGACCACGGTCACCGTCTCCTCAG | SEQ ID NO: 374<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYNSSSYYG<br>MDVWGQGTTVTVSS |
| N0478H | SEQ ID NO: 1 | SEQ ID NO: 2 | SEQ ID NO: 212 AREGYPSSSYYGMDV | SEQ ID NO: 289<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATCCCAGTTCGTCCTAT<br>TATGGTATGGACGTCTGGGGCCAAGGGACCACGGTCACCGTCTCCTCAG | SEQ ID NO: 375<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYPSSSYYG<br>MDVWGQGTTVTVSS |
| N0479H | SEQ ID NO: 1 | SEQ ID NO: 2 | SEQ ID NO: 213 AREGYQSSSYYGMDV | SEQ ID NO: 290<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATCAGAGTTCGTCCTAT<br>TATGGTATGGACGTCTGGGGCCAAGGGACCACGGTCACCGTCTCCTCAG | SEQ ID NO: 376<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYQSSSYYG<br>MDVWGQGTTVTVSS |
| N0480H | SEQ ID NO: 1 | SEQ ID NO: 2 | SEQ ID NO: 214 AREGYRSSSYYGMDV | SEQ ID NO: 291<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGAAGTTCGTCCTAT<br>TATGGTATGGACGTCTGGGGCCAAGGGACCACGGTCACCGTCTCCTCAG | SEQ ID NO: 377<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYRSSSYYG<br>MDVWGQGTTVTVSS |
| N0481H | SEQ ID NO: 1 | SEQ ID NO: 2 | SEQ ID NO: 215 AREGYTSSSYYGMDV | SEQ ID NO: 292<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATACCAGTTCGTCCTAT<br>TATGGTATGGACGTCTGGGGCCAAGGGACCACGGTCACCGTCTCCTCAG | SEQ ID NO: 378<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYTSSSYYG<br>MDVWGQGTTVTVSS |
| N0482H | SEQ ID NO: 1 | SEQ ID NO: 2 | SEQ ID NO: 216 AREGYVSSSYYGMDV | SEQ ID NO: 293<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATGTGAGTTCGTCCTAT<br>TATGGTATGGACGTCTGGGGCCAAGGGACCACGGTCACCGTCTCCTCAG | SEQ ID NO: 379<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYVSSSYYG<br>MDVWGQGTTVTVSS |
| N0483H | SEQ ID NO: 1 | SEQ ID NO: 2 | SEQ ID NO: 217 AREGYWSSSYYGMDV | SEQ ID NO: 294<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATTGAGTTCGTCCTAT<br>TATGGTATGGACGTCTGGGGCCAAGGGACCACGGTCACCGTCTCCTCAG | SEQ ID NO: 380<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYWSSSYYG<br>MDVWGQGTTVTVSS |
| N0484H | SEQ ID NO: 1 | SEQ ID NO: 2 | SEQ ID NO: 218 AREGYYSSSYYGMDV | SEQ ID NO: 295<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATTACAGTTCGTCCTAT<br>TATGGTATGGACGTCTGGGGCCAAGGGACCACGGTCACCGTCTCCTCAG | SEQ ID NO: 381<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYYSSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0485H | SEQ ID NO: 1 | SEQ ID NO: 2 | SEQ ID NO: 219 AREGYSCSSYYGMDV | SEQ ID NO: 296<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTTGCTCGTCCTAT<br>TATGGTATGGACGTCTGGGGCCAAGGGACCACGGTCACCGTCTCCTCAG | SEQ ID NO: 382<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSCSSYYG<br>MDVWGQGTTVTVSS |
| N0486H | SEQ ID NO: 1 | SEQ ID NO: 2 | SEQ ID NO: 220 AREGYSDSSYYGMDV | SEQ ID NO: 297<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTGACTCGTCCTAT<br>TATGGTATGGACGTCTGGGGCCAAGGGACCACGGTCACCGTCTCCTCAG | SEQ ID NO: 383<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSDSSYYG<br>MDVWGQGTTVTVSS |
| N0487H | SEQ ID NO: 1 | SEQ ID NO: 2 | SEQ ID NO: 221 AREGYSESSYYGMDV | SEQ ID NO: 298<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTGAGTCGTCCTAT<br>TATGGTATGGACGTCTGGGGCCAAGGGACCACGGTCACCGTCTCCTCAG | SEQ ID NO: 384<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSESSYYG<br>MDVWGQGTTVTVSS |
| N0488H | SEQ ID NO: 1 | SEQ ID NO: 2 | SEQ ID NO: 223 AREGYSFSSYYGMDV | SEQ ID NO: 299<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTTTCTCGTCCTAT<br>TATGGTATGGACGTCTGGGGCCAAGGGACCACGGTCACCGTCTCCTCAG | SEQ ID NO: 385<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSFSSYYG<br>MDVWGQGTTVTVSS |
| N0489H | SEQ ID NO: 1 | SEQ ID NO: 2 | SEQ ID NO: 224 AREGYSGSSYYGMDV | SEQ ID NO: 300<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTGGCTCGTCCTAT<br>TATGGTATGGACGTCTGGGGCCAAGGGACCACGGTCACCGTCTCCTCAG | SEQ ID NO: 386<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSGSSYYG<br>MDVWGQGTTVTVSS |
| N0490H | SEQ ID NO: 1 | SEQ ID NO: 2 | SEQ ID NO: 225 AREGYSHSSYYGMDV | SEQ ID NO: 301<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTCACTCGTCCTAT<br>TATGGTATGGACGTCTGGGGCCAAGGGACCACGGTCACCGTCTCCTCAG | SEQ ID NO: 387<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSHSSYYG<br>MDVWGQGTTVTVSS |
| N0491H | SEQ ID NO: 1 | SEQ ID NO: 2 | SEQ ID NO: 226 AREGYSISSYYGMDV | SEQ ID NO: 302<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGATATCTCGTCCTAT<br>TATGGTATGGACGTCTGGGGCCAAGGGACCACGGTCACCGTCTCCTCAG | SEQ ID NO: 388<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSISSYYG<br>MDVWGQGTTVTVSS |
| N0492H | SEQ ID NO: 1 | SEQ ID NO: 2 | SEQ ID NO: 227 AREGYSKSSYYGMDV | SEQ ID NO: 303<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAAGTCGTCCTAT<br>TATGGTATGGACGTCTGGGGCCAAGGGACCACGGTCACCGTCTCCTCAG | SEQ ID NO: 389<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSKSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0493H | SEQ ID NO: 1 | SEQ ID NO: 2 | SEQ ID NO: 228 AREGYSLSSYYGMDV | SEQ ID NO: 304<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTCTGTCGTCCTAT<br>TATGGTATGGACGTCTGGGGCCAAGGGACCACGGTCACCGTCTCCTCAG | SEQ ID NO: 390<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSLSSYYG<br>MDVWGQGTTVTVSS |
| N0494H | SEQ ID NO: 1 | SEQ ID NO: 2 | SEQ ID NO: 229 AREGYSMSSYYGMDV | SEQ ID NO: 305<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTATGTCGTCCTAT<br>TATGGTATGGACGTCTGGGGCCAAGGGACCACGGTCACCGTCTCCTCAG | SEQ ID NO: 391<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSMSSYYG<br>MDVWGQGTTVTVSS |
| N0495H | SEQ ID NO: 1 | SEQ ID NO: 2 | SEQ ID NO: 230 AREGYSNSSYYGMDV | SEQ ID NO: 306<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAACTCGTCCTAT<br>TATGGTATGGACGTCTGGGGCCAAGGGACCACGGTCACCGTCTCCTCAG | SEQ ID NO: 392<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSNSSYYG<br>MDVWGQGTTVTVSS |
| N0496H | SEQ ID NO: 1 | SEQ ID NO: 2 | SEQ ID NO: 231 AREGYSPSSYYGMDV | SEQ ID NO: 307<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTCCTCGTCCTAT<br>TATGGTATGGACGTCTGGGGCCAAGGGACCACGGTCACCGTCTCCTCAG | SEQ ID NO: 393<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSPSSYYG<br>MDVWGQGTTVTVSS |
| N0497G | SEQ ID NO: 1 | SEQ ID NO: 2 | SEQ ID NO: 232 AREGYSQSSYYGMDV | SEQ ID NO: 308<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTCAGTCGTCCTAT<br>TATGGTATGGACGTCTGGGGCCAAGGGACCACGGTCACCGTCTCCTCAG | SEQ ID NO: 394<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSQSSYYG<br>MDVWGQGTTVTVSS |
| N0498H | SEQ ID NO: 1 | SEQ ID NO: 2 | SEQ ID NO: 233 AREGYSRSSYYGMDV | SEQ ID NO: 309<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGATCGTCCTAT<br>TATGGTATGGACGTCTGGGGCCAAGGGACCACGGTCACCGTCTCCTCAG | SEQ ID NO: 395<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSRSSYYG<br>MDVWGQGTTVTVSS |
| N0499H | SEQ ID NO: 1 | SEQ ID NO: 2 | SEQ ID NO: 234 AREGYSTSSYYGMDV | SEQ ID NO: 310<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTACCTCGTCCTAT<br>TATGGTATGGACGTCTGGGGCCAAGGGACCACGGTCACCGTCTCCTCAG | SEQ ID NO: 396<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSTSSYYG<br>MDVWGQGTTVTVSS |
| N0500H | SEQ ID NO: 1 | SEQ ID NO: 2 | SEQ ID NO: 235 AREGYSVSSYYGMDV | SEQ ID NO: 311<br>GAGGTGCAGCTGGTGGAGTCTGGGGGAGGCTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTGTGTCGTCCTAT<br>TATGGTATGGACGTCTGGGGCCAAGGGACCACGGTCACCGTCTCCTCAG | SEQ ID NO: 397<br>EVQLVESGGGFVQPGGSL<br>RLSCAVSGFTFNSYWMSW<br>VRQAPGKGLEWVANINQD<br>GSEKFYVASVKGRFTMSR<br>DNAKKSVYVQMNSLRAED<br>TAVYYCAREGYSVSSYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N0501H | SEQ ID NO: 1 | SEQ ID NO: 2 | SEQ ID NO: 236 AREGYSW SSYYGMD V | SEQ ID NO: 312 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATAACGCCAAGAAATCAGTGTATGTACAAATGAACAGCCTGAGAGCCG AGGACACGGCTGTGTATTACTGTGCGAGAGAGGGGTATAGTTGGTCGTCCTAT TATGGTATGGACGTCTGGGGCCAAGGGACCACGGTCACCGTCTCCTCAG | SEQ ID NO: 398 EVQLVESGGGFVQPGGSL RLSCAVSGFTFNSYWMSW VRQAPGKGLEWVANINQD DNAKKSVYVQMNSLRAED TAVYYCAREGYSWSSYYG MDVWGQGTTVTVSS |
| N0502H | SEQ ID NO: 1 | SEQ ID NO: 2 | SEQ ID NO: 237 AREGYSY SSYYGMD V | SEQ ID NO: 313 GAGGTGCAGCTGGTGGAGTCTGGGGGAGGCTTTGTCCAGCCTGGGGGGTCCCT GAGACTCTCCTGTGCAGTCTCTGGATTCACCTTTAATAGCTATTGGATGAGCT GGGTCCGCCAGGCTCCAGGGAAGGGGCTGGAGTGGGTGGCCAACATAAACCAA GATGGAAGTGAGAAATTCTATGTGGCCTCTGTGAAGGGCCGATTCACCATGTC CAGAGACAACGCCAAGAAATCAGTGTATGTACAAATGAACAGCCTGAGAGCCG AGGACACGGCTGTGTATTACTGTGCGAGAGAGGGGTATAGTTACTCGTCCTAT TATGGTATGGACGTCTGGGGCCAAGGGACCACGGTCACCGTCTCCTCAG | SEQ ID NO: 399 EVQLVESGGGFVQPGGSL RLSCAVSGFTFNSYWMSW VRQAPGKGLEWVANINQD GSEKFYVASVKGRFTMSR QDNAKKSVYVQMNSLRAED TAVYYCAREGYSYSSYYG MDVWGQGTTVTVSS |

SEQ ID NO: 400 Consensus HCDR3 of N436 and selected
variants with parent N128H
AREGYSSXSYYGMDV
X is I, L, V, R, W, Q, K, H, E, N, M, S
Representing the N436H CDR3 sequence AREGYSSISYYGMDV in
which the Ile is retained or replaced by Leu, Val, Arg, Trp,
Gln, Lys, His, Glu, Asn, Met or Ser.

SEQ ID NO: 401 Consensus HCDR3 of N436 and selected
variants AREGYSSXSYYGMDV
X is I, L, V, R, W, Q, K, H, E, N or M
Representing the N436H CDR3 sequence AREGYSSISYYGMDV in
which the Ile is retained or replaced by Leu, Val, Arg, Trp,
Gln, Lys, His, Glu, Asn or Met.

SEQ ID NO: 402 Consensus HCDR3 of N436 and selected
hydrophobic or positively charged variants
AREGYSSXSYYGMDV
X is I, L, V, R, W, Q or K
Representing the N436H CDR3 sequence AREGYSSISYYGMDV in
which the Ile is retained or replaced by Leu, Val, Arg, Trp,
Gln or Lys.

SEQ ID NO: 403 Consensus HCDR3 of initial most active
variants AREGYSSXSYYGMDV
X is I, L or V
Representing the N436M CDR3 sequence AREGYSSISYYGMDV in
which the Ile is retained or replaced by Leu or Val.

SEQ ID NO: 406 Consensus HCDR1
GFXGNSYW
X is T or R
Representing the N1280H CDR1 sequence GFRFNSYW (SEQ ID NO: 441) in which the Arg is
retained or replaced by Thr.

SEQ ID NO: 407 Consensus HCDR2
INQX$_1$GX$_2$X$_3$K
X1 is D, G or W. X2 is S or F. X3 is E or R.
Representing the N1280H CDR2 sequence INDGSRK (SEQ ID NO: 436) in which the Asp is
retained or replaced by Gly or Trp, the Ser is retained or replaced by Phe and the
Arg is retained or replaced by Glu.

SEQ ID NO: 634 Consensus HCDR2
INQDGSXK
X is R or E.
Representing the N1280H CDR2 sequence INQDGSRK (SEQ ID NO: 436) in which the Arg is
retained or replaced by Glu.

SEQ ID NO: 408 Consensus HCDR3
AREGYSSX$_1$X$_2$YYGMDV
X1 is S or I. X2 is S or K.
Representing the N1280H CDR3 sequence AREGYSSIKYYGMDV (SEQ ID NO: 433) in
which the Ile is retained or replaced by Ser and the Lys is retained or
replaced by Ser.

SEQ ID NO: 635 Consensus HCDR3
AREGYSSIXYYGMDV
X is K or S.

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| | | | | Reprsenting the N1280H CDR3 sequence AREGYSSIKYYGMDV (SEQ ID NO: 433) in which the Lys is retained or replaced by Ser. | |
| N0511H | SEQ ID NO: 1 | SEQ ID NO: 2 | SEQ ID NO: 433 | SEQ ID NO: 434<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTGAGAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCAAGTAT<br>TATGGTATGGACGTCTGGGGCCAAGGGACCACGGTCACCGTCTCCTCA | SEQ ID NO: 435<br>EVQLVESGGGFVQPGGSL<br>RLSCAVSGFTFNSYWMSW<br>VRQAPGKGLEWVANIKQD<br>GSEKFYVASVKGRFTMSR<br>DNAKKSVYVQMNSLRAED<br>TAVYYCAREGYSSIKYYG<br>MDVWGQGTTVTVSS |
| N1091H | SEQ ID NO: 1 | SEQ ID NO: 436 | SEQ ID NO: 171 | SEQ ID NO: 437<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTAGAAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCTCCTAT<br>TATGGTATGGACGTCTGGGGCCAAGGGACCACGGTCACCGTCTCCTCA | SEQ ID NO: 438<br>EVQLVESGGGFVQPGGSL<br>RLSCAVSGFTFNSYWMSW<br>VRQAPGKGLEWVANINQD<br>GSRKFYVASVKGRFTMSR<br>DNAKKSVYVQMNSLRAED<br>TAVYYCAREGYSISSYYG<br>MDVWGQGTTVTVSS |
| N1172H | SEQ ID NO: 1 | SEQ ID NO: 436 | SEQ ID NO: 433 | SEQ ID NO: 439<br>GAGGTGCAGCTGGTGGAGTCTGGGGGAGGCTTTGTCCAGCCTGGGGGGTCCCT<br>GAGACTCTCCTGTGCAGTCTCTGGATTCACCTTTAATAGCTATTGGATGAGCT<br>GGGTCCGCCAGGCTCCAGGGAAGGGGCTGGAGTGGGTGGCCAACATAAACCAA<br>GATGGAAGTAGAAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCAAGTAT<br>TATGGTATGGACGTCTGGGGCCAAGGGACCACGGTCACCGTCTCCTCA | SEQ ID NO: 440<br>EVQLVESGGGFVQPGGSL<br>RLSCAVSGFTFNSYWMSW<br>VRQAPGKGLEWVANINQD<br>GSRKFYVASVKGRFTMSR<br>DNAKKSVYVQMNSLRAED<br>TAVYYCAREGYSSIKYYG<br>MDVWGQGTTVTVSS |
| N1280H | SEQ ID NO: 441 | SEQ ID NO: 436 | SEQ ID NO: 433 | SEQ ID NO: 442<br>GAGGTGCAGCTGGTGGAGTCTGGGGGAGGCTTTGTCCAGCCTGGGGGGTCCCT<br>GAGACTCTCCTGTGCAGTCTCTGGATTCAGATTTAATAGCTATTGGATGAGCT<br>GGGTCCGCCAGGCTCCAGGGAAGGGGCTGGAGTGGGTGGCCAACATAAACCAA<br>GATGGAAGTAGAAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCAAGTAT<br>TATGGTATGGACGTCTGGGGCCAAGGGACCACGGTCACCGTCTCCTCA | SEQ ID NO: 443<br>EVQLVESGGGFVQPGGSL<br>RLSCAVSGFRFNSYWMSW<br>VRQAPGKGLEWVANINQD<br>GSRKFYVASVKGRFTMSR<br>DNAKKSVYVQMNSLRAED<br>TAVYYCAREGYSSIKYYG<br>MDVWGQGTTVTVSS |
| N1314H | SEQ ID NO: 441 | SEQ ID NO: 444 INQGGSRK | SEQ ID NO: 433 | SEQ ID NO: 445<br>GAGGTGCAGCTGGTGGAGTCTGGGGGAGGCTTTGTCCAGCCTGGGGGGTCCCT<br>GAGACTCTCCTGTGCAGTCTCTGGATTCAGATTTAATAGCTATTGGATGAGCT<br>GGGTCCGCCAGGCTCCAGGGAAGGGGCTGGAGTGGGTGGCCAACATAAACCAA<br>GGCGGAAGTAGAAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCAAGTAT<br>TATGGTATGGACGTCTGGGGCCAAGGGACCACGGTCACCGTCTCCTCA | SEQ ID NO: 446<br>EVQLVESGGGFVQPGGSL<br>RLSCAVSGFRFNSYWMSW<br>VRQAPGKGLEWVANINQG<br>GSRKFYVASVKGRFTMSR<br>DNAKKSVYVQMNSLRAED<br>TAVYYCAREGYSSIKYYG<br>MDVWGQGTTVTVSS |
| N1327H | SEQ ID NO: 441 | SEQ ID NO: 447 INQWGSRK | SEQ ID NO: 433 | SEQ ID NO: 448<br>GAGGTGCAGCTGGTGGAGTCTGGGGGAGGCTTTGTCCAGCCTGGGGGGTCCCT<br>GAGACTCTCCTGTGCAGTCTCTGGATTCAGATTTAATAGCTATTGGATGAGCT<br>GGGTCCGCCAGGCTCCAGGGAAGGGGCTGGAGTGGGTGGCCAACATAAACCAA<br>TGGGGAAGTAGAAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCAAGTAT<br>TATGGTATGGACGTCTGGGGCCAAGGGACCACGGTCACCGTCTCCTCA | SEQ ID NO: 449<br>EVQLVESGGGFVQPGGSL<br>RLSCAVSGFRFNSYWMSW<br>VRQAPGKGLEWVANINQW<br>GSRKFYVASVKGRFTMSR<br>DNAKKSVYVQMNSLRAED<br>TAVYYCAREGYSSIKYYG<br>MDVWGQGTTVTVSS |
| N1333H | SEQ ID NO: 441 | SEQ ID NO: 450 INQDGFRK | SEQ ID NO: 433 | SEQ ID NO: 451<br>GAGGTGCAGCTGGTGGAGTCTGGGGGAGGCTTTGTCCAGCCTGGGGGGTCCCT<br>GAGACTCTCCTGTGCAGTCTCTGGATTCAGATTTAATAGCTATTGGATGAGCT<br>GGGTCCGCCAGGCTCCAGGGAAGGGGCTGGAGTGGGTGGCCAACATAAACCAA<br>GATGGATTCAGAAAATTCTATGTGGCCTCTGTGAAGGGCCGATTCACCATGTC<br>CAGAGACAACGCCAAGAAATCAGTGTATGTACAAATGAACAGCCTGAGAGCCG<br>AGGACACGGCTGTGTATTACTGTGCGAGAGAGGGGTATAGTAGTATCAAGTAT<br>TATGGTATGGACGTCTGGGGCCAAGGGACCACGGTCACCGTCTCCTCA | SEQ ID NO: 452<br>EVQLVESGGGFVQPGGSL<br>RLSCAVSGFRFNSYWMSW<br>VRQAPGKGLEWVANINQD<br>GFRKFYVASVKGRFTMSR<br>DNAKKSVYVQMNSLRAED<br>TAVYYCAREGYSSIKYYG<br>MDVWGQGTTVTVSS |
| N1454H | SEQ ID NO: 441 | SEQ ID NO:436 | SEQ ID NO: 433 | SEQ ID NO: 453<br>GAGGTGCAGCTGGTTGAATCTGGCGGCGGATTTGTTCAGCCTGGCGGCTCTCT<br>GAGACTGAGCTGTGCCGTGTCCGGCTTCCGGTTCAACAGCTACTGGATGTCCT<br>GGGTCCGACAGGCCCCTGGCAAAGGATTGGAGTGGGTCGCCAACATCAACCAG<br>GACGGCAGCCGGAAGTTTTACGTGGCCTCTGTGAAGGGCAGATTCACCATGAG<br>CCGGGACAACGCCAAGAAAGAGGTGTACGTGCAGATGAACAGCCTGAGAGCCG<br>AGGACACCGCCGTGTACTATTGTGCCAGAGAGGGCTACAGCAGCATCAAGTAC<br>TACGGCATGGACGTGTGGGGCCAGGGCACAACAGTGACAGTCTCTTCT | SEQ ID NO: 454<br>EVQLVESGGGFVQPGGSL<br>RLSCAVSGFRFNSYWMSW<br>VRQAPGKGLEWVANINQD<br>GSRKFYVASVKGRFTMSR<br>DNAKKEVYVQMNSLRAED<br>TAVYYCAREGYSSIKYYG<br>MDVWGQGTTVTVSS |

TABLE S-9A-continued

Anti-FIXa VH domain sequences and CRDs

| Ab VH | HCDR1 | HCDR2 | HCDR3 | VH nucleotide sequence | VH amino acid sequence |
|---|---|---|---|---|---|
| N1441H | SEQ ID NO: 441 | SEQ ID NO: 436 | SEQ ID NO: 433 | SEQ ID NO: 455<br>GAGGTGCAGCTGGTTGAATCTGGCGGCGGATTTGTTCAGCCTGGCGGCTCTCT<br>GAGACTGAGCTGTGCCGTGTCCGGCTTCCGGTTCAACAGCTACTGGATGTCCT<br>GGGTCCGACAGGCCCCTGGCAAAGGACTTGAGTGGGTCGCCAACATCAACCAG<br>GACGGCAGCCGGAAGTTTTACGTGGCCTCTGTGAAGGGCAGATTCACCATGAG<br>CCGGGACAACGCCGACAAAAGCGTGTACGTGCAGATGAACAGCCTGAGAGCCG<br>AGGACACCGCCGTGTACTATTGTGCCAGAGAGGGCTACAGCAGCATCAAGTAC<br>TACGGCATGGACGTGTGGGGCCAGGGCACAACAGTGACAGTCTCTTCT | SEQ ID NO: 456<br>EVQLVESGGGFVQPGGSL<br>RLSCAVSGFRFNSYWMSW<br>VRQAPGKGLEWVANINQD<br>GSRKFYVASVKGRFTMSR<br>DNADKSVYVQMNSLRAED<br>TAVYYCAREGYSSIKYYG<br>MDVWGQGTTVTVSS |
| N1442H | SEQ ID NO: 441 | SEQ ID NO: 436 | SEQ ID NO: 433 | SEQ ID NO: 457<br>GAGGTGCAGCTGGTTGAATCTGGCGGCGGATTTGTTCAGCCTGGCGGCTCTCT<br>GAGACTGAGCTGTGCCGTGTCCGGCTTCCGGTTCAACAGCTACTGGATGTCCT<br>GGGTCCGACAGGCCCCTGGCAAAGGACTTGAGTGGGTCGCCAACATCAACCAG<br>GACGGCAGCCGGAAGTTTTACGTGGCCTCTGTGAAGGGCAGATTCACCATGAG<br>CCGGGACAACGCCGAGAAAAGCGTGTACGTGCAGATGAACAGCCTGAGAGCCG<br>AGGACACCGCCGTGTACTATTGTGCCAGAGAGGGCTACAGCAGCATCAAGTAC<br>TACGGCATGGACGTGTGGGGCCAGGGCACAACAGTGACAGTCTCTTCT | SEQ ID NO: 458<br>EVQLVESGGGFVQPGGSL<br>RLSCAVSGFRFNSYWMSW<br>VRQAPGKGLEWVANINQD<br>GSRKFYVASVKGRFTMSR<br>DNAEKSVYVQMNSLRAED<br>TAVYYCAREGYSSIKYYG<br>MDVWGQGTTVTVSS |

TABLE S-9B

Anti-FIXa VH domain framework sequences

| Ab VH | FR1 | FR2 | FR3 | FR4 |
|---|---|---|---|---|
| N0192H | SEQ ID NO: 148<br>EVQLVESGGGLVQP<br>GGSLRLSCAAS | SEQ ID NO: 133 | SEQ ID NO: 149<br>YYVDSVKGRFTISRDNAKNSLYLQMNSLRAEDTAVYYC | SEQ ID NO: 135 |
| N0212H | SEQ ID NO: 148 | SEQ ID NO: 133 | SEQ ID NO: 149 | SEQ ID NO: 135 |
| N0205H | SEQ ID N: 150<br>EVQLVESGGGLVQP<br>GGSLRLSCVAS | SEQ ID NO: 133 | SEQ ID NO: 149 | SEQ ID NO: 135 |
| N0211H | SEQ ID NO: 151<br>EVQLVESGGGLVQP<br>GGSLRLSCAVS | SEQ ID NO: 133 | SEQ ID NO: 152<br>FYVASVKGRFTISRDNAKNSVYLQMNSLRAEDTAVYYC | SEQ ID NO: 135 |
| N0203H | SEQ ID NO: 151 | SEQ ID NO: 133 | SEQ ID NO: 153<br>FYVASVKGRFIISRDNAKNSVYLQMNSLRAEDTAVYYC | SEQ ID NO: 154<br>WGQGTTVSVSS |
| N0128H | SEQ ID NO: 132<br>EVQLVESGGGFVQP<br>GGSLRLSCAVS | SEQ ID NO: 133<br>MSWVRQAPGKGLEWVAN | SEQ ID NO: 134<br>FYVASVKGRFTMSRDNAKKSVYVQMNSLRAEDTAVYYC | SEQ ID NO: 135<br>WGQGTTVTVSS |
| N0215H | SEQ ID NO: 148 | SEQ ID NO: 133 | SEQ ID NO: 149 | SEQ ID NO: 135 |
| N0216H | SEQ ID NO: 132 | SEQ ID NO: 133 | SEQ ID NO: 152 | SEQ ID NO: 135 |
| N0217H | SEQ ID NO: 151 | SEQ ID NO: 133 | SEQ ID NO: 155<br>FYVASVKGRFTMSRDNAKNSVYLQMNSLRAEDTAVYYC | SEQ ID NO: 135 |
| N0218H | SEQ ID NO: 151 | SEQ ID NO: 133 | SEQ ID NO: 156<br>FYVASVKGRFTISRDNAKKSVYLQMNSLRAEDTAVYYC | SEQ ID NO: 135 |
| N0219H | SEQ ID NO: 151 | SEQ ID NO: 133 | SEQ ID NO: 157<br>FYVASVKGRFTISRDNAKNSVYVQMNSLRAEDTAVYYC | SEQ ID NO: 135 |
| N0220H | SEQ ID NO: 132 | SEQ ID NO: 133 | SEQ ID NO: 158<br>FYVASVKGRFTISRDNAKKSVYVQMNSLRAEDTAVYYC | SEQ ID NO: 135 |
| N0221H | SEQ ID NO: 132 | SEQ ID NO: 133 | SEQ ID NO: 159<br>FYVASVKGRFTMSRDNAKNSVYVQMNSLRAEDTAVYYC | SEQ ID NO: 135 |
| N0222H | SEQ ID NO: 132 | SEQ ID NO: 133 | SEQ ID NO: 160<br>FYVASVKGRFTMSRDNAKKSVYLQMNSLRAEDTAVYYC | SEQ ID NO: 135 |
| N0223H | SEQ ID NO: 151 | SEQ ID NO: 133 | SEQ ID NO: 134 | SEQ ID NO: 135 |
| N0224H | SEQ ID NO: 132 | SEQ ID NO: 133 | SEQ ID NO: 155 | SEQ ID NO: 135 |
| N0225H | SEQ ID NO: 132 | SEQ ID NO: 133 | SEQ ID NO: 156 | SEQ ID NO: 135 |

TABLE S-9B-continued

Anti-FIXa VH domain framework sequences

| Ab VH | FR1 | FR2 | FR3 | FR4 |
|---|---|---|---|---|
| N0226H | SEQ ID NO: 132 | SEQ ID NO: 133 | SEQ ID NO: 157 | SEQ ID NO: 135 |
| N0227H | SEQ ID NO: 151 | SEQ ID NO: 133 | SEQ ID NO: 160 | SEQ ID NO: 135 |
| N0228H | SEQ ID NO: 151 | SEQ ID NO: 133 | SEQ ID NO: 159 | SEQ ID NO: 135 |
| N0229H | SEQ ID NO: 151 | SEQ ID NO: 133 | SEQ ID NO: 158 | SEQ ID NO: 135 |
| N0511H | SEQ ID NO: 132 | SEQ ID NO: 133 | SEQ ID NO: 134 | SEQ ID NO: 135 |
| N1091H | SEQ ID NO: 132 | SEQ ID NO: 133 | SEQ ID NO: 134 | SEQ ID NO: 135 |
| N1172H | SEQ ID NO: 132 | SEQ ID NO: 133 | SEQ ID NO: 134 | SEQ ID NO: 135 |
| N1280H | SEQ ID NO: 132 | SEQ ID NO: 133 | SEQ ID NO: 134 | SEQ ID NO: 135 |
| N1314H | SEQ ID NO: 132 | SEQ ID NO: 133 | SEQ ID NO: 134 | SEQ ID NO: 135 |
| N1327H | SEQ ID NO: 132 | SEQ ID NO: 133 | SEQ ID NO: 134 | SEQ ID NO: 135 |
| N1333H | SEQ ID NO: 132 | SEQ ID NO: 133 | SEQ ID NO: 134 | SEQ ID NO: 135 |
| N1441H | SEQ ID NO: 132 | SEQ ID NO: 133 | SEQ ID NO: 459<br>FYVASVKGRFTMSRDNADKSVYVQMNSLRAEDTAVYYC | SEQ ID NO: 135 |
| N1442H | SEQ ID NO: 132 | SEQ ID NO: 133 | SEQ ID NO: 460<br>FYVASVKGRFTMSRDNAEKSVYVQMNSLRAEDTAVYYC | SEQ ID NO: 135 |
| N1454H | SEQ ID NO: 132 | SEQ ID NO: 133 | SEQ ID NO: 461<br>FYVASVKGRFTMSRDNAKKEVYVQMNSLRAEDTAVYYC | SEQ ID NO: 136 |

FX Binding Arm VH Domain Polypeptide Sequences

TABLE S-10A

Anti-FX VH domain sequences and CDRs

| Ab VH | HCDR1 | HCDR2 | HCDR3 | VH nucleotide sequence | VH amino acid sequence |
|---|---|---|---|---|---|
| T02 | SEQ ID NO: 57<br>GYTFTNYA | SEQ ID NO: 58<br>INAGNGFT | SEQ ID NO: 59<br>ARDWAAAISYYGMDV | SEQ ID NO: 60<br>CAGGTCCAGCTTGTGCAGTCTGGGGCTGAGGTGAAGAGGCCTGGGGC<br>CTCAGTGAAGGTTTCCTGCAAGGCTTCTGGATACACCTTCACTAACT<br>ATGCTATACATTGGGTGCGCCAGGCCCCCGGACAGAGGCTTGAGTGG<br>ATGGGATGGATCAACGCTGGCAATGGTTTCACAAAATCTTCACAGAA<br>GTTCCGGGGCAGAGTCACCATTACCAGGGACACATCCGCAACACAG<br>CCTACATGGAACTGAGCAGCCTCAGATCTGAAGACACGGCTATTTAT<br>TACTGTGCGAGAGATTGGGCTGCTGCTATCTCTTACTACGGTATGGA<br>CGTCTGGGGCCAAGGGACCACGGTCACCGTCTCCTCAG | SEQ ID NO: 61<br>QVQLVQSGAEVKRPGASV<br>KVSCKASGYTFTNYAIHW<br>VRQAPGQRLEWMGWINAG<br>NGFTKSSQKFRGRVTITR<br>DTSANTAYMELSSLRSED<br>TAIYYCARDWAAAISYYG<br>MDVWGQGTTVTVSS |
| T05 | SEQ ID NO: 67<br>GFTFSSYG | SEQ ID NO: 68<br>IWYDGTNK | SEQ ID NO: 69<br>ARSGYSSSWYGAMDV | SEQ ID NO: 70<br>CAGGTGCAGCTGGTGGAGTCTGGGGGAGGCGTGGTCCAGCCTGGGAG<br>GTCCCTGAGACTCTCCTGTGCAGCGTCTGGATTCACCTTCAGTAGCT<br>ATGGCATGCACTGGGTCCGCCAGGCTCCAGGCGAGGGGCTGGAGTGG<br>GTGGCAGTTATATGGTATGATGGAAGTAATAAATACTATGCAGACTC<br>CTTGAAGGGCCGATTCACCATCTCCAGAGACAATTCCAAGAACACGC<br>TCTATCTGCAAATGAACAGGCTGAGAGCCGAGGACACGGCTGTGTAT<br>TACTGTGCGAGGTCCGGGTATAGCAGCAGCTGGTACGGCGCTATGGA<br>CGTCTGGGGCCAAGGGACCACGGTCACCGTCTCCTCAG | SEQ ID NO: 71<br>QVQLVESGGGVVQPGRSL<br>RLSCAASGFTFSSYGMHW<br>VRQAPGEGLEWVAVIWYD<br>GTNKYYADSLKGRFTISR<br>DNSKNTLYLQMNRLRAED<br>TAVYYCARSGYSSSWYGA<br>MDVWGQGTTVTVSS |
| T06 | SEQ ID NO: 77<br>GYTFTSYA | SEQ ID NO: 78<br>INAGNGIT | SEQ ID NO: 79<br>ARDWAAAITYYGMDV | SEQ ID NO: 80<br>CAGGTCCAGCTTGTGCAGTCTGGGGCTGAGGTGAAGAGGCCTGGGGC<br>CTCAGTGAAGGTTTCCTGCAAGGCTTCTGGATACACCTTCACAAGCT<br>ACGCCATACATTGGGTGCGCCAGGCCCCCGGACAGAGGCTTGAGTGG<br>ATGGGATGGATCAACGCTGGCAATGGTATCACAAAATCTTCACAGAA<br>GTTCCAGGGCAGAGTCACCATTACCAGGGACACATCCGCAACACAG<br>TTTACCTGGAACTGAGCAGCCTCAGATCTGAAGACACGGCTGTTTAT<br>TATTGTGCGAGAGATTGGGCTGCTGCTATCACCTACTACGGTATGGA<br>CGTCTGGGGCCAAGGGACCACGGTCACCGTCTCCTCAG | SEQ ID NO: 81<br>QVQLVQSGAEVKRPGASV<br>KVSCKASGYTFTSYAIHW<br>VRQAPGQRLEWMGWINAG<br>NGITKSSQKFQGRVTITR<br>DTSANTVYLELSSLRSED<br>TAVYYCARDWAAAITYYG<br>MDVWGQGTTVTVSS |

TABLE S-10A-continued

Anti-FX VH domain sequences and CDRs

| Ab VH | HCDR1 | HCDR2 | HCDR3 | VH nucleotide sequence | VH amino acid sequence |
|---|---|---|---|---|---|
| T12 | SEQ ID NO: 86 EFTFSTA G | SEQ ID NO: 87 ISYDGSN K | SEQ ID NO: 88 AKDFTMV RGVIIMD V | SEQ ID NO: 89 CAGGTGCAGCTGGTGGAGTCTGGGGGAGGCGTACTCCAGCCTGGGAA GTCCTGAGACTCTCTGTGCAGCCTCTGAATTCACCTTCAGTACCG CTGGCATGCACTGGGTCCGCCAGGCTCCAGGCAAGGGGCTGGAGTGG GTGACTTTTATATCATATGATGGAAGTAATAAATACTATGCAGACTC CGTGAAGGGCCGATTCACCATCTCCAGAGACAATTCCAAGGTGTATC TGCAAATGAACAGCCTGAGAACTGAGGACACGGCTGTGTATTACTGT GCGAAAGATTTCACTATGGTTCGGGGAGTTATTATAATGGACGTCTG GGGCCAAGGGACCACGGTCACCGTCTCCTCAG | SEQ ID NO: 90 QVQLVESGGGVLQPGKSL RLSCAASEFTFSTAGMHW VRQAPGKGLEWVTFISYD GSNKYYADSVKGRFTISR DNSKVYLQMNSLRTEDTA VYYCAKDFTMVRGVIIMD VWGQGTTVTVSS |
| T14 | SEQ ID NO: 96 GGSISSY Y | SEQ ID NO: 97 IYYSGST | SEQ ID NO: 98 AKGAAGD Y | SEQ ID NO: 99 CAGGTGCAGCTGCAGGAGTCGGGCCCAGGACTGGTGAAGCCTTCGGA GACCCTGTCCCTCACCTGCACTGTCTCTGGTGGCTCCATCAGTAGTT ATTACTGGAGCTGGATCCGGCAGCCCCCAGGGAAGGGACTGGAGTGG ATTGGGTATATCTATTACAGTGGGAGCACCAACTATAACCCCTCCCT CAAGAGTCGAGTCAACATATCAGTAGACACGTCCAAGAACCAGTTCT CCCTGAGGCTGAGTTCTGTGACCGCTGCGGACACGGCCGTGTATTAT TGTGCGAAAGGGGCAGCTGGGGACTACTGGGGCCAGGGAACCCTGGT CACCGTCTCCTCAG | SEQ ID NO: 100 QVQLQESGPGLVKPSETL SLTCTVSGGSISSYYWSW IRQPPGKGLEWIGYIYYS GSTNYNPSLKSRVNISVD TSKNQFSLRLSSVTAADT AVYYCAKGAAGDYWGQGT LVTVSS |
| T15 | SEQ ID NO: 105 GGSISKY Y | SEQ ID NO: 106 IYYSGNT | SEQ ID NO: 107 ARGLGDY | SEQ ID NO: 108 CAGGTGCAGCTGCAGGAGTCGGGCCCAGGACTGGTGAAGCCTTCGGA GACCCTGTCCCTCACCTGCACTGTCTCTGGTGGCTCCATCAGTAAAT ACTACTGGAGCTGGATCCGGCAGCCCCCAGGGAAGGGACTGGAGTGG ATTGGATATATCTATTACAGTGGGAACACCTACCAGAATCCCTCCCT CAAGAGTCGAGTCACCATATCAATAGACACGTCCAAGAACCAGATCT CCCTGAAGGTGAGCTCTGTGACCGCTGCGGACACGGCCGTCTATTAC TGTGCGAGAGGGCTGGGGGACTACTGGGGCCAGGGAACCCTGGTCAC CGTCTCCTCAG | SEQ ID NO: 109 QVQLQESGPGLVKPSETL SLTCTVSGGSISKYYWSW IRQPPGKGLEWIGYIYYS GNTYQNPSLKSRVTISID TSKNQISLKVSSVTAADT AVYYCARGLGDYWGQGTL VTVSS |
| T23 | SEQ ID NO: 114 GGSISRY Y | SEQ ID NO: 115 IYYSGTT | SEQ ID NO: 116 ARGLGDF | SEQ ID NO: 117 CAGGTGCAGCTGCAGGAGTCGGGCCCAGGACTGGTGAAGCCTTCGGA GACCCTGTCCCTCACCTGCAGTGTCTCTGGTGGCTCCATTAGTAGAT ATTACTGGAGCTGGATCCGGCAGCCCCCAGGGAAGGGACTGGAGTGG ATTGGATATATCTATTACAGTGGGACCACCTACTATAACCCCTCCCT CAAGAGTCGAGTCACCTTTTCAGTAGACACGTCCAAGACCCAGTTCT CCCTGAAACTTAACTCTGTGACCGCTGCGGACACGGCCGTATATTAC TGTGCGAGAGGACTGGGGGACTTCTGGGGCCGGGGAACCCTGGTCAC CGTCTCCTCAG | SEQ ID NO: 118 QVQLQESGPGLVKPSETL SLTCSVSGGSISRYYWSW IRQPPGKGLEWIGYIYYS GTTYNPSLKSRVTFSVD TSKTQFSLKLNSVTAADT AVYYCARGLGDFWGRGTL VTVSS |
| T25 | SEQ ID NO: 122 GGSISSG IYY | SEQ ID NO: 123 INNSGNT | SEQ ID NO: 124 ARGGSGD Y | SEQ ID NO: 125 CAGGTGCAGCTGCAGGAGTCGGGCCCAGGACTGGTGAAGCCTTCAGA GACCCTGTCCCTCACCTGCACTGTCTCTGGTGGCTCCATCAGTAGTG GTATATACTACTGGAGTTGGATCCGCCAGCACCCAGGGAAGGGCCTG GAGTGGATTGGATACATCAATAACAGTGGGAACACCTACTACAACCC GTCCCTCAAGGGTCGAGTTAACATATCAGTAGACACGTCTAAGAAAC AGTTCTCCCTGAAGCTGAGCTCTGTGACTGACGCGGACACGGCCGTC TATTACTGTGCGAGGGGGGATCGGGCGACTACTGGGGCCAGGGAAC CCTGGTCACCGTCTCCTCAG | SEQ ID NO: 126 QVQLQESGPGLVKPSETL SLTCTVSGGSISSGIYYW SWIRQPGKGLEWIGYIN NSGNTYYNPSLKGRVNIS VDTSKKQFSLKLSSVTDA DTAVYYCARGGSGDWGQ GTLVTVSS |

TABLE S-10B

Anti-FX VL domain sequences and CDRs

| Ab VL | LCDR1 | LCDR2 | LCDR3 | VL nucleotide sequence | VL amino acid sequence |
|---|---|---|---|---|---|
| T02 | SEQ ID NO: 62 SSNIGSN Y | SEQ ID NO: 63 RNT | SEQ ID NO: 64 ATWDDSL SAYV | SEQ ID NO: 65 CAGTCTGTCCTGACTCAGCCACCCTCAGCGTCTGGGACCCCCGGGC AGAGGGTCACCATCTCTTGTTCTGGAAGCAGCTCCAACATCGGAAG TAATTATGTATACTGGTACCAGCAGCTCCCAGGAACGGCCCCCAAA CTCCTCATCTATAGGAATACTCAGCGGCCCTCAGAGGTCCCTGACC GATTCTCTGGCTCCAAGTCTGGCGCCTCAGCCTCCCTGGCCATCAG TGGGCTCCGGTCCGAGGATGAGACTGATTATTACTGTGCAACATGG GATGACAGCCTGAGTGCTTATGTCTTCGGAACTGGGACCAAAGTCA CCGTCCTAG | SEQ ID NO: 66 QSVLTQPPSASGTPGQRVT ISCSGSSSNIGSNYVYWYQ QLPGTAPKLLIYRNTQRPS EVPDRFSGSKSGASASLAI SGLRSEDETDYYCATWDDS LSAYVFGTGTKVTVL |
| T05 | SEQ ID NO: 72 SSDVGGY YY | SEQ ID NO: 73 EVN | SEQ ID NO: 74 SSYAGSN TWV | SEQ ID NO: 75 CAGTCTGCCCTGACTCAGCCTCCCTCCGCGTCCGGGTCTCCTGGAC AGTCAGTCACCATCTCCTGCACTGGAACCAGCAGTGACGTTGGTGG TTATTACTATGTCTCCTGGTACCAACAGCACCCAGGCAAAGCCCCC AAACTCATGATTTATGAGGTCAATAAGCGGCCCTCAGGGGTCCCTG | SEQ ID NO: 76 QSALTQPPSASGSPGQSVT ISCTGTSSDVGGYYYVSWY QQHPGKAPKLMIYEVNKRP SGVPDRFSGSKSGITASLT |

TABLE S-10B-continued

Anti-FX VL domain sequences and CDRs

| Ab VL | LCDR1 | LCDR2 | LCDR3 | VL nucleotide sequence | VL amino acid sequence |
|---|---|---|---|---|---|
| | | | | ATCGCTTCTCTGGCTCCAAGTCTGGCATCACGGCCTCCCTGACCGT CTCTGGGCTCCAGTCTGAGGATGAGGCTGATTATTACTGCAGCTCA TATGCAGGCAGCAACACTTGGGTGTTCGGCGGAGGGACCAAGCTGA CCGTCCTAG | VSGLQSEDEADYYCSSYAG SNTWVFGGGTKLTVL |
| T06 | SEQ ID NO: 62 SSNIGSNY | SEQ ID NO: 82 RNN | SEQ ID NO: 83 FGAGTKV TVL | SEQ ID NO: 84 CAGTCTGTGCTGACTCAGCCACCCTCAGTGTCTGGGACCCCCGGGC AGAGGGTCACCATCTCTTGTTCTGGAAGCAGCTCCAACATCGGAAG TAATTATGTATACTGGTACCAGCAGTTCCCAGGAACGGCCCCCAAA CTCCTCATCTATAGGAATAATCAGCGGCCCTCAGAGGTCCCTGACC GATTCTCTGGCTCCAAGTCTGGCGCCTCAGCCTCCCTGGCCATCAG TGGGCTCCGGTCCGAGGATGAGACTGATTATTACTGTGCAACATGG GATGACAGCCTGAGTGCTTATGTCTTCGGAGCTGGGACCAAAGTCA CCGTCCTAG | SEQ ID NO: 85 QSVLTQPPSVSGTPGQRVT ISCSGSSSNIGSNYVYWYQ QFPGTAPKLLIYRNNQRPS EVPDRFSGSKSGASASLAI SGLRSEDETDYYCATWDDS LSAYVFGAGTKVTVL |
| T12 | SEQ ID NO: 91 QDISNY | SEQ ID NO: 92 DAS | SEQ ID NO: 93 QQYDNLP IT | SEQ ID NO: 94 GACATCCAGATGACCCAGTCTCCATCCTCCCTGTCTGTATCTGTAG GAGACAGAGTCACCATCACTTGCCAGGCGAGTCAGGACATTAGCAA CTATTTAAATTGGTATCAGCAGAAACCAGGGAAAGCCCCTAAGCTC CTGATCTACGATGCATCCAATTTGGAAACAGGGGTCCCATCAAGGT TCAGTGGAAGTGGATCTGGGACAGATTTTACTTTCATCATCAGCAG CCTGCAGCCTGAAGATATTGCAACATATTACTGTCAACAGTATGAT AATCTCCCGATCACCTTCGGCCAAGGGACACGACTGGAGATCAAAC | SEQ ID NO: 95 DIQMTQSPSSLSVSVGDRV TITCQASQDISNYLNWYQQ KPGKAPKLLIYDASNLETG VPSRFSGSGSGTDFTFIIS SLQPEDIATYYCQQYDNLP ITFGQGTRLEIK |
| T14 | SEQ ID NO: 101 QSVNSY | SEQ ID NO: 92 DAS | SEQ ID NO: 102 QQRNNWP IT | SEQ ID NO: 103 GAAATTGTGTTGGCACAGTCTCCAGCCACCCTGTCTTTGTCTCCAG GGGAAAGAGCCACGTTCTCCTGCAGGGCCAGTCAGAGTGTTAACAG CTACTTAGCCTGGCACCAACAGAAACCTGGCCAGGCTCCCAGGCTC CTCATCTATGATGCATCCAACAGGGCCACTGGCATCCCAGCCAGGT TCAGTGGCAGTGGGTCCGGGACAGACTTCACTCTCACCATCAGCAG CCTAGAGCCTGAAGATTTTGCAGTTTATTACTGTCAGCAGCGTAAC ATCACTGGCCTATCACCTTCGGCCAAGGGACACGACTGGAGATCAAAC | SEQ ID NO: 104 EIVLAQSPATLSLSPGERA TFSCRASQSVNSYLAWHQQ KPGQAPRLLIYDASNRATG IPARFSGSGSGTDFTLTIS SLEPEDFAVYYCQQRNNWP ITFGQGTRLEIK |
| T15 | SEQ ID NO: 110 QSVSSY | SEQ ID NO: 92 DAS | SEQ ID NO: 111 QQRSNWP LT | SEQ ID NO: 112 GAAATTGTGTTGACACAGTCTCCAGCCACCCTGTCTTTGTCTCCAG GGGAAAGAGCCACCCTCTCCTGCAGGGCCAGTCAGAGTGTTAGCAG CTACTTAGCCTGGCACCAACAGAAACCTGGCCAGGCTCCCAGGCTC CTCATCTATGATGCATCCAACAGGGCCACTGGCATCCCAGCCAGGT TCAGTGGCAGTGGGTCTGGGACAGACTTCACTCTCACCATCAGCAG CCTAGAGCCTGAAGATTTTGCAGTTTATTACTGTCAGCAACGTAGC AACTGGCCTCTCACTTTCGGCGGAGGGACCAAGGTGGAGATCAAAC | SEQ ID NO: 113 EIVLTQSPATLSLSPGERA TLSCRASQSVSSYLAWHQQ KPGQAPRLLIYDASNRATG IPARFSGSGSGTDFTLTIS SLEPEDFAVYYCQQRSNWP LTFGGGTKVEIK |
| T23 | SEQ ID NO: 119 QSVSGY | SEQ ID NO: 92 DAS | SEQ ID NO: 111 QQRSNWP LT | SEQ ID NO: 120 GAAATTGTGTTGACTCAGTCTCCAGCCACCCTGTCATTGTCTCCAG GGGAAAAGGCCACCCTCTCCTGCAGGGCCAGTCAGAGTGTTGGCGG CTACTTAGCCTGGCACCAACAGAAACCTGGCCAGGCTCCCAGGCTC CTCATCTATGATGCATCCAACAGGGCCACTGGCATCCCAGCCAGAT TCAGTGGCAGTGGGTCTGGGACAGACTTCACTCTCACCATCAGCAG CCTAGAGCCTGAAGATTTTGCAGTTTATTACTGTCAGCAACGTAGC AACTGGCCTCTCACTTTCGGCGGAGGGACCAAGGTGGAGATCAAAC | SEQ ID NO: 121 EIVLTQSPATLSLSPGERA TLSCRASQSVSGYLAWHQQ KPGQAPRLLIYDASNRATG IPARFSGSGSGTDFTLTIS SLEPEDFAVYYCQQRSNWP LTFGGGTKVEIK |
| T25 | SEQ ID NO: 128 QSINNY | SEQ ID NO: 92 DAS | SEQ ID NO: 129 QQRNNWP PT | SEQ ID NO: 130 GAAATTGTGTTGACACAGTCTCCAGCCACCCTGTCTTTGTCTCCAG GGGAAAGAGCCACCCTCTCCTGCAGGACCAGTCAGAGTATTAACAA CTACTTAGCCTGGTTCCAACAGAAACCTGGCCAGGCTCCCAGGCTC CTCATCTATGATGCATCCAACAGGGCCCCTGGCATCCCAGCCAGGT TCAGTGGCAGTGGGTCTGGGACAGACTTCACTCTCACCATCAGCAG CCTGGAGCCTGAAGATTTTGTAGTTTATTCTGTCAGCAGCGTAAC CCTGGAGCCTGAAGATTTTGTAGTTTATTCTGTCAGCAGCGTAAC CCTACTTTCGGCCAAGGGACCAAGGTGGAAATCAAAC | SEQ ID NO: 131 EIVLTQSPATLSLSPGERA TLSCRTSQSINNYLAWFQQ KPGQAPRLLIYDASNRAPG IPARFSGSGSGTDFTLTIS SLEPEDFVVYFCQQRNNWP PTFGQGTKVEIK |

TABLE S-10C

Anti-FX VH domain sequences and CDRs
The following TxxxxH VH domains are suitable for pairing with a common light chain VL such as VL domain 0128L or 0325L.

| Ab VH | HCDR1 | HCDR2 | HCDR3 | VH nucleotide sequence | VH amino acid sequence |
|---|---|---|---|---|---|
| T0200H | SEQ ID NO: 462 RYSFTSY | SEQ ID NO: 463 INPKTGD | SEQ ID NO: 464 ARDGYGS | SEQ ID NO: 465 CAGGTGCAGCTGGTGCAGTCTGGGGCTGAGGTGAAAAAGCCTGGGGCCTCAGT GAAGGTTTCCTGCAAGGCATCTAGATACAGCTTCACCAGCTACTATATCTGCATT | SEQ ID NO: 466 QVQLVQSGAEVKKPG ASVKVSCKASRYSFT |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| | Y | T | SARCLQL | GGGTGCGACAGGCCCCTGGACAAGGGCTTGAGTGGATGGGAATAATCAACCCT AAAAACTGGTGACACAAGCTACGCACAGAAGTTCCAGGGCAGAGTCACCATGAC CAGGGACACGTCCACGACCACAGTCTACATGGAGCTGAGCAGCCTGAGATCTG AGGACACGGCCGTGTATTACTGTGCGAGAGATGGGTATGGCAGCTCGGCCCGG TGCCTCCAGCTCTGGGGCCAGGGCACCCTGGTCACCGTCTCCTCA | SYYLHWVRQAPGQGL EWMGIINPKTGDTSY AQKFQGRVTMTRDTS TSTVYMELSSLRSED TAVYYCARDGYGSSA RCLQLWGQGTLVTVS S |
| T0201H | SEQ ID NO: 462 | SEQ ID NO: 467 INPKSGS T | SEQ ID NO: 468 ARDGYGS SSRCLQL | SEQ ID NO: 469 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 470 QVQLIQSGAEVKKPG ASVKVSCKASRYSFT SYYMHWVRQAPGQGL EWMGIINPKSGSTSY AQKFQGRVTMTRDTS TSTVYMELSSLRSED TAVYYCARDGYGSSS RCLQLWGQGTLVTVS S |
| T0202H | SEQ ID NO: 462 | SEQ ID NO: 467 | SEQ ID NO: 468 | SEQ ID NO: 471 CAGGTGCAGCTGATACAGTCTGGGGCTGAGGTGCAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 472 QVQLIQSGAEVQKPG ASVKVSCKASRYSFT SYYMHWVRQAPGQGL EWMGIINPKSGSTSY AQKFQGRVTMTRDTS TSTVYMELSSLRSED TAVYYCARDGYGSSS RCLQLWGQGTLVTVS S |
| T0203H | SEQ ID NO: 462 | SEQ ID NO: 467 | SEQ ID NO: 468 | SEQ ID NO: 473 CAGGTGCAGCTGGTGCAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGATCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 474 QVQLVQSGAEVKKPG ASVKVSCKASRYSFT SYYMHWVRQAPGQGL EWMGIINPKSGSTSY AQKFQGRVTMTRDTS TSTVYMELISLRSED TAVYYCARDGYGSSS RCLQLWGQGTLVTVS S |
| T0204H | SEQ ID NO: 462 | SEQ ID NO: 467 | SEQ ID NO: 468 | SEQ ID NO: 475 CAGGTGCAGCTGGTGCAGTCTGGGGCTGAGGTGCAGAAGACTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 476 QVQLVQSGAEVQKTG ASVKVSCKASRYSFT SYYMHWVRQAPGQGL EWMGIINPKSGSTSY AQKFQGRVTMTRDTS TSTVYMELSSLRSED TAVYYCARDGYGSSS RCLQLWGQGTLVTVS S |
| T0205H | SEQ ID NO: 462 | SEQ ID NO: 477 INPKSGD T | SEQ ID NO: 464 | SEQ ID NO: 478 CAGGTGCAGCTGGTGCAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTGACACAAGCTACGCACAGAAGTTCCAGGGCAGAGTCACCATGAC CAGGGACACGTCCACGAGCACAGTCTACATGGAGCTGAACAGCCTGAGATCTG AGGACACGGCCGTGTATTACTGTGCGAGAGATGGGTATGGCAGCTCGGCCCGG TGCCTCCAGCTCTGGGGCCAGGGCGCCCTGGTCACCGTCTCCTCA | SEQ ID NO: 479 QVQLVQSGAEVKKPG ASVKVSCKASRYSFT SYYMHWVRQAPGQGL EWMGIINPKSGDTSY AQKFQGRVTMTRDTS TSTVYMELNSLRSED TAVYYCARDGYGSSA RCLQLWGQGTLVTVS S |
| T0206H | SEQ ID NO: 462 | SEQ ID NO: 477 | SEQ ID NO: 464 | SEQ ID NO: 480 CAGGTGCAGCTGGTGCAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTGACACAAGCTACGCACAGAAGTTCCAGGGCAGAGTCACCATGAC CAGGGACACGTCCACGAGCACAGTCTACATGGACCTGAGCAGCCTGAGATCTG AGGACACGGCCGTGTATTACTGTGCGAGAGATGGGTATGGCAGCTCGGCCCGG TGCCTCCAGCTCTGGGGCCAGGGCACCCTGGTCACCGTCTCCTCA | SEQ ID NO: 481 QVQLVQSGAEVKKPG ASVKVSCKASRYSFT SYYMHWVRQAPGQGL EWMGIINPKSGDTSY AQKFQGRVTMTRDTS TSTVYMDLSSLRSED TAVYYCARDGYGSSA RCLQLWGQGTLVTVS S |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| T0207H | SEQ ID NO: 462 | SEQ ID NO: 467 | SEQ ID NO: 468 | SEQ ID NO: 482 CAGGTGCAGCTGGTGCAGTCTGGGGCTGAGGTGAAGAAGACTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 483 QVQLVQSGAEVKKTG ASVKVSCKASRYSFT SYYMHWVRQAPGQGL EWMGIINPKSGSTSY AQKFQGRVTMTRDTS TSTVYMELSSLRSED TAVYYCARDGYGSSS RCLQLWGQGTLVTVS S |
| T0208H | SEQ ID NO: 462 | SEQ ID NO: 467 | SEQ ID NO: 468 | SEQ ID NO: 484 CAGGTGCAGCTGGTGCAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGAACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 485 QVQLVQSGAEVKKPG ASVKVSCKASRYSFT SYYMHWVRQAPGQGL EWMGIINPKSGSTSY EQKFQGRVTMTRDTS TSTVYMELSSLRSED TAVYYCARDGYGSSS RCLQLWGQGTLVTVS S |
| T0209H | SEQ ID NO: 462 | SEQ ID NO: 463 | SEQ ID NO: 464 | SEQ ID NO: 486 CAGGTGCAGCTGGTGCAGTCTGGGGCTGAGGTGCAAAAGCCTGGGGCCTCAGT GAAGGTTTCCTGCAAGGCATCTAGATACAGCTTCACCTACTCATT GGGTGCGACAGGCCCCTGGACAAGGGCTTGAGTGGATGGGAATAATCAACCCT AAAACTGGTGACACAAGCTACGCACAGAAGTTCCAGGGCAGAGTCACCATGAC CAGGGACACGTCCACGACCACAGTCTACATGGAGCTGAGCAGCCTGAGATCTG AGGACACGGCCGTGTATTACTGTGCGAGAGATGGGTATGGCAGCTCGGCCCGG TGCCTCCAGCTCTGGGGCCAGGGCACCCTGGTCACCGTCTCCTCA | SEQ ID NO: 487 QVQLVQSGAEVQKPG ASVKVSCKASRYSFT SYYLHWVRQAPGQGL EWMGIINPKTGDTSY AQKFQGRVTMTRDTS TTTVYMELSSLRSED TAVYYCARDGYGSSA RCLQLWGQGTLVTVS S |
| T0210H | SEQ ID NO: 462 | SEQ ID NO: 467 | SEQ ID NO: 468 | SEQ ID NO: 488 CAGGTGCAGCTGGTGCAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAACAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 499 QVQLVQSGAEVKKPG ASVKVSCKASRYSFT SYYMHWVRQAPGQGL EWMGIINPKSGSTSY AQKFQGRVTMTRDTS TSTVYMELNSLRSED TAVYYCARDGYGSSS RCLQLWGQGTLVTVS S |
| T0211H | SEQ ID NO: 462 | SEQ ID NO: 467 | SEQ ID NO: 468 | SEQ ID NO: 500 CAGGTGCAGCTGGTGCAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGACCTGAGCAGCCTGAGATCTG AGGACACGGCCGTGTATTACTGTGCGAGAGATGGGTATGGCAGCTCGTCCCGG TGCCTCCAGCTCTGGGGCCAGGGCACCCTGGTCACCGTCTCCTCA | SEQ ID NO: 501 QVQLVQSGAEVKKPG ASVKVSCKASRYSFT SYYMHWVRQAPGQGL EWMGIINPKSGSTSY AQKFQGRVTMTRDTS TSTVYMDLSSLRSED TAVYYCARDGYGSSS RCLQLWGQGTLVTVS S |
| T0212H | SEQ ID NO: 502 GFSFTSY | SEQ ID NO: 503 INPRSGS T | SEQ ID NO: 504 ARDGYGS SSRCFQY | SEQ ID NO: 505 CAGGTGCAGCTGGTGCAGTCTGGGGCTGAGGTGAAGAAGCCTGGGGCCTCAGT GAAGGTTTCCTGCAAGGCATCTGGATTCTCCTTCACCAGCTACTATATACACT GGGTGCGACAGGCCCCTGGACAAGGGCTTGAGTGGATGGGAATAATCAACCCT AGAAGTGGTAGCAAGCTACGCTCAGAAGTTCCAGGGCAGAGTCACCATGAC CAGGGACACGTCCACGAACACAGTCTACATGGACCTGAGCAGCCTGAGATCTG AGGACACGGCCGTATATTACTGTGCGAGAGATGGGTATGGCAGCTCGTCCCGA TGCTTCCAGTACTGGGGCCAGGGCACCCTGGTCACCGTCTCCTCA | SEQ ID NO: 506 QVQLVQSGAEVKKPG ASVKVSCKASGFSFT SYYIHWVRQAPGQGL EWMGIINPRSGSTSY AQKFQGRVTMTRDTS TNTVYMDLSSLRSED TAVYYCARDGYGSSS RCFQYWGQGTLVTVS S |
| T0213H | SEQ ID NO: 462 | SEQ ID NO: 507 INPKSGT T | SEQ ID NO: 468 | SEQ ID NO: 508 CAGGTGCAGCTGGTGCAGTCTGGGGCTGAGGTGAAGAAGACTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTACTACAAGTTACGCACAGAAGTTCCAGGGCAGAGTCACCATGAC CAGGGACACGTCCACGAGCACAGTCTACATGGAACTGAGCAGCCTGAGATCTG | SEQ ID NO: 509 QVQLVQSGAEVKKTG ASVKVSCKASRYSFT SYYMHWVRQAPGQGL EWMGIINPKSGTTSY AQKFQGRVTMTRDTS |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| | | | | AGGACACGGCCGTGTATTACTGTGCGAGAGATGGGTATGGCAGCTCGTCCCGG<br>TGCCTCCAGCTCTGGGGCCAGGGCACCCTGGTCACCGTCTCCTCA | TSTVYMELSSLRSED<br>TAVYYCARDGYGSSS<br>RCLQLWGQGTLVTVS<br>S |
| T0214H | SEQ ID NO: 462 | SEQ ID NO: 467 | SEQ ID NO: 468 | SEQ ID NO: 510<br>CAGGTGCAGCTGGTGCAGTCTGGGGCTGAGGTGAAGAAGACTGGGGCCTCAGT<br>GAAGGTTTCCTGCCAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>TGCCTCCAGCTCTGGGGCCAGGGCACCCTGGTCACCGTCTCCTCA | SEQ ID NO: 511<br>QVQLVQSGAEVKKT<br>GASVKVSCQASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRCLQLWG<br>QGTLVTVSS |
| T0215H | SEQ ID NO: 462 | SEQ ID NO: 467 | SEQ ID NO: 468 | SEQ ID NO: 512<br>CAGGTGCAGCTGGTGCAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCGGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>TGCCTCCAGCTCTGGGGCCAGGGCACCCTGGTCACCGTCTCCTCA | SEQ ID NO: 513<br>QVQLVQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRCLQLWG<br>QGTLVTVSS |
| T0216H | SEQ ID NO: 462 | SEQ ID NO: 467 | SEQ ID NO: 468 | SEQ ID NO: 514<br>CAGGTGCAGCTGGTGCAGTCTGGGGCTGAGGTGAAGAAGCCTGGGGCCTCAGT<br>GAAGGTTTCCTGCCAAGGCATCTAGATACAGCTTCACCAGCTACTATTTGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>TGCCTCCAGCTCTGGGGCCAGGGCACCCTGGTCACCGTCTCCTCA | SEQ ID NO: 515<br>QVQLVQSGAEVKKT<br>GASVKVSCQASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRCLQLWG<br>QGTLVTVSS |
| T0217H | SEQ ID NO: 462 | SEQ ID NO: 467 | SEQ ID NO: 468 | SEQ ID NO: 516<br>CAGGTGCAGCTGGTGCAGTCTGGGGCTGAGGTGACGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>TGCCTCCAGCTCTGGGGCCAGGGCACCCTGGTCACCGTCTCCTCA | SEQ ID NO: 517<br>QVQLVQSGAEVTKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRCLQLWG<br>QGTLVTVSS |
| T0666H | SEQ ID NO: 462 | SEQ ID NO: 467 | SEQ ID NO: 520<br>ARDGYGS<br>SSRIIQL | SEQ ID NO: 521<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>ATCATCCAGCTCTGGGGCCAGGGCACCCTGGTCACCGTCTCCTCA | SEQ ID NO: 522<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRIIQLWG<br>QGTLVTVSS |
| T0667H | SEQ ID NO: 462 | SEQ ID NO: 467 | SEQ ID NO: 523<br>ARDGYGS<br>SSRLIQL | SEQ ID NO: 524<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>CTGATCCAGCTCTGGGGCCAGGGCACCCTGGTCACCGTCTCCTCA | SEQ ID NO: 525<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRLIQLWG<br>QGTLVTVSS |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| T0668H | SEQ ID NO: 462 | SEQ ID NO: 467 | SEQ ID NO: 526 ARDGYGS SSRQIQL | SEQ ID NO: 527 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG CAGATCCAGCTCTGGGGCCAGGGCACCCTGGTCACCGTCTCCTCA | SEQ ID NO: 528 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSSSRQIQLWG QGTLVTVSS |
| T0669H | SEQ ID NO: 462 | SEQ ID NO: 467 | SEQ ID NO: 529 ARDGYGS SSRILML | SEQ ID NO: 530 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG ATCCTCATGCTCTGGGGCCAGGGCACCCTGGTCACCGTCTCCTCA | SEQ ID NO: 531 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSSSRILMLWG QGTLVTVSS |
| T0670H | SEQ ID NO: 462 | SEQ ID NO: 467 | SEQ ID NO: 532 ARDGYGS SSRLLML | SEQ ID NO: 533 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG CTGCTCATGCTCTGGGGCCAGGGCACCCTGGTCACCGTCTCCTCA | SEQ ID NO: 534 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSSSRLLMLWG QGTLVTVSS |
| T0671H | SEQ ID NO: 462 | SEQ ID NO: 467 | SEQ ID NO: 535 ARDGYGS SSRQLML | SEQ ID NO: 536 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG CAGCTCATGCTCTGGGGCCAGGGCACCCTGGTCACCGTCTCCTCA | SEQ ID NO: 537 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSSSRQLMLWG QGTLVTVSS |
| T0672H | SEQ ID NO: 462 | SEQ ID NO: 467 | SEQ ID NO: 538 ARDGYGS SSRIIML | SEQ ID NO: 539 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG ATCATCATGCTCTGGGGCCAGGGCACCCTGGTCACCGTCTCCTCA | SEQ ID NO: 540 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSSSRIIMLWG QGTLVTVSS |
| T0673H | SEQ ID NO: 462 | SEQ ID NO: 467 | SEQ ID NO: 541 ARDGYGS SSRLIML | SEQ ID NO: 542 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTCGTCCCGG CTGATCATGCTCTGGGGCCAGGGCACCCTGGTCACCGTCTCCTCA | SEQ ID NO: 543 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSSSRLIMLWG QGTLVTVSS |
| T0674H | SEQ ID NO: 462 | SEQ ID NO: 467 | SEQ ID NO: 544 ARDGYGS SSRQIML | SEQ ID NO: 545 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG | SEQ ID NO: 546 QVQLIQSGAEVKKP GASVKVSCKASRYS FTSYYMHWVRQAPG QGLEWMGIINPKSG STSYAQKFQGRVTM |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| | | | | AGGACACGGCCGTGTATTACTGTGCGAGAGATGGGTATGGCAGCTCGTCCCGG<br>CAGATCATGCTCTGGGGCCAGGGCACCCTGGTCACCGTCTCCTCA | TRDTSTSTVYMELS<br>SLRSEDTAVYYCAR<br>DGYGSSSRQIMLWG<br>QGTLVTVSS |
| T0675H | SEQ ID NO: 462 | SEQ ID NO: 467 | SEQ ID NO: 547<br>ARDGYGS<br>SSRVIQL | SEQ ID NO: 548<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>GTGATCCAGCTCTGGGGCCAGGGCACCCTGGTCACCGTCTCCTCA | SEQ ID NO: 549<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRVIQLWG<br>QGTLVTVSS |
| T0676H | SEQ ID NO: 462 | SEQ ID NO: 467 | SEQ ID NO: 550<br>ARDGYGS<br>SSRVLML | SEQ ID NO: 551<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>GTGCTCATGCTCTGGGGCCAGGGCACCCTGGTCACCGTCTCCTCA | SEQ ID NO: 552<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRVLMLWG<br>QGTLVTVSS |
| T0677H | SEQ ID NO: 462 | SEQ ID NO: 467 | SEQ ID NO: 553<br>ARDGYGS<br>SSRVIML | SEQ ID NO: 554<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTCGTCCCGG<br>GTGATCATGCTCTGGGGCCAGGGCACCCTGGTCACCGTCTCCTCA | SEQ ID NO: 555<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSSSRVIMLWG<br>QGTLVTVSS |
| T0678H | SEQ ID NO: 462 | SEQ ID NO: 467 | SEQ ID NO: 556<br>ARDGYGS<br>FSRIIQL | SEQ ID NO: 557<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>ATCATCCAGCTCTGGGGCCAGGGCACCCTGGTCACCGTCTCCTCA | SEQ ID NO: 558<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRIIQLWG<br>QGTLVTVSS |
| T0679H | SEQ ID NO: 462 | SEQ ID NO: 467 | SEQ ID NO: 559<br>ARDGYGS<br>FSRILML | SEQ ID NO: 560<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>ATCCTCATGCTCTGGGGCCAGGGCACCCTGGTCACCGTCTCCTCA | SEQ ID NO: 561<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRILMLWG<br>QGTLVTVSS |
| T0680H | SEQ ID NO: 462 | SEQ ID NO: 467 | SEQ ID NO: 562<br>ARDGYGS<br>FSRIIML | SEQ ID NO: 563<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>ATCATCATGCTCTGGGGCCAGGGCACCCTGGTCACCGTCTCCTCA | SEQ ID NO: 564<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRIIMLWG<br>QGTLVTVSS |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| T0681H | SEQ ID NO: 462 | SEQ ID NO: 467 | SEQ ID NO: 565 ARDGYGS FSRLIQL | SEQ ID NO: 566 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CTGATCCAGCTCTGGGGCCAGGGCACCCTGGTCACCGTCTCCTCA | SEQ ID NO: 567 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSFSRLIQLWG QGTLVTVSS |
| T0682H | SEQ ID NO: 462 | SEQ ID NO: 467 | SEQ ID NO: 568 ARDGYGS FSRLLML | SEQ ID NO: 569 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CTGCTCATGCTCTGGGGCCAGGGCACCCTGGTCACCGTCTCCTCA | SEQ ID NO: 570 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSFSRLLMLWG QGTLVTVSS |
| T0683H | SEQ ID NO: 462 | SEQ ID NO: 467 | SEQ ID NO: 571 ARDGYGS FSRLIML | SEQ ID NO: 572 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CTGATCATGCTCTGGGGCCAGGGCACCCTGGTCACCGTCTCCTCA | SEQ ID NO: 573 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSFSRLIMLWG QGTLVTVSS |
| T0684H | SEQ ID NO: 462 | SEQ ID NO: 467 | SEQ ID NO: 574 ARDGYGS FSRQIQL | SEQ ID NO: 575 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CAGATCCAGCTCTGGGGCCAGGGCACCCTGGTCACCGTCTCCTCA | SEQ ID NO: 576 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSFSRQIQLWG QGTLVTVSS |
| T0685H | SEQ ID NO: 462 | SEQ ID NO: 467 | SEQ ID NO: 577 ARDGYGS FSRQLML | SEQ ID NO: 578 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CAGCTCATGCTCTGGGGCCAGGGCACCCTGGTCACCGTCTCCTCA | SEQ ID NO: 579 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSFSRQLMLWG QGTLVTVSS |
| T0686H | SEQ ID NO: 462 | SEQ ID NO: 467 | SEQ ID NO: 580 ARDGYGS FSRQIML | SEQ ID NO: 581 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CAGATCATGCTCTGGGGCCAGGGCACCCTGGTCACCGTCTCCTCA | SEQ ID NO: 582 QVQLIQSGAEVKKP GASVKVSCKASRYS FTSYYMHWVRQAPG QGLEWMGIINPKSG STSYAQKFQGRVTM TRDTSTSTVYMELS SLRSEDTAVYYCAR DGYGSFSRQIMLWG QGTLVTVSS |
| T0687H | SEQ ID NO: 462 | SEQ ID NO: 467 | SEQ ID NO: 583 ARDGYGS FSRVIQL | SEQ ID NO: 584 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTACAAGTTACGCACAGAAGTTCCAGGGCAGAGTCACCATGAC CAGGGACACGTCCACGAGCACAGTCTACATGGAGCTGAGCAGCCTGAGATCTG | SEQ ID NO: 585 QVQLIQSGAEVKKP GASVKVSCKASRYS FTSYYMHWVRQAPG QGLEWMGIINPKSG STSYAQKFQGRVTM |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| | | | | | AGGACACGGCCGTGTATTACTGTGCGAGAGATGGGTATGGCAGCTTCTCCCGG TRDTSTSTVYMELS<br>GTGATCCAGCTCTGGGGCCAGGGCACCCTGGTCACCGTCTCCTCA SLRSEDTAVYYCAR<br>DGYGSFSRVIQLWG<br>QGTLVTVSS |
| T0688H | SEQ ID NO: 462 | SEQ ID NO: 467 | SEQ ID NO: 586 ARDGYGS FSRVLML | SEQ ID NO: 587<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>GTGCTCATGCTCTGGGGCCAGGGCACCCTGGTCACCGTCTCCTCA | SEQ ID NO: 588<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRVLMLWG<br>QGTLVTVSS |
| T0689H | SEQ ID NO: 462 | SEQ ID NO: 467 | SEQ ID NO: 589 ARDGYGS FSRVIML | SEQ ID NO: 590<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>GTGATCATGCTCTGGGGCCAGGGCACCCTGGTCACCGTCTCCTCA | SEQ ID NO: 591<br>QVQLIQSGAEVKKP<br>GASVKVSCKASRYS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRVIMLWG<br>QGTLVTVSS |
| T0713H | SEQ ID NO: 592 RFSFTSY Y | SEQ ID NO: 467 | SEQ ID NO: 565 | SEQ ID NO: 593<br>CAGGTGCAGTTGATACAGTCTGGGGCTGAGGTGAAGAAGCCTGGGGCCTCAGT<br>GAAGGTTTCCTGCAAGGCATCTAGATTCAGCTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 594<br>QVQLIQSGAEVKKP<br>GASVKVSCKASRFS<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRLIQLWG<br>QGTLVTVSS |
| T0734H | SEQ ID NO: 595 RYHFTSY Y | SEQ ID NO: 467 | SEQ ID NO: 565 | SEQ ID NO: 596<br>CAGGTGCAGTTGATACAGTCTGGGGCTGAGGTGAAGAAGCCTGGGGCCTCAGT<br>GAAGGTTTCCTGCAAGGCATCTAGATACCACTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 597<br>QVQLIQSGAEVKKP<br>GASVKVSCKASRYH<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRLIQLWG<br>QGTLVTVSS |
| T0736H | SEQ ID NO: 598 RYKFTSY Y | SEQ ID NO: 467 | SEQ ID NO: 565 | SEQ ID NO: 599<br>CAGGTGCAGTTGATACAGTCTGGGGCTGAGGTGAAGAAGCCTGGGGCCTCAGT<br>GAAGGTTTCCTGCAAGGCATCTAGATACAAGTTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 600<br>QVQLIQSGAEVKKP<br>GASVKVSCKASRYK<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRLIQLWG<br>QGTLVTVSS |
| T0742H | SEQ ID NO: 601 RYRFTSY Y | SEQ ID NO: 467 | SEQ ID NO: 565 | SEQ ID NO: 602<br>CAGGTGCAGTTGATACAGTCTGGGGCTGAGGTGAAGAAGCCTGGGGCCTCAGT<br>GAAGGTTTCCTGCAAGGCATCTAGATACAGATTCACCAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 603<br>QVQLIQSGAEVKKP<br>GASVKVSCKASRYR<br>FTSYYMHWVRQAPG<br>QGLEWMGIINPKSG<br>STSYAQKFQGRVTM<br>TRDTSTSTVYMELS<br>SLRSEDTAVYYCAR<br>DGYGSFSRLIQLWG<br>QGTLVTVSS |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| T0774H | SEQ ID NO: 604 RYSFKSY Y | SEQ ID NO: 467 | SEQ ID NO: 565 | SEQ ID NO: 605<br>CAGGTGCAGTTGATACAGTCTGGGGCTGAGGTGAAGAAGCCTGGGGCCTCAGT<br>GAAGGTTTCCTGCAAGGCATCTAGATACAGCTTCAAGAGCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 606<br>QVQLIQSGAEVKKP<br>GASVKVSCKASRYS<br>FKSYYMHWVRQAPG<br>QGLEWMGIINPKSG<br>STSYAQKFQGRVTM<br>TRDTSTSTVYMELS<br>SLRSEDTAVYYCAR<br>DGYGSFSRLIQLWG<br>QGTLVTVSS |
| T0785H | SEQ ID NO: 607 RYSFTAY Y | SEQ ID NO: 467 | SEQ ID NO: 565 | SEQ ID NO: 608<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCGCCTACTATATGCACT<br>GGGTGCGACAGGCCCCTGGACAAGGGCTTGAGTGGATGGGAATAATCAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 609<br>QVQLIQSGAEVKKP<br>GASVKVSCKASRYS<br>FTAYYMHWVRQAPG<br>QGLEWMGIINPKSG<br>STSYAQKFQGRVTM<br>TRDTSTSTVYMELS<br>SLRSEDTAVYYCAR<br>DGYGSFSRLIQLWG<br>QGTLVTVSS |
| T0850H | SEQ ID NO: 462 | SEQ ID NO: 610 LNPKSGS T | SEQ ID NO: 565 | SEQ ID NO: 611<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATACTGAACCCT<br>AAAAGTGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 612<br>QVQLIQSGAEVKKP<br>GASVKVSCKASRYS<br>FTSYYMHWVRQAPG<br>QGLEWMGILNPKSG<br>STSYAQKFQGRVTM<br>TRDTSTSTVYMELS<br>SLRSEDTAVYYCAR<br>DGYGSFSRLIQLWG<br>QGTLVTVSS |
| T0925H | SEQ ID NO: 462 | SEQ ID NO: 613 INPKIGS T | SEQ ID NO: 565 | SEQ ID NO: 614<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAATCGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 615<br>QVQLIQSGAEVKKP<br>GASVKVSCKASRYS<br>FTSYYMHWVRQAPG<br>QGLEWMGIINPKIG<br>STSYAQKFQGRVTM<br>TRDTSTSTVYMELS<br>SLRSEDTAVYYCAR<br>DGYGSFSRLIQLWG<br>QGTLVTVSS |
| T0926H | SEQ ID NO: 462 | SEQ ID NO: 616 INPKKGS T | SEQ ID NO: 565 | SEQ ID NO: 617<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAAGGGTAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 618<br>QVQLIQSGAEVKKP<br>GASVKVSCKASRYS<br>FTSYYMHWVRQAPG<br>QGLEWMGIINPKKG<br>STSYAQKFQGRVTM<br>TRDTSTSTVYMELS<br>SLRSEDTAVYYCAR<br>DGYGSFSRLIQLWG<br>QGTLVTVSS |
| T0951H | SEQ ID NO: 462 | SEQ ID NO: 619 INPKSSS T | SEQ ID NO: 565 | SEQ ID NO: 620<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTAGCAGTACAAGTTACGCACAGAAGTTCCAGGGCAGAGTCACCATGAC<br>CAGGGACACGTCCACGAGCACAGTCTACATGGAGCTGAGCAGCCTGAGATCTG<br>AGGACACGGCCGTGTATTACTGTGCGAGAGATGGGTATGGCAGCTTCTCCCGG<br>CTGATCCAGCTCTGGGGCCAGGGCACCCTGGTCACCGTCTCCTCA | SEQ ID NO: 621<br>QVQLIQSGAEVKKP<br>GASVKVSCKASRYS<br>FTSYYMHWVRQAPG<br>QGLEWMGIINPKSS<br>STSYAQKFQGRVTM<br>TRDTSTSTVYMELS<br>SLRSEDTAVYYCAR<br>DGYGSFSRLIQLWG<br>QGTLVTVSS |
| T0958H | SEQ ID NO: 462 | SEQ ID NO: 622 INPKSGD T | SEQ ID NO: 565 | SEQ ID NO: 623<br>CAGGTGCAGTTGATACAGTCTGGGGCTGAGGTGAAGAAGCCTGGGGCCTCAGT<br>GAAGGTTTCCTGCAAGGCATCTAGATACAGCTTCACCAGCTACTATATGCACT<br>GGGTGCGACAGGCCCCTGGACAAGGGCTTGAGTGGATGGGAATAATCAACCCT<br>AAAAGTGGTGACACAAGTTACGCACAGAAGTTCCAGGGCAGAGTCACCATGAC<br>CAGGGACACGTCCACGAGCACAGTCTACATGGAGCTGAGCAGCCTGAGATCTG | SEQ ID NO: 624<br>QVQLIQSGAEVKKP<br>GASVKVSCKASRYS<br>FTSYYMHWVRQAPG<br>QGLEWMGIINPKSG<br>DTSYAQKFQGRVTM |

TABLE S-10C-continued

Anti-FX VH domain sequences and CDRs
The following TxxxxH VH domains are suitable for pairing with a common
light chain VL such as VL domain 0128L or 0325L.

| Ab VH | HCDR1 | HCDR2 | HCDR3 | VH nucleotide sequence | VH amino acid sequence |
|---|---|---|---|---|---|
| | | | | AGGACACGGCCGTGTATTACTGTGCGAGAGATGGGTATGGCAGCTTCTCCCGG CTGATCCAGCTCTGGGGCCAGGGCACCCTGGTCACCGTCTCCTCA | TRDTSTSTVYMELS SLRSEDTAVYYCAR DGYGSFSRLIQLWG QGTLVTVSS |
| T0989H | SEQ ID NO: 462 | SEQ ID NO: 625 INPKSGS R | SEQ ID NO: 565 | SEQ ID NO: 626 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTAGAAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CTGATCCAGCTCTGGGGCCAGGGCACCCTGGTCACCGTCTCCTCA | SEQ ID NO: 627 QVQLIQSGAEVKKP GASVKVSCKASRYS FTSYYMHWVRQAPG QGLEWMGIINPKSG SRSYAQKFQGRVTM TRDTSTSTVYMELS SLRSEDTAVYYCAR DGYGSFSRLIQLWG QGTLVTVSS |
| T0990H | SEQ ID NO: 462 | SEQ ID NO: 628 INPKSGS S | SEQ ID NO: 565 | SEQ ID NO: 629 CAGGTGCAGTTGATACAGTCTGGGGCTGAGGTGAAGAAGCCTGGGGCCTCAGT GAAGGTTTCCTGCAAGGCATCTAGATACAGCTTCACCAGCTACTATATGCACT GGGTGCGACAGGCCCCTGGACAAGGGCTTGAGTGGATGGGAATAATCAACCCT AAAAGTGGTAGTAGCAGTTACGCACAGAAGTTCCAGGGCAGAGTCACCATGAC CAGGGACACGTCCACGAGCACAGTCTACATGGAGCTGAGCAGCCTGAGATCTG AGGACACGGCCGTGTATTACTGTGCGAGAGATGGGTATGGCAGCTTCTCCCGG CTGATCCAGCTCTGGGGCCAGGGCACCCTGGTCACCGTCTCCTCA | SEQ ID NO: 630 QVQLIQSGAEVKKP GASVKVSCKASRYS FTSYYMHWVRQAPG QGLEWMGIINPKSG SSSYAQKFQGRVTM TRDTSTSTVYMELS SLRSEDTAVYYCAR DGYGSFSRLIQLWG QGTLVTVSS |
| T0999H | SEQ ID NO: 598 | SEQ ID NO: 467 | SEQ ID NO: 565 | SEQ ID NO: 631 CAGGTTCAGCTGATTCAGTCCGGCGCCAAAGTGAAGAAACCTGGCGCCTCTGT GAAGGTGTCCTGCAAGGCCTCTCGGTACAAGTTCACCTCCTACTACATGCACT GGGTCCGACAGGCCCCTGGACAAGGATTGGAGTGGATGGGCATCATCAACCCC AAGTCCGGCTCCACCTCTTACGCCCAGAAATTCCAGGGCAGAGTGACCATGAC CAGAGACACCTCTACCTCCACCGTGTACATGGAACTGTCCAGCCTGAGATCCG AGGACACCGCCGTGTACTACTGTGCCAGAGATGGCTACGGCAGCTTCTCCAGA CTGATCCAGTTGTGGGGCCAGGGCACACTGGTCACAGTGTCCTCT | SEQ ID NO: 632 QVQLIQSGAKVKKP GASVKVSCKASRYK FTSYYMHWVRQAPG QGLEWMGIINPKSG STSYAQKFQGRVTM TRDTSTSTVYMELS SLRSEDTAVYYCAR DGYGSFSRLIQLWG QGTLVTVSS |

SEQ ID NO: 636. Consensus HCDR1.
RYXFTSYY
X is K or S
Representing the T0201H VH CDR1 RYSFTSYY (SEQ ID NO: 462) in which the Ser at IMGT
position 29 is retained or replaced by Lys.

SEQ ID NO: 637. Consensus HCDR3.
ARDGYGSX$_1$SRX$_2$X$_3$QL
X1 is F or S. X2 is any amino acid. X3 is I or L.
Representing the T0201H CDR3 ARDGYGSSSRCLQL (SEQ ID NO: 468) in which the
Ser at IMGT position 111A is retained or replaced by Phe, the Cys at IMGT
position 114 is retained or replaced by another amino acid residue, and the
Leu at IMGT position 115 is retained or replaced by Ile.

SEQ ID NO: 638. Consensus HCDR3.
ARDGYGSX$_1$SRX$_2$X$_3$QL
X1 is F or S. X2 is Leu or Val. X3 is I or L.
Representing the T0201H CDR3 ARDGYGSSSRCLQL (SEQ ID NO: 468) in which the
Ser at IMGT position 111A is retained or replaced by Phe, the Cys at IMGT
position 114 is replaced by Leu or Val, and the Leu at IMGT position 115 is
retained or replaced by Ile.

SEQ ID NO: 639. Consensus HCDR3.
ARDGYGSFSRXIQL
X is Leu or Val.
Representing the T0201H CDR3 ARDGYGSSSRCLQL (SEQ ID NO: 468) in which the
Ser at IMGT position 111A is replaced by Phe, the Cys at IMGT position 114
is replaced by Leu or Val, and the Leu at IMGT position is replaced by Ile.

TABLE S-11

| | | Heavy chain sequences |
|---|---|---|
| SEQ ID NO: 418 | Nucleic acid encoding N1280H-IgG4-P K439E; N1280 coding sequence underlined. | <u>GAAGTGCAGCTGGTTGAATCTGGCGGCGGATTTGTTCAGCCTGGCGGCTCTCTGAGACTGTCCTGTGCTGTGTCC<br>GGCTTCCGGTTCAACTCCTACTGGATGTCCTGGGTCCGACAGGCTCCTGGCAAAGGACTGGAATGGGTCGCCAAC<br>ATCAACCAGGACGGCTCCCGGAAGTTCTACGTGGCCTCTGTGAAGGGCAGATTCACCATGTCTCGGGACAACGCC<br>AAGAAATCCGTGTACGTGCAGATGAACTCCCTGAGAGCCGAGGACACCGCCGTGTACTACTGTGCTAGAGAGGGC<br>TACTCCTCCATCAAGTACTACGGCATGGACGTGGGGGCCAGGGCACAACCGTGACAGTCTCTTCCGCTTCCACC</u><br>AAGGGACCCAGCGTTTTCCCTCTGGCTCCTTGCTCCAGATCCACCTCCGAGTCTACAGCTGCTCTGGGCTGCCTG<br>GTCAAGGACTACTTTCCTGAGCCTGTGACCGTGTCCTGGAACTCTGGCGCTCTGACATCTGGCGTGCACACCTTT<br>CCAGCTGTGCTGCAGTCCTCCGGCCTGTACTCTCTGTCCTCTGTCGTGACCGTGCCTTCCAGCTCTCTGGGAACC<br>CAGACCTACACCTGTAATGTGGACCACAAGCCTTCCAACACCAAGGTGGACAAGCGCGTGGAATCTAAGTACGGC<br>CCTCCTTGTCCTCCATGTCCTGCTCCAGAGTTTCTCGGCGGACCCTCCGTGTTTCTGTTCCCTCCAAAGCCTAAG<br>GACACCCTGATGATCTCTCGGACCCCTGAAGTGACCTGCGTGGTGGTGGATGTGTCCAAGAGGATCCCGAGGTG<br>CAGTTCAATTGGTACGTGGACGGCGTGGAAGTGCACAATGCCAAGACCAAGCCTAGAGAGGAACAGTACAACTCC<br>ACCTACAGAGTGGTGTCCGTGCTGACCGTGCTGCACCAGGATTGGCTGAACGGCAAAGAGTACAAGTGCAAGGTG<br>TCCAACAAGGGCCTGCCTAGCTCCATCGAAAAGACCATCTCCAAGGCCAAGGGCCAGCCTCGAGAACCCCAGGTT<br>TACACCCTGCCTCCAAGCCAAGAGGAAATGACCAAGAACCAGGTGTCCCTGACCTGTCTCGTGAAGGGCTTCTAC<br>CCCTCCGATATCGCCGTGGAATGGGAGTCTAATGGCCAGCCAGAGAACAACTACAAGACCACACCTCCAGTGCTG<br>GACTCCGACGGCTCATTCTTTCTGTACTCCAAGCTGACAGTGGACAAGTCCCGGTGGCAAGAGGGCAACGTGTTC<br>TCCTGCTCTGTGATGCACGAGGCCCTGCACAACCACTACACCCAAGAGTCCCTGTCTCTGTCCCCT |
| SEQ ID NO: 419 | N1280H-IgG4-P K439E amino acid sequence | EVQLVESGGGFVQPGGSLRLSCAVSGFRFNSYWMSWVRQAPGKGLEWVANINQDGSRKFYVASVKGRFTMSRDNA<br>KKSVYVQMNSLRAEDTAVYYCAREGYSSIKYYGMDVWGQGTTVTVSSASTKGPSVFPLAPCSRSTSESTAALGCL<br>VKDYFPEPVTVSWNSGALTSGVHTFPAVLQSSGLYSLSSVVTVPSSSLGTQTYTCNVDHKPSNTKVDKRVESKYG<br>PPCPPCPAPEFLGGPSVFLFPPKPKDTLMISRTPEVTCVVVDVSQEDPEVQFNWYVDGVEVHNAKTKPREEQYNS<br>TYRVVSVLTVLHQDWLNGKEYKCKVSNKGLPSSIEKTISKAKGQPREPQVYTLPPSQEEMTKNQVSLTCLVKGFY<br>PSDIAVEWESNGQPENNYKTTPPVLDSDGSFFLYSKLTVDKSRWQEGNVFSCSVMHEALHNHYTQESLSLSP |
| SEQ ID NO: 420 | Nucleic acid encoding T0999H-IgG4-P E356K; T0999H coding sequence underlined | <u>CAGGTTCAGCTGATTCAGTCCGGCGCCAAAGTGAAGAAACCTGGCGCCTCTGTGAAGGTGTCCTGCAAGGCCTCT<br>CGGTACAAGTTCACCTCCTACTACATGCACTGGGTCCGACAGGCCCCTGGACAAGGATTGGAGTGGATGGGCATC<br>ATCAACCCCAAGTCCGGCTCCACCTCTTACGCCCAGAAATTCCAGGGCAGAGTGACCATGACCAGAGACACCTCT<br>ACCTCCACCGTGTACATGGAACTGTCCAGCCTGAGATCCGAGGACACCGCCGTGTACTACTGTGCCAGAGATGGC<br>TACGGCAGCTTCTCCAGATCGATCCAGTTGTGGGGCCAGGGCACACTGGTCACAGTGTCCTCTGCTTCCACCAAG</u><br>GGACCCAGCGTGTTCCCTCTGGCTCCTTGCTCCAGATCCACCTCCGAGTCTACAGCTGCTCTGGGCTGCCTGGTC<br>AAGGACTACTTTCCTGAGCCTGTGACCGTGTCTTGGAACTCTGGCGCTCTGACATCTGGCGTGCACACCTTTCCA<br>GCTGTGCTGCAGTCCTCCGGCCTGTACTCTCTGTCCTCTGTCGTGACCGTGCCTTCCAGCTCTCTGGGAACCCAG<br>ACCTACACCTGTAATGTGGACCACAAGCCTTCCAACACCAAGGTGGACAAGCGCGTGGAATCTAAGTACGGCCCT<br>CCTTGTCCTCCATGTCCTGCTCCAGAGTTTCTCGGCGGACCCTCCGTGTTTCTGTTCCCTCCAAAGCCTAAGGAC<br>ACCCTGATGATCTCTCGGACCCCTGAAGTGACCTGCGTGGTGGTGGATGTGTCCAAGAGGATCCCGAGGTGCAG<br>TTCAATTGGTACGTGGACGGCGTGGAAGTGCACAATGCCAAGACCAAGCCTAGAGAGGAACAGTACAACTCCACC<br>TACAGAGTGGTGTCCGTGCTGACCGTGCTGCACCAGGATTGGCTGAACGGCAAAGAGTACAAGTGCAAGGTGTCC<br>AACAAGGGCCTGCCTAGCTCCATCGAAAAGACCATCTCCAAGGCCAAGGGCCAGCCTCGAGAACCCCAGGTTTAC<br>ACCCTGCCTCCAAGCCAGAAAGAGATGACCAAGAACCAGGTGTCCCTGACCTGCCTCGTGAAGGGCTTCTACCCT<br>TCCGATATCGCCGTGGAATGGGAGAGCAATGGCCAGCCAGAGAACAACTACAAGACCACACCTCCTGTGCTGGAC<br>TCCGATGGCTCATTCTTTCTGTACTCCAAGCTGACAGTGGACAAGTCCCGGTGGCAAGAGGGCAACGTGTTCTCC<br>TGCTCTGTGATGCACGAGGCCCTGCACAACCACTACACCCAGAGTCCCTGTCTCTGTCCCCT |
| SEQ ID NO: 421 | T0999H-IgG4-P E356K amino acid sequence | QVQLIQSGAKVKKPGASVKVSCKASRYKFTSYYMHWVRQAPGQGLEWMGIINPKSGSTSYAQKFQGRVTMTRDTS<br>TSTVYMELSSLRSEDTAVYYCARDGYGSFSRLIQLWGQGTLVTVSSASTKGPSVFPLAPCSRSTSESTAALGCLV<br>KDYFPEPVTVSWNSGALTSGVHTFPAVLQSSGLYSLSSVVTVPSSSLGTQTYTCNVDHKPSNTKVDKRVESKYGP<br>PCPPCPAPEFLGGPSVFLFPPKPKDTLMISRTPEVTCVVVDVSQEDPEVQFNWYVDGVEVHNAKTKPREEQYNST<br>YRVVSVLTVLHQDWLNGKEYKCKVSNKGLPSSIEKTISKAKGQPREPQVYTLPPSQEMTKNQVSLTCLVKGFYP<br>SDIAVEWESNGQPENNYKTTPPVLDSDGSFFLYSKLTVDKSRWQEGNVFSCSVMHEALHNHYTQKSLSLSP |
| SEQ ID NO: 423 | Nucleic acid encoding N1454H-IgG4-P K439E | GAAGTGCAGCTGGTTGAATCTGGCGGCGGATTTGTTCAGCCTGGCGGCTCTCTGAGACTGTCCTGTGCTGTGTCC<br>GGCTTCCGGTTCAACTCCTACTGGATGTCCTGGGTCCGACAGGCTCCTGGCAAAGGACTGGAATGGGTCGCCAAC<br>ATCAACCAGGACGGCTCCCGGAAGTTCTACGTGGCCTCTGTGAAGGGCAGATTCACCATGTCTCGGGACAACGCC<br>AAGAAAGCCGTGTACGTGCAGATGAACTCCCTGAGAGCCGAGGACACCGCCGTGTACTACTGTGCTAGAGAGGGC<br>TACTCCTCCATCAAGTACTACGGCATGGACGTGTGGGGCCAGGGCACAACCGTGACAGTCTCTTCCGCTTCCACC<br>AAGGGACCCAGCGTTTTCCCTCTGGCTCCTTGCTCCAGATCCACCTCCGAGTCTACAGCTGCTCTGGGCTGCCTG<br>GTCAAGGACTACTTTCCTGAGCCTGTGACCGTGTCCTGGAACTCTGGCGCTCTGACATCTGGCGTGCACACCTTT<br>CCAGCTGTGCTGCAGTCCTCCGGCCTGTACTCTCTGTCCTCTGTCGTGACCGTGCCTTCCAGCTCTCTGGGAACC<br>CAGACCTACACCTGTAATGTGGACCACAAGCCTTCCAACACCAAGGTGGACAAGCGCGTGGAATCTAAGTACGGC<br>CCTCCTTGTCCTCCATGTCCTGCTCCAGAGTTTCTCGGCGGACCCTCCGTGTTTCTGTTCCCTCCAAAGCCTAAG<br>GACACCCTGATGATCTCTCGGACCCCTGAAGTGACCTGCGTGGTGGTGGATGTGTCCAAGAGGATCCCGAGGTG<br>CAGTTCAATTGGTACGTGGACGGCGTGGAAGTGCACAATGCCAAGACCAAGCCTAGAGAGGAACAGTACAACTCC<br>ACCTACAGAGTGGTGTCCGTGCTGACCGTGCTGCACCAGGATTGGCTGAACGGCAAAGAGTACAAGTGCAAGGTG<br>TCCAACAAGGGCCTGCCTAGCTCCATCGAAAAGACCATCTCCAAGGCCAAGGGCCAGCCTCGAGAACCCCAGGTT<br>TACACCCTGCCTCCAAGCCAAGAGGAAATGACCAAGAACCAGGTGTCCCTGACCTGTCTCGTGAAGGGCTTCTAC<br>CCCTCCGATATCGCCGTGGAATGGGAGTCTAATGGCCAGCCAGAGAACAACTACAAGACCACACCTCCAGTGCTG<br>GACTCCGACGGCTCATTCTTTCTGTACTCCAAGCTGACAGTGGACAAGTCCCGGTGGCAAGAGGGCAACGTGTTC<br>TCCTGCTCTGTGATGCACGAGGCCCTGCACAACCACTACACCCAAGAGTCCCTGTCTCTGTCCCCT |
| SEQ ID NO: 424 | N1454H-IgG4-P K439E amino acid sequence | EVQLVESGGGFVQPGGSLRLSCAVSGFRFNSYWMSWVRQAPGKGLEWVANINQDGSRKFYVASVKGRFTMSRDNA<br>KKSVYVQMNSLRAEDTAVYYCAREGYSSIKYYGMDVWGQGTTVTVSSASTKGPSVFPLAPCSRSTSESTAALGCL<br>VKDYFPEPVTVSWNSGALTSGVHTFPAVLQSSGLYSLSSVVTVPSSSLGTQTYTCNVDHKPSNTKVDKRVESKYG<br>PPCPPCPAPEFLGGPSVFLFPPKPKDTLMISRTPEVTCVVVDVSQEDPEVQFNWYVDGVEVHNAKTKPREEQYNS<br>TYRVVSVLTVLHQDWLNGKEYKCKVSNKGLPSSIEKTISKAKGQPREPQVYTLPPSQEEMTKNQVSLTCLVKGFY<br>PSDIAVEWESNGQPENNYKTTPPVLDSDGSFFLYSKLTVDKSRWQEGNVFSCSVMHEALHNHYTQESLSLSP |

TABLE S-11-continued

Heavy chain sequences

| SEQ ID NO: 425 | Nucleic acid encoding N1441H-IgG4-P K439E | GAAGTGCAGCTGGTTGAATCTGGCGGCGGATTTGTTCAGCCTGGCGGCTCTCTGAGACTGTCCTGTGCTGTGTCC<br>GGCTTCCGGTTCAACTCCTACTGGATGTCCTGGGTCCGACAGGCTCCTGGCAAAGGACTGGAATGGGTCGCCAAC<br>ATCAACCAGGACGGCTCCCGGAAGTTCTACGTGGCCTCTGTGAAGGGCAGATTCACCATGTCTCGGGACAACGCC<br>GACAAGTCCGTGTACGTGCAGATGAACTCCCTGAGAGCCGAGGACACCGCCGTGTACTACTGTGCTAGAGAGGGC<br>TACTCCTCCATCAAGTACTACGGCATGGACGTGTGGGGCCAGGGCACAACCGTGACAGTCTCTTCCGCTTCCACC<br>AAGGGACCCAGCGTTTTCCCTCTGGCTCCTTGCTCCAGATCACCTCCGAGTCTACAGCTGCTCTGGGCTGCCTG<br>GTCAAGGACTACTTTCCTGAGCCTGTGACCGTGTCCTGGAACTCTGGCGCTCTGACATCTGGCGTGCACACCTTT<br>CCAGCTGTGCTGCAGTCCTCCGGCCTGTACTCTCTGTCCTCTGTCGTGACCGTGCCTTCCAGCTCTCTGGGAACC<br>CAGACCTACACCTGTAATGTGGACCACAAGCCTTCCAACACCAAGGTGGACAAGCGCGTGGAATCTAAGTACGGC<br>CCTCCTTGTCCTCCATGTCCTGCTCCAGAGTTTCTCGGCGGACCCTCCGTGTTTCTGTTCCCTCCAAAGCCTAAG<br>GACACCCTGATGATCTCTCGGACCCCTGAAGTGACCTGCGTGGTGGTGGATGTGTCCAAGAGGATCCCGAGGTG<br>CAGTTCAATTGGTACGTGGACGGCGTGGAAGTGCACAACGCCAAGACCAAGCCTAGAGAGGAACAGTACAACTCC<br>ACCTACAGAGTGGTGTCCGTGCTGACCGTGCTGCACCAGGATTGGCTGAACGGCAAGAGTACAAGTGCAAGGTG<br>TCCAACAAGGGCCTGCCTAGCTCCATCGAAAAGACCATCTCCAAGGCCAAGGGCCAGCCTGAGAACCCCAGGTT<br>TACACCCTGCCTCCAAGCCAAGAGGAAATGACCAAGAACCAGGTGTCCCTGACCTGTCTCGTGAAGGGCTTCTAC<br>CCCTCCGATATCGCCGTGGAATGGGAGTCTAATGGCCAGCCAGAGAACAACTACAAGACCACACCTCCAGTGCTG<br>GACTCCGACGGCTCATTCTTTCTGTACTCCAAGCTGACAGTGGACAAGTCCCGGTGGCAAGAGGGCAACGTGTTC<br>TCCTGCTCTGTGATGCACGAGGCCCTGCACAACCACTACACCCAAGAGTCCCTGTCTCTGTCCCCT |
| --- | --- | --- |
| SEQ ID NO: 426 | N1441H-IgG4-P K439E amino acid sequence | EVQLVESGGGFVQPGGSLRLSCAVSGFRFNSYWMSWVRQAPGKGLEWVANINQDGSRKFYVASVKGRFTMSRDNA<br>DKSVYVQMNSLRAEDTAVYYCAREGYSSIKYYGMDVWGQGTTVTVSSASTKGPSVFPLAPCSRSTSESTAALGCL<br>VKDYFPEPVTVSWNSGALTSGVHTFPAVLQSSGLYSLSSVVTVPSSSLGTQTYTCNVDHKPSNTKVDKRVESKYG<br>PPCPPCPAPEFLGGPSVFLFPPKPKDTLMISRTPEVTCVVVDVSQEDPEVQFNWYVDGVEVHNAKTKPREEQYNS<br>TYRVVSVLTVLHQDWLNGKEYKCKVSNKGLPSSIEKTISKAKGQPREPQVYTLPPSQEEMTKNQVSLTCLVKGFY<br>PSDIAVEWESNGQPENNYKTTPPVLDSDGSFFLYSKLTVDKSRWQEGNVFSCSVMHEALHNHYTQESLSLSP |
| SEQ ID NO: 427 | Nucleic acid encoding N1442H-IgG4-P K439E | GAAGTGCAGCTGGTTGAATCTGGCGGCGGATTTGTTCAGCCTGGCGGCTCTCTGAGACTGTCCTGTGCTGTGTCC<br>GGCTTCCGGTTCAACTCCTACTGGATGTCCTGGGTCCGACAGGCTCCTGGCAAAGGACTGGAATGGGTCGCCAAC<br>ATCAACCAGGACGGCTCCCGGAAGTTCTACGTGGCCTCTGTGAAGGGCAGATTCACCATGTCTCGGGACAACGCC<br>GAGAAGTCCGTGTACGTGCAGATGAACTCCCTGAGAGCCGAGGACACCGCCGTGTACTACTGTGCTAGAGAGGGC<br>TACTCCTCCATCAAGTACTACGGCATGGACGTGTGGGGCCAGGGCACAACCGTGACAGTCTCTTCCGCTTCCACC<br>AAGGGACCCAGCGTTTTCCCTCTGGCTCCTTGCTCCAGATCACCTCCGAGTCTACAGCTGCTCTGGGCTGCCTG<br>GTCAAGGACTACTTTCCTGAGCCTGTGACCGTGTCCTGGAACTCTGGCGCTCTGACATCTGGCGTGCACACCTTT<br>CCAGCTGTGCTGCAGTCCTCCGGCCTGTACTCTCTGTCCTCTGTCGTGACCGTGCCTTCCAGCTCTCTGGGAACC<br>CAGACCTACACCTGTAATGTGGACCACAAGCCTTCCAACACCAAGGTGGACAAGCGCGTGGAATCTAAGTACGGC<br>CCTCCTTGTCCTCCATGTCCTGCTCCAGAGTTTCTCGGCGGACCCTCCGTGTTTCTGTTCCCTCCAAAGCCTAAG<br>GACACCCTGATGATCTCTCGGACCCCTGAAGTGACCTGCGTGGTGGTGGATGTGTCCCAAGAGGATCCCGAGGTG<br>CAGTTCAATTGGTACGTGGACGGCGTGGAAGTGCACAACGCCAAGACCAAGCCTAGAGAGGAACAGTACAACTCC<br>ACCTACAGAGTGGTGTCCGTGCTGACCGTGCTGCACCAGGATTGGCTGAACGGCAAGAGTACAAGTGCAAGGTG<br>TCCAACAAGGGCCTGCCTAGCTCCATCGAAAAGACCATCTCCAAGGCCAAGGGCCAGCCTGAGAACCCCAGGTT<br>TACACCCTGCCTCCAAGCCAAGAGGAAATGACCAAGAACCAGGTGTCCCTGACCTGTCTCGTGAAGGGCTTCTAC<br>CCCTCCGATATCGCCGTGGAATGGGAGTCTAATGGCCAGCCAGAGAACAACTACAAGACCACACCTCCAGTGCTG<br>GACTCCGACGGCTCATTCTTTCTGTACTCCAAGCTGACAGTGGACAAGTCCCGGTGGCAAGAGGGCAACGTGTTC<br>TCCTGCTCTGTGATGCACGAGGCCCTGCACAACCACTACACCCAAGAGTCCCTGTCTCTGTCCCCT |
| SEQ ID NO: 428 | N1442H-IgG4-P K439E amino acid sequence | EVQLVESGGGFVQPGGSLRLSCAVSGFRFNSYWMSWVRQAPGKGLEWVANINQDGSRKFYVASVKGRFTMSRDNA<br>EKSVYVQMNSLRAEDTAVYYCAREGYSSIKYYGMDVWGQGTTVTVSSASTKGPSVFPLAPCSRSTSESTAALGCL<br>VKDYFPEPVTVSWNSGALTSGVHTFPAVLQSSGLYSLSSVVTVPSSSLGTQTYTCNVDHKPSNTKVDKRVESKYG<br>PPCPPCPAPEFLGGPSVFLFPPKPKDTLMISRTPEVTCVVVDVSQEDPEVQFNWYVDGVEVHNAKTKPREEQYNS<br>TYRVVSVLTVLHQDWLNGKEYKCKVSNKGLPSSIEKTISKAKGQPREPQVYTLPPSQEEMTKNQVSLTCLVKGFY<br>PSDIAVEWESNGQPENNYKTTPPVLDSDGSFFLYSKLTVDKSRWQEGNVFSCSVMHEALHNHYTQESLSLSP |
| SEQ ID NO: 429 | Nucleic acid encoding T0736H-IgG4-P E356K | CAGGTTCAGCTGATTCAGTCTGGCGCCGAAGTGAAGAAACCTGGCGCCTCTGTGAAGGTGTCCTGCAAGGCCTCT<br>CGGTACAAGTTCACCTCCTACTACATGCACTGGGTCCGACAGGCCCCTGGACAAGGATTGGAGTGGATGGGCATC<br>ATCAACCCCAAGTCCGGCTCCACCTCTTACGCCCAGAAATTCCAGGGCAGAGTGACCATGACCAGAGACACCTCT<br>ACCTCCACCGTGTACATGGAACTGTCCAGCCTGAGATCCGAGGACACCGCCGTGTACTACTGTGCCAGAGATGGC<br>TACGGCAGCTTCTCCAGGCTGATCCAGTTGTGGGGACAGGGCACACTGGTCACCGTGTCCTGCTTCTACCAAG<br>GGACCCAGCGTGTTCCCTCTGGCTCCTTGCTCCAGATCACCTCCGAGTCTACAGCTGCTCTGGGCTGCCTGGTC<br>AAGGACTACTTTCCTGAGCCTGTGACCGTGTCTTGGAACTCTGGCGCTCTGACATCTGGCGTGCACACCTTTCCA<br>GCTGTGCTGCAGTCCTCCGGCCTGTACTCTCTGTCCTCTGTCGTGACCGTGCCTTCCAGCTCTCTGGGAACCCAG<br>ACCTACACCTGTAATGTGGACCACAAGCCTTCCAACACCAAGGTGGACAAGCGCGTGGAATCTAAGTACGGCCCT<br>CCTTGTCCTCCATGTCCTGCTCCAGAGTTTCTCGGCGGACCCTCCGTGTTTCTGTTCCCTCCAAAGCCTAAGGAC<br>ACCCTGATGATCTCTCGGACCCCTGAAGTGACCTGCGTGGTGGTGGATGTGTCCCAAGAGGATCCCGAGGTGCAG<br>TTCAATTGGTACGTGGACGGCGTGGAAGTGCACAACGCCAAGACCAAGCCTAGAGAGGAACAGTACAACTCCACC<br>TACAGAGTGGTGTCCGTGCTGACCGTGCTGCACCAGGATTGGCTGAACGGCAAAGAGTACAAGTGCAAGGTGTCC<br>AACAAGGGCCTGCCTAGCTCCATCGAAAAGACCATCTCCAAGGCCAAGGGCCAGCCTGAGAACCCCAGGTTTAC<br>ACCCTGCCTCCAAGCCAGAAAGATGACCAAGAACCAGGTGTCCCTGACCTGCCTCGTGAAGGGCTTCTACCCT<br>TCCGATATCGCCGTGGAATGGGAGAGCAATGGCCAGCCAGAGAACAACTACAAGACCACACCTCCTGTGCTGGAC<br>TCCGATGGCTCATTCTTTCTGTACTCCAAGCTGACAGTGGACAAGTCCCGGTGGCAAGAGGGCAACGTGTTCTCC<br>TGCTCTGTGATGCACGAGGCCCTGCACAACCACTACACCCAGAAGTCCCTGTCTCTGTCCCCT |
| SEQ ID NO: 430 | T0736H-IgG4-P E356K amino acid sequence | QVQLIQSGAEVKKPGASVKVSCKASRYKFTSYYMHWVRQAPGQGLEWMGIINPKSGSTSYAQKFQGRVTMTRDTS<br>TSTVYMELSSLRSEDTAVYYCARDGYGSFSRLIQLWGQGTLVTVSSASTKGPSVFPLAPCSRSTSESTAALGCLV<br>KDYFPEPVTVSWNSGALTSGVHTFPAVLQSSGLYSLSSVVTVPSSSLGTQTYTCNVDHKPSNTKVDKRVESKYGP<br>PCPPCPAPEFLGGPSVFLFPPKPKDTLMISRTPEVTCVVVDVSQEDPEVQFNWYVDGVEVHNAKTKPREEQYNST<br>YRVVSVLTVLHQDWLNGKEYKCKVSNKGLPSSIEKTISKAKGQPREPQVYTLPPSQKEMTKNQVSLTCLVKGFYP<br>SDIAVEWESNGQPENNYKTTPPVLDSDGSFFLYSKLTVDKSRWQEGNVFSCSVMHEALHNHYTQKSLSLSP |

TABLE S-11-continued

Heavy chain sequences

| SEQ ID NO: 431 | Nucleic acid encoding T0687H-IgG4-P E356K | CAGGTTCAGCTGATTCAGTCTGGCGCCGAAGTAAGAAACCTGGCGCCTCTGTGAAGGTGTCCTGCAAGGCCTCC<br>AGATACTCCTTCACCTCCTACTACATGCACTGGGTCCGACAGGCCCCTGGACAAGGATTGGAGTGGATGGGCATC<br>ATCAACCCCAAGTCCGGCTCCACCTCTTACGCCCAGAAATTCCAGGGCAGAGTGACCATGACCAGAGACACCTCT<br>ACCTCCACCGTGTACATGGAACTGTCCAGCCTGAGATCCGAGGACACCGCCGTGTACTACTGTGCCAGAGATGGC<br>TACGGCTCCTTCAGCAGAGTGATCCAGTTGTGGGGCCAGGGCACACTGGTCACAGTGTCCTCTGCTTCCACCAAG<br>GGACCCAGCGTGTTCCCTCTGGCTCCTTGCTCCAGATCCACCTCCGAGTCTACAGCTGCTCTGGGCTGCCTGGTC<br>AAGGACTACTTTCCTGAGCCTGTGACCGTGTCTTGGAACTCTGGCGCTCTGACATCGGCGTGCACACCTTTCCA<br>GCTGTGCTGCAGTCCTCCGGCCTGTACTCTCTGTCCTCTGTCGTGACCGTGCCTTCCAGCTCTCTGGGAACCCAG<br>ACCTACACCTGTAATGTGACCACAAGCCTTCCAACACCAAGGTGGACAAGCGCGTGGAATCTAAGTACGGCCCT<br>CCTTGTCCTCCATGTCCTGCTCCAGAGTTTCTCGGCGGACCCTCCGTGTTTCTGTTCCCTCCAAAGCCTAAGGAC<br>ACCCTGATGATCTCTCGGACCCCTGAAGTGACCTGCGTGGTGGTGGATGTGTCCCAAGAGGATCCCGAGGTGCAG<br>TTCAATTGGTACGTGGACGGCGTGGAAGTGCACAACGCCAAGACCAAGCCTAGAGAGGAACAGTACAACTCCACC<br>TACAGAGTGGTGTCCGTGCTGACCGTGCTGCACCAGGATTGGCTGAACGGCAAAGAGTACAAGTGCAAGGTGTCC<br>AACAAGGGCCTGCCTAGCTCCATCGAAAAGACCATCTCCAAGGCCAAGGGCCAGCCTCGAGAACCCCAGGTTTAC<br>ACCCTGCCTCCAAGCCAGAAAGAGATGACCAAGAACCAGGTGTCCCTGACCTGCCTCGTGAAGGGCTTCTACCCT<br>TCCGATATCGCCGTGGAATGGGAGAGCAATGGCCAGCCAGAGAACAACTACAAGACCACACCTCCTGTGCTGGAC<br>TCCGATGGCTCATTCTTTCTGTACTCCAAGCTGACAGTGGACAAGTCCCGGTGGCAAGAGGGCAACGTGTTCTCC<br>TGCTCTGTGATGCACGAGGCCCTGCACAACCACTACACCCAGAAGTCCCTGTCTCTGTCCCCT |
| --- | --- | --- |
| SEQ ID NO: 432 | T0687H-IgG4-P E356K amino acid sequence | QVQLIQSGAEVKKPGASVKVSCKASRYSFTSYYMHWVRQAPGQGLEWMGIINPKSGSTSYAQKFQGRVTMTRDTS<br>TSTVYMELSSLRSEDTAVYYCARDGYGSFSRVIQLWGQGTLVTVSSASTKGPSVFPLAPCSRSTSESTAALGCLV<br>KDYFPEPVTVSWNSGALTSGVHTFPAVLQSSGLYSLSSVVTVPSSSLGTQTYTCNVDHKPSNTKVDKRVESKYGP<br>PCPPCPAPEFLGGPSVFLFPPKPKDTLMISRTPEVTCVVVDVSQEDPEVQFNWYVDGVEVHNAKTKPREEQYNST<br>YRVVSVLTVLHQDWLNGKEYKCKVSNKGLPSSIEKTISKAKGQPREPQVYTLPPSQKEMTKNQVSLTCLVKGFYP<br>SDIAVEWESNGQPENNYKTTPPVLDSDGSFFLYSKLTVDKSRWQEGNVFSCSVMHEALHNHYTQKSLSLSP |

Human Germline Gene Segments

TABLE S-12

Corresponding qermline v and j gene segments
for antibody VH and VL domains

| | V -- J |
| --- | --- |
| Anti-FIX heavy chain | |
| N128 | IGHV3-7*01--IGHJ6*02 |
| N183 | IGHV3-48*02--IGHJ6*02 |
| Anti FX heavy chain | |
| T0200 | IGHV1-46*03--IGHJ1*01 |
| Common light chain | |
| N0128L | IGLV3-21*d01--IGOLJ2*01 |

Common Light Chain Sequences

TABLE S-50A

N0128 and N0325 VL domain sequences and CDRs

| Ab VL | LCDR1 | LCDR2 | LCDR3 | VL nucleotide sequence | VL amino acid sequence |
| --- | --- | --- | --- | --- | --- |
| N128L | SEQ ID NO: 6 NIGRKS | SEQ ID NO: 7 YDS | SEQ ID NO: 8 QVWDGS SDHWV | SEQ ID NO: 9<br>TCCTATGTGCTGACTCAGCCACCCTCAGTGTCAGTGGCCCCAGGAGA<br>GACGGCCAGGATTACCTGTGGGGGAGACAACATTGGAAGGAAAAGTG<br>TGTACTGGTACCAGCAGAAGTCAGGCCAGGCCCCTGTGCTGGTCATC<br>TATTATGATAGCGACCGGCCCTCAGGGATCCCTGAGCGATTCTCTGG<br>GTCCAACTCTGGGAACACGGCGACCCTGACCATCAGCAGGGTCGAAG<br>CCGGGGATGAGGCCGACTATTACTGTCAGGTGTGGGATGAAGTAGT<br>GATCATTGGGTGTTCGGCGAGGGACCAAGTTGACCGTCCTAG | SEQ ID NO: 10<br>SYVLTQPPSVSVAPGETA<br>RITCGGDNIGRKSVYWYQ<br>QKSGQAPVLVIYYDSDRP<br>SGIPERFSGSNSGNTATL<br>TISRVEAGDEADYYCQVW<br>DGSSDHWVFGGGTKLTVL |

TABLE S-50A-continued

N0128 and N0325 VL domain sequences and CDRs

| Ab VL | LCDR1 | LCDR2 | LCDR3 | VL nucleotide sequence | VL amino acid sequence |
|---|---|---|---|---|---|
| N325L | SEQ ID NO: 6 | SEQ ID NO: 7 | SEQ ID NO: 8 | SEQ ID NO: 415<br>TACGTGCTGACCCAGCCTCCTTCCGTGTCTGTTGCTCCTGGCGAGAC<br>AGCCAGAATCACCTGTGGCGGCGATAACATCGGCCGGAAGTCCGTGT<br>ACTGGTATCAGCAGAAGTCCGGCCAGGCTCCTGTGCTGGTCATCTAC<br>TACGACTCCGACCGGCCTTCTGGCATCCCTGAGAGATTCTCCGGCTC<br>CAACTCCGGCAATACCGCCACACTGACCATCTCCAGAGTGGAAGCTG<br>GCGACGAGGCCGACTACTACTGCCAAGTGTGGGACGGCTCCTCTGAC<br>CACTGGGTTTTCGGCGGAGGCACCAAGCTGACAGTGCTG | SEQ ID NO: 416<br>YVLTQPPSVSVAPGETAR<br>ITCGGDNIGRKSVYWYQQ<br>KSGQAPVLVIYYDSDRPS<br>GIPERFSGSNSGNTATLT<br>ISRVEAGDEADYYCQVWD<br>GSSDHWVFGGGTKLTVL |

TABLE S-50B

N0128 and N0325 VL domain framework sequences

| Ab VL | FR1 | FR2 | FR3 | FR4 |
|---|---|---|---|---|
| N128L | SEQ ID NO: 136<br>SYVLTQPPSVSVAP<br>GETARITCGGD | SEQ ID NO: 137<br>VYWYQQKSGQAPVL<br>VIY | SEQ ID NO: 138<br>DRPSGIPERFSGSN<br>SGNTATLTISRVEA<br>GDEADYYC | SEQ ID NO: 139<br>FGGGTKLTVL |
| N325L | SEQ ID NO: 417<br>YVLTQPPSVSVAPG<br>ETARITCGGD | SEQ ID NO: 137 | SEQ ID NO: 138 | SEQ ID NO: 139 |

TABLE S-50C

N0128 and N0325 light chain sequences

| SEQ ID NO: 404 | N0128L-IgL Coding nucleic acid | TCCTATGTGC TGACTCAGCC ACCCTCAGTG TCAGTGGCCC CAGGAGAGAC GGCCAGGATT ACCTGTGGGG GAGACAACAT TGGAAGGAAA AGTGTGTACT GGTACCAGCA GAAGTCAGGC CAGGCCCCTG TGCTGGTCAT CTATTATGAT AGCGACCGGC CCTCAGGGAT CCCTGAGCGA TTCTCTGGGT CCAACTCTGG GAACACGGCG ACCCTGACCA TCAGCAGGGT CGAAGCCGGG GATGAGGCCG ACTATTACTG TCAGGTGTGG GATGGAAGTA GTGATCATTG GGTGTTCGGC GGAGGGACCA AGTTGACCGT CCTAGGTCAG CCCAAGGCTG CCCCCTCGGT CACTCTGTTC CCACCCTCCT CTGAGGAGCT TCAAGCCAAC AAGGCCACAC TGGTGTGTCT CATAAGTGAC TTCTACCCGG GAGCCGTGAC AGTGGCCTGG AAGGCAGATA GCAGCCCCGT CAAGGCGGGA GTGGAGACCA CCACACCCTC CAAACAAAGC AACAACAAGT ACGCGGCCAG CAGCTACCTG AGCCTGACGC CTGAGCAGTG GAAGTCCCAC AAAAGCTACA GCTGCCAGGT CACGCATGAA GGGAGCACCG TGGAGAAGAC AGTGGCCCCT ACAGAATGTT CA |
|---|---|---|
| SEQ ID NO: 405 | N0128L light chain amino acid sequence (mature) | SYVLTQPPSVSVAPGETARITCGGDNIGRKSVYWYQQKSGQAPVLVIYYDSDRPSGIPERFSGSNSGNTATL<br>TISRVEAGDEADYYCQVWDGSSDHWVFGGGTKLTVLGQPKAAPSVTLFPPSSEELQANKATLVCLISDFYPG<br>AVTVAWKADSSPVKAGVETTTPSKQSNNKYAASSYLSLTPEQWKSHKSYSCQVTHEGSTVEKTVAPTECS |
| SEQ ID NO: 413 | N0325L-IgL coding nucleic acid; N0325L coding sequence underlined | <u>TACGTGCTGACCCAGCCTCCTTCCGTGTCTGTTGCTCCTGGCGAGACAGCCAGAATCACCTGTGGCGGCGAT<br>AACATCGGCCGGAAGTCCGTGTACTGGTATCAGCAGAAGTCCGGCCAGGCTCCTGTGCTGGTCATCTACTAC<br>GACTCCGACCGGCCTTCTGGCATCCCTGAGAGATTCTCCGGCTCCAACTCCGGCAATACCGCCACACTGACC<br>ATCTCCAGAGTGGAAGCTGGCGACGAGGCCGACTACTACTGCCAAGTGTGGGACGGCTCCTCTGACCACTGG<br>GTTTTCGGCGGAGGCACCAAGCTGACAGTGCTG</u>GGACAACCTAAGGCCGCTCCTTCTGTGACCCTGTTTCCT<br>CCATCTCCGAGGAACTGCAGGCCAACAAGGCTACCCTCGTGTGCCTGATCTCCGACTTTTACCCTGGCGCT<br>GTGACCGTGGCCTGGAAGGCTGATAGTTCTCCTGTGAAGGCCGGCGTGGAAACCACCACACCTTCCAAGCAG<br>TCCAACAACAAATACGCCGCCTCCTCCTACCTGTCTCTGACCCCTGAACAGTGGAAGTCCCACAAGTCCTAC<br>TCTTGCCAAGTGACCCACGAGGGCTCCACCGTGGAAAAGACAGTGGCTCCTACCGAGTGCTCC |
| SEQ ID NO: 414 | N0325L light chain amino acid sequence (mature) | YVLTQPPSVSVAPGETARITCGGDNIGRKSVYWYQQKSGQAPVLVIYYDSDRPSGIPERFSGSNSGNTATLT<br>ISRVEAGDEADYYCQVWDGSSDHWVFGGGTKLTVLGQPKAAPSVTLFPPSSEELQANKATLVCLISDFYPGA<br>VTVAWKADSSPVKAGVETTTPSKQSNNKYAASSYLSLTPEQWKSHKSYSCQVTHEGSTVEKTVAPTECS |

Recombinant expression of bispecific antibody using common light chain N0128L with its native human Igλ leader sequence (v3-21 leader peptide MAWTALLL-GLLLSHCTGSVT SEQ ID NO: 519) resulted in clipping of the N terminal Ser to produce antibody in which the VL domain was identical to the sequence shown herein for N0325 VL domain. For use with alternative leader sequences in which the mature light chain polypeptide is produced by cleavage after the Ser, the light chain 0325 was generated in order to achieve the same mature product. 0325 omits the N terminal Ser residue of 0128L.

Constant Regions

TABLE S-100

| Antibody constant region sequences | |
|---|---|
| IgG4 PE human heavy chain constant region | SEQ ID NO: 143<br>ASTKGPSVFPLAPCSRSTSESTAALGCLVKDYFPEPVTVSWNSGALTSGVHTFPAVLQSSGLYSLSSVVTVP<br>SSSLGTKTYTCNVDHKPSNTKVDKRVESKYGPPCPPCPAPEFEGGPSVFLFPPKPKDTLMISRTPEVTCVVV<br>DVSQEDPEVQFNWYVDGVEVHNAKTKPREEQFNSTYRVVSVLTVLHQDWLNGKEYKCKVSNKGLPSSIEKTI<br>SKAKGQPREPQVYTLPPSQEEMTKNQVSLTCLVKGFYPSDIAVEWESNGQPENNYKTTPPVLDSDGSFFLYS<br>RLTVDKSRWQEGNVFSCSVMHEALHNHYTQKSLSLSLGK |
| IgG4 human heavy chain constant region with knobs-into-holes mutations and hinge mutation. Type a (IgG4ra) | SEQ ID NO: 144<br>ASTKGPSVFPLAPCSRSTSESTAALGCLVKDYFPEPVTVSWNSGALTSGVHTFPAVLQSSGLYSLSSVVTVP<br>SSSLGTKTYTCNVDHKPSNTKVDKRVESKYGPPCPPCPAPEFEGGPSVFLFPPKPKDTLMISRTPEVTCVVV<br>DVSQEDPEVQFNWYVDGVEVHNAKTKPREEQFNSTYRVVSVLTVLHQDWLNGKEYKCKVSNKGLPSSIEKTI<br>SKAKGQPREPQVCTLPPSQEEMTKNQVSLWCLVKGFYPSDIAVEWESNGQPENNYKTTPPVLDSDGSFFLYS<br>RLTVDKSRWQEGNVFSCSVMHEALHNHYTQKSLSLSLGK |
| IgG4 human heavy chain constant region with knobs-into-holes mutations and hinge mutation. Type b (IgG4yb) | SEQ ID NO: 145<br>ASTKGPSVFPLAPCSRSTSESTAALGCLVKDYFPEPVTVSWNSGALTSGVHTFPAVLQSSGLYSLSSVVTVP<br>SSSLGTKTYTCNVDHKPSNTKVDKRVESKYGPPCPPCPAPEFEGGPSVFLFPPKPKDTLMISRTPEVTCVVV<br>DVSQEDPEVQFNWYVDGVEVHNAKTKPREEQFNSTYRVVSVLTVLHQDWLNGKEYKCKVSNKGLPSSIEKTI<br>SKAKGQPREPQVYTLPPSQCEMTKNQVSLSCAVKGFYPSDIAVEWESNGQPENNYKTTPPVLDSDGSFFLVS<br>RLTVDKSRWQEGNVFSCSVMHEALHNHYTQKSLSLSLGK |
| IgG4 human heavy chain constant region with P (hinge) mutation and K439E | SEQ ID NO: 409<br>ASTKGPSVFPLAPCSRSTSESTAALGCLVKDYFPEPVTVSWNSGALTSGVHTFPAVLQSSGLYSLSSVVTVP<br>SSSLGTQTYTCNVDHKPSNTKVDKRVESKYGPPCPPCPAPEFLGGPSVFLFPPKPKDTLMISRTPEVTCVVV<br>DVSQEDPEVQFNWYVDGVEVHNAKTKPREEQYNSTYRVVSVLTVLHQDWLNGKEYKCKVSNKGLPSSIEKTI<br>SKAKGQPREPQVYTLPPSQEEMTKNQVSLTCLVKGFYPSDIAVEWESNGQPENNYKTTPPVLDSDGSFFLYS<br>KLTVDKSRWQEGNVFSCSVMHEALHNHYTQESLSLSP |
| IgG4 human heavy chain constant region with P (hinge) mutation and E356K | SEQ ID NO: 410<br>ASTKGPSVFPLAPCSRSTSESTAALGCLVKDYFPEPVTVSWNSGALTSGVHTFPAVLQSSGLYSLSSVVTVP<br>SSSLGTQTYTCNVDHKPSNTKVDKRVESKYGPPCPPCPAPEFLGGPSVFLFPPKPKDTLMISRTPEVTCVVV<br>DVSQEDPEVQFNWYVDGVEVHNAKTKPREEQYNSTYRVVSVLTVLHQDWLNGKEYKCKVSNKGLPSSIEKTI<br>SKAKGQPREPQVYTLPPSQKEMTKNQVSLTCLVKGFYPSDIAVEWESNGQPENNYKTTPPVLDSDGSFFLYS<br>KLTVDKSRWQEGNVFSCSVMHEALHNHYTQKSLSLSP |
| IgG4-P K439E encoding nucleic acid | SEQ ID NO: 411<br>GCTTCCACCAAGGGACCCAGCGTTTTCCCTCTGGCTCCTTGCTCCAGATCCACCTCCGAGTCTACAGCTGCT<br>CTGGGCTGCCTGGTCAAGGACTACTTTCCTGAGCCTGTGACCGTGTCCTGGAACTCTGGCGCTCTGACATCT<br>GGCGTGCACACCTTTCCAGCTGTGCTGCAGTCCTCCGGCCTGTACTCTCTGTCCTCTGTCGTGACCGTGCCT<br>TCCAGCTCTCTGGGAACCCAGACCTACACCTGTAATGTGGACCACAAGCCTTCCAACACCAAGGTGGACAAG<br>CGCGTGGAATCTAAGTACGGCCCTCCTTGTCCTCCATGTCCTGCTCCAGAGTTTCTCGGCGGACCCTCCGTG<br>TTTCTGTTCCCTCCAAAGCCTAAGGACACCCTGATGATCTCTCGGACCCCTGAAGTGACCTGCGTGGTGGTG<br>GATGTGTCCCAAGAGGATCCCGAGGTGCAGTTCAATTGGTACGTGGACGGCGTGGAAGTGCACAATGCCAAG<br>ACCAAGCCTAGAGAGGAACAGTACAACTCCACCTACAGAGTGGTGTCCGTGCTGACCGTGCTGCACCAGGAT<br>TGGCTGAACGGCAAAGAGTACAAGTGCAAGGTGTCCAACAAGGGCCTGCCTAGCTCCATCGAAAAGACCATC<br>TCCAAGGCCAAGGGCCAGCCTCGAGAACCCCAGGTTTACACCCTGCCTCCAAGCCAAGAGGAAATGACCAAG<br>AACCAGGTGTCCCTGACCTGTCTCGTGAAGGGCTTCTACCCCTCCGATATCGCCGTGGAATGGGAGTCTAAT<br>GGCCAGCCAGAGAACAACTACAAGACCACACCTCCAGTGCTGGACTCCGACGGCTCATTCTTTCTGTACTCC<br>AAGCTGACAGTGGACAAGTCCCGGTGGCAAGAGGGCAACGTGTTCTCCTGCTCTGTGATGCACGAGGCCCTG<br>CACAACCACTACACCCAAGAGTCCCTGTCTCTGTCCCCT |
| IgG4-P E356K encoding nucleic acid | SEQ ID NO: 412<br>GCTTCCACCAAGGGACCCAGCGTGTTCCCTCTGGCTCCTTGCTCCAGATCCACCTCCGAGTCTACAGCTGCT<br>CTGGGCTGCCTGGTCAAGGACTACTTTCCTGAGCCTGTGACCGTGTCTTGGAACTCTGGCGCTCTGACATCT<br>GGCGTGCACACCTTTCCAGCTGTGCTGCAGTCCTCCGGCCTGTACTCTCTGTCCTCTGTCGTGACCGTGCCT<br>TCCAGCTCTCTGGGAACCCAGACCTACACCTGTAATGTGGACCACAAGCCTTCCAACACCAAGGTGGACAAG<br>CGCGTGGAATCTAAGTACGGCCCTCCTTGTCCTCCATGTCCTGCTCCAGAGTTTCTCGGCGGACCCTCCGTG<br>TTTCTGTTCCCTCCAAAGCCTAAGGACACCCTGATGATCTCTCGGACCCCTGAAGTGACCTGCGTGGTGGTG<br>GATGTGTCCCAAGAGGATCCCGAGGTGCAGTTCAATTGGTACGTGGACGGCGTGGAAGTGCACAACGCCAAG<br>ACCAAGCCTAGAGAGGAACAGTACAACTCCACCTACAGAGTGGTGTCCGTGCTGACCGTGCTGCACCAGGAT<br>TGGCTGAACGGCAAAGAGTACAAGTGCAAGGTGTCCAACAAGGGCCTGCCTAGCTCCATCGAAAAGACCATC<br>TCCAAGGCCAAGGGCCAGCCTCGAGAACCCCAGGTTTACACCCTGCCTCCAAGCCAGAAAGAGATGACCAAG<br>AACCAGGTGTCCCTGACCTGCCTCGTGAAGGGCTTCTACCCTTCCGATATCGCCGTGGAATGGGAGCAAT<br>GGCCAGCCAGAGAACAACTACAAGACCACACCTCCTGTGCTGGACTCCGATGGCTCATTCTTTCTGTACTCC<br>AAGCTGACAGTGGACAAGTCCCGGTGGCAAGAGGGCAACGTGTTCTCCTGCTCTGTGATGCACGAGGCCCTG<br>CACAACCACTACACCCAGAAGTCCCTGTCTCTGTCCCCT |

TABLE S-100-continued

Antibody constant region sequences

| | |
|---|---|
| Nucleic acid encoding IgL human lambda light chain constant region | SEQ ID NO: 633<br>GGACAACCTAAGGCCGCTCCTTCTGTGACCCTGTTTCCTCCATCCTCCGAGGAACTGCAGGCCAACAAGGCT<br>ACCCTCGTGTGCCTGATCTCCGACTTTTACCCTGGCGCTGTGACCGTGGCCTGGAAGGCTGATAGTTCTCCT<br>GTGAAGGCCGGCGTGGAAACCACCACACCTTCCAAGCAGTCCAACAACAAATACGCCGCCTCCTCCTACCTG<br>TCTCTGACCCCTGAACAGTGGAAGTCCCACAAGTCCTACTCTTGCCAAGTGACCCACGAGGGCTCCACCGTG<br>GAAAAGACAGTGGCTCCTACCGAGTGCTCC |
| Human lambda light chain constant region | SEQ ID NO: 146<br>GQPKAAPSVTLFPPSSEELQANKATLVCLISDFYPGAVTVAWKADSSPVKAGVETTTPSKQSNNKYAASSYL<br>SLTPEQWKSHKSYSCQVTHEGSTVEKTVAPTECS |
| Human kappa light chain constant region | SEQ ID NO: 147<br>KRTVAAPSVFIFPPSDEQLKSGTASVVCLLNNFYPREAKVQWKVDNALQSGNSQESVTEQDSKDSTYSLSST<br>LTLSKADYEKHKVYACEVTHQGLSSPVTKSFNRGEC |

TABLE N

N128H Alanine Scanning Mutants

| CDR1 (GFTFNSYW) (SEQ ID NO: 1) | G<br>N400H | F<br>N401H | T<br>N402H | F<br>N403H | N<br>N404H | S<br>N405H | Y<br>N406H | W<br>N407H |
|---|---|---|---|---|---|---|---|---|
| CDR2 (INQDGSEK) (SEQ ID NO: 2) | I<br>N408H | N<br>N409H | Q<br>N410H | D<br>N411H | G<br>N412H | S<br>N413H | E<br>N414H | K<br>N415H |

| CDR3 (AREGYSSSSYYGMDV) (SEQ ID NO: 3) | A<br>N416H | R<br>N417H | E<br>N418H | G<br>N419H | Y<br>N420H | S<br>N421H | S<br>N422H | S<br>N423H | S<br>N424H | Y<br>N425H | Y<br>N426H | G<br>N427H | M<br>N428H | D<br>N429H | V |
|---|---|---|---|---|---|---|---|---|---|---|---|---|---|---|---|

N128H CDR3 Mutants

| CDR3 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| AREGYSSSSYYGMDV (SEQ ID NO: 3) | N420H | N467H | N468H | N469H | N470H | N471H | N472H | N473H | N474H | N475H | N476H | N477H | N478H | N479H | N480H | N128H | N481H | N482H | N483H | N484H |
| AREGYSSSSYYGMDV (SEQ ID NO: 3) | N421H | N485H | N486H | N487H | N488H | N489H | N490H | N491H | N492H | N493H | N494H | N495H | N496H | N497H | N498H | N128H | N499H | N500H | N501H | N502H |
| AREGYSSSSYYGMDV (SEQ ID NO: 3) | N422H | N430H | N431H | N432H | N433H | N434H | N435H | N436H | N437H | N438H | N439H | N440H | N441H | N442H | N443H | N128H | N444H | N445H | N446H | N447H |
| AREGYSSSSYYGMDV (SEQ ID NO: 3) | N423H | N448H | N449H | N450H | N451H | N452H | N453H | N454H | N455H | N456H | N457H | N458H | N459H | N460H | N461H | N128H | N462H | N463H | N464H | N465H |
| AREGYSSSSYYGMDV (SEQ ID NO: 3) | N424H | N542H | N543H | N544H | N545H | N546H | N547H | N548H | N549H | N550H | N551H | N552H | N553H | N554H | N555H | N128H | N556H | N557H | N558H | N559H |
| AREGYSSSSYYGMDV (SEQ ID NO: 3) | N425H | N561H | N562H | N563H | N564H | N565H | N566H | N567H | N568H | N569H | N570H | N571H | N572H | N573H | N574H | N559H | N575H | N576H | N577H | N128H |
| AREGYSSSSYYGMDV (SEQ ID NO: 3) | N426H | N579H | N580H | N581H | N582H | N128H | N583H | N584H | N585H | N586H | N587H | N588H | N589H | N590H | N591H | N592H | N593H | N594H | N595H | N596H |
| AREGYSSSSYYGMDV (SEQ ID NO: 3) | N427H | N597H | N598H | N599H | N600H | N601H | N602H | N603H | N604H | N605H | N128H | N606H | N607H | N608H | N609H | N610H | N611H | N612H | N613H | N614H |
| AREGYSSSSYYGMDV (SEQ ID NO: 3) | N428H | N615H | N616H | N617H | N618H | N619H | N620H | N621H | N622H | N623H | N128H | N624H | N625H | N626H | N627H | N628H | N629H | N630H | N631H | N632H |
| AREGYSSSSYYGMDV (SEQ ID NO: 3) | N429H | N633H | N634H | N635H | N636H | N637H | N638H | N639H | N640H | N641H | N642H | N643H | N644H | N645H | N646H | N647H | N648H | N128H | N649H | N650H |
| AREGYSSSSYYGMDV (SEQ ID NO: 3) | N128H | N651H | N652H | N653H | N654H | N655H | N656H | N657H | N658H | N659H | N660H | N661H | N662H | N663H | N664H | N665H | N666H | N667H | N668H | N669H |
| AREGYSSSSYYGMDV (SEQ ID NO: 3) | N416H | N670H | N671H | N672H | N673H | N674H | N675H | N676H | N677H | N678H | N679H | N680H | N681H | N682H | N128H | N683H | N684H | N685H | N686H | N687H |

TABLE N-continued

| CDR3 | | A | C | D | E | F | G | H | I | K | L | M | N | P | Q | R | S | T | V | W | Y |
|---|---|---|---|---|---|---|---|---|---|---|---|---|---|---|---|---|---|---|---|---|---|
| AREGYSSSSYYGMDV (SEQ ID NO: 3) | | N417H | N689H | N690H | N128H | N691H | N692H | N693H | N694H | N695H | N696H | N697H | N698H | N699H | N700H | N701H | N702H | N703H | N704H | N705H | N706H |
| AREGYSSSSYYGMDV (SEQ ID NO: 3) | | N418H | N707H | N708H | N709H | N710H | N711H | N712H | N713H | N714H | N715H | N716H | N128H | N717H | N718H | N719H | N720H | N721H | N722H | N723H | N724H |
| AREGYSSSSYYGMDV (SEQ ID NO: 3) | | N419H | N725H | N726H | N727H | N728H | N128H | N729H | N730H | N731H | N732H | N733H | N734H | N735H | N736H | N737H | N738H | N739H | N740H | N741H | N128H |

| CDR3 | A | C | D | E | F | G | H | I | K | L | M | N | P | Q | R | S | T | V | W | Y |
|---|---|---|---|---|---|---|---|---|---|---|---|---|---|---|---|---|---|---|---|---|

N436 CDR3 Mutants

| CDR3 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| AREGYSSISYYGMDV (SEQ ID NO: 171) | N503H | N504H | N505H | N506H | N507H | N508H | N509H | N510H | N511H | N512H | N513H | N514H | N515H | N516H | N517H | N436H | N518H | N519H | N520H | N521H |
| AREGYSSISYYGMDV (SEQ ID NO: 171) | N522H | N523H | N524H | N525H | N526H | N527H | N528H | N529H | N530H | N531H | N532H | N533H | N534H | N535H | N436H | N436H | N537H | N538H | N539H | N540H |

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|

N436 CDR1 Mutants

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | N819H | N820H | N821H | N822H | N436H | | N823H | N824H | N825H | N826H | N827H | N828H | N829H | N830H | N831H | N832H | N833H | N834H | N835H | N836H |
| GFTFNSYW (SEQ ID NO: 1) | | N837H | N838H | N839H | N436H | N840H | N841H | N842H | N843H | N844H | N845H | N846H | N847H | N848H | N849H | N850H | N851H | N852H | N853H | N854H |
| GFTFNSYW (SEQ ID NO: 1) | N856H | N857H | N858H | N859H | N436H | N860H | N861H | N862H | N863H | N864H | N865H | N866H | N867H | N868H | N869H | N870H | N436H | N871H | N872H | N873H |
| GFTFNSYW (SEQ ID NO: 1) | | N874H | N875H | N876H | N436H | N877H | N878H | N879H | N880H | N881H | N882H | N436H | N883H | N884H | N885H | N886H | N887H | N889H | N890H | N891H |
| GFTFNSYW (SEQ ID NO: 1) | N892H | N893H | N894H | N895H | N436H | N896H | N897H | N898H | N899H | N900H | N901H | N436H | N902H | N903H | N904H | N905H | N436H | N906H | N907H | N908H |
| GFTFNSYW (SEQ ID NO: 1) | | N910H | N911H | N912H | N913H | N914H | N915H | N916H | N917H | N918H | N919H | N920H | N921H | N922H | N923H | N924H | N436H | N925H | N926H | N927H |
| GFTFNSYW (SEQ ID NO: 1) | | N928H | N929H | N930H | N931H | N932H | N933H | N934H | N935H | N936H | N937H | N938H | N939H | N940H | N941H | N942H | N943H | N944H | N945H | N436H |
| GFTFNSYW (SEQ ID NO: 1) | | N946H | N947H | N948H | N949H | N950H | N951H | N952H | N953H | N954H | N955H | N956H | N957H | N958H | N959H | N960H | N961H | N962H | N963H | |

TABLE N-continued

N436H CDR2 Mutants

| CDR2 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| INQDGSEK (SEQ ID NO: 2) | N964H | N965H | N966H | N967H | N968H | N969H | N970H | N436H | N971H | N972H | N973H | N974H | N975H | N976H | N977H | N978H | N979H | N980H | N981H | N982H |
| INQDGSEK (SEQ ID NO: 2) | N983H | N984H | N985H | N986H | N987H | N988H | N989H | N990H | N991H | N992H | N993H | N436H | N994H | N995H | N996H | N997H | N998H | N999H | N1000H | N1001H |
| INQDGSEK (SEQ ID NO: 2) | N1002H | N1003H | N1004H | N1005H | N1006H | N1007H | N1008H | N1009H | N1010H | N1011H | N1012H | N1013H | N1014H | N436H | N1015H | N1016H | N1017H | N1018H | N1019H | N1020H |
| INQDGSEK (SEQ ID NO: 2) | N1021H | N1022H | N436H | N1023H | N1024H | N1025H | N1026H | N1027H | N1028H | N1029H | N1030H | N1031H | N1032H | N1033H | N1034H | N1035H | N1036H | N1037H | N1038H | N1039H |
| INQDGSEK (SEQ ID NO: 2) | N1040H | N1041H | N1042H | N1043H | N1044H | N436H | N1045H | N1046H | N1047H | N1048H | N1049H | N1050H | N1051H | N1052H | N1053H | N1054H | N1055H | N1056H | N1057H | N1058H |
| INQDGSEK (SEQ ID NO: 2) | N1059H | N1060H | N1061H | N1062H | N1063H | N1064H | N1065H | N1066H | N1067H | N1068H | N1069H | N1070H | N1071H | N1072H | N1073H | N436H | N1074H | N1075H | N1076H | N1077H |
| INQDGSEK (SEQ ID NO: 2) | N1078H | N1079H | N1080H | N436H | N1081H | N1082H | N1083H | N1084H | N1085H | N1086H | N1087H | N1088H | N1089H | N1090H | N1091H | N1092H | N1093H | N1094H | N1095H | N1096H |
| INQDGSEK (SEQ ID NO: 2) | N1097H | N1098H | N1099H | N1100H | N1101H | N1102H | N1103H | N1104H | N436H | N1105H | N1106H | N1107H | N1108H | N1109H | N1110H | N1111H | N1112H | N1113H | N1114H | N1115H |

N511H CDR2 Mutants

| CDR2 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| INQDGSEK (SEQ ID NO: 2) | N1116H | | | | | | | | | | | | | | | N1117H | N1118H | | | |
| INQDGSEK (SEQ ID NO: 2) | | | | | | | | | N1119H | | | | | | | | | | | |
| INQDGSEK (SEQ ID NO: 2) | | | | | | | | | | | | | | | | | | | | |
| INQDGSEK (SEQ ID NO: 2) | N1120H | N1121H | N511H | N1122H | N1123H | N1124H | N1125H | N1126H | N1127H | N1128H | N1129H | N1130H | N1131H | N1132H | N1133H | N1134H | N1135H | N1136H | N1137H | N1138H |
| INQDGSEK (SEQ ID NO: 2) | N1139H | | | | | | | | | | | | | | | | | | | |
| INQDGSEK (SEQ ID NO: 2) | N1140H | N1141H | N1142H | N1143H | N1144H | N1145H | N1146H | N1147H | N1148H | N1149H | N1150H | N1151H | N1152H | N1153H | N1154H | N511H | N1155H | N1156H | N1157H | N1158H |

TABLE N-continued

| CDR1 | | | | | | | | | | | | | | | | | | | | |
|---|---|---|---|---|---|---|---|---|---|---|---|---|---|---|---|---|---|---|---|---|
| INQDGSEK (SEQ ID NO: 2) | N1159H | N1160H | N1161H | N511H | N1162H | N1163H | N1164H | N1165H | N1166H | N1167H | N1168H | N1169H | N1170H | N1171H | N1172H | N1173H | N1174H | N1175H | N1176H | N1177H |
| INQDGSEK (SEQ ID NO: 2) | | | | | | | | | | | | | | | | | | | | |

Selected N436H CDR1 Mutants (batch 1)

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | | | | N825H | | | | | | | N832H | N833H | | | |
| GFTFNSYW (SEQ ID NO: 1) | | | | | | | | | | | | | | | N849H | | | | | |
| GFTFNSYW (SEQ ID NO: 1) | | | | | | | | | N863H | | | N866H | | | | | | | | |
| GFTFNSYW (SEQ ID NO: 1) | | | N875H | | | | N878H | | | | | | | | | | | N889H | | |
| GFTFNSYW (SEQ ID NO: 1) | | | | | | | | | N917H | | | N920H | N921H | | | | | N925H | | |
| GFTFNSYW (SEQ ID NO: 1) | | | | | | | | N934H | | N936H | N937H | | N939H | N940H | N941H | N942H | N943H | N944H | N945H | |
| GFTFNSYW (SEQ ID NO: 1) | N946H | N947H | | N948H | N949H | N950H | N951H | N952H | N953H | N954H | N955H | N956H | N957H | | | | | | | N963H |

N511H CDR1 Mutants

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | | | | N1178H | | | | | | | N1179H | N1180H | | | |
| GFTFNSYW (SEQ ID NO: 1) | | | | | | | | | | | | | | | N1181H | | | | | |
| GFTFNSYW (SEQ ID NO: 1) | | | | | | | | | N1182H | | | N1183H | | | | | | | | |
| GFTFNSYW (SEQ ID NO: 1) | | N1211H | | | | | N1212H | | | | | | | | | | | N1213H | | |

TABLE N-continued

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | | | | | | | | | | | | | | N1187H | |
| GFTFNSYW (SEQ ID NO: 1) | | | | | | | | | N1184H | | | N1185H | N1186H | | | | | | | |
| GFTFNSYW (SEQ ID NO: 1) | | | | | | | | N1188H | | | N1189H | N1190H | | N1191H | N1192H | N1193H | N1194H | N1195H | N1196H | N1197H |
| GFTFNSYW (SEQ ID NO: 1) | N1198H | N1199H | N1200H | N1201H | N1202H | N1203H | N1204H | N1205H | N1206H | N1207H | N1208H | N1209H | | | | | | | N1210H | |

N1172H CDR1 Mutants

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | | | N1214H | | | | | | | N1215H | N1216H | | | |
| GFTFNSYW (SEQ ID NO: 1) | | | | | | | | | | | | | | N1217H | | | | | | |
| GFTFNSYW (SEQ ID NO: 1) | | | | | | | | N1218H | | | N1219H | | | | | | | | | |
| GFTFNSYW (SEQ ID NO: 1) | | | N1247H | | | | N1248H | | | | | | | | | | | N1249H | | |
| GFTFNSYW (SEQ ID NO: 1) | | | | | | | | N1220H | | | N1221H | N1222H | | | | | | N1223H | | |
| GFTFNSYW (SEQ ID NO: 1) | | | | | | | | N1224H | | N1225H | N1226H | | N1227H | N1228H | N1229H | N1230H | N1231H | N1232H | N1233H | |
| GFTFNSYW (SEQ ID NO: 1) | N1234H | N1235H | N1236H | N1237H | N1238H | N1239H | N1240H | N1241H | N1242H | N1243H | N1244H | N1245H | | | | | | | N1246H | |

Selected N436H CDR1 Mutants (batch 2)

| CDR1 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | | | | | | | | | | | | | | | |
| GFTFNSYW (SEQ ID NO: 1) | | | | | | | | | | | | | | N869H | | | | | | |
| GFTFNSYW (SEQ ID NO: 1) | | | | | | | | | | | | | | | | | | N872H | N873H | |

TABLE N-continued

| | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | N877H | | | | | | | | | | | | | | |
| GFTFNSYW (SEQ ID NO: 1) | | | | | | | | | | | | | N886H | | N888H | N889H | | | | N891H |
| GFTFNSYW (SEQ ID NO: 1) | N892H | N893H | N894H | N895H | N896H | N897H | N898H | N899H | N900H | N901H | | | N902H | N903H | N904H | N905H | N906H | N907H | N908H | N909H |
| GFTFNSYW (SEQ ID NO: 1) | | | | | | | N915H | | | | | | | | N923H | | | | N926H | |
| GFTFNSYW (SEQ ID NO: 1) | | | | | | | | | | | N937H | | | | | | | | | |

N511H CDR1 Mutants

| | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | N1253H | | | | | | | | | N1250H | | | N1251H | N1252H | |
| GFTFNSYW (SEQ ID NO: 1) | | | | | | | | | | | | | | | N1254H | | N1255H | N1256H | | N1257H |
| GFTFNSYW (SEQ ID NO: 1) | N1258H | N1259H | N1260H | N1261H | N1262H | N1263H | N1264H | N1265H | N1266H | N1267H | | | N1268H | N1269H | N1270H | N1271H | N1272H | N1273H | N1274H | N1275H |
| GFTFNSYW (SEQ ID NO: 1) | | | | | | | N1276H | | | | | | | | N1277H | | | | N1278H | |
| GFTFNSYW (SEQ ID NO: 1) | | | | | | | | | | | N1279H | | | | | | | | | |

N1172H CDR1 Mutants

| | A | C | D | E | F | G | H | I | K | L | M | N | P | Q | R | S | T | V | W | Y |
|---|---|---|---|---|---|---|---|---|---|---|---|---|---|---|---|---|---|---|---|---|
| GFTFNSYW (SEQ ID NO: 1) | | | | | | | | | | | | | | | | | | | | |
| GFTFNSYW (SEQ ID NO: 1) | | | | | | | | | | | | | | | | | | | | |

TABLE N-continued

| CDR2 | | | | | | | | | | | | | | | | | | | | |
|---|---|---|---|---|---|---|---|---|---|---|---|---|---|---|---|---|---|---|---|---|
| GFTFNSYW (SEQ ID NO: 1) | | | | | | | | | | | | | | | | | | N1280H | N1281H | N1282H |
| GFTFNSYW (SEQ ID NO: 1) | | | | | | | | | | | | | | | | N1283H | | | | |
| GFTFNSYW (SEQ ID NO: 1) | | | | | | | | | | | | | | | | | | N1284H | N1285H N1286H | N1287H |
| GFTFNSYW (SEQ ID NO: 1) | | | | | | | N1288H N1289H N1290H N1291H N1292H N1293H N1294H N1295H N1296H N1297H | | | | | | | | N1298H N1299H N1300H N1301H N1302H N1303H N1304H N1305H | | | | | | |
| GFTFNSYW (SEQ ID NO: 1) | | | | | | | | | | | | | | | | N1306H | | N1307H | | N1308H | |
| GFTFNSYW (SEQ ID NO: 1) | | | | | | | | | | | | N1309H | | | | | | | | | |
| GFTFNSYW (SEQ ID NO: 1) | | | | | | | | | | | | | | | | | | | | | |

N1280H CDR2 Mutants

| CDR2 | A | C | D | E | F | G | H | I | K | L | M | N | P | Q | R | S | T | V | W | Y |
|---|---|---|---|---|---|---|---|---|---

TABLE T

T0201H CDR3 Mutants

| CDR3 | A | C | D | E | F | G | H | I | K | L | M | N | P | Q | R | S | T | V | W | Y |
|---|---|---|---|---|---|---|---|---|---|---|---|---|---|---|---|---|---|---|---|---|
| ARDGYGSSRCLQL (SEQ ID NO: 468) |  | T400H | T401H | T402H | T403H | T404H | T405H | T406H | T407H | T408H | T409H | T410H | T411H | T412H | T413H | T414H | T415H | T416H | T417H | T418H |
| ARDGYGSSRCLQL (SEQ ID NO: 468) | T419H | T420H | T421H | T422H | T423H | T424H | T425H | T426H | T427H | T428H | T429H | T430H | T431H | T432H |  | T433H | T434H | T435H | T436H | T437H |
| ARDGYGSSRCLQL (SEQ ID NO: 468) | T438H | T439H |  | T440H | T441H | T442H | T443H | T444H | T445H | T446H | T447H | T448H | T449H | T450H | T451H | T452H | T453H | T454H | T455H | T456H |
| ARDGYGSSRCLQL (SEQ ID NO: 468) | T457H | T458H | T459H | T460H | T461H |  | T462H | T463H | T464H | T465H | T466H | T467H | T468H | T469H | T470H | T471H | T472H | T473H | T474H | T475H |
| ARDGYGSSRCLQL (SEQ ID NO: 468) | T476H | T477H | T478H | T479H | T480H | T481H | T482H | T483H | T484H | T485H | T486H | T487H | T488H | T489H | T490H | T491H | T492H | T493H | T494H |  |
| ARDGYGSSRCLQL (SEQ ID NO: 468) | T495H | T496H | T497H | T498H | T499H |  | T500H | T501H | T502H | T503H | T504H | T505H | T506H | T507H | T508H | T509H | T510H | T511H | T512H | T513H |
| ARDGYGSSRCLQL (SEQ ID NO: 468) | T514H | T515H | T516H | T517H | T518H | T519H | T520H | T521H | T522H | T523H | T524H | T525H | T526H | T527H | T528H |  | T529H | T530H | T531H | T532H |
| ARDGYGSSRCLQL (SEQ ID NO: 468) | T533H | T534H | T535H | T536H | T537H | T538H | T539H | T540H | T541H | T542H | T543H | T544H | T545H | T546H | T547H |  | T548H | T549H | T550H | T551H |
| ARDGYGSSRCLQL (SEQ ID NO: 468) | T552H | T553H | T554H | T555H | T556H | T557H | T558H | T559H | T560H | T561H | T562H | T563H | T564H | T565H | T566H |  | T567H | T568H | T569H | T570H |
| ARDGYGSSRCLQL (SEQ ID NO: 468) | T571H | T572H | T573H | T574H | T575H | T576H | T577H | T578H | T579H | T580H | T581H | T582H | T583H | T584H |  | T585H | T586H | T587H | T588H | T589H |
| ARDGYGSSRCLQL (SEQ ID NO: 468) | T590H |  | T591H | T592H | T593H | T594H | T595H | T596H | T597H | T598H | T599H | T600H | T601H | T602H | T603H | T604H | T605H | T606H | T607H | T608H |
| ARDGYGSSRCLQL (SEQ ID NO: 468) | T609H | T610H | T611H | T612H | T613H | T614H | T615H | T616H | T617H |  | T618H | T619H | T620H | T621H | T622H | T623H | T624H | T625H | T626H | T627H |
| ARDGYGSSRCLQL (SEQ ID NO: 468) | T628H | T629H | T630H | T631H | T632H | T633H | T634H | T635H | T636H | T637H | T638H | T639H | T640H |  | T641H | T642H | T643H | T644H | T645H | T646H |
| ARDGYGSSRCLQL (SEQ ID NO: 468) | T647H | T648H | T649H | T650H | T651H | T652H | T653H | T654H | T655H | T656H | T657H |  | T658H | T659H | T660H | T661H | T662H | T663H | T664H | T665H |

TABLE T-continued

T0681H CDR1 Mutants

| CDR1 | | A | C | D | E | F | G | H | I | K | L | M | N | P | Q | R | S | T | V | W | Y |
|---|---|---|---|---|---|---|---|---|---|---|---|---|---|---|---|---|---|---|---|---|---|
| RYSFTSYY (SEQ ID NO: 462) | | T690H | T691H | T692H | T693H | T694H | T695H | T696H | T697H | T698H | T699H | T700H | T701H | T702H | T703H | T704H | T705H | T706H | T707H | T708H | |
| RYSFTSYY (SEQ ID NO: 462) | | T709H | T710H | T711H | T712H | T713H | T714H | T715H | T716H | T717H | T718H | T719H | T720H | T721H | T722H | T723H | T724H | T725H | T726H | T727H | |
| RYSFTSYY (SEQ ID NO: 462) | | T728H | T729H | T730H | T731H | T732H | T733H | T734H | T735H | T736H | T737H | T738H | T739H | T740H | T741H | T742H | T743H | T744H | T745H | T746H | |
| RYSFTSYY (SEQ ID NO: 462) | | T747H | T748H | T749H | T750H | T751H | T752H | T753H | T754H | T755H | T756H | T757H | T758H | T759H | T760H | T761H | T762H | T763H | T764H | T765H | |
| RYSFTSYY (SEQ ID NO: 462) | | T766H | T767H | T768H | T769H | T770H | T771H | T772H | T773H | T774H | T775H | T776H | T777H | T778H | T779H | T780H | T781H | T782H | T783H | T784H | |
| RYSFTSYY (SEQ ID NO: 462) | | T785H | T786H | T787H | T788H | T789H | T790H | T791H | T792H | T793H | T794H | T795H | T796H | T797H | T798H | T799H | T800H | T801H | T802H | T803H | |
| RYSFTSYY (SEQ ID NO: 462) | | T804H | T805H | T806H | T807H | T808H | T809H | T810H | T811H | T812H | T813H | T814H | T815H | T816H | T817H | T818H | T819H | T820H | T821H | T822H | |
| RYSFTSYY (SEQ ID NO: 462) | | T823H | T824H | T825H | T826H | T827H | T828H | T829H | T830H | T831H | T832H | T833H | T834H | T835H | T836H | T837H | T838H | T839H | T840H | T841H | |

T0681H CDR2 Mutants

| CDR2 | | A | C | D | E | F | G | H | I | K | L | M | N | P | Q | R | S | T | V | W | Y |
|---|---|---|---|---|---|---|---|---|---|---|---|---|---|---|---|---|---|---|---|---|---|
| INPKSGST (SEQ ID NO: 467) | | T842H | T843H | T844H | T845H | T846H | T847H | T848H | T849H | T850H | T851H | T852H | T853H | T854H | T855H | T856H | T857H | T858H | T859H | T860H | |
| INPKSGST (SEQ ID NO: 467) | | T861H | T862H | T863H | T864H | T865H | T866H | T867H | T868H | T869H | T870H | T871H | T872H | T873H | T874H | T875H | T876H | T877H | T878H | T879H | |
| INPKSGST (SEQ ID NO: 467) | | T880H | T881H | T882H | T883H | T884H | T885H | T886H | T887H | T888H | T889H | T890H | T891H | T892H | T893H | T894H | T895H | T896H | T897H | T898H | |
| INPKSGST (SEQ ID NO: 467) | | T899H | T900H | T901H | T902H | T903H | T904H | T905H | T906H | T907H | T908H | T909H | T910H | T911H | T912H | T913H | T914H | T915H | T916H | T917H | |
| INPKSGST (SEQ ID NO: 467) | | T918H | T919H | T920H | T921H | T922H | T923H | T924H | T925H | T926H | T927H | T928H | T929H | T930H | T931H | T932H | T933H | T934H | T935H | T936H | |
| INPKSGST (SEQ ID NO: 467) | | T937H | T938H | T939H | T940H | T941H | T942H | T943H | T944H | T945H | T946H | T947H | T948H | T949H | T950H | T951H | T952H | T953H | T954H | T955H | |

TABLE T-continued

| | T956H | T957H | T958H | T959H | T960H | T961H | T962H | T963H | T964H | T965H | T966H | T967H | T968H | T969H | T970H | T971H | T972H | T973H | T974H |
|---|---|---|---|---|---|---|---|---|---|---|---|---|---|---|---|---|---|---|---|
| INPKSGST (SEQ ID NO: 467) | | | | | | | | | | | | | | | | | | | |

| | T975H | T976H | T977H | T978H | T979H | T980H | T981H | T982H | T983H | T984H | T985H | T986H | T987H | T988H | T989H | T990H | T991H | T992H | T993H |
|---|---|---|---|---|---|---|---|---|---|---|---|---|---|---|---|---|---|---|---|
| INPKSGST (SEQ ID NO: 467) | | | | | | | | | | | | | | | | | | | |

T678H

CDR2 Mutations

| CDR1 Mutations | T678H INPKSGST (SEQ ID NO: 467) | T850H LNPKSGST (SEQ ID NO: 610) | T925H INPKIGST (SEQ ID NO: 613) | T926H INPKKGST (SEQ ID NO: 616) | T951H INPKSSST (SEQ ID NO: 619) | T958H INPKSGDT (SEQ ID NO: 477) | T989H INPKSGSR (SEQ ID NO: 625) | T990H INPKSGSS (SEQ ID NO: 628) |
|---|---|---|---|---|---|---|---|---|
| T678H RYSFTSYY (SEQ ID NO: 462) | T678H | T850H | T925H | T926H | T951H | T958H | T989H | T990H |
| T713H RFSFTSYY (SEQ ID NO: 592) | T1009H | T1015H | T1022H | T1029H | T1036H | T1043H | T1050H | T1057H |
| T734H RYHFTSYY (SEQ ID NO: 595) | T1010H | T1016H | T1023H | T1030H | T1037H | T1044H | T1051H | T1058H |
| T736H RYKFTSYY (SEQ ID NO: 598) | T1011H | T1017H | T1024H | T1031H | T1038H | T1045H | T1052H | T1059H |
| T742H RYRFTSYY (SEQ ID NO: 601) | T1012H | T1018H | T1025H | T1032H | T1039H | T1046H | T1053H | T1060H |
| T774H RYSFKSYY (SEQ ID NO: 604) | T1013H | T1019H | T1026H | T1033H | T1040H | T1047H | T1054H | T1061H |
| T785H RYSFTAYY (SEQ ID NO: 607) | T1014H | T1020H | T1027H | T1034H | T1041H | T1048H | T1055H | T1062H |
| | | T1021H | T1028H | T1035H | T1042H | T1049H | T1056H | T1063H |

T681H

CDR2 Mutations

| CDR1 Mutations | T678H INPKSGST (SEQ ID NO: 467) | T850H LNPKSGST (SEQ ID NO: 610) | T925H INPKIGST (SEQ ID NO: 613) | T926H INPKKGST (SEQ ID NO: 616) | T951H INPKSSST (SEQ ID NO: 619) | T958H INPKSGDT (SEQ ID NO: 477) | T989H INPKSGSR (SEQ ID NO: 625) | T990H INPKSGSS (SEQ ID NO: 628) |
|---|---|---|---|---|---|---|---|---|
| T681H RYSFTSYY (SEQ ID NO: 462) | T681H | T850H | T925H | T926H | T951H | T958H | T989H | T990H |
| T713H RFSFTSYY (SEQ ID NO: 592) | T713H | T1064H | T1070H | T1076H | T1082H | T1088H | T1094H | T1100H |
| T734H RYHFTSYY (SEQ ID NO: 595) | T734H | T1065H | T1071H | T1077H | T1083H | T1089H | T1095H | T1101H |
| T736H RYKFTSYY (SEQ ID NO: 598) | T736H | T1066H | T1072H | T1078H | T1084H | T1090H | T1096H | T1102H |
| T742H RYRFTSYY (SEQ ID NO: 601) | T742H | T1067H | T1073H | T1079H | T1085H | T1091H | T1097H | T1103H |
| T774H RYSFKSYY (SEQ ID NO: 604) | T774H | T1068H | T1074H | T1080H | T1086H | T1092H | T1098H | T1104H |
| T785H RYSFTAYY (SEQ ID NO: 607) | T785H | T1069H | T1075H | T1081H | T1087H | T1093H | T1099H | T1105H |

TABLE T-continued

| | | T687H | | | | | | | |
|---|---|---|---|---|---|---|---|---|---|
| | | CDR2 Mutations | | | | | | | |
| | CDR1 Mutations | T678H INPKSGST (SEQ ID NO: 467) | T850H LNPKSGST (SEQ ID NO: 610) | T925H INPKIGST (SEQ ID NO: 613) | T926H INPKKGST (SEQ ID NO: 616) | T951H INPKSSST (SEQ ID NO: 619) | T958H INPKSGDT (SEQ ID NO: 477) | T989H INPKSGSR (SEQ ID NO: 625) | T990H INPKSGSS (SEQ ID NO: 628) |
| T687H | RYSFTSYY (SEQ ID NO: 462) | T687H | T1113H | T1120H | T1127H | T1134H | T1141H | T1148H | T1155H |
| T713H | RFSFTSYY (SEQ ID NO: 592) | T1107H | T1114H | T1121H | T1128H | T1135H | T1142H | T1149H | T1156H |
| T734H | RYHFTSYY (SEQ ID NO: 595) | T1108H | T1115H | T1122H | T1129H | T1136H | T1143H | T1150H | T1157H |
| T736H | RYKFTSYY (SEQ ID NO: 598) | T1109H | T1116H | T1123H | T1130H | T1137H | T1144H | T1151H | T1158H |
| T742H | RYRFTSYY (SEQ ID NO: 601) | T1110H | T1117H | T1124H | T1131H | T1138H | T1145H | T1152H | T1159H |
| T774H | RYSFKSYY (SEQ ID NO: 604) | T1111H | T1118H | T1125H | T1132H | T1139H | T1146H | T1153H | T1160H |
| T785H | RYSFTAYY (SEQ ID NO: 607) | T1112H | T1119H | T1126H | T1133H | T1140H | T1147H | T1154H | T1161H |

What is claimed is:

1. A bispecific antibody that binds FIXa and FX and catalyses FIXa-mediated activation of FX, wherein the antibody comprises two immunoglobulin heavy-light chain pairs, wherein
    a first heavy-light chain pair comprises a FIXa binding Fv region comprising a first VH domain paired with a first VL domain, and
    a second heavy-light chain pair comprises a FX binding Fv region comprising a second VH domain paired with a second VL domain, wherein
    the first VH domain comprises a set of HCDRs comprising HCDR1, HCDR2 and HCDR3 with amino acid sequences defined wherein HCDR1 is SEQ ID NO: 441; HCDR2 is SEQ ID NO: 436; and HCDR3 is SEQ ID NO: 433, and wherein the first VH domain is at least 95% identical to the N1280H VH domain SEQ ID NO: 443 at the amino acid sequence level;
    the second VH domain comprises a set of HCDRs comprising HCDR1, HCDR2 and HCDR3 with amino acid sequences defined wherein HCDR1 is SEQ ID NO: 598, SEQ ID NO: 2 is SEQ ID NO: 467 and HCDR3 is SEQ ID NO: 565, and wherein the second VH domain is at least 95% identical to the T0999H VH domain SEQ ID NO: 632 at the amino acid sequence level, and
    the first VL domain and the second VL domain each comprise a set of LCDRs comprising LCDR1, LCDR2 and LCDR3 with amino acid sequences defined wherein LCDR1 is SEQ ID NO: 6, LCDR2 is SEQ ID NO: 7 and LCDR3 is SEQ ID NO: 8, and wherein the first VL domain and the second VL domain are at least 95% identical to the 0128L VL domain SEQ ID NO: 10 at the amino acid sequence level.

2. The bispecific antibody according to claim 1, wherein the first VH domain is the N1280H VH domain SEQ. ID NO: 443.

3. The bispecific antibody according to claim 1, wherein the first domain is the N441H VH domain SEQ ID NO: 456.

4. The bispecific antibody according to claim 1, wherein the second VH domain comprises SEQ ID NO: 632.

5. The bispecific antibody according to claim 1, wherein the first VL domain and the second VL domain are identical in amino acid sequence.

6. The bispecific antibody according to claim 5, wherein the first VL domain and the second VL domain comprise the 0325L amino acid sequence SEQ ID NO: 416.

7. The bispecific antibody according to claim 1, wherein each heavy-light chain pair further comprises a CL constant domain paired with a CH1 domain.

8. The bispecific antibody according to claim 1, wherein the heavy-light chain pairs comprise a common light chain.

9. The bispecific antibody according to claim 8, wherein the common light chain comprises the CL amino acid sequence SEQ ID NO: 146 of the 0128L light chain.

10. The bispecific antibody according to claim 9, wherein the common light chain is the 0325L light chain SEQ ID NO: 414.

11. The bispecific antibody according to claim 1, wherein the heavy chain of each heavy-light chain comprises a heavy chain constant region and wherein the first and second heavy-light chain pairs associate to form tetrameric immunoglobulin through dimerisation of the heavy chain constant regions.

12. The bispecific antibody according to claim 11, wherein the heavy chain constant region of the first heavy-light chain pair comprises a different amino acid sequence from the heavy chain constant region of the second heavy-light chain pair, wherein the different amino acid sequences are engineered to promote heterodimerisation of the heavy chain constant regions.

13. The bispecific antibody according to claim 11, wherein the heavy chain constant region of one or both heavy-light chain pairs is a human IgG4 constant region comprising substitution S228P, wherein constant region numbering is according to the EU numbering system.

14. The bispecific antibody according to claim 11, wherein the heavy chain constant region of one (e.g., the first) heavy-light chain pair comprises SEQ ID NO: 409 and the heavy chain constant region of the other (e.g., the second) heavy-light chain pair comprises SEQ ID NO: 410.

15. The bispecific antibody according to claim 11, comprising
   a first heavy chain comprising a first VH domain amino acid sequence SEQ ID NO: 443 or SEQ ID NO: 456,
   a second heavy chain comprising a second VH domain amino acid sequence SEQ ID NO: 632, and
   a common light chain comprising a VL domain amino acid sequence SEQ ID NO: 416.

16. The bispecific antibody according to claim 11, comprising
   a first heavy chain comprising amino acid sequence SEQ ID NO: 419,
   a second heavy chain comprising amino acid sequence SEQ ID NO: 421, and
   a common light chain comprising amino acid sequence SEQ ID NO: 414.

17. The bispecific antibody according to claim 11, comprising
   a first heavy chain comprising amino acid sequence SEQ ID NO: 426
   a second heavy chain comprising amino acid sequence SEQ ID NO: 421, and
   a common light chain comprising amino acid sequence SEQ ID NO: 414.

* * * * *